(12) United States Patent
Bennett et al.

(10) Patent No.: US 8,143,263 B2
(45) Date of Patent: Mar. 27, 2012

(54) THERAPEUTIC AGENTS

(75) Inventors: Stuart Norman Lile Bennett, Macclesfield (GB); Roger John Butlin, Macclesfield (GB); Leonie Campbell, Macclesfield (GB); Robert Darren Morse Davies, Macclesfield (GB); Graeme Richard Robb, Macclesfield (GB); Rolf Peter Walker, Macclesfield (GB); Michael James Waring, Macclesfield (GB); Helen Claire Pointon, Macclesfield (GB); Mikael Dan Brink, Mölndal (SE); Jonas Rickard Fägerhag, Mölndal (SE); Ulrik Jurva, Mölndal (SE); Volker Schnecke, Mölndal (SE); Anette Marie Svensson Henriksson, Mölndal (SE); Christer Ralf Westerlund, Mölndal (SE); Peter Gustaf Bonn, Mölndal (SE)

(73) Assignee: Astrazeneca AB, Sodertalje (SE)

( * ) Notice: Subject to any disclaimer, the term of this patent is extended or adjusted under 35 U.S.C. 154(b) by 30 days.

(21) Appl. No.: 12/535,293

(22) Filed: Aug. 4, 2009

(65) Prior Publication Data
US 2010/0093757 A1 Apr. 15, 2010

Related U.S. Application Data

(60) Provisional application No. 61/085,919, filed on Aug. 4, 2008, provisional application No. 61/168,048, filed on Apr. 9, 2009.

(51) Int. Cl.
*A01N 43/90* (2006.01)
*A61K 31/519* (2006.01)
*C07D 487/00* (2006.01)

(52) U.S. Cl. ..................................... 514/262.1; 544/262

(58) Field of Classification Search .................. None
See application file for complete search history.

(56) References Cited

U.S. PATENT DOCUMENTS

| | | |
|---|---|---|
| 2,750,393 A | 6/1956 | Elpern |
| 2,967,194 A | 1/1961 | Hauptschein |
| 3,917,625 A | 11/1975 | Lee et al. |
| 3,950,351 A | 4/1976 | Rossignol et al. |
| 4,009,174 A | 2/1977 | Cluzan et al. |
| 4,105,785 A | 8/1978 | Mauvernay et al. |
| 4,146,631 A | 3/1979 | Ford et al. |
| 4,434,170 A | 2/1984 | Dostert et al. |
| 4,474,792 A | 10/1984 | Erickson |
| 4,634,783 A | 1/1987 | Fujii et al. |
| 4,966,891 A | 10/1990 | Fujiu et al. |
| 5,258,407 A | 11/1993 | Washburn et al. |
| 5,273,986 A | 12/1993 | Holland et al. |
| 5,399,702 A | 3/1995 | Holland et al. |
| 5,466,715 A | 11/1995 | Washburn et al. |
| 5,510,478 A | 4/1996 | Sabb |
| 5,661,153 A | 8/1997 | Isobe et al. |
| 5,672,750 A | 9/1997 | Perry |
| 5,712,270 A | 1/1998 | Sabb |
| 5,849,735 A | 12/1998 | Albright et al. |
| 5,939,462 A | 8/1999 | Connell et al. |
| 6,110,945 A | 8/2000 | Head et al. |
| 6,197,798 B1 | 3/2001 | Fink et al. |
| 6,200,995 B1 | 3/2001 | De la Brouse-Elwood et al. |
| 6,207,693 B1 | 3/2001 | Setoi et al. |
| 6,214,878 B1 | 4/2001 | Bernardon et al. |
| 6,242,474 B1 | 6/2001 | Yamasaki et al. |
| 6,245,817 B1 | 6/2001 | Connell et al. |
| 6,255,335 B1 | 7/2001 | Himmler et al. |
| 6,316,482 B1 | 11/2001 | Setoi et al. |
| 6,320,050 B1 | 11/2001 | Bizzarro et al. |
| 6,348,474 B1 | 2/2002 | Kayakiri et al. |
| 6,369,229 B1 | 4/2002 | Head et al. |
| 6,376,515 B2 | 4/2002 | Zhu et al. |
| 6,388,071 B2 | 5/2002 | Mahaney |
| 6,448,399 B1 | 9/2002 | Corbett et al. |
| 6,486,349 B1 | 11/2002 | Flitter et al. |

(Continued)

FOREIGN PATENT DOCUMENTS

CA 2605738 11/2006

(Continued)

OTHER PUBLICATIONS

Alvarez et al. "Evidence that glucokinase regulatory protein is expressed and interacts with glucokinase in rat brain" J. Neurochem. 80(1):45-53 (2002).

Alvarez et al. "Expression of the glucagon-like peptide-1 receptor gene in rat brain" J. Neurochem. 66(3):920-927 (1996).

Anderson et al "Pyridopyrimidines. 6. Nucleophilic substitutions in the pyrido[2,3-d]pyrimidine series" J. Org. Chem. 42(6):993-996 (1977).

Ando et al. "Fluoride salts on alumina as reagents for alkylation of phenols and alcohols" Bull. Chem. Soc. Jpn. 55(8):2504-2507 (1982).

(Continued)

*Primary Examiner* — Jeffrey Murray
(74) *Attorney, Agent, or Firm* — Morgan Lewis & Bockius LLP

(57) ABSTRACT

A compound of Formula (I):

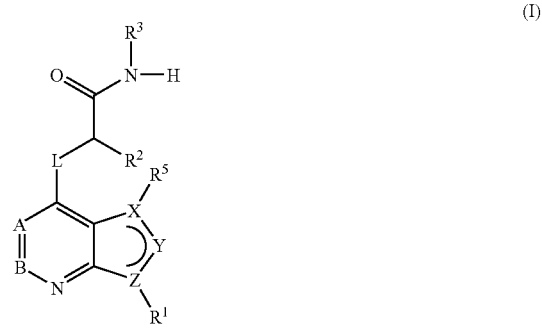

(I)

is useful in the treatment or prevention of a disease or medical condition mediated through glucokinase (GLK or GK), leading to a decreased glucose threshold for insulin secretion.

3 Claims, No Drawings

| | U.S. PATENT DOCUMENTS | | |
|---|---|---|---|
| 6,528,543 B1 | 3/2003 | Bizzarro et al. | |
| 6,545,155 B2 | 4/2003 | Corbett et al. | |
| 6,610,846 B1 | 8/2003 | Bizzarro et al. | |
| 6,613,942 B1 | 9/2003 | Ling et al. | |
| 7,132,546 B2 | 11/2006 | Kato et al. | |
| 7,199,140 B2 | 4/2007 | Hayter et al. | |
| 7,230,108 B2 | 6/2007 | Hargreaves et al. | |
| 7,390,908 B2 | 6/2008 | Boyd et al. | |
| 7,524,957 B2 | 4/2009 | Boyd et al. | |
| 7,642,259 B2 | 1/2010 | McKerrecher et al. | |
| 7,642,263 B2 | 1/2010 | McKerrecher et al. | |
| 7,671,060 B2 | 3/2010 | Martin et al. | |
| 7,696,191 B2 | 4/2010 | McCabe et al. | |
| 7,700,640 B2 | 4/2010 | Cornwall et al. | |
| 7,745,475 B2 | 6/2010 | Johnstone et al. | |
| 7,842,694 B2 | 11/2010 | McKerrecher et al. | |
| 7,902,200 B2 | 3/2011 | Campbell et al. | |
| 2001/0027200 A1 | 10/2001 | De la Brouse-Elwood et al. | |
| 2002/0002183 A1 | 1/2002 | Zhu et al. | |
| 2002/0095044 A1 | 7/2002 | Jagtap et al. | |
| 2003/0162690 A1 | 8/2003 | Zhu et al. | |
| 2003/0228982 A1 | 12/2003 | Helmke et al. | |
| 2004/0014968 A1 | 1/2004 | Bizzarro et al. | |
| 2004/0077555 A1 | 4/2004 | Ishihara et al. | |
| 2004/0214868 A1 | 10/2004 | Hayter et al. | |
| 2005/0080106 A1 | 4/2005 | Boyd et al. | |
| 2005/0148605 A1 | 7/2005 | Grotzfeld et al. | |
| 2005/0165074 A1 | 7/2005 | Grotzfeld et al. | |
| 2005/0171171 A1 | 8/2005 | Mehta et al. | |
| 2005/0171172 A1 | 8/2005 | Lai et al. | |
| 2005/0261315 A1 | 11/2005 | Mehta et al. | |
| 2006/0004010 A1 | 1/2006 | Habashita et al. | |
| 2006/0058353 A1 | 3/2006 | McKerrecher et al. | |
| 2006/0167053 A1 | 7/2006 | Ilno et al. | |
| 2006/0178399 A1 | 8/2006 | Nishizawa et al. | |
| 2006/0258728 A1 | 11/2006 | Tani et al. | |
| 2007/0078168 A1 | 4/2007 | Caulkett | |
| 2007/0093535 A1 | 4/2007 | Hayter et al. | |
| 2007/0112040 A1 | 5/2007 | Hayter et al. | |
| 2007/0255062 A1 | 11/2007 | Johnstone et al. | |
| 2007/0287693 A1 | 12/2007 | Johnstone et al. | |
| 2008/0015203 A1 | 1/2008 | Johnstone et al. | |
| 2008/0057074 A1 | 3/2008 | Takaoka et al. | |
| 2008/0153800 A1 | 6/2008 | McCabe et al. | |
| 2008/0171734 A1 | 7/2008 | Campbell et al. | |
| 2008/0200694 A1 | 8/2008 | Cornwall et al. | |
| 2008/0234273 A1 | 9/2008 | McKerrecher et al. | |
| 2008/0280872 A1 | 11/2008 | Johnstone et al. | |
| 2008/0280874 A1 | 11/2008 | Johnstone et al. | |
| 2008/0300412 A1 | 12/2008 | Hopes et al. | |
| 2008/0312207 A1 | 12/2008 | Johnstone et al. | |
| 2008/0318968 A1 | 12/2008 | Martin et al. | |
| 2009/0018157 A1 | 1/2009 | Johnstone et al. | |
| 2009/0029905 A1 | 1/2009 | McKerrecher et al. | |
| 2009/0062351 A1 | 3/2009 | Caulkett et al. | |
| 2009/0105214 A1 | 4/2009 | McKerrecher et al. | |
| 2009/0105263 A1 | 4/2009 | Caulkett et al. | |
| 2009/0111790 A1 | 4/2009 | McKerrecher et al. | |
| 2009/0118159 A1 | 5/2009 | McKerrecher et al. | |
| 2009/0131403 A1 | 5/2009 | Kusuda et al. | |
| 2009/0227592 A1 | 9/2009 | Boyd et al. | |
| 2009/0253676 A1 | 10/2009 | Johnstone et al. | |
| 2009/0264336 A1 | 10/2009 | McKerrecher et al. | |
| 2010/0094009 A1 | 4/2010 | McCabe et al. | |
| 2010/0210621 A1 | 8/2010 | Bowden et al. | |
| 2010/0210841 A1 | 8/2010 | Butters et al. | |
| 2011/0034432 A1 | 2/2011 | Johnstone et al. | |
| 2011/0053910 A1 | 3/2011 | McKerrecher et al. | |
| 2011/0059941 A1 | 3/2011 | Caulkett et al. | |

FOREIGN PATENT DOCUMENTS

| CS | 173097 | 6/1978 |
|---|---|---|
| EP | 0316704 | 5/1989 |
| EP | 0353452 | 2/1990 |
| EP | 0219436 | 12/1993 |
| EP | 0619116 | 10/1994 |
| EP | 841339 | * 5/1998 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1790637 | 5/2005 |
| EP | 1541563 | 6/2005 |
| EP | 1532980 | 11/2005 |
| EP | 1600442 | 11/2005 |
| EP | 1604981 | 12/2005 |
| EP | 1702919 | 9/2006 |
| EP | 1995246 | 11/2008 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/35944 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |

| | | |
|---|---|---|
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/007472 | 1/2004 |
| WO | WO 2004/009602 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/080966 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/042513 | 5/2005 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/010750 | 2/2006 |
| WO | WO 2006/016174 | 2/2006 |
| WO | WO 2006/016178 | 2/2006 |
| WO | WO 2006/016194 | 2/2006 |
| WO | WO 2006/030925 | 3/2006 |
| WO | WO 2006/034833 | 4/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/030567 | 3/2007 |
| WO | WO 2007/031739 | 3/2007 |
| WO | WO 2007/053657 | 5/2007 |
| WO | WO 2007/060448 | 5/2007 |
| WO | WO 2007/075847 | 7/2007 |
| WO | WO 2007/076474 | 7/2007 |
| WO | WO 2007/105637 | 9/2007 |
| WO | WO 2007/143434 | 12/2007 |
| WO | WO 2008/050101 | 5/2008 |
| WO | WO 2008/050117 | 5/2008 |
| WO | WO 2008/075073 | 6/2008 |
| WO | WO 2008/138918 | 11/2008 |
| WO | WO 2008/148832 | 12/2008 |
| WO | WO 2009/052230 | 4/2009 |
| WO | WO 2009/052231 | 4/2009 |
| WO | WO 2010/015849 | 2/2010 |

OTHER PUBLICATIONS

Atwell et al. "Potential antitumor agents. VI. Bisquaternary salts" J. Med. Chem. 11(2):295-300 (1968).

Baker et al. "Structure and synthesis of Pallescansin E utilising a modified Wadsworth-Emmons reaction" J. Chem. Soc., Perkin Trans. 1, 12:3087-3091 (1981).

Baker et al. "Synthesis of Pallescensin-E: Use of crown ether in the Wadsworth procedure for olefin formation" Tetrahedron Letters 22:161-162 (1981).

Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).

Beilstein Registry No. 6511458 (Apr. 18, 1994) [XP002272206].

Bell et al. "Glucokinase mutations, insulin secretion, and diabetes mellitus" Annu. Rev. Physiol. 58:171-186 (1996).

Beller et al. "Photochemical synthesis of benzo[f]quinolines" J Org Chem. 42(22):3514-3518 (1977).

Berl et al. "Induced fit selection of a barbiturate receptor from a dynamic structural and conformational/ configurational library" European J. Org. Chem. (11):3089-3094 (1999).

Berl et al. "Template-induced and molecular recognition directed hierarchical generation of supramolecular assemblies from molecular strands" Chem. Eur. J. 6(11):1938-1946 (2000).

Bonina et al. "Synthesis and pharmacologic activity of 2-arylethenylthiazol-4-acetic and 4-carboxylic acids" II Farmaco 40(11):875-884 (1985).

Boucherle et al. "Recherches dans la serie des cetones polyphenoliques IV. Thiazoles" Chimica. Therapeutica. 3(5):360-363 (1968) (Translation enclosed).

Bowden et al. "Structure-activity relations. Part 10. Metal-ion-complexation studies of a series of substituted benzamidotetrazoles" J. Chem. Research (Synopses) 11:304 (1991).

Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).

Brenner et al. "Imino-bridged heterocycles. VII. (1) N-aminobenzocycloheptapyridinimines" J. Heterocyclic Chem. 23:1331-1332 (1986).

Brocklehurst et al. "Stimulation of hepatocyte glucose metabolism by novel small molecule glucokinase activators" Diabetes 53:535-541 (2004).

Caira "Crystalline polymorphism of organic compounds" Topics in Current Chemistry 198:163-208 (1998).

Caro et al. "Liver glucokinase: Decreased activity in patients with type II diabetes" Horm. Metab. Res. 27(1):19-22 (1995).

Carroll et al. "The in vitro characterisation of a novel Glucokinase activator" Stress, Signalling and Control, Biochemical Society Meeting 679, University of Essex, UK (Jul. 2-4, 2003).

Caulfield et al. "The first potent and selective inhibitors of the glycine transporter type 2" J. Med. Chem. 44(17):2679-2682 (2001).

Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).

Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].

Chemical Abstracts Service, Columbus, Ohio, US: CAS Registry No. 354767-51-4 (Sep. 5, 2001).

Chemical Abstracts Service, Columbus, Ohio, US: CAS Registry No. 354767-66-1 (Sep. 5, 2001).

Chemical Abstracts Service, Columbus, Ohio, US: CAS Registry No. 438028-05-8 (Nov. 15, 2001); CAS Registry No. 438024-90-9 (Nov. 15, 2001), [XP002272448].

Christesen et al. "The second activating glucokinase mutation (A456V): Implications for glucose homeostasis and diabetes therapy" Diabetes 51(4):1240-1246 (2002).

Ciaceri et al. "Analgesic, antipyretic and anti-inflammatory action of some new acids of the phenylethylenethiazole series" Minerva Medica 63(42):2409-2413 (1972).

Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coghlan et al. "Glucokinase activators in diabetes management" Expert Opin. Investig. Drugs 17(2):145-167 (2008).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al. "The triumvirate: β-cell, muscle, liver. A collusion responsible for NIDDM" Diabetes 37:667-687 (1988).

DeJohn et al. "Functionalization of Substituted 2(1H)- and 4(1H)-Pyridones. III. The preparation of substituted 6-vinyl-1,2-dihydro-2-oxo- and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22: 1686 (1957).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract No. 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methyl-morpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel antidiabetic agents" Biochemical Society Transactions 33(Part 2):371-374 (2005).

Leighton, "Pre-clinical disease models—challenges and success stories"44th Drug Information Association Annual Meeting, Boston, MA, US (2008).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).

Levin et al. "Differential effects of diet and obesity on high and low affinity sulfonylurea binding sites in the rat brain" Brain Research 739(1-2):293-300 (1996).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhurnal Obshchei Khimii 27:3097-3107 (1957) (Translation enclosed).

Lith, "Evaluation of the effects on whole body glucose metabolism after single doses of X2000—A glucose lowering agent" Poster presentation, Master thesis in Pharmaceutical Bioscience, Goteborgs University (2008).

Lynch et al. "Localization of glucokinase gene expression in the rat brain" Diabetes 49(5):693-700 (2000).

Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial polypyridine and polypyrimidine receptors" Angewandte Chemie International Edition 39(3):551-554 (2000).

Mazik et al. "Molecular recognition of carbohydrates by artificial receptors: systematic studies towards recognition motifs for carbohydrates" Chem. Eur. J. 7(3):664-670 (2001).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (May 15, 2006) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328-7336 (1998).

Palmans "Extended-core discotic liquid crystals based on the intramolecular H-bonding in N-acylated 2,2'-bipyridine-3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by Streptomyces purpurogeniscleroticus and Nocardia vaccinii" Journal of Antibiotics (Tokyo), 52(3):245-255 (1999).

Ralph et al. "Glucose Modulation of Glucokinase Activation by Small Molecules" Biochemistry 47(17):5028-5036 (2008).

Rivalle et al. "2,3 Disubstituted furans and pyrroles—XVIII: Synthesis annd rearrangement of 4H-dihydro-9,10 benzo[4,5]cyclohepta[1,2-b]furannones-4" Tetrahedron 32(7):829-834 (1976).

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Sarabu et al., "Glucokinase activators as new type 2 diabetes therapeutic agents" Expert Opinion on Therapeutic Patents 18(7):759-768 (2008).

Schuit et al. "Glucose sensing in pancreatic β-Cells. A model for the study of other glucose-regulated cells in gut, pancreas, and hypothalamus" Diabetes 50:1-11 (2001).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Shorvon, "Pyrrolidone derivatives" Lancet 358(9296):1885-1892 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 (1997).

Takagi et al. "Studies on metabolic fate of 3,4,5-trimethoxy-N-(3-piperidyl)benzamide(KU-54). (2). Metabolism in rats" Accession No. 1984:503556 HCAPLUS, Abstract of Oyo Yakuri 27(6):1167-1174 (1984).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" J Am. Chem. Soc. 124(49):14759-14769 (2002).

Vanderstelt et al. "Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004).

West, Anthony R., "Solid State Chemistry and its Applications" Wiley, New York, pp. 358 and 365 (1988).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).

Wolff, Manfred E. "Burger's Medicinal Chemistry", 5th Edition, Part I, John Wiley & Sons, pp. 975-977 (1995).

Yakushijin et al. "Intramolecular ring formation of phenyl azide and furan moieties" Chem. Pharm. Bull. 30(1):140-151 (1982).

Yakushijin et al. "Intramolecular ring formation of phenyl azide and furan" Heterocycles 12(8):1021-1026 (1979).

Yang et al. "Hypothalamic glucose sensor: similarities to and differences from pancreatic beta-cell mechanisms" Diabetes 48(9):1763-1772 (1999).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

Z.H. Ismail et al., "Synthesis of Some New Biologically Active Sulfur Compounds Containing Pyrazolo[3,4-d]pyrimidine Moiety", Phosphorus, Sulfur and Silicon and the Related Elements 178: 1795-1805 (2003).

J.M. Ready et al., "Asymmetric Catalytic Synthesis of a-Aryloxy Alcohols: Kinetic Resolution of Terminal Epoxides via Highly Enantioselective Ring Opening with Phenols", J. Am. Chem. Soc. 121: 6086-6087 (1999).

* cited by examiner

THERAPEUTIC AGENTS

This application claims the benefit under 35 U.S.C. §119(e) of Application No. 61/085,919 (US) filed on 4 Aug. 2008 and Application No. 61/168,048 (US) filed on 9 Apr. 2009.

The present invention relates to a group of 2-{[1-substituted-1H-pyrazolo[3,4-d]pyrimidin-4-yl](thio, oxy or amino)-N-(heteroaryl)alkanamides which are useful in the treatment or prevention of a disease or medical condition mediated through glucokinase (GLK or GK). GK Activators (GKAs) are known to activate GK in the pancreatic b-cell leading to a decreased glucose threshold for insulin secretion. In addition GKAs activate hepatic GK thereby stimulating hepatic glucose uptake and suppressing hepatic glucose output. The net pharmacological effect of GKAs is to lower blood glucose levels Therefore, such compounds may have utility in the treatment of Type 2 diabetes and obesity. The invention also relates to pharmaceutical compositions comprising said compounds and to methods of treatment of diseases mediated by GLK using said compounds.

The biology of glucokinase and the mechanisms by which GKAs might deliver potential therapeutic benefit in Type 2 diabetes have been extensively reviewed in the literature (see for example Matschinsky F M et al. (2006) Diabetes 55: 1-12, Leighton B, Atkinson A, Coghlan M P (2005) Biochemical Society Transactions 33: 371-374 and "Glucokinase and Glycemic Disease: From Basics to Novel Therapeutics." Frontiers in Diabetes vol 16, eds. Matschinsky F M and Magnuson M A, Karger (Basel) 2005). In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P), which is catalysed by glucokinase (GLK). GLK has a high (6-10 mM) Km for glucose and is not inhibited by physiological concentrations of G-6-P. GLK expression is limited to a few tissues and cell types, most notably pancreatic β-cells and liver cells (hepatocytes). In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes.

In one sub-type of diabetes, Maturity-Onset Diabetes of the Young Type 2 (MODY-2), the diabetes is caused by GLK loss of function mutations. Hyperglycaemia in MODY-2 patients results from defective glucose utilisation in both the pancreas and liver. Defective glucose utilisation in the pancreas of MODY-2 patients results in a raised threshold for glucose stimulated insulin secretion. Conversely, rare activating mutations of GLK reduce this threshold resulting in familial hyperinsulinism. In addition to the reduced GLK activity observed in MODY-2 diabetics, hepatic glucokinase activity is also decreased in type 2 diabetics. Importantly, global or liver selective overexpression of GLK prevents or reverses the development of the diabetic phenotype in both dietary and genetic models of the disease. Moreover, acute treatment of type 2 diabetics with fructose improves glucose tolerance through stimulation of hepatic glucose utilisation. This effect is believed to be mediated through a fructose induced increase in cytosolic GLK activity in the hepatocyte by the mechanism described below.

GLK and the $K_{ATP}$ channel are expressed in neurones of the hypothalamus, a region of the brain that is important in the regulation of energy balance and the control of food intake. These neurones have been shown to express orectic and anorectic neuropeptides and have been assumed to be the glucose-sensing neurones within the hypothalamus that are either inhibited or excited by changes in ambient glucose concentrations. The ability of these neurones to sense changes in glucose levels is defective in a variety of genetic and experimentally induced models of obesity. Intracerebroventricular (icv) infusion of glucose analogues, that are competitive inhibitors of glucokinase, stimulate food intake in lean rats. In contrast, icy infusion of glucose suppresses feeding. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK system can be described as a potential "Diabesity" target (of benefit in both Diabetes and Obesity).

GLK is also expressed in specific entero-endocrine cells where it is believed to control the glucose sensitive secretion of the incretin peptides GIP (glucose-dependent insulinotropic polypeptide) and GLP-1 (Glucagon-Like Peptide-1) from gut K-cells and L-cells respectively. Therefore, small molecule activators of GLK may have additional beneficial effects on insulin secretion, b-cell function and survival and body weight as a consequence of stimulating GIP and GLP-1 secretion from these entero-endocrine cells.

A group of novel activators of GLK has been found containing a 1H-pyrazolo[3,4-d]pyrimidin-4-yl core. N-(Thiazolyl)-2-[(1-phenyl-1H-pyrazolo[3,4-d]pyrimidin-4-yl)thio]acetamide is disclosed in Phosphorus, Sulfur and Silicon, vol 178, 2003, pp 1795-1805 which is concerned with antimicrobial activity of related compounds. Similar compounds are also known from commercially available Chemical Libraries.

WO98/35944 discloses that compounds of formula $R^1R^2N$—C(O)—C($R^3$)($R^4$)—X—$R^5$ in which $R^1$-$R^5$ are each individually selected from a wide range of substituents and X is oxygen or sulfur are useful in treating bulimia and obesity by virtue of their activity at the NPY receptor antagonists. $R^5$ may be 1H-pyrazolo[3,4-d]pyrimidin-4-yl or 4-aminopyrazolo[3,4-d]pyrimidin-6-yl. Specific compounds exemplified are N-(4-cyclohexylphenyl)-2-(1H-pyrazolo[3,4-d]pyrimidin-4-ylsulfanyl)acetamide, N-(4-benzoylphenyl)-2-(1H-pyrazolo[3,4-d]pyrimidin-4-ylsulfanyl)acetamide, 2-(4-amino-1H-pyrazolo[3,4-d]pyrimidin-6-ylsulfanyl)-N-(4-cyclohexylphenyl)acetamide and 2-(4-amino-1H-pyrazolo[3,4-d]pyrimidin-6-ylsulfanyl)-N-(4-benzoylphenyl)acetamide.

Thus, according to the first aspect of the invention there is provided a compound of Formula I:

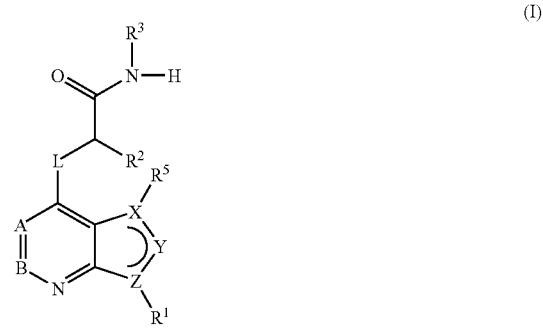

or a pharmaceutically acceptable salt thereof in which:
A and B are each either N or CR$^6$, provided that at least one of A and B is CR$^6$;
X is C or N;
Y is CH or N;
Z is C or N;
wherein X, Y and Z are chosen such that at least two of X, Y and Z are N, the ring containing them is aromatic and any ring nitrogen atom is not quaternised;
R$^1$ is (1-6C)alkyl, aryl, aryl(1-6C)alkyl or HET-1 wherein the aryl, aryl(1-6C)alkyl and HET-1 are optionally substituted by one, two or three groups independently selected from halo, (1-4C)alkyl, (1-4C)alkoxy, trifluoromethyl, (1-6C)alkylthio, (1-6C)alkylsulfinyl, (1-6C)alkylsulfonyl, cyano, carboxy, (1-6C)alkoxycarbonyl, carbamoyl, N-(1-4C)alkylcarbamoyl, N,N-di(1-4C)alkylcarbamoyl, aminosulfonyl, (1-6C)alkylaminosulfonyl, di(1-6C)alkylaminosulfonyl, (1-4C)alkanoylamino, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, di(1-4C)alkylamino(1-4C)alkyl, (1-6C)alkoxycarbonyl(1-4C)alkyl-, (1-6C)alkylsulfonyloxy, (3-6C)cycloalkylsulfonyl, (1-6C)alkylsulfonylamino, azetidinylcarbonyl, pyrrolidinylcarbonyl and HET-3A;
wherein HET-1 is a 5- or 6-membered, C-linked heteroaryl ring, or a fused bicyclic ring system of formula -D-E, wherein ring D is attached to Z and is 6-membered aryl or heteroaryl ring and ring E is a 5- or 6-membered heteroaryl, heterocyclyl or cycloalkyl ring which is fused to ring D at any available position;
R$^2$ is (1-6C)alkyl optionally substituted by one or two hydroxy or by one of the following: carboxy, carbamoyl, N,N-di(1-4C)alkylcarbamoyl, (1-6C)alkoxycarbonyl, a group —N(R$^7$)COR$^8$ or a group NR$^9$R$^{10}$;
or R$^2$ is a group —(CHR$^4$)$_n$—P-Q wherein n is 1, 2, 3 or 4;
P is a linker selected from O, SO$_2$, CONH and NHCO;
Q is selected from (1-6C)alkyl, (3-6C)cycloalkyl and a 4-, 5- or 6-membered heterocyclyl (wherein said heterocyclyl ring contains 1, 2 or 3 heteroatoms independently selected from O, N and S, provided that there are no O—O, S—S or O—S bonds, wherein an available carbon atom in the ring may be oxidised to a carbonyl group, an available sulfur atom in the ring may be oxidised to an SO or SO$_2$ group and wherein there is optionally a double bond in the ring), and Q is optionally substituted on an available carbon atom by hydroxy or (1-4C)alkoxy;
R$^3$ is a group HET-2 wherein HET-2 is a 5- or 6-membered C-linked monocyclic heteroaryl ring, containing a nitrogen atom in the 2-position and optionally 1 or 2 further ring heteroatoms independently selected from O, N and S; or HET-2 is an 8-, 9- or 10-membered C-linked bicyclic heteroaryl ring containing a nitrogen atom in the 2-position with up to five further ring heteroatoms independently selected from O, N and S;
wherein HET-2 is optionally substituted on an available carbon atom, or on a ring nitrogen atom provided it is not thereby quaternised, with 1 or 2 substituents independently selected from R$^H$;
each R$^4$ is independently selected from hydrogen, hydroxy, methyl and ethyl; provided that when n is >1, then no more than two R$^4$ groups are hydroxy;
R$^5$ is H, (1-4C)alkoxy or (1-4C)alkyl;
R$^6$ is H, (1-4C)alkoxy or (1-4C)alkyl;
R$^7$ is H or (1-4C)alkyl;
R$^8$ is (1-4C)alkyl;
R$^9$ is H or (1-4C)alkyl optionally substituted with hydroxy or methoxy;
R$^{10}$ is H or (1-4C)alkyl;
or —NR$^9$R$^{10}$ forms an azetidine optionally substituted by hydroxy;
R$^{11}$ is independently selected from halo, (1-4C)alkyl, (1-4C)alkoxy, trifluoromethyl, (1-6C)alkylthio, (1-6C)alkylsulfinyl, (1-6C)alkylsulfonyl, cyano, carboxy, (1-6C)alkoxycarbonyl, carbamoyl, N-(1-4C)alkylcarbamoyl, N,N-di(1-4C)alkylcarbamoyl, aminosulfonyl, (1-6C)alkylaminosulfonyl, di(1-6C)alkylaminosulfonyl, (1-4C)alkanoylamino, hydroxy(1-4C)alkyl, (1-4C)alkoxy(1-4C)alkyl, (1-4C)alkylS(O)p(1-4C)alkyl (wherein p is 0, 1 or 2), amino(1-4C)alkyl, (1-4C)alkylamino(1-4C)alkyl, di(1-4C)alkylamino(1-4C)alkyl, (1-6C)alkoxycarbonyl(1-4C)alkyl-, (1-6C)alkylsulfonyloxy, (3-6C)cycloalkylsulfonyl, (1-6C)alkylsulfonylamino, azetidinylcarbonyl, pyrrolidinylcarbonyl and HET-3;
HET-3 and HET-3A are each independently either a 5- or 6-membered, C- or N-linked unsubstituted heteroaryl ring containing 1, 2 or 3 ring heteroatoms independently selected from O, N and S, or a 4-, 5- or 6-membered, C- or N-linked unsubstituted saturated heterocyclyl ring containing one ring heteroatom selected from O, N and S;
L is S, O or NR$^{12}$; and
R$^{12}$ is H or (1-4C)alkyl;
but excluding
N-(5-chloro-2-pyridinyl)-2-[(1-phenyl-1H-pyrazolo[3,4-d]pyrimidin-4-yl)thio]propanamide;
N-[1-(1-methylethyl)-1H-pyrazol-5-yl]-2-[(1-phenyl-1H-pyrazolo[3,4-d]pyrimidin-4-yl)thio]propanamide,
N-(5-(methyl)isoxazol-3-yl)-2-[[1-(4-fluorophenyl)-1H-pyrazolo[3,4-d]pyrimidin-4-yl]thio]butanamide;
N-(5-(methyl)isoxazol-3-yl)-2-[[1-(4-fluorophenyl)-1H-pyrazolo[3,4-d]pyrimidin-4-yl]thio]propanamide;
(2R)-2-[1-(3-chloro-2-pyridyl)pyrazolo[4,5-e]pyrimidin-4-yl]oxy-5-hydroxy-N-(5-methyl-2-pyridyl)pentanamide;
(2R)—N-(5-chloro-2-pyridyl)-2-[1-(3-chloro-2-pyridyl)pyrazolo[4,5-e]pyrimidin-4-yl]oxy-5-hydroxy-pentanamide;
(2S)-2-[1-(3-chloro-2-pyridyl)pyrazolo[4,5-e]pyrimidin-4-yl]oxy-N-(5-cyano-2-pyridyl)-3-[(1S)-2-hydroxy-1-methyl-ethoxy]propanamide;
(2R)-2-[1-(2-chlorophenyl)pyrazolo[4,5-e]pyrimidin-4-yl]oxy-N-(5-cyano-2-pyridyl)-3-(2-hydroxyethoxy)propanamide;
(2S)—N-(5-cyano-2-pyridyl)-2-[1-(2,5-dimethylphenyl)pyrazolo[4,5-e]pyrimidin-4-yl]oxy-3-(2-hydroxyethoxy)propanamide;
(2S)-3-(2-hydroxyethoxy)-N-(5-methyl-2-pyridyl)-2-(9-phenylpurin-6-yl)oxy-propanamide;
(2R)-2-[1-(2-chlorophenyl)pyrazolo[4,5-e]pyrimidin-4-yl]oxy-N-(5-fluoro-2-pyridyl)-3-(2-hydroxyethoxy)propanamide;
(2S)—N-(5-chloro-2-pyridyl)-2-[1-(3-chloro-2-pyridyl)pyrazolo[4,5-e]pyrimidin-4-yl]oxy-3-[(2R)-2-hydroxypropoxy]propanamide;
(2R)—N-(5-chloro-2-pyridyl)-2-[1-(3-chloro-2-pyridyl)pyrazolo[4,5-e]pyrimidin-4-yl]oxy-3-[(2R)-2-hydroxypropoxy]propanamide;
(2S)-2-[1-(3-chloro-2-pyridyl)pyrazolo[4,5-e]pyrimidin-4-yl]oxy-N-(5-cyano-2-pyridyl)-3-(3-hydroxycyclobutoxy)propanamide; and
(2S)—N-(5-chloro-2-pyridyl)-2-[1-(3-chloro-2-pyridyl)pyrazolo[4,5-e]pyrimidin-4-yl]oxy-3-(3-hydroxycyclobutoxy)propanamide.
In a further aspect of the invention there is provided a compound of the formula (I) or a pharmaceutically acceptable salt thereof wherein:

A and B are each either N or CR$^6$, provided that at least one of A and B is CR$^6$;

X is C or N;

Y is CH or N;

Z is C or N;

wherein X, Y and Z are chosen such that at least two of X, Y and Z are N, the ring containing them is aromatic and any ring nitrogen atom is not quaternised;

R$^1$ is (1-6C)alkyl, aryl, aryl(1-6C)alkyl or HET-1 wherein the aryl, aryl(1-6C)alkyl and HET-1 are optionally substituted by one, two or three groups independently selected from halo, (1-4C)alkyl, (1-4C)alkoxy, trifluoromethyl, (1-6C)alkylthio, (1-6C)alkylsulfinyl, (1-6C)alkylsulfonyl, cyano, carboxy, (1-6C)alkoxycarbonyl, carbamoyl, N-(1-4C)alkylcarbamoyl, N,N-di(1-4C)alkylcarbamoyl, aminosulfonyl, (1-6C)alkylaminosulfonyl, di(1-6C)alkylaminosulfonyl, (1-4C)alkanoylamino, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, di(1-4C)alkylamino(1-4C)alkyl, (1-6C)alkoxycarbonyl(1-4C)alkyl-, (1-6C)alkylsulfonyloxy, (3-6C)cycloalkylsulfonyl, (1-6C)alkylsulfonylamino, azetidinylcarbonyl, pyrrolidinylcarbonyl and HET-3A;

wherein HET-1 is a 5- or 6-membered, C-linked heteroaryl ring, or a fused bicyclic ring system of formula -D-E, wherein ring D is attached to Z and is 6-membered aryl or heteroaryl ring and ring E is a 5- or 6-membered heteroaryl, heterocyclyl or cycloalkyl ring which is fused to ring D at any available position;

R$^2$ is (1-6C)alkyl optionally substituted by one or two hydroxy or by one of the following: carboxy, carbamoyl, N,N-di(1-4C)alkylcarbamoyl, (1-6C)alkoxycarbonyl, a group —N(R$^7$)COR$^8$ or a group NR$^9$R$^{10}$;

or R$^2$ is a group —(CHR$^4$)$_n$—P-Q wherein n is 1, 2, 3 or 4;

P is a linker selected from O, SO$_2$, SO$_2$NH, NHSO$_2$, CONH and NHCO;

Q is selected from (1-6C)alkyl, (3-6C)cycloalkyl and a 4-, 5- or 6-membered heterocyclyl (wherein said heterocyclyl ring contains 1, 2 or 3 heteroatoms independently selected from O, N and S, provided that there are no O—O, S—S or O—S bonds, wherein an available carbon atom in the ring may be oxidised to a carbonyl group, an available sulfur atom in the ring may be oxidised to an SO or SO$_2$ group and wherein there is optionally a double bond in the ring), and Q is optionally substituted on an available carbon atom by hydroxy or (1-4C)alkoxy;

R$^3$ is a group HET-2 wherein HET-2 is a 5- or 6-membered C-linked monocyclic heteroaryl ring, containing a nitrogen atom in the 2-position and optionally 1 or 2 further ring heteroatoms independently selected from O, N and S; or HET-2 is an 8-, 9- or 10-membered C-linked bicyclic heteroaryl ring containing a nitrogen atom in the 2-position with up to five further ring heteroatoms independently selected from O, N and S;

wherein HET-2 is optionally substituted on an available carbon atom, or on a ring nitrogen atom provided it is not thereby quaternised, with 1 or 2 substituents independently selected from R$^{11}$;

each R$^4$ is independently selected from hydrogen, hydroxy, methyl and ethyl; provided that when n is >1, then no more than two R$^4$ groups are hydroxy;

R$^5$ is H, (1-4C)alkoxy or (1-4C)alkyl;

R$^6$ is H, (1-4C)alkoxy or (1-4C)alkyl;

R$^7$ is H or (1-4C)alkyl;

R$^8$ is (1-4C)alkyl;

R$^9$ is H or (1-4C)alkyl;

R$^{10}$ is H or (1-4C)alkyl;

R$^{11}$ is independently selected from halo, (1-4C)alkyl, (1-4C)alkoxy, trifluoromethyl, (1-6C)alkylthio, (1-6C)alkylsulfinyl, (1-6C)alkylsulfonyl, cyano, carboxy, (1-6C)alkoxycarbonyl, carbamoyl, N-(1-4C)alkylcarbamoyl, N,N-di(1-4C)alkylcarbamoyl, aminosulfonyl, (1-6C)alkylaminosulfonyl, di(1-6C)alkylaminosulfonyl, (1-4C)alkanoylamino, hydroxy(1-4C)alkyl, (1-4C)alkoxy(1-4C)alkyl, (1-4C)alkylS(O)p(1-4C)alkyl (wherein p is 0, 1 or 2), amino(1-4C)alkyl, (1-4C)alkylamino(1-4C)alkyl, di(1-4C)alkylamino(1-4C)alkyl, (1-6C)alkoxycarbonyl(1-4C)alkyl-, (1-6C)alkylsulfonyloxy, (3-6C)cycloalkylsulfonyl, (1-6C)alkylsulfonylamino, azetidinylcarbonyl, pyrrolidinylcarbonyl and HET-3;

HET-3 and HET-3A are each independently either a 5- or 6-membered, C- or N-linked unsubstituted heteroaryl ring containing 1, 2 or 3 ring heteroatoms independently selected from O, N and S, or a 4-, 5- or 6-membered, C- or N-linked unsubstituted saturated heterocyclyl ring containing one ring heteroatom selected from O, N and S;

L is S, O or NR$^{12}$; and

R$^{12}$ is H or (1-4C)alkyl;

but excluding

N-(5-chloro-2-pyridinyl)-2-[(1-phenyl-1H-pyrazolo[3,4-d]pyrimidin-4-yl)thio]propanamide;

N-[1-(1-methylethyl)-1H-pyrazol-5-yl]-2-[(1-phenyl-1H-pyrazolo[3,4-d]pyrimidin-4-yl)thio]propanamide, N-(5-(methyl)isoxazol-3-yl)-2-[[1-(4-fluorophenyl)-1H-pyrazolo[3,4-d]pyrimidin-4-yl]thio]butanamide; and N-(5-(methyl)isoxazol-3-yl)-2-[[1-(4-fluorophenyl)-1H-pyrazolo[3,4-d]pyrimidin-4-yl]thio]propanamide.

The term "aryl" refers to phenyl, naphthyl or a partially saturated bicyclic carbocyclic ring containing between 8 and 12 carbon atoms, preferably between 8 and 10 carbon atoms. Example of partially saturated bicyclic carbocyclic ring include: 1,2,3,4-tetrahydronaphthyl, indanyl, indenyl, 1,2,4a, 5,8,8a-hexahydronaphthyyl or 1,3a-dihydropentalene. Examples of "aryl(1-6C)alkyl" include any of the above examples of "aryl" in conjunction with any of the examples of "(1-6C)alkyl" hereinafter.

Suitable HET-1 groups when HET-1 is a 5- or 6-membered C-linked heteroaryl ring include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl. More suitably HET-1 groups are pyridyl or pyrazinyl, particularly 2-pyridyl, 4-pyridyl and pyrazinyl. Suitable HET-1 groups when HET-1 is of formula -D-E (as hereinbefore defined) include indanyl, benzodioxolyl, benzimidazolyl, benzthiazolyl, benzisothiazolyl, benzoxazolyl, benzisoxazolyl, quinolyl, isoquinolyl, benzofurazanyl, indolyl, indazolyl, cinnolinyl, quinazolinyl, quinoxalinyl, phthalazinyl, 1,5-naphthyridinyl, 1,6-naphthyridinyl, 1,7-naphthyridinyl, 1,8-naphthyridinyl, pyrrolopyridinyl, pyrrolopyrazinyl, pyrazolopyridinyl and imidazopyridinyl.

Suitable examples of HET-2 include pyrrolyl, thiazolyl, isothiazolyl, pyrazolyl, imidazolyl, thiadiazolyl (1,2,4- and 1,3,4-), oxazolyl, isoxazolyl, triazolyl, 1,3,4-oxadiazolyl, 1,2,4-oxadiazolyl, furazanyl, tetrazolyl, pyridyl, pyrazinyl, pyridazinyl, pyrimidinyl, 1,3,5-triazinyl, imidazothiazolyl, benzimidazolyl, benzthiazolyl, benzisothiazolyl, benzoxazolyl, benzisoxazolyl, quinolyl, isoquinolyl, benzofurazanyl, indolyl, indazolyl, cinnolinyl, quinazolinyl, quinoxalinyl, phthalazinyl, 1,5-naphthyridinyl, 1,6-naphthyridinyl, 1,7-naphthyridinyl, 1,8-naphthyridinyl, pyrrolopyridinyl, pyrrolopyrazinyl, pyrazolopyridinyl and imidazopyridinyl.

Suitable examples of HET-3 and HET-3A as heteroaryl rings are furyl, pyrrolyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl and triazolyl. Suitable examples of HET-3 and HET-3A as saturated heterocyclyl rings are oxetane, azetidine, thietane, pyrrolidine, tetrahydrofuran, tetrahydropyran and piperidine.

It will be appreciated that, where definitions of heterocyclyl groups HET-1, HET-2, HET-3 and HET-3A encompass heteroaryl rings which may be substituted on nitrogen, such substitution may not result in charged quaternary nitrogen atoms. It will be appreciated that the definitions of HET-1, HET-2, HET-3 and HET-3A are not intended to include any O—O, O—S or S—S bonds. It will be appreciated that the definitions of HET-1, HET-2, HET-3 and HET-3A are not intended to include unstable structures.

For the avoidance of doubt, reference to the group HET-2 containing a nitrogen in the 2-position, is intended to refer to the 2-position relative to the amide nitrogen atom to which the group is attached. For the avoidance of doubt representative examples are shown below

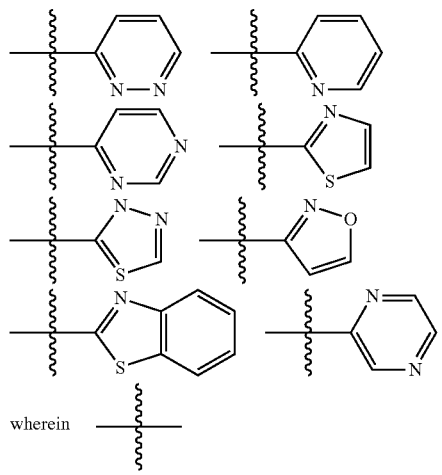

wherein 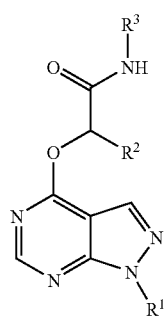 represents the point of attachment to the amide group.

Examples of the group Q as a 4-, 5-, or 6-membered ring heterocycle as hereinbefore defined include azetidinyl, oxetanyl, pyrrolidinyl, pyrrolidonyl, tetrahydrofuryl, tetrahydropyranyl, piperidinyl, morpholinyl, piperazinyl and thiomorpholinyl. Particular examples of Q as a heterocycle include azetidinyl and pyrrolidinyl.

In one aspect of the invention, there is provided a compound of formula (IA) or a pharmaceutically acceptable salt thereof

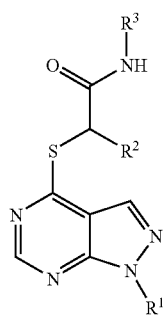

(IA)

wherein $R^1$, $R^2$ and $R^3$ are as defined for a compound of formula (I) hereinbefore.

In another aspect of the invention, there is provided a compound of formula (IB) or a pharmaceutically acceptable salt thereof

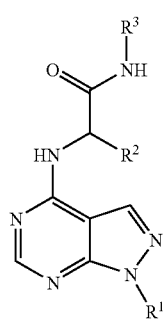

(IB)

wherein $R^1$, $R^2$ and $R^3$ are as defined for a compound of formula (I) hereinbefore.

In another aspect of the invention, there is provided a compound of formula (IC) or a pharmaceutically acceptable salt thereof (IC)

wherein $R^1$, $R^2$ and $R^3$ are as defined for a compound of formula (I) hereinbefore.

Reference herein to a compound of formula (I) will be understood to include reference to a compound of formula (IA), (IB) or (IC).

Compounds of Formula (I) may form salts which are within the ambit of the invention. Pharmaceutically-acceptable salts are preferred although other salts may be useful in, for example, isolating or purifying compounds.

In another aspect, the invention relates to compounds of formula (I) as hereinabove defined or to a pharmaceutically-acceptable salt.

In another aspect, the invention relates to compounds of formula (I) as hereinabove defined or to a pro-drug thereof. Suitable examples of pro-drugs of compounds of formula (I) are in-vivo hydrolysable esters of compounds of formula (I). Therefore in another aspect, the invention relates to compounds of formula (I) as hereinabove defined or to an in-vivo hydrolysable ester thereof In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "(1-4C)alkyl" includes methyl, ethyl, propyl, isopropyl and t-butyl. An analogous convention applies to other generic terms.

Examples of (1-4C)alkyl include methyl, ethyl, propyl, isopropyl, butyl and tert-butyl; examples of (1-6C)alkyl include (1-4C)alkyl, pentyl and hexyl; examples of (1-8C) alkyl include (1-6C)alkyl and heptyl; examples of (1-4C) alkoxy, (1-6C)alkoxy and (1-8C)alkoxy include methoxy, ethoxy, propoxy, isopropoxy and tertbutoxy; examples of (1-6C)alkoxycarbonyl include methoxycarbonyl, ethoxycarbonyl, propoxycarbonyl, isopropoxycarbonyl and tertbutoxycarbonyl; examples of (1-6C)alkoxycarbonyl(1-4C) alkyl include methoxycarbonylmethyl, ethoxycarbonylmethyl, propoxycarbonylethyl, isopropoxycarbonylmethyl and tertbutoxycarbonylmethyl; examples of N-(1-4C)alkylcarbamoyl include methylcarbamoyl, ethylcarbamoyl, propylcarbamoyl, isopropylcarbamoyl and tert-butylcarbamoyl; examples of N,N-di-(1-4C)alkylcarbamoyl include N,N-dimethylcarbamoyl, N,N-diethylcarbamoyl, N-methyl-N-propylcarbamoyl, N,N-di-isopropylcarbamoyl and N-methyl-N-tertbutylcarbamoyl; examples of (3-6C)cycloalkyl include cyclopropyl, cyclobutyl, cyclopentyl and cyclohexyl; examples of halo include fluoro, chloro, bromo and iodo; examples of hydroxy(1-4C)alkyl include hydroxymethyl, 1-hydroxyethyl, 2-hydroxyethyl, 2-hydroxypropyl, 3-hydroxypropyl, 1-hydroxyisopropyl and 4-hydroxybutyl; examples of (1-4C)alkoxy(1-4C)alkyl include methoxymethyl, ethoxymethyl, tert-butoxymethyl, 2-methoxyethyl, 2-ethoxyethyl, methoxypropyl, 2-methoxypropyl and methoxybutyl; examples of (1-4C)alkylS(O)p(1-4C) alkyl include methylsulfinylmethyl, ethylsulfinylmethyl, ethylsulfinylethyl, methylsulfinylpropyl, methylsulfinylbutyl, methylsulfonylmethyl, ethylsulfonylmethyl, ethylsulfonylethyl, methylsulfonylpropyl, methylsulfonylbutyl, methylthiomethyl, ethylthiomethyl, ethylthioethyl, methylthiopropyl, and methylthiobutyl; examples of amino(1-4C)alkyl include aminomethyl, aminoethyl, 2-aminopropyl, 3-aminopropyl, 1-aminoisopropyl and 4-aminobutyl; examples of (1-4C)alkylamino(1-4C)alkyl include (N-methyl)aminomethyl, (N-ethyl)aminomethyl, 1-((N-methyl)amino)ethyl, 2-((N-methyl)amino)ethyl, (N-ethyl)aminoethyl, (N-methyl) aminopropyl, and 4-((N-methyl)amino)butyl; examples of di(1-4C)alkylamino(1-4C)alkyl include dimethylaminomethyl, methyl(ethyl)aminomethyl, methyl(ethyl)aminoethyl, (N,N-diethyl)aminoethyl, (N,N-dimethyl)aminopropyl and (N,N-dimethyl)aminobutyl; examples of (1-4C)alkylamino include methylamino, ethylamino, propylamino, isopropylamino, butylamino and tert-butylamino; examples of di(1-4C)alkylamino include dimethylamino, methyl(ethyl)amino, diethylamino, dipropylamino, di-isopropylamino and dibutylamino; examples of (1-4C)alkylaminosulfonyl include methylaminosulfonyl, ethylaminosulfonyl, propylaminosulfonyl, isopropylaminosulfonyl, butylaminosulfonyl and tert-butylaminosulfonyl; examples of di(1-4C)alkylaminosulfonyl include dimethylaminosulfonyl, methyl(ethyl) aminosulfonyl, diethylaminosulfonyl, dipropylaminosulfonyl, di-isopropylaminosulfonyl and dibutylaminosulfonyl; examples of (1-4C)alkanoylamino include methanoylamino, ethanoylamino, propanoylamino, isopropanoylamino, butanoylamino and tert-butanoylamino; examples of —C(O)(1-4C)alkyl include methylcarbonyl, ethylcarbonyl, propylcarbonyl and tert-butyl carbonyl; examples of (1-4C)alkylthio and (1-6C)alkylthio include methylthio, ethylthio, isopropylthio and tert-butylthio; examples of (1-4C)alkylsulfinyl and (1-6C)alkylsulfinyl include methylsulfinyl, ethylsulfinyl, isopropylsulfinyl and tert-butylsulfinyl; examples of (1-4C)alkylsulfonyl and (1-6C)alkylsulfonyl include methylsulfonyl, ethylsulfonyl, isopropylsulfonyl and tert-butylsulfonyl; example of (1-6C) alkylsulfonyloxy include methylsulfonyloxy, ethylsulfonyloxy, isopropylsulfonyloxy and tert-butylsulfonyloxy; examples of (1-6C)alkylsulfonylamino include methylsulfonylamino, ethylsulfonylamino, isopropylsulfonylamino and tert-butylsulfonylamino; examples of (3-6C)cycloalkylsulfonyl include cyclopropylsulfonyl, cyclobutylsulfonyl, cyclopropylsulfonyl and cyclohexylsulfonyl.

It is to be understood that, insofar as certain of the compounds of Formula (I) defined above may exist in optically active or racemic forms by virtue of one or more asymmetric carbon atoms, the invention includes in its definition any such optically active or racemic form which possesses the property of activating GLK. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK. It will be understood that compounds described in their pyrimidinol form may also be described as the pyrimidinone tautomer and vice versa. This implies nothing about the actual relative proportions of the two in physical samples.

In particular, it will be understood that the carbon atom to which $R^2$ is attached is a chiral centre. In one aspect of the invention, this chiral centre has the S-configuration. In another aspect, this chiral centre has the R-configuration.

It is also to be understood that certain compounds of the formula (1) and salts thereof can exist in solvated as well as unsolvated forms such as, for example, hydrated forms. It is to be understood that the invention encompasses all such solvated forms which activate GLK.

In one embodiment of the invention are provided compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of formula (I).

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I) (including formulas (IA), (IB) and (IC)). Further, each of the following values may be used in combination with one or more of the other following values to limit the broadest definition, or any sub-definition, of formula (I).

1) A is N and B is $CR^6$
2) A is $CR^6$ and B is N
3) X is C, Y is N and Z is N
4) X is N, Y is CH and Z is N
5) X is N, Y is N and Z is C
6) $R^1$ is optionally substituted alkyl
7) $R^1$ is optionally substituted aryl
8) $R^1$ is optionally substituted aryl(1-6C)alkyl
9) $R^1$ is optionally substituted HET-1
10) $R^1$ is optionally substituted phenyl or pyridyl (particularly pyrid-2-yl or pyrid-4-yl, more particularly pyrid-2-yl)
11) $R^1$ is phenyl or pyridyl (particularly pyrid-2-yl), substituted in a 2-position relative to the point of attachment to Z
12) $R^1$ is phenyl or pyridyl (particularly pyrid-2-yl), substituted in a 2-position relative to the point of attachment to Z
13) $R^1$ is phenyl or pyridyl (particularly pyrid-2-yl) and $R^1$ is di-substituted, wherein one substituent is in a 2-position relative to the point of attachment to Z 14) optional substituents on $R^1$ are selected from halo (particularly chloro), (1-4C)alkyl, (1-4C)alkoxy, trifluoromethyl, (1-6C)alkylsulfonyl and cyano 15) $R^1$ is a fused bicyclic ring system of formula -D-E 16) $R^2$ is (1-6C)alkyl optionally substituted by one or two hydroxy or $R^2$ is a group —(CHR$^4$)$_n$—P-Q 17) $R^2$ is a group —(CHR$^4$)$_n$—P-Q 18) $R^2$ is a group —(CHR$^4$)$_n$—P-Q; n is 1, 2, 3, or 4 (particularly 1 or 2); one $R^4$ is optionally hydroxy and the other $R^4$ groups (where applicable) are hydrogen or methyl; P is an oxygen linker and Q is (1-6C)alkyl, (3-6C)cycloalkyl or a 4-, 5- or 6-membered heterocyclyl, and Q is optionally substituted on an available carbon atom by hydroxy or (1-4C)alkoxy 19) $R^2$ is a group —(CHR$^4$)$_n$—P-Q; n is 1, 2, 3, or 4 (particularly 1 or 2); one $R^4$ is optionally hydroxy and the other $R^4$ groups (where applicable) are hydrogen or methyl; P is an oxygen linker and Q is (1-6C)alkyl, optionally substituted by hydroxy or (1-4C)alkoxy 20) $R^2$ is selected from hexyl, butyl, isobutyl, isopropyl, ethyl, methyl, isopropoxymethyl, ethoxymethyl, cyclobutyloxymethyl, methoxymethyl, hydroxyethyl, hydroxypropyl, methylsulfonylethyl, isopropylsulfonylethyl, ethylsulfonylethyl, methylsulfonylaminoethyl, methylsulfonylaminomethyl, cyclopropyloxymethyl, oxetanyloxymethyl, hydroxyethoxymethyl, 1-hydroxyprop-2-yloxymethyl, methoxyethyl, 1-methoxyprop-2yloxymethyl, dimethylaminoethyl, methylcarbonylaminomethyl, carboxyethyl, carbamoylethyl, N-methylcarbamoylethyl, methoxyethoxyethyl, methylcarbonyloxyethyl, 21) $R^2$ is selected from hexyl, butyl, isobutyl, isopropyl, ethyl, methyl, isopropoxymethyl, ethoxymethyl, cyclobutyloxymethyl, methoxymethyl, hydroxyethyl, hydroxypropyl, methylsulfonylethyl, methylsulfonylaminoethyl, hydroxyethoxymethyl, methoxyethyl, 1-methoxyprop-2yloxymethyl, dimethylaminoethyl, methylcarbonylaminomethyl, carboxyethyl, carbamoylethyl, N-methylcarbamoylethyl, methoxyethoxyethyl, methylcarbonyloxyethyl, 22) $R^2$ is selected from isopropoxymethyl, ethoxymethyl, cyclobutyloxymethyl, methoxymethyl, hydroxyethyl, hydroxypropyl, cyclopropyloxymethyl, oxetanyloxymethyl, hydroxyethoxymethyl, 1-hydroxyprop-2-yloxymethyl, methoxyethyl, 1-methoxyprop-2yloxymethyl, methoxyethoxyethyl 23) $R^2$ is selected from isopropoxymethyl, ethoxymethyl, cyclobutyloxymethyl, methoxymethyl, hydroxyethyl, hydroxypropyl, hydroxyethoxymethyl, methoxyethyl, 1-methoxyprop-2yloxymethyl, methoxyethoxyethyl 24) $R^3$ is selected from optionally substituted pyridyl, thiazolyl, pyrimidinyl, pyrazinyl, pyridazinyl, pyrazolyl, isoxazolyl and thiadiazolyl 25) $R^3$ is a 6-membered ring 26) $R^3$ is optionally substituted pyridyl or pyrazinyl 27) $R^3$ is optionally substituted pyridyl 28) $R^3$ is pyridyl, substituted at the para position relative to the point of attachment to the CONH group 29) $R^3$ is 2-pyridyl, substituted at the para position relative to the point of attachment to the CONH group 30) $R^{11}$ is selected from halo, (1-4C)alkyl, (1-6C)alkylsulfonyl, N,N-dialkylcarbamoyl and cyano 31) $R^{11}$ is selected from halo (particularly chloro or fluoro, more particularly chloro) or (1-4C)alkyl (particularly methyl)

32) each $R^4$ is hydrogen 33) n is >1 and only one $R^4$ is not hydrogen 34) n is 1, 2 or 3

35) n is 1 or 2

36) $R^5$ is H

37) $R^6$ is H

38) $R^7$ is H

39) $R^8$ is methyl

40) $R^9$ is H

41) L is O

42) L is S

43) L is NH

44) $R^{10}$ is H

45) $R^{12}$ is H

46) P is an oxygen linger

47) $NR^9R^{10}$ forms an azetidine ring, optionally substituted with hydroxy, hydroxymethyl or methoxy 48) $NR^9R^{10}$ forms an azetidine ring, optionally substituted with hydroxy or hydroxymethyl In a further aspect of the invention, there is provided a compound of formula (IA), or a pharmaceutically-acceptable salt thereof wherein $R^1$ is phenyl or pyridyl, substituted in the 2-position relative to the point of attachment to Z with a substituent selected from halo (particularly chloro), (1-4C)alkyl, (1-4C)alkoxy, trifluoromethyl, (1-6C)alkylsulfonyl and cyano;

$R^2$ is (1-6C)alkyl optionally substituted by one or two hydroxy or $R^2$ is a group —(CHR$^4$)$_n$—P-Q;

n is 1, 2, 3, or 4 (particularly 1 or 2);

one $R^4$ is optionally hydroxy and the other $R^4$ groups (where applicable) are hydrogen or methyl;

is an oxygen linker;

Q is (1-6C)alkyl, (3-6C)cycloalkyl or a 4-, 5- or 6-membered heterocyclyl, and Q is optionally substituted on an available carbon atom by hydroxy or (1-4C)alkoxy;

$R^3$ is pyridyl, substituted at the para position relative to the point of attachment to the CONH group with a substituent selected from $R^{11}$; and $R^{11}$ is selected from halo (particularly fluoro or chloro, more particularly chloro), (1-4C)alkyl, (1-6C)alkylsulfonyl, N,N-dialkylcarbamoyl and cyano.

Reference herein to $R^1$ being substituted in a 2-position relative to the point of attachment to Z will be understood to refer to the following substitution pattern, illustrated for $R^1$ is phenyl and pyrid-2-yl:

-continued

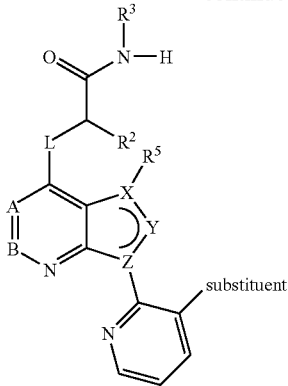

Further preferred compounds of the invention are each of the Examples, each of which provides a further independent aspect of the invention. In further aspects, the present invention also comprises any two or more compounds of the Examples.

Particular compounds of the invention include any one or more of:

2-{[1-(2-chlorophenyl)-1H-pyrazolo[3,4-d]pyrimidin-4-yl]oxy}-3-methoxy-N-(5-methylpyridin-2-yl)propanamide;

(R)-2-{[1-(2-chlorophenyl)-1H-pyrazolo[3,4-d]pyrimidin-4-yl]oxy}-3-methoxy-N-(5-methylpyridin-2-yl)propanamide;

(S)-2-{[1-(2-chlorophenyl)-1H-pyrazolo[3,4-d]pyrimidin-4-yl]oxy}-3-methoxy-N-(5-methylpyridin-2-yl)propanamide;

3-methoxy-2-{[1-(2-methoxyphenyl)-1H-pyrazolo[3,4-d]pyrimidin-4-yl]oxy}-N-(5-methylpyridin-2-yl)propanamide;

(R)-3-methoxy-2-{[1-(2-methoxyphenyl)-1H-pyrazolo[3,4-d]pyrimidin-4-yl]oxy}-N-(5-methylpyridin-2-yl)propanamide;

(S)-3-methoxy-2-{[1-(2-methoxyphenyl)-1H-pyrazolo[3,4-d]pyrimidin-4-yl]oxy}-N-(5-methylpyridin-2-yl)propanamide;

2-{[1-(2,4-dichlorophenyl)-1H-pyrazolo[3,4-d]pyrimidin-4-yl]oxy}-3-methoxy-N-(5-methylpyridin-2-yl)propanamide;

3-methoxy-2-[(1-methyl-1H-pyrazolo[3,4-d]pyrimidin-4-yl)oxy]-N-(5-methylpyridin-2-yl)propanamide;

2-{[1-(2-chlorophenyl)-1H-pyrazolo[3,4-d]pyrimidin-4-yl]oxy}-N-(5-methylpyridin-2-yl)-4-(methylsulfonyl)butanamide;

2-{[1-(2-methoxyphenyl)-1H-pyrazolo[3,4-d]pyrimidin-4-yl]oxy}-N-(5-methylpyridin-2-yl)-4-(methylsulfonyl)butanamide;

(R)-2-{[1-(2-methoxyphenyl)-1H-pyrazolo[3,4-d]pyrimidin-4-yl]oxy}-N-(5-methylpyridin-2-yl)-4-(methylsulfonyl)butanamide;

(S)-2-{[1-(2-methoxyphenyl)-1H-pyrazolo[3,4-d]pyrimidin-4-yl]oxy}-N-(5-methylpyridin-2-yl)-4-(methylsulfonyl)butanamide;

4-methoxy-2-{[1-(3-methoxyphenyl)-1H-pyrazolo[3,4-d]pyrimidin-4-yl]oxy}-N-(5-methylpyridin-2-yl)butanamide;

(R)-4-methoxy-2-{[1-(3-methoxyphenyl)-1H-pyrazolo[3,4-d]pyrimidin-4-yl]oxy}-N-(5-methylpyridin-2-yl)butanamide;

(S)-4-methoxy-2-{[1-(3-methoxyphenyl)-1H-pyrazolo[3,4-d]pyrimidin-4-yl]oxy}-N-(5-methylpyridin-2-yl)butanamide;

4-methoxy-2-{[1-(2-methylphenyl)-1H-pyrazolo[3,4-d]pyrimidin-4-yl]oxy}-N-(5-methylpyridin-2-yl)butanamide;

(S)-4-methoxy-2-{[1-(2-methylphenyl)-1H-pyrazolo[3,4-d]pyrimidin-4-yl]oxy}-N-(5-methylpyridin-2-yl)butanamide;

(R)-4-methoxy-2-{[1-(2-methylphenyl)-1H-pyrazolo[3,4-d]pyrimidin-4-yl]oxy}-N-(5-methylpyridin-2-yl)butanamide;

2-{[1-(2-chlorophenyl)-1H-pyrazolo[3,4-d]pyrimidin-4-yl]oxy}-4-methoxy-N-(5-methylpyridin-2-yl)butanamide;

(R)-2-{[1-(2-chlorophenyl)-1H-pyrazolo[3,4-d]pyrimidin-4-yl]oxy}-4-methoxy-N-(5-methylpyridin-2-yl)butanamide;

(S)-2-{[1-(2-chlorophenyl)-1H-pyrazolo[3,4-d]pyrimidin-4-yl]oxy}-4-methoxy-N-(5-methylpyridin-2-yl)butanamide;

4-methoxy-2-{[1-(2-methoxyphenyl)-1H-pyrazolo[3,4-d]pyrimidin-4-yl]oxy}-N-(5-methylpyridin-2-yl)butanamide;

(R)-4-methoxy-2-{[1-(2-methoxyphenyl)-1H-pyrazolo[3,4-d]pyrimidin-4-yl]oxy}-N-(5-methylpyridin-2-yl)butanamide;

(S)-4-methoxy-2-{[1-(2-methoxyphenyl)-1H-pyrazolo[3,4-d]pyrimidin-4-yl]oxy}-N-(5-methylpyridin-2-yl)butanamide;

2-{[1-(2,4-difluorophenyl)-1H-pyrazolo[3,4-d]pyrimidin-4-yl]oxy}-4-methoxy-N-(5-methylpyridin-2-yl)butanamide;

(R)-2-{[1-(2,4-difluorophenyl)-1H-pyrazolo[3,4-d]pyrimidin-4-yl]oxy}-4-methoxy-N-(5-methylpyridin-2-yl)butanamide;

(S)-2-{[1-(2,4-difluorophenyl)-1H-pyrazolo[3,4-d]pyrimidin-4-yl]oxy}-4-methoxy-N-(5-methylpyridin-2-yl)butanamide;

4-methoxy-N-(5-methylpyridin-2-yl)-2-({1-[2-(trifluoromethyl)phenyl]-1H-pyrazolo[3,4-d]pyrimidin-4-y}oxy)butanamide;

(S)-4-methoxy-N-(5-methylpyridin-2-yl)-2-({1-[2-(trifluoromethyl)phenyl]-1H-pyrazolo[3,4-d]pyrimidin-4-yl}oxy)butanamide;

(R)-4-methoxy-N-(5-methylpyridin-2-yl)-2-({1-[2-(trifluoromethyl)phenyl]-1H-pyrazolo[3,4-d]pyrimidin-4-yl}oxy)butanamide;

4-methoxy-2-{[1-(3-methylphenyl)-1H-pyrazolo[3,4-d]pyrimidin-4-yl]oxy}-N-(5-methylpyridin-2-yl)butanamide;

(R)-4-methoxy-2-{[1-(3-methylphenyl)-1H-pyrazolo[3,4-d]pyrimidin-4-yl]oxy}-N-(5-methylpyridin-2-yl)butanamide;

(S)-4-methoxy-2-{[1-(3-methylphenyl)-1H-pyrazolo[3,4-d]pyrimidin-4-yl]oxy}-N-(5-methylpyridin-2-yl)butanamide;

4-methoxy-N-(5-methylpyridin-2-yl)-2-[(1-pyridin-2-yl-1H-pyrazolo[3,4-d]pyrimidin-4-yl)oxy]butanamide;

4-methoxy-2-{[1-(2-methoxyphenyl)-1H-pyrazolo[3,4-d]pyrimidin-4-yl]oxy}-N-(4-methyl-1,3-thiazol-2-yl)butanamide;

(R)-4-methoxy-2-{[1-(2-methoxyphenyl)-1H-pyrazolo[3,4-d]pyrimidin-4-yl]oxy}-N-(4-methyl-1,3-thiazol-2-yl)butanamide;

(S)-4-methoxy-2-{[1-(2-methoxyphenyl)-1H-pyrazolo[3,4-d]pyrimidin-4-yl]oxy}-N-(4-methyl-1,3-thiazol-2-yl)butanamide;

2-{[1-(2-chlorophenyl)-1H-pyrazolo[3,4-d]pyrimidin-4-yl]oxy}-N-(5-methylpyridin-2-yl)hexanamide;

2-[(1-methyl-1H-pyrazolo[3,4-d]pyrimidin-4-yl)oxy]-N-(5-methylpyridin-2-yl)hexanamide
2-{[1-(2-chlorophenyl)-1H-pyrazolo[3,4-d]pyrimidin-4-yl]oxy}-N-(5-methylpyrazin-2-yl)hexanamide;
2-{[1-(2-chlorophenyl)-1H-pyrazolo[3,4-d]pyrimidin-4-yl]thio}-N-(4-methyl-1,3-thiazol-2-yl)hexanamide;
2-{[1-(2-methoxyphenyl)-1H-pyrazolo[3,4-d]pyrimidin-4-yl]oxy}-N-(5-methylpyridin-2-yl)butanamide;
(2R)-2-{[1-(2-methoxyphenyl)-1H-pyrazolo[3,4-d]pyrimidin-4-yl]oxy}-N-(5-methylpyridin-2-yl)butanamide;
2-{[1-(2-methoxyphenyl)-1H-pyrazolo[3,4-d]pyrimidin-4-yl]oxy}-N-(5-methylpyridin-2-yl)propanamide;
(2S)-2-{[1-(2-chlorophenyl)-1H-pyrazolo[3,4-d]pyrimidin-4-yl]oxy}-4-(dimethylamino)-N-(5-methylpyridin-2-yl)butanamide;
3-acetamido-2-{[1-(2-chlorophenyl)-1H-pyrazolo[3,4-d]pyrimidin-4-yl]oxy}-N-(4-methyl-1,3-thiazol-2-yl)propanamide;
4-{[1-(2-chlorophenyl)-1H-pyrazolo[3,4-d]pyrimidin-4-yl]oxy}-5-[(5-methylpyridin-2-yl)amino]-5-oxopentanoic acid;
2-{[1-(2-chlorophenyl)-1H-pyrazolo[3,4-d]pyrimidin-4-yl]oxy}-N1-(5-methylpyridin-2-yl)pentanediamide;
2-{[1-(2-chlorophenyl)-1H-pyrazolo[3,4-d]pyrimidin-4-yl]oxy}-N5-methyl-N1-(5-methylpyridin-2-yl)pentanediamide;
2-{[1-(2-chlorophenyl)-1H-pyrazolo[3,4-d]pyrimidin-4-yl]thio}-4-(2-methoxyethoxy)-N-(4-methyl-1,3-thiazol-2-yl)butanamide;
2-{[1-(2-chlorophenyl)-1H-pyrazolo[3,4-d]pyrimidin-4-yl]thio}-4-methoxy-N-(4-methyl-1,3-thiazol-2-yl)butanamide;
2-{[1-(2-chlorophenyl)-1H-pyrazolo[3,4-d]pyrimidin-4-yl]thio}-3-methyl-N-(4-methyl-1,3-thiazol-2-yl)pentanamide;
2-{[1-(2-chlorophenyl)-1H-pyrazolo[3,4-d]pyrimidin-4-yl]thio}-N-isoxazol-3-yl-3-methylpentanamide;
2-{[1-(2-chlorophenyl)-1H-pyrazolo[3,4-d]pyrimidin-4-yl]thio}-3-methyl-N-(5-methylpyridin-2-yl)pentanamide;
2-[(1-isopropyl-1H-pyrazolo[3,4-d]pyrimidin-4-yl)thio]-4-(2-methoxyethoxy)-N-(5-methylpyridin-2-yl)butanamide;
2-[(1-isopropyl-1H-pyrazolo[3,4-d]pyrimidin-4-yl)thio]-4-(2-methoxyethoxy)-N-(5-methylpyridin-2-yl)butanamide;
2-{[1-(2-chlorophenyl)-1H-pyrazolo[3,4-d]pyrimidin-4-yl]thio}-N-(4-methyl-1,3-thiazol-2-yl)hexanamide;
2-{[1-(2-chlorophenyl)-1H-pyrazolo[3,4-d]pyrimidin-4-yl]thio}-N-isoxazol-3-ylhexanamide;
2-{[1-(2-Chlorophenyl)-1H-pyrazolo[3,4-d]pyrimidin-4-yl]thio}-4-(2-methoxyethoxy)-N-(4-methyl-1,3-thiazol-2-yl)butanamide;
2-{[1-(2-Chlorophenyl)-1H-pyrazolo[3,4-d]pyrimidin-4-yl]thio}-3-methoxy-N-(5-methylpyridin-2-yl)propanamide;
2-{[1-(2-chlorophenyl)-1H-pyrazolo[3,4-d]pyrimidin-4-yl]thio}-N-(4-methyl-1,3-thiazol-2-yl)octanamide;
2-{[1-(2-chlorophenyl)-1H-pyrazolo[3,4-d]pyrimidin-4-yl]thio}-N-isoxazol-3-yloctanamide;
2-ethoxy-2-{[1-(2-methoxyphenyl)-1H-pyrazolo[3,4-d]pyrimidin-4-yl]thio}-N-(4-methyl-1,3-thiazol-2-yl)acetamide;
2-ethoxy-N-isoxazol-3-yl-2-{[1-(2-methoxyphenyl)-1H-pyrazolo[3,4-d]pyrimidin-4-yl]thio}acetamide;
2-[(1-isopropyl-1H-pyrazolo[3,4-d]pyrimidin-4-yl)oxy]-4-methoxy-N-(5-methylpyridin-2-yl)butanamide;
(R)-2-{[1-(2-chlorophenyl)-1H-pyrazolo[3,4-d]pyrimidin-4-yl]thio}-N-(4-methyl-1,3-thiazol-2-yl)hexanamide;
(S)-2-{[1-(2-chlorophenyl)-1H-pyrazolo[3,4-d]pyrimidin-4-yl]thio}-N-(4-methyl-1,3-thiazol-2-yl)hexanamide;
2-(1-(2-chlorophenyl)-1H-pyrazolo[3,4-d]pyrimidin-4-yloxy)-3-methyl-N-(5-methylpyridin-2-yl)butanamide;
(2S)-2-(1-(2-chlorophenyl)-1H-pyrazolo[3,4-d]pyrimidin-4-yloxy)-3-methyl-N-(5-methylpyridin-2-yl)butanamide;
(2R)-2-(1-(2-chlorophenyl)-1H-pyrazolo[3,4-d]pyrimidin-4-yloxy)-3-methyl-N-(5-methylpyridin-2-yl)butanamide;
(2S)-2-(1-(3-chloropyridin-2-yl)-1H-pyrazolo[3,4-d]pyrimidin-4-yloxy)-3-methyl-N-(5-methylpyridin-2-yl)butanamide;
(2S)-2-(1-(2-chlorophenyl)-1H-pyrazolo[3,4-d]pyrimidin-4-yloxy)-3-methoxy-N-(5-methylpyridin-2-yl)propanamide;
(2R)-2-(1-(2-chlorophenyl)-1H-pyrazolo[3,4-d]pyrimidin-4-yloxy)-3-methoxy-N-(5-methylpyridin-2-yl)propanamide;
(2S)-2-(1-(3-chloropyridin-2-yl)-1H-pyrazolo[3,4-d]pyrimidin-4-yloxy)-3-methoxy-N-(5-methylpyridin-2-yl)propanamide;
(2S)-2-(1-(3-chloropyridin-2-yl)-1H-pyrazolo[3,4-d]pyrimidin-4-yloxy)-3-methoxy-N-(5-methylpyrazin-2-yl)propanamide;
(2S)-2-(1-(3-chloropyridin-2-yl)-1H-pyrazolo[3,4-d]pyrimidin-4-yloxy)-3-isopropoxy-N-(5-methylpyridin-2-yl)propanamide;
(2S)-2-(1-(3-chloropyridin-2-yl)-1H-pyrazolo[3,4-d]pyrimidin-4-yloxy)-3-isopropoxy-N-(5-methylpyrazin-2-yl)propanamide;
(2S)-2-(1-(3-chloropyridin-2-yl)-1H-pyrazolo[3,4-d]pyrimidin-4-yloxy)-3-isopropoxy-N-(3-methyl-1,2,4-thiadiazol-5-yl)propanamide;
(2S)-2-(1-(3-chloropyridin-2-yl)-1H-pyrazolo[3,4-d]pyrimidin-4-yloxy)-3-methyl-N-(5-methylpyrazin-2-yl)butanamide;
(2S)-2-(1-(2-chloro-4-fluorophenyl)-1H-pyrazolo[3,4-d]pyrimidin-4-yloxy)-3-methoxy-N-(5-methylpyrazin-2-yl)propanamide;
(2S)-2-(1-(2-chloro-4-fluorophenyl)-1H-pyrazolo[3,4-d]pyrimidin-4-yloxy)-3-methoxy-N-(5-methylpyridin-2-yl)propanamide;
(2S)-2-(1-(2-cyanophenyl)-1H-pyrazolo[3,4-d]pyrimidin-4-yloxy)-3-methoxy-N-(5-methylpyridin-2-yl)propanamide;
(2S)-2-(1-(2-chlorophenyl)-1H-pyrazolo[3,4-d]pyrimidin-4-yloxy)-3-isopropoxy-N-(5-methylpyridin-2-yl)propanamide;
(2R)-2-(1-(2-chlorophenyl)-1H-pyrazolo[3,4-d]pyrimidin-4-yloxy)-3-isopropoxy-N-(5-methylpyridin-2-yl)propanamide; and/or
(2S)-2-[1-(2-cyanophenyl)pyrazolo[4,5-e]pyrimidin-4-yl]oxy-N-(5-methylpyridin-2-yl)-3-propan-2-yloxypropanamide;
(2S)-2-[1-(2-chlorophenyl)pyrazolo[4,5-e]pyrimidin-4-yl]oxy-N-(3-methyl-1,2,4-thiadiazol-5-yl)-3-propan-2-yloxypropanamide;
(2S)-2-(1-(2-chlorophenyl)-1H-pyrazolo[3,4-d]pyrimidin-4-yloxy)-3-methoxy-N-(3-methyl-1,2,4-thiadiazol-5-yl)propanamide;
(2S)-2-(1-(3-chloropyridin-2-yl)-1H-pyrazolo[3,4-d]pyrimidin-4-yloxy)-4-methoxy-N-(5-methylpyridin-2-yl)butanamide;
(2S)-2-[1-(3-chloropyridin-2-yl)pyrazolo[4,5-e]pyrimidin-4-yl]oxy-3-ethoxy-N-(5-methylpyridin-2-yl)propanamide;

(2S)-2-[1-(3-chloropyridin-2-yl)pyrazolo[4,5-e]pyrimidin-4-yl]oxy-3-ethoxy-N-(5-methylpyrazin-2-yl)propanamide;

(2S)-2-[1-(2-chlorophenyl)pyrazolo[4,5-e]pyrimidin-4-yl]oxy-3-ethoxy-N-(5-methylpyrazin-2-yl)propanamide;

(2S)-3-isopropoxy-N-(5-methylpyrazin-2-yl)-2-(1-(3-methylpyrazin-2-yl)-1H-pyrazolo[3,4-d]pyrimidin-4-yloxy)propanamide;

(S)-3-methoxy-N-(5-methylpyridin-2-yl)-2-(1-phenyl-1H-pyrazolo[3,4-d]pyrimidin-4-yloxy)propanamide;

2-[1-(2-chlorophenyl)pyrazolo[4,5-e]pyrimidin-4-yl]oxy-3-isopropoxy-N-pyrazin-2-yl-propanamide;

2-[1-(2-chlorophenyl)pyrazolo[4,5-e]pyrimidin-4-yl]oxy-3-isopropoxy-N-(5-methyl-1,3,4-thiadiazol-2-yl)propanamide;

2-[1-(2-chlorophenyl)pyrazolo[4,5-e]pyrimidin-4-yl]oxy-3-isopropoxy-N-(5-methylisoxazol-3-yl)propanamide;

2-[1-(2-chlorophenyl)pyrazolo[4,5-e]pyrimidin-4-yl]oxy-3-isopropoxy-N-(5-methylthiazol-2-yl)propanamide;

2-[1-(2-chlorophenyl)pyrazolo[4,5-e]pyrimidin-4-yl]oxy-N-(5-fluoro-2-pyridyl)-3-isopropoxy-propanamide;

2-[1-(2-chlorophenyl)pyrazolo[4,5-e]pyrimidin-4-yl]oxy-N-(5-cyano-2-pyridyl)-3-isopropoxy-propanamide;

2-[1-(2-chlorophenyl)pyrazolo[4,5-e]pyrimidin-4-yl]oxy-3-isopropoxy-N-(1,2,4-thiadiazol-5-yl)propanamide;

2-[1-(2-chlorophenyl)pyrazolo[4,5-e]pyrimidin-4-yl]oxy-N-(5-chloro-2-pyridyl)-3-isopropoxy-propanamide;

2-[1-(2-chlorophenyl)pyrazolo[4,5-e]pyrimidin-4-yl]oxy-3-isopropoxy-N-(4-methyl-2-pyridyl)propanamide;

2-[1-(2-chlorophenyl)pyrazolo[4,5-e]pyrimidin-4-yl]oxy-3-isopropoxy-N-(1,3,4-thiadiazol-2-yl)propanamide;

2-[1-(2-chlorophenyl)pyrazolo[4,5-e]pyrimidin-4-yl]oxy-3-isopropoxy-N-(2-pyridyl)propanamide;

2-[1-(2-chlorophenyl)pyrazolo[4,5-e]pyrimidin-4-yl]oxy-3-isopropoxy-N-isoxazol-3-yl-propanamide;

2-[1-(2-chlorophenyl)pyrazolo[4,5-e]pyrimidin-4-yl]oxy-3-isopropoxy-N-pyrimidin-4-yl-propanamide;

(2S)-2-[1-(2-chlorophenyl)pyrazolo[4,5-e]pyrimidin-4-yl]oxy-3-isopropoxy-N-(5-methylthiazol-2-yl)propanamide;

(2S)-2-[1-(2-chlorophenyl)pyrazolo[4,5-e]pyrimidin-4-yl]oxy-N-(5-fluoro-2-pyridyl)-3-isopropoxy-propanamide;

(2S)-2-[1-(2-chlorophenyl)pyrazolo[4,5-e]pyrimidin-4-yl]oxy-N-(5-cyano-2-pyridyl)-3-isopropoxy-propanamide;

(2S)-2-[1-(2-chlorophenyl)pyrazolo[4,5-e]pyrimidin-4-yl]oxy-N-(5-chloro-2-pyridyl)-3-isopropoxy-propanamide;

(2S)-2-[1-(2-chlorophenyl)pyrazolo[4,5-e]pyrimidin-4-yl]oxy-3-isopropoxy-N-(2-pyridyl)propanamide;

(2S)-3-isopropoxy-N-(5-methylpyridin-2-yl)-2-(1-(3-methylpyridin-2-yl)-1H-pyrazolo[3,4-d]pyrimidin-4-yloxy)propanamide;

(2S)-3-isopropoxy-N-(5-methylpyridin-2-yl)-2-(1-(3-(trifluoromethyl)pyridin-2-yl)-1H-pyrazolo[3,4-d]pyrimidin-4-yloxy)propanamide;

(2S)-2-[1-(3-chloro-2-pyridyl)pyrazolo[4,5-e]pyrimidin-4-yl]oxy-3-isopropoxy-N-(6-methylpyridazin-3-yl)propanamide;

(2S)—N-(5-cyanopyridin-2-yl)-3-isopropoxy-2-(1-(3-methylpyridin-2-yl)-1H-pyrazolo[3,4-d]pyrimidin-4-yloxy)propanamide;

(2S)—N-(5-chloropyridin-2-yl)-3-isopropoxy-2-(1-(3-methylpyridin-2-yl)-1H-pyrazolo[3,4-d]pyrimidin-4-yloxy)propanamide;

(2S)-2-[1-(3-chloro-2-pyridyl)pyrazolo[4,5-e]pyrimidin-4-yl]oxy-N-(5-cyano-2-pyridyl)-3-ethoxy-propanamide;

(2S)-2-[1-(3-chloro-2-pyridyl)pyrazolo[4,5-e]pyrimidin-4-yl]oxy-3-ethoxy-N-(5-fluoro-2-pyridyl)propanamide;

(2S)-2-[1-(3-chloro-2-pyridyl)pyrazolo[4,5-e]pyrimidin-4-yl]oxy-3-ethoxy-N-(2-pyridyl)propanamide;

(2S)-2-[1-(3-chloro-2-pyridyl)pyrazolo[4,5-e]pyrimidin-4-yl]oxy-3-ethoxy-N-pyrimidin-4-yl-propanamide;

(2S)—N-(5-chloro-2-pyridyl)-2-[1-(3-chloro-2-pyridyl)pyrazolo[4,5-e]pyrimidin-4-yl]oxy-3-ethoxy-propanamide;

(2S)-2-[1-(3-chloro-2-pyridyl)pyrazolo[4,5-e]pyrimidin-4-yl]oxy-N-(4-cyanothiazol-2-yl)-3-isopropoxy-propanamide;

(2S)—N-(5-chloro-2-pyridyl)-2-[1-(3-chloro-2-pyridyl)pyrazolo[4,5-e]pyrimidin-4-yl]oxy-3-isopropoxy-propanamide;

(2S)-2-[1-(3-chloro-2-pyridyl)pyrazolo[4,5-e]pyrimidin-4-yl]oxy-N-(5-cyano-2-pyridyl)-3-isopropoxy-propanamide;

(2S)-2-[1-(3-chloro-2-pyridyl)pyrazolo[4,5-e]pyrimidin-4-yl]oxy-3-isopropoxy-N-(2-pyridyl)propanamide;

(2S)-2-[1-(3-chloro-2-pyridyl)pyrazolo[4,5-e]pyrimidin-4-yl]oxy-N-(5-fluoro-2-pyridyl)-3-isopropoxy-propanamide;

(2S)—N-(5-chloropyridin-2-yl)-3-ethoxy-2-[1-(3-methylpyridin-4-yl)pyrazolo[4,5-e]pyrimidin-4-yl]oxypropanamide;

(2S)—N-(5-chloropyridin-2-yl)-3-ethoxy-2-(1-(3-methylpyridin-2-yl)-1H-pyrazolo[3,4-d]pyrimidin-4-yloxy)propanamide;

(2S)-3-isopropoxy-N-(5-methylpyridin-2-yl)-2-(1-(2-(methylsulfonyl)phenyl)-1H-pyrazolo[3,4-d]pyrimidin-4-yloxy)propanamide;

(2S)—N-(5-chloropyridin-2-yl)-3-ethoxy-2-(1-(2-(methylsulfonyl)phenyl)-1H-pyrazolo[3,4-d]pyrimidin-4-yloxy)propanamide;

(2R)-2-[1-(3-chloro-2-pyridyl)pyrazolo[4,5-e]pyrimidin-4-yl]oxy-5-hydroxy-N-(5-methyl-2-pyridyl)pentanamide;

(2S)—N-(5-cyano-2-pyridyl)-3-ethoxy-2-[1-[2-(trifluoromethyl)phenyl]pyrazolo[4,5-e]pyrimidin-4-yl]oxy-propanamide;

(2S)-3-ethoxy-N-(5-methylpyrazin-2-yl)-2-[1-[2-(trifluoromethyl)phenyl]pyrazolo[4,5-e]pyrimidin-4-yl]oxy-propanamide;

(2S)—N-(5-chloro-2-pyridyl)-3-ethoxy-2-[1-[3-(trifluoromethyl)-2-pyridyl]pyrazolo[4,5-e]pyrimidin-4-yl]oxy-propanamide;

(2S)-3-isopropoxy-N-(5-methyl-2-pyridyl)-2-[1-(3-methyl-4-pyridyl)pyrazolo[4,5-e]pyrimidin-4-yl]oxy-propanamide;

(2S)-3-(cyclobutoxy)-N-(5-methylpyrazin-2-yl)-2-[1-(3-methyl-4-pyridyl)pyrazolo[4,5-e]pyrimidin-4-yl]oxy-propanamide;

(2S)-3-(cyclobutoxy)-N-(5-methylpyrazin-2-yl)-2-[1-[3-(trifluoromethyl)-2-pyridyl]pyrazolo[4,5-e]pyrimidin-4-yl]oxy-propanamide;

(2S)-2-[1-[5-chloro-3-(trifluoromethyl)-2-pyridyl]pyrazolo[4,5-e]pyrimidin-4-yl]oxy-3-(cyclobutoxy)-N-(5-methylpyrazin-2-yl)propanamide;

(2S)-2-[1-(3-chloro-2-pyridyl)pyrazolo[4,5-e]pyrimidin-4-yl]oxy-3-ethoxy-N-(5-methylsulfonyl-2-pyridyl)propanamide;

(2S)-3-(cyclobutoxy)-N-(5-methylpyrazin-2-yl)-2-[1-(2-methylsulfonylphenyl)pyrazolo[4,5-e]pyrimidin-4-yl]oxy-propanamide;

(2S)-3-(cyclobutoxy)-N-(5-methylpyrazin-2-yl)-2-[1-(3-methyl-2-pyridyl)pyrazolo[4,5-e]pyrimidin-4-yl]oxy-propanamide;

(2S)-3-(cyclobutoxy)-N-(5-methylpyrazin-2-yl)-2-(1-phenylpyrazolo[4,5-e]pyrimidin-4-yl)oxy-propanamide;

(2S)-2-[1-(3-chloro-2-pyridyl)pyrazolo[4,5-e]pyrimidin-4-yl]oxy-4-hydroxy-N-(5-methyl-2-pyridyl)butanamide;
(2S)-3-(cyclobutoxy)-2-[1-(3-methylpyrazin-2-yl)pyrazolo[4,5-e]pyrimidin-4-yl]oxy-N-(5-methyl-2-pyridyl)propanamide;
(2S)-2-[1-(2-chlorophenyl)pyrazolo[4,5-e]pyrimidin-4-yl]oxy-4-hydroxy-N-(5-methyl-2-pyridyl)butanamide;
(2S)-3-isopropoxy-N-(5-methyl-2-pyridyl)-2-[1-(2-methyl-3-pyridyl)pyrazolo[4,5-e]pyrimidin-4-yl]oxy-propanamide;
6-[[(2S)-2-[1-(3-chloro-2-pyridyl)pyrazolo[4,5-e]pyrimidin-4-yl]oxy-3-ethoxy-propanoyl]amino]-N,N-dimethyl-pyridine-3-carboxamide;
(2S)-3-isopropoxy-N-(5-methyl-2-pyridyl)-2-[1-(4-methyl-3-pyridyl)pyrazolo[4,5-e]pyrimidin-4-yl]oxy-propanamide;
(2S)-3-(cyclobutoxy)-N-(5-methylpyrazin-2-yl)-2-[1-(2-methyl-3-pyridyl)pyrazolo[4,5-e]pyrimidin-4-yl]oxy-propanamide;
(2S)—N-(5-chloro-2-pyridyl)-3-ethoxy-2-[1-(2-methyl-3-pyridyl)pyrazolo[4,5-e]pyrimidin-4-yl]oxy-propanamide;
(2S)-2-[1-(2-chlorophenyl)pyrazolo[4,5-e]pyrimidin-4-yl]oxy-3-[(1S)-2-methoxy-1-methyl-ethoxy]-N-(5-methylpyrazin-2-yl)propanamide;
(2S)-2-[1-(2-chlorophenyl)pyrazolo[4,5-e]pyrimidin-4-yl]oxy-3-[(1S)-2-methoxy-1-methyl-ethoxy]-N-(5-methyl-2-pyridyl)propanamide;
(2S)-2-[1-(2-chlorophenyl)pyrazolo[4,5-e]pyrimidin-4-yl]oxy-3-[(1R)-2-methoxy-1-methyl-ethoxy]-N-(5-methyl-2-pyridyl)propanamide;
(2S)-2-[1-(3-chloro-2-pyridyl)pyrazolo[4,5-e]pyrimidin-4-yl]oxy-3-[(1R)-2-methoxy-1-methyl-ethoxy]-N-(5-methyl-2-pyridyl)propanamide;
(2R)-2-[1-(2-chlorophenyl)pyrazolo[4,5-e]pyrimidin-4-yl]oxy-3-[(1S)-2-methoxy-1-methyl-ethoxy]-N-(5-methylpyrazin-2-yl)propanamide;
(2S)-2-[1-(2-chlorophenyl)pyrazolo[4,5-e]pyrimidin-4-yl]oxy-3-(cyclobutoxy)-N-(5-methylpyrazin-2-yl)propanamide;
(2S)-2-[1-(3-chloro-2-pyridyl)pyrazolo[4,5-e]pyrimidin-4-yl]oxy-3-(cyclobutoxy)-N-(5-methylpyrazin-2-yl)propanamide;
(2S)-2-[1-(3-chloro-2-pyridyl)pyrazolo[4,5-e]pyrimidin-4-yl]oxy-3-(cyclobutoxy)-N-(5-methyl-2-pyridyl)propanamide;
[(3S)-3-[1-(3-chloro-2-pyridyl)pyrazolo[4,5-e]pyrimidin-4-yl]oxy-4-[(5-methyl-2-pyridyl)amino]-4-oxo-butyl]acetate;
(2S)-3-isopropoxy-N-(5-methyl-2-pyridyl)-2-[1-[2-(trifluoromethyl)phenyl]pyrazolo[4,5-e]pyrimidin-4-yl]oxy-propanamide;
(2S)-2-[1-(2-chlorophenyl)pyrazolo[4,5-e]pyrimidin-4-yl]oxy-N-(5-methyl-2-pyridyl)-4-methylsulfonyl-butanamide;
(2S)-2-[1-(3-chloro-2-pyridyl)pyrazolo[4,5-e]pyrimidin-4-yl]oxy-N-(5-cyano-2-pyridyl)-3-(2-hydroxyethoxy)propanamide;
(2S)—N-(5-chloro-2-pyridyl)-2-[1-(3-chloro-2-pyridyl)pyrazolo[4,5-e]pyrimidin-4-yl]oxy-3-(2-hydroxyethoxy)propanamide;
(2S)-2-[1-(2-chlorophenyl)pyrazolo[4,5-e]pyrimidin-4-yl]oxy-4-methanesulfonamido-N-(5-methyl-2-pyridyl)butanamide;
(2S)-2-[1-(3-chloro-2-pyridyl)pyrazolo[4,5-e]pyrimidin-4-yl]oxy-4-hydroxy-N-(5-methylpyrazin-2-yl)butanamide;
(2S)—N-(5-chloro-2-pyridyl)-2-[1-(3-chloro-2-pyridyl)pyrazolo[4,5-e]pyrimidin-4-yl]oxy-4-hydroxy-butanamide;
(2S)-2-[1-(3-chloro-2-pyridyl)pyrazolo[4,5-e]pyrimidin-4-yl]oxy-4-hydroxy-N-(2-pyridyl)butanamide;
(2S)-2-[1-(3-chloro-2-pyridyl)pyrazolo[4,5-e]pyrimidin-4-yl]oxy-N-(5-fluoro-2-pyridyl)-4-hydroxy-butanamide;
(2S)-2-[1-(3-chloro-2-pyridyl)pyrazolo[4,5-e]pyrimidin-4-yl]oxy-N-(5-cyano-2-pyridyl)-4-hydroxy-butanamide;
(2S)-2-[1-(3-chloro-2-pyridyl)pyrazolo[4,5-e]pyrimidin-4-yl]oxy-4-hydroxy-N-pyrimidin-4-yl-butanamide; and/or
(2S)—N-(5-chloropyridin-2-yl)-2-[1-(3-chloropyridin-2-yl)pyrazolo[4,5-e]pyrimidin-4-yl]oxy-3-(3-hydroxyazetidin-1-yl)propanamide;
(2S)-2-[1-(3-chloro-2-methylphenyl)pyrazolo[4,5-e]pyrimidin-4-yl]oxy-N-(5-cyanopyridin-2-yl)-3-(2-hydroxyethoxy)propanamide;
(2S)-2-[1-(3-chloro-2-methylphenyl)pyrazolo[4,5-e]pyrimidin-4-yl]oxy-3-(2-hydroxyethoxy)-N-(5-methylpyridin-2-yl)propanamide;
(2S)—N-(5-cyanopyridin-2-yl)-2-[1-(3-fluoro-2-methylphenyl)pyrazolo[4,5-e]pyrimidin-4-yl]oxy-3-(2-hydroxyethoxy)propanamide;
(2S)-2-[1-(3-fluoro-2-methylphenyl)pyrazolo[4,5-e]pyrimidin-4-yl]oxy-3-(2-hydroxyethoxy)-N-(5-methylpyridin-2-yl)propanamide;
(2S)—N-(5-chloropyridin-2-yl)-2-[1-(3-fluoro-2-methylphenyl)pyrazolo[4,5-e]pyrimidin-4-yl]oxy-3-(2-hydroxyethoxy)propanamide;
(2S)-2-[1-(2-chlorophenyl)pyrazolo[4,5-e]pyrimidin-4-yl]oxy-N-(5-chloropyridin-2-yl)-3-(2-hydroxyethoxy)propanamide;
(2S)-2-[1-(2-chlorophenyl)pyrazolo[4,5-e]pyrimidin-4-yl]oxy-N-(5-cyanopyridin-2-yl)-3-(2-hydroxyethoxy)propanamide;
(2S)-2-[1-(3-chloro-2-methylphenyl)pyrazolo[4,5-e]pyrimidin-4-yl]oxy-N-(5-chloropyridin-2-yl)-3-(2-hydroxyethoxy)propanamide;
(2S)-2-(1-(2-chloro-6-cyanophenyl)-1H-pyrazolo[3,4-d]pyrimidin-4-yloxy)-N-(5-chloropyridin-2-yl)-3-(2-hydroxyethoxy)propanamide;
(2S)-2-(1-(2-chloro-6-cyanophenyl)-1H-pyrazolo[3,4-d]pyrimidin-4-yloxy)-3-((R)-1-hydroxypropan-2-yloxy)-N-(5-methylpyridin-2-yl)propanamide;
(2S)-2-(1-(2-chloro-6-cyanophenyl)-1H-pyrazolo[3,4-d]pyrimidin-4-yloxy)-3-(2-hydroxyethoxy)-N-(5-methylpyridin-2-yl)propanamide;
(2S)-2-(1-(3-chloropyridin-2-yl)-1H-pyrazolo[3,4-d]pyrimidin-4-yloxy)-3-isopropoxy-N-(5-(methylsulfonyl)pyridin-2-yl)propanamide;
6-((2S)-2-(1-(3-chloropyridin-2-yl)-1H-pyrazolo[3,4-d]pyrimidin-4-yloxy)-3-isopropoxypropanamido)-N,N-dimethylnicotinamide;
(2S)—N-(5-chloropyridin-2-yl)-2-(1-(2,5-dimethylphenyl)-1H-pyrazolo[3,4-d]pyrimidin-4-yloxy)-3-(2-hydroxyethoxy)propanamide;
(2S)—N-(5-chloropyridin-2-yl)-2-(1-(5-fluoro-2-methylphenyl)-1H-pyrazolo[3,4-d]pyrimidin-4-yloxy)-3-(2-hydroxyethoxy)propanamide;
(S)-2-(1-benzyl-1H-pyrazolo[3,4-d]pyrimidin-4-yloxy)-3-(2-hydroxyethoxy)-N-(5-methylpyridin-2-yl)propanamide;
(2S)—N-(5-cyanopyridin-2-yl)-2-(1-(5-fluoro-2-methylphenyl)-1H-pyrazolo[3,4-d]pyrimidin-4-yloxy)-3-(2-hydroxyethoxy)propanamide;
(2S)-2-(1-(5-chloro-2-methylphenyl)-1H-pyrazolo[3,4-d]pyrimidin-4-yloxy)-N-(5-cyanopyridin-2-yl)-3-(2-hydroxyethoxy)propanamide;

(2S)-2-(1-(5-cyano-2-methylphenyl)-1H-pyrazolo[3,4-d]pyrimidin-4-yloxy)-3-(2-hydroxyethoxy)-N-(5-methylpyridin-2-yl)propanamide;

(2S)—N-(5-chloropyridin-2-yl)-2-(1-(5-cyano-2-methylphenyl)-1H-pyrazolo[3,4-d]pyrimidin-4-yloxy)-3-(2-hydroxyethoxy)propanamide;

(2S)—N-(5-cyanopyridin-2-yl)-2-(1-(2,5-dimethylphenyl)-1H-pyrazolo[3,4-d]pyrimidin-4-yloxy)-3-ethoxypropanamide;

(2S)—N-(5-chloropyridin-2-yl)-3-ethoxy-2-(1-(4-methylpyridin-3-yl)-1H-pyrazolo[3,4-d]pyrimidin-4-yloxy)propanamide;

(2S)-3-cyclobutoxy-N-(5-methylpyrazin-2-yl)-2-(1-(4-methylpyridin-3-yl)-1H-pyrazolo[3,4-d]pyrimidin-4-yloxy)propanamide;

(2S)-2-(1-(3-chloropyridin-2-yl)-1H-pyrazolo[3,4-d]pyrimidin-4-yloxy)-N-(5-cyanopyridin-2-yl)-3-((R)-1-hydroxypropan-2-yloxy)propanamide;

(2S)—N-(5-chloropyridin-2-yl)-2-(1-(3-chloropyridin-2-yl)-1H-pyrazolo[3,4-d]pyrimidin-4-yloxy)-3-((R)-1-hydroxypropan-2-yloxy)propanamide;

(2S)-2-(1-(3-chloropyridin-2-yl)-1H-pyrazolo[3,4-d]pyrimidin-4-yloxy)-N-(5-fluoropyridin-2-yl)-3-((R)-1-hydroxypropan-2-yloxy)propanamide;

(2S)-2-(1-(3-chloropyridin-2-yl)-1H-pyrazolo[3,4-d]pyrimidin-4-yloxy)-N-(5-fluoropyridin-2-yl)-3-((S)-1-hydroxypropan-2-yloxy)propanamide;

(2S)—N-(5-chloropyridin-2-yl)-2-(1-(3-chloropyridin-2-yl)-1H-pyrazolo[3,4-d]pyrimidin-4-yloxy)-3-((S)-1-hydroxyprop an-2-yloxy)propanamide;

(2S)-2-(1-(2-chlorophenyl)-1H-pyrazolo[3,4-d]pyrimidin-4-yloxy)-3-(2-hydroxyethoxy)-N-(5-methylpyridin-2-yl)propanamide;

(2S)-2-(3-(2-chlorophenyl)-3H-[1,2,3]triazolo[4,5-d]pyrimidin-7-yloxy)-3-(2-hydroxyethoxy)-N-(5-methylpyridin-2-yl)propanamide;

(2S)-3-(2-(tert-butyldiphenylsilyloxy)ethoxy)-2-(3-(2-chlorophenyl)-3H-[1,2,3 ]triazolo[4,5-d]pyrimidin-7-yloxy)-N-(5-methylpyridin-2-yl)propanamide;

(2S)-2-(3-(2-chlorophenyl)-3H-[1,2,3 ]triazolo[4,5-d]pyrimidin-7-yloxy)-N-(5-cyanopyridin-2-yl)-3-ethoxypropanamide;

(2S)—N-(5-chloropyridin-2-yl)-3-(2-hydroxyethoxy)-2-(3-o-tolyl-3H-[1,2,3 ]triazolo[4,5-d]pyrimidin-7-yloxy)propanamide;

(2S)-3-(2-hydroxyethoxy)-N-(pyridin-2-yl)-2-(1-(2-(trifluoromethyl)phenyl)-1H-pyrazolo[3,4-d]pyrimidin-4-yloxy)propanamide;

(2S)-2-(1-(2-chlorophenyl)-1H-pyrazolo[3,4-d]pyrimidin-4-yloxy)-3-((R)-1-hydroxypropan-2-yloxy)-N-(pyridin-2-yl)propanamide;

(2S)-2-(1-(2-chlorophenyl)-1H-pyrazolo[3,4-d]pyrimidin-4-yloxy)-3-(2-hydroxyethoxy)-N-(pyridin-2-yl)propanamide;

(2S)—N-(5-chloropyridin-2-yl)-2-(1-(2,3-dichlorophenyl)-1H-pyrazolo[3,4-d]pyrimidin-4-yloxy)-3-(2-hydroxyethoxy)propanamide;

(2S)—N-(5-cyanopyridin-2-yl)-2-(1-(2,3-dichlorophenyl)-1H-pyrazolo[3,4-d]pyrimidin-4-yloxy)-3-(2-hydroxyethoxy)propanamide;

(2S)-2-(1-(3-chloropyridin-2-yl)-1H-pyrazolo[3,4-d]pyrimidin-4-yloxy)-3-((S)-2-hydroxypropoxy)-N-(5-methylpyridin-2-yl)propanamide;

(2S)-2-(1-(2-chlorophenyl)-1H-pyrazolo[3,4-d]pyrimidin-4-yloxy)-3-(3-hydroxyazetidin-1-yl)-N-(5-methylpyridin-2-yl)propanamide;

(2S)-2-(1-(3-chloropyridin-2-yl)-1H-pyrazolo[3,4-d]pyrimidin-4-yloxy)-3-(3-hydroxyazetidin-1-yl)-N-(5-methylpyridin-2-yl)propanamide;

(2S)-2-(1-(3-cyano-2-methylphenyl)-1H-pyrazolo[3,4-d]pyrimidin-4-yloxy)-N-(5-cyanopyridin-2-yl)-3-(2-hydroxyethoxy)propanamide;

(2S)-2-(1-(3-cyano-2-methylphenyl)-1H-pyrazolo[3,4-d]pyrimidin-4-yloxy)-3-(2-hydroxyethoxy)-N-(5-methylpyridin-2-yl)propanamide;

(2S)—N-(5-chloropyridin-2-yl)-2-(1-(3-cyano-2-methylphenyl)-1H-pyrazolo[3,4-d]pyrimidin-4-yloxy)-3-(2-hydroxyethoxy)propanamide;

(2S)—N-(5-chloropyridin-2-yl)-3-ethoxy-2-(1-(1-methyl-1H-imidazol-2-yl)-1H-pyrazolo[3,4-d]pyrimidin-4-yloxy)propanamide;

(2S)-3-isopropoxy-2-(1-(1-methyl-1H-imidazol-2-yl)-1H-pyrazolo[3,4-d]pyrimidin-4-yloxy)-N-(5-methylpyridin-2-yl)propanamide;

(2S)—N-(5-chloropyridin-2-yl)-2-(1-(3-chloropyridin-2-yl)-1H-pyrazolo[3,4-d]pyrimidin-4-yloxy)-5-hydroxypentanamide;

(2S)-2-(1-(3-chloropyridin-2-yl)-1H-pyrazolo[3,4-d]pyrimidin-4-yloxy)-N-(5-cyanopyridin-2-yl)-5-hydroxypentanamide;

(2S)—N-(5-cyanopyridin-2-yl)-2-(1-(2,3-dichlorophenyl)-1H-pyrazolo[3,4-d]pyrimidin-4-yloxy)-3-ethoxypropanamide;

(2S)-2-[1-(2-chlorophenyl)pyrazolo[4,5-e]pyrimidin-4-yl]oxy-N-(5-fluoro-2-pyridyl)-3-(3-hydroxyazetidin-1-yl)propanamide;

(2S)-2-[1-(2-chloro-6-cyano-phenyl)pyrazolo[4,5-e]pyrimidin-4-yl]oxy-N-(5-chloro-2-pyridyl)-3-[(1R)-2-hydroxy-1-methyl-ethoxy]propanamide;

(2S)-2-[1-(2-chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide;

(2S)-2-[1-(2,6-dichlorophenyl)pyrazolo[4,5-e]pyrimidin-4-yl]oxy-N-(5-fluoro-2-pyridyl)-3-(2-hydroxyethoxy)propanamide;

(2S)-2-[1-(2-chlorophenyl)pyrazolo[4,5-e]pyrimidin-4-yl]oxy-3-(3-hydroxyazetidin-1-yl)-N-(5-methylpyrazin-2-yl)propanamide;

(2S)-2-[1-(2,6-dichlorophenyl)pyrazolo[4,5-e]pyrimidin-4-yl]oxy-3-(3-hydroxyazetidin-1-yl)-N-(5-methylpyrazin-2-yl)propanamide;

(2S)-3-(azetidin-1-yl)-2-[1-(2-chloro-6-cyano-phenyl)pyrazolo[3,4-d]pyrimidin-4-yl]oxy-N-(2-pyridyl)propanamide;

(2S)-2-[1-(2-chloro-6-fluoro-phenyl)pyrazolo[3,4-d]pyrimidin-4-yl]oxy-3-(3-hydroxyazetidin-1-yl)-N-(2-pyridyl)propanamide;

(2S)-2-[1-(2-chlorophenyl)pyrazolo[3,4-d]pyrimidin-4-yl]oxy-N-(5-cyano-2-pyridyl)-3-(3-hydroxyazetidin-1-yl)propanamide;

(2S)-2-[1-(2-chloro-6-cyano-phenyl)pyrazolo[3,4-d]pyrimidin-4-yl]oxy-N-(5-cyano-2-pyridyl)-3-(3-hydroxyazetidin-1-yl)propanamide (2S)-2-[1-(2-chlorophenyl)pyrazolo[3,4-d]pyrimidin-4-yl]oxy-3-(3-hydroxyazetidin-1-yl)-N-(2-pyridyl)propanamide;

(2S)-2-[1-(2-chlorophenyl)pyrazolo[3,4-d]pyrimidin-4-yl]oxy-N-(5-chloro-2-pyridyl)-3-(3-hydroxyazetidin-1-yl)propanamide;

(2S)-3-[(1R)-2-hydroxy-1-methyl-ethoxy]-N-(5-methyl-2-pyridyl)-2-[1-(4-methyl-3-thienyl)pyrazolo[3,4-d]pyrimidin-4-yl]oxy-propanamide;

(2S)-2-[1-(2-chlorophenyl)pyrazolo[3,4-d]pyrimidin-4-yl]
 oxy-3-[3-(hydroxymethyl)azetidin-1-yl]-N-(2-pyridyl)
 propanamide;
(2S)-2-[1-(2-chloro-6-fluoro-phenyl)pyrazolo[3,4-d]pyrimi-
 din-4-yl]oxy-N-(5-fluoro-2-pyridyl)-3-(3-hydroxyazeti-
 din-1-yl)propanamide;
(2S)-2-[1-(2,6-dichlorophenyl)pyrazolo[3,4-d]pyrimidin-4-
 yl]oxy-N-(5-fluoro-2-pyridyl)-3-(3-hydroxyazetidin-1-
 yl)propanamide;
(2S)-2-[1-(2-chloro-6-cyano-phenyl)pyrazolo[3,4-d]pyrimi-
 din-4-yl]oxy-3-[(1R)-2-hydroxy-1-methyl-ethoxy]-N-(2-
 pyridyl)propanamide;
(2S)-2-[1-(3-chloro-2-pyridyl)pyrazolo[3,4-d]pyrimidin-4-
 yl]oxy-3-[(1R)-2-hydroxy-1-methyl-ethoxy]-N-(5-me-
 thyl-2-pyridyl)propanamide;
(2S)-2-[1-(2,6-dichlorophenyl)pyrazolo[3,4-d]pyrimidin-4-
 yl]oxy-3-(3-hydroxyazetidin-1-yl)-N-(2-pyridyl)pro-
 panamide;
(2S)—N-(5-cyano-2-pyridyl)-2-[1-(2,6-dichlorophenyl)
 pyrazolo[3,4-d]pyrimidin-4-yl]oxy-3-(3-hydroxyazeti-
 din-1-yl)propanamide;
(2S)—N-(5-cyano-2-pyridyl)-2-[1-(2,6-dichlorophenyl)
 pyrazolo[3,4-d]pyrimidin-4-yl]oxy-3-(2-hydroxyethoxy)
 propanamide;
(2S)—N-(5-chloro-2-pyridyl)-2-[1-(2,6-dicyanophenyl)
 pyrazolo[3,4-d]pyrimidin-4-yl]oxy-3-[(1R)-2-hydroxy-1-
 methyl-ethoxy]propanamide;
(2S)-2-[1-(2-chloro-6-cyano-phenyl)pyrazolo[3,4-d]pyrimi-
 din-4-yl]oxy-N-(5-fluoro-2-pyridyl)-3-(2-hydroxy-
 ethoxy)propanamide;
(2S)-2-[1-(2-chloro-6-cyano-phenyl)pyrazolo[3,4-d]pyrimi-
 din-4-yl]oxy-3-(2-hydroxyethoxy)-N-(2-pyridyl)pro-
 panamide;
(2S)-2-[1-(2-chloro-6-cyano-phenyl)pyrazolo[3,4-d]pyrimi-
 din-4-yl]oxy-3-(3-hydroxyazetidin-1-yl)-N-(5-meth-
 ylpyrazin-2-yl)propanamide;
(2S)-2-[1-(2-chloro-6-cyano-phenyl)pyrazolo[3,4-d]pyrimi-
 din-4-yl]oxy-N-(5-chloro-2-pyridyl)-3-(3-hydroxyazeti-
 din-1-yl)propanamide;
(2S)-2-[1-(3-chloro-2-pyridyl)pyrazolo[3,4-d]pyrimidin-4-
 yl]oxy-3-(3-hydroxyazetidin-1-yl)-N-(2-pyridyl)pro-
 panamide;
(2S)-2-[1-(2-chloro-6-cyano-phenyl)pyrazolo[3,4-d]pyrimi-
 din-4-yl]oxy-N-(5-fluoro-2-pyridyl)-3-(3-hydroxyazeti-
 din-1-yl)propanamide;
(2S)-2-[1-(3-chloro-2-pyridyl)pyrazolo[3,4-d]pyrimidin-4-
 yl]oxy-N-(5-fluoro-2-pyridyl)-3-(3-hydroxyazetidin-1-
 yl)propanamide;
(2S)-2-[1-(2-chloro-6-fluoro-phenyl)pyrazolo[3,4-d]pyrimi-
 din-4-yl]oxy-N-(5-fluoro-2-pyridyl)-3-(2-hydroxy-
 ethoxy)propanamide;
(2S)-2-[1-(2-chlorophenyl)pyrazolo[3,4-d]pyrimidin-4-yl]
 oxy-N-(5-fluoro-2-pyridyl)-3-[(1R)-2-hydroxy-1-methyl-
 ethoxy]propanamide;
(2S)-2-[1-(2-chloro-6-cyano-phenyl)pyrazolo[3,4-d]pyrimi-
 din-4-yl]oxy-N-(5-fluoro-2-pyridyl)-3-[(1R)-2-hydroxy-
 1-methyl-ethoxy]propanamide;
(2S)-2-[1-(2-chlorophenyl)pyrazolo[3,4-d]pyrimidin-4-yl]
 oxy-3-[(1R)-2-hydroxy-1-methyl-ethoxy]-N-(5-meth-
 ylpyrazin-2-yl)propanamide;
(2S)-2-[1-(2-chlorophenyl)pyrazolo[3,4-d]pyrimidin-4-yl]
 oxy-N-(5-fluoro-2-pyridyl)-3-(2-hydroxyethoxy)pro-
 panamide;
(2S)-2-[1-(3-chloro-2-pyridyl)pyrazolo[3,4-d]pyrimidin-4-
 yl]oxy-3-(3-hydroxyazetidin-1-yl)-N-(5-methylthiazol-2-
 yl)propanamide;
(2S)-2-[1-(2,6-dichlorophenyl)pyrazolo[3,4-d]pyrimidin-4-
 yl]oxy-3-(2-hydroxyethoxy)-N-(2-pyridyl)propanamide;
(2S)-2-[1-(2-chloro-6-cyano-phenyl)pyrazolo[3,4-d]pyrimi-
 din-4-yl]oxy-N-(5-cyano-2-pyridyl)-3-[(1R)-2-hydroxy-
 1-methyl-ethoxy]propanamide;
(2S)-2-[1-(2-chlorophenyl)pyrazolo[3,4-d]pyrimidin-4-yl]
 oxy-N-(5-cyano-2-pyridyl)-3-[(1R)-2-hydroxy-1-methyl-
 ethoxy]propanamide;
or a pharmaceutically acceptable salt thereof. The term "any one or more of" means any number of the above compounds from 1 to 258.

In another aspect the present invention provides a compound selected from one or more (that is any number from 1 to 12) of the following:
(2S)—N-(5-chloropyridin-2-yl)-2-(1-(3-chloropyridin-2-
 yl)-1H-pyrazolo[3,4-d]pyrimidin-4-yloxy)-3-(3-hy-
 droxyazetidin-1-yl)propanamide;
(2S)-2-(1-(2-chloro-6-cyanophenyl)-1H-pyrazolo[3,4-d]py-
 rimidin-4-yloxy)-N-(5-chloropyridin-2-yl)-3-(2-hydroxy-
 ethoxy)propanamide;
(2S)—N-(5-chloropyridin-2-yl)-2-(1-(3-chloropyridin-2-
 yl)-1H-pyrazolo[3,4-d]pyrimidin-4-yloxy)-3-((R)-1-hy-
 droxypropan-2-yloxy)propanamide;
(2S)-2-[1-(2-chlorophenyl)pyrazolo[4,5-e]pyrimidin-4-yl]
 oxy-N-(5-fluoro-2-pyridyl)-3-(3-hydroxyazetidin-1-yl)
 propanamide;
(2S)-2-[1-(2-chloro-6-cyano-phenyl)pyrazolo[4,5-e]pyrimi-
 din-4-yl]oxy-N-(5-chloro-2-pyridyl)-3-[(1R)-2-hydroxy-
 1-methyl-ethoxy]propanamide;
(2S)-2-[1-(2-chloro-6-cyano-phenyl)pyrazolo[4,5-e]pyrimi-
 din-4-yl]oxy-3-[(1R)-2-hydroxy-1-methyl-ethoxy]-N-(5-
 methylpyrazin-2-yl)propanamide;
(2S)-2-[1-(2,6-dichlorophenyl)pyrazolo[4,5-e]pyrimidin-4-
 yl]oxy-N-(5-fluoro-2-pyridyl)-3-(2-hydroxyethoxy)pro-
 panamide;
(2S)-2-[1-(2-chlorophenyl)pyrazolo[4,5-e]pyrimidin-4-yl]
 oxy-3-(3-hydroxyazetidin-1-yl)-N-(5-methylpyrazin-2-
 yl)propanamide;
(2S)-2-[1-(2,6-dichlorophenyl)pyrazolo[4,5-e]pyrimidin-4-
 yl]oxy-3-(3-hydroxyazetidin-1-yl)-N-(5-methylpyrazin-
 2-yl)propanamide;
(2S)-2-[1-(2-chlorophenyl)pyrazolo[3,4-d]pyrimidin-4-yl]
 oxy-N-(5-chloro-2-pyridyl)-3-(3-hydroxyazetidin-1-yl)
 propanamide;
(2S)-2-[1-(2,6-dichlorophenyl)pyrazolo[3,4-d]pyrimidin-4-
 yl]oxy-N-(5-fluoro-2-pyridyl)-3-(3-hydroxyazetidin-1-
 yl)propanamide; and
(2S)-2-[1-(2-chloro-6-cyano-phenyl)pyrazolo[3,4-d]pyrimi-
 din-4-yl]oxy-N-(5-fluoro-2-pyridyl)-3-(3-hydroxyazeti-
 din-1-yl)propanamide;
or a pharmaceutically acceptable salt thereof.

Depending on the computer naming package used certain compounds of the invention are named as pyrazolo[3,4-d]pyrimidin-4-yl compounds and others are named as pyrazolo[4,5-e]pyrimidin-4-yl compounds. It will be understood by those skilled in the art that these terms describe the same heterocyclic ring.

In another aspect the present invention provides a compound of formula I as defined in any of the definitions above but excluding any one of the compounds in either of the lists of compounds immediately above.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen;
c) H. Bundgaard, Chapter 5 "Design and Application of Prodrugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988); and
f) N. Kakeya, et al., Chem Pharm Bull, 32, 692 (1984).

The contents of the above cited documents are incorporated herein by reference.

Examples of pro-drugs are as follows. An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $C_6$alkanoyloxymethyl esters for example pivaloyloxymethyl, phthalidyl esters, $C_3$ to $C_8$cycloalkoxycarbonyloxy$C_1$ to $C_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In one aspect, a suitable acid-addition salt may be one with hydrochloric, sulphuric, methanesulfonic or citric acid. It will be understood that an acid addition salt may be formed with any sufficiently basic group which may for example be in HET-1 or may for example be a substituent $R^2$. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

A further feature of the invention is a pharmaceutical composition comprising a compound of Formula (I) as defined above, or a pharmaceutically-acceptable salt thereof, together with a pharmaceutically-acceptable diluent or carrier.

According to another aspect of the invention there is provided a compound of
Formula (I) as defined above or a pharmaceutically-acceptable salt thereof for use as a medicament.

According to another aspect of the invention there is provided a compound of Formula (I), or a pharmaceutically-acceptable salt thereof as defined above for use as a medicament for treatment of a disease mediated through GLK, in particular type 2 diabetes.

Further according to the invention there is provided the use of a compound of Formula (I) or a pharmaceutically-acceptable salt thereof in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of Formula (I) or a pharmaceutically-acceptable salt thereof, including the compounds mentioned in the provisos, to a mammal in need of such treatment.

Specific diseases which may be treated by a compound or composition of the invention include: blood glucose lowering in Type 2 Diabetes Mellitus without a serious risk of hypoglycaemia (and potential to treat type 1), dyslipidemia, obesity, insulin resistance, metabolic syndrome X, impaired glucose tolerance.

As discussed above, thus the GLK system can be described as a potential "Diabesity" target (of benefit in both Diabetes and Obesity). Thus, according to another aspect of the invention there is provided the use of a compound of Formula (I) or a pharmaceutically-acceptable salt thereof, in the preparation of a medicament for use in the combined treatment or prevention, particularly treatment, of diabetes and obesity.

According to another aspect of the invention there is provided the use of a compound of Formula (I) or a pharmaceutically-acceptable salt thereof, in the preparation of a medicament for use in the treatment or prevention of obesity.

According to a further aspect of the invention there is provided a method for the combined treatment of obesity and diabetes by administering an effective amount of a compound of Formula (I) or a pharmaceutically-acceptable salt thereof, to a mammal in need of such treatment.

According to another aspect of the invention there is provided a compound of Formula (I) or a pharmaceutically-acceptable salt thereof as defined above for use as a medicament for treatment or prevention, particularly treatment of obesity.

According to a further aspect of the invention there is provided a method for the treatment of obesity by administering an effective amount of a compound of Formula (I) or a pharmaceutically-acceptable salt thereof, to a mammal in need of such treatment.

Compounds of the invention may be particularly suitable for use as pharmaceuticals, for example because of favourable physical and/or pharmacokinetic properties and/or toxicity profile.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or in combination with one or more other substances and/or treatments for the indication being treated. In another aspect the invention provides a pharmaceutical combination comprising a compound of Formula I and another pharmacologically active substance particularly wherein the other pharmacologically active substance is a medicament for the treatment of type 2 diabetes or obesity or a related condition.

Such conjoint treatment may be achieved by way of the simultaneous, sequential or separate administration of the individual components of the treatment. Simultaneous treatment may be in a single tablet or in separate tablets. For example in the treatment of diabetes mellitus, chemotherapy may include the following main categories of treatment:

1) Insulin and insulin analogues;
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors e.g. saxagliptin, sitagliptin, vildagliptin or alogliptin and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1, 6 bisphosphatase inhibitors, glycogen phopsphorylase inhibitors, glycogen synthase kinase inhibitors);
6) Agents designed to reduce the absorption of glucose from the intestine (for example acarbose);
7) Agents that prevent the reabsorption of glucose by the kidney (SGLT inhibitors for example dapagliflozin);
8) Agents designed to treat the complications of prolonged hyperglycaemia (for example aldose reductase inhibitors);
9) Anti-obesity agents (for example sibutramine and orlistat);
10) Anti-dyslipidaemia agents such as, HMG-CoA reductase inhibitors (eg statins); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
11) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
12) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;
13) Agents which antagonise the actions of glucagon; and
14) Anti-inflammatory agents, such as non-steroidal anti-inflammatory drugs (eg. aspirin) and steroidal anti-inflammatory agents (eg. cortisone).

According to another aspect of the present invention there is provided individual compounds produced as end products in the Examples set out below and salts thereof.

A compound of the invention, or a salt thereof, may be prepared by any process known to be applicable to the preparation of such compounds or structurally related compounds. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

Processes for the synthesis of compounds of Formula (I) are provided as a further feature of the invention. Thus, according to a further aspect of the invention there is provided a process for the preparation of a compound of Formula (I).

Compounds of formula (I) may be prepared by reacting a compound of formula (II)

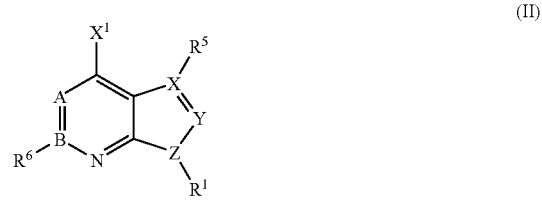

For example:

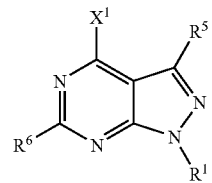

in which $R^1$, $R^2$, $R^3$, $R^5$ and $R^6$ are as defined above and $X^1$ is a leaving group, for example halo, particularly chloro, with a compound of formula (III)

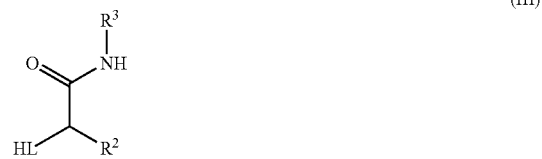

in which $R^2$, $R^3$ and L are as defined above in an inert solvent, for example tetrahydrofuran, in the presence of a base, for example lithium bis(trimethylsilyl)amide or sodium hydride, at a temperature in the range of −25° C. to 150° C.

Compounds of formula (I) may be also prepared by reacting a compound of formula (IV)

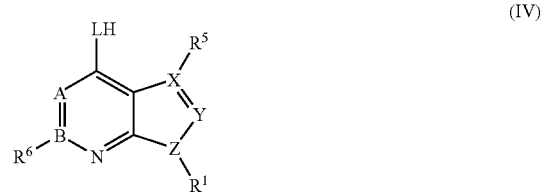

For example

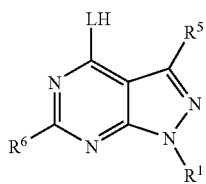

in which $R^1$, $R^5$, $R^6$ and L are as defined above with a compound of formula (V)

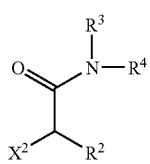
(V)

in which $R^2$, $R^3$ and L are as defined above and $X^2$ is a leaving group for example halo particularly chloro, in an inert solvent, for example tetrahydrofuran or dimethylformamide, in the presence of a base, for example potassium carbonate, at a temperature in the range of $-25°$ C. to $150°$ C.

Compounds of formula (I) may be also prepared by reacting a compound of formula (IV)

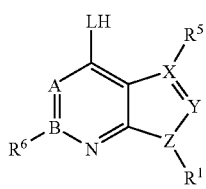
(IV)

for example

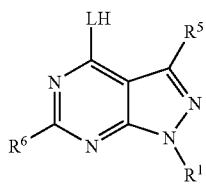

in which $R^1$, $R^5$ and $R^6$ are as defined above and L is, for example, S with a compound of formula (V) as defined above wherein the compound of formula (V) is formed in situ by reacting a compound of formula (VI)

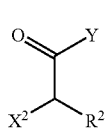
(VI)

in which $R^2$ is as defined above and $X^2$ is a leaving group, for example halo, particularly bromo, and Y is chloro with a compound of formula (VII)

(VII)

in which $R^3$ is as previously defined in the presence of a base, for example di-iso-propylethylamine, in an inert solvent for example dichloromethane at a temperature in the range of $-25°$ C. to $150°$ C.

Or where $X^2$ is hydroxy and Y is alkoxy eg. methoxy in the presence of a Lewis acid such as trimethyl aluminium or isopropylmagnesium bromide.

Compounds of formula (I) may be also prepared by reacting a compound of formula (VIII)

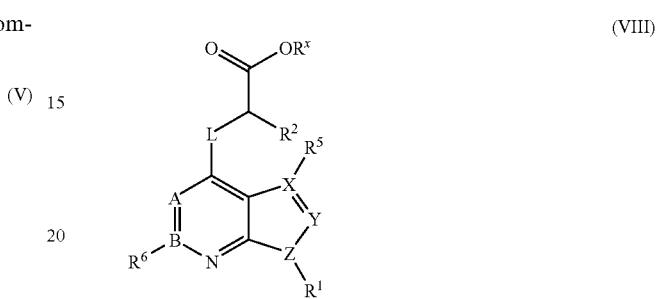
(VIII)

For example

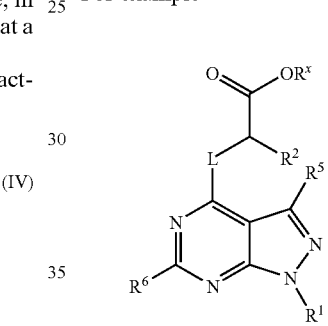

in which $R^1$, $R^5$, $R^6$ and L are as defined above and $R^x$ is a (1-4C)alkyl with a compound of formula (VII) as defined above in an inert solvent, for example tetrahydrofuran, in the presence of a base, for example sodium hydride, at a temperature in the range of $-25°$ C. to $150°$ C. or in the presence of a Lewis acid, for example trimethyl aluminium in a suitable solvent such as toluene.

Certain intermediates of formula (II) and (IV) are believed to be novel and comprise an independent aspect of the invention.

When $R^2$ is (1-6C)alkoxymethyl, compounds of formula (III) may be made as outlined in Scheme 1 below, wherein R is (1-6C)alkyl. The process shown in Scheme 1 comprises a further aspect of the invention.

Ring opening of epoxyesters by alcohols as shown in step a) of Scheme 1 is known in the art, see Synthetic Communications, Vol 33 (2003), pp 687-692. The reaction generally requires the use of a Lewis acid catalyst, and specifically magnesium perchlorate $(Mg(ClO_4)_2)$ is known in the above reference, used without any added solvent. We have found that this process carries a risk of spontaneous decomposition with rapid gas evolution and/or explosion, which may be reduced both by changing Lewis acid and by adding solvent to the reaction. In particular, step a) is carried out in the presence of magnesium trifluoromethanesulfonate, suitably in ethyl acetate, toluene or dichloromethane, most particularly in ethyl acetate. This process is exemplified in Intermediate C7a hereinafter.

Therefore in a further aspect of the invention there is provided the reaction of methyl oxirane-2-carboxylate (IX) with an alcohol ROH (wherein R is (1-6C)alkyl, (3-6C)cycloalkyl or $R^x_3SiO(2\text{-}4C)$alkyl (wherein each $R^x$ is independently selected from (1-6C)alkyl and phenyl) in the presence of magnesiumtrifluoromethanesulfonate in ethyl acetate, to give a compound of formula (X).

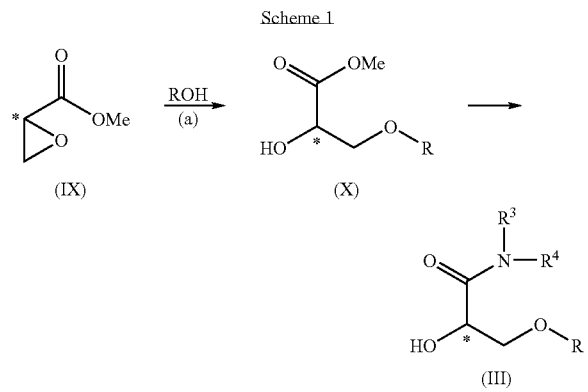

Suitable examples of ROH wherein R is $R^x_3SiO(2\text{-}4C)$ alkyl include

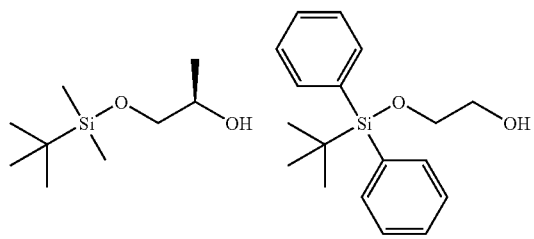

In an analogous procedure amines may be used prepare azetidines:

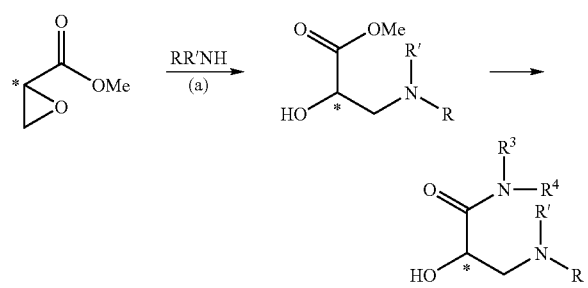

Suitable examples of RR'NH include

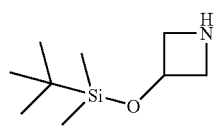

In one aspect R is (1-6C)alkyl. In another aspect, R is methyl, ethyl, isopropyl or cyclobutyl.

Although compound of formula (IX) is a methyl ester, other alkyl esters may also be used.

It will be appreciated that when the compound of formula (IX) is enantiomerically enriched then the compounds of formula (X) and (III) made therefrom will also be enantiomerically enriched.

The compound of formula (X) may alternatively be reacted with a compound of formula (II) to give a compound of formula (VIII).

Compounds of Formula (II) may be Made According to the Following Processes a) to b)

a) by reaction of a compound of formula (XI) wherein $X^3$ is a leaving group such as halo (for example chloro), or a precursor to the linker group L such as OH, or SH, or a precursor to the leaving group such as OH, SMe, S(p-tolyl) or $NH_2$; and wherein LG is a leaving group such as chloro, bromo, iodo or trifluoromethanesulfonyl; $R^1$, $R^5$, $R^6$, A, B, X, Y and Z are as previously defined;

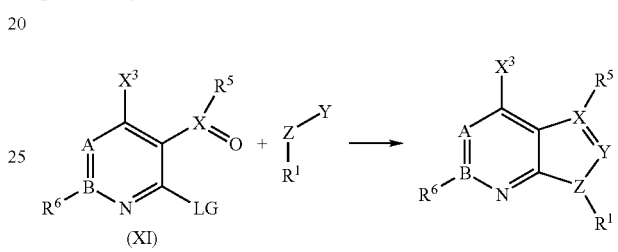

Compounds of the formula (XI) may be made by processes known in the art.

It will be appreciated that a compound where $X^3$ is OH may be transformed into a compound where $X^3$ is Cl by reaction with a chlorinating agent such as $POCl_3$.

b) By reaction of a compound of formula (XII) with a compound of formula (XIII), wherein $R^1$, $R^5$, $R^6$, A, B, X, $X^3$, Y and Z are as previously defined; $LG^2$ is a leaving group such as chloro, bromo, iodo or trifluoromethanesulfonyl when Z=C, and $LG^2$ is H when Z=N; Met is a group suitable for coupling reactions, such as $-B(OH)_2$ and $-SnBu_3$, mediated by catalysts containing transition metals such as $Pd^0$ or $Cu^I$, such as $PdPPh_3$ or CuI.

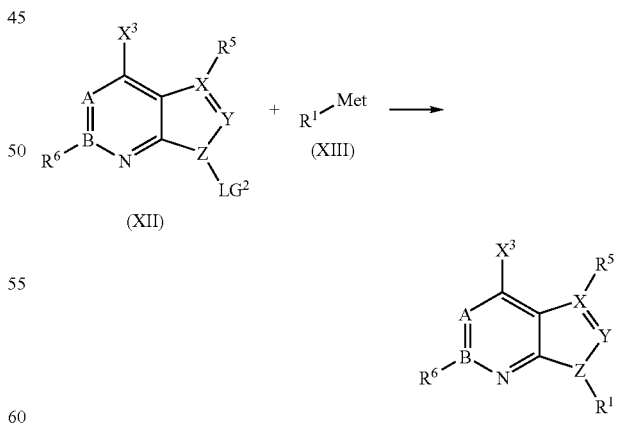

It will be appreciated that the above reaction may alternatively be carried out by the equivalent procedure wherein the Met group is a substitutent on Z and $LG^2$ is attached to $R^1$, wherein $LG^2$ is a leaving group such as chloro, bromo, iodo or trifluoromethanesulfonyl and Met is as previously defined when Z=C but wherein Met is H when Z=N.

It will be understood that compounds such as those of formulae (XI) and (XII) when $X^3$ is OH may exist in two tautomeric forms, although they are drawn herein in the enol form.

Compounds of the formula (XII) may be made by processes known in the art or by analogy to processes known in the art. For example for X=Y=Z=N the following process may be used:

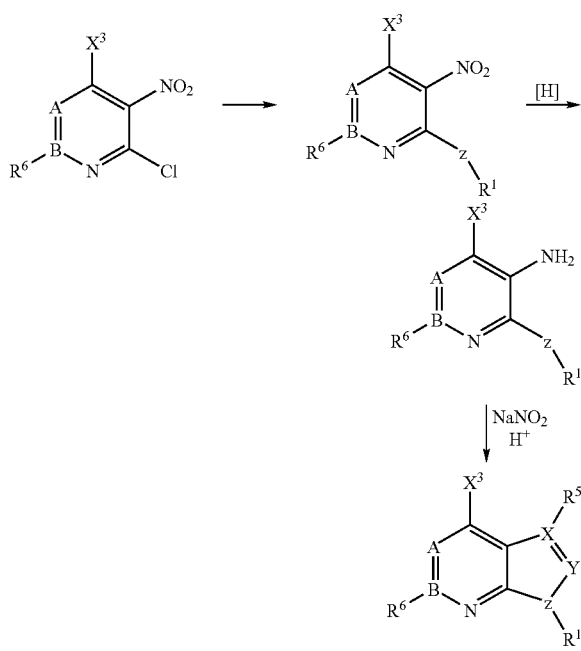

or for example according to the scheme below, using a reagent such as methyl formate, a mixture of formic acid and sulfuric acid, or trimethylorthoformate when B is C and a reagent such as nitrous acid when B is N.

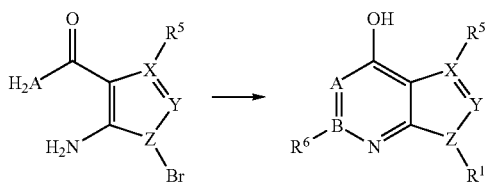

During the preparation process, it may be advantageous to use a protecting group for a functional group within the molecule. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal- or enzymically-catalysed hydrolysis.

Examples of hydroxy protecting groups include methyl, t-butyl, lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); tetrahydropyran-2-yl; aryl lower alkyl groups (e.g. benzyl) groups; and triaryl lower alkyl groups (e.g. triphenylmethyl). Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, nucleophilic displacement, acid-, base, metal- or enzymically-catalysed hydrolysis, catalytic hydrogenolysis/hydrogenation or photolytically for groups such as o-nitrobenzyloxycarbonyl, or with fluoride ions for silyl groups. For example, methylether protecting groups for hydroxy groups may be removed by trimethylsilyliodide. A tert-butyl ether protecting group for a hydroxy group may be removed by hydrolysis, for example by use of hydrochloric acid in methanol.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with eerie ammonium nitrate. Finally alk-1-enyl groups may be introduced by reacting the amide with the appropriate aldehyde and removed with acid.

In the above other pharmaceutical composition, process, method, use and medicament manufacture features, the alternative and preferred aspects and embodiments of the compounds of the invention described herein also apply.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation under reduced pressure and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet; sextet (v) intermediates were not generally fully characterised and purity was assessed by thin layer chromatography (TLC), high-performance liquid chromatography (HPLC), infra-red (IR) or NMR analysis;

(vi) flash chromatography was carried out on silica unless otherwise stated;

(vii) Enantiomeric excesses (ee's) were determined by HPLC using a chiral stationary phase such as Chiralcel OJ or Chiralpak AD-H and/or by NMR using an appropriate chiral shift reagent such as (1S)-[1,1'-binaphthalene]-2,2'-diol (CAS 18531-99-2) or (1R)-[1,1'-binaphthalene]-2,2'-diol (CAS 18531-94-7).

ABBREVIATIONS

ACN Acetonitrile
n-BuLi n-Butyllithium
m-CPBA 3-Chloroperbenzoic acid
DCM Dichloromethane
DIPEA Di-iso-propylethylamine
DMAP 4-Di(methylamino)pyridine
DMF N,N-Dimethylformamide
DMSO dimethylsulfoxide
EtOAc Ethyl acetate
EtOH Ethanol
FMOC 9-Fluorenylmethyl carbamate
IPA Isopropyl alcohol
LHMDS Lithium bis(trimethylsilyl)amide
MeOH Methanol
TBDMSCl tert-Butyldimethylsilyl chloride
THF Tetrahydrofuran
ESI Electrospray ionisation
rt Room temperature
cat Catalytic
ee Enantiomeric excess
HPLC High performance liquid chromatography
EDCI 1-(3-Dimethylaminopropyl)-2-ethylcarbodiimide hydrochloride
Method 1

EXAMPLE 1

2-{[1-(2-chlorophenyl)-1H-pyrazolo[3,4-d]pyrimidin-4-yl]oxy}-3-methoxy-N-(5-methylpyridin-2-yl)propanamide

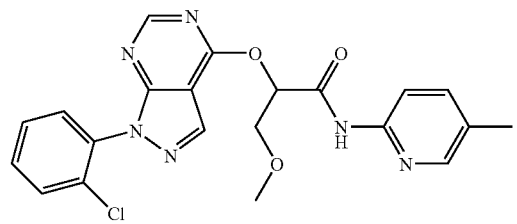

LHMDS (1.40 mL, 1.0 M in THF, 1.40 mmol) was added slowly to a stirred solution of 2-hydroxy-3-methoxy-N-(5-methylpyridin-2-yl)propanamide (200 mg, 0.951 mmol) in anhydrous THF (5 mL). The reaction mixture was kept at ambient temperature for 10 minutes, and a solution of 4-chloro-1-(2-chlorophenyl)-1H-pyrazolo[3,4-d]pyrimidine (265 mg, 1.00 mmol) in anhydrous THF (3 mL) was added. The reaction mixture was heated at 50° C. for ½ hrs (another 3 equivalents of LHMDS were added and the reaction heated for 18 hrs at 50° C. in example 49). Water and EtOAc were added, and the two phases were separated. The organic phase was washed with water, dried over MgSO$_4$ and concentrated in vacuo. The residue was purified with column chromatography (silica gel, eluting with DCM/EtOAc:2/1) to give the title compound as a colourless solid (323 mg), $^1$H NMR (500 MHz, CDCl$_3$) δ 8.67 (br s, 1H), 8.62 (s, 1H), 8.48 (s, 1H), 8.18 (d, 1H), 8.12 (s, 1H), 7.65 (d, 1H), 7.52 (m, 4H), 6.13 (t, 1H), 4.14 (m, 2H), 4.06 (m, 1H), 3.49 (s, 3H), 2.32 (s, 3H), HRMS: calcd for (M+H$^+$) C$_{21}$H$_{20}$$^{35}$ClN$_6$O$_3$: 439.1285. Found: 439.1287.

EXAMPLE 2

(R)-2-{[1-(2-chlorophenyl)-1H-pyrazolo[3,4-d]pyrimidin-4-yl]oxy}-3-methoxy-N-(5-methylpyridin-2-yl)propanamide

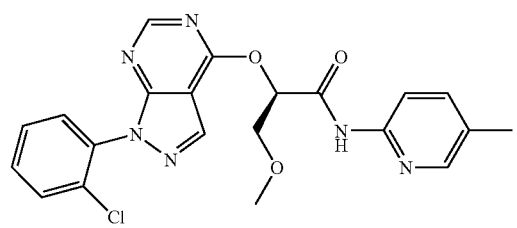

AND EXAMPLE 3

(S)-2-{[1-(2-chlorophenyl)-1H-pyrazolo[3,4-d]pyrimidin-4-yl]oxy}-3-methoxy-N-(5-methylpyridin-2-yl)propanamide

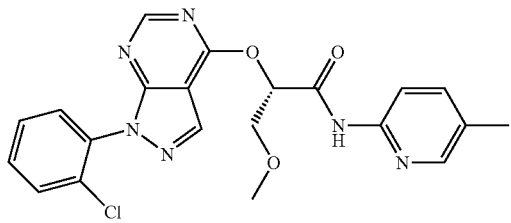

The enantiomers of racemic 2-{[1-(2-chlorophenyl)-1H-pyrazolo[3,4-d]pyrimidin-4-yl]oxy}-3-methoxy-N-(5-methylpyridin-2-yl)propanamide (100 mg) were separated by preparative HPLC: Column Chiralpak AS (250×20 mm, 5 μm); Mobile phase heptane/IPA:60/40; Flow 15 ml/min; UV 275 nm; Temperature 40° C. This gave (R)-2-{[1-(2-chlorophenyl)-1H-pyrazolo[3,4-d]pyrimidin-4-yl]oxy}-3-methoxy-N-(5-methylpyridin-2-yl)propanamide (44.1 mg, >99% ee), $^1$H NMR (300 MHz, CDCl$_3$) δ 8.70 (br s, 1H), 8.59 (s, 1H), 8.44 (s, 1H), 8.15 (d, 1H), 8.10 (s, 1H), 7.62 (m, 1H), 7.51 (m, 4H), 6.10 (t, 1H), 4.07 (m, 2H), 3.46 (s, 3H), 2.29 (s, 3H), and (S)-2-{[1-(2-chlorophenyl)-1H-pyrazolo[3,4-d]pyrimidin-4-yl]oxy}-3-methoxy-N-(5-methylpyridin-2-yl)propanamide (45.7 mg, >99% ee), $^1$H NMR (300 MHz, CDCl$_3$) δ 8.69 (br s, 1H), 8.59 (s, 1H), 8.44 (s, 1H), 8.15 (d, 1H), 8.10 (s, 1H), 7.62 (m, 1H), 7.50 (m, 4H), 6.10 (t, 1H), 4.07 (m, 2H), 3.46 (s, 3H), 2.29 (s, 3H).

EXAMPLE 4

3-methoxy-2-{[1-(2-methoxyphenyl)-1H-pyrazolo[3,4-d]pyrimidin-4-yl]oxy}-N-(5-methylpyridin-2-yl)propanamide

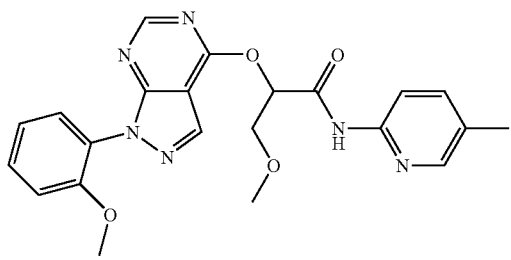

Method 1 from Intermediates A2 and B3

$^1$H NMR (300 MHz, CDCl$_3$) δ 8.67 (br s, 1H), 8.56 (s, 1H), 8.42 (s, 1H), 8.15 (d, 1H), 8.10 (s, 1H), 7.48 (m, 3H), 7.12 (m, 2H), 6.11 (t, 1H), 4.12 (m, 1H), 4.02 (m, 1H), 3.79 (s, 3H), 3.46 (s, 3H), 2.29 (s, 3H), HRMS: calcd for (M+H$^+$) C$_{22}$H$_{23}$N$_6$O$_4$: 435.1780. Found: 435.1773.

EXAMPLE 5

(R)-3-methoxy-2-{[1-(2-methoxyphenyl)-1H-pyrazolo[3,4-d]pyrimidin-4-yl]oxy}-N-(5-methylpyridin-2-yl)propanamide

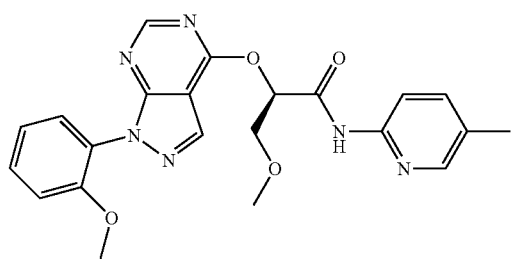

AND EXAMPLE 6

(S)-3-methoxy-2-{[1-(2-methoxyphenyl)-1H-pyrazolo[3,4-d]pyrimidin-4-yl]oxy}-N-(5-methylpyridin-2-yl)propanamide

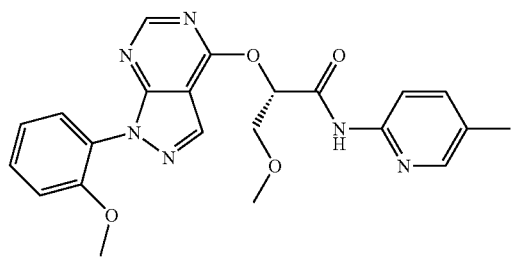

The enantiomers of racemic 3-methoxy-2-{[1-(2-methoxyphenyl)-1H-pyrazolo[3,4-d]pyrimidin-4-yl]oxy}-N-(5-methylpyridin-2-yl)propanamide (100 mg) were separated by preparative HPLC: Column Chiralpak AD (250×20 mm, 5 μm); Mobile phase heptane/IPA:40/60; Flow 15 ml/min; UV 275 nm; Temperature 40° C. This gave (R)-3-methoxy-2-{[1-(2-methoxyphenyl)-1H-pyrazolo[3,4-d]pyrimidin-4-yl]oxy}-N-(5-methylpyridin-2-yl)propanamide (39.0 mg, >99% ee), $^1$H NMR (300 MHz, CDCl$_3$) δ 8.69 (br s, 1H), 8.56 (s, 1H), 8.41 (s, 1H), 8.15 (d, 1H), 8.09 (d, 1H), 7.48 (m, 3H), 7.12 (m, 2H), 6.10 (dd, 1H), 4.06 (m, 2H), 3.78 (s, 3H), 3.46 (s, 3H), 2.29 (s, 3H), and (S)-3-methoxy-2-{[1-(2-methoxyphenyl)-1H-pyrazolo[3,4-d]pyrimidin-4-yl]oxy}-N-(5-methylpyridin-2-yl)propanamide (41.1 mg, >99% ee), $^1$H NMR (300 MHz, CDCl$_3$) δ 8.69 (br s, 1H), 8.56 (s, 1H), 8.41 (s, 1H), 8.15 (d, 1H), 8.10 (d, 1H), 7.48 (m, 3H), 7.11 (m, 2H), 6.10 (dd, 1H), 4.06 (m, 2H), 3.78 (s, 3H), 3.46 (s, 3H), 2.29 (s, 3H).

EXAMPLE 7

2-{[1-(2,4-Dichlorophenyl)-1H-pyrazolo[3,4-d]pyrimidin-4-yl]oxy}-3-methoxy-N-(5-methylpyridin-2-yl)propanamide

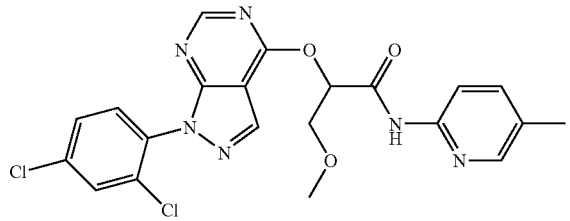

Method 1 from Intermediates A2 and B6

$^1$H NMR (400 MHz, CDCl$_3$) δ 9.37 (br s, 1H), 8.08 (m, 1H), 7.86 (s, 1H), 7.59 (s, 1H), 7.23 (s, 1H), 7.15 (m, 1H), 6.98 (m, 1H), 6.78 (m, 1H), 5.63 (m, 1H), 3.70 (m, 1H), 3.55 (m, 1H), 2.99 (s, 3H), 1.86 (s, 3H), HRMS: calcd for (M+H$^+$) C$_{22}$H$_{19}$$^{35}$Cl$_2$N$_6$O$_3$: 473.0895. Found: 473.0904.

EXAMPLE 8

3-methoxy-2-[(1-methyl-1H-pyrazolo[3,4-d]pyrimidin-4-yl)oxy]-N-(5-methylpyridin-2-yl)propanamide

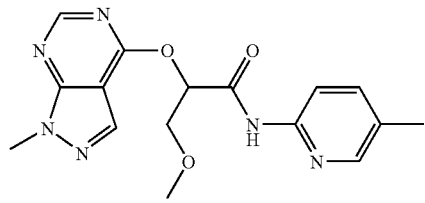

Method 1 from Intermediates A2 and B 11

$^1$H NMR (500 MHz, CDCl$_3$) δ 8.65 (br s, 1H), 8.56 (s, 1H), 8.19 (s, 1H), 8.13 (d, 1H), 8.08 (s, 1H), 7.52 (d, 1H), 6.07 (t, 1H), 4.12 (s, 3H), 4.09 (m, 1H), 4.00 (m, 1H), 3.44 (s, 3H), 2.28 (s, 3H), HRMS: calcd for (M+H$^+$) C$_{16}$H$_{19}$N$_6$O$_3$: 343.1518. Found: 343.1529.

EXAMPLE 9

2-{[1-(2-chlorophenyl)-1H-pyrazolo[3,4-d]pyrimidin-4-yl]oxy}-N-(5-methylpyridin-2-yl)-4-(methylsulfonyl)butanamide

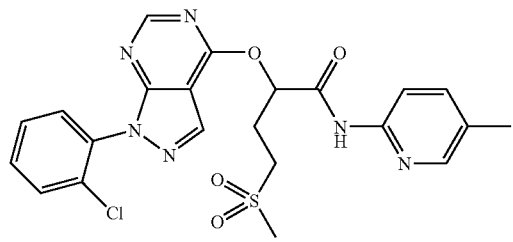

Method 1 from Intermediates A1 and B1

$^1$H NMR (500 MHz, CDCl$_3$) δ 9.01 (br s, 1H), 8.58 (s, 1H), 8.39 (s, 1H), 8.07 (m, 2H), 7.60 (d, 1H), 7.49 (m, 4H), 6.07 (t, 1H), 3.36 (m, 2H), 2.96 (s, 3H), 2.72 (m, 2H), 2.27 (s, 3H), HRMS: calcd for (M+H$^+$) C$_{22}$H$_{22}$$^{35}$ClN$_6$O$_4$S: 501.1111. Found: 501.1070.

EXAMPLE 10

2-{[1-(2-methoxyphenyl)-1H-pyrazolo[3,4-d]pyrimidin-4-yl]oxy}-N-(5-methylpyridin-2-yl)-4-(methylsulfonyl)butanamide

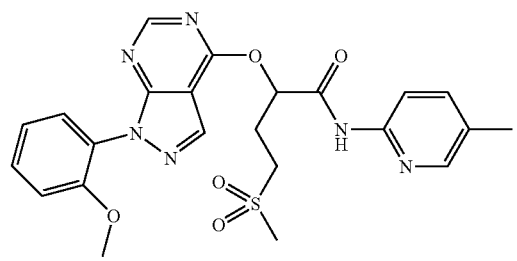

Method 1 from Intermediates A1 and B3

$^1$H NMR (300 MHz, CDCl$_3$) δ 9.00 (br s, 1H), 8.55 (s, 1H), 8.35 (s, 1H), 8.07 (m, 2H), 7.47 (m, 3H), 7.11 (m, 2H), 6.08 (t, 1H), 3.78 (s, 3H), 3.35 (m, 2H), 2.97 (s, 3H), 2.72 (m, 2H), 2.26 (s, 3H), HRMS: calcd for (M+H) C$_{23}$H$_{25}$N$_6$O$_5$S: 497.1607. Found: 497.1630.

EXAMPLE 11

(R)-2-{[1-(2-methoxyphenyl)-1H-pyrazolo[3,4-d]pyrimidin-4-yl]oxy}-N-(5-methylpyridin-2-yl)-4-(methylsulfonyl)butanamide

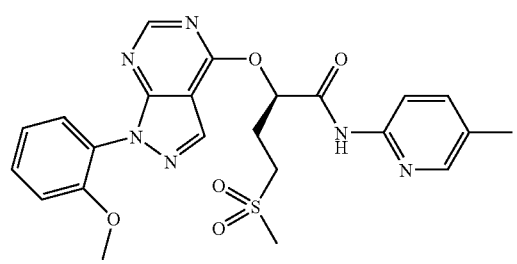

AND EXAMPLE 12

(S)-2-{[1-(2-methoxyphenyl)-1H-pyrazolo[3,4-d]
pyrimidin-4-yl]oxy}-N-(5-methylpyridin-2-yl)-4-
(methylsulfonyl)butanamide

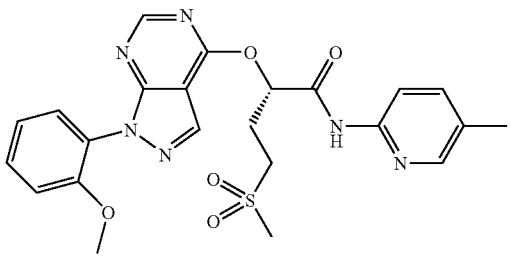

The enantiomers of racemic 2-{[1-(2-methoxyphenyl)-1H-pyrazolo[3,4-d]pyrimidin-4-yl]oxy}-N-(5-methylpyridin-2-yl)-4-(methylsulfonyl)butanamide (48.5 mg) were separated by preparative HPLC: Column Chiralcel OD (250×20 mm, 10 µm); Mobile phase heptane/EtOH:30/70; Flow 20 ml/min; UV 240 nm; Ambient temperature. This gave (R)-2-{[1-(2-methoxyphenyl)-1H-pyrazolo[3,4-d]pyrimidin-4-yl]oxy}-N-(5-methylpyridin-2-yl)-4-(methylsulfonyl)butanamide (15.0 mg, >99% ee), $^1$H NMR (300 MHz, CDCl$_3$) δ 8.79 (br s, 1H), 8.57 (s, 1H), 8.37 (s, 1H), 8.09 (m, 2H), 7.49 (m, 3H), 7.13 (m, 2H), 6.10 (t, 1H), 3.79 (s, 3H), 3.34 (m, 2H), 2.98 (s, 3H), 2.74 (m, 2H), 2.30 (s, 3H), and (S)-2-{[1-(2-methoxyphenyl)-1H-pyrazolo[3,4-d]pyrimidin-4-yl]oxy}-N-(5-methylpyridin-2-yl)-4-(methylsulfonyl)butanamide (20.0 mg, >99% ee), $^1$H NMR (300 MHz, CDCl$_3$) δ 8.77 (br s, 1H), 8.58 (s, 1H), 8.38 (s, 1H), 8.10 (m, 2H), 7.48 (m, 3H), 7.13 (m, 2H), 6.11 (t, 1H), 3.79 (s, 3H), 3.34 (m, 2H), 2.98 (s, 3H), 2.73 (m, 2H), 2.30 (s, 3H).

EXAMPLE 13

4-methoxy-2-{[1-(3-methoxyphenyl)-1H-pyrazolo[3,4-d]pyrimidin-4-yl]oxy}-N-(5-methylpyridin-2-yl)butanamide

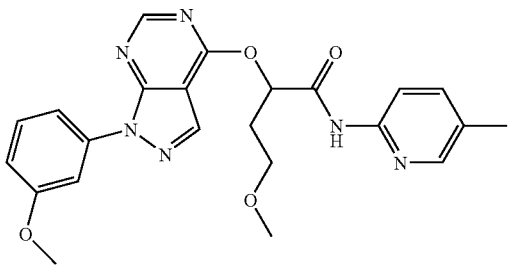

Method 1 from Intermediates A12 and B5

$^1$H NMR (500 MHz, CDCl$_3$) δ 8.72 (br s, 1H), 8.64 (s, 1H), 8.32 (s, 1H), 8.12 (d, 1H), 8.08 (s, 1H), 7.81 (d, 1H), 7.79 (m, 1H), 7.51 (d, 1H), 7.43 (t, 1H), 6.91 (d, 1H), 5.96 (t, 1H), 3.90 (s, 3H), 3.63 (t, 2H), 3.33 (s, 3H), 2.44 (m, 2H), 2.28 (s, 3H). HRMS: calcd for (M+H$^+$) C$_{23}$H$_{25}$N$_6$O$_4$: 449.1937. Found: 449.1936.

EXAMPLE 14

(R)-4-methoxy-2-{[1-(3-methoxyphenyl)-1H-pyrazolo[3,4-d]pyrimidin-4-yl]oxy}-N-(5-methylpyridin-2-yl)butanamide

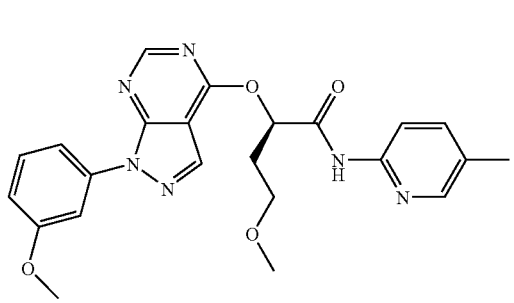

AND EXAMPLE 15

(S)-4-methoxy-2-{[1-(3-methoxyphenyl)-1H-pyrazolo[3,4-d]pyrimidin-4-yl]oxy}-N-(5-methylpyridin-2-yl)butanamide

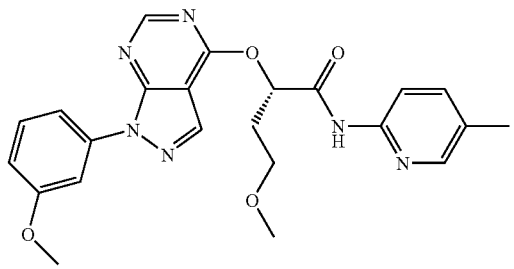

The enantiomers of racemic 4-methoxy-2-{[1-(3-methoxyphenyl)-1H-pyrazolo[3,4-d]pyrimidin-4-yl]oxy}-N-(5-methylpyridin-2-yl)butanamide (140.0 mg) were separated by preparative HPLC: Column Chiralpak IA (250×20 mm, 5 µm); Mobile phase heptane/EtOH:30/70; Flow 12 ml/min; UV 254 nm; Temperature 40° C. This gave (R)-4-methoxy-2-{[1-(3-methoxyphenyl)-1H-pyrazolo[3,4-d]pyrimidin-4-yl]oxy}-N-(5-methylpyridin-2-yl)butanamide (63.4 mg, >98% ee), $^1$H NMR (300 MHz, CDCl$_3$) δ 8.90 (br s, 1H), 8.63 (s, 1H), 8.31 (s, 1H), 8.11 (m, 2H), 7.81 (m, 2H), 7.51 (d, 1H), 7.42 (t, 1H), 6.90 (d, 1H), 5.95 (t, 1H), 3.89 (s, 3H), 3.63 (t, 2H), 3.32 (s, 3H), 2.43 (m, 2H), 2.27 (s, 3H), and (S)-4-methoxy-2-{[1-(3-methoxyphenyl)-1H-pyrazolo[3,4-d]pyrimidin-4-yl]oxy}-N-(5-methylpyridin-2-yl)butanamide (62.7 mg, 99.7% ee), $^1$H NMR (300 MHz, CDCl$_3$) δ 8.92 (br s, 1H), 8.63 (s, 1H), 8.31 (s, 1H), 8.12 (m, 2H), 7.79 (m, 2H), 7.52 (d, 1H), 7.42 (t, 1H), 6.90 (d, 1H), 5.95 (t, 1H), 3.89 (s, 3H), 3.63 (t, 2H), 3.32 (s, 3H), 2.43 (m, 2H), 2.27 (s, 3H).

EXAMPLE 16

4-methoxy-2-{[1-(2-methylphenyl)-1H-pyrazolo[3,4-d]pyrimidin-4-yl]oxy}-N-(5-methylpyridin-2-yl)butanamide

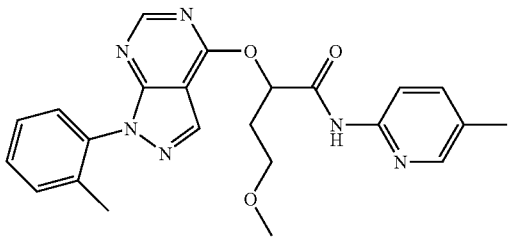

Method 1 from Intermediates A12 and B2

$^1$H NMR (500 MHz, CDCl$_3$) δ 8.90 (br s, 1H), 8.56 (s, 1H), 8.36 (s, 1H), 8.15 (d, 1H), 8.12 (s, 1H), 7.53 (d, 1H), 7.39 (m, 4H), 5.96 (t, 1H), 3.66 (m, 2H), 3.36 (s, 3H), 2.45 (m, 2H), 2.29 (s, 3H), 2.17 (s, 3H), HRMS: calcd for (M+H$^+$) C$_{23}$H$_{25}$N$_6$O$_3$: 433.1988. Found: 433.1984.

EXAMPLE 17

(S)-4-methoxy-2-{[1-(2-methylphenyl)-1H-pyrazolo[3,4-d]pyrimidin-4-yl]oxy}-N-(5-methylpyridin-2-yl)butanamide

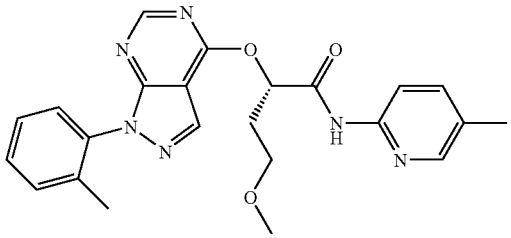

AND EXAMPLE 18

(R)-4-methoxy-2-{[1-(2-methylphenyl)-1H-pyrazolo[3,4-d]pyrimidin-4-yl]oxy}-N-(5-methylpyridin-2-yl)butanamide

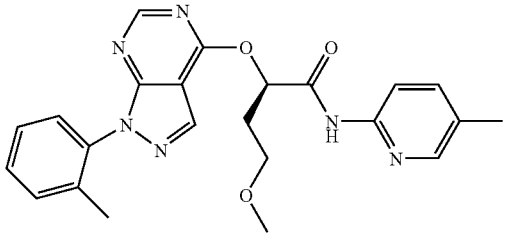

The enantiomers of racemic 4-methoxy-2-{[1-(2-methylphenyl)-1H-pyrazolo[3,4-d]pyrimidin-4-yl]oxy}-N-(5-methylpyridin-2-yl)butanamide (122.0 mg) were separated by preparative HPLC: Column Chiralcel OD (250×20 mm, 5 μm); Mobile phase MeOH; Flow 15 ml/min; UV 230 nm; Ambient temperature. This gave (S)-4-methoxy-2-{[1-(2-methylphenyl)-1H-pyrazolo[3,4-d]pyrimidin-4-yl]oxy}-N-(5-methylpyridin-2-yl)butanamide (49.1 mg, >99% ee), $^1$H NMR (300 MHz, CDCl$_3$) δ 8.67 (br s, 1H), 8.57 (s, 1H), 8.36 (s, 1H), 8.12 (m, 2H), 7.53 (d, 1H), 7.39 (m, 4H), 5.96 (t, 1H), 3.65 (t, 2H), 3.34 (s, 3H), 2.46 (m, 2H), 2.29 (s, 3H), 2.16 (s, 3H), and (R)-4-methoxy-2-{[1-(2-methylphenyl)-1H-pyrazolo[3,4-d]pyrimidin-4-yl]oxy}-N-(5-methylpyridin-2-yl)butanamide (53.5 mg, >99% ee), $^1$H NMR (300 MHz, CDCl$_3$) δ 8.66 (br s, 1H), 8.56 (s, 1H), 8.35 (s, 1H), 8.13 (d, 1H), 8.09 (d, 1H), 7.52 (dd, 1H), 7.38 (m, 4H), 5.95 (t, 1H), 3.65 (t, 2H), 3.34 (s, 3H), 2.44 (m, 2H), 2.29 (s, 3H), 2.16 (s, 3H).

EXAMPLE 19

2-{[1-(2-Chlorophenyl)-1H-pyrazolo[3,4-d]pyrimidin-4-yl]oxy}-4-methoxy-N-(5-methylpyridin-2-yl)butanamide

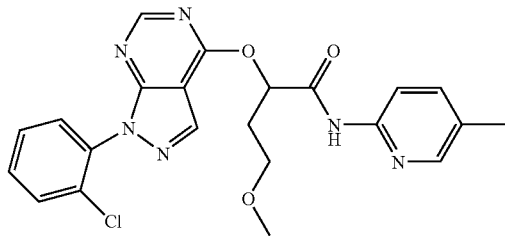

Method 1 from Intermediates A12 and B1

$^1$H NMR (300 MHz, CDCl$_3$) δ 8.70 (br s, 1H), 8.58 (s, 1H), 8.39 (s, 1H), 8.11 (dd, 2H), 7.61 (m, 1H), 7.49 (m, 4H), 5.95 (t, 1H), 3.64 (t, 2H), 3.34 (s, 3H), 2.44 (m, 2H), 2.29 (s, 3H), HRMS: calcd for (M+H$^+$) C$_{22}$H$_{22}$$^{35}$ClN$_6$O$_3$: 453.1442. Found: 453.1452.

EXAMPLE 20

(R)-2-{[1-(2-Chlorophenyl)-1H-pyrazolo[3,4-d]pyrimidin-4-yl]oxy}-4-methoxy-N-(5-methylpyridin-2-yl)butanamide

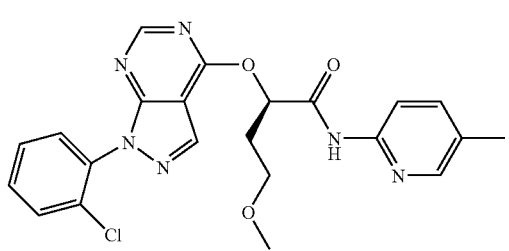

AND EXAMPLE 21

(S)-2-{[1-(2-chlorophenyl)-1H-pyrazolo[3,4-d]pyrimidin-4-yl]oxy}-4-methoxy-N-(5-methylpyridin-2-yl)butanamide

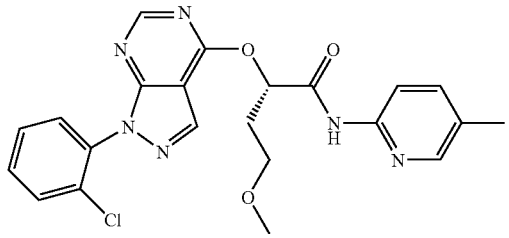

The enantiomers of racemic 2-{[1-(2-chlorophenyl)-1H-pyrazolo[3,4-d]pyrimidin-4-yl]oxy}-4-methoxy-N-(5-methylpyridin-2-yl)butanamide (200 mg) were separated by preparative HPLC: Column Chiralcel OJ (250×20 mm, 5 μm); Mobile phase heptane/EtOH:30/70; Flow 19 ml/min; UV 285 nm; Temperature 20° C. This gave (R)-2-{[1-(2-chlorophenyl)-1H-pyrazolo[3,4-d]pyrimidin-4-yl]oxy}-4-methoxy-N-(5-methylpyridin-2-yl)butanamide (89 mg, >99% ee), $^1$H NMR (300 MHz, CDCl$_3$) δ 8.76 (br s, 1H), 8.58 (s, 1H), 8.38 (s, 1H), 8.11 (m, 2H), 7.61 (m, 1H), 7.48 (m, 4H), 5.94 (t, 1H), 3.64 (t, 2H), 3.33 (s, 3H), 2.44 (m, 2H), 2.28 (s, 3H), and (S)-2-{[1-(2-chlorophenyl)-1H-pyrazolo[3,4-d]pyrimidin-4-yl]oxy}-4-methoxy-N-(5-methylpyridin-2-yl)butanamide (93 mg, >99% ee), $^1$H NMR (300 MHz, CDCl$_3$) δ 8.67 (br s, 1H), 8.58 (s, 1H), 8.39 (s, 1H), 8.12 (m, 2H), 7.61 (m, 1H), 7.49 (m, 4H), 5.95 (t, 1H), 3.64 (t, 2H), 3.34 (s, 3H), 2.44 (m, 2H), 2.29 (s, 3H).

EXAMPLE 22

4-Methoxy-2-{[1-(2-methoxyphenyl)-1H-pyrazolo[3,4-d]pyrimidin-4-yl]oxy}-N-(5-methylpyridin-2-yl)butanamide

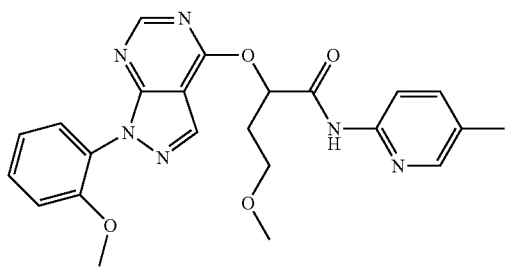

Method 1 from Intermediates A12 and B3

$^1$H NMR (300 MHz, CDCl$_3$) δ 8.67 (br s, 1H), 8.56 (s, 1H), 8.37 (s, 1H), 8.14 (d, 1H), 8.09 (m, 1H), 7.51 (t, 2H), 7.44 (m, 1H), 7.12 (m, 2H), 5.96 (m, 1H), 3.79 (s, 3H), 3.64 (t, 2H), 3.34 (s, 3H), 2.44 (d, 2H), 2.29 (s, 3H), HRMS: calcd for (M+H$^+$) C$_{23}$H$_{25}$N$_6$O$_4$: 449.1937. Found: 449.1951.

EXAMPLE 23

(R)-4-Methoxy-2-{[1-(2-methoxyphenyl)-1H-pyrazolo[3,4-d]pyrimidin-4-yl]oxy}-N-(5-methylpyridin-2-yl)butanamide

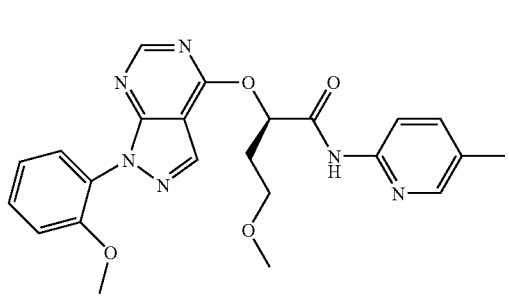

AND EXAMPLE 24

(S)-4-methoxy-2-{[1-(2-methoxyphenyl)-1H-pyrazolo[3,4-d]pyrimidin-4-yl]oxy}-N-(5-methylpyridin-2-yl)butanamide

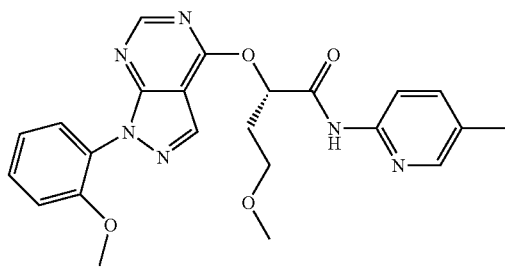

The enantiomers of racemic 4-methoxy-2-{[1-(2-methoxyphenyl)-1H-pyrazolo[3,4-d]pyrimidin-4-yl]oxy}-N-(5-methylpyridin-2-yl)butanamide (100 mg) were separated by preparative HPLC: Column Chiralpak AS (250×20 mm, 5 μm); Mobile phase heptane/IPA:60/40; Flow 13 ml/min; UV 275 nm; Temperature 40° C. This gave (R)-4-methoxy-2-{[1-(2-methoxyphenyl)-1H-pyrazolo[3,4-d]pyrimidin-4-yl]oxy}-N-(5-methylpyridin-2-yl)butanamide (54.4 mg, >99% ee), $^1$H NMR (300 MHz, CDCl$_3$) δ 8.66 (br s, 1H), 8.56 (s, 1H), 8.36 (s, 1H), 8.12 (m, 2H), 7.46 (m, 3H), 7.12 (m, 2H), 5.95 (t, 1H), 3.79 (s, 3H), 3.64 (t, 2H), 3.34 (s, 3H), 2.45 (m, 2H), 2.29 (s, 3H), and (S)-4-methoxy-2-{[1-(2-methoxyphenyl)-1H-pyrazolo[3,4-d]pyrimidin-4-yl]oxy}-N-(5-methylpyridin-2-yl)butanamide (53.7 mg, >99% ee), $^1$H NMR (300 MHz, CDCl$_3$) δ 8.65 (br s, 1H), 8.56 (s, 1H), 8.36 (s, 1H), 8.12 (m, 2H), 7.47 (m, 3H), 7.12 (m, 2H), 5.95 (t, 1H), 3.79 (s, 3H), 3.64 (t, 2H), 3.34 (s, 3H), 2.44 (d, 2H), 2.29 (s, 3H).

EXAMPLE 25

2-{[1-(2,4-Difluorophenyl)-1H-pyrazolo[3,4-d]pyrimidin-4-yl]oxy}-4-methoxy-N-(5-methylpyridin-2-yl)butanamide

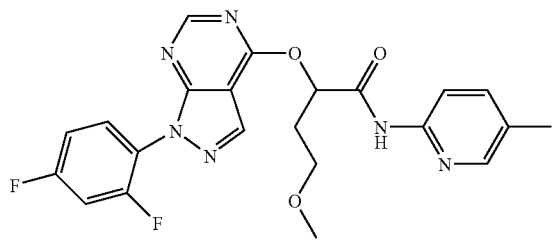

Method 1 from Intermediates A12 and B7

$^1$H NMR (400 MHz, CDCl$_3$) δ 9.01 (br s, 1H), 8.55 (s, 1H), 8.35 (s, 1H), 8.09 (d, 1H), 8.04 (m, 1H), 7.56 (m, 1H), 7.49 (dd, 1H), 7.03 (m, 2H), 5.91 (t, 1H), 3.60 (t, 2H), 3.29 (s, 3H), 2.44 (s 3H), 2.40 (m, 2H), HRMS: calcd for (M+H$^+$) C$_{22}$H$_{21}$F$_2$N$_6$O$_3$: 455.1643. Found: 455.1657.

EXAMPLE 26

(R)-2-{[1-(2,4-Difluorophenyl)-1H-pyrazolo[3,4-d]pyrimidin-4-yl]oxy}-4-methoxy-N-(5-methylpyridin-2-yl)butanamide

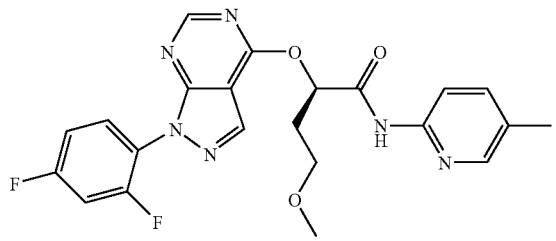

AND EXAMPLE 27

(S)-2-{[1-(2,4-difluorophenyl)-1H-pyrazolo[3,4-d]pyrimidin-4-yl]oxy}-4-methoxy-N-(5-methylpyridin-2-yl)butanamide

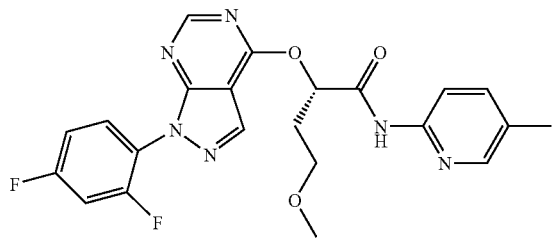

The enantiomers of racemic 2-{[1-(2,4-difluorophenyl)-1H-pyrazolo[3,4-d]pyrimidin-4-yl]oxy}-4-methoxy-N-(5-methylpyridin-2-yl)butanamide (160 mg) were separated by preparative HPLC: Column Chiralpak AS (250×20 mm, 5 µm); Mobile phase heptane/EtOH:75/25; Flow 18 ml/min; UV 230 nm; Temperature 22° C. This gave (R)-2-{[1-(2,4-difluorophenyl)-1H-pyrazolo[3,4-d]pyrimidin-4-yl]oxy}-4-methoxy-N-(5-methylpyridin-2-yl)butanamide (37.6 mg, >99% ee), $^1$H NMR (400 MHz, CDCl$_3$) δ 9.17 (br s, 1H), 8.57 (s, 1H), 8.42 (s, 1H), 8.18 (d, 1H), 8.05 (s, 1H), 7.59 (m, 2H), 7.05 (m, 2H), 5.94 (t, 1H), 3.62 (t, 1H), 3.31 (s, 3H), 2.42 (m, 2H), 2.29 (s, 3H), and (S)-2-{[1-(2,4-difluorophenyl)-1H-pyrazolo[3,4-d]pyrimidin-4-yl]oxy}-4-methoxy-N-(5-methylpyridin-2-yl)butanamide (53.7 mg, >99% ee), $^1$H NMR (400 MHz, CDCl$_3$) δ 9.38 (br s, 1H), 8.56 (s, 1H), 8.44 (s, 1H), 8.22 (d, 1H), 8.04 (s, 1H), 7.59 (m, 2H), 7.05 (m, 2H), 5.94 (t, 1H), 3.62 (t, 1H), 3.31 (s, 3H), 2.42 (m, 2H), 2.30 (s, 3H).

EXAMPLE 28

4-Methoxy-N-(5-methylpyridin-2-yl)-2-({1-[2-(trifluoromethyl)phenyl]-1H-pyrazolo[3,4-d]pyrimidin-4-yl}oxy)butanamide

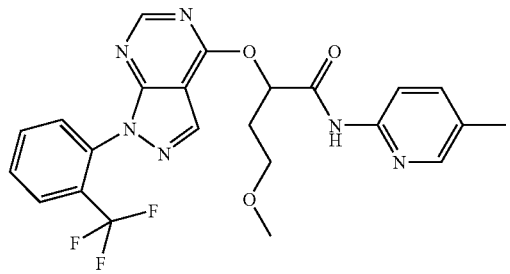

Method 1 from Intermediates A12 and B4

$^1$H NMR (400 MHz, CDCl$_3$) δ 9.20 (br s, 1H), 8.54 (s, 1H), 8.35 (s, 1H), 8.12 (m, 2H), 7.88 (d, 1H), 7.73 (m, 1H), 7.66 (m, 1H), 7.52 (m, 2H), 5.94 (t, 1H), 3.64 (m, 2H), 3.31 (s, 3H), 2.43 (m, 2H), 2.26 (s, 3H), HRMS: calcd for (M+H$^+$) C$_{23}$H$_{22}$F$_3$N$_6$O$_3$: 487.1705. Found: 487.1708.

EXAMPLE 29

(S)-4-Methoxy-N-(5-methylpyridin-2-yl)-2-({1-[2-(trifluoromethyl)phenyl]-1H-pyrazolo[3,4-d]pyrimidin-4-yl}oxy)butanamide

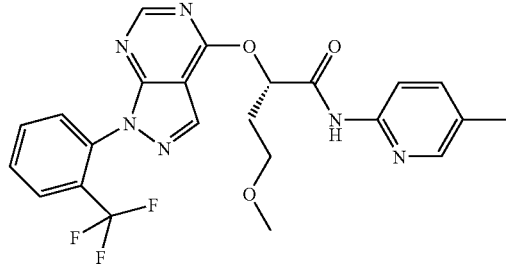

AND EXAMPLE 30

(R)-4-methoxy-N-(5-methylpyridin-2-yl)-2-({1-[2-(trifluoromethyl)phenyl]-1H-pyrazolo[3,4-d]pyrimidin-4-yl}oxy)butanamide

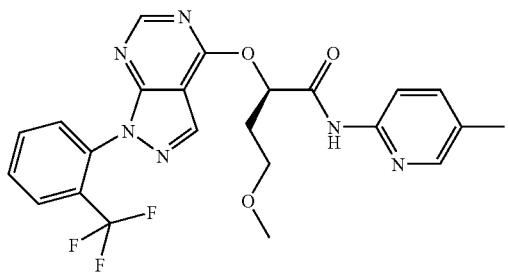

The enantiomers of racemic 4-methoxy-N-(5-methylpyridin-2-yl)-2-({1-[2-(trifluoromethyl)phenyl]-1H-pyrazolo[3,4-d]pyrimidin-4-yl}oxy)butanamide (178 mg) were separated by preparative HPLC: Column Chiralpak AD (250×20 mm, 5 μm); Mobile phase heptane/EtOH:30/70; Flow 18 ml/min; UV 254 nm; Temperature 20° C. This gave (S)-4-methoxy-N-(5-methylpyridin-2-yl)-2-({1-[2-(trifluoromethyl)phenyl]-1H-pyrazolo[3,4-d]pyrimidin-4-yl}oxy)butanamide (61.6 mg, >98% ee), $^1$H NMR (500 MHz, CDCl$_3$) δ 8.65 (br s, 1H), 8.58 (s, 1H), 8.39 (s, 1H), 8.14 (m, 2H), 7.92 (d, 1H), 7.78 (t, 1H), 7.71 (t, 1H), 7.55 (t, 2H), 5.98 (m, 1H), 3.67 (t, 2H), 3.36 (s, 3H), 2.47 (m, 2H), 2.31 (s, 3H), and (R)-4-methoxy-N-(5-methylpyridin-2-yl)-2-({1-[2-(trifluoromethyl)phenyl]-1H-pyrazolo[3,4-d]pyrimidin-4-yl}oxy)butanamide (52.0 mg, >99% ee), $^1$H NMR (500 MHz, CDCl$_3$) δ 8.66 (br s, 1H), 8.58 (s, 1H), 8.39 (s, 1H), 8.14 (m, 2H), 7.92 (d, 1H), 7.78 (t, 1H), 7.71 (t, 1H), 7.55 (t, 2H), 5.98 (t, 1H), 3.67 (t, 2H), 3.36 (s, 3H), 2.47 (m, 2H), 2.31 (s, 3H).

EXAMPLE 31

4-Methoxy-2-{[1-(3-methylphenyl)-1H-pyrazolo[3,4-d]pyrimidin-4-yl]oxy}-N-(5-methylpyridin-2-yl)butanamide

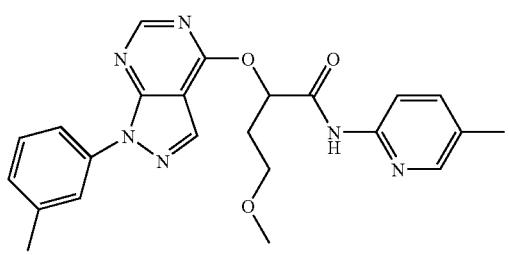

Method 1 from Intermediates A12 and B10

$^1$H NMR (400 MHz, CDCl$_3$) δ 9.19 (br s, 1H), 8.56 (s, 1H), 8.27 (s, 1H), 8.08 (d, 1H), 8.03 (d, 1H), 7.90 (m, 2H), 7.45 (dd, 1H), 7.35 (t, 1H), 7.10 (d, 1H), 5.90 (t, 1H), 3.59 (t, 2H), 3.26 (s, 3H), 2.40 (m, 5H), 2.21 (s, 3H), HRMS: calcd for (M+H$^+$) C$_{23}$H$_{25}$N$_6$O$_3$: 433.1988. Found: 433.2008.

EXAMPLE 32

(R)-4-Methoxy-2-{[1-(3-methylphenyl)-1H-pyrazolo[3,4-d]pyrimidin-4-yl]oxy}-N-(5-methylpyridin-2-yl)butanamide

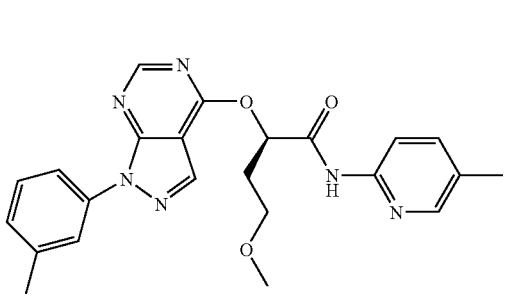

AND EXAMPLE 33

(S)-4-methoxy-2-{[1-(3-methylphenyl)-1H-pyrazolo[3,4-d]pyrimidin-4-yl]oxy}-N-(5-methylpyridin-2-yl)butanamide

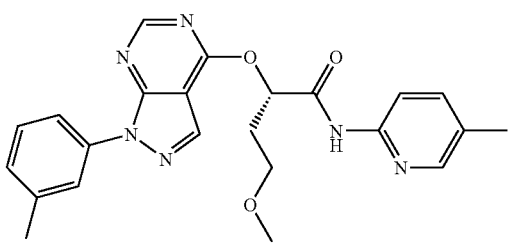

The enantiomers of racemic 4-methoxy-2-{[1-(3-methylphenyl)-1H-pyrazolo[3,4-d]pyrimidin-4-yl]oxy}-N-(5-methylpyridin-2-yl)butanamide (159 mg) were separated by preparative HPLC: Column Chiralpak IA (250×20 mm, 5 μm); Mobile phase heptane/IPA:30/70; Flow 14 ml/min; UV 265 nm; Temperature 40° C. This gave (R)-4-methoxy-2-{[1-(3-methylphenyl)-1H-pyrazolo[3,4-d]pyrimidin-4-yl]oxy}-N-(5-methylpyridin-2-yl)butanamide (59 mg, >99% ee), $^1$H NMR (500 MHz, CDCl$_3$) δ 8.66 (s, 1H), 8.64 (br s, 1H), 8.35 (s, 1H), 8.14 (d, 1H), 8.10 (s, 1H), 7.98 (d, 2H), 7.54 (dd, 1H), 7.44 (t, 1H), 7.20 (d, 1H), 5.99 (dd, 1H), 3.65 (t, 2H), 3.35 (s, 3H), 2.49 (d, 3H), 2.48 (s, 2H), 2.31 (s, 3H), and (S)-4-methoxy-2-{[1-(3-methylphenyl)-1H-pyrazolo[3,4-d]pyrimidin-4-yl]oxy}-N-(5-methylpyridin-2-yl)butanamide (54 mg, >99% ee), $^1$H NMR (500 MHz, CDCl$_3$) δ 8.66 (s, 1H), 8.65 (br s, 1H), 8.35 (s, 1H), 8.14 (d, 1H), 8.10 (s, 1H), 7.98 (d, 2H), 7.54 (m, 1H), 7.44 (t, 1H), 7.20 (d, 1H), 5.99 (dd, 1H), 3.65 (t, 2H), 3.35 (s, 3H), 2.49 (s, 3H), 2.45 (dd, 2H), 2.30 (s, 3H).

EXAMPLE 34

4-Methoxy-N-(5-methylpyridin-2-yl)-2-[(1-pyridin-2-yl-1H-pyrazolo[3,4-d]pyrimidin-4-yl)oxy]butanamide

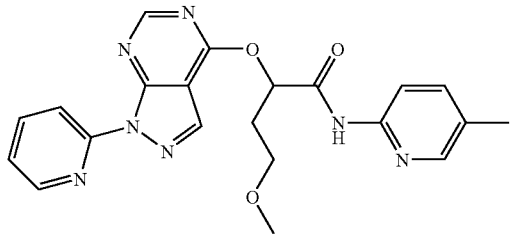

Method 1 from Intermediates A12 and B8

$^1$H NMR (400 MHz, CDCl$_3$) δ 9.34 (br s, 1H), 8.62 (m, 2H), 8.18 (s, 1H), 8.09 (m, 1H), 7.99 (s, 1H), 7.83 (m, 1H), 7.45 (d, 1H), 7.22 (m, 1H), 5.87 (t, 1H), 3.57 (t, 2H), 3.23 (s, 3H), 2.36 (m, 2H), 2.19 (s, 3H), HRMS: calcd for (M+H$^+$) C$_{21}$H$_{22}$N$_7$O$_3$: 420.1784. Found: 420.1797.

EXAMPLE 35

4-Methoxy-2-{[1-(2-methoxyphenyl)-1H-pyrazolo[3,4-d]pyrimidin-4-yl]oxy}-N-(4-methyl-1,3-thiazol-2-yl)butanamide

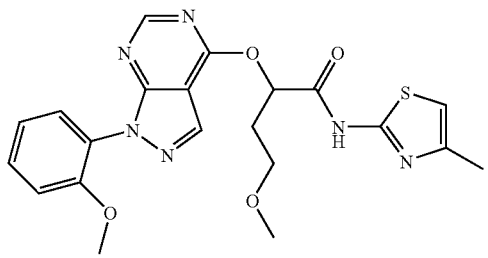

Method 1 from Intermediates A13 and B3

$^1$H NMR (300 MHz, CDCl$_3$) δ 8.77 (br s, 1H), 8.52 (s, 1H), 8.34 (s, 1H), 7.46 (m, 2H), 7.11 (m, 2H), 6.52 (s, 1H), 6.01 (t, 1H), 3.77 (d, 3H), 3.62 (m, 2H), 3.32 (d, 3H), 2.42 (m, 2H), 2.31 (s, 3H), HRMS: calcd for (M+H$^-$) C$_{22}$H$_{23}$N$_6$O$_4$S: 455.1501. Found: 455.1490.

EXAMPLE 36

(R)-4-Methoxy-2-{[1-(2-methoxyphenyl)-1H-pyrazolo[3,4-d]pyrimidin-4-yl]oxy}-N-(4-methyl-1,3-thiazol-2-yl)butanamide

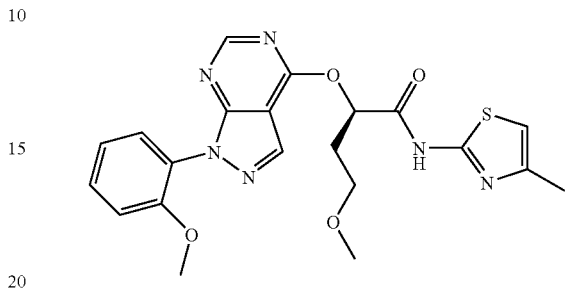

AND EXAMPLE 37

(S)-4-methoxy-2-{[1-(2-methoxyphenyl)-1H-pyrazolo[3,4-d]pyrimidin-4-yl]oxy}-N-(4-methyl-1,3-thiazol-2-yl)butanamide

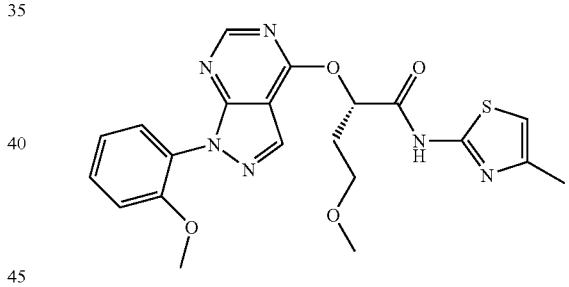

The enantiomers of racemic 4-methoxy-2-{[1-(2-methoxyphenyl)-1H-pyrazolo[3,4-d]pyrimidin-4-yl]oxy}-N-(4-methyl-1,3-thiazol-2-yl)butanamide (90 mg) were separated by preparative HPLC: Column Chiralpak AD (250×20 mm, 5 µm); Mobile phase heptane/ethanol:50/50; Flow 15 ml/min; UV 270 nm; Temperature 20° C. This gave (R)-4-methoxy-2-{[1-(2-methoxyphenyl)-1H-pyrazolo[3,4-d]pyrimidin-4-yl]oxy}-N-(4-methyl-1,3-thiazol-2-yl)butanamide (24 mg, >99% ee), $^1$H NMR (500 MHz, CDCl$_3$) δ 9.80 (br s, 1H), 8.58 (s, 1H), 8.35 (s, 1H), 7.51 (m, 1H), 7.46 (m, 1H), 7.14 (m, 2H), 6.57 (d, 1H), 6.06 (t, 1H), 3.81 (s, 3H), 3.65 (t, 2H), 3.34 (s, 3H), 2.46 (m, 2H), 2.35 (d, 3H), and (S)-4-methoxy-2-{[1-(2-methoxyphenyl)-1H-pyrazolo[3,4-d]pyrimidin-4-yl]oxy}-N-(4-methyl-1,3-thiazol-2-yl)butanamide (26.1 mg, >99% ee), $^1$H NMR (500 MHz, CDCl$_3$) δ 9.87 (br s, 1H), 8.59 (s, 1H), 8.35 (s, 1H), 7.51 (m, 1H), 7.46 (m, 1H), 7.14 (m, 2H), 6.57 (d, 1H), 6.05 (t, 1H), 3.81 (s, 3H), 3.64 (t, 2H), 3.34 (s, 3H), 2.45 (m, 2H), 2.35 (d, 3H).

EXAMPLE 38

2-{[1-(2-chlorophenyl)-1H-pyrazolo[3,4-d]pyrimidin-4-yl]oxy}-N-(5-methylpyridin-2-yl)hexanamide

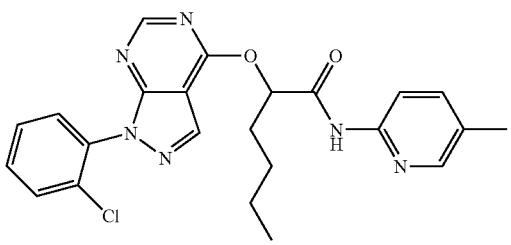

Method 1 from Intermediates A3 and B1
$^1$H NMR (300 MHz, CDCl$_3$) δ 8.59 (s, 1H), 8.47 (br s, 1H), 8.40 (s, 1H), 8.15 (d, 1H), 8.08 (s, 1H), 7.62 (m, 1H), 7.50 (m, 4H), 5.85 (t, 1H), 2.29 (s, 3H), 2.17 (m, 2H), 1.54 (m, 2H), 1.42 (m, 2H), 0.94 (t, 3H), HRMS: calcd for (M+H$^+$) C$_{23}$H$_{24}$$^{35}$ClN$_6$O$_2$: 451.1649. Found: 451.1656.

EXAMPLE 39

2-[(1-methyl-1H-pyrazolo[3,4-d]pyrimidin-4-yl)oxy]-N-(5-methylpyridin-2-yl)hexanamide

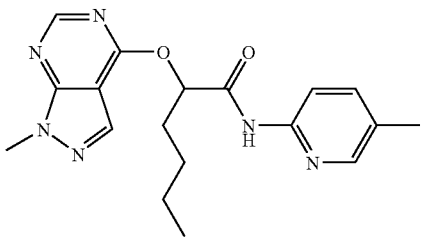

Method 1 from Intermediates A3 and B11
$^1$H NMR (500 MHz, CDCl$_3$) δ 8.60 (br s, 1H), 8.56 (s, 1H), 8.15 (m, 2H), 8.07 (s, 1H), 7.53 (d, 1H), 5.84 (t, 1H), 4.13 (s, 3H), 2.29 (s, 3H), 2.15 (m, 2H), 1.52 (m, 2H), 1.39 (m, 2H), 0.92 (t, 3H), HRMS: calcd for (M+H$^+$) C$_{18}$H$_{23}$N$_6$O$_2$: 355.1882. Found: 355.1892.

EXAMPLE 40

2-{[1-(2-chlorophenyl)-1H-pyrazolo[3,4-d]pyrimidin-4-yl]oxy}-N-(5-methylpyrazin-2-yl)hexanamide

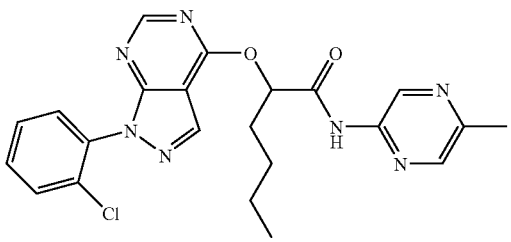

Method 1 from Intermediates A4 and B1
$^1$H NMR (300 MHz, CDCl$_3$) δ 9.46 (s, 1H), 8.59 (s, 1H), 8.48 (br s, 1H), 8.40 (s, 1H), 8.10 (s, 1H), 7.62 (m, 1H), 7.50 (m, 3H), 5.89 (t, 1H), 2.53 (s, 3H), 2.19 (m, 2H), 1.55 (m, 2H), 1.44 (m, 2H), 0.94 (t, 3H), HRMS: calcd for (M+H$^+$) C$_{22}$H$_{23}$$^{35}$ClN$_7$O$_2$: 452.1601. Found: 452.1576.

EXAMPLE 41

2-{[1-(2-chlorophenyl)-1H-pyrazolo[3,4-d]pyrimidin-4-yl]thio}-N-(4-methyl-1,3-thiazol-2-yl)hexanamide

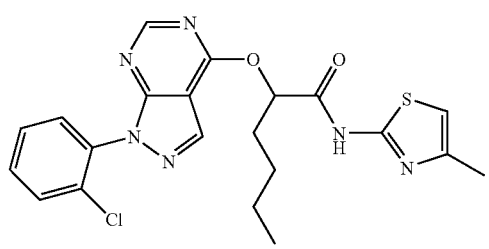

Method 1 from Intermediates A5 and B1
$^1$H NMR (300 MHz, CDCl$_3$) δ 9.44 (br s, 1H), 8.58 (s, 1H), 8.38 (s, 1H), 7.62 (m, 1H), 7.51 (m, 3H), 6.56 (s, 1H), 5.95 (t, 1H), 2.33 (s, 3H), 2.17 (m, 2H), 1.53 (m, 2H), 1.41 (m, 2H), 0.93 (t, 3H), HRMS: calcd for (M+H$^+$) C$_{21}$H$_{22}$$^{35}$ClN$_6$O$_2$S: 457.1213. Found: 457.1238.

EXAMPLE 42

2-{[1-(2-Methoxyphenyl)-1H-pyrazolo[3,4-d]pyrimidin-4-yl]oxy}-N-(5-methylpyridin-2-yl)butanamide

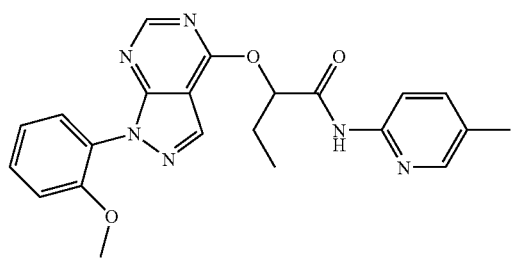

Method 1 from Intermediates A9 and B3
$^1$H NMR (300 MHz, CDCl$_3$) δ 8.72 (br s, 1H), 8.56 (s, 1H), 8.39 (s, 1H), 8.17 (d, 1H), 8.07 (s, 1H), 7.49 (m, 3H), 7.12 (m, 2H), 5.81 (t, 1H), 3.79 (s, 3H), 2.29 (s, 3H), 2.21 (m, 2H), 1.15 (t, 3H), HRMS: calcd for (M+H$^+$) C$_{22}$H$_{23}$N$_6$O$_3$: 419.1831. Found: 419.1810.

EXAMPLE 43

(2R)-2-{[1-(2-Methoxyphenyl)-1H-pyrazolo[3,4-d]pyrimidin-4-yl]oxy}-N-(5-methylpyridin-2-yl)butanamide

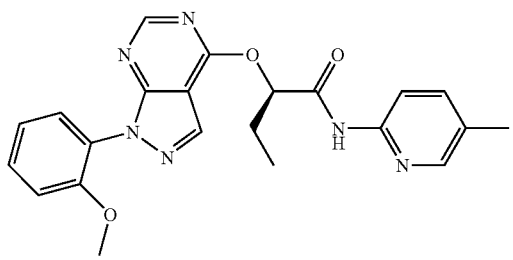

Method 1 from Intermediates A8 and B3

$[\alpha]^{20}_D$ −31.8° (1.0 g/100 ml in ACN), $^1$H NMR (500 MHz, CDCl$_3$) δ 8.70 (br s, 1H), 8.58 (s, 1H), 8.40 (s, 1H), 8.19 (d, 1H), 8.10 (s, 1H), 7.55 (dd, 1H), 7.50 (m, 1H), 7.46 (dd, 1H), 7.13 (m, 2H), 5.83 (m, 1H), 3.81 (s, 3H), 2.31 (s, 3H), 2.22 (m, 2H), 1.13 (m, 3H), HRMS: calcd for (M+H$^+$) C$_{22}$H$_{23}$N$_6$O$_3$: 419.1831. Found: 419.1854.

EXAMPLE 44

2-{[1-(2-Methoxyphenyl)-1H-pyrazolo[3,4-d]pyrimidin-4-yl]oxy}-N-(5-methylpyridin-2-yl)propanamide

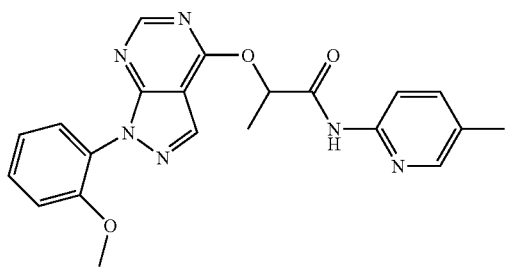

Method 1 from Intermediates A10 and B3

$^1$H NMR (300 MHz, CDCl$_3$) δ 8.88 (br s, 1H), 8.57 (s, 1H), 8.38 (s, 1H), 8.17 (d, 1H), 8.07 (s, 1H), 7.48 (m, 3H), 7.12 (m, 2H), 5.94 (q, 1H), 3.79 (s, 3H), 2.30 (s, 3H), 1.80 (d, 3H), HRMS: calcd for (M+H$^+$) C$_{21}$H$_{21}$N$_6$O$_3$: 405.1675. Found: 405.1676.

There are no examples 45 and 46.

EXAMPLE 47

(2S)-2-{[1-(2-chlorophenyl)-1H-pyrazolo[3,4-d]pyrimidin-4-yl]oxy}-4-(dimethylamino)-N-(5-methylpyridin-2-yl)butanamide

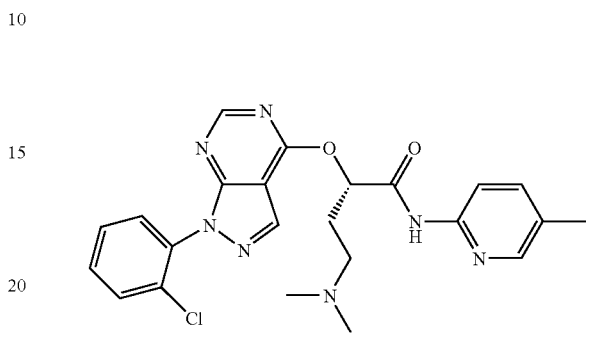

Method 1 from Intermediates A11 and B1

$[\alpha]^{20}_D$ +7.3° (1.0 g/100 ml in ACN), $^1$H NMR (300 MHz, CDCl$_3$) δ 9.61 (br s, 1H), 8.53 (s, 1H), 8.35 (s, 1H), 8.09 (m, 2H), 7.57 (m, 1H), 7.46 (m, 4H), 5.86 (t, 1H), 2.55 (m, 2H), 2.30 (m, 11H), HRMS: calcd for (M+H$^+$) C$_{23}$H$_{25}$$^{35}$ClN$_7$O$_2$: 466.1758. Found: 466.1763.

EXAMPLE 48

3-Acetamido-2-{[1-(2-chlorophenyl)-1h-pyrazolo[3,4-d]pyrimidin-4-yl]oxy}-n-(4-methyl-1,3-thiazol-2-yl)propanamide

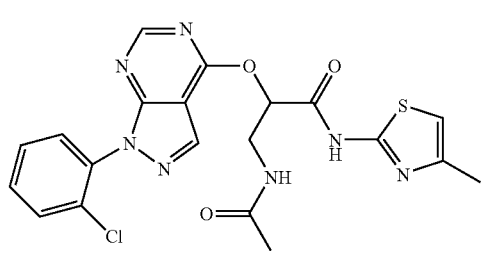

Method 1 from Intermediates A14 and B1

$^1$H NMR (500 MHz, CDCl$_3$) δ 8.59 (s, 1H), 8.39 (s, 1H), 7.62 (m, 1H), 7.50 (m, 3H), 6.55 (s, 1H), 6.18 (br t, 1H), 6.04 (t, 1H), 4.04 (m, 2H), 2.32 (s, 3H), 2.01 (s, 3H), HRMS: calcd for (M+H$^+$) C$_{20}$H$_{19}$$^{35}$ClN$_7$O$_3$S: 472.0958. Found: 472.0971.

EXAMPLE 49

4-{[1-(2-chlorophenyl)-1H-pyrazolo[3,4-d]pyrimidin-4-yl]oxy}-5-[(5-methylpyridin-2-yl)amino]-5-oxopentanoic acid

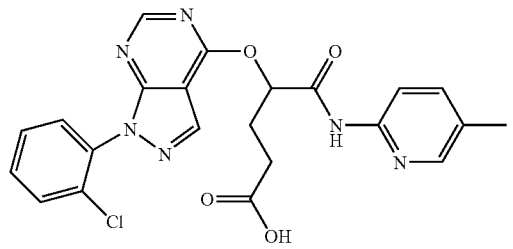

Method 1 from Intermediates A15 and B1

$^1$H NMR (400 MHz, CDCl$_3$) δ 11.44 (br s, 1H), 8.42 (s, 1H), 8.37 (s, 1H), 8.23 (d, 1H), 7.89 (s, 1H), 7.56 (m, 2H), 7.43 (m, 3H), 5.95 (m, 1H), 2.98 (m, 1H), 2.73 (m, 1H), 2.61 (m, 1H), 2.34 (m, 1H), 2.26 (s, 3H), HRMS: calcd for (M+H$^+$) C$_{22}$H$_{20}$$^{35}$ClN$_6$O$_4$: 467.1234. Found: 467.1233.

EXAMPLE 50

2-{[1-(2-chlorophenyl)-1H-pyrazolo[3,4-d]pyrimidin-4-yl]oxy}-N1-(5-methylpyridin-2-yl)pentanediamide

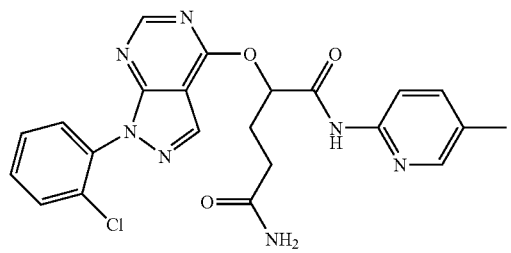

A solution of 4-{[1-(2-chlorophenyl)-1H-pyrazolo[3,4-d]pyrimidin-4-yl]oxy}-5-[(5-methylpyridin-2-yl)amino]-5-oxopentanoic acid (5.0 mg, 0.011 mmol), ammonium chloride (3.0 mg, 0.054 mmol), DIPEA (7.0 mg, 0.054 mmol) and TBTU (7.0 mg, 0.021 mmol) in THF (1 mL) was stirred at ambient temperature for 3 hrs. Water (1 mL) was added and the reaction mixture was purified by preparative HPLC: Mobile phase A: 100% ACN, Mobile phase B: 5% ACN+95% 0.1M NH$_4$OAc in water; Gradient: 0% A to 50% A over 45 min; Flow: 25 ml/min; UV: 235 nm, to give the title compound (3.0 mg). $^1$H NMR (500 MHz, CDCl$_3$) δ 9.18 (br s, 1H), 8.59 (s, 1H), 8.42 (s, 1H), 8.16 (d, 1H), 8.09 (s, 1H), 7.64 (m, 1H), 7.53 (m, 4H), 5.94 (s, 1H), 5.75 (br s, 1H), 5.57 (br s, 1H), 2.58 (m, 4H), 2.32 (s, 3H), HRMS: calcd for (M+H$^+$) C$_{22}$H$_{21}$$^{35}$ClN$_7$O$_3$: 466.1394. Found: 467.1426.

EXAMPLE 51

2-{[1-(2-chlorophenyl)-1H-pyrazolo[3,4-d]pyrimidin-4-yl]oxy}-N5-methyl-N1-(5-methylpyridin-2-yl)pentanediamide

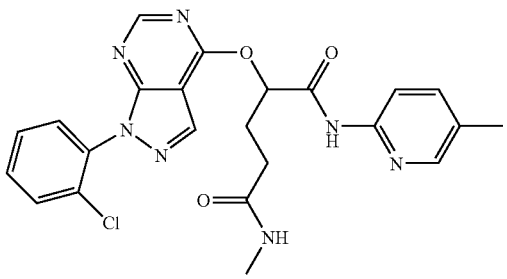

A solution of 4-{[1-(2-chlorophenyl)-1H-pyrazolo[3,4-d]pyrimidin-4-yl]oxy}-5-[(5-methylpyridin-2-yl)amino]-5-oxopentanoic acid (5.0 mg, 0.011 mmol), methylamine (0.021 ml (2M in THF), 0.043 mmol) and TBTU (7.0 mg, 0.021 mmol) in THF (1 mL) was stirred at ambient temperature for 5 hrs. Water (1 mL) was added and the reaction mixture was purified by preparative HPLC: Mobile phase A: 100% ACN, Mobile phase B: 5% ACN+95% 0.1M NH$_4$OAc in water; Gradient: 0% A to 50% A over 45 min; Flow: 25 ml/min; UV: 235 nm, to give the title compound (3.0 mg). $^1$H NMR (500 MHz, CDCl$_3$) δ 8.88 (br s, 1H), 8.57 (s, 1H), 8.39 (s, 1H), 8.11 (m, 2H), 7.62 (m, 1H), 7.51 (m, 4H), 5.91 (m, 1H), 5.63 (br s, 1H), 2.82 (d, 3H), 2.51 (m, 4H), 2.30 (s, 3H), HRMS: calcd for (M+H$^+$) C$_{23}$H$_{23}$$^{35}$ClN$_7$O$_3$: 480.1551. Found: 480.1503.
Method 2

EXAMPLE 52

2-{[1-(2-chlorophenyl)-1H-pyrazolo[3,4-d]pyrimidin-4-yl]thio}-4-(2-methoxyethoxy)-N-(4-methyl-1,3-thiazol-2-yl)butanamide

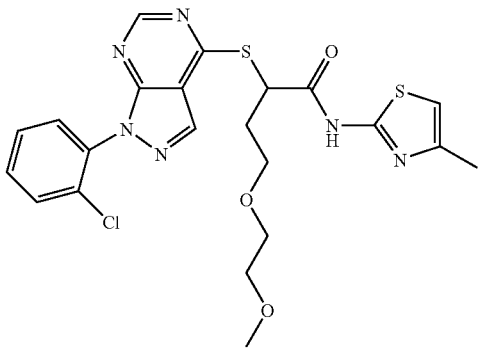

A solution of 2-bromo-4-(2-methoxyethoxy)-N-(4-methyl-1,3-thiazol-2-yl)butanamide (104 mg, 0.308 mmol) in DMF (1 mL) was added to a stirred solution of 1-(2-chlorophenyl)-1H-pyrazolo[3,4-d]pyrimidine-4-thiol (81.0 mg, 0.308 mmol) and K$_2$CO$_3$ (51.1 mg, 0.370 mmol) in DMF (2 mL). The reaction mixture was kept at ambient temperature for 3 hrs (45° C. and 17 hrs for example 54, 55 and 56). Water and EtOAc were added, and the two phases were separated.

The aqueous phase was extracted with EtOAc. The organic extracts were combined and washed with water, dried over MgSO$_4$ and concentrated in vacuo. The residue was purified with column chromatography (silica gel, eluting with DCM/EtOAc:1/1) to give the title compound as a colourless viscous oil (145 mg), $^1$H NMR (300 MHz, CDCl$_3$) δ 11.06 (br s, 1H), 8.93 (s, 1H), 8.30 (s, 1H), 7.62 (m, 1H), 7.49 (m, 3H), 6.51 (s, 1H), 5.14 (t, 1H), 3.77 (m, 1H), 3.67 (m, 1H), 3.59 (m, 2H), 3.50 (m, 2H), 3.33 (s, 3H), 2.60 (m, 1H), 2.27 (m, 4H), HRMS: calcd for (M+H$^+$) C$_{22}$H$_{24}$$^{35}$ClN$_6$O$_3$S$_2$: 518.1040. Found: 519.1050.

EXAMPLE 53

2-{[1-(2-chlorophenyl)-1H-pyrazolo[3,4-d]pyrimidin-4-yl]thio}-4-methoxy-N-(4-methyl-1,3-thiazol-2-yl)butanamide

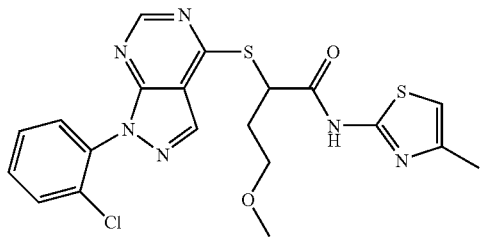

Method 2 from Intermediates A18 and B12

$^1$H NMR (500 MHz, CDCl$_3$) δ 11.08 (br s, 1H), 8.95 (s, 1H), 8.30 (s, 1H), 7.62 (d, 1H), 7.49 (m, 3H), 6.51 (s, 1H), 5.09 (t, 1H), 3.66 (m, 1H), 3.57 (m, 1H), 3.34 (s, 3H), 2.59 (m, 1H), 2.30 (s, 3H), 2.22 (m, 1H), HRMS: calcd for (M+H$^+$) C$_{20}$H$_{20}$$^{35}$ClN$_6$O$_2$S$_2$: 475.0777. Found: 475.0764.

EXAMPLE 54

2-{[1-(2-chlorophenyl)-1H-pyrazolo[3,4-d]pyrimidin-4-yl]thio}-3-methyl-N-(4-methyl-1,3-thiazol-2-yl)pentanamide

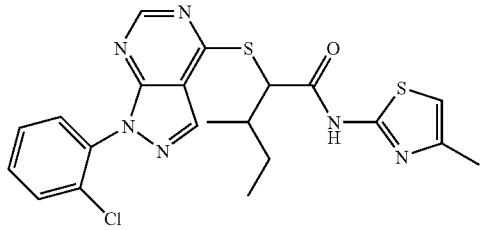

Method 2 from Intermediates A19 and B12

$^1$H NMR (300 MHz, CDCl$_3$) δ 10.48 (br s, 1H), 8.89 (d, 1H), 8.31 (d, 1H), 7.63 (m, 1H), 7.49 (m, 3H), 6.51 (s, 1H), 4.91 (d, 0.56H), 4.81 (d, 0.44H), 2.43 (m, 1H), 2.30 (s, 3H), 1.87 (m, 0.44H), 1.55 (m, 2.56H), 1.21 (m, 3H), 0.99 (t, 3H), HRMS: calcd for (M+H$^+$) C$_{21}$H$_{22}$$^{35}$ClN$_6$OS$_2$: 473.0985. Found: 473.0985.

EXAMPLE 55

2-{[1-(2-chlorophenyl)-1H-pyrazolo[3,4-d]pyrimidin-4-yl]thio}-N-isoxazol-3-yl-3-methylpentanamide

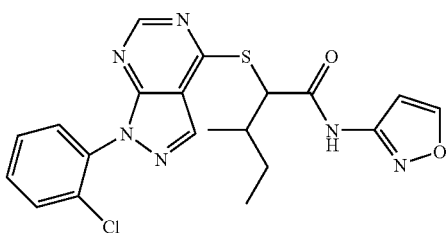

Method 2 from Intermediates A21 and B 12

$^1$H NMR (300 MHz, CDCl$_3$) δ 10.06 (br d, 1H), 8.85 (s, 1H), 8.32 (d, 1H), 8.26 (s, 1H), 7.62 (m, 1H), 7.49 (m, 3H), 7.06 (d, 1H), 4.81 (d, 0.57H), 4.73 (d, 0.43H), 2.40 (m, 1H), 1.90 (m, 0.43H), 1.63 (m, 0.57H), 1.47 (m, 1H), 1.22 (m, 3H), 0.99 (m, 3H), HRMS: calcd for (M+H$^+$) C$_{20}$H$_{20}$$^{35}$ClN$_6$O$_2$S: 443.1057. Found: 443.1057.

EXAMPLE 56

2-{[1-(2-chlorophenyl)-1H-pyrazolo[3,4-d]pyrimidin-4-yl]thio}-3-methyl-N-(5-methylpyridin-2-yl)pentanamide

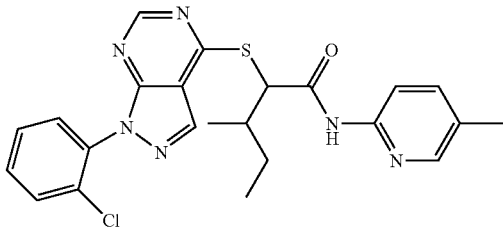

Method 2 from Intermediates A20 and B 12

$^1$H NMR (300 MHz, CDCl$_3$) δ 9.33 (br d, 1H), 8.85 (d, 1H), 8.30 (d, 1H), 8.11 (d, 1H), 8.05 (s, 1H), 7.62 (m, 1H), 7.48 (m, 4H), 4.92 (d, 0.69H), 4.82 (d, 0.31H), 2.40 (m, 1H), 2.26 (s, 3H), 1.88 (m, 0.39H), 1.68 (m, 0.61H), 1.48 (m, 1H), 1.22 (m, 3H), 0.99 (m, 3H), HRMS: calcd for (M+H$^+$) C$_{23}$H$_{24}$$^{35}$ClN$_6$OS: 467.1420. Found: 467.1420.

EXAMPLE 57

2-[(1-Isopropyl-1H-pyrazolo[3,4-d]pyrimidin-4-yl)thio]-4-(2-methoxyethoxy)-N-(4-methyl-1,3-thiazol-2-yl)butanamide

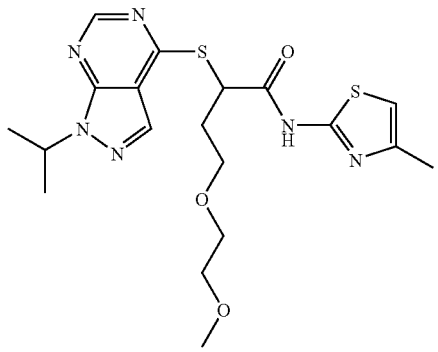

Method 2 from Intermediates A16 and B14

$^1$H NMR (400 MHz, CDCl$_3$) δ 8.82 (s, 1H), 7.98 (s, 1H), 6.43 (d, 1H), 5.14 (m, 1H), 5.03 (t, 1H), 3.68 (m, 1H), 3.60 (m, 1H), 3.51 (m, 2H), 3.42 (m, 2H), 3.24 (s, 3H), 2.50 (m, 1H), 2.23 (s, 3H), 1.99 (m, 1H), 1.51 (t, 6H), HRMS: calcd for (M+H$^-$) C$_{19}$H$_{27}$N$_6$O$_3$S$_2$: 451.1586. Found: 451.1598.

EXAMPLE 58

2-[(1-Isopropyl-1H-pyrazolo[3,4-d]pyrimidin-4-yl)thio]-4-(2-methoxyethoxy)-N-(5-methylpyridin-2-yl)butanamide

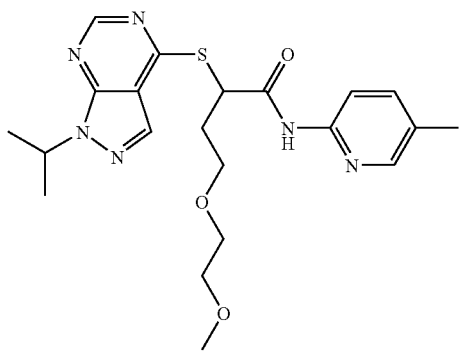

Method 2 from Intermediates A17 and B14

$^1$H NMR (400 MHz, CDCl$_3$) δ 10.01 (br s, 1H), 8.83 (s, 1H), 8.02 (m, 3H), 7.44 (dd, 1H), 5.15 (m, 1H), 5.07 (t, 1H), 3.69 (m, 1H), 3.64 (m, 1H), 3.54 (m, 2H), 3.45 (m, 2H), 3.28 (s, 3H), 2.50 (m, 1H), 2.22 (s, 3H), 2.15 (m, 1H), 1.53 (t, 6H), HRMS: calcd for (M+H$^+$) C$_{21}$H$_{29}$$^{35}$ClN$_6$O$_3$S: 445.2021. Found: 445.2016.

Method 3

EXAMPLE 59

2-{[1-(2-chlorophenyl)-1h-pyrazolo[3,4-]pyrimidin-4-yl]thio}-n-(4-methyl-1,3-thiazol-2-yl)hexanamide

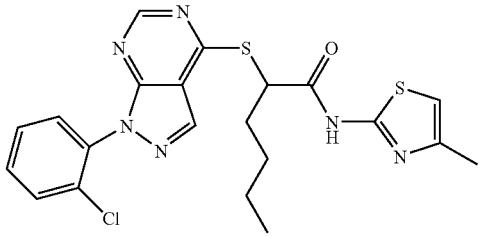

A stirred solution of 2-bromo-hexanoic acid (2.00 g, 10.25 mmol) in thionyl chloride (1.59 g, 13.36 mmol) was refluxed for 30 minutes. The reaction mixture was concentrated in vacuo to remove excess thionyl chloride. The freshly prepared acid chloride (117 mg, 0.548 mmol) was added slowly to a stirred solution of 2-amino-4-methylthiazole (62.1 mg, 0.544 mmol) and DIPEA (67.2 mg, 0.520 mmol) in DCM (2 mL). The reaction mixture was kept at ambient temperature for 25 minutes before it was added to a solution of 1-(2-chlorophenyl)-1H-pyrazolo[3,4-d]pyrimidine-4-thiol (130 mg, 0.495 mmol) and anhydrous potassium carbonate (102.6 mg, 0.742 mmol) in DMF (3 mL). The reaction mixture was kept at ambient temperature for 3 hrs. Water and EtOAc were added and the two phases were separated. The aqueous phase was extracted with EtOAc. The organic extracts were combined and washed three times with water, dried over MgSO$_4$ and concentrated in vacuo. The residue was purified with column chromatography (silica gel, eluting with DCM/EtOAc:5/1) to give the title compound (99 mg), $^1$H NMR (300 MHz, CDCl$_3$) δ 10.92 (s, 1H), 8.95 (s, 1H), 8.29 (s, 1H), 7.63 (m, 1H), 7.50 (m, 3H), 6.51 (s, 1H), 4.80 (t, 1H), 2.30 (m, 4H), 1.97 (m, 1H), 1.57 (m, 2H), 1.42 (m, 2H), 0.94 (t, 3H), HRMS: calcd for (M+H$^+$) C$_{21}$H$_{22}$$^{35}$ClN$_6$OS$_2$: 473.0985. Found: 473.1027.

EXAMPLE 60

2-{[1-(2-chlorophenyl)-1H-pyrazolo[3,4-d]pyrimidin-4-yl]thio}-N-isoxazol-3-ylhexanamide

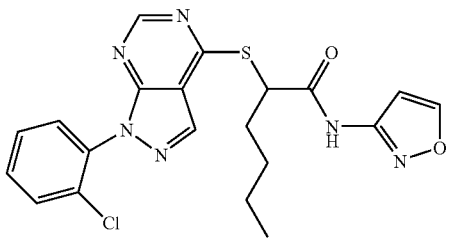

Method 3 from 2-bromo-hexanoic acid, 3-aminoisoxazole and Intermediate B12

$^1$H NMR (300 MHz, CDCl$_3$) δ 10.44 (br s, 1H), 8.89 (s, 1H), 8.30 (s, 1H), 8.26 (d, 1H), 7.63 (m, 1H), 7.50 (m, 3H), 7.05 (d, 1H), 4.73 (t, 1H), 2.26 (m, 1H), 1.93 (m, 1H), 1.55 (m, 2H), 1.42 (m, 2H), 0.95 (t, 3H), HRMS: calcd for (M+H$^+$) C$_{20}$H$_{20}$$^{35}$ClN$_6$O$_2$S: 443.1057. Found: 443.1081.

EXAMPLE 61

2-{[1-(2-Chlorophenyl)-1H-pyrazolo[3,4-d]pyrimidin-4-yl]thio}-4-(2-methoxyethoxy)-N-(4-methyl-1,3-thiazol-2-yl)butanamide

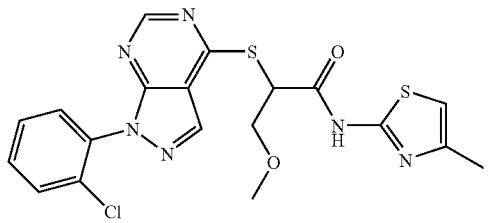

Method 3 from 2-chloro-3-methoxy-propionic acid, 2-amino-4-methylthiazole and Intermediate B12.

$^1$H NMR (300 MHz, CDCl$_3$) δ 8.87 (s, 1H), 8.31 (s, 1H), 7.63 (m, 1H), 7.50 (m, 3H), 6.53 (s, 1H), 5.24 (t, 1H), 4.05 (d, 2H), 3.50 (s, 3H), 2.31 (s, 3H), HRMS: calcd for (M+H$^+$) C$_{19}$H$_{18}$$^{35}$ClN$_6$O$_2$S$_2$: 461.0621. Found: 461.0631.

EXAMPLE 62

2-{[1-(2-Chlorophenyl)-1H-pyrazolo[3,4-d]pyrimidin-4-yl]thio}-3-methoxy-N-(5-methylpyridin-2-yl)propanamide

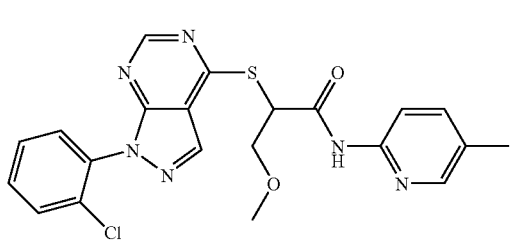

Method 3 from 2-chloro-3-methoxy-propionic acid, 2-amino-5-picoline and Intermediate B12

$^1$H NMR (300 MHz, $_{CDCl3}$) δ 9.54 (br s, 1H), 8.87 (s, 1H), 8.31 (s, 1H), 8.08 (m, 2H), 7.63 (m, 1H), 7.49 (m, 4H), 5.22 (t, 1H), 4.04 (m, 2H), 3.50 (s, 3H), 2.27 (s, 3H), HRMS: calcd for (M+H$^+$) C$_{21}$H$_{20}$$^{35}$ClN$_6$O$_2$S: 455.1057. Found: 455.1085.

EXAMPLE 63

2-{[1-(2-chlorophenyl)-1H-pyrazolo[3,4-d]pyrimidin-4-yl]thio}-N-(4-methyl-1,3-thiazol-2-yl)octanamide

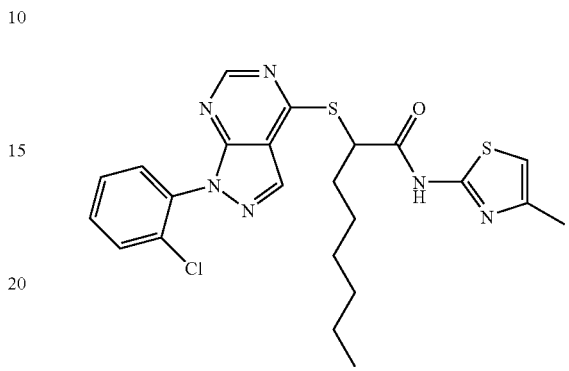

Method 3 from 2-bromo-octanoic acid, 2-amino-4-methylthiazole and Intermediate B 12

$^1$H NMR (300 MHz, CDCl$_3$) δ 10.90 (br s, 1H), 8.94 (s, 1H), 8.29 (s, 1H), 7.63 (m, 1H), 7.50 (m, 3H), 6.51 (s, 1H), 4.80 (t, 1H), 2.30 (m, 4H), 1.95 (m, 1H), 1.59 (m, 2H), 1.32 (m, 6H), 0.88 (t, 3H), HRMS: calcd for (M+H$^+$) C$_{23}$H$_{26}$$^{35}$ClN$_6$OS$_2$: 501.1298. Found: 501.1298.

EXAMPLE 64

2-{[1-(2-chlorophenyl)-1H-pyrazolo[3,4-d]pyrimidin-4-yl]thio}-N-isoxazol-3-yloctanamide

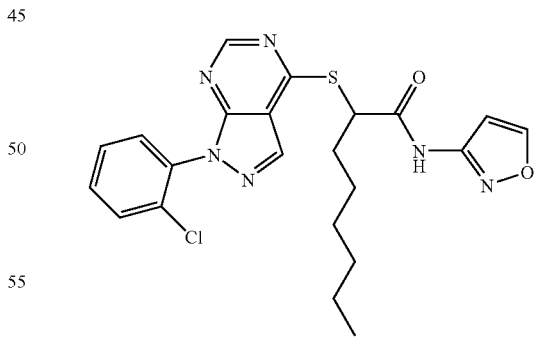

Method 3 from 2-bromo-octanoic acid, 3-aminoisoxazole and Intermediate B12

$^1$H NMR (300 MHz, CDCl$_3$) δ 10.47 (br s, 1H), 8.88 (s, 1H), 8.30 (s, 1H), 8.26 (d, 1H), 7.62 (m, 1H), 7.48 (m, 3H), 7.05 (d, 1H), 4.74 (t, 1H), 2.27 (m, 1H), 1.93 (m, 1H), 1.55 (m, 2H), 1.35 (m, 6H), 0.88 (t, 3H), HRMS: calcd for (M+H$^+$) C$_{22}$H$_{24}$$^{35}$ClN$_6$O$_2$S: 471.1370. Found: 471.1370.

There are no examples 65-70.
Method 4

EXAMPLE 71

2-Ethoxy-2-{[1-(2-methoxyphenyl)-1H-pyrazolo[3,4-d]pyrimidin-4-yl]thio}-N-(4-methyl-1,3-thiazol-2-yl)acetamide

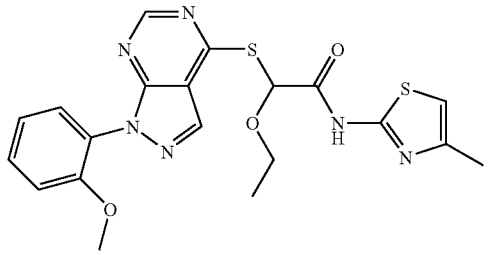

Sodium hydride (95%, 3.7 mg, 0.15 mmol) was added to a stirred solution of 2-amino-4-methylthiazol (17.6 mg, 0.154 mmol) in anhydrous THF (4 mL). The reaction mixture was kept at ambient temperature for 5 minutes before ethyl ethoxy{[1-(2-methoxyphenyl)-1H-pyrazolo[3,4-d]pyrimidin-4-yl]thio}acetate (50 mg, 0.129 mmol) was added. The reaction mixture was stirred at ambient temperature for 1 h. Water and DCM were added and the two phases were separated. The organic phase was dried over MgSO$_4$ and concentrated in vacuo. The residue was purified with column chromatography (silica gel, eluting with a gradient consisting of 40-100% EtOAc in heptane) to give the title compound as a colourless oil (1.1 mg), $^1$H NMR (300 MHz, CDCl$_3$) δ 10.03 (br s, 1H), 8.74 (s, 1H), 8.26 (s, 1H), 7.47 (m, 2H), 7.12 (m, 2H), 6.91 (s, 1H), 6.58 (s, 1H), 4.02 (m, 1H), 3.81 (m, 4H), 2.38 (s, 3H), 1.34 (t, 3H), HRMS: calcd for (M+H$^+$) C$_{20}$H$_{21}$N$_6$O$_3$S$_2$: 457.1116. Found: 457.1116.

EXAMPLE 72

2-Ethoxy-N-isoxazol-3-yl-2-{[1-(2-methoxyphenyl)-1H-pyrazolo[3,4-d]pyrimidin-4-yl]thio}acetamide

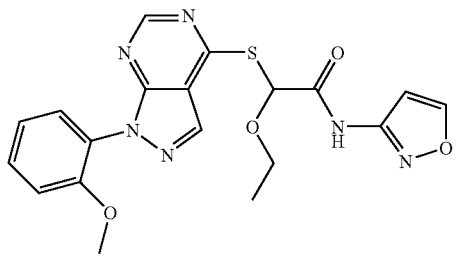

Method 4 from 3-aminoisoxazole and Intermediate A24

$^1$H NMR (300 MHz, CDCl$_3$) δ 9.51 (br s, 1H), 8.75 (s, 1H), 8.33 (s, 1H), 8.27 (s, 1H), 7.47 (m, 2H), 7.13 (t, 3H), 6.82 (s, 1H), 4.03 (m, 1H), 3.82 (m, 5H), 1.35 (t, 3H), HRMS: calcd for (M+H$^+$) C$_{19}$H$_{19}$$^{35}$ClN$_6$O$_4$S: 427.1188. Found: 427.1181.

There is no example 73.
Method 5

REFERENCE EXAMPLE 74

N-2-[1-(2-chlorophenyl)-1H-pyrazolo[3,4-d]pyrimidin-4-yl]-N-(5-methyl-1,3-thiazol-2-yl)glycinamide

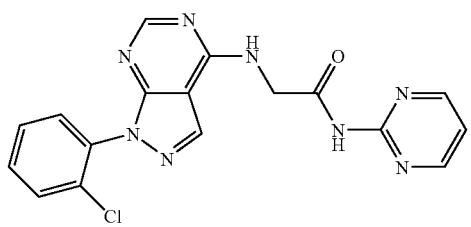

Sodium hydride (95%, 19.08 mg, 0.76 mmol) was added to a stirred solution of 2-aminopyrimidine (62.9 mg, 0.66 mmol) in anhydrous THF (3 mL). The reaction mixture was kept at ambient temperature for 3 hrs before it was added to a solution of methyl N-[1-(2-chlorophenyl)-1H-pyrazolo[3,4-d]pyrimidin-4-yl]glycinate (200 mg, 0.63 mmol) in anhydrous THF (3 mL). The reaction mixture was stirred at ambient temperature for 1 h. Water and EtOAc were added and the two phases were separated. The aqueous phase was extracted with EtOAc. The organic extracts were combined and concentrated in vacuo. The residue was triturated sequentially with DCM, MeOH and EtOAc. The remaining solid was dissolved in hot DMSO and precipitated by the addition of water to give the title compound as a solid (37 mg), $^1$H NMR (300 MHz, DMSO) δ 10.80 (br s, 1H), 8.87 (br t, 1H), 8.67 (d, 2H), 8.49 (s, 1H), 8.22 (s, 1H), 7.70 (m, 1H), 7.56 (m, 3H), 7.18 (t, 1H), 4.59 (d, 2H), HRMS: calcd for (M+H$^+$) C$_{17}$H$_{14}$$^{35}$ClN$_8$O: 381.0979. Found: 381.0980.

There is no example 75.

EXAMPLE 76

2-[(1-isopropyl-1H-pyrazolo[3,4-d]pyrimidin-4-yl)oxy]-4-methoxy-N-(5-methylpyridin-2-yl)butanamide

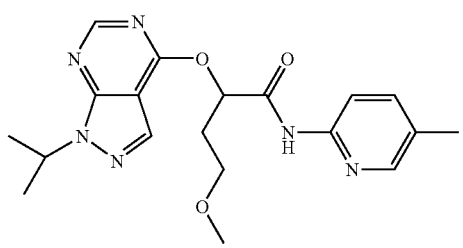

Method 1 from Intermediates A12 and B9

$^1$H NMR (400 MHz, CDCl$_3$) δ 8.92 (br s, 1H), 8.46 (s, 1H), 8.09 (s, 1H), 8.07 (s, 1H), 7.46 (dd, 1H), 5.87 (dd, 1H), 5.13 (m, 1H), 3.56 (t, 2H), 3.25 (s, 3H), 2.35 (m, 2H), 2.22 (s, 3H), 1.52 (dd, 6H), HRMS: calcd for (M+H$^+$) C$_{19}$H$_{25}$N$_6$O$_3$: 385.1988. Found: 385.2007.

There are no examples with Example numbers 77 to 80.

EXAMPLE 81

(R)-2-{[1-(2-chlorophenyl)-1H-pyrazolo[3,4-d]pyrimidin-4-yl]thio}-N-(4-methyl-1,3-thiazol-2-yl)hexanamide

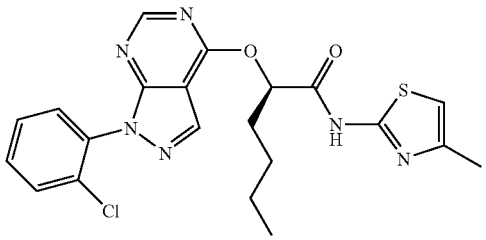

AND EXAMPLE 82

(S)-2-{[1-(2-chlorophenyl)-1H-pyrazolo[3,4-d]pyrimidin-4-yl]thio}-N-(4-methyl-1,3-thiazol-2-yl)hexanamide

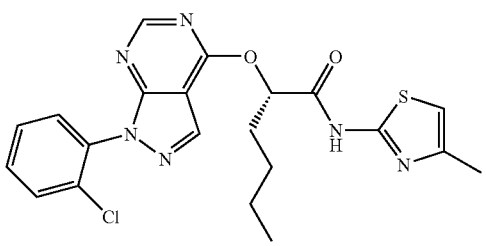

The enantiomers of 2-{[1-(2-chlorophenyl)-1H-pyrazolo[3,4-d]pyrimidin-4-yl]thio}-N-(4-methyl-1,3-thiazol-2-yl)hexanamide Example 41 (40 mg) were separated by chiral preparative HPLC: Column Chiralpak AD (250×20 mm, 5 μm), eluting with heptane/ethanol 85/5. This gave (R)-2-{[1-(2-chlorophenyl)-1H-pyrazolo[3,4-d]pyrimidin-4-yl]thio}-N-(4-methyl-1,3-thiazol-2-yl)hexanamide (17 mg, >99% ee).

$^1$H NMR (300 MHz, CDCl$_3$) δ 9.44 (br s, 1H), 8.58 (s, 1H), 8.38 (s, 1H), 7.62 (m, 1H), 7.51 (m, 3H), 6.56 (s, 1H), 5.95 (t, 1H), 2.33 (s, 3H), 2.17 (m, 2H), 1.53 (m, 2H), 1.41 (m, 2H), 0.93 (t, 3H)

and (S)-2-{[1-(2-chlorophenyl)-1H-pyrazolo[3,4-d]pyrimidin-4-yl]thio}-N-(4-methyl-1,3-thiazol-2-yl)hexanamide (17 mg, >99% ee). $^1$H NMR (300 MHz, CDCl$_3$) δ 9.44 (br s, 1H), 8.58 (s, 1H), 8.38 (s, 1H), 7.62 (m, 1H), 7.51 (m, 3H), 6.56 (s, 1H), 5.95 (t, 1H), 2.33 (s, 3H), 2.17 (m, 2H), 1.53 (m, 2H), 1.41 (m, 2H), 0.93 (t, 3H)

EXAMPLE 83

2-(1-(2-chlorophenyl)-1H-pyrazolo[3,4-d]pyrimidin-4-yloxy)-3-methyl-N-(5-methylpyridin-2-yl)butanamide

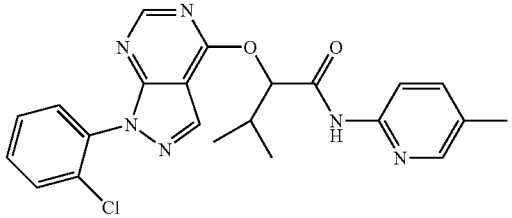

A solution of LHMDS (0.999 mL, 1.00 mmol) in anhydrous THF (15 mL) was added dropwise to a stirred solution of racemic 2-hydroxy-3-methyl-N-(5-methylpyridin-2-yl)butanamide C1 (208 mg, 1.00 mmol) in anhydrous THF (15 mL) over a period of 3 minutes under nitrogen. The resulting suspension was stirred at ambient temperature for 10 minutes, then a solution of 4-chloro-1-(2-chlorophenyl)-1H-pyrazolo[3,4-d]pyrimidine B1 (265 mg, 1.00 mmol) in anhydrous THF (3 mL) was added dropwise over 1 minute and the resulting mixture heated to 50° C. for 3 hours. The mixture was allowed to cool to room temperature then diluted with EtOAc (50 mL), and washed sequentially with water (2×25 mL) and saturated brine (25 mL). The organic layer was dried over MgSO$_4$, filtered and evaporated to afford crude product. The material was purified by flash silica chromatography, elution gradient 30 to 50% EtOAc in DCM. Pure fractions were evaporated to dryness to afford 2-(1-(2-chlorophenyl)-1H-pyrazolo[3,4-d]pyrimidin-4-yloxy)-3-methyl-N-(5-methylpyridin-2-yl)butanamide (320 mg).

$^1$H NMR (400 MHz, CDCl$_3$) δ 8.58 (1H, s), 8.40 (1H, s), 8.38 (1H, s), 8.16 (1H, d), 8.08-8.07 (1H, m), 7.63-7.60 (1H, m), 7.54-7.51 (2H, m), 7.50-7.44 (2H, m), 5.71 (1H, d), 2.59-2.55 (1H, m), 2.28 (3H, s), 1.21 (3H, d), 1.15 (3H, d), m/z (ESI+) (M+H)+=437; HPLC t$_R$=2.56 min.

The following examples (84-96) were prepared in an analogous fashion from the appropriate alcohol and chloroderivative.

EXAMPLE 84

(2S)-2-(1-(2-chlorophenyl)-1H-pyrazolo[3,4-d]pyrimidin-4-yloxy)-3-methyl-N-(5-methylpyridin-2-yl)butanamide

EXAMPLE 85

(2R)-2-(1-(2-chlorophenyl)-1H-pyrazolo[3,4-d]pyrimidin-4-yloxy)-3-methyl-N-(5-methylpyridin-2-yl)butanamide

EXAMPLE 86

(2S)-2-(1-(3-chloropyridin-2-yl)-1H-pyrazolo[3,4-d]pyrimidin-4-yloxy)-3-methyl-N-(5-methylpyridin-2-yl)butanamide

EXAMPLE 87

(2S)-2-(1-(2-chlorophenyl)-1H-pyrazolo[3,4-d]pyrimidin-4-yloxy)-3-methoxy-N-(5-methylpyridin-2-yl)propanamide

EXAMPLE 88

(2R)-2-(1-(2-chlorophenyl)-1H-pyrazolo[3,4-d]pyrimidin-4-yloxy)-3-methoxy-N-(5-methylpyridin-2-yl)propanamide

EXAMPLE 89

(2S)-2-(1-(3-chloropyridin-2-yl)-1H-pyrazolo[3,4-d]pyrimidin-4-yloxy)-3-methoxy-N-(5-methylpyridin-2-yl)propanamide

EXAMPLE 90

(2S)-2-(1-(3-chloropyridin-2-yl)-1H-pyrazolo[3,4-d]pyrimidin-4-yloxy)-3-methoxy-N-(5-methylpyrazin-2-yl)propanamide

EXAMPLE 91

(2S)-2-(1-(3-chloropyridin-2-yl)-1H-pyrazolo[3,4-d]pyrimidin-4-yloxy)-3-isopropoxy-N-(5-methylpyridin-2-yl)propanamide

EXAMPLE 92

(2S)-2-(1-(3-chloropyridin-2-yl)-1H-pyrazolo[3,4-d]pyrimidin-4-yloxy)-3-isopropoxy-N-(5-methylpyrazin-2-yl)propanamide

EXAMPLE 93

(2S)-2-(1-(3-chloropyridin-2-yl)-1H-pyrazolo[3,4-d]pyrimidin-4-yloxy)-3-isopropoxy-N-(3-methyl-1,2,4-thiadiazol-5-yl)propanamide

EXAMPLE 94

(2S)-2-(1-(3-chloropyridin-2-yl)-1H-pyrazolo[3,4-d]pyrimidin-4-yloxy)-3-methyl-N-(5-methylpyrazin-2-yl)butanamide

EXAMPLE 95

(2S)-2-(1-(2-chloro-4-fluorophenyl)-1H-pyrazolo[3,4-d]pyrimidin-4-yloxy)-3-methoxy-N-(5-methylpyrazin-2-yl)propanamide

EXAMPLE 96

(2S)-2-(1-(2-chloro-4-fluorophenyl)-1H-pyrazolo[3,4-d]pyrimidin-4-yloxy)-3-methoxy-N-(5-methylpyridin-2-yl)propanamide

EXAMPLE 97

(2S)-2-(1-(2-cyanophenyl)-1H-pyrazolo[3,4-d]pyrimidin-4-yloxy)-3-methoxy-N-(5-methylpyridin-2-yl)propanamide

EXAMPLE 97a (2S)-2-[1-(2-cyanophenyl)pyrazolo[4,5-e]pyrimidin-4-yl]oxy-N-(5-methylpyridin-2-yl)-3-propan-2-yloxypropanamide

| | STRUCTURE | M/Z | $^1$H nmr data (400 MHz) |
|---|---|---|---|
| 84 | 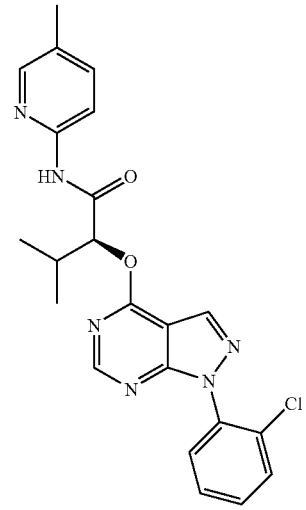 | ESI+ (M + H)+ = 437; HPLC $t_R$ = 2.55 min | (CDCl$_3$) δ 8.58 (1 H, s), 8.40 (1 H, s), 8.38 (1 H, s), 8.16 (1 H, d), 8.08-8.07 (1 H, m), 7.63-7.60 (1 H, m), 7.54-7.51 (2 H, m), 7.50-7.44 (2 H, m), 5.71 (1 H, d), 2.59-2.55 (1 H, m), 2.28 (3 H, s), 1.21 (3 H, d), 1.15 (3 H, d) |

| | STRUCTURE | M/Z | ¹H nmr data (400 MHz) |
|---|---|---|---|
| 85 | 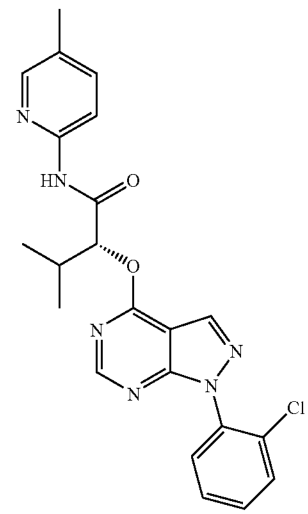 | ESI+<br>(M + H)+ = 437;<br>HPLC t_R = 2.60 min | (CDCl₃) δ 8.58 (1 H, s), 8.40 (1 H, s), 8.38 (1 H, s), 8.16 (1 H, d), 8.08-8.07 (1 H, m), 7.63-7.60 (1 H, m), 7.54-7.51 (2 H, m), 7.50-7.44 (2 H, m), 5.71 (1 H, d), 2.59-2.55 (1 H, m), 2.28 (3 H, s), 1.21 (3 H, d), 1.15 (3 H, d) |
| 86 | 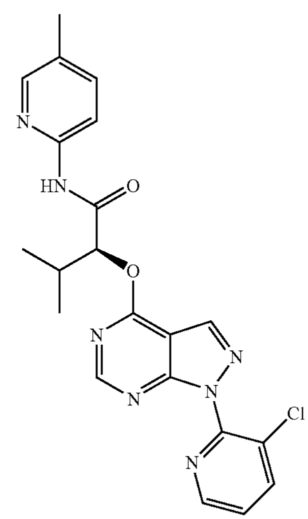 | ESI+<br>(M + H)+ = 438;<br>HPLC t_R = 2.11 min | (DMSO-d₆) δ 10.83 (1 H, s), 8.71 (1 H, s), 8.69 (1 H, dd), 8.55 (1 H, s), 8.37 (1 H, dd), 8.19 (1 H, d), 7.92 (1 H, d), 7.76 (1 H, dd), 7.60 (1 H, dd), 5.57 (1 H, d), 2.49-2.40 (1 H, m), 2.25 (3 H, s), 1.13 (6 H, d) |
| 87 | 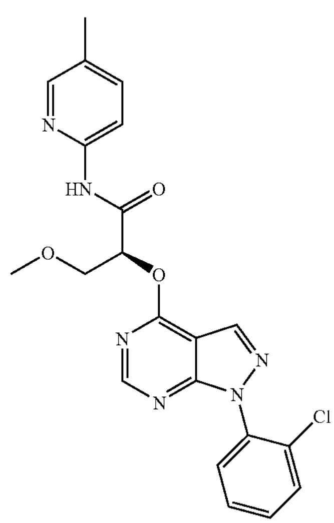 | ESI+<br>(M + H)+ = 439;<br>HPLC t_R = 2.21 min | (DMSO-d₆) δ 10.85 (1 H, s), 8.62 (1 H, s), 8.54 (1 H, s), 8.18 (1 H, d), 7.88 (1 H, d), 7.76 (1 H, dd), 7.65-7.56 (4 H, m), 5.95-5.94 (1 H, m), 4.06-4.01 (1 H, m), 3.94-3.90 (1 H, m), 3.40 (3 H, s), 2.24 (3 H, s) |

| STRUCTURE | M/Z | ¹H nmr data (400 MHz) |
|---|---|---|
| 88 | ESI+ (M + H)+ = 439; HPLC $t_R$ = 2.20 min | (DMSO-d$_6$) δ 10.85 (1 H, s), 8.62 (1 H, s), 8.54 (1 H, s), 8.18 (1 H, d), 7.88 (1 H, d), 7.76 (1 H, dd), 7.65-7.56 (4 H, m), 5.95-5.94 (1 H, m), 4.06-4.01 (1 H, m), 3.94-3.90 (1 H, m), 3.40 (3 H, s), 2.24 (3 H, s) |
| 89 | ESI+ (M + H)+ = 440; HPLC $t_R$ = 1.77 min | (DMSO-d$_6$) δ 10.86 (1 H, s), 8.67 (1 H, s), 8.66 (1 H, s), 8.56 (1 H, s), 8.33 (1 H, dd), 8.17 (1 H, d), 7.88 (1 H, d), 7.75 (1 H, dd), 7.58 (1 H, d), 5.95-5.94 (1 H, m), 4.07-4.00 (1 H, m), 3.94-3.91 (1 H, m), 3.40 (3 H, s), 2.24 (3 H, s) |
| 90 | ESI+ (M + H)+ = 441; HPLC $t_R$ = 1.59 min | (DMSO-d$_6$) δ 11.18 (1 H, s), 9.10 (1 H, d), 8.68 (1 H, s), 8.66 (1 H, dd), 8.57 (1 H, s), 8.32 (1 H, dd), 8.31 (1 H, d), 7.74 (1 H, dd), 5.99-5.96 (1 H, m), 4.10-3.93 (2 H, m), 3.41 (3 H, s), 2.44 (3 H, s) |

| | STRUCTURE | M/Z | $^1$H nmr data (400 MHz) |
|---|---|---|---|
| 91 | 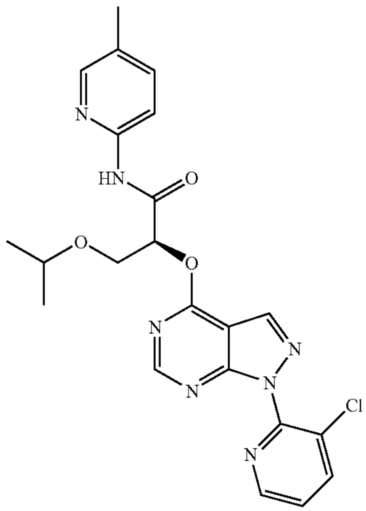 | ESI+<br>(M + H)+ = 468;<br>HPLC $t_R$ = 2.02 min | (CDCl$_3$) δ 8.69 (1 H, s), 8.63 (1 H, s), 8.62 (1 H, dd), 8.46 (1 H, s), 8.13 (1 H, d), 8.10-8.09 (1 H, m), 8.00 (1 H, dd), 7.52 (1 H, dd), 7.47 (1 H, dd), 6.02 (1 H, t), 4.08 (2 H, d), 3.78-3.65 (1 H, m), 2.29 (3 H, s), 1.18 (6 H, m) |
| 92 | 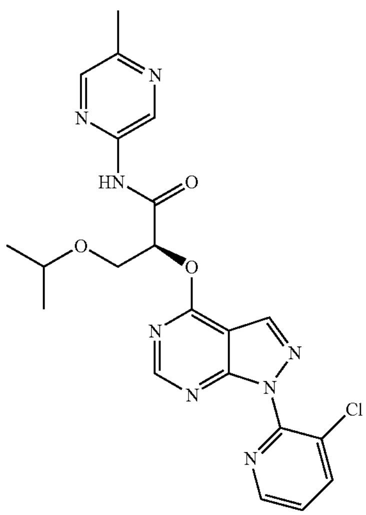 | ESI+<br>(M + H)+ = 469;<br>HPLC $t_R$ = 1.82 min | (CDCl$_3$) δ 1.18-1.21 (6 H, m), 2.54 (3 H, s), 3.70-3.76 (1 H, m), 4.12 (2 H, d), 6.04 (1 H, t), 7.46 (1 H, dd), 8.00 (1 H, dd), 8.12 (1 H, d), 8.46 (1 H, s), 8.62 (1 H, dd), 8.64 (1 H, s), 8.71 (1 H, s), 9.43 (1 H, d) |
| 93 | 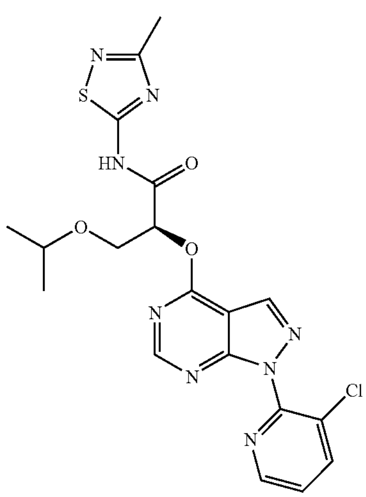 | ESI−<br>(M + H)− = 473;<br>HPLC $t_R$ = 2.08 min | (CDCl$_3$) δ 1.17-1.21 (6 H, m), 2.55 (3 H, s), 3.65-3.76 (1 H, m), 4.11 (2 H, d), 6.14 (1 H, t), 7.48 (1 H, dd), 8.02 (1 H, dd), 8.44 (1 H, s), 8.61-8.63 (1 H, m), 8.62 (1 H, s), 9.96 (1 H, s) |

| | STRUCTURE | M/Z | ¹H nmr data (400 MHz) |
|---|---|---|---|
| 94 | 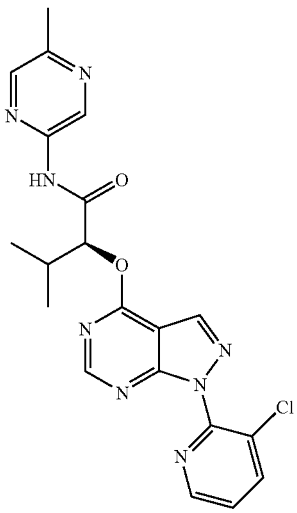 | ESI+<br>(M + H)+ = 439;<br>HPLC $t_R$ = 1.95 min | (CDCl₃) δ 1.15-1.17 (3 H, d), 1.22 (3 H, d), 2.53 (3 H, s), 2.57-2.61 (1 H, m), 5.75 (1 H, d), 7.46-7.49 (1 H, m), 8.00-8.03 (1 H, m), 8.09 (1 H, d), 8.37 (1 H, s), 8.45 (1 H, s), 8.61-8.62 (1 H, m), 8.63 (1 H, s), 9.46 (1 H, d) |
| 95 | 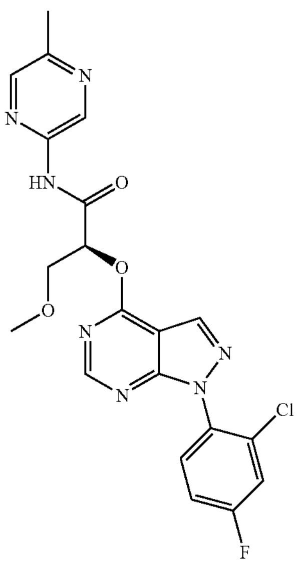 | ESI+<br>(M + H)+ = 458;<br>HPLC $t_R$ = 2.16 min | (CDCl₃) δ 2.54 (3 H, s), 3.48 (3 H, s), 4.03-4.07 (1 H, m), 4.10-4.14 (1 H, m), 6.12 (1 H, t), 7.16-7.21 (1 H, m), 7.35-7.38 (1 H, m), 7.50-7.54 (1 H, m), 8.12 (1 H, d), 8.43 (1 H, s), 8.59 (1 H, s), 8.63 (1 H, s), 9.45 (1 H, d) |
| 96 | 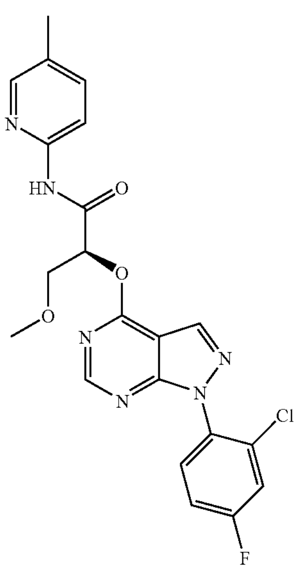 | ESI+<br>(M + H)+ = 457;<br>HPLC $t_R$ = 2.27 min | (CDCl₃) δ 2.29 (3 H, s), 3.46 (3 H, s), 4.01-4.05 (1 H, m), 4.09-4.13 (1 H, m), 6.09 (1 H, t), 7.16-7.20 (1 H, m), 7.35-7.38 (1 H, m), 7.50-7.54 (2 H, m), 8.10 (1 H, d), 8.14 (1 H, d), 8.42 (1 H, d), 8.58 (1 H, s), 8.73 (1 H, s) |

| STRUCTURE | M/Z | ¹H nmr data (400 MHz) |
|---|---|---|
| 97 | ESI+ (M + H)⁺ = 430; HPLC $t_R$ = 1.94 min | (DMSO-$d_6$) δ 2.24 (3 H, s), 3.40 (3 H, s), 3.90-3.96 (1 H, m), 4.01-4.09 (1 H, m), 5.93-5.98 (1 H, m), 7.56-7.60 (1 H, m), 7.71-7.77 (1 H, m), 7.85-7.91 (1 H, m), 7.94-7.98 (2 H, m), 8.12 (1 H, d), 8.17 (1 H, s), 8.64 (1 H, s), 8.64 (1 H, s), 10.87 (1 H, s), |
| 97a | (ESI+) (M + H)+ = 458; HPLC $t_R$ = 2.29 min. | (CDCl₃) δ 1.18 (3 H, d), 1.20 (3 H, d), 2.29 (3 H, s), 3.66-3.78 (1 H, m), 4.09 (2 H, d), 6.02 (1 H, t), 7.52 (1 H, dd), 7.56 (1 H, ddd), 7.79 (1 H, ddd), 7.89 (1 H, dd), 7.92 (1 H, dd), 8.09-8.11 (1 H, m), 8.12 (1 H, d), 8.48 (1 H, s), 8.63 (1 H, s), 8.71 (1 H, s) |

EXAMPLE 98

(2S)-2-(1-(2-chlorophenyl)-1H-pyrazolo[3,4-d]pyrimidin-4-yloxy)-3-isopropoxy-N-(5-methylpyridin-2-yl)propanamide

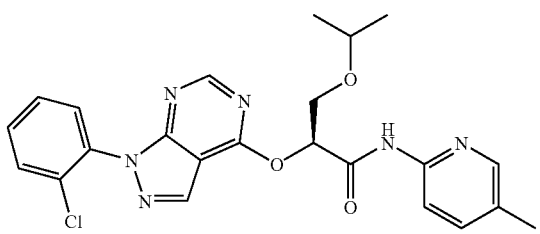

O-(7-Azabenzotriazol-1-yl)-N,N,N',N'-tetramethyluronium hexafluorophosphate (333 mg, 0.88 mmol) was added to (2S)-2-(1-(2-chlorophenyl)-1H-pyrazolo[3,4-d]pyrimidin-4-yloxy)-3-isopropoxypropanoic acid D2 (300 mg, 0.80 mmol), 5-methylpyridin-2-amine (95 mg, 0.88 mmol) and N-ethyldiisopropylamine (0.153 mL, 0.88 mmol) in DCM (15 mL) at room temperature under nitrogen. The resulting solution was stirred at room temperature for 24 hours. The reaction mixture was diluted with DCM (25 mL) and washed with saturated brine (20 mL). The aqueous layer was re-extracted with DCM (30 mL). The combined organics were evaporated to afford crude product. The crude product was purified by flash silica chromatography, elution gradient 20 to 50% EtOAc in isohexane. Pure fractions were evaporated to dryness to afford (2S)-2-(1-(2-chlorophenyl)-1H-pyrazolo[3, 4-d]pyrimidin-4-yloxy)-3-isopropoxy-N-(5-methylpyridin-2-yl)propanamide (175 mg, 47.1%), 10% ee. 143 mg of this material was further purified by chiral preparative HPLC on Chiralcel OJ (50 mm×20 μm), eluent isohexane/EtOH/MeOH 70/15/15 to afford (2S)-2-(1-(2-chlorophenyl)-1H-pyrazolo[3,4-d]pyrimidin-4-yloxy)-3-isopropoxy-N-(5-methylpyridin-2-yl)propanamide (56 mg, >99% ee which eluted after the R enantiomer).

¹H NMR (400 MHz, CDCl₃) 1.17-1.20 (6H, m), 2.29 (3H, s), 3.72 (1H, quin), 4.09 (2H, d), 6.02 (1H, t), 7.44-7.55 (4H, m), 7.61-7.63 (1H, m), 8.09-8.10 (1H, m), 8.13 (1H, d), 8.42 (1H, s), 8.59 (1H, s), 8.69 (1H, s); m/z (ESI)+(M+H)+=467; HPLC $t_R$=2.63 min

EXAMPLE 99

(2R)-2-(1-(2-chlorophenyl)-1H-pyrazolo[3,4-d]pyrimidin-4-yloxy)-3-isopropoxy-N-(5-methylpyridin-2-yl)propanamide

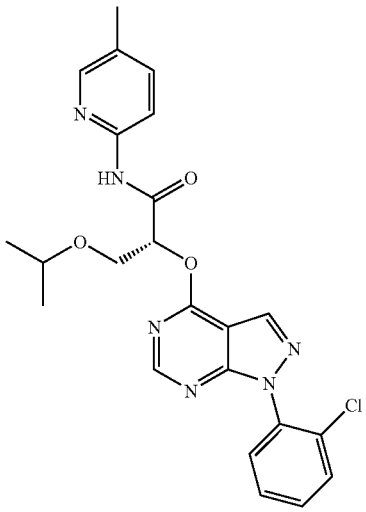

143 mg of (2S)-2-(1-(2-chlorophenyl)-1H-pyrazolo[3,4-d]pyrimidin-4-yloxy)-3-isopropoxy-N-(5-methylpyridin-2-yl)propanamide (10% ee) obtained in the preparation of Example 98 was purified by chiral preparative HPLC on Chiralcel OJ (50 mm×20 μm), eluent isohexane/EtOH/MeOH 70/15/15 to afford (2R)-2-(1-(2-chlorophenyl)-1H-pyrazolo[3,4-d]pyrimidin-4-yloxy)-3-isopropoxy-N-(5-methylpyridin-2-yl)propanamide (60 mg, >99% ee which eluted before the S enantiomer).

$^1$H NMR (400 MHz, CDCl$_3$) 1.17-1.20 (6H, m), 2.29 (3H, s), 3.72 (1H, quin), 4.09 (2H, d), 6.02 (1H, t), 7.44-7.55 (4H, m), 7.61-7.63 (1H, m), 8.09-8.10 (1H, m), 8.13 (1H, d), 8.42 (1H, s), 8.59 (1H, s), 8.69 (1H, s); m/z (ESI)+(M+H)+=467; HPLC t$_R$=2.64 min

EXAMPLE 100

(2S)-2-[1-(2-Chlorophenyl)pyrazolo[4,5-e]pyrimidin-4-yl]oxy-N-(3-methyl-1,2,4-thiadiazol-5-yl)-3-propan-2-yloxypropanamide

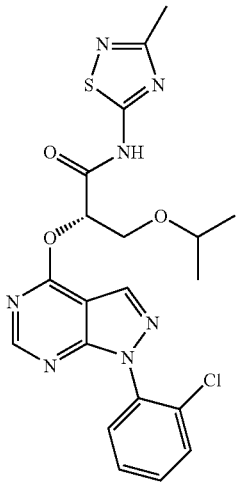

A solution of lithium bis(trimethylsilyl)amide (0.82 mL, 0.82 mmol) was added dropwise to a stirred solution of (S)-2-hydroxy-3-isopropoxy-N-(3-methyl-1,2,4-thiadiazol-5-yl)propanamide (Intermediate C9) (200 mg, 0.82 mmol) in anhydrous THF (5 mL) over a period of 3 minutes under nitrogen. The resulting suspension was stirred at ambient temperature for 10 minutes and then a solution of 4-chloro-1-(2-chlorophenyl)-1H-pyrazolo[3,4-d]pyrimidine (Intermediate B1) in dry THF (1.5 mL) was added dropwise over 1 minute and the reaction heated to 50° C. for 20 hours. The mixture was cooled, diluted with EtOAc (50 mL), washed with water (10 mL) and brine (10 mL). The combined aqueous extracts were acidified with 1M citric acid and extracted with EtOAc (2×20 mL), the combined organic extracts were dried (MgSO$_4$) and evaporated. The resulting residue was purified by flash silica chromatography, eluting with an increasing gradient of 60 to 100% EtOAc in isohexane to afford (2S)-2-[1-(2-chlorophenyl)pyrazolo[4,5-e]pyrimidin-4-yl]oxy-N-(3-methyl-1,2,4-thiadiazol-5-yl)-3-propan-2-yloxypropanamide (300 mg, 78%).

$^1$H NMR (400 MHz, CDCl$_3$) δ 1.18 (3H, d), 1.21 (3H, d), 2.55 (3H, s), 3.68-3.76 (1H, m), 4.10 (2H, d), 6.14 (1H, t), 7.45-7.57 (3H, m), 7.62 (1H, dd), 8.40 (1H, s), 8.57 (1H, s), 9.98 (1H, s). m/z (ESI−) (M−H)−=472; HPLC t$_R$=2.33 min.

EXAMPLE 101

(2S)-2-(1-(2-Chlorophenyl)-1H-pyrazolo[3,4-d]pyrimidin-4-yloxy)-3-methoxy-N-(3-methyl-1,2,4-thiadiazol-5-yl)propanaide

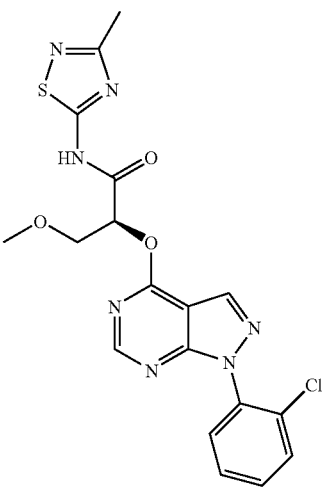

A solution of lithium bis(trimethylsilyl)amide (0.947 mL, 0.95 mmol) was added dropwise to a stirred solution of (S)-2-hydroxy-3-methoxy-N-(3-methyl-1,2,4-thiadiazol-5-yl)propanamide (Intermediate E1) (187 mg, 0.86 mmol) in anhydrous THF (5 mL) over a period of 3 minutes under nitrogen. The resulting suspension was stirred at ambient temperature for 10 minutes and then a solution of 4-chloro-1-(2-chlorophenyl)-1H-pyrazolo[3,4-d]pyrimidine (Intermediate B1) (228 mg, 0.86 mmol) in dry THF (1.5 mL) added dropwise over 1 minute and the reaction heated to 50° C. for 16 hours. Reaction was cooled, diluted with EtOAc (50 mL), washed with 1M citric acid (25 mL) and brine (25 mL), dried (MgSO$_4$), and evaporated. The residue was purified by flash silica chromatography, elution gradient 0 to 100% EtOAc in isohexane to afford (2S)-2-(1-(2-chlorophenyl)-1H-pyrazolo[3,4-d]pyrimidin-4-yloxy)-3-methoxy-N-(3-methyl-1,2,4-thiadiazol-5-yl)propanamide (44 mg, 11%) $^1$H NMR (400 MHz, CDCl$_3$) δ 2.48 (3H, s), 3.41 (3H, s), 4.01 (2H, ddd), 6.13 (1H, t), 7.38-7.48 (3H, m), 7.56 (1H, dd), 8.34 (1H, s), 8.51 (1H, s), 9.90 (1H, s). m/z (ESI+) (M+H)+=446.08; HPLC t$_R$=2.02 min.

EXAMPLE 102

(2S)-2-(1-(3-Chloropyridin-2-yl)-1H-pyrazolo[3,4-d]pyrimidin-4-yloxy)-4-methoxy-N-(5-methylpyridin-2-yl)butanamide

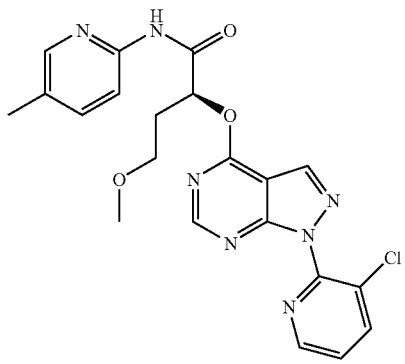

4-Chloro-1-(3-chloropyridin-2-yl)-1H-pyrazolo[3,4-d]pyrimidine (Intermediate B15) (219 mg, 0.82 mmol) was added to sodium methanesulfinate (75 mg, 0.73 mmol) and sodium hydride (38.0 mg, 0.95 mmol) in THF (5 mL) at 23° C. under nitrogen. The resulting suspension was stirred at ambient temperature for 5 minutes. (S)-2-Hydroxy-4-methoxy-N-(5-methylpyridin-2-yl)butanamide (Intermediate F1) (142 mg, 0.63 mmol) was added dropwise and the suspension was stirred at ambient temperature for a further 30 minutes. The mixture was diluted with EtOAc (50 mL), and washed sequentially with water (2×25 mL) and saturated brine (25 mL). The organic layer was dried (MgSO$_4$) and evaporated. The residue was purified by flash silica chromatography, elution gradient 40 to 100% EtOAc in isohexane to afford (2S)-2-(1-(3-chloropyridin-2-yl)-1H-pyrazolo[3,4-d]pyrimidin-4-yloxy)-4-methoxy-N-(5-methylpyridin-2-yl)butanamide (250 mg, 87%).

1H NMR (400 MHz, CDCl$_3$) δ 2.29 (3H, s), 2.42-2.47 (2H, m), 3.33 (3H, s), 3.64 (2H t), 5.96-5.99 (1H, m), 7.45-7.48 (1H, m), 7.50-7.53 (1H, m), 7.99-8.02 (1H, m), 8.08-8.09 (1H, m), 8.12 (1H d), 8.43 (1H, s), 8.60-8.63 (3H, m); m/z (ESI+) (M+H)+=454; HPLC t$_R$=1.77 min.

EXAMPLE 103

(2S)-2-[1-(3-Chloropyridin-2-yl)pyrazolo[4,5-e]pyrimidin-4-yl]oxy-3-ethoxy-N-(5-methylpyridin-2-yl)propanamide

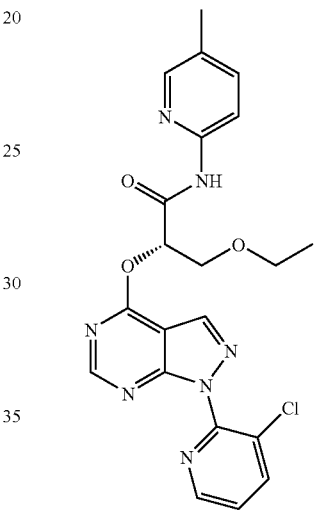

A solution of lithium bis(trimethylsilyl)amide (3.26 mL, 3.26 mmol) was added dropwise to a stirred solution of (S)-3-ethoxy-2-hydroxy-N-(5-methylpyridin-2-yl)propanamide (Intermediate G1) (730 mg, 3.26 mmol) in anhydrous THF (15 mL) over a period of 3 minutes under nitrogen. The resulting suspension was stirred at ambient temperature for 10 minutes and then a solution of 4-chloro-1-(3-chloropyridin-2-yl)-1H-pyrazolo[3,4-d]pyrimidine (Intermediate B15) (866 mg, 3.26 mmol) in dry THF (3 mL) added dropwise over 1 minute and the reaction heated to 50° C. for 3hours. The reaction mixture was diluted with EtOAc (50 mL), and washed sequentially with water (2×25 mL) and saturated brine (25 mL). The organic layer was dried (MgSO$_4$) and evaporated. The residue was purified by flash silica chromatography eluting with EtOAc to afford (2S)-2-[1-(3-chloropyridin-2-yl)pyrazolo[4,5-e]pyrimidin-4-yl]oxy-3-ethoxy-N-(5-methylpyridin-2-yl)propanamide (930 mg, 63%). $^1$H NMR (400 MHz, CDCl$_3$) δ 1.20 (3H, t), 2.29 (3H, s), 3.59-3.67 (2H, m), 4.06-4.17 (2H, m), 6.06-6.08 (1H, m), 7.47 (1H, dd), 7.53 (1H, dd), 8.00 (1H, dd), 8.09-8.10 (1H, m), 8.13 (1H, d), 8.48 (1H, s), 8.62 (1H, dd), 8.63 (1H, s), 8.65 (1H, s); m/z (ESI+) (M+H)+=454.3; HPLC tR=1.97 min.

EXAMPLE 104

(2S)-2-[1-(3-Chloropyridin-2-yl)pyrazolo[4,5-e]pyrimidin-4-yl]oxy-3-ethoxy-N-(5-methylpyrazin-2-yl)propanamide

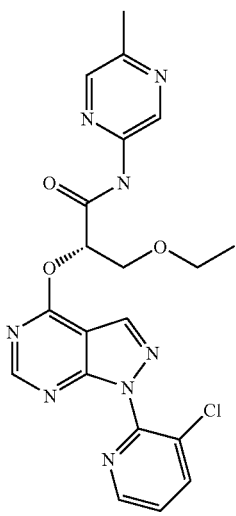

A solution of lithium bis(trimethylsilyl)amide (1.40 mL, 1.40 mmol) was added dropwise to a stirred solution of (S)-3-ethoxy-2-hydroxy-N-(5-methylpyrazin-2-yl)propanamide (Intermediate H1) (315 mg, 1.40 mmol) in THF (15 mL) over a period of 3 minutes under nitrogen. The resulting suspension was stirred at ambient temperature for 10 minutes and then a solution of 4-chloro-1-(3-chloropyridin-2-yl)-1H-pyrazolo[3,4-d]pyrimidine (Intermediate B15) (372 mg, 1.40 mmol) in anhydrous THF (3 mL) added dropwise over 1 minute and the reaction heated to 50° C. for 3 hours. The reaction mixture was diluted with EtOAc (50 mL), and washed sequentially with water (2×25 mL) and saturated brine (25 mL). The organic layer was dried (MgSO$_4$) and evaporated. The residue was purified by flash silica chromatography eluting with EtOAc to afford (2S)-2-[1-(3-chloropyridin-2-yl)pyrazolo[4,5-e]pyrimidin-4-yl]oxy-3-ethoxy-N-(5-methylpyrazin-2-yl)propanamide (330 mg, 52%). $^1$H NMR (400 MHz, CDCl$_3$) δ 1.24 (3H, t), 2.54 (3H, s), 3.60-3.68 (2H, m), 4.07-4.16 (2H, m), 6.09 (1H, t), 7.47 (1H, dd), 8.01 (1H, dd), 8.12 (1H, d), 8.47 (1H, s), 8.62 (1H, dd), 8.64 (1H, s), 8.66 (1H, s), 9.44 (1H, d); m/z (ESI+) (M+H)+=455; HPLC $t_R$=1.77 min.

EXAMPLE 105

(2S)-2-[1-(2-chlorophenyl)pyrazolo[4,5-e]pyrimidin-4-yl]oxy-3-ethoxy-N-(5-methylpyrazin-2-yl)propanamide

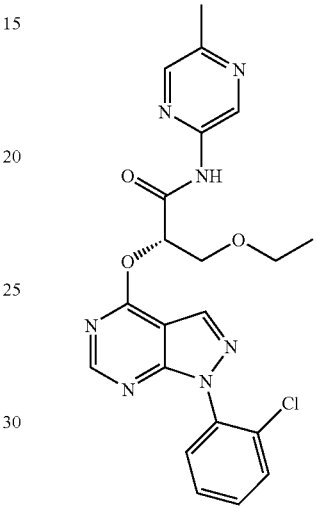

A solution of lithium bis(trimethylsilyl)amide (1.398 mL, 1.40 mmol) was added dropwise to a stirred solution of (S)-3-ethoxy-2-hydroxy-N-(5-methylpyrazin-2-yl)propanamide (Intermediate H1) (315 mg, 1.40 mmol) in anhydrous THF (15 mL) over a period of 3 minutes under nitrogen. The resulting suspension was stirred at ambient temperature for 10 minutes and then a solution of 4-chloro-1-(2-chlorophenyl)-1H-pyrazolo[3,4-d]pyrimidine (Intermediate B1) (371 mg, 1.40 mmol) in dry THF (3 mL) added dropwise over 1 minute and the reaction heated to 50° C. for 3 hours. The reaction mixture was diluted with EtOAc (50 mL), and washed sequentially with water (2×25 mL) and saturated brine (25 mL). The organic layer was dried (MgSO$_4$) and evaporated. The residue was purified by flash silica chromatography with EtOAc to afford (2S)-2-[1-(2-chlorophenyl)pyrazolo[4,5-e]pyrimidin-4-yl]oxy-3-ethoxy-N-(5-methylpyrazin-2-yl)propanamide (460 mg, 72%).

$^1$H NMR (400 MHz, CDCl$_3$) δ 1.23 (3H, t), 2.54 (3H, s), 3.61-3.69 (2H, m), 4.07-4.16 (2H, m), 6.09 (1H, t), 7.47-7.55 (3H, m), 7.61-7.63 (1H, m), 8.12 (1H, d), 8.44 (1H, s), 8.60 (1H, s), 8.68 (1H, s), 9.45 (1H, d); m/z (ESI+) (M+H)+= 454.3; HPLC $t_R$=2.16 min.

EXAMPLE 106

(2S)-3-Isopropoxy-N-(5-methylpyrazin-2-yl)-2-(1-(3-methylpyrazin-2-yl)-1H-pyrazolo[3,4-d]pyrimidin-4-yloxy)propanamide

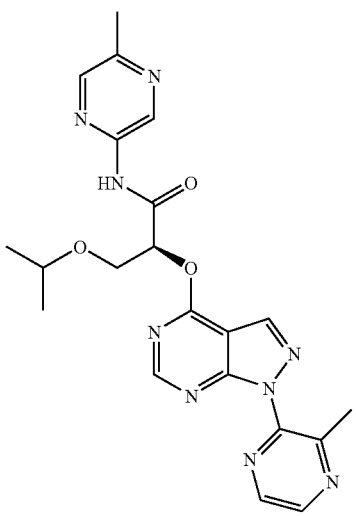

Sodium hydride (22.06 mg, 0.55 mmol) was added to (S)-2-hydroxy-3-isopropoxy-N-(5-methylpyrazin-2-yl)propanamide (Intermediate C8) (110 mg, 0.46 mmol) in anhydrous THF (5 mL) at 0° C. under nitrogen. The resulting solution was stirred at 0° C. for 10 minutes and then 4-chloro-1-(3-methylpyrazin-2-yl)-1H-pyrazolo[3,4-d]pyrimidine (Intermediate I4) (125 mg, 0.51 mmol) in THF (2 mL) was added. The reaction mixture was allowed to warm to room temperature and stirred for 1 hour. Further sodium hydride (22.06 mg, 0.55 mmol) was added and the reaction stirred for another hour at room temperature. The reaction mixture was neutralised with 1M citric acid, and then diluted with water (20 mL) and EtOAc (50 mL). The organic layer was separated and the aqueous layer re-extracted with EtOAc (2×50 mL). The combined organics were washed with saturated brine (75 mL), dried (MgSO$_4$), filtered and evaporated. The residue was purified by flash silica chromatography, elution gradient 50 to 100% EtOAc in isohexane to afford (2S)-3-isopropoxy-N-(5-methylpyrazin-2-yl)-2-(1-(3-methylpyrazin-2-yl)-1H-pyrazolo[3,4-d]pyrimidin-4-yloxy)propanamide (98 mg, 47.4%).

$^1$H NMR (400 MHz, CDCl$_3$) 1.20 (6H t), 2.54 (3H, s), 2.61 (3H, s), 3.71-3.77 (1H, m), 4.10 (2H d), 6.04 (1H t), 8.12 (1H, s), 8.45 (1H, s), 8.51-8.52 (1H, m), 8.64-8.66 (2H, m), 8.71 (1H, s), 9.43 (1H, s), m/z (ESI+) (M+H)+=450; HPLC t$_R$=1.73 min.

EXAMPLE 107

(S)-3-Methoxy-N-(5-methylpyridin-2-yl)-2-(1-phenyl-1H-pyrazolo[3,4-d]pyrimidin-4-yloxy)propanamide

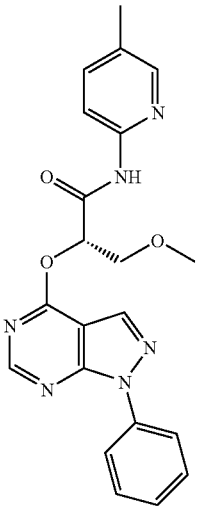

Palladium (10% on Carbon) (25.5 mg, 0.24 mmol) was added to (2S)-2-(1-(2-chlorophenyl)-1H-pyrazolo[3,4-d]pyrimidin-4-yloxy)-3-methoxy-N-(5-methylpyridin-2-yl)propanamide (Example 3) (105 mg, 0.24 mmol) in methanol (2.5 mL) at ambient temperature under nitrogen. This was then purged with hydrogen and the resulting solution was stirred at ambient temperature for 24 hours. The mixture was filtered through celite and evaporated. The residue was purified by flash silica chromatography eluting with 0 to 100% EtOAc in isohexane to afford (S)-3-methoxy-N-(5-methylpyridin-2-yl)-2-(1-phenyl-1H-pyrazolo[3,4-d]pyrimidin-4-yloxy)propanamide (20.0 mg, 20.7%).

$^1$NMR (400 MHz, DMSO) δ 2.24 (s, 3H), 3.39 (s, 3H), 3.88-4.07 (m, 2H), 5.92-5.98 (m, 1H), 7.38-7.44 (m, 1H), 7.56-7.62 (m, 3H), 7.85-7.90 (m, 1H), 8.15-8.20 (m, 3H), 8.62 (s, 1H), 8.66 (s, 1H), 10.84 (s, 1H); m/z (ESI+) (M+H)+= 405.35

EXAMPLE 108

2-[1-(2-Chlorophenyl)pyrazolo[4,5-e]pyrimidin-4-yl]oxy-3-isopropoxy-N-pyrazin-2-yl-propanamide

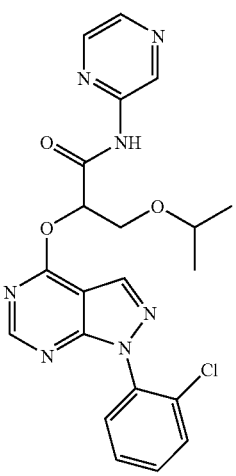

O-(7-Azabenzotriazol-1-yl)-N,N,N',N'-tetramethyluronium hexafluorophosphate (333 mg, 0.88 mmol) was added to (2S)-2-(1-(2-chlorophenyl)-1H-pyrazolo[3,4-d]pyrimidin-4-yloxy)-3-isopropoxypropanoic acid (Intermediate D2) (300 mg, 0.80 mmol), aminopyrazine (CAS no. 5049-61-6) (84 mg, 0.88 mmol) and N-ethyldiisopropylamine (0.153 mL, 0.88 mmol) in DCM (15 mL) at room temperature under nitrogen. The resulting solution was stirred at room temperature for 24 hours. The reaction mixture was diluted with DCM (10 mL) and water (10 mL) and the organic phase separated using a phase separation cartridge and evaporated. The residue was purified using reverse phase chromatography, eluting with 25-75% acetonitrile in water to give 2-[1-(2-chlorophenyl)pyrazolo[4,5-e]pyrimidin-4-yl]oxy-3-isopropoxy-N-pyrazin-2-yl-propanamide (142 mg, 39%). $^1$H NMR (400 MHz, CDCl$_3$) 1.18-1.22 (6H, m), 3.70-3.78 (1H, m), 4.10 (2H, d), 6.08 (1H, t), 7.40-7.50 (2H, m), 7.51-7.55 (1H, m), 7.62-7.64 (1H, m), 8.24 (1H, s), 8.35 (1H, s), 8.60 (1H, s), 8.80 (1H, s), 9.58 (1H, s); (M+H)+=454; HPLC t$_R$=2.26.

The following examples were prepared from the appropriate amine using an analogous procedure.

EXAMPLE 109

2-[1-(2-chlorophenyl)pyrazolo[4,5-e]pyrimidin-4-yl]oxy-3-isopropoxy-N-(5-methyl-1,3,4-thiadiazol-2-yl)propanamide

EXAMPLE 110

2-[1-(2-chlorophenyl)pyrazolo[4,5-e]pyrimidin-4-yl]oxy-3-isopropoxy-N-(5-methylisoxazol-3-yl)propanamide

EXAMPLE 111

2-[1-(2-chlorophenyl)pyrazolo[4,5-e]pyrimidin-4-yl]oxy-3-isopropoxy-N-(5-methylthiazol-2-yl)propanamide

EXAMPLE 112

2-[1-(2-chlorophenyl)pyrazolo[4,5-e]pyrimidin-4-yl]oxy-N-(5-fluoro-2-pyridyl)-3-isopropoxy-propanamide

EXAMPLE 113

2-[1-(2-chlorophenyl)pyrazolo[4,5-e]pyrimidin-4-yl]oxy-N-(5-cyano-2-pyridyl)-3-isopropoxy-propanamide

EXAMPLE 114

2-[1-(2-chlorophenyl)pyrazolo[4,5-e]pyrimidin-4-yl]oxy-3-isopropoxy-N-(1,2,4-thiadiazol-5-yl)propanamide

EXAMPLE 115

2-[1-(2-chlorophenyl)pyrazolo[4,5-e]pyrimidin-4-yl]oxy-N-(5-chloro-2-pyridyl)-3-isopropoxy-propanamide

EXAMPLE 116

2-[1-(2-chlorophenyl)pyrazolo[4,5-e]pyrimidin-4-yl]oxy-3-isopropoxy-N-(4-methyl-2-pyridyl)propanamide

EXAMPLE 117

2-[1-(2-chlorophenyl)pyrazolo[4,5-e]pyrimidin-4-yl]oxy-3-isopropoxy-N-(1,3,4-thiadiazol-2-yl)propanamide

EXAMPLE 118

2-[1-(2-chlorophenyl)pyrazolo[4,5-e]pyrimidin-4-yl]oxy-3-isopropoxy-N-(2-pyridyl)propanamide

EXAMPLE 119

2-[1-(2-chlorophenyl)pyrazolo[4,5-e]pyrimidin-4-yl]oxy-3-isopropoxy-N-isoxazol-3-yl-propanamide

EXAMPLE 120

2-[1-(2-chlorophenyl)pyrazolo[4,5-e]pyrimidin-4-yl]oxy-3-isopropoxy-N-pyrimidin-4-yl-propanamide

| Example no. | Structure | M/Z | $^1$H nmr data (400 MHz, CDCl$_3$) |
|---|---|---|---|
| 109 | 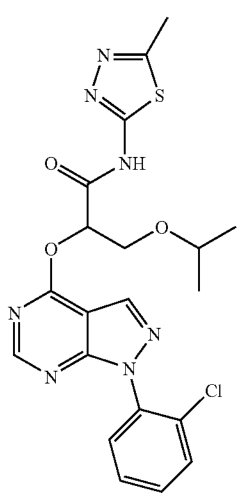 | MH– = 472<br>t$_R$ = 1.47 min. | 1.18-1.22 (6 H, m), 3.38 (3 H, s), 3.70-3.76 (1 H, m), 4.10 (2 H, d), 6.1 (1 H, t), 7.45-7.50 (2 H, m), 7.50-7.55 (1 H, m), 7.60-7.62 (1 H, m), 8.40 (1 H, s), 8.60 (1 H, s) |

-continued
| Example no. | Structure | M/Z | ¹H nmr data (400 MHz, CDCl₃) |
|---|---|---|---|
| 110 | 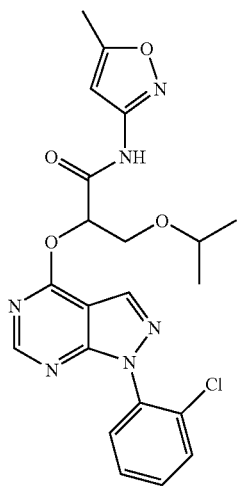 | (M + H)+ = 457<br>t_R = 2.52 min. | 1.18-1.22 (6 H, m), 2.40 (3 H, s), 3.70-3.76 (1 H, m), 4.08 (2 H, d), 6.0 (1 H, t), 7.45-7.50 (2 H, m), 7.50-7.55 (1 H, m), 7.60-7.62 (1 H, m), 8.40 (1 H, s), 8.60 (1 H, s), 8.78 (1 H, m). |
| 111 | 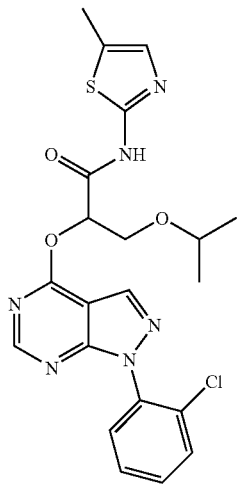 | MH− = 471<br>t_R = 2.32 min | 1.18-1.22 (6 H, m), 2.40 (3 H, s), 3.65-3.74 (1 H, m), 4.10 (2 H, d), 6.1 (1 H, t), 7.10 (1 H, s), 7.45-7.50 (2 H, m), 7.50-7.55 (1 H, m), 7.60-7.62 (1 H, m), 8.40 (1 H, s), 8.60 (1 H, s). |
| 112 | 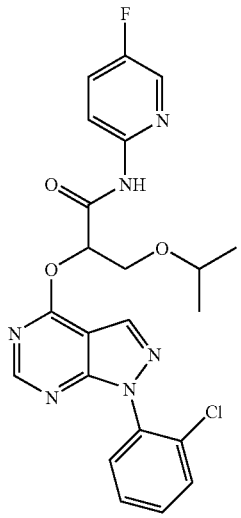 | (M + H)+ = 471<br>t_R = 2.68 min | 1.18-1.22 (6 H, m), 3.70-3.76 (1 H, m), 4.10 (2 H, d), 6.0 (1 H, t), 7.45-7.55 (3 H, m), 7.61-7.63 (1 H, m), 8.1 (1 H, m), 8.24 (1 H, m), 8.42 (1 H, s), 8.58 (1 H, s), 8.8 (1 H, s). |

-continued
| Example no. | Structure | M/Z | ¹H nmr data (400 MHz, CDCl₃) |
|---|---|---|---|
| 113 | 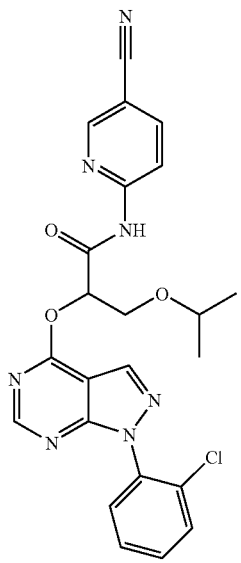 | MH− = 476<br>$t_R$ = 2.66 | 1.18-1.22 (6 H, m), 3.70-3.78 (1 H, m), 4.10 (2 H, d), 6.0 (1 H, t), 7.45-7.55 (2 H, m), 7.60-7.63 (1 H, m), 7.94-7.98 (1 H, m), 8.38 (1 H, d), 8.40 (1 H, s), 8.56-8.58 (2 H, m), 9.10 (1 H, s). |
| 114 | 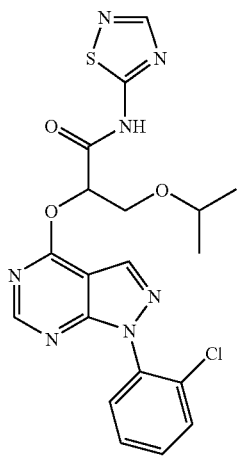 | MH− = 458<br>$t_R$ = 1.31 min | 1.18-1.22 (6 H, m), 3.68-3.76 (1 H, m), 4.10 (2 H, d), 6.15 (1 H, t), 7.45-7.50 (2 H, m), 7.50-7.55 (1 H, m), 7.60-7.62 (1 H, m), 8.37 (2 H, m), 8.60 (1 H, s), 10.44 (1 H, s) |
| 115 | 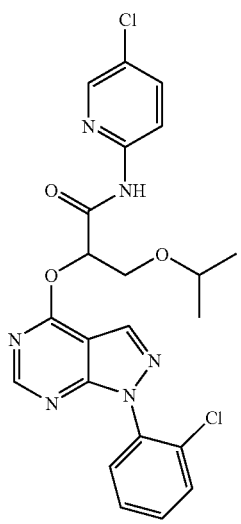 | (M + H)+ = 488<br>$t_R$ = 2.92 min | 1.18-1.22 (6 H, m), 3.70-3.76 (1 H, m), 4.10 (2 H, d), 6.0 (1 H, t), 7.41-7.50 (2 H, m), 7.55 (1 H, m), 7.61 (1 H, m), 7.6-7.70 (1 H, d), 8.2 (2 H, d), 8.40 (1 H, s), 8.60 (1 H, s), 8.70 (1 H, s) |

-continued
| Example no. | Structure | M/Z | ¹H nmr data (400 MHz, CDCl₃) |
|---|---|---|---|
| 116 | 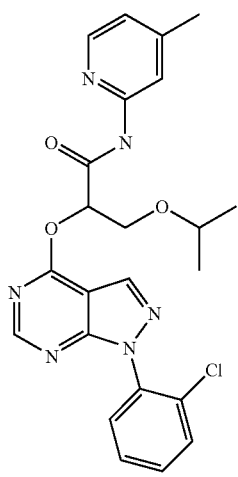 | MH− = 465<br>$t_R$ = 2.66 min | 1.18-1.22 (6 H, m), 2.35 (3 H, s), 3.70-3.76 (1 H, m), 4.10 (2 H, d), 6.0 (1 H, t), 6.80 (1 H, d), 7.45-7.55 (3 H, m), 7.61-7.63 (1 H, m), 8.1 (1 H, s), 8.14 (1 H, d), 8.42 (1 H, s), 8.60 (1 H, s), 8.70 (1 H, s) |
| 117 | 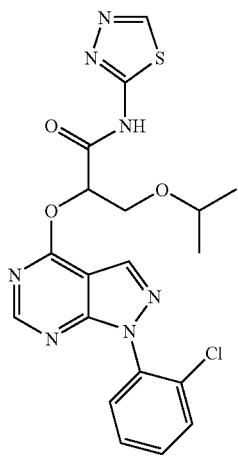 | MH− = 458<br>$t_R$ = 1.23 min | 1.18-1.22 (6 H, m), 3.68-3.76 (1 H, m), 4.10 (2 H, d), 6.15 (1 H, t), 7.45-7.50 (3 H, m), 7.60 (1 H, m), 8.40 (1 H, s), 8.58 (1 H, s), 8.85 (1 H, s) |
| 118 | 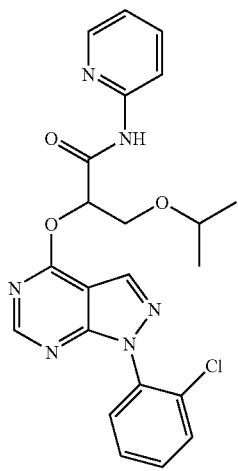 | (M + H)+ = 453<br>$t_R$ = 2.53 min | 1.19-1.25 (6 H, m), 3.70-3.75 (1 H, m), 4.10 (2 H, d), 6.0 (1 H, t), 7.0-7.1 (1 H, m), 7.45-7.55 (2 H, m), 7.56-7.59 (1 H, m), 7.64-7.68 (1 H, m), 7.70-7.72 (1 H, m), 8.20-8.40 (2 H, m), 8.40 (1 H, s), 8.60 (1 H, s), 8.75 (1 H, s) |

| Example no. | Structure | M/Z | ¹H nmr data (400 MHz, CDCl₃) |
|---|---|---|---|
| 119 | 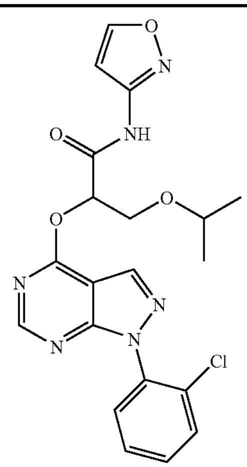 | (M + H)+ = 443<br>$t_R$ = 2.36 min | 1.18-1.22 (6 H, m), 3.68-3.76 (1 H, m), 4.10 (2 H, d), 6.17 (1 H, t), 7.10 (1 H, s), 7.45-7.50 (3 H, m), 7.60 (1 H, m), 8.30 (1 H, s), 8.40 (1 H, s), 8.58 (1 H, s), 8.85 (1 H, s) |
| 120 | 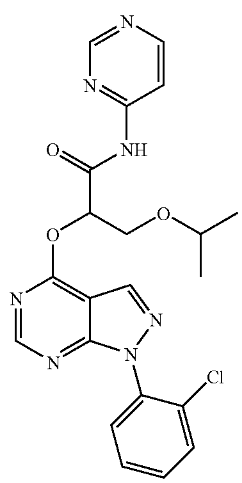 | (M + H)+ = 454<br>$t_R$ = 1.58 min | 1.19-1.25 (6 H, m), 3.70-3.77 (1 H, m), 4.10 (2 H, d), 5.98 (1 H, t), 7.0-7.1 (1 H, m), 7.45-7.55 (2 H, m), 7.56-7.59 (1 H, m), 7.64-7.68 (1 H, m), 7.70-7.72 (1 H, m), 8.19 (2 H, d), 8.41 (1 H, s), 8.60 (1 H, s). |

The examples below were prepared from the examples above by chiral chromatography using either Chiralcel OJ or Chiralcel AD as a chiral stationary phase and eluting with an appropriate mixture of isohexane, ethanol, methanol and triethylamine.

EXAMPLE 111a (2S)-2-[1-(2-chlorophenyl)pyrazolo[4,5-e]pyrimidin-4-yl]oxy-3-isopropoxy-N-(5-methylthiazol-2-yl)propanamide

EXAMPLE 112a (2S)-2-[1-(2-chlorophenyl)pyrazolo[4,5-e]pyrimidin-4-yl]oxy-N-(5-fluoro-2-pyridyl)-3-isopropoxy-propanamide

EXAMPLE 113a (2S)-2-[1-(2-chlorophenyl)pyrazolo[4,5-e]pyrimidin-4-yl]oxy-N-(5-cyano-2-pyridyl)-3-isopropoxy-propanamide

EXAMPLE 115a (2S)-2-[1-(2-chlorophenyl)pyrazolo[4,5-e]pyrimidin-4-yl]oxy-N-(5-chloro-2-pyridyl)-3-isopropoxy-propanamide EXAMPLE 118a
(2S)-2-[1-(2-chlorophenyl)pyrazolo[4,5-e]pyrimidin-4-yl]oxy-3-isopropoxy-N-(2-pyridyl)propanamide
| Example no. | Structure | M/Z | $^1$H nmr data (400 MHz, CDCl$_3$) |
|---|---|---|---|
| 111a | 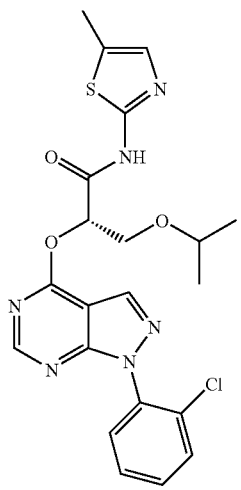 | MH− = 471<br>$t_R$ = 2.32 min | 1.17-1.20 (6 H, m), 2.40 (3 H, s), 3.70-3.76 (1 H, m), 4.10 (2 H, d), 6.1 (1 H, t), 7.10 (1 H, s), 7.45-7.50 (2 H, m), 7.50-7.55 (1 H, m), 7.60-7.62 (1 H, m), 8.37 (1 H, s), 8.57 (1 H, s). |
| 112a | 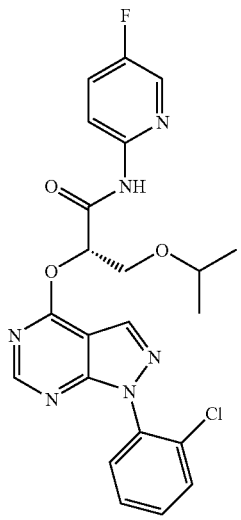 | (M + H)+ = 471<br>$t_R$ = 2.68 min | 1.18-1.22 (6 H, m), 3.70-3.76 (1 H, m), 4.10 (2 H, d), 6.0 (1 H, t), 7.45-7.55 (3 H, m), 7.61-7.63 (1 H, m), 8.1 (1 H, m), 8.24 (1 H, m), 8.42 (1 H, s), 8.58 (1 H, s), 8.8 (1 H, s). |

| Example no. | Structure | M/Z | ¹H nmr data (400 MHz, CDCl₃) |
|---|---|---|---|
| 113a | 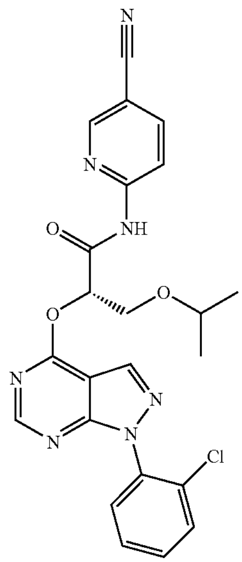 | MH− = 476<br>$t_R$ = 2.66 min | 1.19-1.25 (6 H, m), 3.70-3.75 (1 H, m), 4.10 (2 H, d), 6.0 (1 H, t), 7.45-7.55 (2 H, m), 7.60-7.63 (1 H, m), 7.94-7.97 (1 H, m), 8.38 (1 H, d), 8.40 (1 H, s), 8.56-8.58 (2 H, m), 9.10 (1 H, s). |
| 115a | 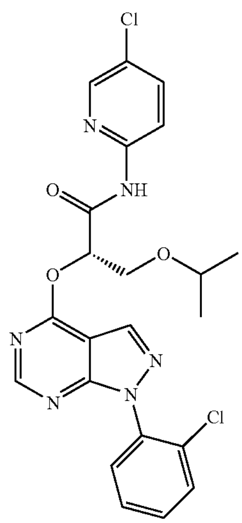 | (M + H)+ = 488<br>$t_R$ = 2.92 min | 1.11-1.15 (6 H, m), 3.60-3.65 (1 H, m), 4.0 (2 H, d), 5.94 (1 H, t), 7.41-7.50 (3 H, m), 7.54 (1 H, m) 7.56 (1 H, d), 7.6-7.62 (1 H, m), 8.17 (1 H, s), 8.30 (1 H, s), 8.50 (1 H, s), 8.74 (1 H, s). |
| 118a | 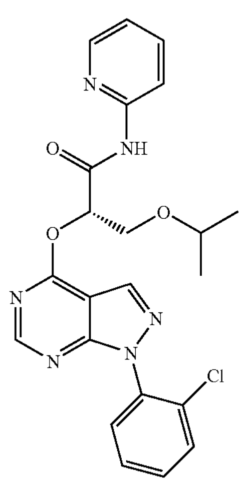 | (M + H)+ = 453<br>$t_R$ = 2.53 min | 1.17-1.20 (6 H, m), 3.70-3.76 (1 H, m), 4.10 (2 H, d), 6.02 (1 H, t), 7.0-7.1 (1 H, m), 7.45-7.49 (2 H, m), 7.54-7.57 (1 H, m), 7.64-7.68 (1 H, m), 7.70-7.73 (1 H, m), 8.20-8.40 (2 H, m), 8.40 (1 H, s), 8.60 (1 H, s), 8.70 (1 H, s). |

EXAMPLE 125

(2S)-3-Isopropoxy-N-(5-methylpyridin-2-yl)-2-(1-(3-methylpyridin-2-yl)-1H-pyrazolo[3,4-d]pyrimidin-4-yloxy)propanamide

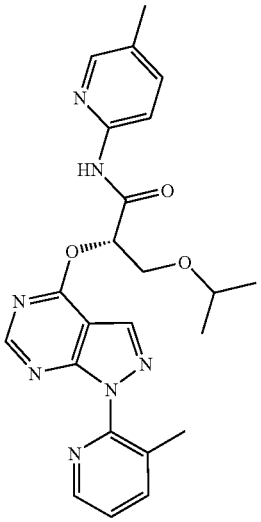

A 2M solution of trimethylaluminium in hexane (0.404 mL, 0.81 mmol) was added to 5-methylpyridin-2-amine (84 mg, 0.77 mmol) in toluene (22 mL) at 5° C. under nitrogen. The resulting solution was stirred at 5° C. for 20 minutes. (2S)-Methyl 3-isopropoxy-2-(1-(3-methylpyridin-2-yl)-1H-pyrazolo[3,4-d]pyrimidin-4-yloxy)propanoate (300 mg, 0.70 mmol) (Intermediate J5) in toluene (6 mL) was added dropwise at 5° C. After the addition was complete, the solution was allowed to warm to ambient temperature and was then heated to reflux for 16 hours. The solution was allowed to cool to ambient temperature. The reaction mixture was concentrated, diluted with EtOAc (100 mL) and washed sequentially with 1M citric acid (50 mL), then saturated brine (50 mL). The organic layer was separated, dried (MgSO$_4$) and evaporated. The residue was purified by flash silica chromatography, eluting with EtOAc to afford (2S)-3-isopropoxy-N-(5-methylpyridin-2-yl)-2-(1-(3-methylpyridin-2-yl)-1H-pyrazolo[3,4-d]pyrimidin-4-yloxy)propanamide (160 mg, 51%). $^1$H NMR (400 MHz, CDCl$_3$) δ 1.09-1.12 (6H, m), 2.23 (3H, s), 2.26 (3H, s), 3.62-3.68 (1H, m), 4.00-4.09 (2H, m), 5.97 (1H, t), 7.30-7.33 (1H, m), 7.56-7.59 (1H, d), 7.70-7.73 (1H, d), 8.01-8.01 (1H, s), 8.21 (1H, d), 8.44 (1H, s), 8.46 (1H, m) 8.53 (1H, s), 9.5 (1H, broad s); m/z (ESI+) (M+H)+=448; HPLC $t_R$=1.98 min.

EXAMPLE 126

(2S)-3-Isopropoxy-N-(5-methylpyridin-2-yl)-2-(1-(3-(trifluoromethyl)pyridin-2-yl)-1H-pyrazolo[3,4-d]pyrimidin-4-yloxy)propanamide

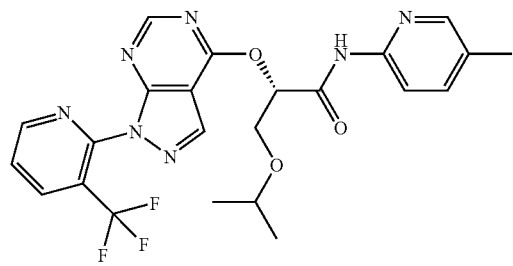

(2S)-2-(1-(5-Chloro-3-(trifluoromethyl)pyridin-2-yl)-1H-pyrazolo[3,4-d]pyrimidin-4-yloxy)-3-isopropoxy-N-(5-methylpyridin-2-yl)propanamide (Intermediate K6) (1 g, 0.73 mmol), and 10% Palladium on Carbon (100 mg, 0.09 mmol) in MeOH (25 mL) were stirred under an atmosphere of hydrogen for 16 hours. The reaction mixture was filtered through celite. 10% Palladium on Carbon (100 mg, 0.09 mmol) added and stirred under an atmosphere of hydrogen for a further 16 hours. The reaction mixture was filtered through celite and evaporated. The residue was purified by flash silica chromatography, elution gradient 1 to 5% MeOH in DCM to afford (2S)-3-isopropoxy-N-(5-methylpyridin-2-yl)-2-(1-(3-(trifluoromethyl)pyridin-2-yl)-1H-pyrazolo[3,4-d]pyrimidin-4-yloxy)propanamide (0.173 g, 47%). $^1$H NMR (400 MHz, DMSO) δ 1.08-1.14 (6H, m), 2.24 (3H, s), 3.73-3.79 (1H, m), 3.96-4.05 (2H, m), 5.90 (1H, s), 7.57-7.60 (1H, m), 7.86-7.90 (1H, m), 7.94-7.98 (1H, m), 8.17 (1H, s), 8.55 (1H, s), 8.58-8.61 (1H, m), 8.65 (1H, s), 8.97-9.00 (1H, m), 10.82 (1H, s). m/z (ESI+) (M+H)+=502; HPLC $t_R$=2.30 min.

The following Examples were prepared using a method analogous to that described for Example 125 using the appropriate ester and arylamine.

EXAMPLE 127

(2S)-2-[1-(3-chloro-2-pyridyl)pyrazolo[4,5-e]pyrimidin-4-yl]oxy-3-isopropoxy-N-(6-methylpyridazin-3-yl)propanamide

EXAMPLE 127a (2S)—N-(5-cyanopyridin-2-yl)-3-isopropoxy-2-(1-(3-methylpyridin-2-yl)-1H-pyrazolo[3,4-d]pyrimidin-4-yloxy)propanamide

EXAMPLE 127b (2S)—N-(5-chloropyridin-2-yl)-3-isopropoxy-2-(1-(3-methylpyridin-2-yl)-1H-pyrazolo[3,4-d]pyrimidin-4-yloxy)propanamide

EXAMPLE 127c (2S)-2-[1-(3-chloro-2-pyridyl)pyrazolo[4,5-e]pyrimidin-4-yl]oxy-N-(5-cyano-2-pyridyl)-3-ethoxy-propanamide

EXAMPLE 127d (2S)-2-[1-(3-chloro-2-pyridyl)pyrazolo[4,5-e]pyrimidin-4-yl]oxy-3-ethoxy-N-(5-fluoro-2-pyridyl)propanamide

EXAMPLE 127e (2S)-2-[1-(3-chloro-2-pyridyl)pyrazolo[4,5-e]pyrimidin-4-yl]oxy-3-ethoxy-N-(2-pyridyl)propanamide

EXAMPLE 127f (2S)-2-[1-(3-chloro-2-pyridyl)pyrazolo[4,5-e]pyrimidin-4-yl]oxy-3-ethoxy-N-pyrimidin-4-yl-propanamide

EXAMPLE 127g (2S)—N-(5-chloro-2-pyridyl)-2-[1-(3-chloro-2-pyridyl)pyrazolo[4,5-e]pyrimidin-4-yl]oxy-3-ethoxy-propanamide

EXAMPLE 127h (2S)-2-[1-(3-chloro-2-pyridyl)pyrazolo[4,5-e]pyrimidin-4-yl]oxy-N-(4-cyanothiazol-2-yl)-3-isopropoxy-propanamide

EXAMPLE 127i (2S)—N-(5-chloro-2-pyridyl)-2-[1-(3-chloro-2-pyridyl)pyrazolo[4,5-e]pyrimidin-4-yl]oxy-3-isopropoxy-propanamide

EXAMPLE 127j (2S)-2-[1-(3-chloro-2-pyridyl)pyrazolo[4,5-e]pyrimidin-4-yl]oxy-N-(5-cyano-2-pyridyl)-3-isopropoxy-propanamide

EXAMPLE 127k (2S)-2-[1-(3-chloro-2-pyridyl)pyrazolo[4,5-e]pyrimidin-4-yl]oxy-3-isopropoxy-N-(2-pyridyl)propanamide

EXAMPLE 127l (2S)-2-[1-(3-chloro-2-pyridyl)pyrazolo[4,5-e]pyrimidin-4-yl]oxy-N-(5-fluoro-2-pyridyl)-3-isopropoxy-propanamide

| Example no. | Structure | m/z | $^1$H NMR data (400 MHz) |
|---|---|---|---|
| 127 | 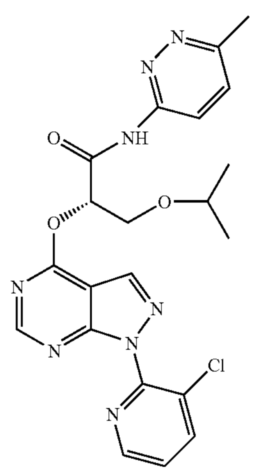 | (M + H)+ = 470<br>$t_R$ = 1.78 min | (CDCl$_3$) 1.18-1.22 (6H, m), 2.03 (3H, s) 3.70-3.78 (1H, m), 4.10 (2H, d), 6.08 (1H, t), 7.30 (1H, d), 7.46-7.50 (1H, m), 8.0 (1H, d), 8.40 (1H, d), 8.60 (2H, m), 9.30 (1H, s). |
| 127a | 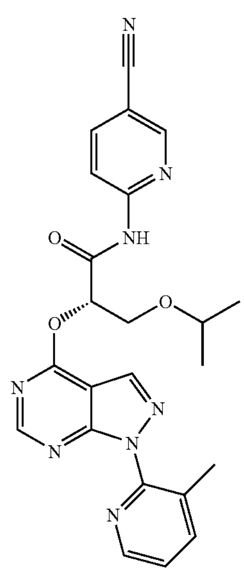 | (M + H)+ = 459;<br>$t_R$ = 2.15 min.<br>ee 89% | (DMSO-d$_6$) 1.10-1.13 (6H, m), 2.11 (3H, s), 3.73-3.80 (1H, m), 3.99-4.08 (2H, m), 5.91 (1H, q), 7.56-7.59 (1H, m), 7.98-8.00 (1H, m), 8.13 (1H, d), 8.23-8.26 (1H, m), 8.50 (1H, t), 8.48-8.55 (1H, m), 8.60 (1H, s), 8.82 (1H, q), 11.50 (1H, s) |

-continued

| Example no. | Structure | m/z | ¹H NMR data (400 MHz) |
|---|---|---|---|
| 127b | 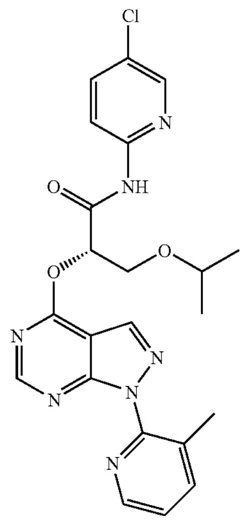 | (M + H)+ = 468; $t_R$ = 2.24 min. ee 89% | (DMSO-d$_6$) 1.11-1.13 (6H, m), 2.11 (3H, s), 3.73-3.79 (1H, m), 3.97-4.06 (2H, m), 5.90 (1H, q), 7.56-7.59 (1H, m), 7.88-7.90 (1H, m), 7.98-8.03 (2H, m), 8.40-8.41 (1H, m), 8.49 (1H, q), 8.53 (1H, s), 8.59 (1H, s), 11.13 (1H, s). |
| 127c | 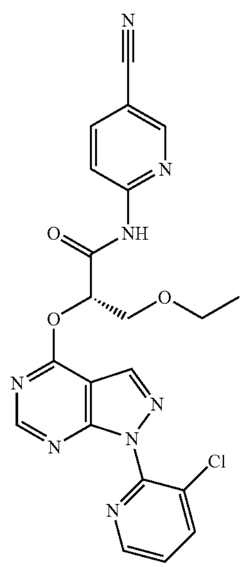 | (M + H)+ = 465.33; $t_R$ = 2.08 min | (DMSO-d$_6$) 1.14 (3H, t), 3.59-3.69 (2H, m), 3.98-4.01 (1H, m), 4.06-4.10 (1H, m), 5.95 (1H, q), 7.72-7.78 (2H, m), 8.02-8.05 (1H, m), 8.34-8.36 (2H, m), 8.58 (1H, s), 8.68 (2H, t), 11.10 (1H, s) |
| 127d | 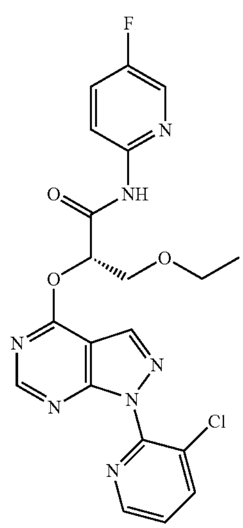 | (M + H)+ = 458.33; $t_R$ = 2.09 min. | (DMSO-d$_6$) 1.14 (3H, t), 3.59-3.69 (2H, m), 4.00-4.03 (1H, m), 4.08-4.12 (1H, m), 5.97 (1H, q), 7.75-7.78 (1H, m), 8.14 (1H, d), 8.24-8.27 (1H, m), 8.34-8.36 (1H, m), 8.58 (1H, s), 8.68 (2H, d), 8.84 (1H, q), 11.55 (1H, s) |

| Example no. | Structure | m/z | 1H NMR data (400 MHz) |
|---|---|---|---|
| 127e | 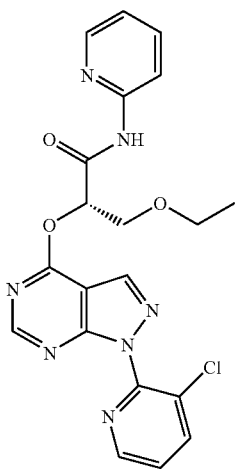 | (M + H)+ = 440.63; $t_R$ = 1.87 min. | (DMSO-$d_6$) 1.15 (3H, t), 3.60-3.69 (2H, m), 3.98-4.02 (1H, m), 4.06-4.11 (1H, m), 5.96-5.97 (1H, m), 7.12-7.15 (1H, m), 7.75-7.78 (2H, m), 7.99 (1H, d), 8.34-8.37 (2H, m), 8.58 (1H, s), 8.69 (2H, q), 10.97 (1H, s) |
| 127f | 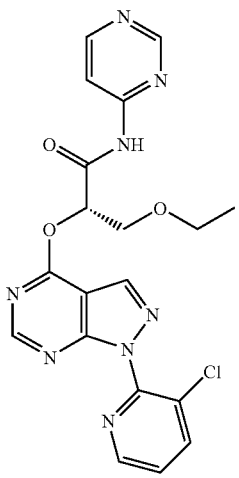 | (M + H)+ = 441.32; $t_R$ = 1.65 min. | (DMSO-$d_6$) 1.14 (3H, t), 3.57-3.7 (2H, m), 4.00-4.03 (1H, m), 4.08-4.12 (1H, m), 5.96 (1H, q), 7.75-7.78 (1H, m), 7.98-8.00 (1H, m), 8.34-8.36 (1H, m), 8.58 (1H, s), 8.66-8.68 (1H, m), 8.67-8.69 (2H, m), 8.94 (1H, d), 11.46 (1H, ) |
| 127g | 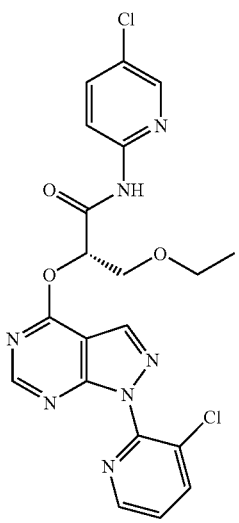 | (M + H)+ = 474.28; $t_R$ = 2.32 min. | (DMSO-$d_6$) 1.13 (3H, t), 3.56-3.69 (2H, m), 3.96-4.00 (1H, m), 4.05-4.09 (1H, m), 5.94 (1H, q), 7.73-7.77 (1H, m), 7.87-7.90 (1H, m), 8.02 (1H, d), 8.32-8.35 (1H, m), 8.39-8.42 (1H, m), 8.56 (1H, s), 8.66-8.68 (2H, m), 1.17 (1H, s) |

-continued
| Example no. | Structure | m/z | ¹H NMR data (400 MHz) |
|---|---|---|---|
| 127h | 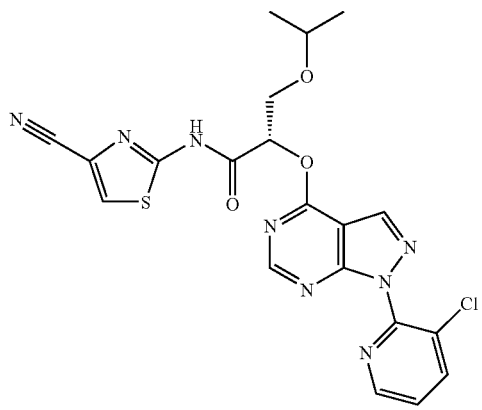 | (M + H)+ = 485; $t_R$ = 2.24 min | (CDCl₃) 1.20-1.24 (6H, m), 3.70-3.77 (1H, m), 4.10 (2H, d), 6.10 (1H, t), 7.47-7.50 (1H, m), 7.67 (1H, s), 8.01-8.03 (1H, m), 8.45 (1H, s), 8.61-8.63 (2H, m). |
| 127i | 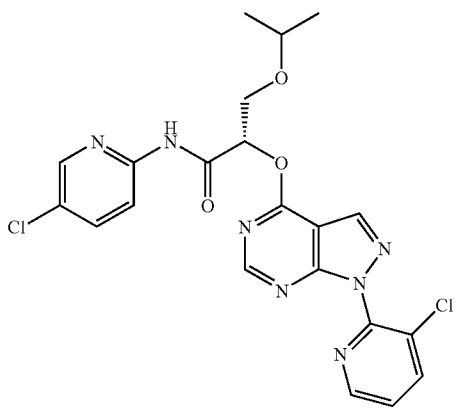 | (M + H)+ = 489; $t_R$ = 2.38 min | (DMSO-d₆) 1.11-1.14 (6H, m), 3.7-3.8 (1H, m), 3.9-4.0 (2H, m), 5.9-5.93 (1H, m), 7.75-7.78 (1H, m), 7.9-7.92 (1H, m), 8.03 (1H, d), 8.33-8.36 (1H, m), 8.40-8.41 (1H, m), 8.56 (1H, m), 8.66-8.69 (2H, m), 11.1 (1, s) |
| 127j | 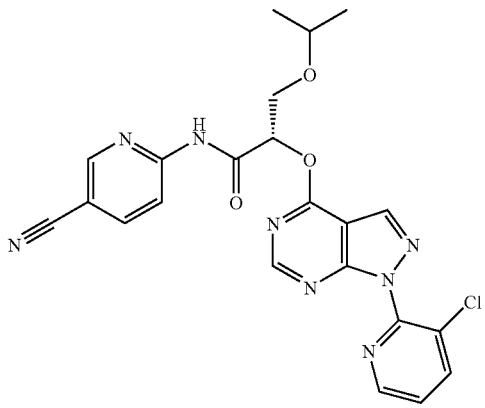 | MH− = 479; $t_R$ = 1.83 min | (DMSO-d₆) 1.13 (6H, t), 3.75-3.81 (1H, m), 4.01-4.10 (2H, m), 5.92-5.94 (1H, m), 7.75-7.78 (1H, m), 8.13-8.16 (1H, m), 8.24-8.27 (1H, m), 8.34-8.36 (1H, m), 8.57 (1H, s), 8.67-8.69 (2H, m), 8.84 (1H, q), 11.52 (1H, s) |

-continued

| Example no. | Structure | m/z | ¹H NMR data (400 MHz) |
|---|---|---|---|
| 127k | 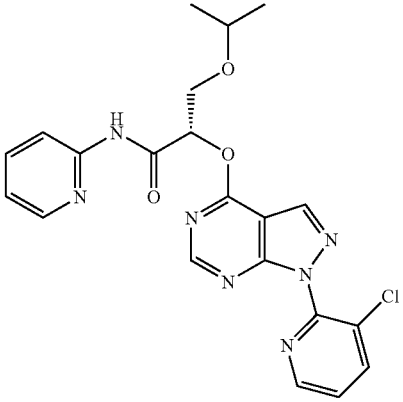 | (M + H)+ = 454; t_R = 1.91 min | (DMSO-d$_6$) 1.11-1.15 (6H, m), 3.75-3.81 (1H, m), 3.99-4.08 (2H, m), 5.92-5.93 (1H, m), 7.11-7.15 (1H, m), 7.75-7.80 (2H, m), 8.03 (1H, d), 8.33-8.36 (2H, m), 8.57 (1H, m), 8.66-8.69 (2H, m), 11.1 (1H, s) |
| 127l | 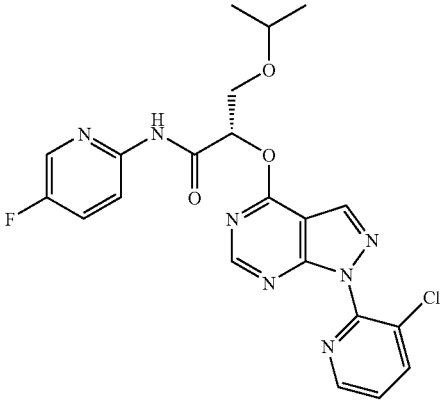 | (M + H)+ = 471; t_R = 2.14 min | (DMSO-d$_6$) 1.12-1.14 (6H, m), 3.75-3.8 (1H, m), 3.99-4.08 (2H, m), 5.9-5.92 (1H, m), 7.11-7.18 (2H, m), 8.0-8.15 (1H, d), 8.33-8.36 (2H, m), 8.57 (1H, m), 8.66-8.69 (2H, m), 11.1 (1H, s) |

EXAMPLE 128

(2S)—N-(5-Chloropyridin-2-yl)-3-ethoxy-2-[1-(3-methylpyridin-4-yl)pyrazolo[4,5-e]pyrimidin-4-yl]oxypropanamide

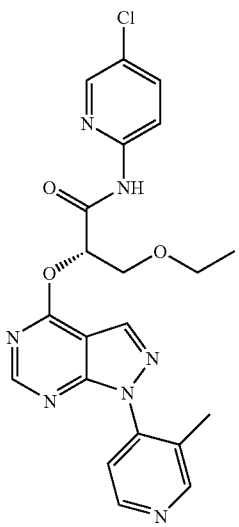

60% Sodium hydride in mineral oil (48.8 mg, 1.22 mmol) was added in one portion to (S)—N-(5-chloropyridin-2-yl)-3-ethoxy-2-hydroxypropanamide (Intermediate H3) (199 mg, 0.81 mmol) in anhydrous THF (5 mL) cooled to 0° C. under nitrogen. The resulting suspension was stirred at 0° C. for 10 minutes and then 4-chloro-1-(3-methylpyridin-4-yl)-1H-pyrazolo[3,4-d]pyrimidine (Intermediate M1) (200 mg, 0.81 mmol) added portionwise over 1 minute. The mixture was stirred at 0° C. for 15 mins, allowed to warm slowly to ambient temperature and stirred for 2 hours. 1M citric acid (2 mL) was added and the mixture extracted with ethyl acetate (2×20 mL). The organic extracts were washed with water (15 mL) and brine (15 mL), dried (MgSO$_4$) and evaporated. The residue was purified by flash silica chromatography, elution gradient 0 to 10% MeOH in EtOAc to afford (2S)—N-(5-chloropyridin-2-yl)-3-ethoxy-2-[1-(3-methylpyridin-4-yl)pyrazolo[4,5-e]pyrimidin-4-yl]oxypropanamide (370 mg, 100%). ¹H NMR (400 MHz, CDCl$_3$) δ 1.23 (3H, t), 2.34 (3H, s), 3.61-3.69 (2H, m), 4.06-4.14 (2H, m), 6.05 (1H, t), 7.49 (1H, d), 7.68 (1H, dd), 8.22 (1H, dd), 8.23-8.25 (1H, m), 8.44 (1H, s), 8.61 (1H, s), 8.63 (1H, dd), 8.69 (1H, s), 8.76 (1H, s); m/z (ESI+) (M+H)+=454; HPLC t$_R$=1.93 min.

The following Examples were prepared using a method analogous to that described for Example 128 using the alcohol and chloro derivative.

EXAMPLE 128a (2S)—N-(5-chloropyridin-2-yl)-3-ethoxy-2-(1-(3-methylpyridin-2-yl)-1H-pyrazolo[3,4-d]pyrimidin-4-yloxy)propanamide Phosphorus oxychloride (1.864 ml, 20.00 mmol) was added to 1-(2-(methylsulfonyl)phenyl)-1H-pyrazolo[3,4-d]pyrimidin-4-ol (Intermediate N1) (0.290 g, 1 mmol), at ambient temperature. The resulting mixture was stirred at 100° C. for 4 hours. The solution was allowed to cool to ambient

| Example no. | Structure | m/z | $^1$H NMR data |
|---|---|---|---|
| 128a | 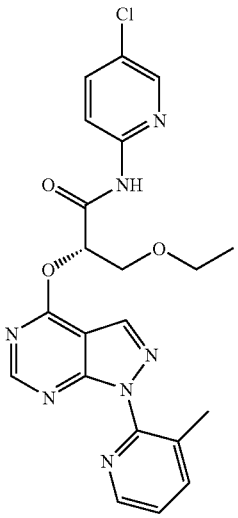 | (M + H)+ = 454; $t_R$ = 2.08 min. ee 99% | 400 MHz, DMSO-$d_6$ 1.11-1.15 (3 H, m), 2.11 (3 H, s), 3.56-3.69 (2 H, m), 3.96-4.06 (2 H, m), 5.93 (1 H, m), 7.56-7.59 (1 H, m), 7.88-7.90 (1 H, m), 7.98-8.00 (1 H, m), 8.01-8.03 (1 H, m), 8.40-8.41 (1 H, m), 8.48-8.53 (2 H, m), 8.61 (1 H, t), 11.16 (1 H, s) |

EXAMPLE 129

(2S)-3-isopropoxy-N-(5-methylpyridin-2-yl)-2-(1-(2-(methylsulfonyl)phenyl)-1H-pyrazolo[3,4-d]pyrimidin-4-yloxy)propanamide

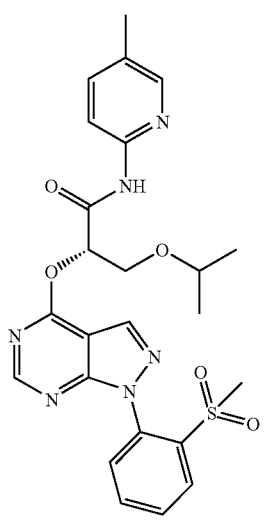

temperature. The reaction mixture was evaporated. The residue was dissolved in DCM (30 mL). MP-Carbonate was added and the mixture stirred for 30 minutes then evaporated. The residue was dissolved in THF (5 mL). Sodium hydride (55.9 mg, 1.40 mmol) was added to (S)-2-hydroxy-3-isopropoxy-N-(5-methylpyridin-2-yl)propanamide (Intermediate C7) (238 mg, 1.00 mmol) in anhydrous THF (10 mL) at 0° C. under nitrogen. The resulting solution was stirred at 0° C. for 15 minutes and then the THF solution prepared above was added. The reaction mixture was allowed to warm to ambient temperature and was stirred for 16 hours. The reaction mixture was concentrated, diluted with water (10 mL) and EtOAc (50 mL). The organic layer was separated and the aqueous layer re-extracted with EtOAc (25 mL). The combined organics were washed with saturated brine (25 mL), dried (MgSO$_4$) and evaporated. The residue was purified by preparative HPLC (Waters XBridge Prep C18 OBD column, 5μ silica, 50 mm diameter, 150 mm length), using decreasingly polar mixtures of water (containing 0.1% formic acid) and MeCN as eluent to afford (2S)-3-isopropoxy-N-(5-methylpyridin-2-yl)-2-(1-(2-(methylsulfonyl)phenyl)-1H-pyrazolo[3,4-d]pyrimidin-4-yloxy)propanamide (242 mg, 47.5%, 81% ee). $^1$H NMR (400 MHz, DMSO-d6) δ 1.12 (6H, dd), 2.24 (3H, s), 3.38 (3H, s), 3.72-3.80 (1H, m), 3.96-4.05 (2H, m), 5.87-5.91 (1H, m), 7.58 (1H, dd), 7.77 (1H, dd), 7.86-7.92 (2H, m), 7.94-7.99 (1H, m), 8.16-8.21 (2H, m), 8.53 (1H, s), 8.60 (1H, s), 10.82 (1H, s); m/z (ESI+) (M+H)+=511; HPLC $t_R$=2.07 min.

EXAMPLE 130

(2S)—N-(5-chloropyridin-2-yl)-3-ethoxy-2-(1-(2-(methylsulfonyl)phenyl)-1H-pyrazolo[3,4-d]pyrimidin-4-yloxy)propanamide

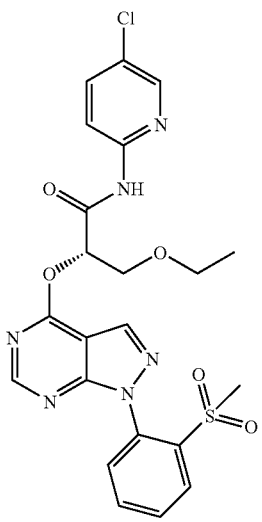

Prepared in an analogous fashion to Example 129 from (Intermediate H3).

$^1$H NMR (400 MHz, DMSO) δ 1.13 (3H, t), 3.34 (3H, s), 3.58-3.68 (2H, m), 3.95-4.09 (2H, m), 5.91-5.95 (1H, m), 7.76 (1H, dd), 7.87-8.05 (4H, m), 8.19 (1H, dd), 8.40 (1H, d), 8.53 (1H, s), 8.53 (1H, s), 11.18 (1H, s); m/z (ESI+) (M+H)+= 517; HPLC $t_R$=2.41 min; ee 98%.

EXAMPLE 131

(2S)-2-[1-(3-chloropyridin-2-yl)pyrazolo[4,5-e]pyrimidin-4-yl]oxy-5-hydroxy-N-(5-methylpyridin-2-yl)pentanamide

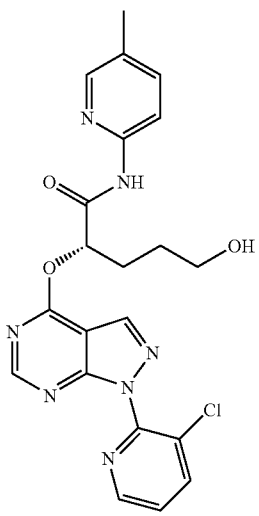

A solution of tetrabutylammonium fluoride 2M in THF (0.449 mL, 0.45 mmol) was added in one portion to a stirred solution of (2S)-5-(tert-butyldimethylsilyloxy)-2-(1-(3-chloropyridin-2-yl)-1H-pyrazolo[3,4-d]pyrimidin-4-yloxy)-N-(5-methylpyridin-2-yl)pentanamide (Intermediate O1) (170 mg, 0.30 mmol) in THF (5 mL). The resulting solution was stirred at ambient temperature for 4 hours, evaporated and the residue dissolved in ethyl acetate (30 mL). This was washed with water (20 mL) and brine (20 mL), dried (MgSO$_4$) and evaporated. The residue was purified by flash silica chromatography, eluting with 0 to 10% MeOH in ethyl acetate to afford the product (100 mg, 73%). $^1$H NMR (400 MHz, CDCl$_3$) δ 1.61-1.68 (1H, m), 1.84-1.88 (2H, m), 2.23-2.36 (2H, m), 2.30 (3H, s), 3.72-3.82 (2H, m), 5.94-5.98 (1H, m), 7.46 (1H, dd), 7.54 (1H, dd), 8.01 (1H, dd), 8.08-8.10 (1H, m), 8.12-8.15 (1H, m), 8.45 (1H, s), 8.61-8.62 (2H, m), 8.63 (1H, s); m/z (ESI+)(M+H)+=454; HPLC $t_R$=1.51 min.

EXAMPLE 132

(2S)—N-(5-cyanopyridin-2-yl)-3-ethoxy-2-[1-[2-(trifluoromethyl)phenyl]pyrazolo[4,5-e]pyrimidin-4-yl]oxypropanamide

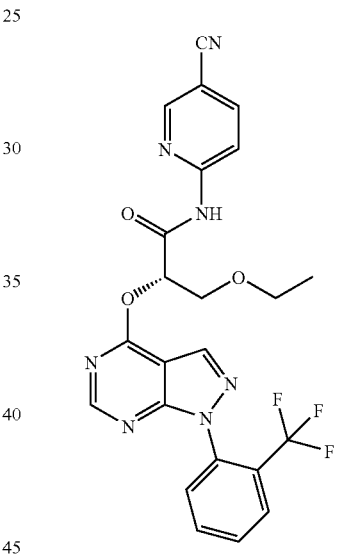

60% Sodium hydride (60.0 mg, 1.50 mmol) was added in one portion to (S)—N-(5-cyanopyridin-2-yl)-3-ethoxy-2-hydroxypropanamide (Intermediate H4) (235 mg, 1.00 mmol) in anhydrous THF (5 mL) and the mixture was cooled to 0° C. under nitrogen. The resulting suspension was stirred at 0° C. for 10 minutes and 4-chloro-1-(2-(trifluoromethyl)phenyl)-1H-pyrazolo[3,4-d]pyrimidine (Intermediate P1) (298.6 mg, 1.00 mmol) as suspension in dry THF (4 mL) was added dropwise over 1 minute. The mixture was stirred at 0° C. for 15 mins, allowed to warm slowly to ambient temperature and stirred for 2 hours. 1M Citric acid (4 mL) was added and the mixture extracted with ethyl acetate (2×25 mL). The combined organic extracts were washed with water (25 mL) and brine (25 mL), dried (MgSO$_4$) and evaporated. The crude product was purified by flash silica chromatography, eluting with 20 to 100% ethyl acetate in isohexane to give the product (430 mg, 86%). $^1$H NMR (400 MHz, CDCl$_3$) δ 1.25 (3H, t), 3.62-3.70 (2H, m), 4.08-4.14 (2H, m), 6.04 (1H, t), 7.53-7.55 (1H, m), 7.68-7.77 (2H, m), 7.91 (1H, dd), 7.97 (1H, dd), 8.39 (1H, dd), 8.41 (1H, s), 8.56 (1H, s), 8.57-8.59 (1H, m), 9.02 (1H, s); m/z (ESI−) (M−H)$^-$=496; HPLC tR=2.55 min.

EXAMPLE 133

(2S)-3-ethoxy-N-(5-methylpyrazin-2-yl)-2-[1-[2-(trifluoromethyl)phenyl]pyrazolo[4,5-e]pyrimidin-4-yl]oxypropanamide

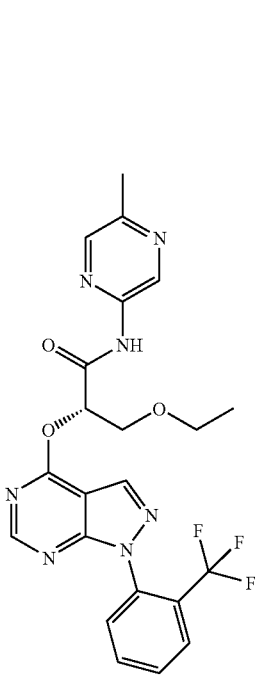

60% Sodium hydride (60.0 mg, 1.50 mmol) was added in one portion to (S)-3-ethoxy-2-hydroxy-N-(5-methylpyrazin-2-yl)propanamide (Intermediate H1) (225 mg, 1.00 mmol) in anhydrous THF (5 mL) and the mixture was cooled to 0° C. under nitrogen. The resulting suspension was stirred at 0° C. for 10 minutes and then 4-chloro-1-(2-(trifluoromethyl)phenyl)-1H-pyrazolo[3,4-d]pyrimidine (Intermediate P1) (298.6 mg, 1.00 mmol) as suspension in dry THF (4 mL) added dropwise over 1 minute. The mixture was stirred at 0° C. for 15 mins, allowed to warm to ambient temperature and stirred for 2 hours. 1M Citric acid (2 mL) was added and the mixture extracted with ethyl acetate (2×20 mL). The organic extracts were washed with water (15 mL) and brine (15 mL), dried (MgSO$_4$) and evaporated. The residue was purified by flash silica chromatography, eluting with 60 to 100% ethyl acetate in isohexane to give the product (440 mg, 88%).

$^1$H NMR (400 MHz, CDCl$_3$) δ 1.25 (3H, t), 2.54 (3H, s), 3.61-3.69 (2H, m), 4.08-4.16 (2H, m), 6.08 (1H, t), 7.52-7.57 (1H, m), 7.65-7.72 (1H, m), 7.74-7.76 (1H, m), 7.90 (1H, dd), 8.12 (1H, d), 8.41 (1H, s), 8.57 (1H, s), 8.68 (1H, s), 9.45 (1H, d); m/z (ESI+) (M+H)+=488; HPLC tR=2.27 min.

EXAMPLE 134

(2S)—N-(5-chloropyridin-2-yl)-3-ethoxy-2-[1-[3-(trifluoromethyl)pyridin-2-yl]pyrazolo[4,5-e]pyrimidin-4-yl]oxypropanamide

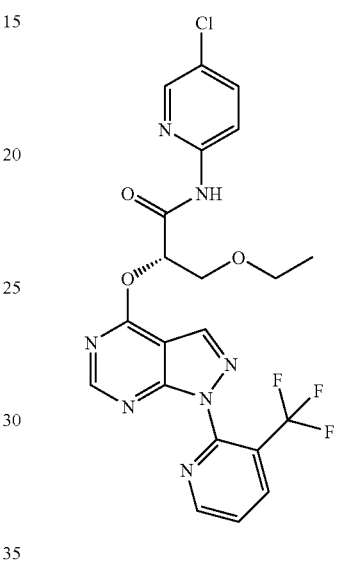

A solution of trimethylaluminium (2M in hexane) (0.322 mL, 0.64 mmol) was added dropwise to a stirred solution of 5-chloropyridin-2-amine (CAS no. 1072-98-6) (79 mg, 0.62 mmol) in toluene (5 mL) at 0° C., over a period of 1 minute under nitrogen. The resulting solution was stirred at 0° C. for 20 minutes. A solution of (2S)-methyl 3-ethoxy-2-(1-(3-(trifluoromethyl)pyridin-2-yl)-1H-pyrazolo[3,4-d]pyrimidin-4-yloxy)propanoate (Intermediate Q1) (230 mg, 0.56 mmol) in toluene (5 mL) was added dropwise over a period of 2 minutes. The resulting solution was stirred at 0° C. for 10 minutes, allowed to warm to ambient temperature and then heated at 60° C. for 20 hours. The resulting mixture was allowed to cool and 1M citric acid (10 mL) added with vigorous stirring. Ethyl acetate (35 mL) and water (10 mL) were added and the organic phase was separated, washed with water (20 mL) and brine (20 mL), dried (MgSO$_4$) and evaporated. The residue was purified by flash silica chromatography, eluting with 50 to 100% ethyl acetate in isohexane and then chiral preparative HPLC to give the product (90 mg, 31%). $^1$H NMR (400 MHz, CDCl$_3$) δ 1.22 (3H, t), 3.60-3.68 (2H, m), 4.06-4.15 (2H, m), 6.05 (1H, t), 7.64-7.70 (2H, m), 8.22-8.25 (2H, m), 8.29 (1H, dd), 8.43 (1H, s), 8.62 (1H, s), 8.84 (1H, s)8.89 (1H, dd); m/z (ESI+) (M+H)+=508: HPLC tR=2.35 min.

EXAMPLE 135

(2S)—N-(5-methylpyridin-2-yl)-2-[1-(3-methylpyridin-4-yl)pyrazolo[4,5-e]pyrimidin-4-yl]oxy-3-propan-2-yloxypropaamide

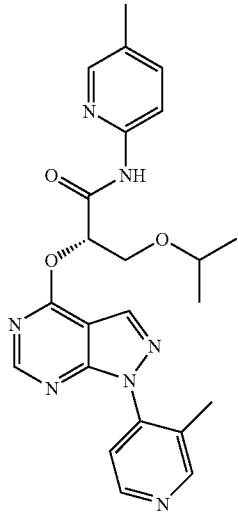

60% Sodium hydride in mineral oil (48.8 mg, 1.22 mmol) was added in one portion to (S)-2-hydroxy-3-isopropoxy-N-(5-methylpyridin-2-yl)propanamide (Intermediate C7) (194 mg, 0.81 mmol) in anhydrous THF (5 mL) cooled to 0° C. under nitrogen. The resulting suspension was stirred at 0° C. for 10 minutes and then 4-chloro-1-(3-methylpyridin-4-yl)-1H-pyrazolo[3,4-d]pyrimidine (Intermediate M1) (200 mg, 0.81 mmol) as suspension in dry THF (4 mL) added dropwise over 1 minute. The mixture was stirred at 0° C. for 15 mins, allowed to warm slowly to ambient temperature and stirred for 2 hours. 1M Citric acid (2 mL) was added and the mixture extracted with ethyl acetate (2×20 mL). The combined organic extracts were washed with water (15 mL) and brine (15 mL), dried (MgSO$_4$) and evaporated. The residue was purified by flash silica chromatography with ethyl acetate to give the product (300 mg, 82%). $^1$H NMR (400 MHz, CDCl$_3$) δ 1.17 (3H, d), 1.19 (3H, d), 2.29 (3H, s), 2.34 (3H, s), 3.69-3.76 (1H, m), 4.09 (2H, d), 6.01 (1H, t), 7.51 (1H, d), 7.53 (1H, dd), 8.09-8.10 (1H, m), 8.13 (1H, d), 8.43 (1H, s), 8.60 (1H, s), 8.62 (1H, dd), 8.67 (1H, s), 8.68 (1H, s); m/z (ESI+) (M+H)+=448; HPLC t$_R$=1.78 min.

EXAMPLE 136

(2S)-3-cyclobutyloxy-N-(5-methylpyrazin-2-yl)-2-[1-(3-methylpyridin-4-yl)pyrazolo[4,5-e]pyrimidin-4-yl]oxypropanamide 60% Sodium hydride in mineral oil (48.8 mg, 1.22 mmol) was added in one portion to (S)-3-cyclobutoxy-2-hydroxy-N-(5-methylpyrazin-2-yl)propanamide (Intermediate R1) (205 mg, 0.81 mmol) in anhydrous THF (5 mL) cooled to 0° C. under nitrogen. The resulting suspension was stirred at 0° C. for 10 minutes and then 4-chloro-1-(3-methylpyridin-4-yl)-1H-pyrazolo[3,4-d]pyrimidine (Intermediate M1) (200 mg, 0.81 mmol) as suspension in dry THF (4 mL) added dropwise over 1 minute. The mixture was stirred at 0° C. for 15 mins, allowed to warm slowly to ambient temperature and stirred for 2 hours. 1M Citric mins, allowed to warm slowly to ambient temperature and stirred for 2 hours. 1M Citric combined organic extracts were washed with water (15 mL) and brine (15 mL), dried (MgSO$_4$) and evaporated. The residue was purified by flash silica chromatography, eluting (MgSO$_4$) and evaporated. The residue was purified by flash silica chromatography, eluting with 0 to 10% MeOH in ethyl acetate to give the product (360 mg, 96%). $^1$H NMR (400 (2H, m), 2.35 (3H, s), 2.54 (3H, s), 3.97-4.10 (3H, m), 6.05 (1H, t), 7.49 (1H, d), 8.12 (1H, d), 8.44 (1H, s), 8.61 (1H, s), 8.62-8.65 (2H, m), 8.69 (1H, s), 9.44 (1H, d); m/z (ESI+) (M+H)+=461; HPLC t$_R$=1.67 min.

EXAMPLE 137

(2S)-3-cyclobutyloxy-N-(5-methylpyrazin-2-yl)-2-[1-[3-(trifluoromethyl)pyridin-2-yl]pyrazolo[4,5-e]pyrimidin-4-yl]oxypropanamide

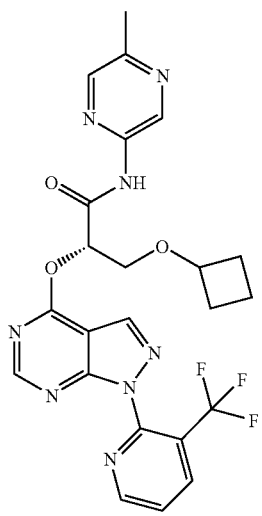

10% Palladium on carbon (200 mg, 1.88 mmol) and (2S)-2-(1-(5-chloro-3-(trifluoromethyl)pyridin-2-yl)-1H-pyrazolo[3,4-d]pyrimidin-4-yloxy)-3-cyclobutoxy-N-(5-methylpyrazin-2-yl)propanamide (Example 138) (501 mg, 0.91 mmol) in ethanol was stirred under an atmosphere of hydrogen at ambient temperature for 20 hours. The mixture was filtered and fresh catalyst (200 mg) added and the mixture stirred under hydrogen atmosphere for 8 hours. The mixture was filtered, triethylamine (1 mL) added, and the mixture evaporated. The residue was purified by flash silica chromatography eluting with ethyl acetate to give the product (150 mg, 32%). $^1$H NMR (400 MHz, CDCl$_3$) δ 1.46-1.60 (1H, m), 1.64-1.71 (1H, m), 1.92-1.97 (2H, m), 2.18-2.23 (2H, m), 2.54 (3H, s), 3.98-4.07 (3H, m), 6.05 (1H, t), 7.65-7.68 (1H, m), 8.12 (1H, d), 8.29 (1H, dd), 8.44 (1H, s), 8.62-8.67 (1H, m), 8.65 (1H, s), 8.89 (1H, dd), 9.45 (1H, d); m/z (ESI+) (M+H)+=515; HPLC $t_R$=2.25 min.

EXAMPLE 138

(2S)-2-[1-[5-chloro-3-(trifluoromethyl)pyridin-2-yl]pyrazolo[4,5-e]pyrimidin-4-yl]oxy-3-cyclobutyloxy-N-(5-methylpyrazin-2-yl)propanamide

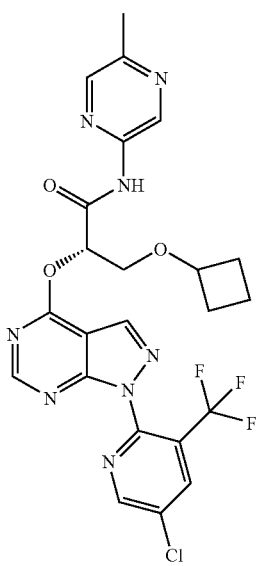

60% Sodium hydride in mineral oil (60 mg, 1.50 mmol) was added in one portion to (S)-3-cyclobutoxy-2-hydroxy-N-(5-methylpyrazin-2-yl)propanamide (Intermediate R1) (251 mg, 1.00 mmol) in anhydrous THF (5 mL) at 0° C. under nitrogen. The resulting suspension was stirred at 0° C. for 10 minutes and then 4-chloro-1-(5-chloro-3-(trifluoromethyl)pyridin-2-yl)-1H-pyrazolo[3,4-d]pyrimidine (Intermediate K3) (334 mg, 1.00 mmol) as suspension in dry THF (2.5 mL) added dropwise over 1 minute. The mixture was stirred at 0° C. for 15 mins, allowed to warm to ambient temperature and stirred for 6 hours. 1M Citric acid (10 mL) was added and the mixture extracted with ethyl acetate (2×25 mL). The combined organic extracts were washed with water (25 mL) and brine (25 mL), dried (MgSO$_4$) and evaporated. The residue was purified by flash silica chromatography, eluting with 50 to 100% ethyl acetate in isohexane to give the product (550 mg, 100%). $^1$H NMR (400 MHz, CDCl$_3$) δ 1.46-1.54 (1H, m), 1.66-1.74 (1H, m), 1.89-2.01 (2H, m), 2.18-2.25 (2H, m), 2.54 (3H, s), 3.98-4.08 (3H, m), 6.04 (1H, t), 8.12 (1H, d), 8.25 (1H, d), 8.43 (1H, s), 8.62 (1H, s), 8.63-8.65 (1H, m), 8.82 (1H, d), 9.44 (1H, d); m/z (ESI+) (M+H)+=549; HPLC $t_R$=2.56 min.

EXAMPLE 139

(2S)-2-(1-(3-chloropyridin-2-yl)-1H-pyrazolo[3,4-d]
pyrimidin-4-yloxy)-3-ethoxy-N-(5-(methylsulfonyl)
pyridin-2-yl)propanamide

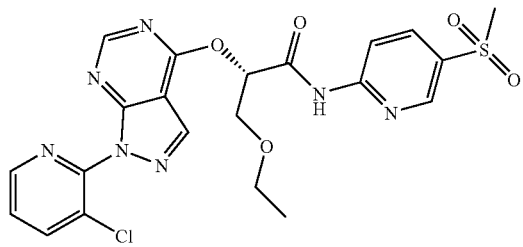

A solution of 3-chloroperoxybenzoic acid (85 mg, 0.38 mmol) in DCM (10 mL) was added dropwise to a stirred solution of (2S)-2-(1-(3-chloropyridin-2-yl)-1H-pyrazolo[3,4-d]pyrimidin-4-yloxy)-3-ethoxy-N-(5-(methylthio)pyridin-2-yl)propanamide (Intermediate S1) (92 mg, 0.19 mmol), in DCM (10 mL), at 22° C., over a period of 10 minutes. The resulting solution was stirred at 22° C. for 3 hours. The reaction mixture was diluted with DCM (20 mL) washed with 2M NaOH (20 mL), dried (MgSO$_4$) and evaporated. The residue was purified by flash silica chromatography, eluting with 10 to 100% ethyl acetate in isohexane to afford the product (80 mg). $^1$H NMR (400 MHz, DMSO) δ 1.13 (3H, t), 3.26 (3H, s), 3.56-3.70 (2H, m), 3.99-4.05 (2H, m), 5.96 (1H, q), 7.74-7.77 (1H, m), 8.18-8.21 (1H, m), 8.26-8.29 (1H, m), 8.32-8.35 (1H, m), 8.56 (1H, s), 8.66-9.68 (2H, m), 8.83-8.84 (1H, m), 11.59 (1H, s); m/z (ES+) (M+H)$^+$=518; HPLC tR=1.88 min.

EXAMPLE 140

(2S)-3-cyclobutoxy-N-(5-methylpyrazin-2-yl)-2-(1-(2-(methylsulfonyl)phenyl)-1H-pyrazolo[3,4-d]pyrimidin-4-yloxy)propanamide

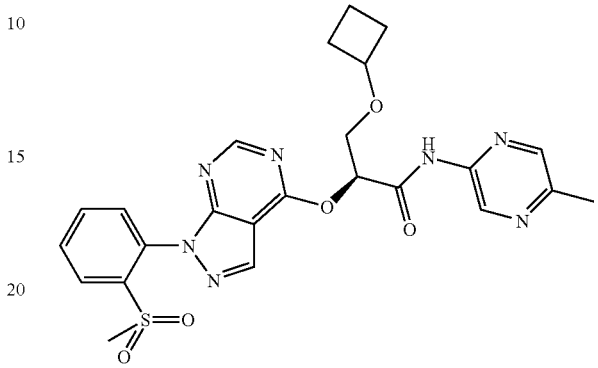

Prepared in an analogous fashion to Example 129 from Intermediate N1 and (S)-3-cyclobutoxy-2-hydroxy-N-(5-methylpyrazin-2-yl)propanamide (Intermediate R1). $^1$H NMR (400 MHz, DMSO) δ 1.42-1.50 (1H, m), 1.62 (1H, q), 1.80-1.92 (2H, m), 2.16-2.23 (2H, m), 2.45 (3H, s), 3.38 (3H, s), 3.90-3.93 (1H, m), 3.99 (1H, q), 4.08-4.15 (1H, m), 5.92 (1H, q), 7.76-7.78 (1H, m), 7.88-7.92 (1H, m), 7.95-7.99 (1H, m), 8.18-8.21 (1H, m), 8.32 (1H, d), 8.53 (1H, s), 8.63 (1H, s), 9.11 (1H, s), 11.19 (1H, s); m/z (ESI+) (M+H)$^+$=524; HPLC t$_R$=1.97 min.

EXAMPLE 141

(2S)-3-cyclobutoxy-N-(5-methylpyrazin-2-yl)-2-(1-(3-methylpyridin-2-yl)-1H-pyrazolo[3,4-d]pyrimidin-4-yloxy)propanamide

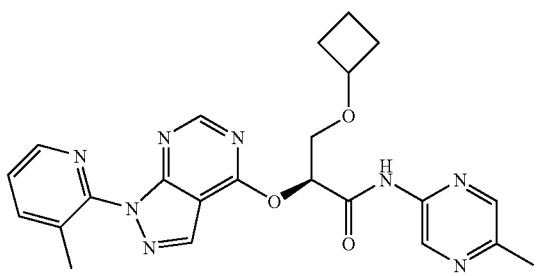

Prepared in an analogous fashion to Example 106 from Intermediate J4 and (S)-3-cyclobutoxy-2-hydroxy-N-(5-methylpyrazin-2-yl)propanamide (Intermediate R1).

$^1$H NMR (400 MHz, CDCl$_3$) δ 1.39-1.46 (1H, m), 1.58-1.68 (1H, m), 1.82-1.94 (2H, m), 2.10-2.19 (2H, m), 2.23 (3H, s), 2.47 (3H, s), 3.90-4.01 (3H, m), 5.98 (1H, t), 7.31-7.34 (1H, m), 7.73 (1H, d), 8.05 (1H, s), 8.36 (1H, s), 8.47 (1H, d), 8.55 (1H, s), 8.59 (1H, s), 9.38 (1H, s); m/z (ESI+) (M+H)$^+$= 461; HPLC tR=1.92 min.

EXAMPLE 142

(S)-3-cyclobutoxy-N-(5-methylpyrazin-2-yl)-2-(1-phenyl-1H-pyrazolo[3,4-d]pyrimidin-4-yloxy)propanamide

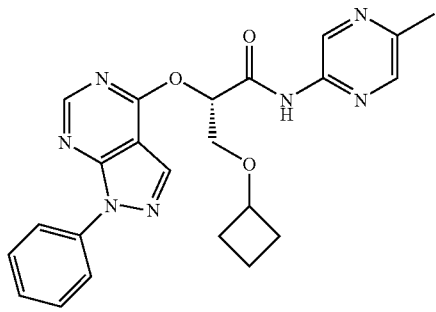

(2S)-2-(1-(2-Chlorophenyl)-1H-pyrazolo[3,4-d]pyrimidin-4-yloxy)-3-cyclobutoxy-N-(5-methylpyrazin-2-yl)propanamide (Example 156) (102 mg, 0.21 mmol) and 10% palladium on carbon (25 mg, 0.02 mmol) in ethanol (20 mL) were stirred under an atmosphere of hydrogen for 16 hours. The suspension was filtered through celite. 10% Palladium on carbon (25 mg, 0.02 mmol) was added and the resulting suspension was stirred under an atmosphere of hydrogen for 24 hours. The reaction mixture was filtered through celite and evaporated. The residue was purified by flash silica chromatography, eluting with 0 to 50% ethyl acetate in isohexane to afford the product (16.0 mg, 16.9%).

$^1$H NMR (400 MHz, DMSO) δ 1.39-1.51 (1H, m), 1.56-1.66 (1H, m), 1.78-1.90 (2H, m), 2.13-2.23 (2H, m), 2.44 (3H, s), 3.89-4.14 (3H, m), 5.89-5.94 (1H, m), 7.41 (1H, t), 7.59 (2H, t), 8.17 (1H, s), 8.17 (1H, s), 8.32 (1H, s), 8.63 (1H, s), 8.66 (1H, s), 9.09 (1H, s). 11.17 (1H, s); m/z (ESI+) (M+H)$^+$=446; HPLC tR=2.70 min.

EXAMPLE 143

(2S)-2-[1-(3-chloro-2-pyridyl)pyrazolo[4,5-e]pyrimidin-4-yl]oxy-4-hydroxy-N-(5-methyl-2-pyridyl)butanamide

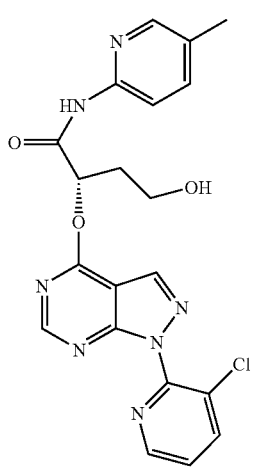

Trimethylaluminium (0.347 mL, 0.69 mmol) was added to 5-methylpyridin-2-amine (71.7 mg, 0.66 mmol) in toluene (8 mL) cooled to 0° C. under nitrogen. The resulting solution was stirred at 0° C. for 20 minutes. (3S)-3-(1-(3-chloropyridin-2-yl)-1H-pyrazolo[3,4-d]pyrimidin-4-yloxy)dihydrofuran-2(3H)-one (Intermediate T1) (200 mg, 0.60 mmol) in toluene (2 mL) and the reaction was allowed to warm to room temperature and stirred for 1 hour. The reaction was then heated at 50° C. for 2 hours. The reaction mixture was allowed to cool and was neutralised with citric acid (1M, aq.) and then diluted with water (50 mL) and ethyl acetate (50 mL). The organic layer was separated and the aqueous layer re-extracted with ethyl acetate (50 mL). The combined organics were dried (MgSO$_4$), filtered and evaporated. The crude product was purified by flash silica chromatography, eluting with 0 to 10% MeOH in DCM to afford the product (185 mg, 69.8%). $^1$H NMR (400 MHz, CDCl$_3$) 2.30 (3H, s) 2.33-2.40 (1H, m), 2.44-2.52 (1H, m), 2.55 (1h, s), 3.83-3.92 (2H, m), 6.07-6.10 (1H, m), 7.46-7.49 (1H, m), 7.52-7.55 (1H, m), 8.00-8.02 (1H, m), 8.09-8.10 (1H, m), 8.13 (1H, d), 8.47 (1H, s), 8.61-8.62 (1H, m), 8.64 (1H, s), 8.68 (1H, s); m/z (ESI+) (M+H)+=440; HPLC t$_R$=1.68 min.

The following examples were prepared using an analogous procedure using Intermediate T1 and the appropriate amine:

| No. | STRUCTURE | NAME | M/Z | $^1$H NMR data (400 MHz, CDCl$_3$) |
|---|---|---|---|---|
| 143a | 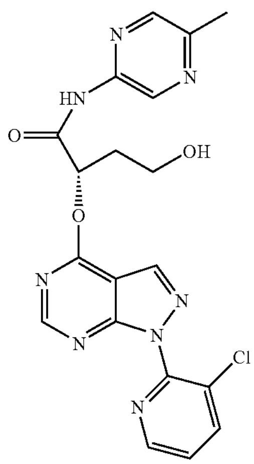 | (2S)-2-[1-(3-chloro-2-pyridyl)pyrazolo[4,5-e]pyrimidin-4-yl]oxy-4-hydroxy-N-(5-methylpyrazin-2-yl)butanamide | ESI+ (M + H)+ = 441; HPLC t$_R$ = 1.39 min | δ 2.35-2.52 (2H, m), 2.54 (3H, s), 3.85-3.98 (2H, m), 6.10-6.13 (1H, m), 7.46-7.50 (1H, m), 8.00-8.03 (1H, m), 8.11 (1H, d), 8.45 (1H, s), 8.60-8.63 (1H, m), 8.64 (1H, s), 8.77 (1H, s), 9.43 (1H, d) |
| 143b | 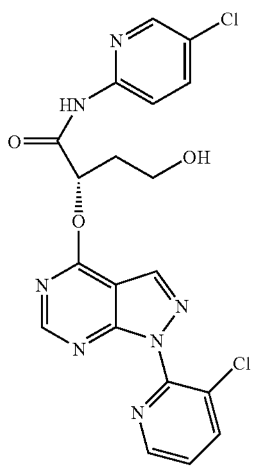 | (2S)-N-(5-chloro-2-pyridyl)-2-[1-(3-chloro-2-pyridyl)pyrazolo[4,5-e]pyrimidin-4-yl]oxy-4-hydroxy-butanamide | ESI+ (M + H)+ = 460; HPLC t$_R$ = 1.82 min | δ 2.33-2.52 (3H, m), 3.83-3.97 (2H, m), 6.07-6.10 (1H, m), 7.46-7.50 (1H, m), 7.67-7.70 (1H, m), 8.00-8.03 (1H, m), 8.22-8.23 (1H, m), 8.23 (1H, d), 8.46 (1H, s), 8.61-8.63 (1H, m), 8.64 (1H, s), 8.81 (1H, s) |
| 143c | 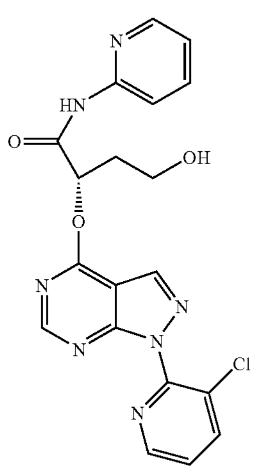 | (2S)-2-[1-(3-chloro-2-pyridyl)pyrazolo[4,5-e]pyrimidin-4-yl]oxy-4-hydroxy-N-(2-pyridyl)butanamide | (ESI+) (M + H)+ = 426; HPLC t$_R$ = 1.40 min | δ 2.33-2.53 (3H, m), 3.84-3.94 (2H, m), 6.08-6.11 (1H, m), 7.06-7.09 (1H, m), 7.46-7.49 (1H, m), 7.70-7.75 (1H, m), 8.00-8.02 (1H, m), 8.24 (1H, d), 8.28-8.30 (1H, m), 8.47 (1H, s), 8.59-8.63 (1H, m), 8.65 (1H, s), 8.76 (1H, s) |

-continued

| No. | STRUCTURE | NAME | M/Z | ¹H NMR data (400 MHz, CDCl₃) |
|---|---|---|---|---|
| 143d | 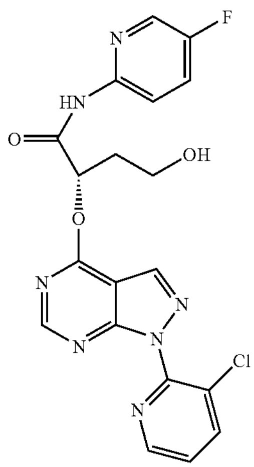 | (2S)-2-[1-(3-chloro-2-pyridyl)pyrazolo[4,5-e]pyrimidin-4-yl]oxy-N-(5-fluoro-2-pyridyl)-4-hydroxy-butanamide | (ESI+) (M + H)+ = 444; HPLC t$_R$ = 1.62 min | δ 2.33-2.41 (1H, m), 2.44-2.52 (2H, m), 3.83-3.98 (2H, m), 6.07-6.11 (1H, m), 7.43-7.50 (2H, m), 8.00-8.03 (1H, m), 8.14 (1H, s), 8.25-8.28 (1H, m), 8.46 (1H, s), 8.59-8.63 (1H, m), 8.64 (1H, s), 8.80 (1H, s) |
| 143e | 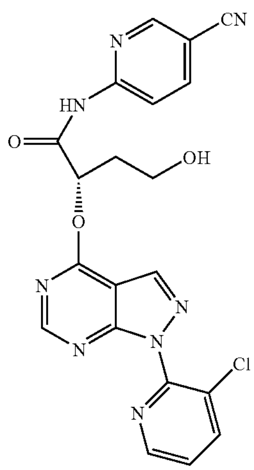 | (2S)-2-[1-(3-chloro-2-pyridyl)pyrazolo[4,5-e]pyrimidin-4-yl]oxy-N-(5-cyano-2-pyridyl)-4-hydroxy-butanamide | (ESI+) (M − H)− = 449; HPLC t$_R$ = 1.63 min | δ 2.27 (1H, t), 2.35-2.52 (2H, m), 3.85-3.99 (2H, m), 6.07-6.10 (1H, m), 7.47-7.50 (1H, m), 7.95-7.98 (1H, m), 8.01-8.03 (1H, m), 8.37-8.40 (1H, m), 8.46 (1H, s), 8.56-8.57 (1H, m), 8.61-8.63 (1H, m), 8.64 (1H, s), 9.06 (1H, s) |
| 143f | 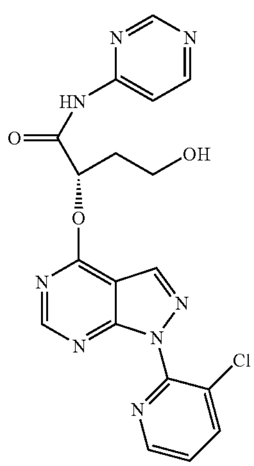 | (2S)-2-[1-(3-chloro-2-pyridyl)pyrazolo[4,5-e]pyrimidin-4-yl]oxy-4-hydroxy-N-pyrimidin-4-yl-butanamide | (ESI+) (M − H)− = 425; HPLC t$_R$ = 1.37 min | δ 2.31 (1H, s), 2.35-2.52 (2H, m), 3.86-3.97 (2H, m), 6.05-6.09 (1H, m), 7.44-7.50 (1H, m), 8.00-8.03 (1H, m), 8.19-8.20 (1H, m), 8.46 (1H, s), 8.59-8.67 (3H, m), 8.89 (1H, d), 8.94 (1H, s) |

EXAMPLE 144

(2S)-3-(cyclobutoxy)-2-[1-(3-methylpyrazin-2-yl)pyrazolo[4,5-e]pyrimidin-4-yl]oxy-N-(5-methyl-2-pyridyl)propanamide

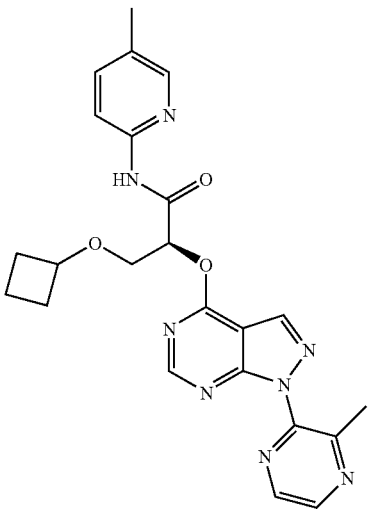

Prepared using an analogous procedure to that described for Example 106 using 4-Chloro-1-(3-methylpyrazin-2-yl)-1H-pyrazolo[3,4-d]pyrimidine (Intermediate I4) with (S)-3-cyclobutoxy-2-hydroxy-N-(5-methylpyridin-2-yl)propanamide (Intermediate U1).

$^1$H NMR (400 MHz, CDCl$_3$) δ 1.43-1.55 (1H, m), 1.64-1.73 (1H, m), 1.89-2.00 (2H, m), 2.17-2.24 (2H, m), 2.30 (3H, s), 2.61 (3H, s), 3.97-4.08 (3H, m), 6.02-6.05 (1H, m), 7.51-7.54 (1H, m), 8.09-8.10 (1H, m), 8.13 (1H, d), 8.47 (1H, s), 8.51-8.52 (1H, m), 8.64 (1H, s), 8.65 (2H, d); m/z (ESI+) (M+H)+=461; HPLC t$_R$=2.05 min.

EXAMPLE 145

(2S)-2-[1-(2-chlorophenyl)pyrazolo[4,5-e]pyrimidin-4-yl]oxy-4-hydroxy-N-(5-methyl-2-pyridyl)butanamide

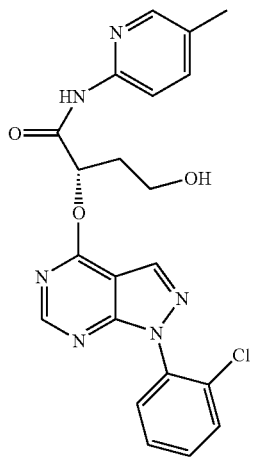

Prepared using an analogous procedure to that described for Example 143 using (3S)-3-(1-(2-chlorophenyl)-1H-pyrazolo[3,4-d]pyrimidin-4-yloxy)dihydrofuran-2(3H)-one (Intermediate T2). $^1$H NMR (400 MHz, CDCl$_3$) δ 2.29 (3H, s), 2.32-2.40 (1H, m), 2.44-2.52 (1H, m), 2.73 (1H, s), 3.83-3.97 (2H, m), 6.07-6.10 (1H, m), 7.44-7.63 (5H, m), 8.09-8.10 (1H, m), 8.13 (1H, d), 8.43 (1H, s), 8.59 (1H, s), 8.76 (1H, s); m/z (ESI+) (M+H)+=439; HPLC t$_R$=1.81 min

EXAMPLE 146

(2S)-3-isopropoxy-N-(5-methyl-2-pyridyl)-2-[1-(2-methyl-3-pyridyl)pyrazolo[4,5-e]pyrimidin-4-yl]oxy-propanamide

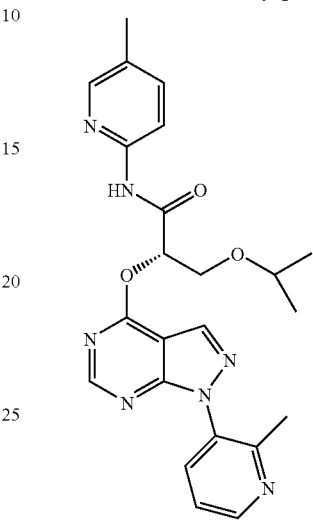

Prepared using an analogous procedure to that described for Example 106 using Intermediate C7 and Intermediate V5.
$^1$H NMR (400 MHz, CDCl$_3$) δ 1.19 (6H, t), 2.30 (3H, s), 2.45 (3H, s), 3.70-3.76 (1H, m), 4.09-4.10 (2H, m), 6.01 (1H, t), 7.33-7.37 (1H, m), 7.52-7.55 (1H, m), 7.75-7.77 (1H, m), 8.10-8.15 (2H, m), 8.44 (1H, s), 8.58 (1H, s), 8.66-8.67 (1H, m), 8.70 (1H, s); m/z (ESI+) (M+H)+=448; HPLC t$_R$=1.83 min

EXAMPLE 147

6-[[(2S)-2-[1-(3-chloro-2-pyridyl)pyrazolo[4,5-e]pyrimidin-4-yl]oxy-3-ethoxy-propanoyl]amino]-N,N-dimethyl-pyridine-3-carboxamide

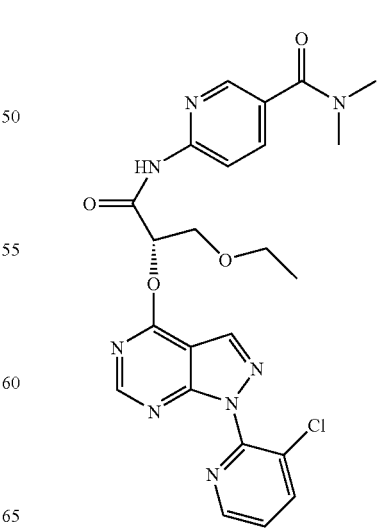

Prepared using an analogous procedure to that described for Example 125 using Intermediate W1 and Intermediate L2. $^1$H NMR (400 MHz, CDCl$_3$) δ 1.20-1.28 (3H, m), 3.04 (3H, s), 3.09 (3H, s), 3.58-3.70 (2H, m), 4.07-4.15 (2H, m), 6.06 (1H, t), 7.46-7.49 (1H, m), 7.79-7.82 (1H, m), 8.00-8.02 (1H, m), 8.27-8.30 (1H, m), 8.39-8.40 (1H, m), 8.48 (1H, s), 8.61-8.62 (1H, m), 8.63 (1H, s), 8.86 (1H, s); m/z (ESI+) (M+H)+= 511; HPLC tR=1.72 min.

EXAMPLE 148

(2S)-3-isopropoxy-N-(5-methyl-2-pyridyl)-2-[1-(4-methyl-3-pyridyl)pyrazolo[4,5-e]pyrimidin-4-yl]oxy-propanamide

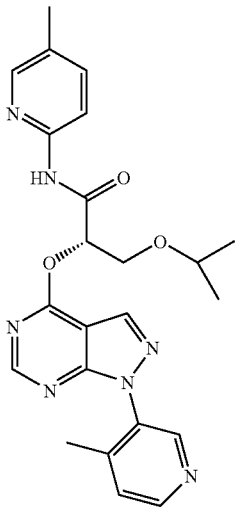

Prepared using a procedure analogous to that described for Example 106 using Intermediate C7 and Intermediate X5. $^1$H NMR (400 MHz, CDCl$_3$) δ 1.19 (6H, t), 2.25 (3H, s), 2.29 (3H, s), 3.70-3.76 (1H, m), 4.09 (2H, d), 6.02 (1H, t), 7.35 (1H, d), 7.51-7.54 (1H, m), 8.09-8.10 (1H, m), 8.13 (1H, d), 8.44 (1H, s), 8.57 (1H, s), 8.60 (1H, d), 8.65 (1H, s), 8.71 (1H, s); m/z (ES+) (M+H)+=448.5; HPLC tR=1.93 min.

EXAMPLE 149

(2S)-3-cyclobutoxy-N-(5-methylpyrazin-2-yl)-2-(1-(2-methylpyridin-3-yl)-1H-pyrazolo[3,4-d]pyrimidin-4-yloxy)propanamide

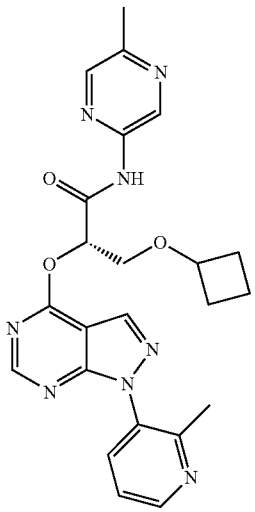

Sodium hydride (19.54 mg, 0.49 mmol) was added to (S)-3-cyclobutoxy-2-hydroxy-N-(5-methylpyrazin-2-yl)propanamide (Intermediate R1) (102 mg, 0.41 mmol) in anhydrous THF (5 mL) at 0° C. under nitrogen. The resulting solution was stirred at 0° C. for 10 minutes and then 4-chloro-1-(2-methylpyridin-3-yl)-1H-pyrazolo[3,4-d]pyrimidine (Intermediate V5) (100 mg, 0.41 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and ethyl acetate (50 mL). The organic layer was separated and the aqueous layer re-extracted with ethyl acetate (2×50 mL). The combined organics were washed with saturated brine (25 mL), dried (MgSO$_4$) and evaporated. The crude product was purified by flash silica chromatography, eluting with 0 to 5% MeOH in DCM to afford the product (78 mg, 41.6%). $^1$H NMR (400 MHz, DMSO) δ 1.23-1.36 (m, 1H), 1.38-1.51 (m, 1H), 1.60-1.75 (m, 2H), 1.96-2.07 (m, 2H), 2.13 (s, 3H), 2.27 (s, 3H), 3.71-3.87 (m, 2H), 3.89-3.98 (m, 1H), 5.71-5.78 (m, 1H), 7.28-7.34 (m, 1H), 7.75 (d, 1H), 8.15 (s, 1H), 8.39 (s, 1H), 8.45-8.51 (m, 2H), 8.93 (s, 1H), 11.01 (s, 1H). m/z (ESI+) (M+H)+=461.48; HPLC tR=1.75 min

EXAMPLE 150

(2S)—N-(5-chloropyridin-2-yl)-3-ethoxy-2-(1-(2-methylpyridin-3-yl)-1H-pyrazolo[3,4-d]pyrimidin-4-yloxy)propanamide

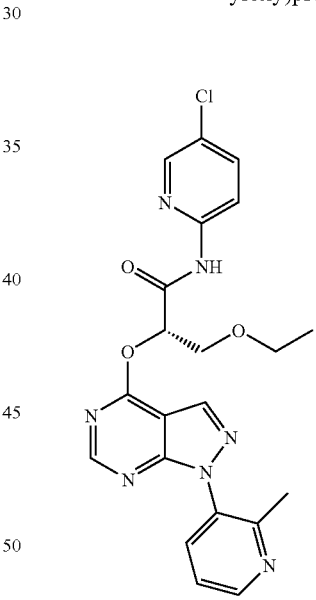

Sodium hydride (21.49 mg, 0.54 mmol) was added to (S)—N-(5-chloropyridin-2-yl)-3-ethoxy-2-hydroxypropanamide (110 mg, 0.45 mmol) in anhydrous THF (5 mL) at 0° C. under nitrogen. The resulting solution was stirred at 0° C. for 10 minutes and then 4-chloro-1-(2-methylpyridin-3-yl)-1H-pyrazolo[3,4-d]pyrimidine (110 mg, 0.45 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and ethyl acetate (50 mL). The organic layer was separated and the aqueous layer re-extracted with ethyl acetate (2×20 mL). The combined organics were washed with saturated brine (10 mL), dried (MgSO$_4$) and evaporated. The crude product was purified by flash silica chromatography, eluting with 0 to 5% MeOH in DCM to afford the product (24.0 mg, 11.8%). $^1$H NMR (400 MHz, CDCl$_3$) δ1.23 (t, 3H), 2.45 (s, 3H), 3.59-3.72 (m, 2H), 4.05-4.16 (m, 2H), 6.06 (t, 1H), 7.31-7.38 (m, 1H), 7.66-7.71 (m, 1H), 7.73-7.78 (m, 1H), 8.21-8.27 (m, 2H), 8.42 (s, 1H), 8.57 (s, 1H), 8.64-8.69 (m, 1H), 8.89 (s, 1H). m/z (ESI+) (M+H)+=454.31; HPLC tR=1.83 min

EXAMPLE 151

(2S)-2-(1-(2-chlorophenyl)-1H-pyrazolo[3,4-d]pyrimidin-4-yloxy)-3-((S)-1-methoxypropan-2-yloxy)-N-(5-methylpyrazin-2-yl)propanamide

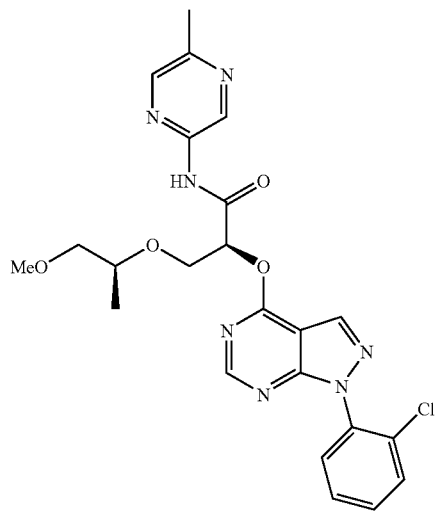

Sodium hydride (23.17 mg, 0.58 mmol) was added in one portion to a stirred solution of (S)-2-hydroxy-3-((S)-1-methoxypropan-2-yloxy)-N-(5-methylpyrazin-2-yl)propanamide (Intermediate Y3) (78 mg, 0.29 mmol) in anhydrous THF (5 mL) at 0° C. The resulting mixture was stirred for 10 minutes and then a solution of 4-chloro-1-(2-chlorophenyl)-1H-pyrazolo[3,4-d]pyrimidine (Intermediate B1) (115 mg, 0.43 mmol) in dry THF (2 mL) added dropwise over 1 minute and the reaction was allowed to warm up to ambient temperature and stirred for 1 hour. The reaction mixture was diluted with ethyl acetate (20 mL), and washed sequentially with water (10 mL) and saturated brine (5 mL). The organic layer was dried (MgSO$_4$) and evaporated. The crude product was purified by flash silica chromatography, eluting with 0-100% ethyl acetate in isohexane to afford the product (115 mg, 80%). $^1$H NMR (400 MHz, CDCl$_3$) δ 1.20 (d, 3H), 2.53 (s, 3H), 3.35-3.50 (m, 5H), 3.79-3.88 (m, 1H), 4.08-4.16 (m, 1H), 4.21-4.28 (m, 1H), 5.94-5.99 (m, 1H), 7.43-7.55 (m, 3H), 7.60-7.63 (m, 1H), 8.12-8.13 (m, 1H), 8.40 (s, 1H), 8.58 (s, 1H), 9.18 (s, 1H), 9.42 (d, 1H). m/z (ESI+) (M+H)+=498.36; HPLC $t_R$=2.25 min.

EXAMPLE 152

(2S)-2-(1-(2-chlorophenyl)-1H-pyrazolo[3,4-d]pyrimidin-4-yloxy)-3-((S)-1-methoxypropan-2-yloxy)-N-(5-methylpyridin-2-yl)propanamide

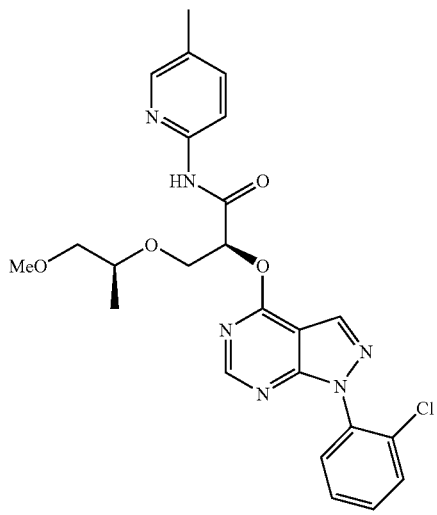

Sodium hydride (21.24 mg, 0.53 mmol) was added to (S)-2-hydroxy-3-((S)-1-methoxypropan-2-yloxy)-N-(5-methylpyridin-2-yl)propanamide (Intermediate Y5) (95 mg, 0.35 mmol) in anhydrous THF (5 mL) at 0° C. under nitrogen. The resulting solution was stirred at 0° C. for 10 minutes and then 4-chloro-1-(2-chlorophenyl)-1H-pyrazolo[3,4-d]pyrimidine (Intermediate B1) (122 mg, 0.46 mmol) in dry THF (2 mL) was added. The reaction was allowed to warm up to room temperature and stirred for 1 hour. The reaction mixture was diluted with ethyl acetate (20 mL), and washed sequentially with water (10 mL) and saturated brine (5 mL). The organic layer was dried (MgSO$_4$) and evaporated. The crude product was purified by flash silica chromatography, eluting with 0-100% ethyl acetate in isohexane to afford the product (160 mg, 91%). $^1$H NMR (400 MHz, DMSO) δ 1.09 (d, 3H), 2.24 (s, 3H), 3.23 (s, 3H), 3.26-3.38 (m, 2H), 3.77-3.86 (m, 1H), 4.00-4.16 (m, 2H), 5.85-5.91 (m, 1H), 7.55-7.70 (m, 4H), 7.73-7.78 (m, 1H), 7.88 (d, 1H), 8.16-8.19 (m, 1H), 8.54 (s, 1H), 8.59 (s, 1H), 10.79 (s, 1H). m/z (ESI+) (M+H)+=497.20; HPLC $t_R$=2.36 min.

EXAMPLE 153

(2S)-2-(1-(2-chlorophenyl)-1H-pyrazolo[3,4-d]pyrimidin-4-yloxy)-3-((R)-1-methoxypropan-2-yloxy)-N-(5-methylpyridin-2-yl)propanamide

EXAMPLE 154

(2S)-2-(1-(3-chloropyridin-2-yl)-1H-pyrazolo[3,4-d]pyrimidin-4-yloxy)-3-((R)-1-methoxypropan-2-yloxy)-N-(5-methylpyridin-2-yl)propanamide

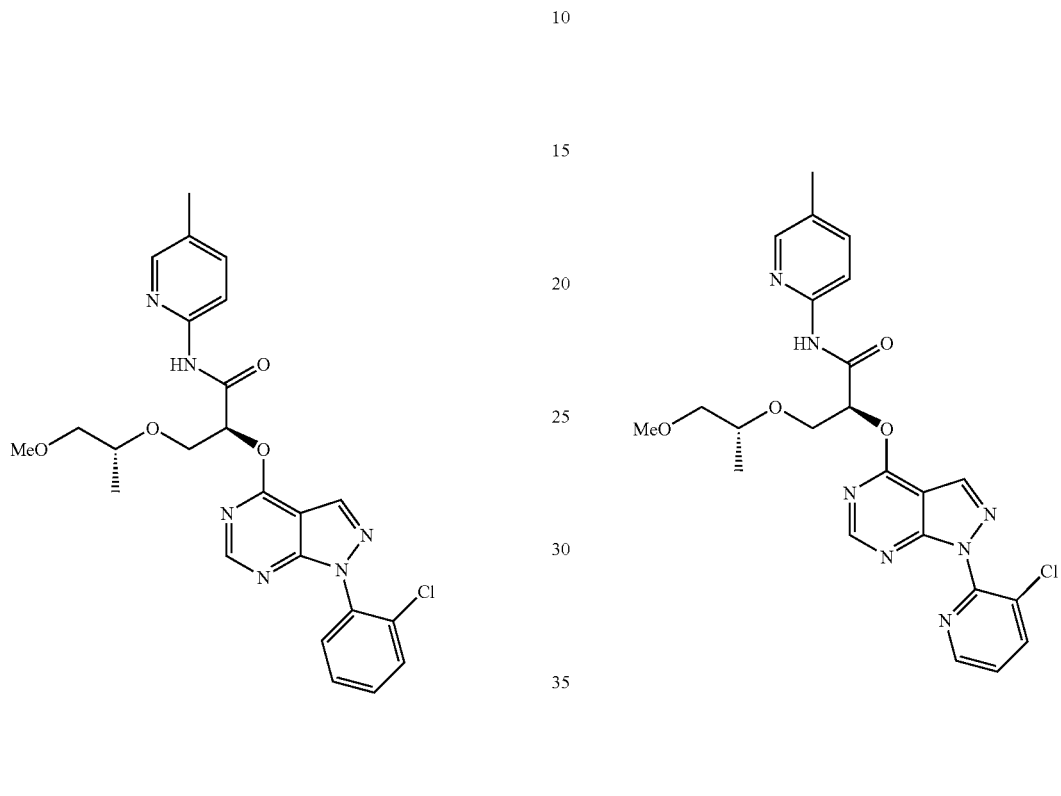

Trimethylaluminium (2M in hexane) (0.489 mL, 0.98 mmol) was added to 5-methylpyridin-2-amine (101 mg, 0.94 mmol) in toluene (3 mL) cooled to 0° C. under nitrogen. The resulting solution was stirred at 0° C. for 20 minutes. (2S)-Methyl 2-(1-(2-chlorophenyl)-1H-pyrazolo[3,4-d]pyrimidin-4-yloxy)-3-((R)-1-methoxypropan-2-yloxy) propanoate (Intermediate Y7) (358 mg, 0.85 mmol) in toluene (5 mL) was added and the reaction was allowed to warm up to room temperature and then heated at reflux for 4 hours. The reaction mixture was neutralised with 1M citric acid and then diluted with sodium potassium tartrate solution (20%, aq) (20 ml) and ethyl acetate (20 mL) before stirring vigorously for 2 hours. The phases were separated and the organic layer was dried (MgSO$_4$) and evaporated. The crude product was purified by flash silica chromatography, eluting with 0 to 100% ethyl acetate in isohexane to afford the product (167 mg, 39.5%). $^1$H NMR (400 MHz, DMSO) δ 1.08 (d, 3H), 2.24 (s, 3H), 3.21 (s, 3H), 3.22-3.38 (m, 2H), 3.75-3.85 (m, 1H), 3.98-4.15 (m, 2H), 5.85-5.93 (m, 1H), 7.55-7.70 (m, 4H), 7.73-7.78 (m, 1H), 7.88 (d, 1H), 8.15-8.19 (m, 1H), 8.53 (s, 1H), 8.59 (s, 1H), 10.82 (s, 1H). m/z (ESI+) (M+H)+=497.37; HPLC t$_R$=2.37 min.

Trimethylaluminium (0.334 mL, 0.67 mmol) was added to 5-methylpyridin-2-amine (69.1 mg, 0.64 mmol) in toluene (8 mL) cooled to 0° C. under nitrogen. The resulting solution was stirred at 0° C. for 20 minutes. (2S)-Methyl 2-(1-(3-chloropyridin-2-yl)-1H-pyrazolo[3,4-d]pyrimidin-4-yloxy)-3-((R)-1-methoxypropan-2-yloxy)propanoate (Intermediate Y8) (245 mg, 0.58 mmol) in toluene (2 mL) was added and the reaction was allowed to warm to room temperature and then heated at reflux for 24 hours. The reaction mixture was allowed to cool and neutralised with citric acid (1M, aq) and then diluted with water (50 mL) and ethyl acetate (50 mL). The organic layer was separated and the aqueous layer re-extracted with ethyl acetate (50 mL). The combined organics were dried (MgSO$_4$), filtered and evaporated. The crude product was purified by preparative HPLC (Phenomenex Gemini C 18 110A (axia) column, 5μ silica, 19 mm diameter, 100 mm length), using decreasingly polar mixtures of water (containing 0.1% formic acid) and MeCN as eluents to afford the product (137 mg, 47.4%). $^1$H NMR (400 MHz, DMSO) δ 1.10 (d, 3H), 2.26 (s, 3H), 3.23-3.42 (m, 5H), 3.76-3.85 (m, 1H), 4.10-4.16 (m, 2H), 5.95-6.00 (m, 1H), 7.55-7.60 (m, 1H), 7.68-7.73 (m, 1H), 7.86 (d, 1H), 8.14-8.18 (m, 1H), 8.24-8.29 (m, 1H), 8.54 (s, 2H), 8.62-8.67 (m, 1H), 10.21 (s, 1H) m/z (ESI+) (M+H)+=498.16; HPLC t$_R$=1.84 min.

EXAMPLE 155

(2S)-2-(1-(2-chlorophenyl)-1H-pyrazolo[3,4-d]pyrimidin-4-yloxy)-3-((R)-1-methoxypropan-2-yloxy)-N-(5-methylpyrazin-2-yl)propanamide

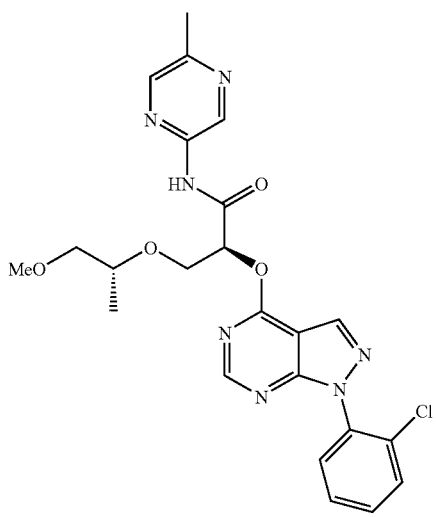

Sodium hydride (14.26 mg, 0.36 mmol) was added to (S)-2-hydroxy-3-((R)-1-methoxypropan-2-yloxy)-N-(5-methylpyrazin-2-yl)propanamide (Intermediate Y12) (64 mg, 0.24 mmol) in anhydrous THF (5 mL) at 0° C. under nitrogen. The resulting mixture was stirred for 10 minutes at 0° C. and 4-chloro-1-(2-chlorophenyl)-1H-pyrazolo[3,4-d]pyrimidine (86 mg, 0.32 mmol) was added and the reaction was allowed to warm up to room temperature and stirred for 1 hour. The reaction mixture was diluted with ethyl acetate (20 mL), and washed sequentially with water (10 mL) and saturated brine (5 mL). The organic layer was dried (MgSO$_4$) and evaporated. The crude product was purified by flash silica chromatography, eluting with 0-100% ethyl acetate in isohexane to afford the product (75 mg, 63.4%). $^1$H NMR (400 MHz, CDCl$_3$) δ 1.16 (d, 3H), 2.52 (s, 3H), 3.33-3.48 (m, 5H), 3.80-3.89 (m, 1H), 4.16-4.27 (m, 2H), 6.01 (t, 1H), 7.45-7.55 (m, 3H), 7.60-7.64 (m, 1H), 8.11-8.12 (m, 1H), 8.41 (s, 1H), 8.59 (s, 1H), 8.94 (s, 1H), 9.42 (d, 1H). m/z (ESI+) (M+H)+= 498.36; HPLC t$_R$=2.19 min.

EXAMPLE 156

(2S)-2-(1-(2-chlorophenyl)-1H-pyrazolo[3,4-d]pyrimidin-4-yloxy)-3-cyclobutoxy-N-(5-methylpyrazin-2-yl)propanamide

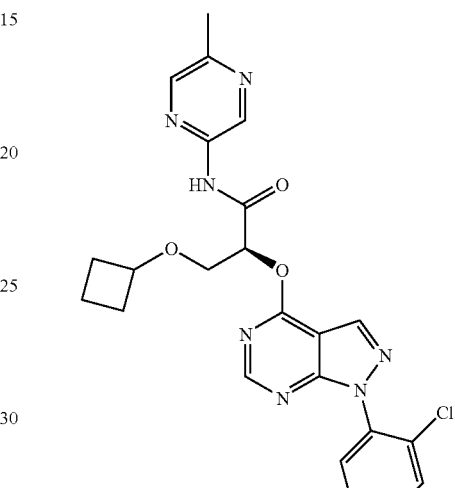

Sodium hydride (44.4 mg, 1.11 mmol) was added to (S)-3-cyclobutoxy-2-hydroxy-N-(5-methylpyrazin-2-yl)propanamide (Intermediate R1) (186 mg, 0.74 mmol) in anhydrous THF (5 mL) at 0° C. under nitrogen. The resulting mixture was stirred for 10 minutes at 0° C. and 4-chloro-1-(2-chlorophenyl)-1H-pyrazolo[3,4-d]pyrimidine (Intermediate B1) (255 mg, 0.96 mmol) was added and the reaction was allowed to warm up to room temperature and stirred for 30 minutes. The reaction mixture was diluted with ethyl acetate (20 mL), and washed sequentially with water (10 mL) and saturated brine (5 mL). The organic layer was dried (MgSO$_4$) and evaporated. The crude product was purified by flash silica chromatography, eluting with 0-100% ethyl acetate in isohexane to afford the product (262 mg, 73.8%). $^1$H NMR (400 MHz, DMSO) δ 1.39-1.52 (m, 1H), 1.56-1.67 (m, 1H), 1.77-1.91 (m, 2H), 2.13-2.24 (m, 2H), 2.44 (s, 3H), 3.88-4.02 (m, 2H), 4.06-4.15 (m, 1H), 5.89-5.94 (m, 1H), 7.56-7.70 (m, 3H), 7.73-7.78 (m, 1H), 8.31-8.33 (m, 1H), 8.54 (s, 1H), 8.63 (s, 1H), 9.10 (s, 1H), 11.17 (s, 1H). m/z (ESI+) (M+H)+= 480.33; HPLC t$_R$=2.45 min.

EXAMPLE 157

(2S)-2-(1-(3-chloropyridin-2-yl)-1H-pyrazolo[3,4-d]pyrimidin-4-yloxy)-3-cyclobutoxy-N-(5-methylpyrazin-2-yl)propanamide

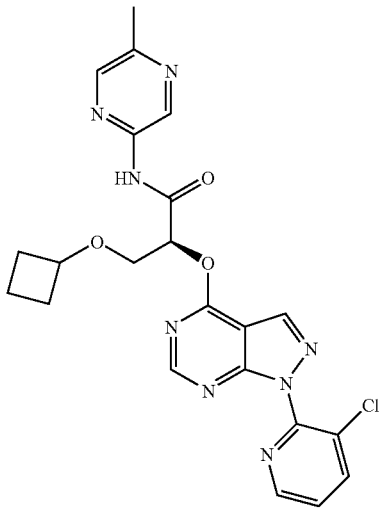

Prepared using an analogous procedure to that described for Example 156 using Intermediate R1 and Intermediate B15. ¹H NMR (400 MHz, DMSO) δ 1.40-1.52 (m, 1H), 1.56-1.67 (m, 1H), 1.78-1.92 (m, 2H), 2.14-2.23 (m, 2H), 2.45 (s, 3H), 3.89-4.01 (m, 2H), 4.06-4.15 (m, 1H), 5.89-5.95 (m, 1H), 7.73-7.78 (m, 1H), 8.31-8.33 (m, 1H), 8.35 (d, 1H), 8.56 (s, 1H), 8.65-8.69 (m, 2H), 9.09 (s, 1H), 11.18 (s, 1H). m/z (ESI+) (M+H)+=481.30; HPLC $t_R$=2.06 min.

EXAMPLE 158

(2S)-2-(1-(3-chloropyridin-2-yl)-1H-pyrazolo[3,4-d]pyrimidin-4-yloxy)-3-cyclobutoxy-N-(5-methylpyridin-2-yl)propanamide

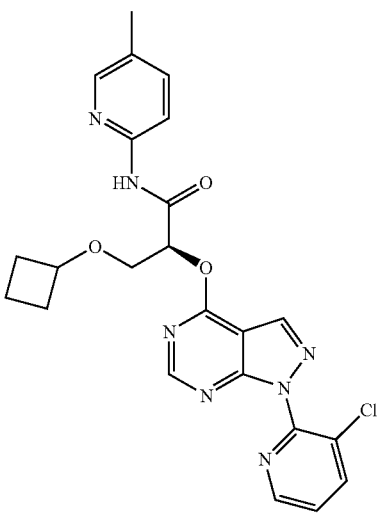

Prepared using an analogous procedure to that described for Example 156 using Intermediate R6 and Intermediate B15. ¹H NMR (400 MHz, DMSO) δ 1.41-1.52 (m, 1H), 1.56-1.67 (m, 1H), 1.78-1.91 (m, 2H), 2.13-2.23 (m, 2H), 2.24 (s, 3H), 3.86-3.99 (m, 2H), 4.06-4.15 (m, 1H), 5.86-5.92 (m, 1H), 7.56-7.61 (m, 1H), 7.73-7.77 (m, 1H), 7.84-7.90 (m, 1H), 8.16-8.19 (m, 1H), 8.32-8.35 (m, 1H), 8.56 (s, 1H), 8.65-8.69 (m, 2H), 10.86 (s, 1H). m/z (ESI+) (M+H)+= 480.35; HPLC $t_R$=2.27 min.

EXAMPLE 159

[(3S)-3-[1-(3-chloropyridin-2-yl)pyrazolo[4,5-e]pyrimidin-4-yl]oxy-4-[(5-methylpyridin-2-yl)amino]-4-oxobutyl]acetate

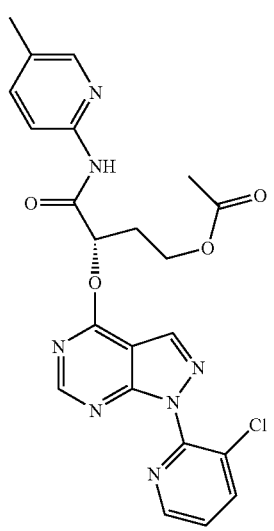

Acetic anhydride (0.035 mL, 0.38 mmol) was added to (2S)-2-(1-(3-chloropyridin-2-yl)-1H-pyrazolo[3,4-d]pyrimidin-4-yloxy)-4-hydroxy-N-(5-methylpyridin-2-yl)butanamide (Example 143) (150 mg, 0.34 mmol), N,N-Diisopropylethylamine (0.089 mL, 0.51 mmol) and 4-dimethylaminopyridine (4.17 mg, 0.03 mmol) in DCM (2 mL) at 0° C. over a period of 5 minutes under nitrogen. The resulting solution was stirred at 0° C. for 25 minutes. The volatiles were removed under reduced pressure and the crude product was purified by flash silica chromatography, eluting with 0 to 100% ethyl acetate in isohexane to afford the product (75 mg, 45.6%). ¹H NMR (400 MHz, CDCl₃) δ 1.95 (3H, s), 2.29 (3H, s), 2.54 (2H, q), 4.31-4.39 (2H, m), 6.00 (1H, t), 7.45-7.49 (1H, m), 7.53 (1H, d), 8.00-8.02 (1H, m), 8.10-8.14 (2H, m), 8.43 (1H, s), 8.61 (1H, q), 8.64 (1H, s), 8.80 (1H, s); m/z (ES+) (M+H)+=482; HPLC tR=2.04 min.

EXAMPLE 160

(2S)-3-isopropoxy-N-(5-methylpyridin-2-yl)-2-(1-(2-(trifluoromethyl)phenyl)-1H-pyrazolo[3,4-d]pyrimidin-4-yloxy)propanamide

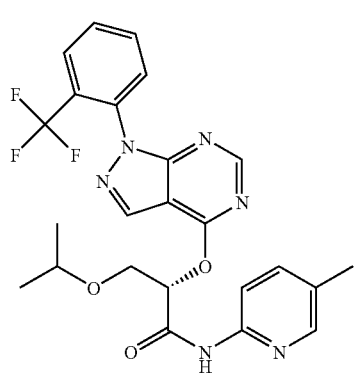

Sodium hydride (10.78 mg, 0.27 mmol) was added to (S)-2-hydroxy-3-isopropoxy-N-(5-methylpyridin-2-yl)propanamide (Intermediate C7) (53.5 mg, 0.22 mmol) in anhydrous THF (50 mL) at 0° C. under nitrogen. The resulting solution was stirred at 0° C. for 10 minutes and then 4-phenoxy-1-(2-(trifluoromethyl)phenyl)-1H-pyrazolo[3,4-d]pyrimidine (Intermediate Z1) (80 mg, 0.22 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and ethyl acetate (50 mL). The organic layer was separated and the aqueous layer re-extracted with ethyl acetate (2×100 mL). The combined organics were washed with saturated brine (75 mL), dried (MgSO$_4$) and evaporated. The crude product was purified by flash silica chromatography, eluting with 50 to 100% ethyl acetate in isohexane. The residue was purified by preparative HPLC using decreasingly polar mixtures of water (containing 1% ammonia) and MeCN as eluents to afford the product (60.0 mg, 53.4%). $^1$H NMR (400 MHz, CDCl$_3$) δ 1.17-1.20 (6H, m), 2.30 (3H, s), 3.69-3.75 (1H, m), 4.09 (2H, d), 6.01 (1H, t), 7.52-7.56 (2H, m), 7.69 (1H, t), 7.76 (1H, t), 7.91 (1H, d), 8.10-8.15 (2H, m), 8.42 (1H, s), 8.56 (1H, s), 8.72 (1H, s); m/z (ES+) (M+H)+=501; HPLC tR=2.70 min.

EXAMPLE 161

(2S)-2-(1-(2-chlorophenyl)-1H-pyrazolo[3,4-d]pyrimidin-4-yloxy)-N-(5-methylpyridin-2-yl)-4-(methylsulfonyl)butanamide

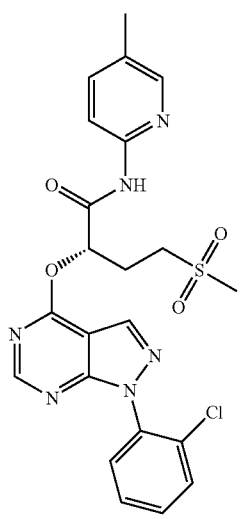

Trimethylaluminium (0.135 mL, 0.27 mmol) was added to 2-amino-5-methylpyridine (28.0 mg, 0.26 mmol) in toluene (5 mL) cooled to 0° C. under nitrogen. (2S)-methyl 2-(1-(2-chlorophenyl)-1H-pyrazolo[3,4-d]pyrimidin-4-yloxy)-4-(methylsulfonyl)butanoate (Intermediate AA1) (100 mg, 0.24 mmol) was added and the reaction was heated to 100° C. for 3 hours in the microwave reactor and then allowed to cool. The reaction mixture was neutralised with citric acid (1M, aq) and then diluted with water (30 mL) and ethyl acetate (50 mL). The aqueous layer was washed with ethyl acetate. The combined organics were dried (MgSO$_4$) and evaporated. The crude product was purified by flash silica chromatography, eluting with 30 to 50% ethyl acetate in isohexane to afford the product (90 mg, 76%) $^1$H NMR (400 MHz, CDCl$_3$) δ 2.31 (3H, s), 2.71-2.77 (2H, m), 2.98 (3H, s), 3.32-3.38 (2H, m), 6.12 (1H, t), 7.45-7.56 (4H, m), 7.62-7.64 (1H, m), 8.09-8.11 (2H, m), 8.41 (1H, s), 8.61 (1H, s), 8.69 (1H, s); m/z (ES+) (M+H)+=501; HPLC tR=2.05 min.

EXAMPLE 162

(2S)-2-(1-(3-chloropyridin-2-yl)-1H-pyrazolo[3,4-d]pyrimidin-4-yloxy)-N-(5-cyanopyridin-2-yl)-3-(2-hydroxyethoxy)propanamide

EXAMPLE 163

(2S)—N-(5-chloropyridin-2-yl)-2-(1-(3-chloropyridin-2-yl)-1H-pyrazolo[3,4-d]pyrimidin-4-yloxy)-3-(2-hydroxyethoxy)propanamide

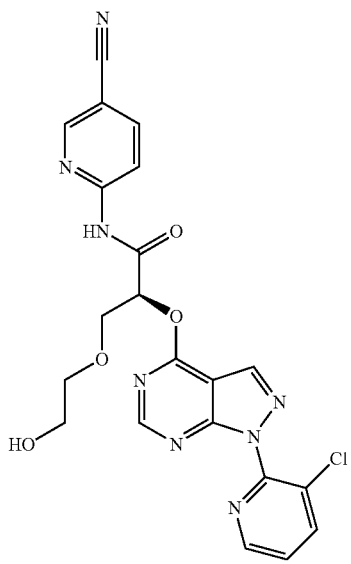

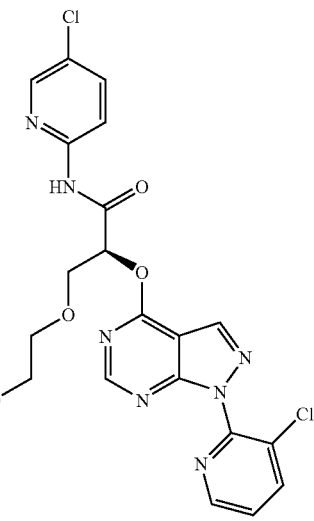

Tetrabutylammonium fluoride (1M in THF) (0.139 mL, 0.14 mmol) was added to (2S)-3-(2-(tert-butyldiphenylsilyloxy)ethoxy)-2-(1-(3-chloropyridin-2-yl)-1H-pyrazolo[3,4-d]pyrimidin-4-yloxy)-N-(5-cyanopyridin-2-yl)propanamide (Intermediate AB1) (100 mg, 0.14 mmol) in THF (2 mL) under nitrogen. The resulting mixture was stirred at ambient temperature for 1 hour. The reaction mixture was quenched with saturated NH$_4$Cl (1 mL), diluted with DCM (10 ml) and poured onto a phase separator. The organic layer was collected and evaporated. The residue was purified by flash silica chromatography, eluting with 0 to 100% ethyl acetate in isohexane to afford the product (38.0 mg, 56.8%). $^1$H NMR (300 MHz, CDCl$_3$) δ 2.36 (1H, s), 3.70-3.86 (4H, m), 4.16-4.27 (2H, m), 6.07 (1H, t), 7.45-7.52 (1H, m), 7.93-8.05 (2H, m), 8.32-8.38 (1H, m), 8.46 (1H, s), 8.55-8.58 (1H, m), 8.60-8.65 (2H, m), 9.28 (1H, s). m/z (ES+) (M+H)+=481.31; HPLC tR=1.63 min.

Tetrabutylammonium fluoride (1M in THF) (0.790 mL, 0.79 mmol) was added to (2S)-3-(2-(tert-butyldiphenylsilyloxy)ethoxy)-N-(5-chloropyridin-2-yl)-2-(1-(3-chloropyridin-2-yl)-1H-pyrazolo[3,4-d]pyrimidin-4-yloxy)propanamide (Intermediate AB4) (576 mg, 0.79 mmol) in THF (2 mL) under nitrogen. The resulting mixture was stirred at ambient temperature for 1 hour. The reaction mixture was quenched with saturated NH$_4$Cl (1 mL), diluted with DCM (10 ml) and poured onto a phase separator. The organic layer was collected and evaporated. The residue was purified by preparative HPLC (Waters XBridge Prep C18 OBD column, 5μ silica, 50 mm diameter, 150 mm length), using decreasingly polar mixtures of water (containing 1% NH3) and MeCN as eluents. The resulting product decomposed to an extent during evaporation and so was re-purified by flash silica chromatography, eluting with 0 to 10% MeOH in ethyl acetate to afford the product (82 mg, 21%). $^1$H NMR (400 MHz, CDCl$_3$) δ 2.49-2.56 (1H, m), 3.69-3.85 (4H, m), 4.14-4.25 (2H, m), 6.08 (1H, t), 7.45-7.50 (1H, m), 7.67-7.72 (1H, m), 7.98-8.04 (1H, m), 8.15-8.28 (2H, m), 8.47 (1H, s), 8.58-8.65 (2H, m), 8.99 (1H, s); m/z (ES+) (M+H)+=490.35; HPLC tR=1.82 min.

EXAMPLE 164

(2S)-2-(1-(2-chlorophenyl)-1H-pyrazolo[3,4-d]pyrimidin-4-yloxy)-N-(5-methylpyridin-2-yl)-4-(methylsulfonamido)butanamide

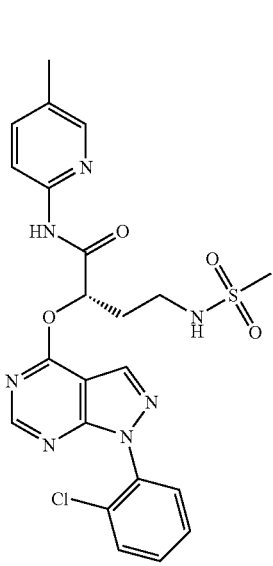

Trimethylaluminium (2M in hexane) (0.164 mL, 0.33 mmol) was added to 5-methylpyridin-2-amine (33.8 mg, 0.31 mmol) in toluene (5 mL) cooled to 0° C. under nitrogen. The resulting solution was stirred at 0° C. for 20 minutes. (3S)-3-(1-(2-chlorophenyl)-1H-pyrazolo[3,4-d]pyrimidin-4-yloxy)-1-(methylsulfonyl)pyrrolidin-2-one (Intermediate AC1) (116 mg, 0.28 mmol) in toluene (1 mL) was added and the reaction was allowed to warm to room temperature and stirred for 1 hour. The reaction was then heated to reflux for 2.5 hours. The reaction mixture was allowed to cool and concentrated in vacuo. The residue was neutralised with citric acid and sodium potassium tartrate solution (sat.) and stirred vigorously for 45 mins. The mixture was separated and the aqueous re-extracted with ethyl acetate, the organic layer was dried ($MgSO_4$) and evaporated. The residue was purified by preparative HPLC (Waters XBridge Prep C18 OBD column, 5μ silica, 50 mm diameter, 150 mm length), using decreasingly polar mixtures of water (containing 0.1% formic acid) and MeCN as eluents to afford the product (52.0 mg, 35.4%). $^1$H NMR (400 MHz, $CDCl_3$) δ 2.30 (3H, s), 2.37-2.55 (2H, m), 2.98 (3H, s), 3.35-3.55 (2H, m), 4.95-5.10 (1H, m), 6.04 (1H, t), 7.44-7.58 (4H, m), 7.60-7.65 (1H, m), 8.07-8.15 (2H, m), 8.44 (1H, s), 8.61 (1H, s), 8.69 (1H, s); m/z (ES+) (M+H)+=516.28; HPLC tR=1.84 min.

EXAMPLE 165

(2S)—N-(5-chloropyridin-2-yl)-2-[1-(3-chloropyridin-2-yl)pyrazolo[4,5-e]pyrimidin-4-yl]oxy-3-(3-hydroxyazetdin-1-yl)propanamide

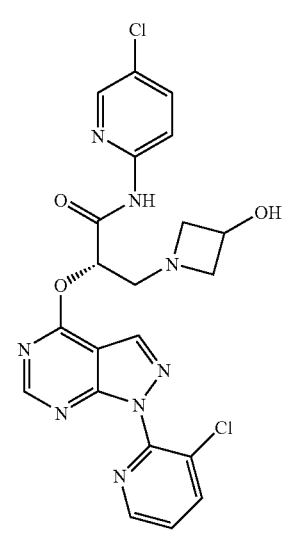

Tetrabutylammonium fluoride (1M in THF) (5.96 mL, 5.96 mmol) was added to (2S)-3-(3-(tert-butyldimethylsilyloxy)azetidin-1-yl)-N-(5-chloropyridin-2-yl)-2-(1-(3-chloropyridin-2-yl)-1H-pyrazolo[3,4-d]pyrimidin-4-yloxy)propanamide (Intermediate AD1) (3.67 g, 5.96 mmol) in THF (75 mL) under nitrogen. The resulting mixture was stirred at ambient temperature for 20 hours, saturated ammonium chloride (50 mL) added, diluted with DCM (100 mL) and poured onto a phase separator. The organic layer was evaporated and the crude product was purified by flash silica chromatography, eluting with 0 to 10% MeOH in EtOAc to afford the product (1.7 g, 57%). $^1$H NMR (400 MHz, DMSO) δ 2.95-3.10 (3H, m), 3.10-3.15 (1H, m), 3.60-3.70 (2H, m), 4.14-4.21 (1H, m), 5.26 (1H, d), 5.73-5.75 (1H, m), 7.74 (1H, dd), 7.88 (1H, dd), 8.01-8.07 (1H, m), 8.33 (1H, dd), 8.39-8.40 (1H, m), 8.55 (1H, s), 8.66 (1H, s), 8.68 (1H, dd), 11.13 (1H, s); m/z (ESI+) (M+H)+=501; HPLC $t_R$=1.27 min.

EXAMPLE 166

(2S)-2-[1-(3-chloro-2-methylphenyl)pyrazolo[4,5-e]
pyrimidin-4-yl]oxy-N-(5-cyanopyridin-2-yl)-3-(2-
hydroxyethoxy)propanamide

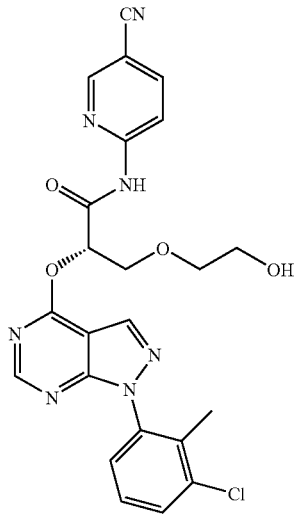

A solution of tetrabutylammonium fluoride (1M in THF) (1.557 mL, 1.56 mmol) was added dropwise to a stirred solution of (2S)-3-(2-(tert-butyldiphenylsilyloxy)ethoxy)-2-(1-(3-chloro-2-methylphenyl)-1H-pyrazolo[3,4-d]pyrimidin-4-yloxy)-N-(5-cyanopyridin-2-yl)propanamide (Intermediate AE1) (950 mg, 1.30 mmol) in THF (15 mL) over a period of 1 minute and the resulting solution was stirred at ambient temperature for 3 hours. Saturated ammonium chloride (20 mL) was added to the reaction mixture which was then diluted with EtOAc (25 mL) and washed sequentially with water (25 mL) and saturated brine (25 mL). The organic layer was dried (MgSO$_4$), filtered and evaporated in vacuo. The crude product was purified by flash silica chromatography, elution gradient 60 to 100% EtOAc in isohexane and fractions were evaporated to dryness to afford the product as a white foam containing ~10-15% of the opposite enantiomer. Chiral HPLC followed by reverse phase HPLC (acetonitrile/water with 0.1% formic acid modifier gave (350 mg, 54%) as a colourless amorphous foam. $^1$H NMR (400 MHz, DMSO) δ 2.06 (3H, s), 3.51-3.57 (2H, m), 3.58-3.68 (2H, m), 4.03-4.07 (1H, m), 4.11-4.15 (1H, m), 4.55-4.67 (1H, m), 5.91-5.98 (1H, m), 7.42-7.47 (2H, m), 7.64-7.69 (1H, m), 8.13 (1H, dd), 8.25 (1H, dd), 8.54 (1H, s), 8.62 (1H, s), 8.82 (1H, dd), 11.53 (1H, s); m/z (ESI−) (M−H)−=492; HPLC $t_R$=2.25 min.

EXAMPLE 167

(2S)-2-[1-(3-chloro-2-methylphenyl)pyrazolo[4,5-e]
pyrimidin-4-yl]oxy-3-(2-hydroxyethoxy)-N-(5-methylpyridin-2-yl)propanamide

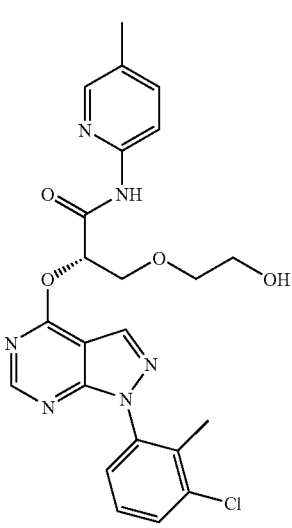

A solution of tetrabutylammonium fluoride (1M in THF) (0.832 mL, 0.83 mmol) was added dropwise to a stirred solution of (2S)-3-(2-(tert-butyldiphenylsilyloxy)ethoxy)-2-(1-(3-chloro-2-methylphenyl)-1H-pyrazolo[3,4-d]pyrimidin-4-yloxy)-N-(5-methylpyridin-2-yl)propanamide (Intermediate AE3) (500 mg, 0.69 mmol) in THF (15 mL) over a period of 1 minute and the resulting solution stirred at ambient temperature for 3 hours. Saturated ammonium chloride (20 mL) was added to the reaction mixture which was then diluted with EtOAc (25 mL) and washed sequentially with water (25 mL) and saturated brine (25 mL). The organic layer was dried (MgSO$_4$), filtered and evaporated in vacuo. The crude product was purified by flash silica chromatography, elution gradient 60 to 100% EtOAc in isohexane. This was further purified by chiral HPLC to give the product (76 mg, 52%). $^1$H NMR (400 MHz, DMSO) δ 2.06 (3H, s), 2.24 (3H, s), 3.53-3.58 (2H, m), 3.58-3.68 (2H, m), 4.00-4.05 (1H, m), 4.08-4.13 (1H, m), 4.61 (1H, t), 5.93-6.01 (1H, m), 7.45-7.02 (2H, m), 7.57-7.60 (1H, m), 7.66-7.69 (1H, m), 7.88-7.95 (1H, m), 8.17-8.18 (1H, m), 8.54 (1H, s), 8.62 (1H, s), 10.86 (1H, s); m/z (ESI+) (M+H)$^+$=483; HPLC $t_R$=2.14 min.

EXAMPLE 168

(2S)—N-(5-cyanopyridin-2-yl)-2-[1-(3-fluoro-2-methylphenyl)pyrazolo[4,5-e]pyrimidin-4-yl]oxy-3-(2-hydroxyethoxy)propanamide

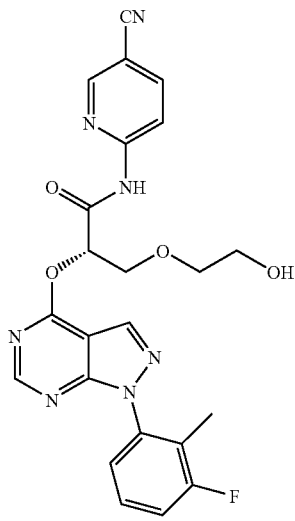

A solution of tetrabutylammonium fluoride (1M in THF, 1.504 mL, 1.50 mmol) was added dropwise to a stirred solution of (2S)-3-(2-(tert-butyldiphenylsilyloxy)ethoxy)-N-(5-cyanopyridin-2-yl)-2-(1-(3-fluoro-2-methylphenyl)-1H-pyrazolo[3,4-d]pyrimidin-4-yloxy)propanamide (Intermediate AF1) (520 mg, 0.73 mmol) in THF (15 mL) over a period of 1 minute and the resulting solution stirred at ambient temperature for 3 hours. Saturated ammonium chloride (20 mL) was added to the reaction mixture which was then diluted with EtOAc (25 mL), and washed sequentially with water (25 mL) and saturated brine (25 mL). The organic layer was dried (MgSO$_4$), filtered and evaporated in vacuo. The crude product was purified by flash silica chromatography, elution gradient 60 to 100% EtOAc in isohexane and then by chiral HPLC to afford the product (250 mg, 72%).

$^1$H NMR (400 MHz, DMSO) δ 1.99 (3H, d), 3.50-3.55 (2H, m), 3.58-3.67 (2H, m), 4.03-4.07 (1H, m), 4.11-4.15 (1H, m), 4.52-4.65 (1H, m), 5.92-5.98 (1H, m), 7.31-7.34 (1H, m), 7.40-7.50 (2H, m), 8.12-8.14 (1H, m), 8.22-8.25 (1H, m), 8.55 (1H, s), 8.62 (1H, s), 8.81-8.85 (1H, m), 11.5 (1H, s); m/z (ESI−) (M−H)−=476; HPLC t$_R$=2.10 min.

EXAMPLE 169

(2S)-2-[1-(3-fluoro-2-methylphenyl)pyrazolo[4,5-e]pyrimidin-4-yl]oxy-3-(2-hydroxyethoxy)-N-(5-methylpyridin-2-yl)propanamide

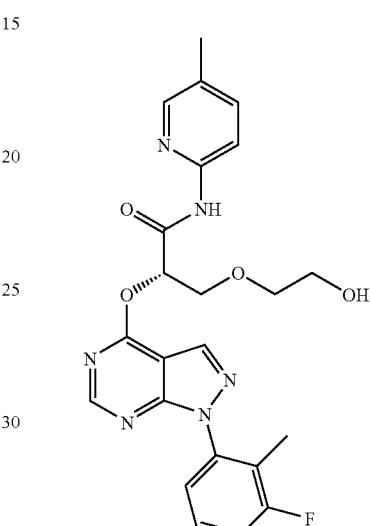

A solution of tetrabutylammonium fluoride (1M in THF) (1.504 mL, 1.50 mmol) was added dropwise to a stirred solution of (2S)-3-(2-(tert-butyldiphenylsilyloxy)ethoxy)-2-(1-(3-fluoro-2-methylphenyl)-1H-pyrazolo[3,4-d]pyrimidin-4-yloxy)-N-(5-methylpyridin-2-yl)propanamide (Intermediate AF2) (430 mg, 0.61 mmol) in THF (15 mL) over a period of 1 minute and the resulting solution stirred at ambient temperature for 3 hours. Saturated ammonium chloride (20 mL) was added to the reaction mixture which was then diluted with EtOAc (25 mL), and washed sequentially with water (25 mL) and saturated brine (25 mL). The organic layer was dried (MgSO$_4$), filtered and evaporated to afford crude product which was purified by flash silica chromatography, elution gradient 60 to 100% EtOAc in isohexane then by chiral HPLC to afford the product (160 mg, 56%). 1H NMR (400 MHz, DMSO) δ 1.99 (3H, d), 2.24 (3H, s), 3.50-3.56 (2H, m), 3.58-3.68 (2H, m), 4.00-4.05 (1H, m), 4.08-4.13 (1H, m), 4.61 (1H, t), 5.91-5.96 (1H, m), 7.30-7.33 (1H, m), 7.40-7.51 (2H, m), 7.57-7.60 (1H, m), 7.85-7.88 (1H, m), 8.17-8.18 (1H, m), 8.54 (1H, s), 8.61 (1H, s), 10.85 (1H, s); m/z (ESI+) (M+H)$^+$=467; HPLC t$_R$=1.98 min.

EXAMPLE 170

(2S)—N-(5-chloropyridin-2-yl)-2-[1-(3-fluoro-2-methylphenyl)pyrazolo[4,5-e]pyrimidin-4-yl]oxy-3-(2-hydroxyethoxy)propanamde

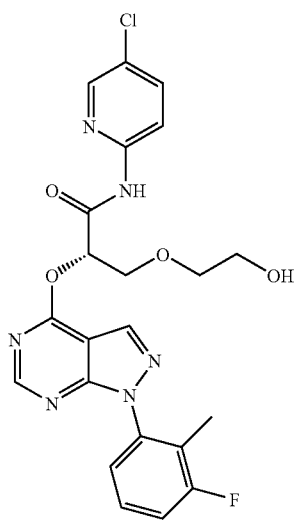

A solution of tetrabutylammonium fluoride (1M in THF) (1.504 mL, 1.50 mmol) was added dropwise to a stirred solution of (2S)-3-(2-(tert-butyldiphenylsilyloxy)ethoxy)-N-(5-chloropyridin-2-yl)-2-(1-(3-fluoro-2-methylphenyl)-1H-pyrazolo[3,4-d]pyrimidin-4-yloxy)propanamide (Intermediate AF3) (600 mg, 0.83 mmol) in THF (15 mL) over a period of 1 minute and the resulting solution stirred at ambient temperature for 3 hours. Saturated ammonium chloride (20 mL) was added to the reaction mixture which was then diluted with EtOAc (25 mL), and washed sequentially with water (25 mL) and saturated brine (25 mL). The organic layer was dried (MgSO$_4$), filtered and evaporated in vacuo. The crude product was purified by flash silica chromatography, elution gradient 60 to 100% EtOAc in isohexane then by chiral HPLC to afford the product (252 mg, 62%). $^1$H NMR (400 MHz, DMSO) δ 2.07 (3H, s), 3.53-3.62 (2H, m), 3.65-3.72 (2H, m), 4.06-4.22 (2H, m), 4.61-4.71 (1H, m), 5.96-6.05 (1H, m), 7.36-7.42 (1H, m), 7.44-7.55 (2H, m), 7.92-7.96 (1H, m), 8.08 (1H, d), 8.45 (1H, dd), 8.60 (1H, s), 8.71 (1H, s), 11.18 (1H, s); m/z (ESI−) (M−H)−=485; HPLC t$_R$=2.29 min.

EXAMPLE 171

(2S)-2-[1-(2-chlorophenyl)pyrazolo[4,5-e]pyrimidin-4-yl]oxy-N-(5-chloropyridin-2-yl)-3-(2-hydroxyethoxy)propanamide

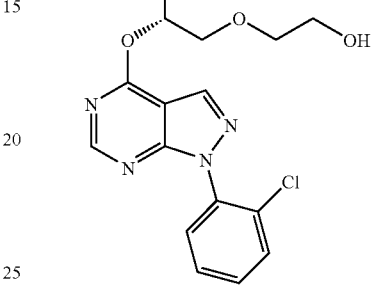
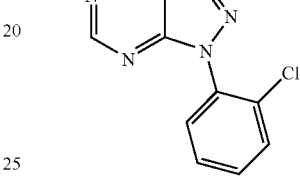

Prepared from (2S)-3-[2-(tert-butyl-dimethylsilyl)oxy-ethoxy]-2-[1-(2-chlorophenyl)pyrazolo[4,5-e]pyrimidin-4-yl]oxy-N-(5-chloropyridin-2-yl)propanamide (Intermediate AG1) (980 mg, 1.35 mmol) according to the method for Example 167. $^1$H NMR (400 MHz, DMSO) δ 3.54-3.64 (2H, m), 3.65-3.78 (2H, m), 4.05-4.24 (2H, m), 4.62-4.71 (1H, m), 5.96-6.04 (1H, m), 7.60-7.78 (3H, m), 7.76 (1H, dd), 7.88 (1H, dd), 8.06 (1H, d), 8.45 (1H, dd), 8.60 (1H, s), 8.68 (1H, s), 11.18 (1H, s); m/z (ESI−) (M−H)−=487; HPLC t$_R$=2.17 min.

EXAMPLE 172

(2S)-2-[1-(2-chlorophenyl)pyrazolo[4,5-e]pyrimidin-4-yl]oxy-N-(5-cyanopyridin-2-yl)-3-(2-hydroxyethoxy)propanamide

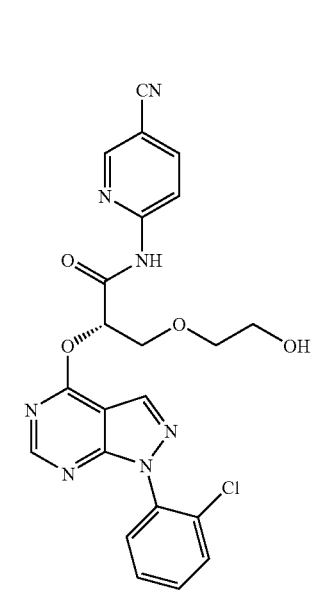

Prepared according to the method for Example 171 from (2S)-3-(2-(tert-butyldiphenylsilyloxy)ethoxy)-2-(1-(2-chlorophenyl)-1H-pyrazolo[3,4-d]pyrimidin-4-yloxy)-N-(5-cyanopyridin-2-yl)propanamide (Intermediate AG3). $^1$H NMR (400 MHz, DMSO) δ 3.52-3.61 (2H, m), 3.56-3.64 (2H, m), 3.65-3.76 (2H, m), 4.04-4.25 (2H, m), 4.61-4.75 (1H, m), 5.96-6.04 (1H, m), 7.57-7.78 (3H, m), 7.80-7.84 (1H, dd), 8.18 (1H, d), 8.30 (1H, dd), 8.60 (1H, s), 8.70 (1H, s), 8.87-8.91 (1H, m), 11.53 (1H, s); m/z (ESI−) (M−H)−=478; HPLC $t_R$=1.99 min.

EXAMPLE 173

(2S)-2-[1-(3-chloro-2-methylphenyl)pyrazolo[4,5-e]pyrimidin-4-yl]oxy-N-(5-chloropyridin-2-yl)-3-(2-hydroxyethoxy)propnamide

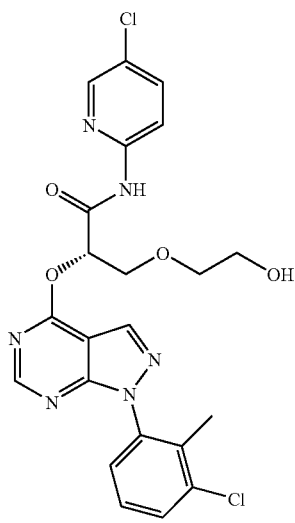

Prepared according to the method for Example 166 from (2S)-3-(2-(tert-butyldiphenylsilyloxy)ethoxy)-2-(1-(3-chloro-2-methylphenyl)-1H-pyrazolo[3,4-d]pyrimidin-4-yloxy)-N-(5-chloropyridin-2-yl)propanamide (Intermediate AE4).

1H NMR (400 MHz, CDCl$_3$) δ 2.09 (3H, s), 3.67-3.74 (4H, m), 4.08-4.18 (2H, m), 6.02 (1H, t), 7.22-7.29 (2H, m), 7.47-7.49 (1H, m), 7.63 (1H, dd), 8.12-8.16 (1H, m), 8.14-8.17 (1H, m), 8.34 (1H, s), 8.51 (1H, s), 8.95 (1H, s) (OH signal not observed); m/z (ESI+) (M+H)$^+$=503; HPLC $t_R$=2.49 min.

EXAMPLE 174

(2S)-2-(1-(2-chloro-6-cyanophenyl)-1H-pyrazolo[3,4-d]pyrimidin-4-yloxy)-N-(5-chloropyridin-2-yl)-3-(2-hydroxyethoxy)propanamide

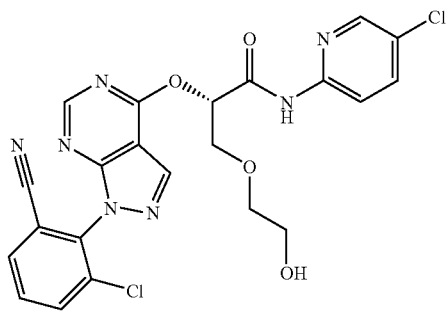

Tetrabutylammonium fluoride (1M in THF) (0.611 mL, 0.61 mmol) was added to (2S)-3-(2-(tert-butyldiphenylsilyloxy)ethoxy)-2-(1-(2-chloro-6-cyanophenyl)-1H-pyrazolo[3,4-d]pyrimidin-4-yloxy)-N-(5-chloropyridin-2-yl)propanamide (Intermediate AH1) in THF (5 mL) under nitrogen. The resulting mixture was stirred at ambient temperature for 1 hour. The reaction mixture was quenched with saturated NH$_4$Cl (2 mL), diluted with DCM (25 mL) and poured through a phase separator. The organic phase was reduced to give a gum. This was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. Fractions containing the desired compound were evaporated to dryness to afford (2S)-2-(1-(2-chloro-6-cyanophenyl)-1H-pyrazolo[3,4-d]pyrimidin-4-yloxy)-N-(5-chloropyridin-2-yl)-3-(2-hydroxyethoxy)propanamide (194 mg, 61.7%, 84% ee). $^1$H NMR (400 MHz, DMSO) δ 3.53 (2H, m), 3.70-3.58 (2H, m), 4.05 (1H, m), 4.13 (1H, m), 4.62 (1H, t), 5.95 (1H, s), 7.92-7.86 (2H, m), 8.06-8.00 (1H, m), 8.17 (1H, m), 8.19 (1H, m), 8.42-8.38 (1H, m), 8.61 (1H, s), 8.79 (1H, d), 11.21 (1H, s). m/z (ES+) (M+H)$^+$=514; HPLC $t_R$=2.10 min.

EXAMPLE 175

(2S)-2-(1-(2-chloro-6-cyanophenyl)-1H-pyrazolo[3,4-d]pyrimidin-4-yloxy)-3-((R)-1-hydroxypropan-2-yloxy)-N-(5-methylpyridin-2-yl)propanamide

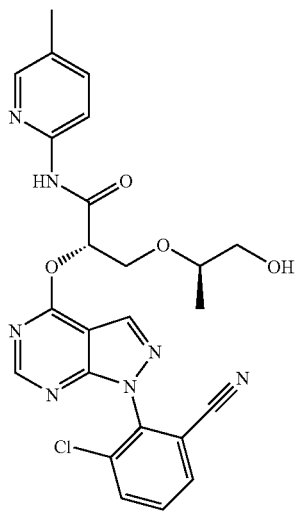

1M tetrabutylammonium fluoride in THF (0.503 mL, 0.50 mmol) was added to (2S)-2-(1-(2-chloro-6-cyanophenyl)-1H-pyrazolo[3,4-d]pyrimidin-4-yloxy)-N-(5-methylpyridin-2-yl)-3-((R)-1-(triisopropylsilyloxy)propan-2-yloxy)propanamide (Intermediate AH8) (334 mg, 0.50 mmol) in THF (10 mL) under nitrogen. The resulting mixture was stirred at ambient temperature for 1 hour. The reaction mixture was quenched with saturated NH$_4$Cl (2 mL), diluted with DCM (25 mL) and poured onto a phase separator. The organic phase was reduced and the residue was purified by preparative HPLC (Waters XBridge Prep C18 OBD column, 5µ silica, 50 mm diameter, 150 mm length), using decreasingly polar mixtures of water (containing 0.1% formic acid) and MeCN as eluents to afford the product (129 mg, 50.5%). $^1$H NMR (400 MHz, CDCl$_3$) d 1.21-1.14 (3H, m), 2.30 (3H, s), 3.62 (2H, m), 3.78 (1H, m), 4.14-4.03 (1H, m), 4.28 (1H, dd), 6.10-6.03 (1H, m), 7.54 (1H, dd), 7.62 (1H, t), 7.79 (1H, m), 7.86 (1H, m), 8.07 (2H, d), 8.51 (1H, d), 8.62 (1H, d), 9.28-9.18 (1H, m), OH not observed. m/z (ES+) (M+H)$^+$=508; HPLC t$_R$=1.92 min. ee 90%

EXAMPLE 176

(2S)-2-(1-(2-chloro-6-cyanophenyl)-1H-pyrazolo[3,4-d]pyrimidin-4-yloxy)-3-(2-hydroxyethoxy)-N-(5-methylpyridin-2-yl)propanamide

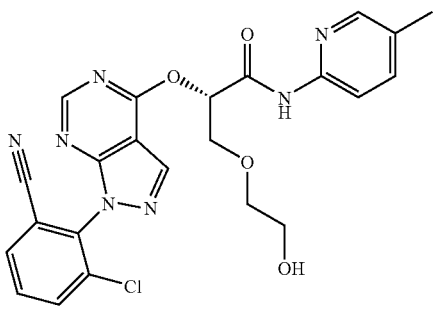

Tetrabutylammonium fluoride (1M in THF) (0.203 mL, 0.20 mmol) was added to (2S)-3-(2-(tert-butyldiphenylsilyloxy)ethoxy)-2-(1-(2-chloro-6-cyanophenyl)-1H-pyrazolo[3,4-d]pyrimidin-4-yloxy)-N-(5-methylpyridin-2-yl)propanamide (Intermediate AH9) (149 mg, 0.20 mmol) in THF (5 mL) under nitrogen. The resulting mixture was stirred at ambient temperature for 1 hour. The reaction mixture was quenched with saturated NH$_4$Cl (2 mL), diluted with DCM (25 mL) and poured onto a phase separator. The organic phase was reduced to give a gum. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents to afford the product (45.0 mg, 44.8%, 58% ee). $^1$H NMR (400 MHz, CDCl$_3$) d 2.23 (3H, s), 3.77-3.62 (4H, m), 4.20-4.04 (2H, m), 6.01 (1H, m), 7.51-7.46 (1H, m), 7.55 (1H, t), 7.72 (1H, dd), 7.84-7.76 (1H, m), 8.03 (2H, d), 8.46 (1H, d), 8.55 (1H, d), 9.19-8.96 (1H, m) OH not observed. m/z (ES+) (M+H)$^+$=494; HPLC t$_R$=1.82 min.

EXAMPLE 177

(2S)-2-(1-(3-chloropyridin-2-yl)-1H-pyrazolo[3,4-d]pyrimidin-4-yloxy)-3-isopropoxy-N-(5-(methylsulfonyl)pyridin-2-yl)propanamide

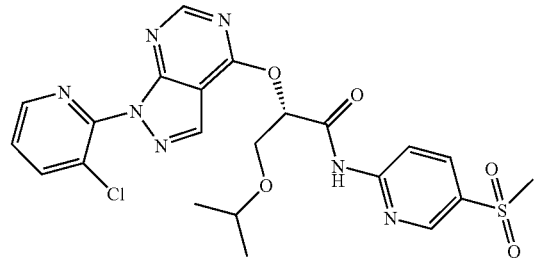

A solution of 3-chloroperoxybenzoic acid (284 mg, 1.27 mmol) in DCM (10 mL) was added dropwise to a stirred solution of (2S)-2-(1-(3-chloropyridin-2-yl)-1H-pyrazolo[3,4-d]pyrimidin-4-yloxy)-3-isopropoxy-N-(5-(methylthio)pyridin-2-yl)propanamide (Intermediate AI3) (317 mg, 0.63 mmol), in DCM (10 mL) at 22° C., over a period of 10 minutes. The resulting solution was stirred at 22° C. for 2 hours. The reaction mixture was diluted with DCM (20 mL), washed with 2M NaOH (20 mL), brine (20 mL), dried (MgSO$_4$) and reduced in vacuo. The residue was purified by flash silica chromatography, elution gradient 50 to 100% EtOAc in isohexane to afford the product (273 mg, 81%) $^1$H NMR (400 MHz, DMSO) d 1.14-1.10 (6H, m), 3.27 (3H, s), 3.77 (1H, m), 4.10-3.99 (2H, m), 5.92 (1H, m), 7.75 (1H, dd), 8.20 (1H, d), 8.28 (1H, dd), 8.34 (1H, dd), 8.56 (1H, s), 8.69-8.65 (2H, m), 8.85-8.82 (1H, s), 11.56 (1H, s). m/z (ES+) (M+H)$^+$=532; HPLC t$_R$=2.03 min. ee 98%

EXAMPLE 178

6-((2S)-2-(1-(3-chloropyridin-2-yl)-1H-pyrazolo[3,4-d]pyrimidin-4-yloxy)-3-isopropoxypropanamido)-N,N-dimethylnicotinamide

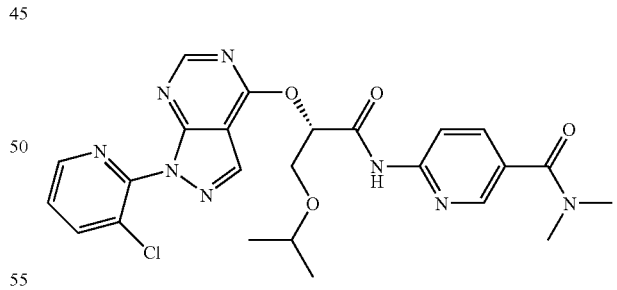

Trimethylaluminium (2M in hexane, 0.376 mL, 0.75 mmol) was added to 6-amino-N,N-dimethylnicotinamide (CAS no. 827588-33-0) (108 mg, 0.65 mmol) in toluene (20 mL) at 0° C. under Nitrogen. The resulting solution was stirred at 0° C. for 20 minutes. (2S)-Methyl 2-(1-(3-chloropyridin-2-yl)-1H-pyrazolo[3,4-d]pyrimidin-4-yloxy)-3-isopropoxypropanoate (Intermediate L1) (256 mg, 0.65 mmol) in toluene (6 mL) was added dropwise at this temperature. After the addition was complete, the solution was allowed to warm to ambient temperature and was then heated to reflux for 16 hours. Allowed to cool to ambient temperature. The reaction mixture was concentrated and diluted with EtOAc (100 mL) and washed with saturated brine (50 mL). The organic layer was dried (MgSO4), filtered and evaporated. 2M Trimethylaluminium in hexane (0.376 mL, 0.75 mmol) was added to 6-amino-N,N-dimethylnicotinamide (108 mg, 0.65 mmol) in toluene (20 mL) at 0° C. under Nitrogen. The resulting solution was stirred at 0° C. for 20 minutes. The residue from the above evaporation was dissolved in toluene (6 mL) and added dropwise. After the addition was complete, the solution was allowed to warm to ambient temperature and was then heated to reflux for 16 hours. Allowed to cool to ambient temperature. The reaction mixture was concentrated and diluted with EtOAc (100 mL) and washed with saturated brine (50 mL). The organic layer was dried (MgSO4), filtered and evaporated to afford crude product.

This was purified by preparative HPLC (Waters XBridge Prep C18 OBD column, 5µ silica, 50 mm diameter, 150 mm length) column, using decreasingly polar mixtures of water (containing 0.5% NH3) and MeCN as eluents to afford the product (30.0 mg, 8.75%). $^1$H NMR (400 MHz, DMSO) δ 1.13 (6H, dd), 2.50, 2.97 (6H, s), 3.78 (1H, m), 4.04 (2H, m), 5.93 (1H, s), 7.76 (1H, dd), 7.86 (1H, dd), 8.03 (1H, d), 8.34 (1H, dd), 8.43 (1H, m), 8.57 (1H, s), 8.64-8.70 (2H, m), 11.16 (1H, s). m/z (ES+) (M+H)$^+$=500; HPLC $t_R$=2.41 min.

EXAMPLE 179

(2S)—N-(5-chloropyridin-2-yl)-2-(1-(2,5-dimethylphenyl)-1H-pyrazolo[3,4-d]pyrimidin-4-yloxy)-3-(2-hydroxyethoxy)propanamide

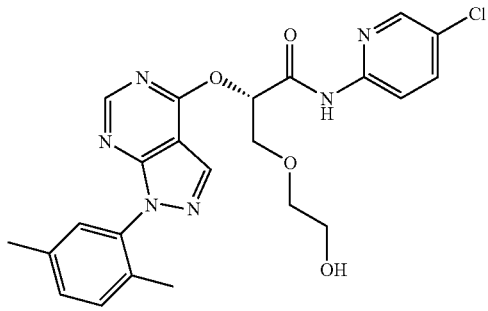

Tetrabutylammonium fluoride (1M in THF) (0.455 mL, 0.45 mmol) was added to (2S)-3-(2-(tert-butyldiphenylsilyloxy)ethoxy)-N-(5-chloropyridin-2-yl)-2-(1-(2,5-dimethylphenyl)-1H-pyrazolo[3,4-d]pyrimidin-4-yloxy)propanamide (Intermediate AJ1) (328 mg, 0.45 mmol) in THF (5 mL) under nitrogen. The resulting mixture was stirred at ambient temperature for 1 hour. The reaction mixture was quenched with saturated NH4Cl (2 mL), diluted with DCM (25 mL) and poured onto a phase separator. The organic layer was loaded onto a silica column and purified by flash silica chromatography, elution gradient 50 to 100% EtOAc in isohexane. This was further purified by preparative HPLC (Waters XBridge Prep C18 OBD column, 5µ silica, 50 mm diameter, 150 mm length), using decreasingly polar mixtures of water (containing 0.1% formic acid) and MeCN as eluents to afford the product (93 mg, 42.4%). $^1$H NMR (400 MHz, DMSO) δ 2.00 (3H, s), 2.33 (3H, s), 3.53 (2H, m), 3.57-3.68 (2H, m), 4.03 (1H, m), 4.11 (1H, m), 4.66 (1H, t), 5.92 (1H, m), 7.23 (1H, s), 7.28 (1H, d), 7.34 (1H, d), 7.90 (1H, dd), 8.02 (1H, d), 8.41 (1H, d), 8.52 (1H, s), 8.57 (1H, s), 11.23 (1H, s). m/z (ES+) (M+H)$^+$=481; HPLC $t_R$=2.35 min.

EXAMPLE 180

(2S)—N-(5-chloropyridin-2-yl)-2-(1-(5-fluoro-2-methylphenyl)-1H-pyrazolo[3,4-d]pyrimidin-4-yloxy)-3-(2-hydroxyethoxy)propanamide

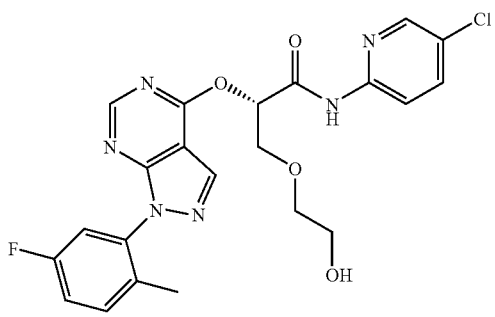

Tetrabutylammonium fluoride (1M in THF) (0.538 mL, 0.54 mmol) was added to (2S)-3-(2-(tert-butyldiphenylsilyloxy)ethoxy)-N-(5-chloropyridin-2-yl)-2-(1-(5-fluoro-2-methylphenyl)-1H-pyrazolo[3,4-d]pyrimidin-4-yloxy)propanamide (Intermediate AK5) (390 mg, 0.54 mmol) in THF (5 mL) under nitrogen. The resulting mixture was stirred at ambient temperature for 1 hour. The reaction mixture was quenched with saturated NH4Cl (2 mL), diluted with DCM (25 mL) and poured onto a phase separator. The organic phase was evaporated to give the crude product. This was purified by preparative HPLC (Waters XBridge Prep C18 OBD column, 5µ silica, 50 mm diameter, 150 mm length), using decreasingly polar mixtures of water (containing 0.1% formic acid) and MeCN as eluents to afford the product (136 mg, 51.9%, 75% ee). $^1$H NMR (400 MHz, DMSO) δ 1.88 (3H, s), 3.35 (2H, m), 3.43 (2H, m), 3.84 (1H, dd), 3.92 (1H, dd), 4.47 (1H, t), 5.74 (1H, m), 7.19 (2H, m), 7.36-7.29 (1H, m), 7.71 (1H, dd), 7.83 (1H, d), 8.23 (1H, d), 8.37 (1H, s), 8.43 (1H, s), 11.05 (1H, s). m/z (ES+) (M+H)$^+$=487; HPLC $t_R$=2.28 min.

EXAMPLE 181

(S)-2-(1-benzyl-1H-pyrazolo[3,4-d]pyrimidin-4-yloxy)-3-(2-hydroxyethoxy)-N-(5-methylpyridin-2-yl)propanamide

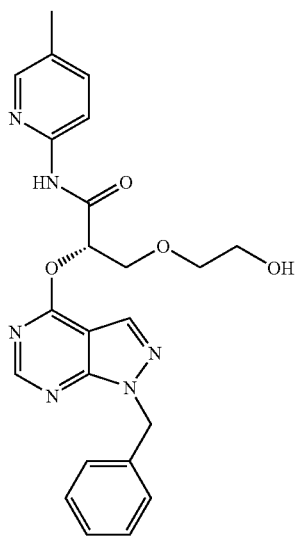

A solution of tetrabutylammonium fluoride (1M in THF) (0.896 mL, 0.90 mmol) was added to a stirred solution of (S)-2-(1-benzyl-1H-pyrazolo[3,4-d]pyrimidin-4-yloxy)-3-(2-(tert-butyldiphenylsilyloxy)ethoxy)-N-(5-methylpyridin-2-yl)propanamide (Intermediate AL1) (342 mg, 0.50 mmol) in tetrahydrofuran (20 mL). The resulting solution was stirred at ambient temperature for 30 minutes. The reaction mixture was quenched with saturated NH$_4$Cl (10 mL), and diluted with water (20 mL) and EtOAc (70 mL). The organic layer was separated and the aqueous layer extracted with EtOAc (70 mL), The combined organics were dried (MgSO$_4$), filtered and evaporated to afford crude product. The crude product was purified by flash silica chromatography, elution gradient 80 to 100% EtOAc in isohexane to afford the product (170 mg, 76%). $^1$H NMR (400 MHz, CDCl$_3$) 2.28 (3H, s), 2.91 (1H, s), 3.68-3.74 (4H, m), 4.09-4.20 (2H, m), 5.65 (2H, s), 6.05 (1H, t), 7.25-7.36 (5H, m), 7.50-7.53 (1H, m), 8.05-8.07 (2H, m), 8.21 (1H, s), 8.57 (1H, s), 8.88 (1H, s); m/z (ES+) (M+H)$^+$=449; HPLC t$_R$=1.90 min.

EXAMPLE 182

(2S)—N-(5-cyanopyridin-2-yl)-2-(1-(5-fluoro-2-methylphenyl)-1H-pyrazolo[3,4-d]pyrimidin-4-yloxy)-3-(2-hydroxyethoxy)propanamide

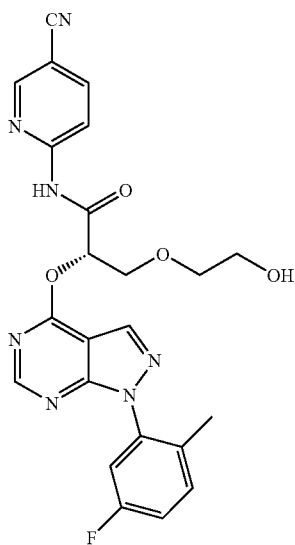

Prepared in an analogous fashion to Example 181 from Intermediate AK6. 1H NMR (400 MHz, CDCl$_3$) 2.14 (3H, s), 2.42 (1H, t), 3.73-3.83 (4H, m), 4.17-4.25 (2H, m), 6.07 (1H, t), 7.13-7.18 (2H, m), 7.35-7.38 (1H, m), 7.96-7.98 (1H, m), 8.35-8.38 (1H, m), 8.40 (1H, s), 8.57 (1H, q), 8.58 (1H, s), 9.32 (1H, s); m/z (ES+) (M+H)$^+$=478; HPLC t$_R$=2.10 min.

EXAMPLE 183

(2S)-2-(1-(5-cyano-2-methylphenyl)-1H-pyrazolo[3,4-d]pyrimidin-4-yloxy)-N-(5-cyanopyridin-2-yl)-3-(2-hydroxyethoxy)propanamide

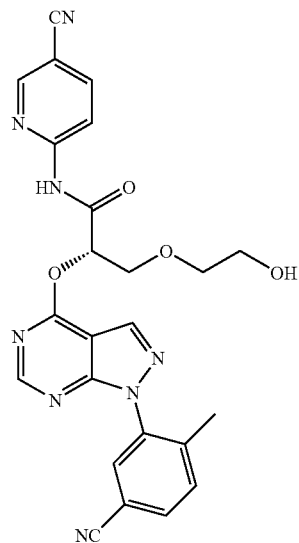

Prepared in an analogous fashion to Example 181 using Intermediate AM1. $^1$H NMR (400 MHz, CDCl$_3$) 2.30 (3H, s), 3.74-3.84 (4H, m), 4.17-4.25 (2H, m), 6.07 (1H, t), 7.53 (1H, d), 7.69-7.72 (1H, m), 7.74 (1H, s), 7.96-7.99 (1H, m), 8.35-8.37 (1H, m), 8.43 (1H, s), 8.57 (1H, q), 8.59 (1H, s), 9.33 (1H, s) (no OH observed); m/z (ES+) (M+H)$^+$=485; HPLC t$_R$=1.90 min.

EXAMPLE 184

(2S)-2-(1-(5-cyano-2-methylphenyl)-1H-pyrazolo[3,4-d]pyrimidin-4-yloxy)-3-(2-hydroxyethoxy)-N-(5-methylpyridin-2-yl)propanamide

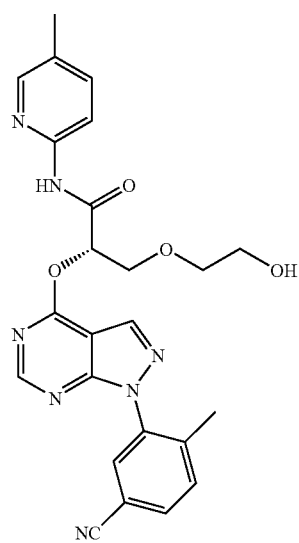

Prepared in an analogous fashion to Example 181 using Intermediate AM6. ¹H NMR (400 MHz, CDCl₃) 2.29 (3H, s), 2.30 (3H, s), 3.74-3.81 (4H, m), 4.17-4.25 (2H, m), 6.09 (1H, t), 7.52-7.56 (2H, m), 7.69-7.75 (2H, m), 8.06-8.10 (2H, m), 8.44 (1H, s), 8.59 (1H, s), 8.95 (1H, s); m/z (ES+) (M+H)⁺=474; HPLC t$_R$=1.79 min.

EXAMPLE 185

(2S)—N-(5-chloropyridin-2-yl)-2-(1-(5-cyano-2-methylphenyl)-1H-pyrazolo[3,4-d]pyrimidin-4-yloxy)-3-(2-hydroxyethoxy)propanamide

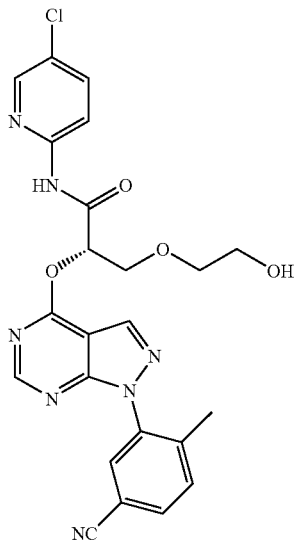

Prepared in an analogous fashion to Example 181 using Intermediate AM8. ¹H NMR (400 MHz, CDCl₃) 2.30 (3H, s), 3.74-3.81 (4H, m), 4.18-4.22 (2H, m), 6.08 (1H, t), 7.53 (1H, d), 7.69-7.75 (3H, m), 8.19-8.21 (1H, m), 8.23-8.24 (1H, m), 8.43 (1H, s), 8.59 (1H, s), 9.06 (1H, s) (no OH observed); m/z (ES+) (M+H)⁺=494; HPLC t$_R$=2.09 min.

EXAMPLE 186

(2S)—N-(5-cyanopyridin-2-yl)-2-(1-(2,5-dimethylphenyl)-1H-pyrazolo[3,4-d]pyrimidin-4-yloxy)-3-ethoxypropanamide

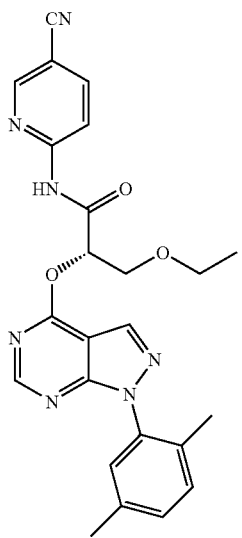

Prepared in an analogous fashion to Intermediate 181 using Intermediate H4 and Intermediate AJ3. ¹H NMR (400 MHz, CDCl₃) 1.24 (3H, t), 2.09 (3H, s), 2.38 (3H, s), 3.62-3.70 (2H, m), 4.07-4.15 (2H, m), 6.03-6.05 (1H, m), 7.19-7.29 (3H, m), 7.94-7.97 (1H, m), 8.39 (1H, s), 8.38-8.40 (1H, m), 8.56 (1H, s), 8.57 (1H, q), 9.03 (1H, s); m/z (ES+) (M−H)−=456; HPLC t$_R$=2.57 min.

EXAMPLE 187

(2S)—N-(5-chloropyridin-2-yl)-3-ethoxy-2-(1-(4-methylpyridin-3-yl)-1H-pyrazolo[3,4-d]pyriidin-4-yloxy)propanamide

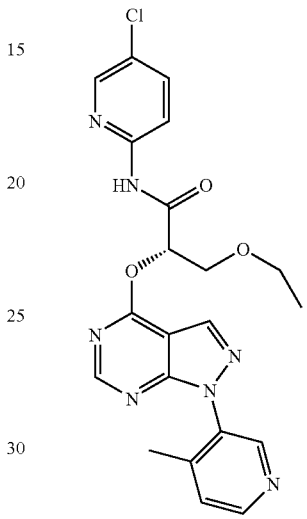

Prepared in an analogous fashion to Intermediate 181 from Intermediate X5 and Intermediate H3. ¹H NMR (400 MHz, CDCl₃) 1.21-1.26 (3H, m), 2.26 (3H, s), 3.61-3.69 (2H, m), 4.06-4.15 (2H, m), 6.06 (1H, t), 7.35 (1H, d), 7.67-7.70 (1H, m), 8.24 (2H, dd), 8.44 (1H, s), 8.58 (1H, s), 8.60 (1H, d), 8.65 (1H, s), 8.78 (1H, s); m/z (ES+) (M+H)⁺=454; HPLC t$_R$=2.07 min.

EXAMPLE 188

(2S)-3-cyclobutoxy-N-(5-methylpyrazin-2-yl)-2-(1-(4-methylpyridin-3-yl)-1H-pyrazolo[3,4-d]pyrimidin-4-yloxy)propanamide

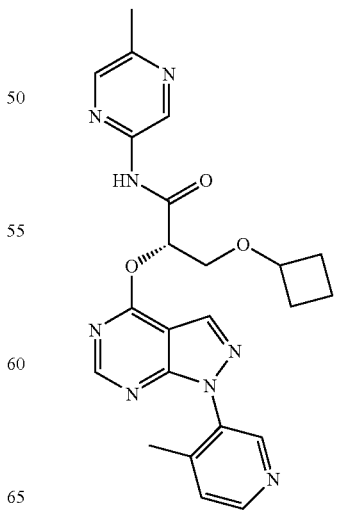

Prepared in an analogous fashion to Intermediate 1 from Intermediate X5 and Intermediate R1. $^1$H NMR (400 MHz, CDCl$_3$) 1.48-1.55 (1H, m), 1.69-1.75 (1H, m), 1.91-2.00 (2H, m), 2.19-2.27 (5H, m), 2.54 (3H, s), 3.98-4.08 (3H, m), 6.05 (1H, t), 7.36 (1H, d), 8.12-8.13 (1H, m), 8.45 (1H, s), 8.58 (1H, s), 8.60 (1H, d), 8.65 (1H, s), 8.68 (1H, s), 9.45 (1H, d); m/z (ES+) (M+H)$^+$=461; HPLC t$_R$=1.82 min.

EXAMPLE 189

(2S)-2-(1-(3-chloropyridin-2-yl)-1H-pyrazolo[3,4-d]pyrimidin-4-yloxy)-N-(5-cyanopyridin-2-yl)-3-((R)-1-hydroxypropan-2-yloxy)propanamide

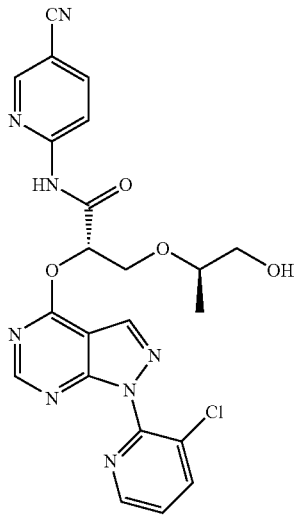

EXAMPLE 190

(2S)—N-(5-chloropyridin-2-yl)-2-(1-(3-chloropyridin-2-yl)-1H-pyrazolo[3,4-d]pyrimidin-4-yloxy)-3-((R)-1-hydroxypropan-2-yloxy)propanamide

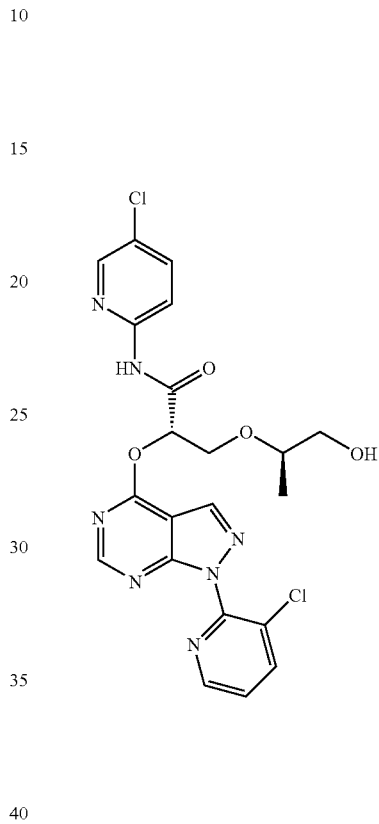

Tetrabutylammonium fluoride (1M in THF) (0.973 mL, 0.97 mmol) was added to (2S)-3-((R)-1-(tert-butyldimethylsilyloxy)propan-2-yloxy)-2-(1-(3-chloropyridin-2-yl)-1H-pyrazolo[3,4-d]pyrimidin-4-yloxy)-N-(5-cyanopyridin-2-yl)propanamide (Intermediate AN3) (395 mg, 0.65 mmol) in THF (10 mL) under nitrogen. The resulting mixture was stirred at room temperature for 1 hour. The reaction mixture was quenched with saturated NH$_4$Cl (10 mL), extracted with Et$_2$O (3×15 mL), the combined organic layers were back washed with water (10 mL), dried (MgSO$_4$), and evaporated to afford crude product. The crude product was purified by preparative chiral-HPLC on a Merck 50 mm 20 μm Chiralpak column, eluting isocratically with 30% EtOH in isohexane (modified with Et$_3$N) as eluent to afford the product (95 mg, 29.6%). $^1$H NMR (400 MHz, CDCl$_3$) δ1.17 (d, 3H), 2.71-2.78 (m, 1H), 3.56-3.72 (m, 2H), 3.78-3.87 (m, 1H), 4.09-4.16 (m, 1H), 4.26-4.32 (m, 1H), 6.01-6.05 (m, 1H), 7.46-7.50 (m, 1H), 7.94-7.98 (m, 1H), 7.99-8.04 (m, 1H), 8.32-8.36 (m, 1H), 8.45 (s, 1H), 8.54-8.56 (m, 1H), 8.60-8.63 (m, 1H), 8.64 (s, 1H), 9.51 (s, 1H); m/z (ESI+) (M+H)$^+$=495.42; HPLC t$_R$=1.75 min Tetrabutylammonium fluoride (1M in THF) (0.892 mL, 0.89 mmol) was added to (2S)-3-((R)-1-(tert-butyldimethylsilyloxy)propan-2-yloxy)-N-(5-chloropyridin-2-yl)-2-(1-(3-chloropyridin-2-yl)-1H-pyrazolo[3,4-d]pyrimidin-4-yloxy) propanamide (Intermediate AN4) (460 mg, 0.74 mmol) in THF (5 mL) under nitrogen. The resulting mixture was stirred at room temperature for 1 hour. The reaction mixture was quenched with saturated NH$_4$Cl (10 mL), extracted with EtOAc (3×15 mL), the combined organic layers were back washed with water (10 mL), dried (MgSO$_4$), and evaporated to afford crude product. The crude product was purified by flash silica chromatography, eluting with 0 to 90% EtOAc in isohexane to afford the product (256 mg, 68.3%). $^1$H NMR (400 MHz, DMSO) δ1.07 (d, 3H), 3.26-3.37 (m, 1H), 3.38-3.47 (m, 1H), 3.61-3.71 (m, 1H), 4.07-4.18 (m, 2H), 4.57 (t, 1H), 5.87-5.93 (m, 1H), 7.74-7.79 (m, 1H), 7.88-7.93 (m, 1H), 8.00-8.06 (m, 1H), 8.32-8.37 (m, 1H), 8.41 (d, 1H), 8.57 (s, 1H), 8.66 (s, 1H), 8.67-8.70 (m, 1H), 11.15 (s, 1H) m/z (ESI+) (M+H)$^+$=504.37; HPLC t$_R$=1.96 min

EXAMPLE 191

(2S)-2-(1-(3-chloropyridin-2-yl)-1H-pyrazolo[3,4-d]pyrimidin-4-yloxy)-N-(5-fluoropyridin-2-yl)-3-((R)-1-hydroxypropan-2-yloxy)propanamide

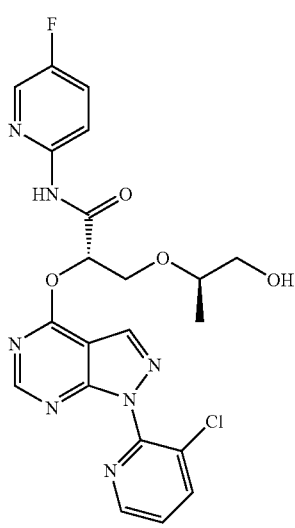

Tetrabutylammonium fluoride (1M in THF) (604 µl, 0.60 mmol) was added to (2S)-3-((R)-1-(tert-butyldimethylsilyloxy)propan-2-yloxy)-2-(1-(3-chloropyridin-2-yl)-1H-pyrazolo[3,4-d]pyrimidin-4-yloxy)-N-(5-fluoropyridin-2-yl)propanamide (Intermediate AN5) (303 mg, 0.50 mmol) in THF (5 mL) under nitrogen. The resulting mixture was stirred at room temperature for 1 hour. The reaction mixture was quenched with saturated NH$_4$Cl (10 mL), extracted with Et$_2$O (3×15 mL), the combined organic layers were back washed with water (10 mL), dried (MgSO$_4$) and evaporated to afford crude product. The crude product was purified by preparative chiral-HPLC on a Merck 50 mm 20 µm Chiralpak AS column, eluting isocratically with 30% EtOH in isohexane (modified with Et$_3$N) as eluent to afford the product (112 mg, 45.6%). $^1$H NMR (400 MHz, CDCl$_3$) δ1.17 (d, 3H), 2.99-3.05 (m, 1H), 3.54-3.61 (m, 1H), 3.62-3.70 (m, 1H), 3.75-3.84 (m, 1H), 4.07-4.13 (m, 1H), 4.25-4.31 (m, 1H), 6.04-6.09 (m, 1H), 7.43-7.50 (m, 2H), 7.99-8.03 (m, 1H), 8.13 (d, 1H), 8.18-8.23 (m, 1H), 8.45 (s, 1H), 8.61-8.63 (m, 1H), 8.64 (s, 1H), 9.17 (s, 1H); m/z (ESI+) (M+H)$^+$=488.42; HPLC t$_R$=1.74 min

EXAMPLE 192

(2S)-2-(1-(3-chloropyridin-2-yl)-1H-pyrazolo[3,4-d]pyrimidin-4-yloxy)-N-(5-fluoropyridin-2-yl)-3-((S)-1-hydroxypropan-2-yloxy)propanamide

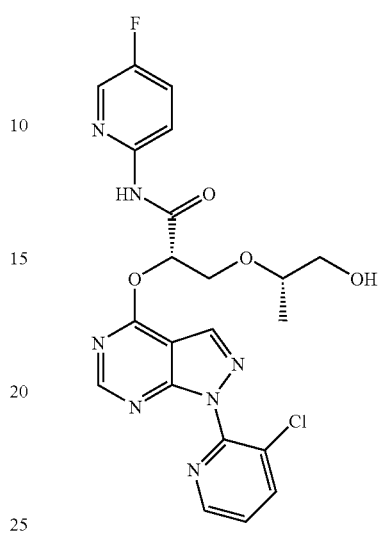

HCl (4M in Dioxane) (0.530 mL, 2.12 mmol) was added to (2S)-3-((S)-1-(tert-butyldimethylsilyloxy)propan-2-yloxy)-2-(1-(3-chloropyridin-2-yl)-1H-pyrazolo[3,4-d]pyrimidin-4-yloxy)-N-(5-fluoropyridin-2-yl)propanamide (Intermediate AO3) (638 mg, 1.06 mmol) in THF (5 mL) at room temperature. The resulting solution was stirred for 20 minutes. The reaction mixture was evaporated and the residue partitioned between EtOAc (25 mL) and sat NaHCO$_3$ (10 mL). The organic layer was dried (MgSO$_4$) and evaporated. The crude product was purified by preparative chiral-HPLC on a Merck 50 mm 20 µm Chiralpak AS column, eluting isocratically with 30% EtOH in isohexane (modified with Et3N) as eluent to afford the product (397 mg, 77%). $^1$H NMR (400 MHz, CDCl$_3$) δ1.16 (d, 3H), 2.73 (s, 1H), 3.51-3.68 (m, 2H), 3.69-3.78 (m, 1H), 4.12-4.28 (m, 2H), 6.06 (t, 1H), 7.42-7.50 (m, 2H), 7.99-8.03 (m, 1H), 8.13 (d, 1H), 8.21-8.26 (m, 1H), 8.47 (s, 1H), 8.60-8.65 (m, 2H), 9.09 (s, 1H); m/z (ESI+) (M+H)$^+$=488.42; HPLC t$_R$=1.75 min

EXAMPLE 193

(2S)—N-(5-chloropyridin-2-yl)-2-(1-(3-chloropyridin-2-yl)-1H-pyrazolo[3,4-d]pyrimidin-4-yloxy)-3-((S)-1-hydroxypropan-2-yloxy)propanamide

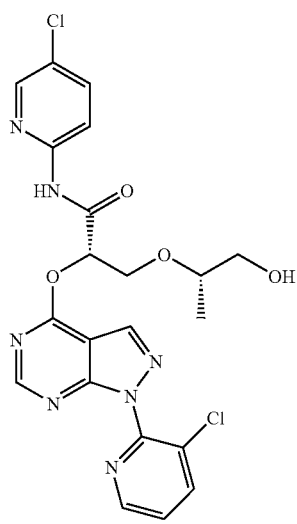

HCl (4M in Dioxane) (0.606 mL, 2.42 mmol) was added to (2S)-3-((S)-1-(tert-butyldimethylsilyloxy)propan-2-yloxy)-N-(5-chloropyridin-2-yl)-2-(1-(3-chloropyridin-2-yl)-1H-pyrazolo[3,4-d]pyrimidin-4-yloxy)propanamide (Intermediate AO4) (300 mg, 0.48 mmol) in THF (5 mL) and water (0.5 mL) at room temperature. The resulting solution was stirred at room temperature for 10 minutes. The reaction mixture was evaporated and the residue partitioned between EtOAc (25 mL) and sat NaHCO$_3$ (10 mL). The organic layer was dried (MgSO$_4$) and evaporated. The crude product was purified by preparative chiral-HPLC on a Merck 50 mm 20 μm Chiralpak AS column, eluting isocratically with 30% EtOH in isohexane (modified with Et3N) as eluent. The fractions containing the desired compound were evaporated to dryness to afford the product (173 mg, 70.7%). $^1$H NMR (400 MHz, CDCl$_3$) δ 1.17 (d, 3H), 2.64 (s, 1H), 3.51-3.67 (m, 2H), 3.69-3.79 (m, 1H), 4.11-4.28 (m, 2H), 6.05 (t, 1H), 7.45-7.50 (m, 1H), 7.66-7.71 (m, 1H), 7.99-8.04 (m, 1H), 8.18-8.25 (m, 2H), 8.47 (s, 1H), 8.60-8.65 (m, 2H), 9.10 (s, 1H) m/z (ESI+) (M+H)$^+$=504.40; HPLC t$_R$=1.96 min

EXAMPLE 194

(2S)-2-(1-(2-chlorophenyl)-1H-pyrazolo[3,4-d]pyrimidin-4-yloxy)-3-(2-hydroxyethoxy)-N-(5-methylpyridin-2-yl)propanamide

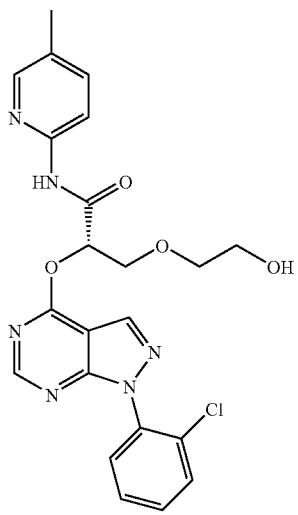

Tetrabutylammonium fluoride (1M in THF) (0.271 mL, 0.27 mmol) was added to (2S)-3-(2-(tert-butyldiphenylsilyloxy)ethoxy)-2-(1-(2-chlorophenyl)-1H-pyrazolo[3,4-d]pyrimidin-4-yloxy)-N-(5-methylpyridin-2-yl)propanamide (Intermediate AG4) (96 mg, 0.14 mmol) in THF (5 mL) under nitrogen. The resulting mixture was stirred at room temperature for 1 hour. The reaction mixture was quenched with saturated NH$_4$Cl (10 mL), extracted with Et$_2$O (3×15 mL), the combined organic layers were back washed with water (10 mL), dried (MgSO$_4$), and evaporated to afford crude product. The crude product was purified by flash silica chromatography, eluting with 0 to 10% MeOH in DCM to afford the product (50.0 mg, 79%). $^1$H NMR (400 MHz, CDCl$_3$) δ2.28 (s, 3H), 3.32 (s, 1H), 3.70-3.81 (m, 4H), 4.13-4.26 (m, 2H), 6.08 (t, 1H), 7.43-7.55 (m, 4H), 7.59-7.63 (m, 1H), 8.05-8.10 (m, 2H), 8.44 (s, 1H), 8.59 (s, 1H), 9.11 (s, 1H); m/z (ESI+) (M+H)$^+$=469.45; HPLC t$_R$=1.86 min

EXAMPLE 195

(2S)-2-(3-(2-chlorophenyl)-3H-[1,2,3]triazolo[4,5-d]pyrimidin-7-yloxy)-3-(2-hydroxyethoxy)-N-(5-methylpyridin-2-yl)propanamide

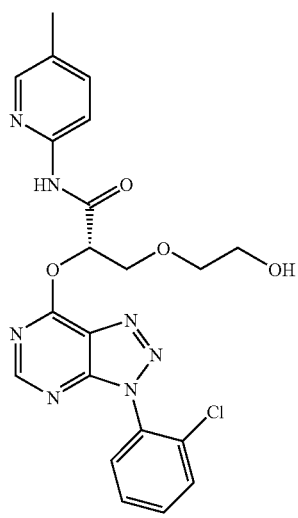

Hydrochloric acid (10%, 2 mL) was added to (2S)-3-(2-(tert-butyldiphenylsilyloxy)ethoxy)-2-(3-(2-chlorophenyl)-3H-[1,2,3]triazolo[4,5-d]pyrimidin-7-yloxy)-N-(5-methylpyridin-2-yl)propanamide (Intermediate AP3) (335 mg, 0.47 mmol) in methanol (30.0 mL) at 0° C. The resulting solution was stirred at 0° C. for 10 minutes and allowed to warm to room temperature and stirred for 1 hour. The reaction mixture was quenched with saturated NH$_4$Cl (25 mL) and most of the MeOH was removed by evaporation. The aqueous residue was extracted with EtOAc (3×25 mL), the organic layer was dried (MgSO$_4$), filtered and evaporated to afford crude product. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents to afford the product (67.0 mg, 30.1%). $^1$H NMR (400 MHz, CDCl$_3$) δ2.31 (s, 3H), 3.73-3.85 (m, 4H), 4.20-4.35 (m, 2H), 6.06 (t, 1H), 7.49-7.63 (m, 4H), 7.68 (d, 1H), 8.05 (s, 1H), 8.09-8.22 (m, 2H), 8.68 (s, 1H), OH not observed; m/z (ESI+) (M+H)$^+$=470.41; HPLC t$_R$=1.80 min

EXAMPLE 196

(2S)-3-(2-(tert-butyldiphenylsilyloxy)ethoxy)-2-(3-(2-chlorophenyl)-3H-[1,2,3]triazolo[4,5-d]pyrimidin-7-yloxy)-N-(5-methylpyridin-2-yl)propanamide

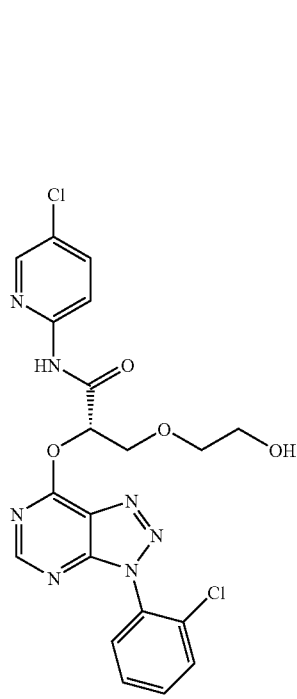

Hydrochloric acid (10%, 1 mL) was added dropwise to (2S)-3-(2-(tert-butyldiphenylsilyloxy)ethoxy)-2-(3-(2-chlorophenyl)-3H-[1,2,3]triazolo[4,5-d]pyrimidin-7-yloxy)-N-(5-chloropyridin-2-yl)propanamide (Intermediate AP4) (180 mg, 0.25 mmol) in methanol (20.00 mL) at room temperature. The resulting solution was stirred for 4 hours. Most of the methanol was evaporated and the remaining aq. soln was diluted with saturated NH$_4$Cl and extracted with EtOAc (2×30 mL). The organic layers were combined, dried (MgSO$_4$) and evaporated to give crude product. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford (2S)-2-(3-(2-chlorophenyl)-3H-[1,2,3]triazolo[4,5-d]pyrimidin-7-yloxy)-N-(5-chloropyridin-2-yl)-3-(2-hydroxyethoxy)propanamide (38.0 mg, 31.4%). $^1$H NMR (400 MHz, CDCl$_3$) δ3.72-3.83 (m, 4H), 4.19-4.32 (m, 2H), 6.15 (t, 1H), 7.50-7.63 (m, 3H), 7.66-7.72 (m, 2H), 8.15-8.27 (m, 2H), 8.72 (s, 1H), 9.16 (s, 1H) OH not observed; m/z (ESI+) (M+H)$^+$=490.16; HPLC $t_R$=2.15 min

EXAMPLE 197

(2S)-2-(3-(2-chlorophenyl)-3H-[1,2,3]triazolo[4,5-d]pyrimidin-7-yloxy)-N-(5-cyanopyridin-2-yl)-3-ethoxypropanamide

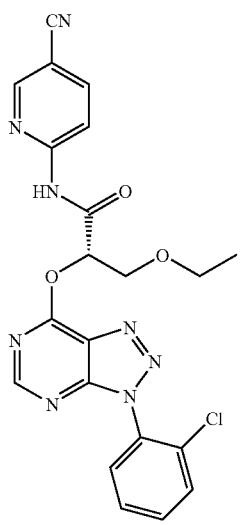

Sodium hydride (82 mg, 2.05 mmol) was added to (S)—N-(5-cyanopyridin-2-yl)-3-ethoxy-2-hydroxypropanamide (Intermediate H4) (177 mg, 0.75 mmol) in anhydrous THF (5 mL) at 0° C. under nitrogen. The resulting solution was stirred at 0° C. for 10 minutes and then 7-chloro-3-(2-chlorophenyl)-3H-[1,2,3]triazolo[4,5-d]pyrimidine (Intermediate AP2) (200 mg, 0.75 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×50 mL). The combined organics were washed with saturated brine (25 mL), dried (MgSO$_4$) and evaporated. The crude product was purified by flash silica chromatography, eluting with 0 to 60% EtOAc in isohexane to afford the product (136 mg, 38.9%). $^1$H NMR (400 MHz, CDCl$_3$) δ1.24 (t, 3H), 3.61-3.74 (m, 2H), 4.13-4.21 (m, 2H), 6.13 (t, 1H), 7.51-7.62 (m, 3H), 7.67-7.71 (m, 1H), 7.93-7.98 (m, 1H), 8.36-8.40 (m, 1H), 8.57-8.59 (m, 1H), 8.71 (s, 1H), 9.19 (s, 1H); m/z (ESI+) (M+H)$^+$=463.23; HPLC $t_R$=2.43 min

EXAMPLE 198

(2S)—N-(5-chloropyridin-2-yl)-3-(2-hydroxy-ethoxy)-2-(3-o-tolyl-3H-[1,2,3]triazolo[4,5-d]pyrimidin-7-yloxy)propanamide

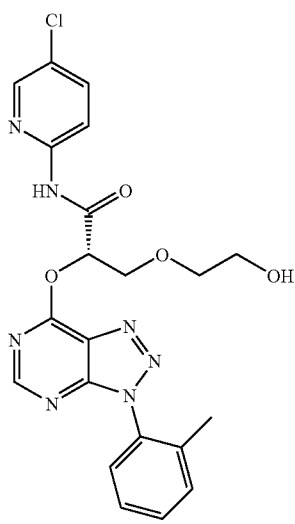

Hydrochloric acid (10%, 1 mL) was added dropwise to (2S)-3-(2-(tert-butyldiphenylsilyloxy)ethoxy)-N-(5-chloropyridin-2-yl)-2-(3-o-tolyl-3H-[1,2,3]triazolo[4,5-d]pyrimidin-7-yloxy)propanamide (Intermediate AP7) (250 mg, 0.35 mmol) in methanol (20.00 mL) at room temperature. The resulting solution was stirred for 4 hours. Most of the methanol was evaporated and the remaining aq. soln was diluted with saturated NH$_4$Cl and extracted with EtOAc (2×30 mL). The organic layers were combined, dried (MgSO$_4$) and evaporated to give crude product. The crude product was purified by flash silica chromatography, eluting with 0 to 100% EtOAc in isohexane to afford the product (81 mg, 48.8%). $^1$H NMR (400 MHz, CDCl$_3$) δ 2.20 (s, 3H), 2.60-2.66 (m, 1H), 3.73-3.83 (m, 4H), 4.20-4.32 (m, 2H), 6.15 (t, 1H), 7.41-7.54 (m, 4H), 8.17-8.21 (m, 1H), 8.23-8.25 (m, 1H), 8.70 (s, 1H), 9.20 (s, 1H), OH not observed; m/z (ESI+) (M+H)$^+$=470.43; HPLC t$_R$=2.25 min

EXAMPLE 199

(2S)-3-(2-hydroxyethoxy)-N-(pyridin-2-yl)-2-(1-(2-(trifluoromethyl)phenyl)-1H-pyrazolo[3,4-d]pyrimidin-4-yloxy)propanamide

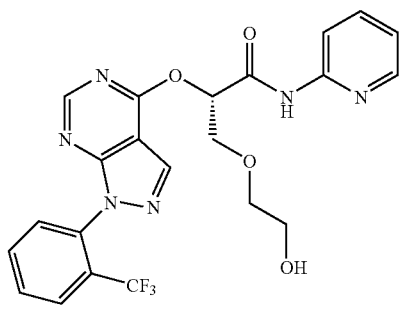

A solution of tetrabutylammonium fluoride (1M in THF) (1.275 mL, 1.28 mmol) was added in one portion to a stirred solution of (2S)-3-(2-(tert-butyldiphenylsilyloxy)ethoxy)-N-(pyridin-2-yl)-2-(1-(2-(trifluoromethyl)phenyl)-1H-pyrazolo[3,4-d]pyrimidin-4-yloxy)propanamide (0.927 g, 1.28 mmol) (Intermediate AQ1) in tetrahydrofuran (15 mL). The resulting solution was stirred at ambient temperature for 30 minutes. The reaction mixture was quenched with saturated NH4Cl (10 mL), and diluted with water (20 mL) and EtOAc (50 mL). The organic layer was separated and the aqueous layer extracted with EtOAc (50 mL), The combined organics were dried (MgSO$_4$), filtered and evaporated to afford crude product. The crude product was purified by flash silica chromatography, elution gradient 80 to 100% EtOAc in isohexane to afford the product (0.226 g, 36.3%). $^1$H NMR: (400 MHz, CDCl$_3$) δ 2.90 (1H, s), 3.75-3.80 (4H, m), 4.16-4.25 (2H, m), 6.09 (1H, t), 7.06-7.10 (1H, m), 7.53-7.92 (5H, m), 8.18-8.20 (1H, m), 8.28-8.30 (1H, m), 8.41 (1H, s), 8.57 (1H, s), 9.01 (1H, s); m/z (ES+) (M+H)$^+$=489.31; HPLC t$_R$=1.74 min.

EXAMPLE 200

(2S)-2-(1-(2-chlorophenyl)-1H-pyrazolo[3,4-d]pyrimidin-4-yloxy)-3-((R)-1-hydroxypropan-2-yloxy)-N-(pyridin-2-yl)propanamide

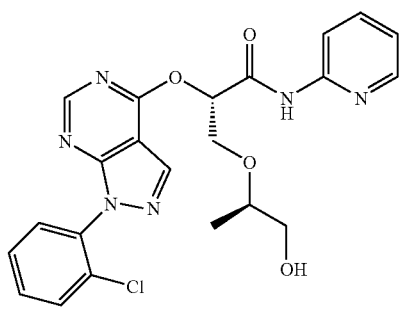

A solution of tetrabutylammonium fluoride (1M in THF) (0.526 mL, 0.53 mmol) was added in one portion to a stirred solution of (2S)-2-(1-(2-chlorophenyl)-1H-pyrazolo[3,4-d]pyrimidin-4-yloxy)-N-(pyridin-2-yl)-3-((R)-1-(triisopropylsilyloxy)propan-2-yloxy)propanamide (0.329 g, 0.53 mmol)

(Intermediate AQ3) in tetrahydrofuran (15 mL). The resulting solution was stirred at ambient temperature for 30 minutes. The reaction mixture was quenched with saturated NH$_4$Cl (10 mL), and diluted with water (20 mL) and EtOAc (50 mL). The organic layer was separated and the aqueous layer extracted with EtOAc (50 mL), The combined organics were dried (MgSO$_4$), filtered and evaporated to afford crude product. The crude product was purified by flash silica chromatography, elution gradient 80 to 100% EtOAc in isohexane to afford the product (0.247 g, 100%). $^1$H NMR: (400 MHz, CDCl$_3$) δ 1.16-1.19 (3H, m), 3.45-3.85 (4H, m), 4.1-4.31 (2H, m), 6.06-6.09 (1H, m), 7.05-7.09 (1H, m), 7.46-7.63 (4H, m), 7.73-7.75 (1H, m), 8.17 (1H, d), 8.26-8.28 (1H, m), 8.43 (1H, d), 8.60 (1H, s), 9.23 (1H, s); m/z (ES+) (M+H)$^+$=469.24; HPLC $t_R$=1.91 min.

EXAMPLE 201

(2S)-2-(1-(2-chlorophenyl)-1H-pyrazolo[3,4-d]pyrimidin-4-yloxy)-3-(2-hydroxyethoxy)-N-(pyridin-2-yl)propanamide

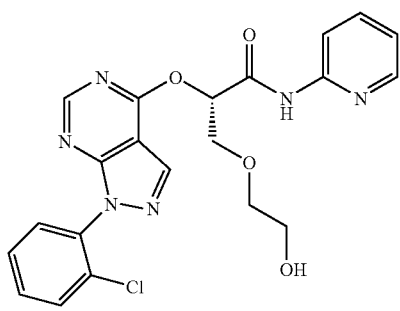

A solution of tetrabutylammonium fluoride (1M in THF) (0.984 mL, 0.98 mmol) was added in one portion to a stirred solution of (2S)-3-(2-(tert-butyldiphenylsilyloxy)ethoxy)-2-(1-(2-chlorophenyl)-1H-pyrazolo[3,4-d]pyrimidin-4-yloxy)-N-(pyridin-2-yl)propanamide (Intermediate AQ5) (0.682 g, 0.98 mmol) in tetrahydrofuran (15 mL). The resulting solution was stirred at ambient temperature for 30 minutes. The reaction mixture was quenched with saturated NH$_4$Cl (10 mL), and diluted with water (20 mL) and EtOAc (50 mL). The organic layer was separated and the aqueous layer extracted with EtOAc (50 mL), The combined organics were dried (MgSO$_4$), filtered and evaporated to afford crude product. The crude product was purified by flash silica chromatography, elution gradient 80 to 100% EtOAc in isohexane to afford the product (0.335 g, 74.9%). $^1$H NMR: (400 MHz, CDCl$_3$) δ 2.91 (1H, s), 3.74-3.79 (4H, m), 4.15-4.25 (2H, m), 6.10 (1H, t), 7.06-7.10 (1H, m), 7.45-7.63 (4H, m), 7.71-7.75 (1H, m), 8.19 (1H, d), 8.27-8.29 (1H, m), 8.44 (1H, s), 8.60 (1H, s), 9.01 (1H, s); m/z (ES+) (M+H)$^+$=455; HPLC $t_R$=1.76 min.

EXAMPLE 202

(2S)—N-(5-chloropyridin-2-yl)-2-(1-(2,3-dichlorophenyl)-1H-pyrazolo[3,4-d]pyrimidin-4-yloxy)-3-(2-hydroxyethoxy)propanamide

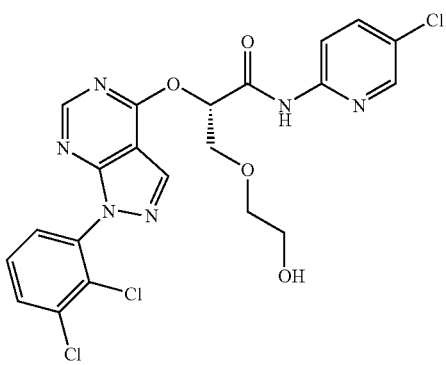

Trimethylaluminium (2M in toluene) (0.638 mL, 1.28 mmol) was added to 5-chloropyridin-2-amine (164 mg, 1.28 mmol) in toluene (2 mL) under nitrogen. The resulting solution was stirred at room temperature for 15 minutes. (2S)-Methyl 3-(2-(tert-butyldiphenylsilyloxy)ethoxy)-2-(1-(2,3-dichlorophenyl)-1H-pyrazolo[3,4-d]pyrimidin-4-yloxy) propanoate (Intermediate AR1) (425 mg, 0.64 mmol) in toluene (8 mL) was added sealed into a 20 mL microwave tube. The reaction was heated to 120° C. for 4 hours in the microwave reactor and cooled to RT. The reaction mixture was allowed to cool and concentrated in vacuo. The residue was neutralised with citric acid (1M, aq) and then diluted with water (30 mL) and extracted with EtOAc (2×50 mL). The combined organics were dried (MgSO$_4$) and evaporated. The crude product was purified by flash silica chromatography, elution gradient 0 to 50% EtOAc in isohexane to afford (2S)-3-(2-(tert-butyldiphenylsilyloxy)ethoxy)-N-(5-chloropyridin-2-yl)-2-(1-(2,3-dichlorophenyl)-1H-pyrazolo[3,4-d]pyrimidin-4-yloxy)propanamide (460 mg, 95%). m/z (ES+) (M+H)$^+$=763; HPLC $t_R$=3.94 min.

A solution of tetrabutylammonium fluoride (1M in THF) (0.661 mL, 0.66 mmol) was added dropwise to a stirred solution of (2S)-3-(2-(tert-butyldiphenylsilyloxy)ethoxy)-N-(5-chloropyridin-2-yl)-2-(1-(2,3-dichlorophenyl)-1H-pyrazolo[3,4-d]pyrimidin-4-yloxy)propanamide (420 mg, 0.55 mmol) in THF (15 mL) over a period of 1 minute. The resulting solution was stirred at ambient temperature for 3 hours. Saturated ammonium chloride (20 mL) was added to the reaction mixture which was then diluted with EtOAc (25 mL), and washed sequentially with water (25 mL) and saturated brine (25 mL). The organic layer was dried (MgSO$_4$), filtered and evaporated to afford crude product. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. Fractions containing the desired compound were concentrated to remove most of the MeCN and then EtOAc was added. The organic phase was washed sequentially with saturated NaHCO$_3$ and water the organic layer was evaporated to dryness to afford the product (120 mg, 41.6%). $^1$H NMR (400 MHz, CDCl$_3$) δ 3.75 (4H, m), 4.16 (1H, dd), 4.22 (1H, dd), 6.06 (1H, t), 7.42 (2H, m), 7.66 (2H, m), 8.20 (2H, m), 8.43 (1H, d), 8.58 (1H, s), 9.17 (1H, s); m/z (ES+) (M+H)$^+$=525; HPLC $t_R$=2.32 min.

EXAMPLE 203

(2S)—N-(5-cyanopyridin-2-yl)-2-(1-(2,3-dichlorophenyl)-1H-pyrazolo[3,4-d]pyrimidin-4-yloxy)-3-(2-hydroxyethoxy)propanamide

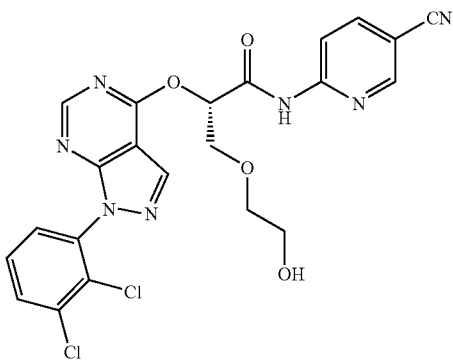

Trimethylaluminium (2M in toluene) (0.638 mL, 1.28 mmol) was added to 6-aminonicotinonitrile (152 mg, 1.28 mmol) in toluene (2 mL) under nitrogen. The resulting solution was stirred at room temperature for 15 minutes. (2S)-methyl 3-(2-(tert-butyldiphenylsilyloxy)ethoxy)-2-(1-(2,3-dichlorophenyl)-1H-pyrazolo[3,4-d]pyrimidin-4-yloxy) propanoate (Intermediate AR1) (425 mg, 0.64 mmol) in toluene (8 mL) was added sealed into a 20 mL microwave tube. The reaction was heated to 120° C. for 4 hours in the microwave reactor and cooled to RT. The reaction mixture was allowed to cool and concentrated in vacuo. The residue was neutralised with citric acid (1M, aq) and then diluted with water (30 mL) and extracted with EtOAc (2×50 mL). The combined organics were dried (MgSO$_4$) and evaporated. The crude product was purified by flash silica chromatography, elution gradient 0 to 50% EtOAc in isohexane to afford (2S)-3-(2-(tert-butyldiphenylsilyloxy)ethoxy)-N-(5-cyanopyridin-2-yl)-2-(1-(2,3-dichlorophenyl)-1H-pyrazolo[3,4-d]pyrimidin-4-yloxy)propanamide (450 mg, 94%).

m/z (ES+) (M+H)$^+$=752; HPLC $t_R$=3.74 min.

A solution of tetrabutylammonium fluoride (1M in THF) (0.701 mL, 0.70 mmol) was added dropwise to a stirred solution of (2S)-3-(2-(tert-butyldiphenylsilyloxy)ethoxy)-N-(5-cyanopyridin-2-yl)-2-(1-(2,3-dichlorophenyl)-1H-pyrazolo[3,4-d]pyrimidin-4-yloxy)propanamide (440 mg, 0.58 mmol) in THF (15 mL) over a period of 1 minute. The resulting solution was stirred at ambient temperature for 3 hours. Saturated ammonium chloride (20 mL) was added to the reaction mixture which was then diluted with EtOAc (25 mL), and washed sequentially with water (25 mL) and saturated brine (25 mL). The organic layer was dried (MgSO$_4$), filtered and evaporated to afford crude product. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. Fractions containing the desired compound were concentrated to remove most of the MeCN and then EtOAc was added. The organic phase was washed sequentially with saturated NaHCO$_3$ and water the organic layer was evaporated to dryness to afford the product (240 mg, 80%). $^1$H NMR (400 MHz, CDCl$_3$) δ 2.37 (1H, s), 3.81-3.62 (4H, m), 4.14 (2H, m), 6.00 (1H, t), 7.44-7.28 (2H, m), 7.60 (1H, dd), 7.90 (1H, dd), 8.29 (1H, dd), 8.36 (1H, s), 8.49 (1H, dd), 8.52 (1H, s), 9.26 (1H, s); m/z (ES+) (M+H)$^+$=514; HPLC $t_R$=2.13 min.

EXAMPLE 204

(2S)-2-(1-(3-chloropyridin-2-yl)-1H-pyrazolo[3,4-d]pyrimidin-4-yloxy)-3-((S)-2-hydroxypropoxy)-N-(5-methylpyridin-2-yl)propanamide

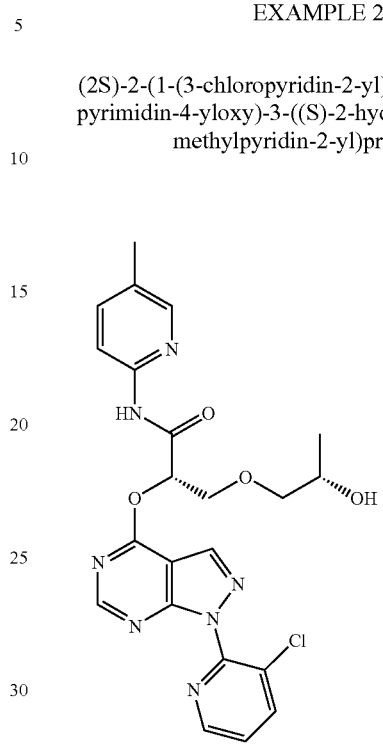

Tetrabutylammonium fluoride (1M in THF) (1.342 mL, 1.34 mmol) was added to (2S)-3-((S)-2-(tert-butyldimethylsilyloxy)propoxy)-2-(1-(3-chloropyridin-2-yl)-1H-pyrazolo[3,4-d]pyrimidin-4-yloxy)-N-(5-methylpyridin-2-yl)propanamide (Intermediate AS1) (803 mg, 1.34 mmol) in THF (6 mL) under nitrogen. The resulting mixture was stirred at ambient temperature for 16 hours. A further portion of Tetrabutylammonium fluoride (1M in THF) (1.342 mL, 1.34 mmol) was added and stirring continued for a further 5 hours. The reaction mixture was quenched with saturated NH4Cl, diluted with DCM and poured onto a phase separator. The organic layer was evaporated to a gum. The crude product was purified by flash silica chromatography, elution gradient 0 to 100% EtOAc in isohexane. 336 mg of material was isolated but was found to contain co-running imps. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. The relevant fractions were concentrated to remove the acetonitrile, then the remaining aqueous was basified with sat bicarb and extracted into ethylacetate x2. The organics were washed with brine, dried (MgSO$_4$) and concentrated to give (2S)-2-(1-(3-chloropyridin-2-yl)-1H-pyrazolo[3,4-d]pyrimidin-4-yloxy)-3-((S)-2-hydroxypropoxy)-N-(5-methylpyridin-2-yl)propanamide (193 mg, 29.7%, 77% ee). $^1$H NMR (400 MHz, CDCl$_3$) δ 1.14 (3H, d), 2.29 (3H, s), 2.98 (1H, s), 3.37-3.44 (1H, m), 3.60-3.65 (1H, m), 3.97-4.05 (1H, m), 4.10-4.26 (2H, m), 6.09 (1H, t), 7.44-7.50 (1H, m), 7.51-7.57 (1H, m), 7.99-8.03 (1H, m), 8.05-8.12 (2H, m), 8.47 (1H, s), 8.60-8.63 (1H, m), 8.64 (1H, s), 8.86 (1H, s); m/z (ES+) (M+H)$^+$=484.46; HPLC $t_R$=1.62 min.

EXAMPLE 205

(2S)-2-(1-(2-chlorophenyl)-1H-pyrazolo[3,4-d]pyrimidin-4-yloxy)-3-(3-hydroxyazetidin-1-yl)-N-(5-methylpyridin-2-yl)propanamide

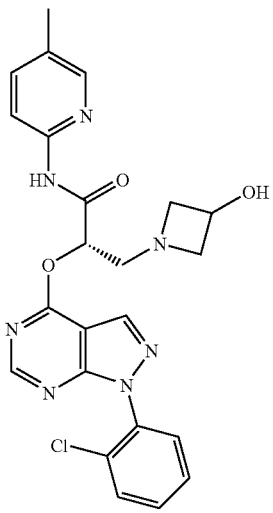

Tetrabutylammonium fluoride (1M in THF) (1.515 mL, 1.51 mmol) was added to (2S)-3-(3-(tert-butyldimethylsilyloxy)azetidin-1-yl)-2-(1-(2-chlorophenyl)-1H-pyrazolo[3,4-d]pyrimidin-4-yloxy)-N-(5-methylpyridin-2-yl)propanamide (Intermediate AD7) (0.9 g, 1.51 mmol) in THF (10 mL) under nitrogen. The resulting mixture was stirred at ambient temperature for 2.5 hours. The reaction mixture was quenched with saturated NH$_4$Cl, diluted with DCM and poured onto a phase separator. The organic layer was evaporated to a gum. The crude product was purified by flash silica chromatography, elution gradient 0 to 10% MeOH in EtOAc to afford the product (0.313 g, 43.1%, 98% ee). $^1$H NMR (400 MHz, CDCl$_3$) δ 2.29 (3H, s), 2.50-2.78 (1H, m), 3.15-3.31 (4H, m), 3.79-3.89 (2H, m), 4.47-4.55 (1H, m), 5.91 (1H, t), 7.42-7.56 (4H, m), 7.59-7.65 (1H, m), 8.08-8.14 (2H, m), 8.37 (1H, s), 8.59 (1H, s), 9.53 (1H, s); m/z (ES+) (M+H)$^+$=480.41; HPLC t$_R$=1.19 min.

EXAMPLE 206

(2S)-2-(1-(3-chloropyridin-2-yl)-1H-pyrazolo[3,4-d]pyrimidin-4-yloxy)-3-(3-hydroxyazetidin-1-yl)-N-(5-methylpyridin-2-yl)propanamide

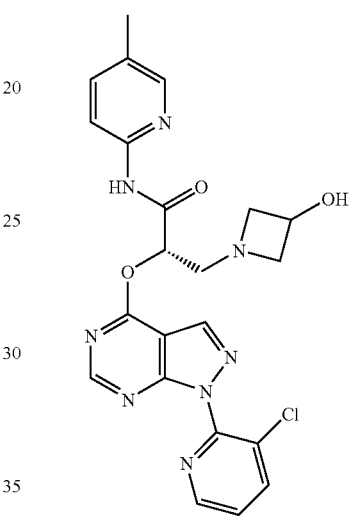

Tetrabutylammonium fluoride (1M in THF) (0.328 mL, 0.33 mmol) was added to (2S)-3-(3-(tert-butyldimethylsilyloxy)azetidin-1-yl)-2-(1-(3-chloropyridin-2-yl)-1H-pyrazolo[3,4-d]pyrimidin-4-yloxy)-N-(5-methylpyridin-2-yl)propanamide (Intermediate AD9) (195 mg, 0.33 mmol) in THF (2 mL) under nitrogen. The resulting mixture was stirred at ambient temperature for 6 hours. The reaction mixture was quenched with saturated NH4Cl, diluted with DCM and poured onto a phase separator. The organic layer was evaporated to a gum. The crude product was purified by flash silica chromatography, elution gradient 0 to 10% MeOH in EtOAc to afford the product (38.0 mg, 24.12%). $^1$H NMR (400 MHz, CDCl$_3$) δ 1.23-1.29 (1H, m), 2.29 (3H, s), 3.16-3.32 (4H, m), 3.76-3.87 (2H, m), 4.46-4.53 (1H, m), 5.91 (1H, t), 7.44-7.49 (1H, m), 7.50-7.55 (1H, m), 7.97-8.03 (1H, m), 8.07-8.15 (2H, m), 8.42 (1H, s), 8.59-8.65 (2H, m), 9.58 (1H, s) m/z (ES+) (M+H)$^+$=481.51; HPLC t$_R$=1.14 min.

EXAMPLE 207

(2S)-2-(1-(3-cyano-2-methylphenyl)-1H-pyrazolo[3,4-d]pyrimidin-4-yloxy)-N-(5-cyanopyridin-2-yl)-3-(2-hydroxyethoxy)propanamide

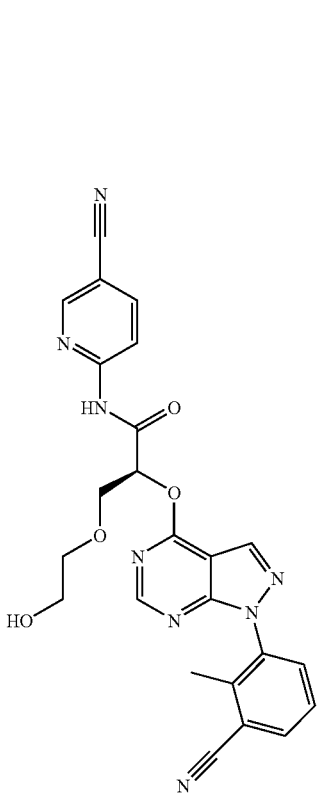

Tetrabutylammonium fluoride (1M in THF) (0.346 mL, 0.35 mmol) was added to (2S)-3-(2-(tert-butyldiphenylsilyloxy)ethoxy)-2-(1-(3-cyano-2-methylphenyl)-1H-pyrazolo[3,4-d]pyrimidin-4-yloxy)-N-(5-cyanopyridin-2-yl)propanamide (Intermediate AT1) (250 mg, 0.35 mmol) in THF (2 mL) under nitrogen. The resulting mixture was stirred at ambient temperature for 90 minutes. The reaction mixture was quenched with saturated NH4Cl, diluted with DCM and poured onto a phase separator. The organic layer was evaporated to a gum. The crude product was purified by flash silica chromatography, elution gradient 50 to 100% EtOAc in isohexane to afford the product (69.0 mg, 41.2%, 92% ee). $^1$H NMR (400 MHz, CDCl$_3$) δ 2.37-2.44 (4H, m), 3.73-3.86 (4H, m), 4.15-4.26 (2H, m), 6.07 (1H, t), 7.49 (1H, t), 7.63-7.68 (1H, m), 7.77-7.82 (1H, m), 7.94-8.00 (1H, m), 8.34-8.38 (1H, m), 8.43 (1H, s), 8.55-8.60 (2H, m), 9.34 (1H, s); m/z (ES-) (M-H)-=483.52; HPLC t$_R$=1.95 min.

EXAMPLE 208

(2S)-2-(1-(3-cyano-2-methylphenyl)-1H-pyrazolo[3,4-d]pyrimidin-4-yloxy)-3-(2-hydroxyethoxy)-N-(5-methylpyridin-2-yl)propanamide

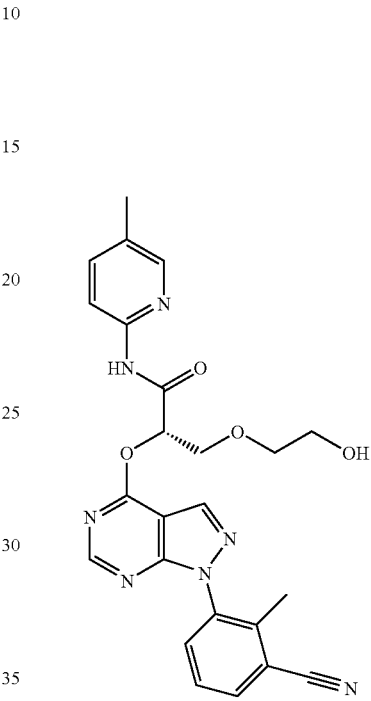

Tetrabutylammonium fluoride (1M in THF) (0.440 mL, 0.44 mmol) was added to (2S)-3-(2-(tert-butyldiphenylsilyloxy)ethoxy)-2-(1-(3-cyano-2-methylphenyl)-1H-pyrazolo[3,4-d]pyrimidin-4-yloxy)-N-(5-methylpyridin-2-yl)propanamide (Intermediate AT6) (313 mg, 0.44 mmol) in THF (2 mL) under nitrogen. The resulting mixture was stirred at ambient temperature for 2 hours. The reaction mixture was quenched with saturated NH$_4$Cl, diluted with DCM and poured onto a phase separator. The organic layer was evaporated to a gum. The crude product was purified by flash silica chromatography, elution gradient 0 to 10% methanol in ethyl acetate to afford the product (59.0 mg, 28.3%, 84% ee). $^1$H NMR (400 MHz, CDCl$_3$) δ 2.30 (3H, s), 2.40 (3H, s), 3.02 (1H, s), 3.72-3.83 (4H, m), 4.13-4.26 (2H, m), 6.09 (1H, t), 7.45-7.57 (2H, m), 7.63-7.68 (1H, m), 7.76-7.81 (1H, m), 8.03-8.12 (2H, m), 8.43 (1H, s), 8.58 (1H, s), 8.95 (1H, s); m/z (ES+) (M+H)$^+$=474.49; HPLC t$_R$=1.83 min.

EXAMPLE 209

(2S)—N-(5-chloropyridin-2-yl)-2-(1-(3-cyano-2-methylphenyl)-1H-pyrazolo[3,4-d]pyrimidin-4-yloxy)-3-(2-hydroxyethoxy)propanamide

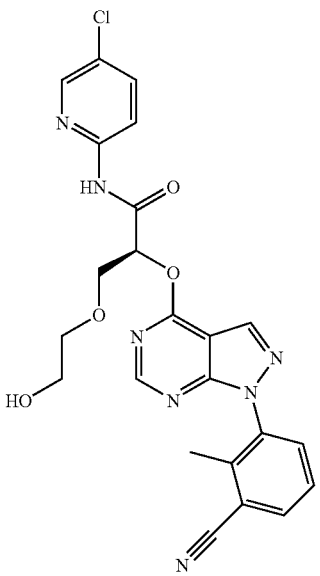

Tetrabutylammonium fluoride (1M in THF) (1.174 mL, 1.17 mmol) was added to (2S)-3-(2-(tert-butyldiphenylsilyloxy)ethoxy)-N-(5-chloropyridin-2-yl)-2-(1-(3-cyano-2-methylphenyl)-1H-pyrazolo[3,4-d]pyrimidin-4-yloxy)propanamide (Intermediate AT7) (860 mg, 1.17 mmol) in THF (2 mL) under nitrogen. The resulting mixture was stirred at ambient temperature for 2 hours. The reaction mixture was quenched with saturated NH4Cl (1 mL), diluted with DCM (10 mL) and poured onto a phase separator. The organic layer was evaporated to a gum. The crude product was purified by flash silica chromatography, elution gradient 0 to 100% EtOAc in isohexane to afford the product (284 mg, 49.0%, 91% ee). $^1$H NMR (300 MHz, CDCl$_3$) δ 2.40 (3H, s), 2.55-2.65 (1H, m), 3.70-3.86 (4H, m), 4.14-4.27 (2H, m), 6.08 (1H, t), 7.49 (1H, t), 7.63-7.73 (2H, m), 7.76-7.82 (1H, m), 8.15-8.25 (2H, m), 8.44 (1H, s), 8.59 (1H, s), 9.03 (1H, s); m/z (ES+) (M+H)$^+$=494.45; HPLC $t_R$=2.13 min.

EXAMPLE 210

(2S)—N-(5-chloropyridin-2-yl)-3-ethoxy-2-(1-(1-methyl-1H-imidazol-2-yl)-1H-pyrazolo[3,4-d]pyrimidin-4-yloxy)propanaide

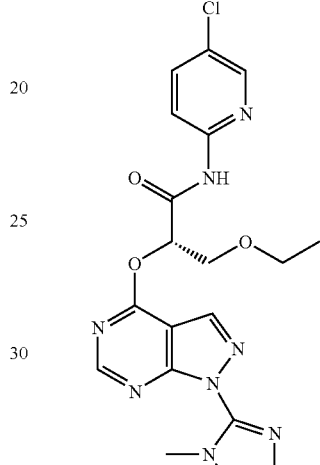

Sodium hydride (60% in oil) (29.2 mg, 0.73 mmol) was added to (S)—N-(5-chloropyridin-2-yl)-3-ethoxy-2-hydroxypropanamide (Intermediate H3) (149 mg, 0.61 mmol) in anhydrous THF (5 mL) at 0° C. under nitrogen. The resulting solution was stirred at 0° C. for 10 minutes and then 1-(1-methyl-1H-imidazol-2-yl)-4-phenoxy-1H-pyrazolo[3,4-d]pyrimidine (Intermediate AV1) (196 mg, 0.67 mmol) was added. The reaction mixture was allowed to warm to room temperature and stirred for 4 hours. The reaction mixture was quenched with 1M citric (2 mL), extracted with EtOAc, the organic layer was washed with water ×2 and brine, dried (MgSO$_4$), filtered and evaporated to afford orange oil. The crude product was purified by preparative HPLC (Waters XBridge Prep C18 OBD column, 5μ silica, 50 mm diameter, 150 mm length), using decreasingly polar mixtures of water (containing 1% NH$_3$) and MeCN as eluents to afford the product (111 mg, 41.2%, 95% ee). $^1$H NMR (400 MHz, CDCl$_3$) δ 1.22 (3H, t), 3.56-3.72 (5H, m), 4.03-4.15 (2H, m), 6.05 (1H, t), 7.02 (1H, d), 7.17 (1H, d), 7.65-7.71 (1H, m), 8.19-8.26 (2H, m), 8.43 (1H, s), 8.65 (1H, s), 8.78 (1H, s); m/z (ES+) (M+H)$^+$=443.40; HPLC $t_R$=1.92 min.

EXAMPLE 211

(2S)-3-isopropoxy-2-(1-(1-methyl-1H-imidazol-2-yl)-1H-pyrazolo[3,4-d]pyrimidin-4-yloxy)-N-(5-methylpyridin-2-yl)propanamide

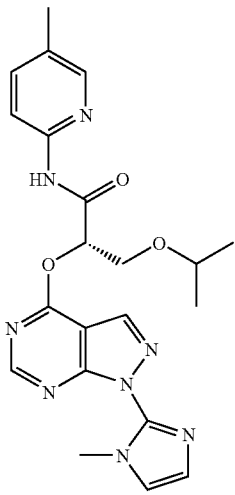

EXAMPLE 212

(2S)—N-(5-chloropyridin-2-yl)-2-(1-(3-chloropyridin-2-yl)-1H-pyrazolo[3,4-d]pyrimidin-4-yloxy)-5-hydroxypentanamide

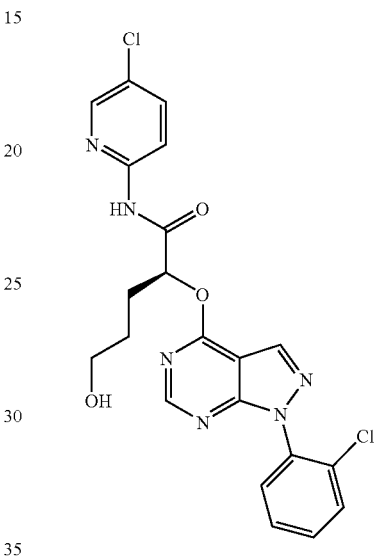

Sodium hydride (60% in oil) (28.8 mg, 0.72 mmol) was added to (S)-2-hydroxy-3-isopropoxy-N-(5-methylpyridin-2-yl)propanamide (Intermediate C7) (143 mg, 0.60 mmol) in anhydrous THF (5 mL) at 0° C. under nitrogen. The resulting solution was stirred at 0° C. for 10 minutes and then 1-(1-methyl-1H-imidazol-2-yl)-4-phenoxy-1H-pyrazolo[3,4-d]pyrimidine (Intermediate AV1) (193 mg, 0.66 mmol) in THF (1 mL) was added. The reaction mixture was allowed to warm to room temperature and stirred for 2 hours. The reaction mixture was quenched with 1M citric (2 mL), extracted with EtOAc, the organic layer was washed with water ×2 and brine, dried (MgSO$_4$), filtered and evaporated to afford orange oil. The crude product was purified by preparative HPLC (Waters XBridge Prep C18 OBD column, 5μ silica, 50 mm diameter, 150 mm length), using decreasingly polar mixtures of water (containing 1% NH$_3$) and MeCN as eluents to afford the product (90 mg, 34.4%, 100% ee). $^1$H NMR (400 MHz, CDCl$_3$) δ 1.18 (6H, t), 2.29 (3H, s), 3.65 (3H, s), 3.67-3.76 (1H, m), 4.08 (2H, d), 6.01 (1H, t), 7.01 (1H, d), 7.17 (1H, d), 7.49-7.55 (1H, m), 8.06-8.14 (2H, m), 8.42 (1H, s), 8.65 (1H, s), 8.68 (1H, s); m/z (ES+) (M+H)$^+$=437.51; HPLC t$_R$=1.89 min.

Tetrabutylammonium fluoride (1M in THF) (1.177 mL, 1.18 mmol) was added to (2S)-5-(tert-butyldimethylsilyloxy)-N-(5-chloropyridin-2-yl)-2-(1-(3-chloropyridin-2-yl)-1H-pyrazolo[3,4-d]pyrimidin-4-yloxy)pentanamide (Intermediate AW1) (693 mg, 1.18 mmol) in THF (5 mL) under nitrogen. The resulting mixture was stirred at ambient temperature for 1 hour. The reaction mixture was quenched with saturated NH4Cl (2 mL), diluted with DCM (25 mL) and poured onto a phase separator. The organic layer was loaded onto a silica column and purified by flash silica chromatography, elution gradient 50 to 100% EtOAc in isohexane to afford the product (171 mg, 30.6%, 95% ee). $^1$H NMR (400 MHz, CDCl$_3$) δ 1.59 (1H, t), 1.81-1.91 (2H, m), 2.21-2.39 (2H, m), 3.73-3.86 (2H, m), 5.95 (1H, t), 7.44-7.50 (1H, m), 7.64-7.72 (1H, m), 7.98-8.04 (1H, m), 8.20-8.27 (2H, m), 8.44 (1H, s), 8.59-8.65 (2H, m), 8.72 (1H, s); m/z (ES+) (M+H)$^+$=474.36; HPLC t$_R$=1.89 min.

EXAMPLE 213

(2S)-2-(1-(3-chloropyridin-2-yl)-1H-pyrazolo[3,4-d]
pyrimidin-4-yloxy)-N-(5-cyanopyridin-2-yl)-5-hy-
droxypentanamide

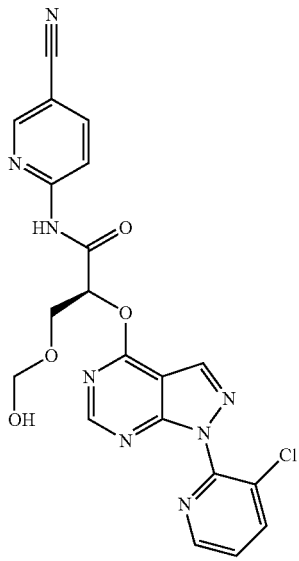

Tetrabutylammonium fluoride (1M in THF) (1.376 mL, 1.38 mmol) was added to (2S)-5-(tert-butyldimethylsilyloxy)-2-(1-(3-chloropyridin-2-yl)-1H-pyrazolo[3,4-d]pyrimidin-4-yloxy)-N-(5-cyanopyridin-2-yl)pentanamide (Intermediate AW2) (797 mg, 1.38 mmol) in THF (5 mL) under nitrogen. The resulting mixture was stirred at ambient temperature for 1 hour. The reaction mixture was quenched with saturated NH4Cl (2 mL), diluted with DCM (25 mL) and poured onto a phase separator. The organic layer was loaded onto a silica column and purified by flash silica chromatography, elution gradient 50 to 100% EtOAc in isohexane to afford the product (166 mg, 25.9%, 100% ee). $^1$H NMR (400 MHz, CDCl$_3$) δ 1.61 (1H, t), 1.81-1.92 (2H, m), 2.22-2.40 (2H, m), 3.76-3.88 (2H, m), 5.95 (1H, t), 7.45-7.50 (1H, m), 7.93-7.98 (1H, m), 7.99-8.04 (1H, m), 8.35-8.41 (1H, m), 8.44 (1H, s), 8.53-8.57 (1H, m), 8.60-8.64 (2H, m), 9.03 (1H, s); m/z (ES−) (M−H)−=463.37; HPLC t$_R$=1.68 min.

EXAMPLE 214

(2S)—N-(5-cyanopyridin-2-yl)-2-(1-(2,3-dichlo-
rophenyl)-1H-pyrazolo[3,4-d]pyrimidin-4-yloxy)-3-
ethoxypropanamide Sodium hydride (60% in oil) (80 mg, 2.00 mmol) was added to (S)—N-(5-cyanopyridin-2-yl)-3-ethoxy-2-hydroxypropanamide (Intermediate H4) (314 mg, 1.34 mmol) in THF (10 mL) at 0° C. under nitrogen. The resulting mixture was stirred at 0° C. for 10 minutes. 4-chloro-1-(2,3-dichlorophenyl)-1H-pyrazolo[3,4-d]pyrimidine (Intermediate AR4) (400 mg, 1.34 mmol) in THF (2 mL) was then added dropwise and stirred at 0° C. for a further 10 mins. The reaction was then allowed to warm to r.t. and stirred for 3½ hours. The reaction mixture was quenched with 1M citric acid, extracted with EtOAc and washed with water ×2. The organic layer was dried (MgSO$_4$), filtered and evaporated to afford yellow gum (835 mg). The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents to afford the product (285 mg, 42.8%, 96% ee). $^1$H NMR (400 MHz, CDCl$_3$) δ 1.24 (3H, t), 3.58-3.74 (2H, m), 4.04-4.17 (2H, m), 6.04 (1H, t), 7.37-7.48 (2H, m), 7.64-7.69 (1H, m), 7.93-7.99 (1H, m), 8.36-8.41 (1H, m), 8.43 (1H, s), 8.56-8.58 (1H, m), 8.58 (1H, s), 9.02 (1H, s); m/z (ES−) (M−H)−=496.33; HPLC t$_R$=2.70 min.

EXAMPLE 215

(2S)-2-[1-(2-chlorophenyl)pyrazolo[4,5-e]pyrimidin-4-yl]oxy-N-(5-fluoro-2-pyridyl)-3-(3-hydroxyazetidin-1-yl)propanamide

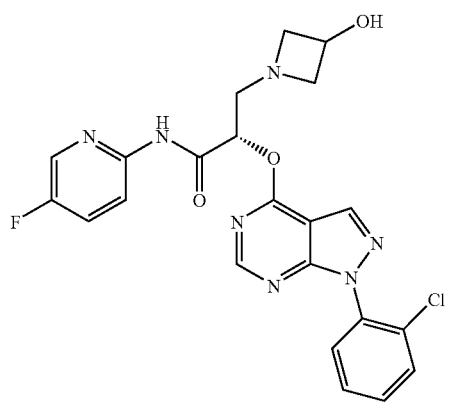

A solution of tetrabutylammonium fluoride (1M in THF) (7.14 mL, 7.14 mmol) was added in one portion to a stirred solution of (2S)-3-(3-(tert-butyldimethylsilyloxy)azetidin-1-yl)-2-(1-(2-chlorophenyl)-1H-pyrazolo[3,4-d]pyrimidin-4-yloxy)-N-(5-fluoropyridin-2-yl)propanamide (Intermediate AX1) (4.27 g, 7.14 mmol) in tetrahydrofuran (100 mL). The resulting solution was stirred at ambient temperature for 30 minutes. The reaction mixture was quenched with saturated NH$_4$Cl (30 mL), concentrated to approximately 50 mL and then diluted with water (50 mL) and EtOAc (100 mL). The organic layer was separated and the aqueous layer extracted with EtOAc (100 mL). The combined organics were dried (MgSO$_4$), filtered and evaporated to afford crude product. The crude product was purified by flash silica chromatography, elution gradient 0 to 10% MeOH in EtOAc to afford the product (2.54 g, 73.6%). $^1$H NMR (400 MHz, CDCl$_3$) δ 2.35 (1H, s), 3.15-3.21 (3H, m), 3.27-3.31 (1H, m), 3.84-3.91 (2H, m), 4.50-4.57 (1H, m), 5.90-5.93 (1H, m), 7.41-7.54 (4H, m), 7.61-7.63 (1H, m), 8.14 (1H, d), 8.23-8.26 (1H, m), 8.37 (1H, s), 8.59 (1H, s), 9.74 (1H, s); m/z (ES$^+$) (M+H)$^+$=484.17; HPLC t$_R$=1.65 min.

EXAMPLE 216

(2S)-2-[1-(2-chloro-6-cyano-phenyl)pyrazolo[4,5-e]pyrimidin-4-yl]oxy-N-(5-chloro-2-pyridyl)-3-[(1R)-2-hydroxy-1-methyl-ethoxy]propanamide

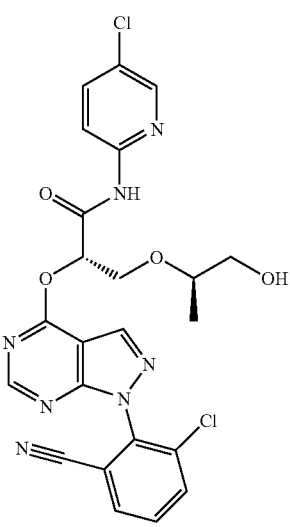

A solution of tetrabutylammonium fluoride (1M in THF) (0.891 mL, 0.89 mmol) was added in one portion to a stirred solution of (2S)-2-(1-(2-chloro-6-cyanophenyl)-1H-pyrazolo[3,4-d]pyrimidin-4-yloxy)-N-(5-chloropyridin-2-yl)-3-((R)-1-(triisopropylsilyloxy)propan-2-yloxy)propanamide (Intermediate AY1) (610 mg, 0.89 mmol) in tetrahydrofuran (15 mL). The resulting solution was stirred at ambient temperature for 30 minutes. The reaction mixture was quenched with saturated NH$_4$Cl (10 mL), and diluted with water (20 mL) and EtOAc (70 mL). The organic layer was separated and the aqueous layer extracted with EtOAc (70 mL). The combined organics were dried (MgSO$_4$), filtered and evaporated to afford crude product. The crude product was purified by flash silica chromatography, elution gradient 50 to 80% EtOAc in isohexane to afford the product (281 mg, 59.7%). $^1$H NMR (400 MHz, DMSO) δ 1.07 (3H, d), 3.33 (1H, q), 3.40-3.46 (1H, m), 3.61-3.69 (1H, m), 4.09-4.16 (2H, m), 4.57 (1H, t), 5.90 (1H, s), 7.87-7.91 (2H, m), 8.01-8.05 (1H, m), 8.16-8.19 (2H, m), 8.40-8.41 (1H, m), 8.61 (1H, s), 8.78 (1H, t), 11.17 (1H, d); m/z (ES$^-$) (M−H)$^-$=526; HPLC t$_R$=2.94 min.

EXAMPLE 217

(2S)-2-[1-(2-chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide

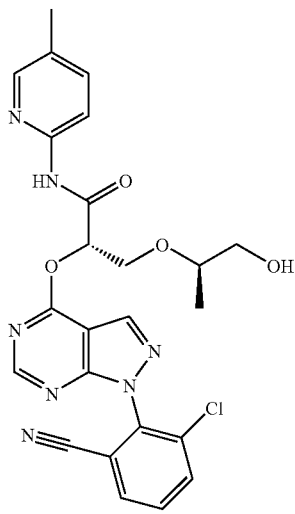

| Angle 2-Theta (2θ) | Intensity % |
|---|---|
| 4.234 | 100.0 |
| 20.902 | 95.6 |
| 14.456 | 95.2 |
| 17.730 | 77.8 |
| 13.278 | 69.4 |
| 11.065 | 63.2 |
| 21.237 | 61.5 |
| 19.725 | 59.4 |
| 26.458 | 59.2 |
| 8.463 | 54.9 |
| 26.192 | 54.8 |

EXAMPLE 217

(2S)-2-[1-(2-chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide
Alternative Method

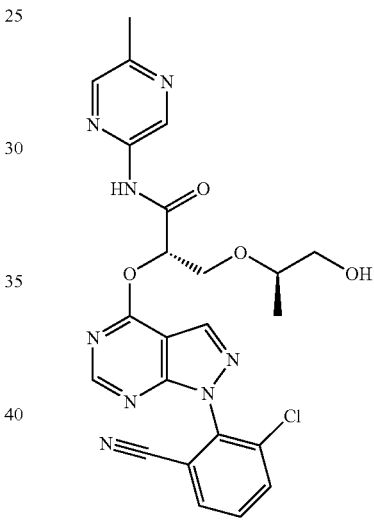

A solution of tetrabutylammonium fluoride (1M in THF) (0.887 mL, 0.89 mmol) was added in one portion to a stirred solution of (2S)-2-(1-(2-chloro-6-cyanophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide (Intermediate AZ1) (0.59 g, 0.89 mmol) in tetrahydrofuran (15 mL). The resulting solution was stirred at ambient temperature for 30 minutes. The reaction mixture was quenched with saturated NH$_4$Cl (10 mL), and diluted with water (20 mL) and EtOAc (70 mL). The organic layer was separated and the aqueous layer extracted with EtOAc (70 mL), The combined organics were dried (MgSO$_4$), filtered and evaporated to afford crude product. The crude product was purified by flash silica chromatography, elution gradient 50 to 80% EtOAc in isohexane to afford the product (0.367 g, 81%). $^1$H NMR (400 MHz, CDCl$_3$) δ 1.14-1.20 (3H, m), 2.54 (3H, s), 2.70-2.84 (1H, m), 3.54-3.72 (2H, m), 3.77-3.83 (1H, m), 4.09-4.16 (1H, m), 4.28-4.32 (1H, m), 6.08-6.11 (1H, m), 7.63 (1H, t), 7.78-7.81 (1H, m), 7.85-7.88 (1H, m), 8.12 (1H, s), 8.50-8.53 (1H, m), 8.62 (1H, d), 9.04-9.12 (1H, m), 9.41 (1H, s); m/z (ES$^+$) (M+H)$^+$=509.06; HPLC t$_R$=2.41 min.

(2S)-2-(1-(2-chloro-6-cyanophenyl)-1H-pyrazolo[3,4-d]pyrimidin-4-yloxy)-3-((R)-1-hydroxypropan-2-yloxy)-N-(5-methylpyrazin-2-yl)propanamide (220 mg, 0.43 mmol) was taken up into Et$_2$O (20 mL) and warmed to boiling under reflux. The material dissolved and then began to crystallise. The mixture was allowed to cool and stood at ambient temperature for 1 hour. The solid was filtered off to give (2S)-2-(1-(2-chloro-6-cyanophenyl)-1H-pyrazolo[3,4-d]pyrimidin-4-yloxy)-3-((R)-1-hydroxypropan-2-yloxy)-N-(5-methylpyrazin-2-yl)propanamide (200 mg) which was shown to be crystalline by x-ray powder diffraction.

1M TBAF in THF (5.11 mL, 5.11 mmol) was added to (2S)-2-(1-(2-chloro-6-cyanophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide (Intermediate AZ1) (3.4 g, 5.11 mmol) and acetic acid (0.307 g, 5.11 mmol) in THF (35 mL). The resulting solution was stirred at 22° C. for 20 hours. It was quenched with NH$_4$Cl solution (sat., 25 mL) and diluted with EtOAc (50 mL). The organic phase was washed with saturated sodium bicarbonate (25 mL), water (20 mL), brine (20 mL), dried (MgSO$_4$) and evaporated. The crude product was purified by flash silica chromatography, eluting with EtOAc to afford the product (2.23 g, 85%). This was crystallised from EtOAc (10 mL) and iso-hexane (6 mL) to give the desired product as a white crystalline powder (1.9 g, 73%) confirmed to be of the same crystalline form as that described previously.

1H NMR (400 MHz, DMSO-d$_6$) δ 1.06-1.07 (3H, m), 2.44 (3H, s), 3.25-3.47 (2H, m), 3.62-3.67 (1H, m), 4.09-4.16 (2H, m), 4.53-4.61 (1H, m), 5.90-5.96 (1H, m), 7.89 (1H, dd), 8.16-8.20 (2H, m), 8.31-8.32 (1H, m), 8.62 (1H, s), 8.76-8.78 (1H, m), 9.10-9.12 (1H, m), 11.17 (1H, s); m/z (ES$^-$) (M-H)$^-$= 507; HPLC t$_R$=2.44 min.

EXAMPLE 218

(2S)-2-[1-(2,6-dichlorophenyl)pyrazolo[4,5-e]pyrimidin-4-yl]oxy-N-(5-fluoro-2-pyridyl)-3-(2-hydroxyethoxy)propanamide

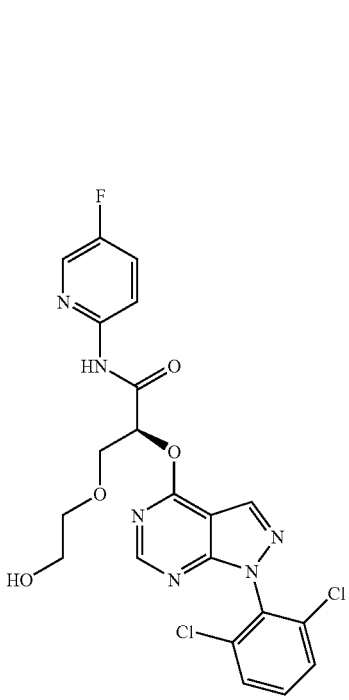

Tetrabutylammonium fluoride (1M in THF) (0.838 mL, 0.84 mmol) was added dropwise to (S)-3-(2-(tert-butyldiphenylsilyloxy)ethoxy)-2-(1-(2,6-dichlorophenyl)-1H-pyrazolo[3,4-d]pyrimidin-4-yloxy)-N-(5-fluoropyridin-2-yl)propanamide (Intermediate BA1) (0.625 g, 0.84 mmol) in THF (10.34 mL) at ambient temperature under nitrogen. The resulting solution was stirred at ambient temperature for 1 hour. The reaction mixture was quenched with saturated NH$_4$Cl (10 mL), and diluted with water (20 mL) and EtOAc (70 mL). The organic layer was separated and the aqueous layer extracted with EtOAc (70 mL). The combined organics were dried (MgSO$_4$), filtered and evaporated to afford crude product. The crude product was purified by flash silica chromatography, elution gradient 25 to 100% EtOAc in isohexane to afford the product (0.307 g, 72.1%). $^1$H NMR (400 MHz, CDCl$_3$) δ 2.60 (1H, t), 3.71-3.81 (4H, m), 4.16-4.25 (2H, m), 6.10 (1H, t), 7.43-7.49 (2H, m), 7.53-7.55 (2H, m), 8.14 (1H, d), 8.22-8.25 (1H, m), 8.48 (1H, s), 8.60 (1H, s), 9.00 (1H, s); m/z (ES$^-$) (M+H)$^+$=507.31; HPLC t$_R$=2.67 min.

EXAMPLE 219

(2S)-2-[1-(2-chlorophenyl)pyrazolo[4,5-e]pyrimidin-4-yl]oxy-3-(3-hydroxyazetidin-1-yl)-N-(5-methylpyrazin-2-yl)propanamide

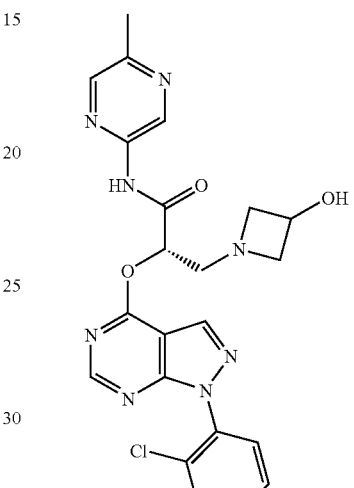

Tetrabutylammonium fluoride (1M in THF) (0.87 mL, 0.87 mmol) was added to (2S)-3-(3-(tert-butyldimethylsilyloxy)azetidin-1-yl)-2-(1-(2-chlorophenyl)-1H-pyrazolo[3,4-d]pyrimidin-4-yloxy)-N-(5-methylpyrazin-2-yl)propanamide (Intermediate BB1) (520 mg, 0.87 mmol) in tetrahydrofuran (25 mL) under nitrogen. The resulting mixture was stirred at ambient temperature for 2 hours. Further tetrabutylammonium fluoride (1M in THF) (1.7 mL, 1.7 mmol) added and the mixture stirred overnight. The reaction mixture was quenched with saturated ammonium chloride solution (20 mL), diluted with ethyl acetate (50 mL) and stirred for 10 minutes. The organic layer was separated, washed with water (50 mL) and brine (50 mL), dried (MgSO$_4$), filtered and evaporated. The crude product was purified by flash silica chromatography, eluting with 0 to 10% methanol in ethyl acetate, to afford the product (130 mg). $^1$H NMR (400 MHz, DMSO-d6) δ 2.50 (3H, m), 2.98-3.09 (3H, m), 3.15-3.21 (1H, m), 3.67-3.77 (2H, m), 4.19-4.29 (1H, m), 5.31 (1H, d), 5.77-5.84 (1H, m), 7.60-7.76 (3H, m), 7.80-7.82 (1H, m), 8.35-8.37 (1H, m), 8.57 (1H, s), 8.64 (1H, s), 9.11-9.12 (1H, m), 11.17 (1H, s); m/z (ESI$^+$) (M+H)$^+$=481; HPLC t$_R$=1.52 min.

EXAMPLE 220

(2S)-2-[1-(2,6-dichlorophenyl)pyrazolo[4,5-e]pyrimidin-4-yl]oxy-3-(3-hydroxyazetidin-1-yl)-N-(5-methylpyrazin-2-yl)propanamide

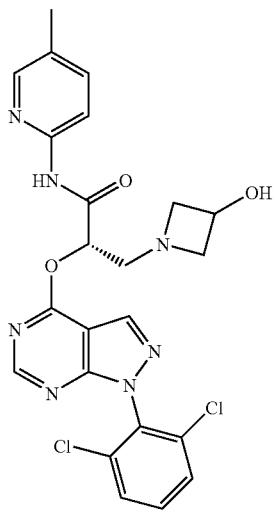

A solution of tetrabutylammonium fluoride (1M in THF) (0.61 mL, 0.61 mmol) was added in one portion to a stirred solution of (S)-3-(3-(tert-butyldimethylsilyloxy)azetidin-1-yl)-2-(1-(2,6-dichlorophenyl)-1H-pyrazolo[3,4-d]pyrimidin-4-yloxy)-N-(5-methylpyrazin-2-yl)propanamide (Intermediate BB3) (385 mg, 0.61 mmol) in tetrahydrofuran (15 mL). The resulting solution was stirred at ambient temperature for 30 minutes. The reaction mixture was quenched with saturated ammonium chloride solution (10 mL), and diluted with water (20 mL) and ethyl acetate (70 mL). The organic layer was separated and the aqueous layer extracted with ethyl acetate (70 mL). The combined organics were dried (MgSO₄), filtered and evaporated. The crude product was purified by flash silica chromatography, eluting with 0 to 10% methanol in ethyl acetate, to afford the product (197 mg, 62.5%, 99.4% ee). $^1$H NMR (400 MHz, CDCl$_3$) δ 2.54 (3H, s), 3.19-3.24 (3H, m), 3.30-3.35 (1H, m), 3.88-3.93 (2H, m), 4.53-4.58 (1H, m), 5.93-5.96 (1H, m), 7.43-7.47 (1H, m), 7.52-7.55 (2H, m), 8.13 (1H, d), 8.41 (1H, s), 8.59 (1H, s), 9.42 (1H, d), 9.81 (1H, s); m/z (ES$^+$) (M+H)$^+$=515; HPLC t$_R$=1.58 min.

Amorphous (S)-2-(1-(2,6-dichlorophenyl)-1H-pyrazolo[3,4-d]pyrimidin-4-yloxy)-3-(3-hydroxyazetidin-1-yl)-N-(5-methylpyrazin-2-yl)propanamide (1700 mg) was heated in refluxing t-butyl methyl ether (800 mL) for 30 minutes. The suspension was filtered, and the filtrate then reduced to a volume of approximately 100 mL. This solution was stirred overnight allowing the temperature to return to ambient. A solid was filtered off and was then dried under vacuum at 60° C. for 4 days to give crystalline (S)-2-(1-(2,6-dichlorophenyl)-1H-pyrazolo[3,4-d]pyrimidin-4-yloxy)-3-(3-hydroxyazetidin-1-yl)-N-(5-methylpyrazin-2-yl)propanamide (1121 mg).

| Angle 2-Theta (2θ) | Intensity % |
|---|---|
| 12.297 | 100.0 |
| 15.433 | 88.2 |
| 12.175 | 78.8 |
| 19.607 | 77.2 |
| 22.653 | 77.0 |
| 19.955 | 72.9 |
| 27.095 | 72.7 |
| 27.141 | 72.1 |
| 15.766 | 70.8 |
| 16.021 | 67.8 |

EXAMPLE 221

(2S)-3-(azetidin-1-yl)-2-[1-(2-chloro-6-cyano-phenyl)pyrazolo[3,4-d]pyrimidin-4-yl]oxy-N-(2-pyridyl)propanamide

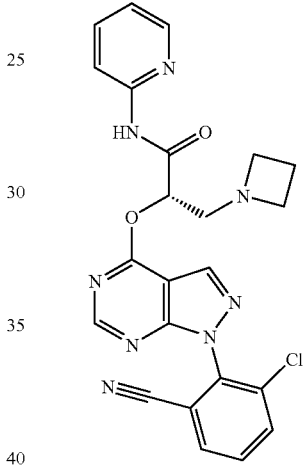

Sodium hydride (116 mg, 2.90 mmol) was added to (S)-3-(azetidin-1-yl)-2-hydroxy-N-(pyridin-2-yl)propanamide (Intermediate BC1) (232 mg, 1.05 mmol) in anhydrous THF (50 mL) at 0° C. under nitrogen. The resulting solution was stirred at 0° C. for 10 minutes and then a solution of 3-chloro-2-(4-chloro-1H-pyrazolo[3,4-d]pyrimidin-1-yl)benzonitrile (Intermediate AH6) (280 mg, 0.97 mmol) in anhydrous THF (20 mL) was added dropwise over 1 minute. The mixture was stirred at 0° C. for 10 minutes and then allowed to warm to ambient temperature for 2 hours. It was then cooled to 0° C., 20% Rochelle salt (20 mL) added and the mixture stirred for 10 minutes. It was extracted with EtOAc (50 mL), the organic phase was washed with water (10 mL) and brine (20 mL), dried (MgSO₄), filtered and evaporated. The residue was triturated with EtOAc (10 mL), filtered and the filtrates evaporated. The residue was purified by flash silica chromatography, elution gradient 0 to 20% MeOH in EtOAc and further purified by preparative HPLC (Phenomenex Luna C18 100A column, 5μ silica, 21 mm diameter, 150 mm length), using decreasingly polar mixtures of water (containing 1% formic acid) and MeCN as eluents to afford the product (100 mg, 22%).

$^1$H NMR (400 MHz, CDCl$_3$) δ 2.17-2.25 (2H, m), 3.08-3.17 (1H, m), 3.20-3.29 (1H, m), 3.40-3.52 (4H, m), 5.84-5.91 (1H, m), 7.02-7.08 (1H, m), 7.57-7.64 (1H, m), 7.65-7.71 (1H, m), 7.77-7.80 (1H, m), 7.82-7.87 (1H, m), 8.21-

8.25 (1H, m), 8.31-8.32 (1H, m), 8.44-8.47 (1H, d), 8.58-8.61 (1H, d), 9.8 (0.4H, s), 10.08 (0.6H, s) (Mixture of rotamers); m/z (ESI$^+$) (M+H)$^+$=475; HPLC $t_R$=1.16 min.

The following examples were prepared using a procedure analogous to that described for Example 218 using the appropriate intermediate.

| Example number | Structure | $^1$H NMR (400 MHz) δ | LCMS | Intermediate reference |
|---|---|---|---|---|
| 222 | 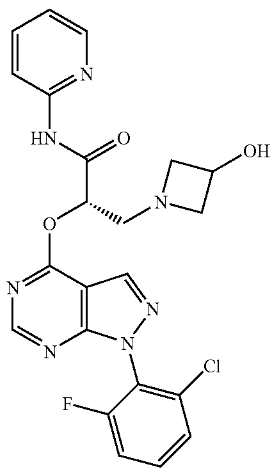 | (DMSO-d6) 3.00-3.13 (3H, m), 3.14-3.23 (1H, m), 3.67-3.76 (2H, m), 4.18-4.27 (1H, m), 5.30 (1H, d), 5.77-5.84 (1H, m), 5.30 (1H, d), 5.77-5.84 (1H, m), 7.72-7.20 (1H, m), 7.60-7.68 (1H, m), 7.69-7.71 (1H, m), 7.76-7.85 (2H, m), 8.00-8.08 (1H, m), 8.35-8.40 (1H, m), 8.60 (1H, s), 8.71 (1H, s), 10.95 (1H, d) | m/z (ES+) (M + H)+ = 484; HPLC tR = 1.17 min. | BD1 |
| 223 | 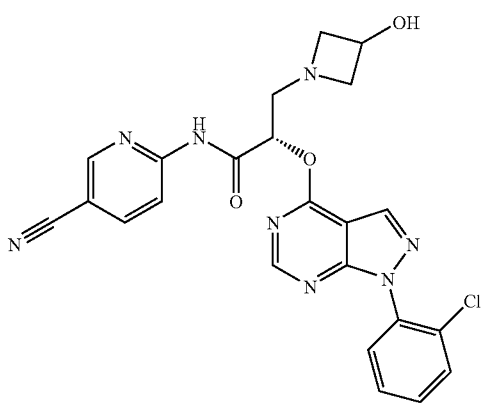 | (CDCl$_3$) 2.14 (1H, s, broad), 3.16-3.27 (1H, m), 3.20-3.24 (2H, m), 3.30-3.35 (1H, m), 3.90-3.94 (2H, m), 4.55-4.61 (1H, m), 5.89-5.92 (1H, m), 7.45-7.51 (2H, m), 7.52-7.55 (1H, m), 7.61-7.63 (1H, m), 7.92-7.95 (1H, m), 8.33-8.35 (1H, m), 8.36 (1H, s), 8.56-8.58 (1H, m), 8.59 (1H, s), 10.41 (1H, s) | m/z (ES+) (M + H)+ = 491; HPLC tR = 1.27 min. | BD2 |
| 224 | 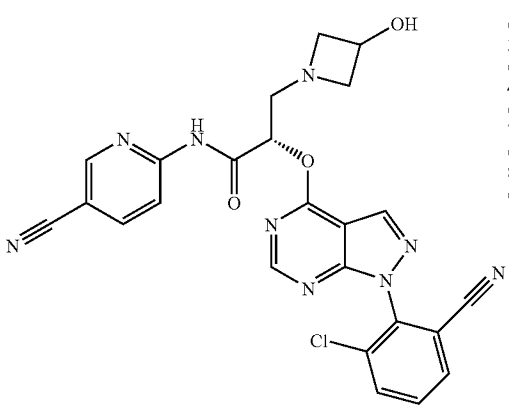 | (CDCl$_3$) 2.10 (1H, s. broad), 3.17-3.26 (3H, m), 3.27-3.38 (1H, m), 3.91-3.96 (2H, m), 4.58-4.65 (1H, m), 5.85-5.93 (1H, m), 7.60-7.65 (1H, m), 7.78-7.81 (1H, m), 7.85-7.88 (1H, m), 7.92-7.96 (1H, m), 8.33-8.36 (1H, m), 8.44-8.46 (1H, m), 8.57-8.62 (2H, m), 10.30 (0.5H, s), 10.60 (0.5H, s). | m/z (ES+) (M + H)+ = 516; HPLC tR = 1.23 min. | BD3 |

-continued
| Example number | Structure | $^1$H NMR (400 MHz) δ | LCMS | Intermediate reference |
|---|---|---|---|---|
| 225 | 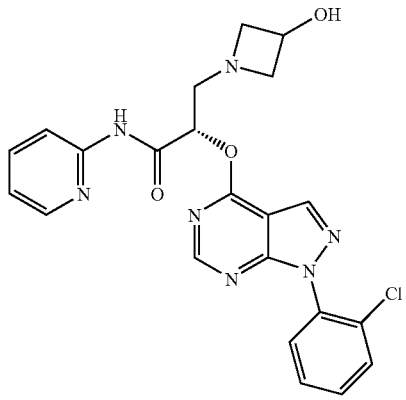 | (DMSO-d6) 2.98-3.12 (3H, m), 3.14-3.19 (1H, m), 3.66-3.74 (2H, m), 4.18-4.27 (1H, m), 5.31 (1H, d), 5.76-5.83 (1H, m), 7.15-7.19 (1H, m), 7.60-7.75 (3H, m), 7.76-7.82 (2H, m), 8.06 (1H, d), 8.37-8.40 (1H, m), 8.53 (1H, s), 8.58 (1H, s), 10.90 (1H, s) | m/z (ES+) (M + H)+ = 466; HPLC tR = 1.22 min. | BD4 |
| 226 | 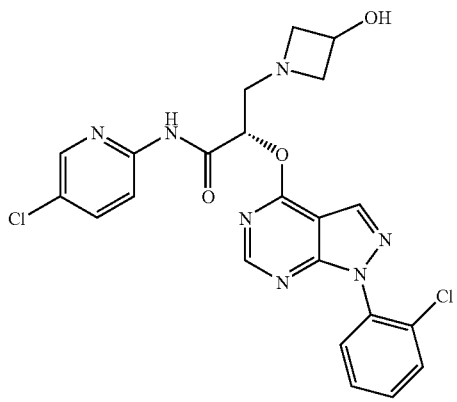 | (DMSO-d6) 2.96-3.05 (3H, m), 3.10-3.15 (1H, m), 3.60-3.66 (2H, m), 4.14-4.20 (1H, m), 5.22-5.27 (1H, m), 5.72-5.75 (1H, m), 7.56-7.70 (3H, m), 7.74 (1H, dd), 7.88 (1H, dd), 8.02 (1H, d), 8.39-8.41 (1H, m), 8.52 (1H, s), 8.58 (1H, s), 11.12 (1H, s) | m/z (ES+) (M + H)+ = 500; HPLC tR = 1.44 min. | BD5 |
| 227 | 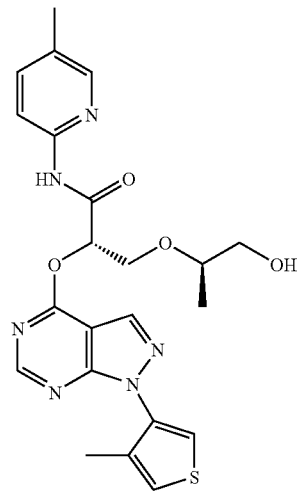 | (DMSO-d6) 1.06 (3H, d), 2.10 (3H, d), 2.24 (3H, s), 3.30-3.40 (1H, m), 3.41-3.46 (1H, m), 3.61-3.68 (1H, m), 4.03-4.11 (2H, m), 4.55 (1H, t), 5.88-5.98 (1H, m), 7.40-7.43 (1H, m), 7.62 (1H, dd), 7.86 (1H, d), 7.92-7.97 (1H, m), 8.19-9.02 (1H, m), 8.60 (1H, s), 8.62 (1H, s), 10.85 (1H, s) | m/z (ES+) (M + H)+ = 469; HPLC tR = 2.0 | |

| Example number | Structure | ¹H NMR (400 MHz) δ | LCMS | Intermediate reference |
|---|---|---|---|---|
| 228 | 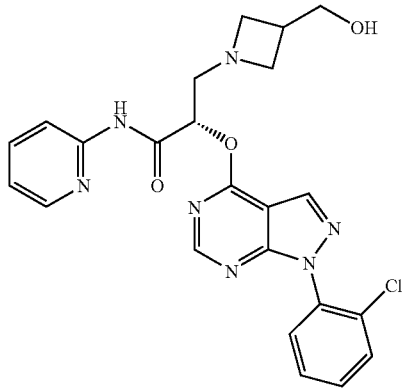 | (CDCl₃) 2.39 (1H, s), 2.68-2.71 (1H, m), 3.15-3.27 (2H, m), 3.37-3.40 (2H, m), 3.54-3.59 (2H, m), 3.83-3.85 (2H, m), 5.88-5.91 (1H, m), 7.03-7.06 (1H, m), 7.46-7.50 (2H, m), 7.52-7.55 (1H, m), 7.61-7.63 (1H, m), 7.67-7.72 (1H, m), 8.19 (1H, d, 8.4 Hz), 8.29-8.31 (1H, m), 8.36 (1H, s), 8.58 (1H, s), 10.20 (1H, s) | m/z (ES+) (M + H)+ = 480; HPLC tR = 1.63 min. | BD7 |
| 229 | 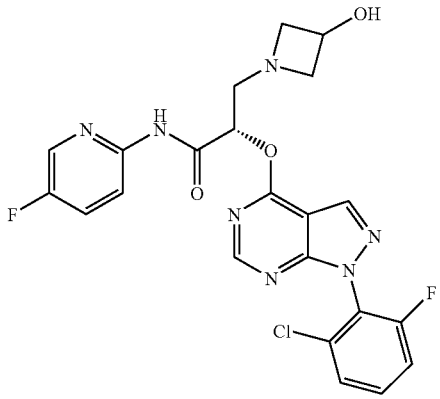 | (CDCl₃) 2.26 (1H, s), 3.15-3.22 (3H, m), 3.26-3.32 (1H, m), 3.85-3.91 (2H, m), 4.53-4.55 (1H, m), 5.89-5.93 (1H, m), 7.22-7.27 (1H, m), 7.41-7.52 (3H, m), 8.14-8.15 (1H, m), 8.22-8.27 (1H, m), 8.41 (1H, s), 8.59 (1H, s), 9.74 (1H, d) | m/z (ES+) (M + H)+ = 502; HPLC tR = 1.72 min. | BD8 |
| 230 | 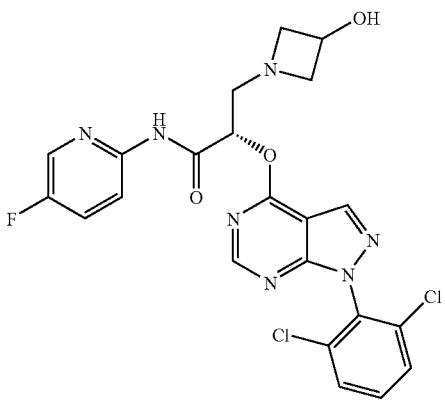 | (CDCl₃) 3.16-3.22 (3H, m), 3.27-3.32 (1H, m), 3.86-3.92 (2H, m), 4.54 (1H, s), 5.90-5.93 (1H, m), 7.41-7.47 (2H, m), 7.52-7.55 (2H, m), 8.15 (1H, d), 8.23-8.27 (1H, m), 8.41 (1H, s), 8.59 (1H, s), 9.74 (1H, s) | m/z (ES+) (M + H)+ = 518; HPLC tR = 1.78 min. | BD9 |

-continued
| Example number | Structure | $^1$H NMR (400 MHz) δ | LCMS | Intermediate reference |
|---|---|---|---|---|
| 231 | 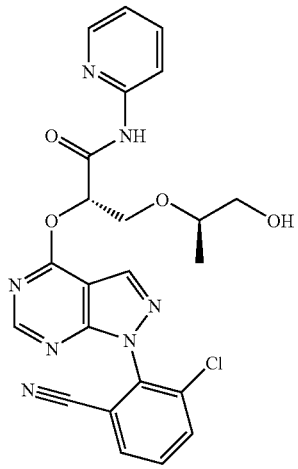 | (DMSO-d6) 1.07 (3H, d), 3.34 (1H, q), 3.40-3.46 (1H, m), 3.64-3.68 (1H, m), 4.08-4.17 (2H, m), 4.55-4.58 (1H, m), 5.91 (1H, s), 7.11-7.14 (1H, m), 7.74-7.79 (1H, m), 7.89 (1H, t), 7.99 (1H, t), 8.13-8.19 (2H, m), 8.33-8.35 (1H, m), 8.61 (1H, d), 8.78 (1H, t), 10.96 (1H, d) | m/z (ES+) (M + H)+ = 494; HPLC tR = 2.51 min. | BD10 |
| 232 | 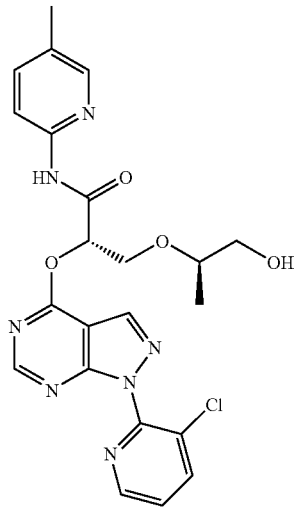 | (CDCl$_3$) 1.15-1.17 (3H, m), 2.29 (3H, s), 3.50-3.69 (3H, m), 3.75-3.80 (1H, m), 4.07-4.11 (1H, m), 4.26-4.29 (1H, m), 6.05-6.08 (1H, m), 7.45-7.48 (1H, m), 7.52-7.55 (1H, m), 7.97-8.10 (3H, m), 8.45 (1H, s), 8.60-8.62 (1H, m), 8.64 (1H, s), 9.15 (1H, s) | m/z (ES+) (M + H)+ = 484; HPLC tR = 2.43 min. | BD11 |
| 233 | 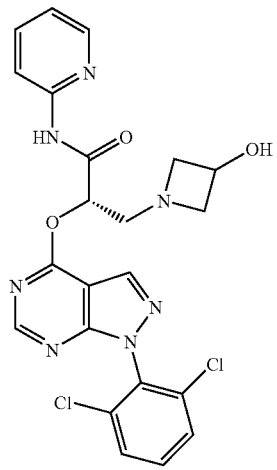 | (CDCl$_3$) 3.18-3.32 (4H, m), 3.83-3.90 (2H, m), 4.50-4.56 (1H, m), 5.90-5.93 (1H, m), 7.04-7.08 (1H, m), 7.43-7.47 (1H, m), 7.52-7.55 (2H, m), 7.69-7.73 (1H, m), 8.22-8.24 (1H, m), 8.28-8.30 (1H, m), 8.42 (1H, s), 8.59 (1H, s), 9.66 (1H, s) | m/z (ES+) (M + H)+ = 500; HPLC tR = 1.29 min. | BD12 |

| Example number | Structure | ¹H NMR (400 MHz) δ | LCMS | Intermediate reference |
|---|---|---|---|---|
| 234 | 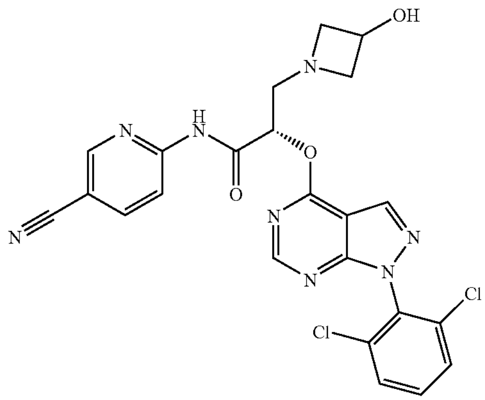 | (CDCl₃) 3.17-3.25 (3H, m), 3.31-3.36 (1H, m), 3.90-3.95 (2H, m), 4.56-4.62 (1H, m), 5.88-5.91 (1H, m), 7.44-7.55 (3H, m), 7.93-7.95 (1H, m), 8.34-8.36 (1H, m), 8.41 (1H, s), 8.57-8.59 (2H, m), 10.44 (1H, s) | m/z (ES+) (M + H)+ = 525; HPLC tR = 1.38 min. | BD13 |
| 235 | 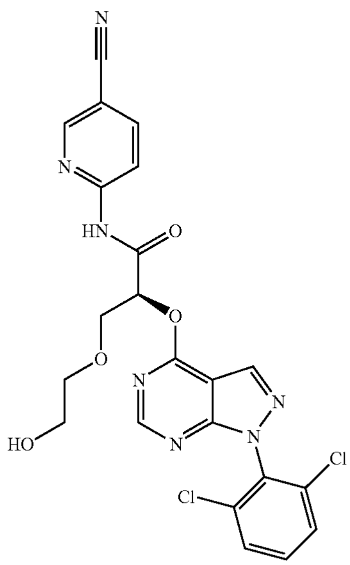 | (CDCl₃) 3.73-3.83 (4H, m), 4.17-4.25 (2H, m), 6.07 (1H, t), 7.44-7.48 (1H, m), 7.52-7.56 (2H, m), 7.96-7.99 (1H, m), 8.36-8.39 (1H, m), 8.48 (1H, s), 8.57 (1H, q), 8.59 (1H, s), 9.32 (1H, s) | m/z (ES+) (M + H)+ = 514; HPLC tR = 2.04 min. | BD14 |
| 236 | 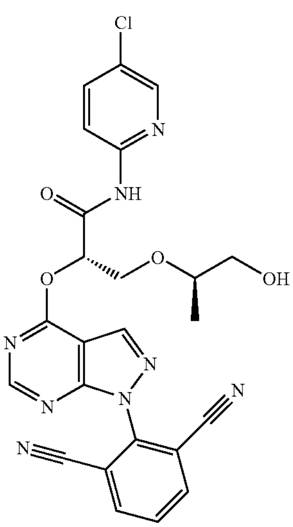 | (CDCl₃) d 1.17 (d, 3H), 3.55-3.71 (m, 2H), 3.76-3.85 (m, 1H), 4.07-4.14 (m, 2H), 4.25-4.31 (m, 1H), 6.04-6.08 (m, 1H), 7.66-7.72 (m, 1H), 7.78 (t, 1H), 8.10 (d, 2H), 8.17 (d, 1H), 8.24 (d, 1H), 8.56 (s, 1H), 8.67 (s, 1H), 9.25 (s, 1H) | m/z (ES+), (M + H)+ = 519.31; HPLC tR = 2.74 min | BD15 |

| Example number | Structure | ¹H NMR (400 MHz) δ | LCMS | Intermediate reference |
|---|---|---|---|---|
| 237 | 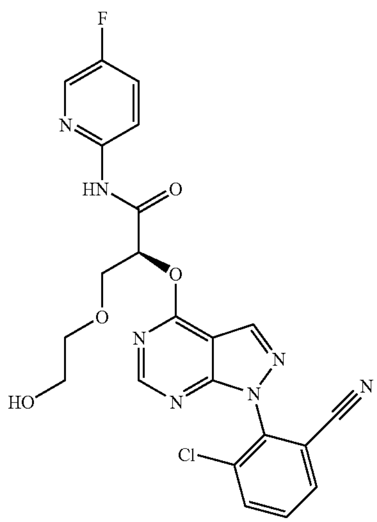 | (DMSO-d6) d 3.50-3.56 (m, 2H), 3.58-3.70 (m, 2H), 3.99-4.16 (m, 2H), 4.61 (t, 1H), 5.91-5.97 (m, 1H), 7.68-7.77 (m, 1H), 7.89 (t, 1H), 8.00-8.07 (m, 1H), 8.15-8.21 (m, 2H), 8.34-8.37 (m, 1H), 8.61 (s, 1H), 8.79 (d, 1H), 11.12 (s, 1H) | m/z (ES+), (M + H)+ = 498.36; HPLC tR = 1.88 min | BD16 |
| 238 | 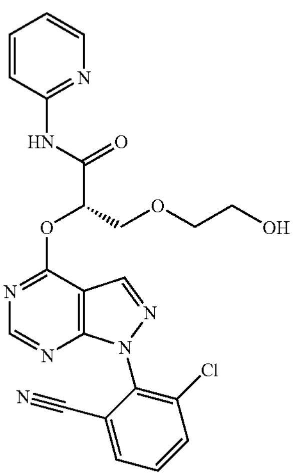 | (DMSO-d6) d 3.50-3.57 (m, 2H), 3.58-3.70 (m, 2H), 4.01-4.17 (m, 2H), 4.62 (t, 1H), 5.93-5.98 (m, 1H), 7.10-7.16 (m, 1H), 7.73-7.80 (m, 1H), 7.89 (t, 1H), 7.96-8.02 (m, 1H), 8.15-8.21 (m, 2H), 8.33-8.37 (m, 1H), 8.61 (s, 1H), 8.80 (d, 1H), 11.00 (s, 1H) | m/z (ES+), (M + H)+ = 480.29; HPLC tR = 1.66 min | BD17 |
| 239 | 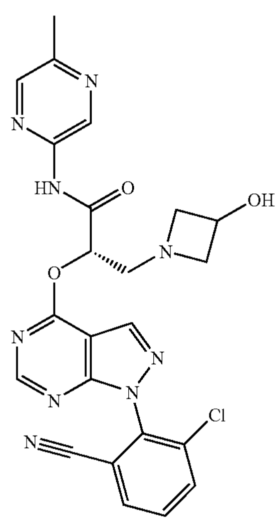 | (CDCl₃) d 9.93 (1H, s), 9.58 (0H, s), 9.34 (1H, s), 8.54 (1H, d), 8.39 (1H, d), 8.06 (1H, s), 7.80 (1H, d), 7.72 (1H, d), 7.56 (1H, t), 5.87 (1H, q), 4.45-4.52 (1H, m), 3.84 (2H, t), 3.25 (2H, q), 3.08-3.19 (2H, m), 2.47 (3H, s) | m/z (ES+), (M + H)+ = 506; HPLC tR = 1.17 min. | BD18 |

-continued
| Example number | Structure | ¹H NMR (400 MHz) δ | LCMS | Intermediate reference |
|---|---|---|---|---|
| 240 | 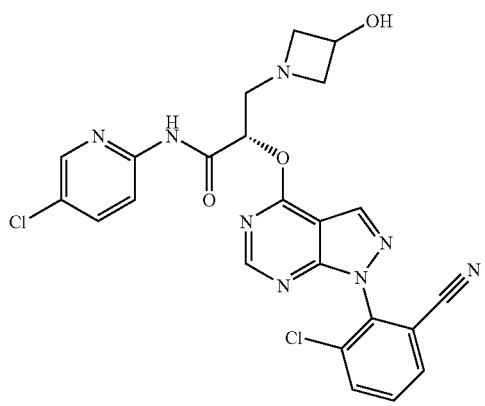 | (CDCl₃) d 3.08-3.17 (2H, m), 3.20-3.26 (1H, m), 3.41 (1H, q), 3.77-3.87 (2H, m), 4.47 (1H, q), 5.80-5.86 (1H, m), 7.52-7.62 (2H, m), 7.70-7.81 (4H, m), 8.12-8.19 (2H, m), 8.39 (1H, d), 8.54 (1H, d), 9.68 (0H, s), 9.90 (1H, s) | m/z (ES+), (M + H)+ = 525; 5 min Acid, HPLC tR = 1.39 min | BD19 |
| 241 | 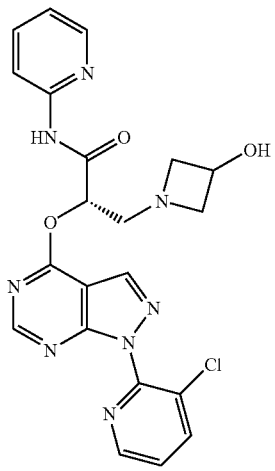 | (CDCl₃) 3.15-3.31 (4H, m), 3.83-3.90 (2H, m), 4.52 (1H, t), 5.91-5.94 (1H, m), 7.04-7.07 (1H, m), 7.45-7.48 (1H, m), 7.68-7.72 (1H, m), 8.00-8.02 (1H, m), 8.21 (1H, d), 8.28-8.30 (1H, m), 8.41 (1H, s), 8.61-8.63 (2H, m), 9.54 (1H, s) | m/z (ES+) (M + H)+ = 467.04; HPLC tR = 1.4 min. | BD20 |
| 242 | 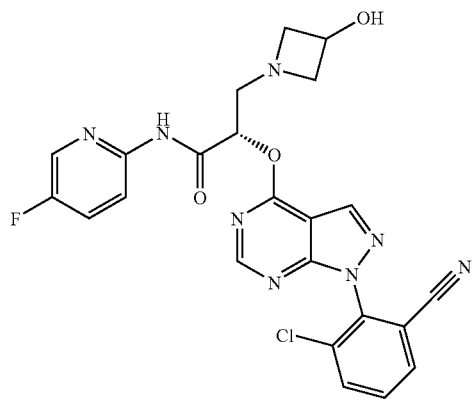 | (CDCl₃) 3.17-3.33 (4H, m), 3.87-3.93 (2H, m), 4.55 (1H, q), 5.90-5.93 (1H, m), 7.41-7.46 (1H, m), 7.62 (1H, t), 7.78-7.81 (1H, m), 7.85-7.88 (1H, m), 8.15 (1H, d), 8.23-8.26 (1H, m), 8.46 (1H, d), 8.61 (1H, d), 9.64-9.87 (1H, m) | m/z (ES+) (M + H)+ = 509.13; HPLC tR = 1.59 min. | BD21 |

| Example number | Structure | ¹H NMR (400 MHz) δ | LCMS | Intermediate reference |
|---|---|---|---|---|
| 243 | 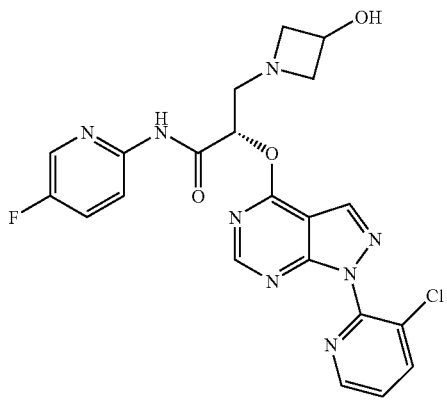 | (CDCl₃) 3.14-3.22 (3H, m), 3.27-3.32 (1H, m), 3.89 (2H, q), 4.54 (1H, t), 5.91-5.94 (1H, m), 7.41-7.52 (2H, m), 8.00-8.02 (1H, m), 8.14 (1H, d), 8.22-8.25 (1H, m), 8.41 (1H, s), 8.61-8.63 (1H, m), 8.63 (1H, s), 9.67 (1H, s) | m/z (ES+) (M + H)+ = 485; HPLC tR = 1.44 min. | BD22 |
| 244 | 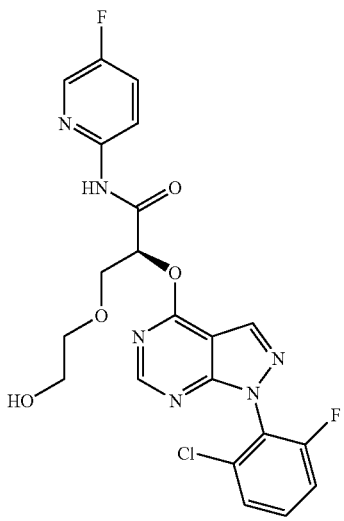 | (CDCl₃), 2.55 (1H, d), 3.71-3.79 (4H, m), 4.15-4.25 (2H, m), 6.09 (1H, t), 7.22-7.27 (1H, m), 7.40-7.52 (3H, m), 8.14 (1H, t), 8.21-8.25 (1H, m), 8.48 (1H, s), 8.60 (1H, s), 8.98 (1H, d) | m/z (ES+) (M + H)+ = 491.09; HPLC tR = 2.68 min. | BD23 |
| 245 | 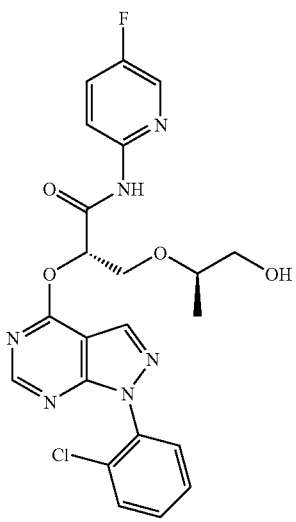 | (CDCl₃) 1.17 (3H, d), 3.05 (1H, d), 3.55-3.61 (1H, m), 3.64-3.69 (1H, m), 3.76-3.83 (1H, m), 4.08-4.12 (1H, m), 4.26-4.30 (1H, m), 6.06-6.08 (1H, m), 7.44-7.55 (4H, m), 7.61-7.63 (1H, m), 8.13 (1H, d), 8.20-8.23 (1H, m), 8.42 (1H, s), 8.60 (1H, s), 9.18 (1H, s) | m/z (ES+) (M + H)+ = 487.09; HPLC tR = 2.8 min. | BD24 |

-continued

| Example number | Structure | ¹H NMR (400 MHz) δ | LCMS | Intermediate reference |
|---|---|---|---|---|
| 246 | 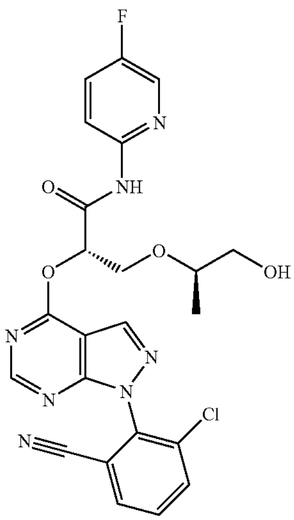 | (DMSO-d6) 1.07 (3H, d), 3.33 (1H, q), 3.40-3.46 (1H, m), 3.63-3.69 (1H, m), 4.09-4.16 (2H, m), 4.57 (1H, t), 5.89 (1H, s), 7.69-7.76 (1H, m), 7.89 (1H, t), 8.02 (1H, d), 8.17-8.19 (2H, m), 8.35 (1H, d), 8.61 (1H, s), 8.77 (1H, t), 11.09 (1H, d) | m/z (ES+) (M + H)+ = 512.14; HPLC tR = 2.7 min. | BD25 |
| 247 | 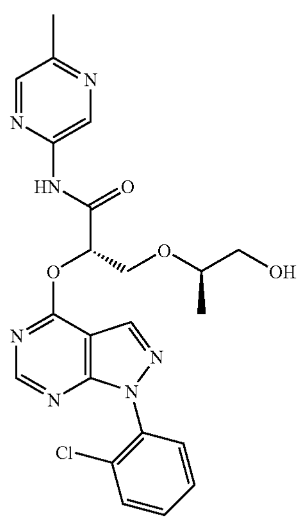 | (CDCl₃) 1.17 (3H, d), 2.54 (3H, s), 2.76-2.79 (1H, m), 3.54-3.60 (1H, m), 3.64-3.69 (1H, m), 3.76-3.82 (1H, m), 4.09-4.15 (1H, m), 4.28-4.32 (1H, m), 6.09 (1H, d), 7.45-7.52 (2H, m), 7.44-7.55 (1H, m), 7.62-7.63 (1H d, m), 8.11 (1H, d), 8.42 (1H, s), 8.61 (1H, s), 9.05 (1H, s), 9.40-9.42 (1H, m) | m/z (ES+) (M + H)+ = 484; HPLC tR = 2.52 min. | BD26 |
| 248 | 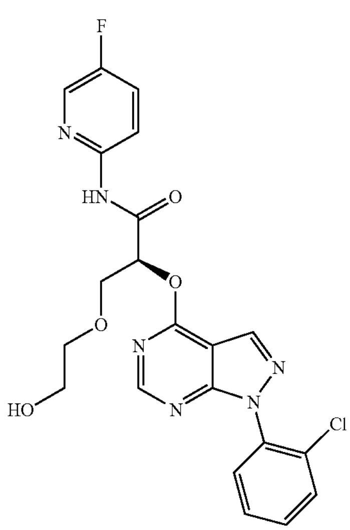 | (CDCl₃) 2.59 (1H, d), 3.73-3.79 (4H, m), 4.15-4.25 (2H, m), 6.10 (1H, t), 7.44-7.55 (4H, m), 7.61-7.64 (1H, m), 8.14 (1H, d), 8.22-8.25 (1H, m), 8.44 (1H, s), 8.60 (1H, s), 9.00 (1H, s) | m/z (ES+) (M + H)+ = 473.44; HPLC tR = 1.97 min. | BD27 |

| Example number | Structure | ¹H NMR (400 MHz) δ | LCMS | Intermediate reference |
|---|---|---|---|---|
| 249 | 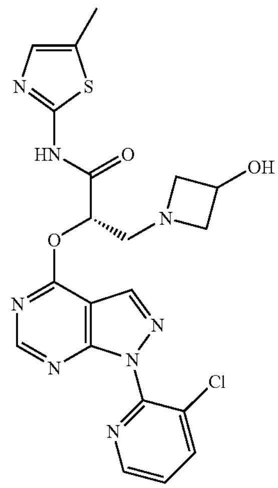 | (CDCl₃) 1.66-1.74 (1H, m), 2.40 (3H, s), 3.12-3.44 (4H, m), 3.86-3.95 (2H, m), 4.52-4.61 (1H, m), 5.97-6.03 (1H, m), 7.10 (1H, s), 7.43-7.49 (1H, m), 7.98-8.03 (1H, m), 8.37 (1H, s), 8.58-8.64 (2H, m), 10.74-11.53 (1H, m) | m/z (ES−) (M − H)− = 485.31; HPLC tR = 1.55 min. | BD28 |
| 250 | 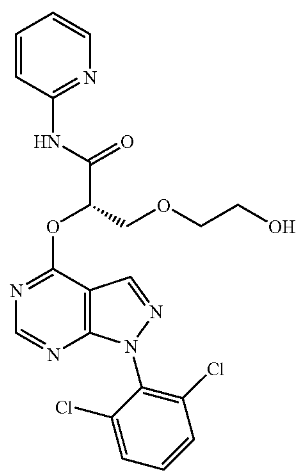 | (CDCl₃) 2.92 (1H, s), 3.73-3.80 (4H, m), 4.16-4.26 (2H, m), 6.10 (1H, t), 7.06-7.09 (1H, m), 7.43-7.47 (1H, m), 7.52-7.54 (2H, m), 7.71-7.75 (1H, m), 8.20 (1H, d), 8.27-8.29 (1H, m), 8.48 (1H, s), 8.60 (1H, s), 9.02 (1H, s) | m/z (ES+) (M + H)+ = 489.31; HPLC tR = 2.53 min. | BD29 |
| 251 | 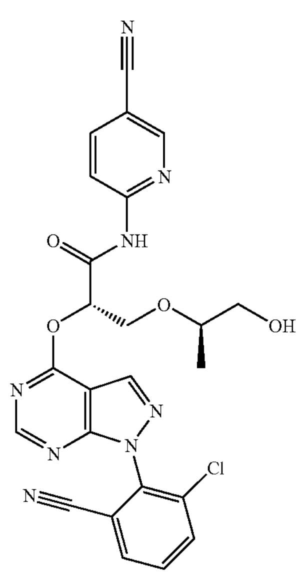 | (DMSO-d6) 1.05-1.09 (3H, m), 3.25-3.36 (1H, m), 3.40-3.46 (1H, m), 3.61-3.68 (1H, m), 4.10-4.18 (2H, m), 4.58 (1H, t), 5.91-5.93 (1H, m), 7.89 (1H, t), 8.12-8.19 (3H, m), 8.22-8.26 (1H, m), 8.61 (1H, s), 8.77-8.79 (1H, m), 8.82-8.83 (1H, m), 11.53 (1H, s) | m/z (ES−) (M − H)− = 517.37; HPLC tR = 2.53 min. | BD30 |

-continued

| Example number | Structure | $^1$H NMR (400 MHz) δ | LCMS | Intermediate reference |
|---|---|---|---|---|
| 252 | 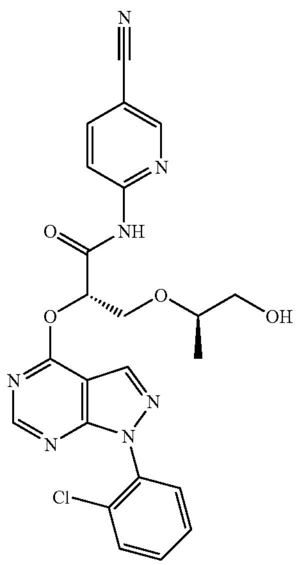 | (DMSO-d6) 1.06-1.09 (3H, m), 3.33 (1H, t), 3.40-3.45 (1H, m), 3.61-3.69 (1H, m), 4.09-4.17 (2H, m), 4.57 (1H, t), 5.89-5.92 (1H, m), 7.56-7.69 (3H, m), 7.74-7.77 (1H, m), 8.12-8.14 (1H, m), 8.23-8.26 (1H, m), 8.54 (1H, s), 8.61 (1H, d), 8.82 (1H, m), 11.51 (1H, s) | m/z (ES−) (M − H)− = 492.40; HPLC tR = 2.62 min. | BD31 |

EXAMPLE 222

(2S)-2-[1-(2-chloro-6-fluoro-phenyl)pyrazolo[3,4-d]pyrimidin-4-yl]oxy-3-(3-hydroxyazetidin-1-yl)-N-(2-pyridyl)propanamide

EXAMPLE 223

(2S)-2-[1-(2-chlorophenyl)pyrazolo[3,4-d]pyrimidin-4-yl]oxy-N-(5-cyano-2-pyridyl)-3-(3-hydroxyazetidin-1-yl)propanamide

EXAMPLE 224

(2S)-2-[1-(2-chloro-6-cyano-phenyl)pyrazolo[3,4-d]pyrimidin-4-yl]oxy-N-(5-cyano-2-pyridyl)-3-(3-hydroxyazetidin-1-yl)propanamide

EXAMPLE 225

(2S)-2-[1-(2-chlorophenyl)pyrazolo[3,4-d]pyrimidin-4-yl]oxy-3-(3-hydroxyazetidin-1-yl)-N-(2-pyridyl)propanamide

EXAMPLE 226

(2S)-2-[1-(2-chlorophenyl)pyrazolo[3,4-d]pyrimidin-4-yl]oxy-N-(5-chloro-2-pyridyl)-3-(3-hydroxyazetidin-1-yl)propanamide

EXAMPLE 227

(2S)-3-[(1R)-2-hydroxy-1-methyl-ethoxy]-N-(5-methyl-2-pyridyl)-2-[1-(4-methyl-3-thienyl)pyrazolo[3,4-d]pyrimidin-4-yl]oxy-propanamide

EXAMPLE 228

(2S)-2-[1-(2-chlorophenyl)pyrazolo[3,4-d]pyrimidin-4-yl]oxy-3-[3-(hydroxymethyl)azetidin-1-yl]-N-(2-pyridyl)propanamide

EXAMPLE 229

(2S)-2-[1-(2-chloro-6-fluoro-phenyl)pyrazolo[3,4-d]pyrimidin-4-yl]oxy-N-(5-fluoro-2-pyridyl)-3-(3-hydroxyazetidin-1-yl)propanamide

EXAMPLE 230

(2S)-2-[1-(2,6-dichlorophenyl)pyrazolo[3,4-d]pyrimidin-4-yl]oxy-N-(5-fluoro-2-pyridyl)-3-(3-hydroxyazetidin-1-yl)propanamide

EXAMPLE 231

(2S)-2-[1-(2-chloro-6-cyano-phenyl)pyrazolo[3,4-d]pyrimidin-4-yl]oxy-3-[(1R)-2-hydroxy-1-methyl-ethoxy]-N-(2-pyridyl)propanamide

EXAMPLE 232

(2S)-2-[1-(3-chloro-2-pyridyl)pyrazolo[3,4-d]pyrimidin-4-yl]oxy-3-[(1R)-2-hydroxy-1-methyl-ethoxy]-N-(5-methyl-2-pyridyl)propanamide

EXAMPLE 233

(2S)-2-[1-(2,6-dichlorophenyl)pyrazolo[3,4-d]pyrimidin-4-yl]oxy-3-(3-hydroxyazetidin-1-yl)-N-(2-pyridyl)propanamide

EXAMPLE 234

(2S)—N-(5-cyano-2-pyridyl)-2-[1-(2,6-dichlorophenyl)pyrazolo[3,4-d]pyrimidin-4-yl]oxy-3-(3-hydroxyazetidin-1-yl)propanamide

EXAMPLE 235

(2S)—N-(5-cyano-2-pyridyl)-2-[1-(2,6-dichlorophenyl)pyrazolo[3,4-d]pyrimidin-4-yl]oxy-3-(2-hydroxyethoxy)propanamide

EXAMPLE 236

(2S)—N-(5-chloro-2-pyridyl)-2-[1-(2,6-dicyanophenyl)pyrazolo[3,4-d]pyrimidin-4-yl]oxy-3-[(1R)-2-hydroxy-1-methyl-ethoxy]propanamide

EXAMPLE 237

(2S)-2-[1-(2-chloro-6-cyano-phenyl)pyrazolo[3,4-d]pyrimidin-4-yl]oxy-N-(5-fluoro-2-pyridyl)-3-(2-hydroxyethoxy)propanamide

EXAMPLE 238

(2S)-2-[1-(2-chloro-6-cyano-phenyl)pyrazolo[3,4-d]pyrimidin-4-yl]oxy-3-(2-hydroxyethoxy)-N-(2-pyridyl)propanamide

EXAMPLE 239

(2S)-2-[1-(2-chloro-6-cyano-phenyl)pyrazolo[3,4-d]pyrimidin-4-yl]oxy-3-(3-hydroxyazetidin-1-yl)-N-(5-methylpyrazin-2-yl)propanamide

EXAMPLE 240

(2S)-2-[1-(2-chloro-6-cyano-phenyl)pyrazolo[3,4-d]pyrimidin-4-yl]oxy-N-(5-chloro-2-pyridyl)-3-(3-hydroxyazetidin-1-yl)propanamide

EXAMPLE 241

(2S)-2-[1-(3-chloro-2-pyridyl)pyrazolo[3,4-d]pyrimidin-4-yl]oxy-3-(3-hydroxyazetidin-1-yl)-N-(2-pyridyl)propanamide

EXAMPLE 242

(2S)-2-[1-(2-chloro-6-cyano-phenyl)pyrazolo[3,4-d]pyrimidin-4-yl]oxy-N-(5-fluoro-2-pyridyl)-3-(3-hydroxyazetidin-1-yl)propanamide

EXAMPLE 243

(2S)-2-[1-(3-chloro-2-pyridyl)pyrazolo[3,4-d]pyrimidin-4-yl]oxy-N-(5-fluoro-2-pyridyl)-3-(3-hydroxyazetidin-1-yl)propanamide

EXAMPLE 244

(2S)-2-[1-(2-chloro-6-fluoro-phenyl)pyrazolo[3,4-d]pyrimidin-4-yl]oxy-N-(5-fluoro-2-pyridyl)-3-(2-hydroxyethoxy)propanamide

EXAMPLE 245

(2S)-2-[1-(2-chlorophenyl)pyrazolo[3,4-d]pyrimidin-4-yl]oxy-N-(5-fluoro-2-pyridyl)-3-[(1R)-2-hydroxy-1-methyl-ethoxy]propanamide

EXAMPLE 246

(2S)-2-[1-(2-chloro-6-cyano-phenyl)pyrazolo[3,4-d]pyrimidin-4-yl]oxy-N-(5-fluoro-2-pyridyl)-3-[(1R)-2-hydroxy-1-methyl-ethoxy]propanamide

EXAMPLE 247

(2S)-2-[1-(2-chlorophenyl)pyrazolo[3,4-d]pyrimidin-4-yl]oxy-3-[(1R)-2-hydroxy-1-methyl-ethoxy]-N-(5-methylpyrazin-2-yl)propanamide

EXAMPLE 248

(2S)-2-[1-(2-chlorophenyl)pyrazolo[3,4-d]pyrimidin-4-yl]oxy-N-(5-fluoro-2-pyridyl)-3-(2-hydroxyethoxy)propanamide

EXAMPLE 249

(2S)-2-[1-(3-chloro-2-pyridyl)pyrazolo[3,4-d]pyrimidin-4-yl]oxy-3-(3-hydroxyazetidin-1-yl)-N-(5-methylthiazol-2-yl)propanamide

EXAMPLE 250

(2S)-2-[1-(2,6-dichlorophenyl)pyrazolo[3,4-d]pyrimidin-4-yl]oxy-3-(2-hydroxyethoxy)-N-(2-pyridyl)propanamide

EXAMPLE 251

(2S)-2-[1-(2-chloro-6-cyano-phenyl)pyrazolo[3,4-d]pyrimidin-4-yl]oxy-N-(5-cyano-2-pyridyl)-3-[(1R)-2-hydroxy-1-methyl-ethoxy]propanamide

EXAMPLE 252

(2S)-2-[1-(2-chlorophenyl)pyrazolo[3,4-d]pyrimidin-4-yl]oxy-N-(5-cyano-2-pyridyl)-3-[(1R)-2-hydroxy-1-methyl-ethoxy]propanamide Preparation of Intermediates Intermediate A1: 2-hydroxy-N-(5-methylpyridin-2-yl)-4-(methylsulfonyl)butanamide

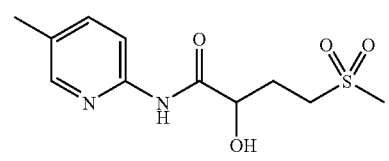

Step 1: tert-butyl(dimethyl)silyl 2-{[tert-butyl(dimethyl)silyl]oxy}-4-(methylthio)butanoate

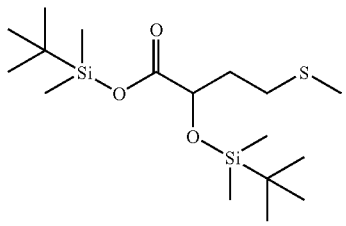

Imidazole (21.76 g, 320 mmol) and TBDMSCl (24.08 g, 151 mmol) was added to a stirred solution of 2-hydroxy-4-(methylthio)butyric acid (6.10 g, 40.6 mmol) in DMF (100 mL). The reaction mixture was kept at ambient temperature for 18 hrs. Water and EtOAc were added, and the two phases were separated. The aqueous phase was extracted with EtOAc. The organic extracts were combined and washed three times with water, dried over MgSO$_4$ and concentrated in vacuo. The residue was purified with column chromatography (silica gel, eluting with a gradient consisting of 0-100% EtOAc in DCM) to give the title compound as a colourless oil (10.20 g), $^1$H NMR (300 MHz, CDCl$_3$) δ 4.29 (t, 1H), 2.59 (m, 2H), 2.09 (s, 3H), 1.98 (m, 2H), 0.94 (s, 9H), 0.91 (s, 9H), 0.28 (d, 6H), 0.08 (d, 6H).

Step 2: tert-butyl(dimethyl)silyl 2-{[tent-butyl(dimethyl)silyl]oxy}-4-(methylsulfonyl)butanoate

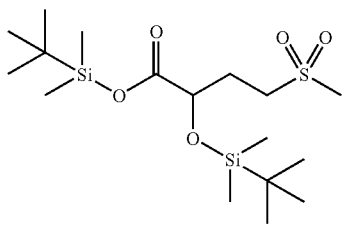

m-CPBA (77%, 5.70 g, 25.4 mmol) in DCM (10 mL) was added in portions to a stirred solution of tert-butyl(dimethyl) silyl 2-{[tert-butyl(dimethyl)silyl]oxy}-4-(methylthio)butanoate (Step 1) (5.00 g, 13.2 mmol) in DCM (15 mL). The reaction mixture was kept at ambient temperature for 1½ hrs. Water was added and the two phases were separated. The organic phase was washed two times with sodium pyrosulfite (5% in water), dried over MgSO$_4$ and concentrated in vacuo. The residue was purified with column chromatography (silica gel, eluting with a gradient consisting of 0-100% EtOAc in DCM) to give the title compound (2.12 g), $^1$H NMR (300 MHz, CDCl$_3$) δ 4.33 (t, 1H), 3.18 (m, 1H), 3.04 (m, 1H), 2.91 (s, 3H), 2.26 (m, 2H), 0.94 (s, 9H), 0.91 (s, 9H), 0.29 (d, 6H), 0.10 (m, 6H).

Step 3: 2-{[tert-butyl(dimethyl)silyl]oxy}-N-(5-methylpyridin-2-yl)-4-(methylsulfonyl)butanamide

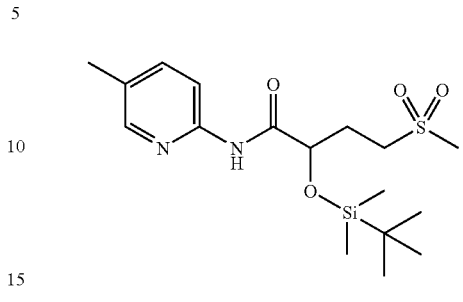

Oxalyl chloride (0.74 g, 5.84 mmol) in DCM (2 mL) was added slowly to a stirred solution of tert-butyl(dimethyl)silyl 2-{[tert-butyl(dimethyl)silyl]oxy}-4-(methylsulfonyl)butanoate (Step 2) (2.00 g, 4.87 mmol) in DCM (8 mL) and DMF (three drops). After 1 h at ambient temperature, gas evolution had subsided and the reaction mixture was concentrated in vacuo to remove excess oxalyl chloride. The residue was dissolved in DCM (8 mL) and pyridine (0.50 g, 6.33 mmol) and 2-amino-5-picoline (0.58 g, 5.36 mmol) were added. The reaction mixture was kept at ambient temperature for 1 h. Water was added and the two phases were separated. The aqueous phase was extracted with DCM. The organic extracts were combined and washed with water, dried over MgSO$_4$ and concentrated in vacuo. The residue was purified with column chromatography (silica gel, eluting with DCM/EtOAc:10/1) to give the title compound as a colourless oil (1.23 g), $^1$H NMR (300 MHz, CDCl$_3$) δ 8.92 (br s, 1H), 8.13 (d, 1H), 8.08 (d, 1H), 7.53 (dd, 1H), 4.44 (t, 1H), 3.19 (m, 1H), 3.05 (m, 1H), 2.90 (s, 3H), 2.44 (m, 1H), 2.28 (m, 4H), 0.97 (s, 9H), 0.19 (d, 6H).

Step 4: 2-hydroxy-N-(5-methylpyridin-2-yl)-4-(methylsulfonyl)butanamide

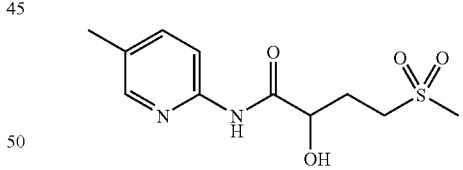

Tetrabutylammoniumfluoride trihydrate (1.43 g, 4.54 mmol) was added to a stirred solution of 2-{[tert-butyl(dimethyl)silyl]oxy}-N-(5-methylpyridin-2-yl)-4-(methylsulfonyl)butanamide (Step 3) (1.17 g, 3.03 mmol) in THF (10 mL). The reaction mixture was kept at ambient temperature for 30 minutes. Water and EtOAc were added and the two phases were separated. The aqueous phase was extracted with EtOAc. The organic extracts were combined and washed with water, dried over MgSO$_4$ and concentrated in vacuo. The residue was recrystallised from EtOAc to give the title compound as colourless solid (0.57 g), $^1$H NMR (500 MHz, DMSO) δ 8.14 (d, 1H), 7.99 (d, 1H), 7.62 (dd, 1H), 4.23 (m, 1H), 3.17 (m, 2H), 2.96 (s, 3H), 2.24 (s, 3H), 2.16 (m, 1H), 1.98 (m, 1H).

Intermediate A2: 2-hydroxy-3-methoxy-N-(5-methylpyridin-2-yl)propanamide

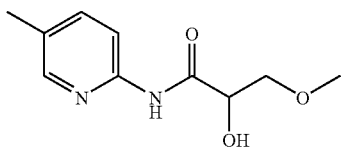

Step 1: 2-bromo-3-methoxy-N-(5-methylpyridin-2-yl)propanamide

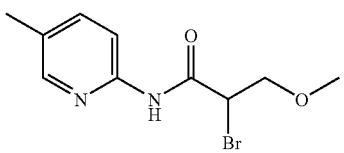

Bromine (3.38 g, 21.13 mmol) was added to a stirred solution of 3-methoxypropionic acid (2.00 g, 19.21 mmol) in thionyl chloride (11.4 g, 96.0 mmol). The reaction mixture was heated at 60° C. for 3 hrs before it was concentrated in vacuo to remove excess reagents. The residue was dissolved in DCM (10 mL) and a solution of DIPEA (2.73 g, 21.13 mmol) and 2-amino-5-picoline (2.28 g, 21.13 mmol) in DCM (10 mL) was added slowly at 0° C.

The reaction mixture was stirred at ambient temperature for 45 minutes. Water was added and the two phases were separated. The aqueous phase was extracted with DCM. The organic extracts were combined and washed with water, dried over $MgSO_4$ and concentrated in vacuo. The residue was purified with column chromatography (silica gel, eluting with DCM/EtOAc:5/1) to give the title compound (2.30 g), $^1$H NMR (300 MHz, $CDCl_3$) δ 9.09 (br s, 1H), 8.10 (m, 2H), 7.55 (dd, 1H), 4.49 (t, 1H), 3.93 (d, 2H), 3.46 (s, 3H), 2.31 (s, 3H).

Step 2: 1-(methoxymethyl)-2-[(5-methylpyridin-2-yl)amino]-2-oxoethyl acetate

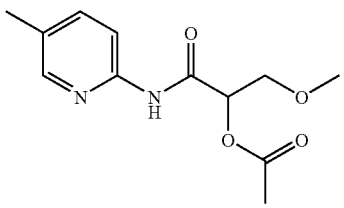

Potassium acetate (2.01 g, 20.50 mmol) was added to a stirred solution of 2-bromo-3-methoxy-N-(5-methylpyridin-2-yl)propanamide (Step 1) (1.40 g, 5.13 mmol) in ACN (20 mL). The reaction mixture was refluxed for 5 hrs. The reaction mixture was filtered and concentrated in vacuo. The residue was purified with column chromatography (silica gel, eluting with DCM/EtOAc:2/1) to give the title compound as a colourless solid (1.15 g), $^1$H NMR (300 MHz, $CDCl_3$) δ 8.57 (br s, 1H), 8.11 (m, 2H), 7.52 (dd, 1H), 5.44 (dd, 1H), 3.89 (dd, 1H), 3.78 (dd, 1H), 3.39 (s, 3H), 2.30 (s, 3H), 2.25 (s, 3H).

Step 3: 2-hydroxy-3-methoxy-N-(5-methylpyridin-2-yl)propanamide

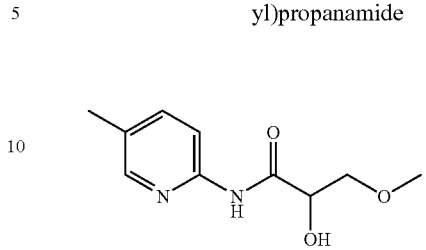

Anhydrous potassium carbonate (50 mg, 0.36 mmol) was added to a stirred solution of 1-(methoxymethyl)-2-[(5-methylpyridin-2-yl)amino]-2-oxoethyl acetate (Step 2) (1.10 g, 4.36 mmol) in MeOH (10 mL). The reaction mixture was kept at ambient temperature for 1 h before it was concentrated in vacuo. The residue was purified with column chromatography (silica gel, eluting with EtOAc) to give the title compound as a colourless solid (0.81 g), $^1$H NMR (300 MHz, $CDCl_3$) δ 9.39 (br s, 1H), 8.14 (d, 1H), 8.09 (d, 1H), 7.53 (dd, 1H), 4.92 (br s, 1H), 4.41 (dd, 1H), 3.75 (m, 2H), 3.42 (s, 3H), 2.30 (s, 3H).

Intermediate A3: 2-hydroxy-N-(5-methylpyridin-2-yl)hexanamide

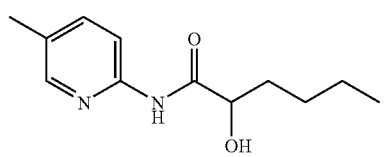

Step 1: ethyl 2-{[tert-butyl(dimethyl)silyl]oxy}hexanoate

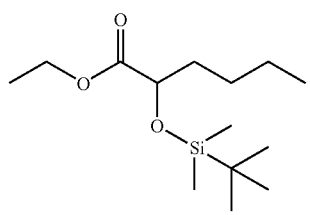

Imidazole (4.10 g, 60.22 mmol) and TBDMSCl (3.60 g, 23.89 mmol) was added to a stirred solution of 2-hydroxyhexanoic acid ethyl ester (3.20 g, 19.97 mmol) in DMF (25 mL). The reaction mixture was kept at ambient temperature for 18 hrs. Water and diethyl ether were added and the two phases were separated. The aqueous phase was extracted with diethyl ether. The organic extracts were combined and washed sequentially with 0.5 M HCl and water, dried over $MgSO_4$ and concentrated in vacuo to give the title product (5.30 g), $^1$H NMR (300 MHz, $CDCl_3$) δ 4.18 (m, 3H), 1.69 (m, 2H), 1.35 (m, 4H), 1.28 (t, 3H), 0.91 (m, 12H), 0.07 (d, 6H).

Step 2: 2-{[tert-butyl(dimethyl)silyl]oxy}-N-(5-methylpyridin-2-yl)hexanamide

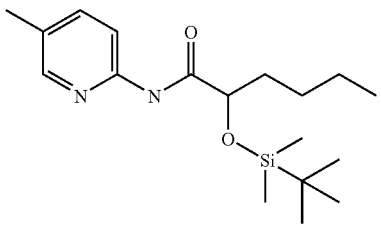

n-BuLi (2.25 mL, 1.6 M in hexanes, 3.60 mmol) was added slowly to a stirred solution of 2-amino-5-picoline (390 mg, 3.60 mmol) in anhydrous THF (6 mL). The reaction mixture was kept at ambient temperature for 10 minutes before it was added to a solution of ethyl 2-{[tert-butyl(dimethyl)silyl]oxy}hexanoate (Step 1) (820 mg, 3.00 mmol) in anhydrous THF (4 mL). The reaction mixture was stirred at ambient temperature for 1 h. Water and EtOAc were added and the two phases were separated. The organic phase was washed with water, dried over MgSO$_4$ and concentrated in vacuo. The residue was purified with column chromatography (silica gel, eluting with a gradient consisting of 0-100% EtOAc in heptane) to give the title compound as a colourless oil (223 mg), $^1$H NMR (300 MHz, CDCl$_3$) δ 8.87 (br s, 1H), 8.13 (m, 2H), 7.51 (dd, 1H), 4.25 (t, 1H), 2.29 (s, 3H), 1.79 (m, 2H), 1.35 (m, 4H), 0.98 (s, 8H), 0.89 (t, 3H), 0.14 (d, 6H).

Step 3: 2-hydroxy-N-(5-methylpyridin-2-yl)hexanamide

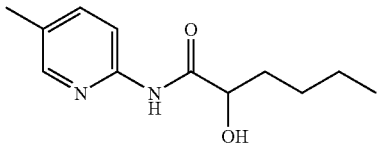

Tetrabutylammoniumfluoride trihydrate (302 mg, 0.96 mmol) was added to a stirred solution of 2-{[tert-butyl(dimethyl)silyl]oxy}-N-(5-methylpyridin-2-yl)hexanamide (Step 2) (215 mg, 0.64 mmol) in THF (5 mL). The reaction mixture was kept at ambient temperature for 1 h. Water and EtOAc were added and the two phases were separated. The organic phase was washed with water, dried over MgSO$_4$ and concentrated in vacuo. The residue was purified with column chromatography (silica gel, eluting with DCM/EtOAc:2/1) to give the title compound as a colourless solid (135 mg), $^1$H NMR (300 MHz, CDCl$_3$) δ 9.46 (br s, 1H), 8.20 (d, 1H), 8.04 (d, 1H), 7.55 (dd, 1H), 5.47 (br s, 1H), 4.29 (m, 1H), 2.31 (s, 3H), 1.98 (m, 1H), 1.76 (m, 1H), 1.52 (m, 2H), 1.38 (m, 2H), 0.92 (t, 3H).

Intermediate A4: 2-hydroxy-N-(5-methylpyrazin-2-yl)hexanamide

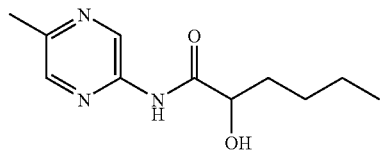

The title compound was prepared in a manner similar to that described for Intermediate A3, starting from ethyl 2-{[tert-butyl(dimethyl)silyl]oxy}hexanoate and 2-amino-5-methylpyrazine, $^1$H NMR (300 MHz, CDCl$_3$) δ 9.46 (s, 1H), 8.98 (br s, 1H), 8.12 (s, 1H), 4.32 (m, 1H), 2.98 (d, 1H), 2.54 (s, 3H), 1.96 (m, 1H), 1.78 (m, 1H), 1.44 (m, 4H), 0.93 (t, 3H).

Intermediate A5: 2-hydroxy-N-(4-methyl-1,3-thiazol-2-yl)hexanamide

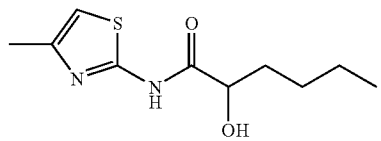

The title compound was prepared in a manner similar to that described for Intermediate A3, starting from ethyl 2-{[tert-butyl(dimethyl)silyl]oxy}hexanoate and 2-amino-4-methylthiazole, $^1$H NMR (300 MHz, CDCl$_3$) δ 10.30 (br s, 1H), 6.54 (s, 1H), 5.12 (br s, 1H), 4.41 (m, 1H), 2.35 (s, 3H), 2.00 (m, 1H), 1.76 (m, 1H), 1.48 (m, 2H), 1.39 (m, 2H), 0.92 (t, 3H).

Intermediate A6: 2-hydroxy-N-(5-methylpyridin-2-yl)acetamide

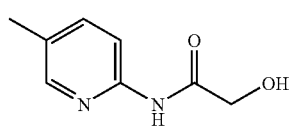

The title compound was prepared in a manner similar to that described for Intermediate A3, starting from methyl glycolate and 2-amino-5-picoline, $^1$H NMR (300 MHz, CDCl$_3$) δ 9.24 (br s, 1H), 8.19 (d, 1H), 8.07 (d, 1H), 7.57 (dd, 1H), 5.59 (br s, 1H), 4.26 (s, 2H), 2.31 (s, 3H).

Intermediate A7: 2-hydroxy-N-(4-methyl-1,3-thiazol-2-yl)acetamide

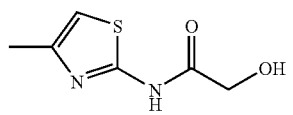

The title compound was prepared in a manner similar to that described for Intermediate A3, starting from methyl glycolate and 2-amino-4-methylthiazole, $^1$H NMR (300 MHz, CDCl$_3$) δ 10.11 (br s, 1H), 6.55 (s, 1H), 5.58 (br s, 1H), 4.36 (s, 2H), 2.34 (s, 3H).

Intermediate A8: (2R)-2-Hydroxy-N-(5-methylpyridin-2-yl)butanamide

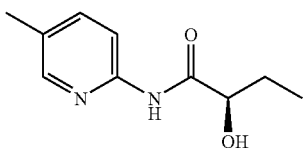

Step 1: tert-Butyl(dimethyl)silyl(2R)-2-{[tert-butyl(dimethyl)silyl]oxy}butanoate

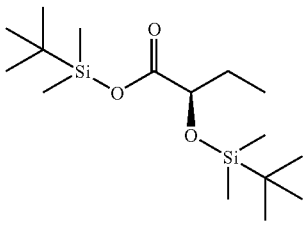

Imidazole (2.61 g, 38.43 mmol) and TBDMSCl (3.62 g, 24.02 mmol) was added to a stirred solution of (R)-2-hydroxy-butyric acid (1.0 g, 9.61 mmol) in DMF (20 mL). The reaction was stirred at ambient temperature for 18 hrs. Water and EtOAc were added and the two phases were separated. The aqueous phase was extracted with EtOAc. The organic extracts were combined and washed three times with water, dried over MgSO$_4$ and concentrated in vacuo. The residue was purified with column chromatography (silica gel, eluting with heptane/EtOAc:5/2) to give the title compound as a colorless oil (2.77 g), $^1$H NMR (300 MHz, CDCl$_3$) δ 4.09 (dd, 1H), 1.72 (m, 2H), 0.93 (m, 21H), 0.27 (d, 6H), 0.07 (d, 6H).

Step 2: (2R)-2-{[tert-Butyl(dimethyl)silyl]oxy}-N-(5-methylpyridin-2-yl)butanamide

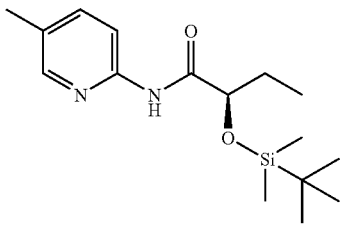

Oxalyl chloride (1.32 g, 10.43 mmol was added slowly to a stirred solution of tert-butyl(dimethyl)silyl (2R)-2-{[tert-butyl(dimethyl)silyl]oxy}butanoate (Step 1) (2.77 g, 8.69 mmol) in DCM (10 mL) and DMF (three drops). After 1 h at ambient temperature, gas evolution had subsided and the reaction mixture was concentrated in vacuo to remove excess oxalyl chloride. The residue was dissolved in DCM (10 mL) and 2-amino-5-picoline (1.03 g, 9.56 mmol) were added. The reaction mixture was kept at ambient temperature for 2 hrs. Water was added and the two phases were separated. The aqueous phase was extracted with DCM. The organic extracts were combined and washed with water, dried over MgSO$_4$ and concentrated in vacuo. The residue was purified with column chromatography (silica gel, eluting with heptane/EtOAc:5/2) to give the title compound as a colourless oil (2.0 g). $^1$H NMR (500 MHz, CDCl$_3$) δ 8.91 (br s, 1H), 8.15 (d, 2H), 7.53 (m, 1H), 4.26 (t, 1H), 2.31 (s, 3H), 1.85 (m, 2H), 0.96 (m, 12H), 0.17 (m, 6H).

Step 3: (2R)-2-Hydroxy-N-(5-methylpyridin-2-yl)butanamide

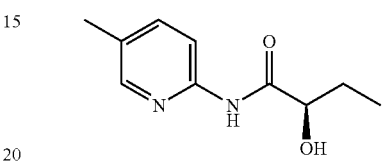

Tetrabutylammoniumfluoride trihydrate (3.21 g, 10.19 mmol) was added to a stirred solution of (2R)-2-{[tert-butyl(dimethyl)silyl]oxy}-N-(5-methylpyridin-2-yl)butanamide (Step 2) (2.00 g, 6.79 mmol) in THF (20 mL). The reaction mixture was kept at ambient temperature for 2 hrs. Water and EtOAc were added and the two phases were separated. The aqueous phase was extracted with EtOAc. The organic extracts were combined and washed with water, dried over MgSO$_4$ and concentrated in vacuo. The residue was recrystallised from diethyl ether to give the title compound as colourless crystals (1.14 g).
$^1$H NMR (500 MHz, CDCl$_3$) δ 9.35 (br s, 1H), 8.21 (d, 1H), 8.08 (s, 1H), 7.57 (d, 1H), 5.03 (br s, 1H), 4.25 (m, 1H), 2.32 (s, 3H), 2.01 (m, 1H), 1.82 (m, 1H), 1.10 (t, 3H).

Intermediate A9: 2-Hydroxy-N-(5-methylpyridin-2-yl)butanamide

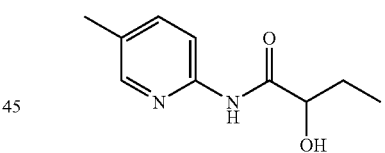

The title compound was prepared in a manner similar to that described for Intermediate A8, starting from 2-hydroxy-butyric acid and 2-amino-5-picoline,
$^1$H NMR (300 MHz, CD$_3$OD) δ 8.10 (d, 1H), 8.05 (d, 1H), 7.63 (dd, 1H), 4.10 (dd, 1H), 2.30 (s, 3H), 1.87 (m, 1H), 1.71 (m, 1H), 1.00 (t, 3H).

Intermediate A10: 2-Hydroxy-N-(5-methylpyridin-2-yl)propanamide

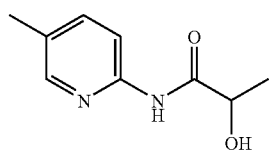

The title compound was prepared in a manner similar to that described for Intermediate A8, starting from 2-hydroxypropionic acid and 2-amino-5-picoline, ¹H NMR (300 MHz, CD₃OD) δ 8.11 (d, 1H), 8.05 (d, 1H), 7.64 (dd, 1H), 4.26 (q, 1H), 2.30 (s, 3H), 1.43 (d, 3H).

Intermediate A11: (2S)-4-(dimethylamino)-2-hydroxy-N-(5-methylpyridin-2-yl)butanamide

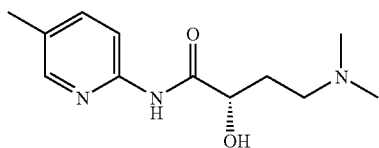

Step 1: ethyl (2S)-4-(dimethylamino)-2-hydroxybutanoate

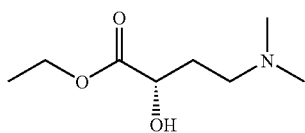

Formic acid (7.0 mL) and formaldehyde (6 mL, 36% in water) was added to (S)-4-amino-2-hydroxybutyric acid (2.00 g, 16.79 mmol). The reaction mixture was refluxed under stirring for 6 hrs when gas evolution had subsided. The reaction mixture was cooled to ambient temperature and concentrated HCl (2 mL) was added. The reaction mixture was concentrated in vacuo and EtOH was added. The solution was refluxed for 5 minutes before it again was concentrated in vacuo. The residue was treated with EtOAc and sodium bicarbonate (5% in water). The two phases were separated and the organic phase was dried over MgSO₄ and concentrated in vacuo. The residue was purified with column chromatography (silica gel, eluting with a gradient consisting of 0-100% EtOAc in DCM) to give the title compound as a colourless oil (1.81 g), ¹H NMR (300 MHz, DMSO) δ 4.08 (m, 2H), 3.10 (m, 5H), 2.70 (s, 6H), 2.06 (m, 1H), 1.92 (m, 1H), 1.20 (t, 1H).

Step 2: ethyl (2S)-2-{[tert-butyl(dimethyl)silyl]oxy}-4-(dimethylamino)butanoate

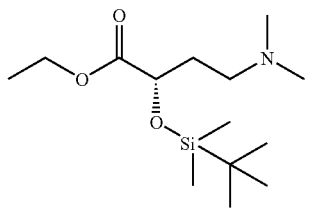

Imidazole (1.98 g, 29.10 mmol) and TBDMSCl (2.34 g, 15.52 mmol) was added to a stirred solution of ethyl (2S)-4-(dimethylamino)-2-hydroxybutanoate (Step 1) (3.20 g, 19.97 mmol) in DMF (25 mL). The reaction mixture was kept at ambient temperature for 18 hrs. Water and EtOAc were added and the two phases were separated. The aqueous phase was extracted with EtOAc. The organic extracts were combined and washed three times with water, dried over MgSO₄ and concentrated in vacuo. The residue was purified with column chromatography (silica gel, eluting with heptane/EtOAc:2/1) to give the title compound as a colourless oil (2.73 g), ¹H NMR (300 MHz, DMSO) δ 4.28 (m, 1H), 4.18 (m, 2H), 2.44 (m, 1H), 2.30 (m, 1H), 2.22 (s, 6H), 1.87 (m, 2H), 1.28 (t, 3H), 0.90 (s, 9H), 0.08 (d, 6H).

Step 3: (2S)-2-{[tert-butyl(dimethyl)silyl]oxy}-4-(dimethylamino)-N-(5-methylpyridin-2-yl)butanamide

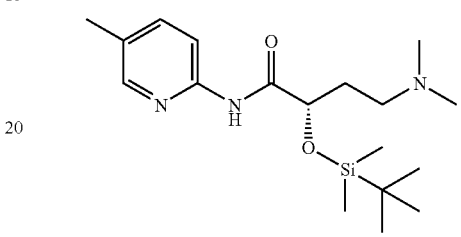

n-BuLi (3.40 mL, 1.6 M in hexanes, 5.44 mmol) was added slowly to a stirred solution of 2-amino-5-picoline (616 mg, 5.70 mmol) in anhydrous THF (8 mL). The reaction mixture was kept at ambient temperature for 10 minutes before a solution of ethyl (2S)-2-{[tert-butyl(dimethyl)silyl]oxy}-4-(dimethylamino)butanoate (Step 2) (1.50 g, 5.18 mmol) in anhydrous THF (2 mL) was added. The reaction mixture was stirred at ambient temperature for 1 h. Water and EtOAc were added and the two phases were separated. The aqueous phase was extracted with EtOAc. The organic extracts were combined and washed with water, dried over MgSO₄ and concentrated in vacuo. The residue was purified with column chromatography (silica gel, eluting with EtOAc) to give the title compound (320 mg), ¹H NMR (300 MHz, CDCl₃) δ 8.89 (br s, 1H), 8.12 (m, 2H), 7.51 (dd, 1H), 4.32 (t, 1H), 2.47 (m, 1H), 2.31 (m, 4H), 2.21 (s, 6H), 1.97 (m, 2H), 0.98 (s, 9H), 0.15 (d, 6H).

Step 4: (2S)-4-(dimethylamino)-2-hydroxy-N-(5-methylpyridin-2-yl)butanamide

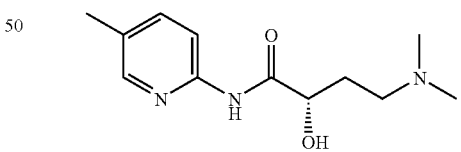

Tetrabutylammoniumfluoride trihydrate (417 mg, 1.32 mmol) was added to a stirred solution of (2S)-2-{[tert-butyl(dimethyl)silyl]oxy}-4-(dimethylamino)-N-(5-methylpyridin-2-yl)butanamide (Step 3) (310 mg, 0.88 mmol) in THF (5 mL). The reaction mixture was kept at ambient temperature for 30 minutes. Water and EtOAc were added and the two phases were separated. The organic phase was dried over MgSO₄ and concentrated in vacuo. The residue was purified with column chromatography (silica gel, eluting with EtOAc/MeOH:10/1) to give the title compound as a solid (110 mg), ¹H NMR (300 MHz, CDCl₃) δ 9.44 (br s, 1H), 8.15 (d, 1H), 8.12 (d, 1H), 7.51 (dd, 1H), 4.39 (dd, 1H), 2.63 (m, 2H), 2.28 (m, 9H), 2.09 (m, 1H), 1.92 (m, 1H).

Intermediate A12: 2-hydroxy-4-methoxy-N-(5-methylpyridin-2-yl)butanamide

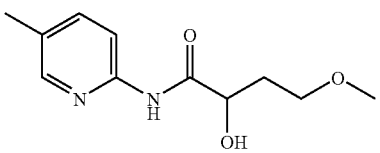

The title compound was prepared in a manner similar to that described for Intermediate A16 and Intermediate A2 (Step 2-Step 3) starting from diethyl malonate, 2-bromoethyl methyl ether and 2-amino-5-picoline, $^1$H NMR (300 MHz, CDCl$_3$) δ 9.24 (br s, 1H), 8.14 (m, 2H), 7.52 (dd, 1H), 4.48 (br s, 1H), 4.39 (m, 1H), 3.69 (m, 2H), 3.39 (s, 3H), 2.25 (m, 4H), 2.09 (m, 1H).

Intermediate A13: 2-Hydroxy-4-methoxy-N-(4-methyl-1,3-thiazol-2-yl)butanamide

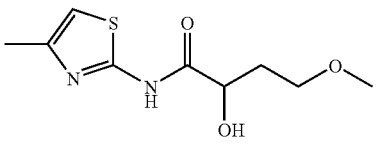

The title compound was prepared in a manner similar to that described for Intermediate A16 and Intermediate A2 (Step 2-Step 3) starting from diethyl malonate, 2-bromoethyl methyl ether and 2-amino-4-methylthiazol, $^1$H NMR (300 MHz, CDCl$_3$) δ 10.07 (br s, 1H), 6.53 (d, 1H), 4.68 (br s, 1H), 4.48 (dd, 1H), 3.68 (m, 2H), 3.37 (s, 3H), 2.33 (s, 3H), 2.20 (m, 1H), 2.14 (m, 1H).

Intermediate A14: 3-acetamido-2-hydroxy-N-(4-methyl-1,3-thiazol-2-yl)propanamide

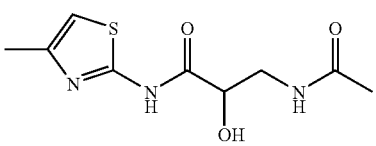

Step 1: 2-(tert-Butyl-dimethyl-silanyloxy)-3-(9H-fluoren-9-ylmethoxycarbonylamino)-propionic acid

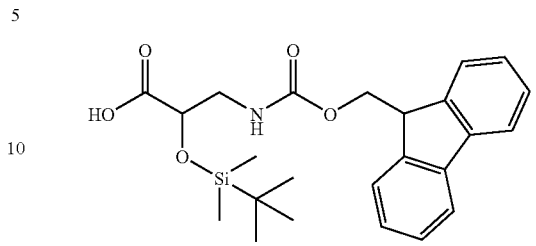

TBDMSCl (1.01 g, 6.72 mmol), DMAP (0.19 g, 1.52 mmol) and pyridine (0.97 g, 12.2 mmol) were added to a stirred solution of FMOC-isoserine (1.00 g, 3.05 mmol) in DMF (20 mL). The reaction mixture was heated at 50° C. for 18 hrs. Water (10 mL) was added and the reaction mixture was concentrated in vacuo. DCM and HCl (0.5 M) were added and the two phases were separated. The aqueous phase was extracted two times with DCM. The organic extracts were combined concentrated in vacuo. The residue was purified with column chromatography (silica gel, eluting with a gradient consisting of 20-100% EtOAc in heptane) to give the title compound (1.3 g). $^1$H NMR (500 MHz, CDCl$_3$) δ 7.76 (d, 2H), 7.59 (m, 2H), 7.40 (t, 2H), 7.30 (m, 2H), 5.14 (br s, 1H), 4.29 (m, 4H), 3.53 (m, 2H), 0.91 (s, 9H), 0.10 (s, 6H).

Step 2: 9H-fluoren-9-ylmethyl(2-{[tert-butyl(dimethyl)silyl]oxy}-3-[(4-methyl-1,3-thiazol-2-yl)amino]-3-oxopropyl)carbamate

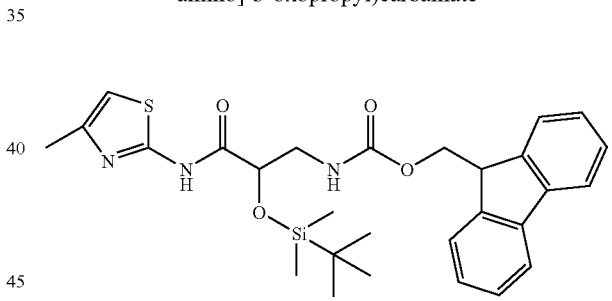

Oxalyl chloride (1.12 g, 8.83 mmol) in DCM (5 mL) was added slowly to a stirred solution of 2-(tert-butyl-dimethyl-silanyloxy)-3-(9H-fluoren-9-ylmethoxycarbonylamino)-propionic acid (Step 1) (1.30 g, 2.94 mmol) in DCM (25 ml) and DMF (50 µl) at 0° C. After 3 hrs at ambient temperature, gas evolution had subsided and the reaction mixture was concentrated in vacuo. THF (20 mL) and DIPEA (0.57 g, 4.4 mmol) were added, followed by the addition of 2-amino-4-methylthiazole (0.403 g, 3.53 mmol) in DCM (5 mL). The reaction mixture was kept at ambient temperature for 3 hrs. Water (0.5 mL) was added and the reaction mixture was concentrated in vacuo. The residue was purified by column chromatography (silica gel, eluting with a gradient consisting of 0-40% EtOAc in heptane) to give the title compound as a colorless oil (0.10 g). $^1$H NMR (500 MHz, CDCl$_3$) δ 9.60 (br s, 1H), 7.75 (d, 2H), 7.57 (d, 2H), 7.39 (t, 2H), 7.30 (t, 2H), 6.56 (s, 1H), 5.19 (br s, 1H), 4.41 (t, 1H), 4.37 (d, 2H), 4.21 (t, 1H), 3.66 (m, 1H), 3.49 (m, 1H), 2.35 (s, 3H), 0.98 (s, 9H), 0.20 (s, 6H).

Step 3: 3-acetamido-2-hydroxy-N-(4-methyl-1,3-thiazol-2-yl)propanamide

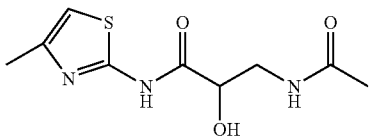

Tetrabutylammoniumfluoride (0.28 mL, 1M in THF, 0.28 mmol) was added to a stirred solution of 9H-fluoren-9-ylmethyl (2-{[tert-butyl(dimethyl)silyl]oxy}-3-[(4-methyl-1,3-thiazol-2-yl)amino]-3-oxopropyl)carbamate (Step 2) (0.10 g, 0.186 mmol) in THF (5 mL). The reaction mixture was kept at ambient temperature for 3 hrs before DIPEA (0.036 g, 0.28 mmol) and acetyl chloride (0.018 g, 0.22 mmol) were added. The reaction mixture was stirred for another 3 hrs at ambient temperature and water (1 mL) was added and the reaction mixture was concentrated in vacuo. The residue was purified by column chromatography (silica gel, eluting with a gradient consisting of 0-20% MeOH in DCM) to give the title compound as a colorless oil (0.04 g). $^1$H NMR (500 MHz, CD$_3$OD) δ 6.71 (s, 1H), 4.38 (dd, 1H), 3.64 (dd, 1H), 3.48 (dd, 1H), 2.33 (s, 3H), 1.96 (s, 3H).

Intermediate A15: methyl 4-hydroxy-5-[(5-methylpyridin-2-yl)amino]-5-oxopentanoate

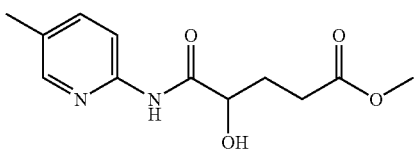

Step 1: 5-oxotetrahydrofuran-2-carboxylic acid

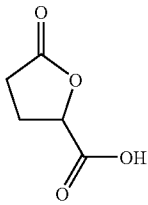

Amberlite(R) IR-120 (3.0 g, washed with 4×20 ml THF) was added to a stirred suspension of α-hydroxyglutaric acid zinc salt (0.40 g, 1.90 mmol) in THF (15 mL). The reaction mixture was kept at ambient temperature for 16 hrs. The reaction mixture was filtered and the resin was washed three times with THF. The combined extracts was concentrated in vacuo and the residue was purified by column chromatography (silica gel, eluting with a gradient consisting of 5-50% MeOH in DCM) to give the title compound as a colorless oil (0.215 g). $^1$H NMR (500 MHz, D$_2$O) δ 5.00 (t, 1H), 2.53 (m, 3H), 2.20 (m, 1H).

Step 2: 5-Oxo-tetrahydro-furan-2-carboxylic acid (5-methyl-pyridin-2-yl)-amide

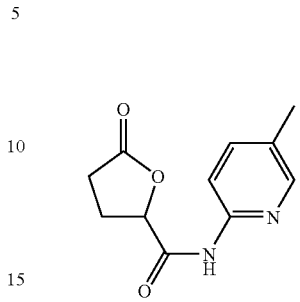

Oxalyl chloride (0.252 g, 1.63 mmol) in DCM (5 mL) was added slowly to a stirred solution of 5-oxotetrahydrofuran-2-carboxylic acid (Step 1) (0.215 g, 1.65 mmol) in DCM (10 ml) and DMF (50 µl) at 0° C. After 3 hrs at ambient temperature, gas evolution had subsided. DIPEA (0.64, 4.95 mmol) was added followed by the addition of 2-amino-5-picoline (0.357 g, 3.3 mmol) in DCM (5 mL). The reaction mixture was kept at ambient temperature for 3 hrs. Water (0.5 mL) was added and the reaction mixture was concentrated in vacuo. The residue was purified by column chromatography (silica gel, eluting with a gradient consisting of 0-40% MeOH in DCM) to give the title compound as a colorless oil (0.138 g). $^1$H NMR (500 MHz, CDCl$_3$) δ 8.74 (br s, 1H), 8.13 (d, 1H), 8.08 (d, 1H), 7.54 (dd, 1H), 4.99 (t, 1H), 2.71 (m, 1H), 2.63 (m, 2H), 2.48 (m, 1H), 2.31 (s, 3H).

Step 3: methyl 4-hydroxy-5-[(5-methylpyridin-2-yl)amino]-5-oxopentanoate

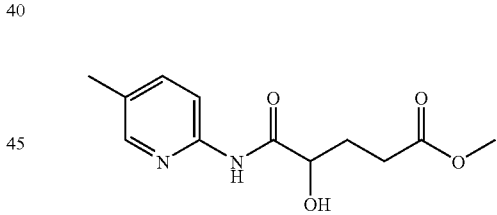

Amberlyst 15 (2.0 g, washed with 4×20 ml of MeOH) was added to a stirred solution of 5-oxo-tetrahydro-furan-2-carboxylic acid (5-methyl-pyridin-2-yl)-amide (Step 2) (0.138 g, 0.63 mmol) in MeOH (10 mL). The reaction mixture was kept at ambient temperature for 16 hrs. HCl (1 M, 5 mL) was added and the reaction mixture was stirred for another hour at ambient temperature. The reaction mixture was filtered and the resin was washed two times with MeOH (10 mL) and HCl (1 M, 2 mL). The combined extracts was concentrated in vacuo and the residue was purified by column chromatography (silica gel, eluting with a gradient consisting of 0-40% MeOH in DCM) to give the title compound as a colorless oil (0.02 g). $^1$H NMR (500 MHz, THF) δ 9.24 (br s, 1H), 8.16 (d, 1H), 8.09 (s, 1H), 7.53 (d, 1H), 5.34 (d, 1H), 4.17 (m, 1H), 3.62 (s, 3H), 2.47 (m, 2H), 2.28 (s, 3H), 2.17 (m, 1H), 1.95 (m, 1H).

Intermediate A16: 2-bromo-4-(2-methoxyethoxy)-N-(4-methyl-1,3-thiazol-2-yl)butanamide

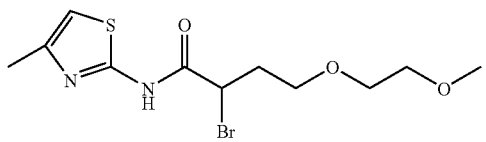

Step 1: diethyl[2-(2-methoxyethoxy)ethyl]malonate

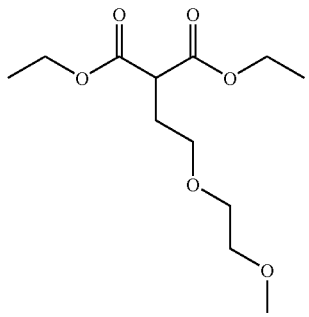

Sodium (0.72 g, 31.31 mmol) was added in portions to EtOH (99.5%, 35 mL) under stirring. When all sodium had dissolved, diethyl malonate (4.80 g, 29.97 mmol) was added slowly during 5 minutes and the reaction mixture was stirred for another 15 minutes. 1-Bromo-2-(2-methoxyethoxy)-ethane (5.50 g, 30.05 mmol) was added and the reaction mixture was refluxed for 2 hrs. Any solids were filtered off and the clear solution was concentrated in vacuo. The residue was taken up in water and diethyl ether and the two phases were separated. The organic phase was dried over MgSO$_4$ and concentrated in vacuo. The residue was purified with column chromatography (silica gel, eluting with EtOAc/MeOH:20/1) to give the title compound as a colourless oil (3.80 g), $^1$H NMR (300 MHz, CDCl$_3$) δ 4.19 (q, 4H), 3.54 (m, 7H), 3.38 (s, 3H), 2.19 (m, 2H), 1.27 (t, 6H).

Step 2: [2-(2-methoxyethoxy)ethyl]malonic acid

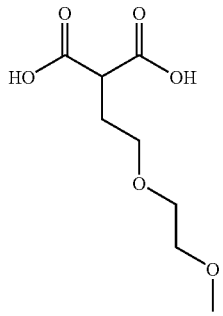

Sodium hydroxide (2.00 g, 50.00 mmol) in water (15 mL) was added to a stirred solution of diethyl[2-(2-methoxy-ethoxy)ethyl]malonate (Step 1) (2.35 g, 8.96 mmol). The reaction was kept at ambient temperature for 10 minutes before MeOH was removed in vacuo. The resulting solution was acidified to pH=1 by the addition of HCl (5 M). Diethyl ether was added and the two phases were separated. The aqueous phase was extracted three times with diethyl ether. The organic extracts were combined, dried over MgSO$_4$ and concentrated in vacuo to give the title compound as a colourless oil (1.81 g), $^1$H NMR (300 MHz, CDCl$_3$) δ 7.16 (br s, 2H), 3.58 (m, 7H), 3.40 (s, 3H), 2.23 (m, 2H).

Step 3: bromo[2-(2-methoxyethoxy)ethyl]malonic acid

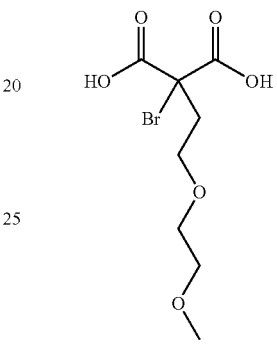

HBr (4.1 M in acetic acid, two drops) and bromine (1.44 g, 9.01 mmol) was added to a stirred solution of [2-(2-methoxy-ethoxy)ethyl]malonic acid (Step 2) (1.75 g, 8.49 mmol) in diethyl ether. The reaction mixture was kept at ambient temperature for 20 minutes when most of the bromine colour had disappeared. Sodium pyrosulfite (5% in water) was added and the two phases were separated. The aqueous phase was extracted with diethyl ether two times. The organic extracts were combined and washed with water. The organic phase was dried over MgSO$_4$ and concentrated in vacuo to give the title product as a colourless solid (1.91 g), $^1$H NMR (300 MHz, CDCl$_3$) δ 6.91 (br s, 2H), 3.75 (t, 2H), 3.62 (m, 4H), 3.42 (s, 3H), 2.70 (t, 2H).

Step 4: 2-bromo-4-(2-methoxyethoxy)butanoic acid

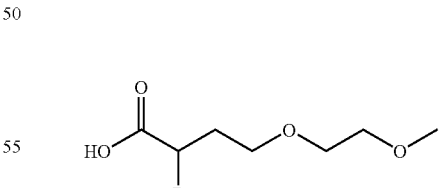

Bromo[2-(2-methoxyethoxy)ethyl]malonic acid (Step 3) (1.15 g, 4.04 mmol) was heated at 150° C. under stirring. The heating was discontinued after 10 minutes when gas evolution had ceased. This gave the title compound as a yellowish oil (941 mg), $^1$H NMR (300 MHz, CDCl$_3$) δ 7.01 (br s, 1H), 4.56 (dd, 1H), 3.60 (m, 6H), 3.40 (s, 3H), 2.42 (m, 1H), 2.20 (m, 1H).

Step 5: 2-bromo-4-(2-methoxyethoxy)-N-(4-methyl-1,3-thiazol-2-yl)butanamide

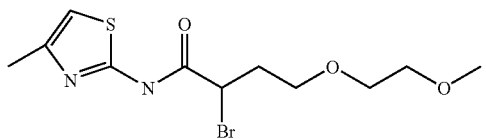

A stirred solution of 2-bromo-4-(2-methoxyethoxy)butanoic acid (Step 4) (200 mg, 0.83 mmol) in thionyl chloride (4 mL) was refluxed for 30 minutes. The reaction mixture was concentrated in vacuo to remove excess thionyl chloride. The residue was dissolved in DCM (2 mL) and was added slowly to a stirred solution of 2-amino-4-methylthiazole (99.5 mg, 0.871 mmol) and DIPEA (117.9 mg, 0.913 mmol) in DCM (4 mL). The reaction mixture was kept at ambient temperature for 1 h before water was added and the two phases were separated. The organic phase was dried over MgSO$_4$ and concentrated in vacuo. The residue was purified with column chromatography (silica gel, eluting with EtOAc/MeOH:1/1) to give the title compound as an oil (105 mg), $^1$H NMR (300 MHz, CDCl$_3$) δ 6.57 (d, 1H), 4.72 (dd, 1H), 3.66 (m, 2H), 3.60 (m, 2H), 3.51 (m, 2H), 3.36 (s, 3H), 2.50 (m, 1H), 2.31 (m, 4H).

Intermediate A17: 2-bromo-4-(2-methoxyethoxy)-N-(5-methylpyridin-2-yl)butanamide

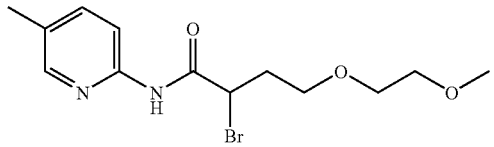

The title compound was prepared in a manner similar to that described for Intermediate A16 (Step 5) starting from 2-bromo-4-(2-methoxyethoxy)butanoic acid and 2-amino-5-picoline.

Intermediate A18: 2-bromo-4-methoxy-N-(4-methyl-1,3-thiazol-2-yl)butanamide

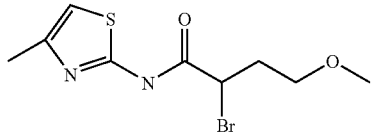

The title compound was prepared in a manner similar to that described for Intermediate A16 starting from diethyl malonate and 2-bromoethyl methyl ether, $^1$H NMR (500 MHz, CDCl$_3$) δ 10.35 (br s, 1H), 6.61 (d, 1H), 4.66 (dd, 1H), 3.57 (t, 2H), 3.34 (s, 3H), 2.49 (m, 1H), 2.40 (d, 3H), 2.28 (m, 1H).

Intermediate A19: 2-bromo-3-methyl-N-(4-methyl-1,3-thiazol-2-yl)pentanamide

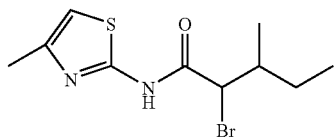

The title compound was prepared in a manner similar to that described for Intermediate A16 (Step 5) starting from 2-methyl-3-methylpentanoic acid and 2-amino-4-methylthiazol, (Diastereomers) $^1$H NMR (300 MHz, CDCl$_3$) δ 9.72 (br s, 1H), 6.58 (d, 1H), 4.62 (d, 0.37H), 4.45 (d, 0.63H), 2.37 (d, 3H), 2.19 (m, 1H), 1.59 (m, 0.74H), 1.41 (m, 1.26H), 1.07 (d, 1.89H), 0.95 (m, 4.11H).

Intermediate A20: 2-bromo-3-methyl-N-(5-methylpyridin-2-yl)pentanamide

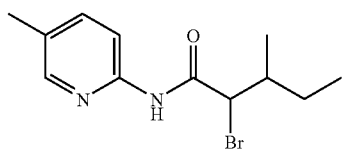

The title compound was prepared in a manner similar to that described for Intermediate A16 (Step 5) starting from 2-methyl-3-methylpentanoic acid and 2-amino-5-picoline, (Diastereomers) $^1$H NMR (300 MHz, CDCl$_3$) δ 8.83 (br s, 0.35H), 8.70 (br s, 0.65H), 8.13 (s, 1H), 8.08 (d, 1H), 7.54 (d, 1H), 4.53 (d, 0.35H), 4.35 (d, 0.65H), 2.31 (s, 3H), 2.20 (m, 1H), 1.66 (m, 1H), 1.37 (m, 1H), 1.08 (d, 1.95H), 1.01 (d, 1.05H), 0.94 (m, 3H).

Intermediate A21: 2-bromo-N-isoxazol-3-yl-3-methylpentanamide

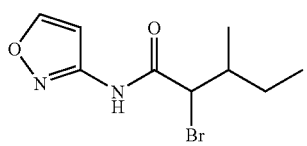

The title compound was prepared in a manner similar to that described for Intermediate A16 (Step 5) starting from 2-methyl-3-methylpentanoic acid and 3-aminoisoxazol, (Diastereomers) $^1$H NMR (300 MHz, CDCl$_3$) δ 9.57 (br s, 0.62H), 9.47 (br s, 0.38H), 8.33 (d, 1H), 7.10 (dd, 1H), 4.53 (d, 0.38H), 4.37 (d, 0.62H), 2.19 (m, 1H), 1.70 (m, 0.62H), 1.43 (m, 1.38H), 1.08 (d, 1.86H), 1.04 (d, 1.14H), 0.95 (m, 3H).

Intermediate A22:
2-bromo-N-(5-methylpyridin-2-yl)acetamide

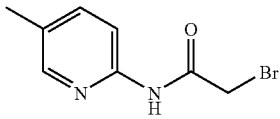

The title compound was prepared in a manner similar to that described for Intermediate A16 (Step 5) starting from bromoacetyl bromide and 2-amino-5-picoline.

Intermediate A23:
2-Bromo-N-(4-methyl-1,3-thiazol-2-yl)acetamide

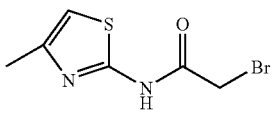

The title compound was prepared in a manner similar to that described for Intermediate A16 (Step 5) starting from bromoacetyl bromide and 2-amino-4-methylthiazole.

Intermediate A24: ethyl ethoxy{[1-(2-methoxyphenyl)-1H-pyrazolo[3,4-d]pyrimidin-4-yl]thio}acetate

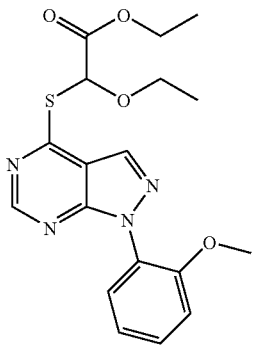

The title compound was prepared in a manner similar to that described for Example 54 starting from 2-chloro-2-ethoxyacetic acid ethyl ester and Intermediate B13, $^1$H NMR (300 MHz, CDCl$_3$) δ 8.76 (s, 1H), 8.26 (s, 1H), 7.46 (m, 2H), 7.13 (m, 2H), 6.88 (s, 1H), 4.32 (m, 2H), 3.90 (m, 1H), 3.78 (m, 4H), 1.31 (m, 6H).

Intermediate A25: ethyl 2-{[1-(2-chlorophenyl)-1H-pyrazolo[3,4-d]pyrimidin-4-yl]thio}-4-phenylbutanoate

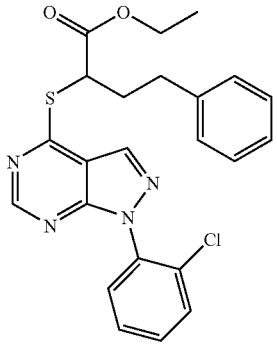

The title compound was prepared in a manner similar to that described for Example 54 starting from ethyl 2-bromo-4-phenylbutanoate and Intermediate B12, $^1$H NMR (300 MHz, CDCl$_3$) δ 8.69 (s, 1H), 8.29 (s, 1H), 7.62 (m, 1H), 7.50 (m, 3H), 7.27 (m, 5H), 4.99 (t, 1H), 4.24 (m, 2H), 2.86 (m, 2H), 2.39 (m, 2H), 1.30 (t, 3H).

Intermediate A26: methyl N-[1-(2-chlorophenyl)-1H-pyrazolo[3,4-d]pyrimidin-4-yl]glycinate

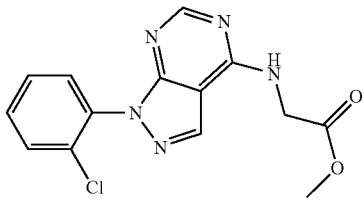

Step 1: N-[1-(2-chlorophenyl)-1H-pyrazolo[3,4-d]pyrimidin-4-yl]glycine

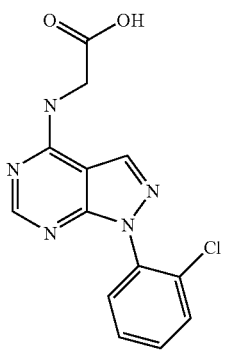

4-chloro-1-(2-chlorophenyl)-1H-pyrazolo[3,4-d]pyrimidine (1.3 g, 4.90 mmol) was added to a stirred solution of glycine (0.72 g, 9.59 mmol) and anhydrous sodium carbonate (0.58 g, 5.48 mmol) in water (10 mL). The reaction was refluxed for 2 hrs. The reaction mixture was acidified by the addition of formic acid. The precipitate was filtered, washed with water and dried in vacuo to give the title compound as a colourless solid (1.23 g), $^1$H NMR (300 MHz, CD$_3$OD) δ 8.32 (s, 1H), 8.24 (s, 1H), 7.66 (m, 1H), 7.54 (m, 3H), 4.34 (s, 2H).

Step 2: methyl N-[1-(2-chlorophenyl)-1H-pyrazolo[3,4-d]pyrimidin-4-yl]glycinate

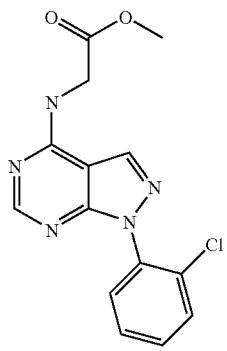

Trimethylsilyldiazomethane (2 M in diethyl ether) was added slowly to a stirred solution of N-[1-(2-chlorophenyl)-1H-pyrazolo[3,4-d]pyrimidin-4-yl]glycine (Step 1) (0.80 g, 2.63 mmol) in DCM (4 mL) and MeOH (1 mL) until a yellow colour persisted. A few drops of acetic acid was added after 1 minute followed by the addition of DCM and water. The two phases were separated and the organic phase was concentrated in vacuo to give the title compound (795 mg), $^1$H NMR (300 MHz, CD3OD) δ 8.32 (s, 1H), 8.24 (s, 1H), 7.66 (m, 1H), 7.54 (m, 3H), 4.39 (s, 2H), 3.77 (s, 3H).

Intermediate B1: 4-chloro-1-(2-chlorophenyl)-1H-pyrazolo[3,4-d]pyrimidine

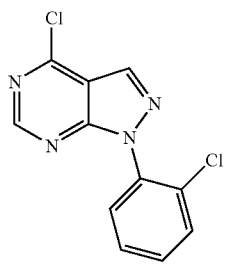

The title compound was prepared using the methods described in *Journal of Organic Chemistry* 1956, 21, 1240-1256 and WO2004/009602A1, $^1$H NMR (300 MHz, CDCl$_3$) δ 8.82 (s, 1H), 8.40 (s, 1H), 7.63 (m, 1H), 7.51 (m, 3H).

Intermediate B2: 4-chloro-1-(2-methylphenyl)-1H-pyrazolo[3,4-d]pyrimidine

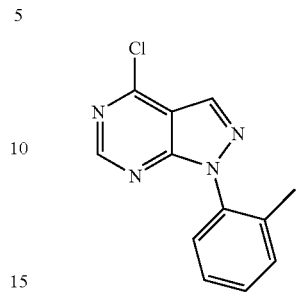

The title compound was prepared using the methods described in *Journal of Organic Chemistry* 1956, 21, 1240-1256 and WO2004/009602A1, $^1$H NMR (500 MHz, CDCl$_3$) δ 8.82 (s, 1H), 8.40 (s, 1H), 7.45 (m, 4H), 2.17 (s, 3H).

Intermediate B3: 4-chloro-1-(2-methoxyphenyl)-1H-pyrazolo[3,4-d]pyrimidine

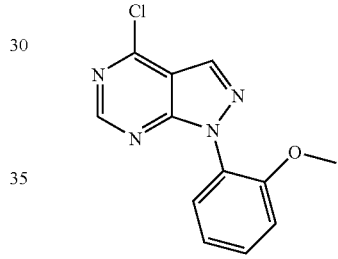

The title compound was prepared using the methods described in *Journal of Organic Chemistry* 1956, 21, 1240-1256 and WO2004/009602A1, $^1$H NMR (300 MHz, CDCl$_3$) δ 8.79 (s, 1H), 8.36 (s, 1H), 7.49 (m, 2H), 7.14 (m, 2H), 3.77 (s, 3H).

Intermediate B4: 4-Chloro-1-[2-(trifluoromethyl)phenyl]-1H-pyrazolo[3,4-d]pyrimidine

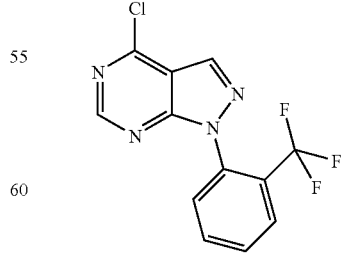

The title compound was prepared using the methods described in *Journal of Organic Chemistry* 1956, 21, 1240-1256 and WO2004/009602A1.

Intermediate B5: 4-chloro-1-(3-methoxyphenyl)-1H-pyrazolo[3,4-d]pyrimidine

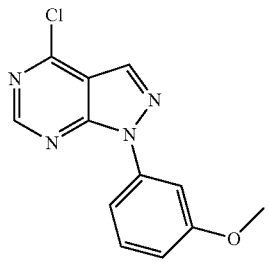

The title compound was prepared using the methods described in *Journal of Organic Chemistry* 1956, 21, 1240-1256 and WO2004/009602A1, $^1$H NMR (500 MHz, CDCl$_3$) δ 8.88 (s, 1H), 8.33 (s, 1H), 7.82 (m, 2H), 7.45 (t, 1H), 6.94 (m, 1H), 3.89 (s, 3H).

Intermediate B6: 4-Chloro-1-(2,4-dichlorophenyl)-1H-pyrazolo[3,4-d]pyrimidine

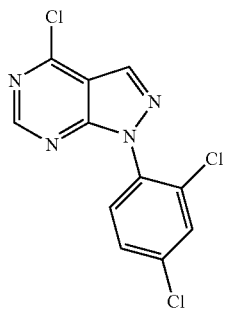

The title compound was prepared using the methods described in *Journal of Organic Chemistry* 1956, 21, 1240-1256 and WO2004/009602A1.

Intermediate B7: 4-Chloro-1-(2,4-difluorophenyl)-1H-pyrazolo[3,4-d]pyrimidine

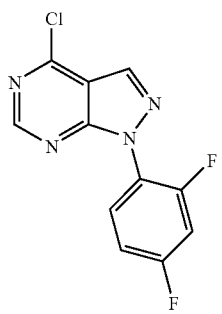

The title compound was prepared using the methods described in *Journal of Organic Chemistry* 1956, 21, 1240-1256 and WO2004/009602A1, $^1$H NMR (400 MHz, DMSO) δ 8.90 (s, 1H), 8.78 (s, 1H), 7.80 (m, 1H), 7.64 (m, 1H), 7.35 (m, 1H).

Intermediate B8: 4-Chloro-1-pyridin-2-yl-1H-pyrazolo[3,4-d]pyrimidine

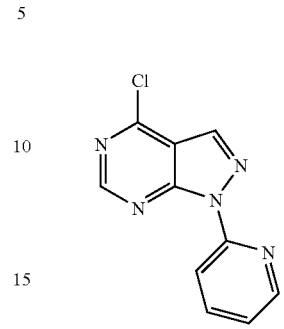

The title compound was prepared using the methods described in *Journal of Organic Chemistry* 1956, 21, 1240-1256 and WO2004/009602A1, $^1$H NMR (400 MHz, DMSO) δ 8.95 (s, 1H), 8.73 (s, 1H), 8.62 (d, 1H), 8.05 (m, 2H), 7.50 (m, 1H).

Intermediate B9: 4-Chloro-1-isopropyl-1H-pyrazolo[3,4-d]pyrimidine

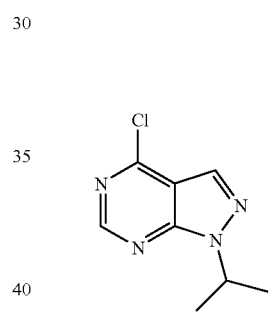

The title compound was prepared using the methods described in *Journal of Organic Chemistry* 1956, 21, 1240-1256 and WO2004/009602A1, $^1$H NMR (400 MHz, CDCl$_3$) δ 8.64 (s, 1H), 8.05 (s, 1H), 5.12 (q, 1H), 1.50 (d, 6H).

Intermediate B10: 4-Chloro-1-(3-methylphenyl)-1H-pyrazolo[3,4-d]pyrimidine

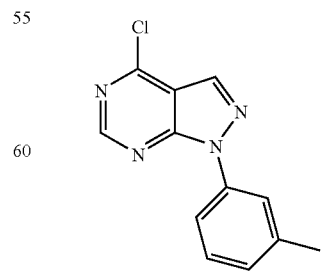

The title compound is commercially available.

Intermediate B11: 4-Chloro-1-methyl-1H-pyrazolo[3,4-d]pyrimidine

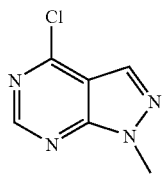

The title compound is commercially available.

Intermediate B12: 1-(2-chlorophenyl)-1H-pyrazolo[3,4-d]pyrimidine-4-thiol

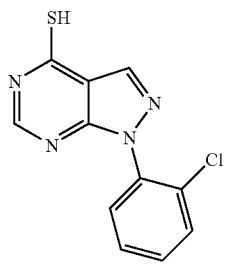

The title compound was prepared using the method described in *Journal of Organic Chemistry* 1956, 21, 1240-1256 and WO2004/009602A1, $^1$H NMR (300 MHz, DMSO) δ 13.82 (br s, 1H), 8.46 (s, 1H), 8.19 (s, 1H), 7.74 (m, 1H), 7.61 (m, 3H).

Intermediate B13: 1-(2-methoxyphenyl)-1H-pyrazolo[3,4-d]pyrimidine-4-thiol

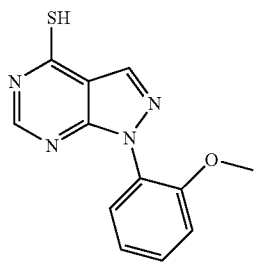

The title compound was prepared using the method described in *Journal of Organic Chemistry* 1956, 21, 1240-1256 and WO2004/009602A1, $^1$H NMR (300 MHz, CDCl3) δ 12.68 (br s, 1H), 8.46 (s, 1H), 7.89 (s, 1H), 7.44 (m, 2H), 7.08 (m, 2H), 3.77 (s, 3H).

Intermediate B14: 1-isopropyl-1,5-dihydro-4H-pyrazolo[3,4-d]pyrimidine-4-thiol

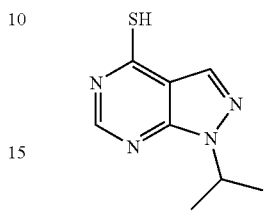

The title compound was prepared using the method described in *Journal of Organic Chemistry* 1956, 21, 1240-1256 and WO2004/009602A1.

Intermediate C1: 2-hydroxy-3-methyl-N-(5-methylpyridin-2-yl)butanamide

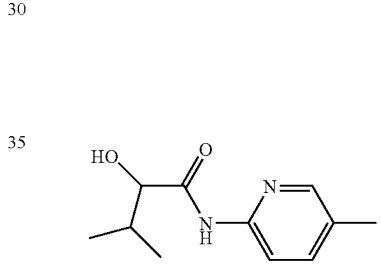

5-Methylpyridin-2-amine (CAS 1603-41-4) (2.014 g, 18.6 mmol) was added in one portion to 2-hydroxy-3-methylbutanoic acid (CAS 4026-18-0) (2.0 g, 16.9 mmol), 2-(3H-[1,2,3]triazolo[4,5-b]pyridin-3-yl)-1,1,3,3-tetramethylisouronium hexafluorophosphate(V) (7.08 g, 18.6 mmol) and N-ethyl-N-isopropylpropan-2-amine (5.80 mL, 33.9 mmol) in DCM (40 mL). The resulting suspension was stirred at ambient temperature for 70 hours. The reaction mixture was concentrated, diluted with EtOAc (150 mL) and washed sequentially with water (150 mL) and saturated brine (75 mL). The organic layer was dried over MgSO$_4$, filtered and evaporated to afford crude product. The crude product was purified by flash silica chromatography, elution gradient 20 to 50% EtOAc in isohexane to afford 2-hydroxy-3-methyl-N-(5-methylpyridin-2-yl)butanamide (500 mg).

$^1$H NMR (400 MHz, DMSO-d$_6$) δ 0.87 (3H, d), 0.97 (3H, d), 2.06-2.16 (1H, m), 2.29 (3H, s), 3.94-3.98 (1H, m), 5.87 (1H, d), 7.65 (1H, dd), 8.05 (1H, d), 8.16 (1H, d), 9.50 (1H, s), m/z (ESI+) (M+H)+=209; HPLC t$_R$=1.11 min.

Intermediates C2 and C3 were prepared in an analogous fashion from enantiopure starting materials (CAS 17407-55-5 and 17407-56-6).

| | | | |
|---|---|---|---|
| C2 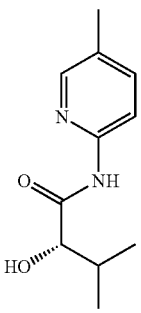 | (S)-2-hydroxy-3-methyl-N-(5-methylpyridin-2-yl)butanamide | ESI+ (M + H)+ = 209; HPLC $t_R$ = 1.13 min | $^1$H NMR (400 MHz, DMSO-$d_6$) δ 0.87 (3 H, d), 0.97 (3 H, d), 2.06-2.16 (1 H, m), 2.29 (3 H, s), 3.94-3.98 (1 H, m), 5.87 (1 H, d), 7.65 (1 H, dd), 8.05 (1 H, d), 8.16 (1 H, d), 9.50 (1 H, s) |
| C3 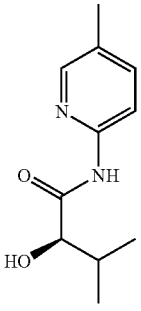 | (R)-2-hydroxy-3-methyl-N-(5-methylpyridin-2-yl)butanamide | ESI+ (M + H)+ = 209; HPLC $t_R$ = 1.12 min | $^1$H NMR (400 MHz, DMSO-$d_6$) δ 0.82 (3 H, d), 0.95 (3 H, d), 2.02-2.10 (1 H, m), 2.24 (3 H, s), 3.89-3.91 (1 H, m), 5.80 (1 H, d), 7.61 (1 H, dd), 8.00 (1 H, d), 8.13 (1 H, d), 9.45 (1 H, s) |

Intermediate C4: (S)-2-hydroxy-3-methoxy-N-(5-methylpyridin-2-yl)propanamide

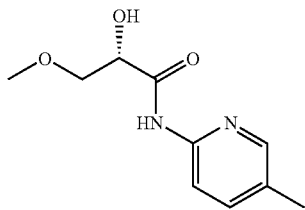

Step 1: Synthesis of C4a: (S)-methyl 2-hydroxy-3-methoxypropanoate

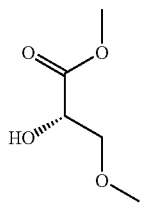

Magnesium perchlorate (0.820 g, 3.67 mmol) was added in one portion to (S)-methyl oxirane-2-carboxylate (CAS 2868-37-3) (1.5 g, 14.7 mmol) and methanol (0.714 mL, 17.6 mmol) cooled to 10° C. The resulting suspension was stirred at 10° C. for 10 minutes and then warmed to 45° C. for 20 hours. The crude reaction mixture was purified by flash silica chromatography, elution gradient 20 to 50% Et$_2$O in DCM to afford (S)-methyl 2-hydroxy-3-methoxypropanoate (1.4 g).
$^1$H NMR (400 MHz, CDCl$_3$) δ 3.01 (1H, d), 3.40 (3H, s), 3.65-3.72 (2H, m), 3.81 (3H, s), 4.29-4.33 (1H, m)

Step 2: Synthesis of C4b: (S)-methyl 2-(tert-butyldimethylsilyloxy)-3-methoxypropanoate

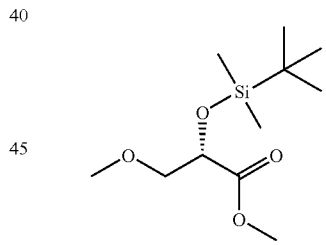

A solution of tert-butylchlorodimethylsilane (661 mg, 4.38 mmol) in DMF (2.5 mL) was added dropwise to a stirred solution of (S)-methyl 2-hydroxy-3-methoxypropanoate C4a (490 mg, 3.65 mmol) and 1H-imidazole (497 mg, 7.31 mmol) in DMF (5 mL) at 20° C., over a period of 2 minutes. The resulting solution was stirred at ambient temperature for 3 hours. The reaction mixture was concentrated, diluted with EtOAc (50 mL) and washed sequentially with water (4×15 mL) and saturated brine (20 mL). The organic layer was dried over MgSO$_4$, filtered and evaporated to afford crude product. Purification by flash silica chromatography, elution gradient 20 to 50% EtOAc in isohexane afforded (S)-methyl 2-(tert-butyldimethylsilyloxy)-3-methoxypropanoate (750 mg).
$^1$H NMR (400 MHz, CDCl$_3$) δ 0.11 (3H, s), 0.13 (3H, s), 0.94 (9H, s), 3.40 (3H, s), 3.56-3.64 (2H, m), 3.76 (3H, s), 4.37-4.41 (1H, m)

Step 3: Synthesis of C4c: (S)-2-(tert-butyldimethylsilyloxy)-3-methoxypropanoic acid

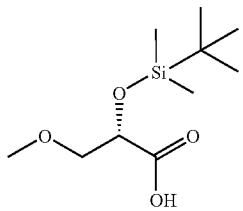

Lithium iodide (535 mg, 3.99 mmol) was added in one portion to (S)-methyl 2-(tert-butyldimethylsilyloxy)-3-methoxypropanoate C4b (248 mg, 1.00 mmol) in EtOAc (5 mL). The resulting suspension was protected from light and stirred at reflux (75° C.) for 24 hours. The reaction mixture was diluted with EtOAc (10 mL) and washed sequentially with water (5 mL), 1M sodium metabisulphite (5 mL) and saturated brine (5 mL). The organic layer was dried over MgSO$_4$, filtered and evaporated to afford crude product, an approximate 3:1 mixture of (S)-2-(tert-butyldimethylsilyloxy)-3-methoxypropanoic acid and (S)-methyl 2-(tert-butyldimethylsilyloxy)-3-methoxypropanoate. The material was carried through to the next step without purification.

Step 4: Synthesis of C4d: (S)-2-(tert-butyldimethylsilyloxy)-3-methoxy-N-(5-methylpyridin-2-yl)propanamide

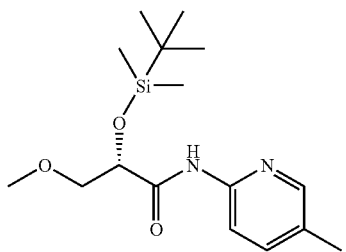

A solution of 1-chloro-N,N,2-trimethylprop-1-en-1-amine (1.55 mL, 11.7 mmol) in DCM (5 mL) was added dropwise to a stirred solution of (S)-2-(tert-butyldimethylsilyloxy)-3-methoxypropanoic acid C4c (2.5 g, 10.7 mmol) in DCM (15 mL) under nitrogen. The resulting solution was stirred at ambient temperature for 30 minutes. N-Ethyl-N-isopropylpropan-2-amine (2.74 mL, 16.0 mmol) was added in one portion followed by 5-methylpyridin-2-amine (CAS 1603-41-4) (1.27 g, 11.73 mmol) in DCM (5 mL) dropwise. The resulting solution was stirred at ambient temperature for 1 hour. 1M Citric acid (10 mL) was added and the mixture extracted with EtOAc (20 mL). The organic phase was washed with water (5 mL) and brine (5 mL), dried over MgSO$_4$, filtered and evaporated to provide the crude product. Purification by flash silica chromatography, elution gradient 20 to 100% EtOAc in isohexane furnished (S)-2-(tert-butyldimethylsilyloxy)-3-methoxy-N-(5-methylpyridin-2-yl)propanamide (1.4 g). $^1$H NMR (400 MHz, CDCl$_3$) δ 0.2 (6H, s), 1.01 (9H, s), 2.32 (3H, s), 3.41 (3H, s), 3.66-3.75 (2H, m), 4.40-4.42 (1H, m), 7.52 (1H, d), 7.14-7.16 (2H, m), 9.04 (1H, s), m/z (ESI+) (M+H)+=326; HPLC t$_R$=2.75 min.

Step 5: Synthesis of C4: (S)-2-hydroxy-3-methoxy-N-(5-methylpyridin-2-yl)propanamide

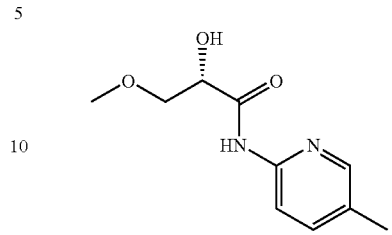

A solution of tetrabutylammonium fluoride (1M in THF) (8.63 mL, 8.63 mmol) was added in one portion to a stirred solution of (S)-2-(tert-butyldimethylsilyloxy)-3-methoxy-N-(5-methylpyridin-2-yl)propanamide C4d (1.4 g, 4.31 mmol) in THF (20 mL). The resulting solution was stirred at ambient temperature for 4 hours. The reaction mixture was concentrated, diluted with EtOAc (50 mL) and washed sequentially with water (20 mL) and saturated brine (20 mL). The organic layer was dried over MgSO$_4$, filtered and evaporated to afford crude product as an oil. Trituration with 1:1 isohexane:EtOAc afforded (S)-2-hydroxy-3-methoxy-N-(5-methylpyridin-2-yl)propanamide (340 mg). The residue was purified by flash silica chromatography with EtOAc to afford a second batch of (S)-2-hydroxy-3-methoxy-N-(5-methylpyridin-2-yl)propanamide (220 mg).

$^1$H NMR (400 MHz, CDCl$_3$) δ 2.31 (3H, s), 3.44 (3H, s), 3.73-3.80 (2H, m), 4.38-4.42 (1H, m), 4.63 (1H, d), 7.54 (1H, dd), 8.10-8.11 (1H, d), 8.14 (1H, d), 9.33 (1H, s) m/z (ESI+) (M+H)+=211; HPLC t$_R$=0.77 min.

Intermediate C5: (R)-2-hydroxy-3-methoxy-N-(5-methylpyridin-2-yl)propanamide

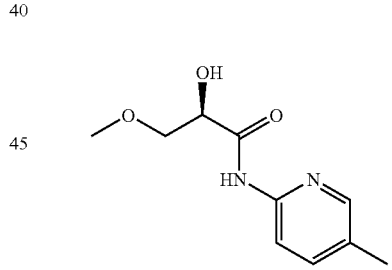

Step 1: Synthesis of C5a: (R)-methyl 2-hydroxy-3-methoxypropanoate

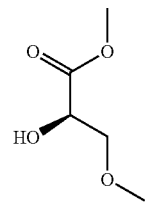

C5a was prepared in an analogous fashion to intermediate C4a from (R)-methyl oxirane-2-carboxylate (CAS 111058-32-3). $^1$H NMR (400 MHz, CDCl$_3$) δ 3.01 (1H, d), 3.40 (3H, s), 3.65-3.72 (2H, m), 3.81 (3H, s), 4.29-4.33 (1H, m)

Step 2: Synthesis of C5b: (R)-methyl 2-(tert-butyldimethylsilyloxy)-3-methoxypropanoate

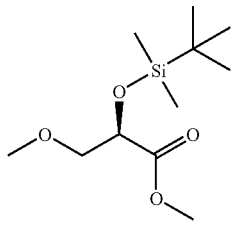

C5b was prepared in an analogous fashion to intermediate C4b from (R)-methyl 2-hydroxy-3-methoxypropanoate C5a. $^1$H NMR (400 MHz, CDCl$_3$) δ 0.11 (3H, s), 0.13 (3H, s), 0.94 (9H, s), 3.40 (3H, s), 3.56-3.64 (2H, m), 3.76 (3H, s), 4.37-4.41 (1H, m)

Step 3: Synthesis of C5c: (R)-2-(tert-butyldimethylsilyloxy)-3-methoxy-N-(5-methylpyridin-2-yl)propanamide

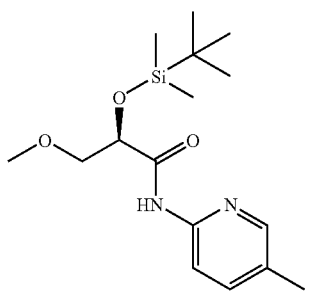

A solution of n-butyllithium (2.5M in hexanes) (2.04 mL, 3.26 mmol) was added dropwise to a stirred solution of 5-methylpyridin-2-amine (CAS 1603-41-4) (353 mg, 3.26 mmol) in THF (10 mL) cooled to 10° C. under nitrogen. The resulting solution was stirred at ambient temperature for 10 minutes and then added to a solution of (R)-methyl 2-(tert-butyldimethylsilyloxy)-3-methoxypropanoate C5b (810 mg, 3.26 mmol) in THF (10 mL) at 10° C. The resulting solution was stirred at ambient temperature for 1 hour. The reaction mixture was diluted with EtOAc (75 mL) and washed sequentially with saturated ammonium chloride (50 mL), water (25 mL) and saturated brine (25 mL). The organic layer was dried over MgSO$_4$, filtered and evaporated to afford crude product. Purification by flash silica chromatography, elution gradient 20 to 50% EtOAc in isohexane provided (R)-2-(tert-butyldimethylsilyloxy)-3-methoxy-N-(5-methylpyridin-2-yl)propanamide (300 mg). $^1$H NMR (400 MHz, CDCl$_3$) δ 0.15 (3H, s), 0.16 (3H, s), 0.88 (9H, s), 2.12 (3H, s), 3.46 (3H, s), 3.61-3.65 (2H, m), 4.35-4.42 (1H, m), 7.47 (1H, d), 8.19 (1H, d), 8.20 (1H, s), 8.97 (1H, s), m/z (ESI+) (M+H)+=325; HPLC t$_R$=3.08 min.

Step 4: Synthesis of C5:(R)-2-hydroxy-3-methoxy-N-(5-methylpyridin-2-yl)propanamide

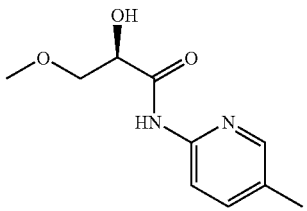

C5 was prepared in an analogous fashion to C4 (step 5) from (R)-2-(tert-butyldimethylsilyloxy)-3-methoxy-N-(5-methylpyridin-2-yl)propanamide C5c.
$^1$H NMR (400 MHz, CDCl$_3$) δ 2.31 (3H, s), 3.44 (3H, s), 3.73-3.78 (2H, m), 4.36-4.44 (1H, m), 4.46-4.50 (1H, m), 7.54 (1H, dd), 8.10 (1H, d), 8.14 (1H, d), 9.30 (1H, s), m/z (ESI+) (M+H)+=211; HPLC t$_R$=0.74 min.

Intermediate C6: (S)-2-hydroxy-3-methoxy-N-(5-methylpyrazin-2-yl)propanamide

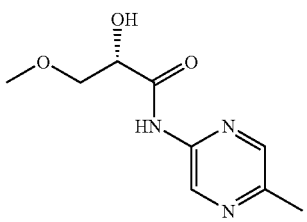

Step 1:Synthesis of C6a: (S)-2-(tert-butyldimethylsilyloxy)-3-methoxy-N-(5-methylpyrazin-2-yl)propanamide

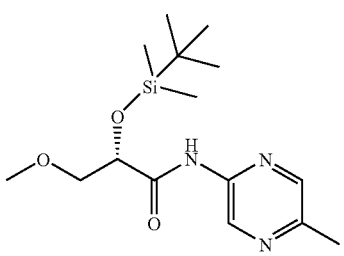

C6a was prepared in an analogous fashion to C4d from (S)-2-(tert-butyldimethylsilyloxy)-3-methoxypropanoic acid C4c and 5-methylpyrazine-2-amine (CAS 5521-58-4).
$^1$H NMR (400 MHz, CDCl$_3$) δ 0.18 (3H, s), 0.19 (3H, s), 1.01 (9H, s), 2.54 (3H, s), 3.39 (3H, s), 3.70 (2H, d), 4.41 (1H, t), 8.14 (1H, d), 9.01 (1H, s), 9.42 (1H, d), m/z )ESI+) (M+H)+=326; HPLC t$_R$=2.67 min.

Step 2: Synthesis of C6: (S)-2-hydroxy-3-methoxy-N-(5-methylpyrazin-2-yl)propanamide

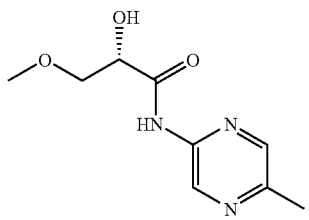

C6 was prepared in an analogous fashion to intermediate C4 (step 5) from (S)-2-(tert-butyldimethylsilyloxy)-3-methoxy-N-(5-methylpyrazin-2-yl)propanamide C6a. $^1$H NMR (400 MHz, CDCl$_3$) δ 2.55 (3H, s), 3.45 (3H, s), 3.74-3.82 (2H, m), 3.85 (1H, s), 4.41 (1H, t), 8.14 (1H, d), 9.18 (1H, s), 9.45 (1H, d), m/z (ESI+) (M+H)+=212; HPLC t$_R$=0.78 min.

Intermediate C7: (S)-2-hydroxy-3-isopropoxy-N-(5-methylpyridin-2-yl)propanamide

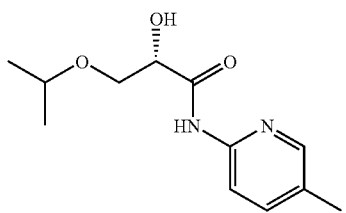

Step 1: Synthesis of C7a(S)-methyl 2-hydroxy-3-isopropoxypropanoate

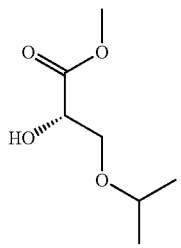

Magnesium perchlorate (2.73 g, 12.24 mmol) was added in one portion to (S)-methyl oxirane-2-carboxylate (CAS 2868-37-3) (5.0 g, 48.98 mmol) and propan-2-ol (4.69 mL, 61.22 mmol) at 10° C. The resulting suspension was stirred at 10° C. for 10 minutes and then allowed to warm to ambient temperature for 30 minutes during which most of the solids dissolve. Heated to 100° C. for 30 minutes in a microwave reactor. The material was used without purification in the next step.

Alternatively C7a may be prepared as follows.

(S)-Methyl oxirane-2-carboxylate (2.04 g, 19.98 mmol), magnesium trifluoromethanesulfonate (1.611 g, 5.00 mmol) and propan-2-ol (1.84 mL, 24.0 mmol) in ethyl acetate (10 mL) were heated at reflux for 90 hours. The mixture was diluted with EtOAc (20 mL), filtered and evaporated. The residue was purified by flash silica chromatography, elution gradient 20 to 50% EtOAc in isohexane to afford (S)-methyl 2-hydroxy-3-isopropoxypropanoate (2.45 g, 76%). $^1$H NMR (400 MHz, CDCl$_3$) δ 1.13 (3H, d), 1.16 (3H, d), 3.00 (1H, d), 3.58-3.64 (1H, m), 3.68-3.74 (2H, m), 3.69-3.73 (1H, m), 3.80 (3H, s), 4.28-4.31 (1H, m)

Step 2: Synthesis of C7b: (S)-methyl 2-(tert-butyldimethylsilyloxy)-3-isopropoxypropanoate

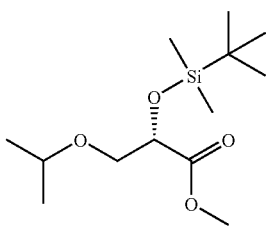

C7b was prepared in an analogous fashion to C4b from crude (S)-methyl 2-hydroxy-3-isopropoxypropanoate C7a. $^1$H NMR (400 MHz, CDCl$_3$) δ 0.10 (3H, s), 0.11 (3H, s), 0.90 (9H, d), 1.14 (6H, d), 3.50-3.7 (3H, m), 3.73 (3H, s), 4.33-4.36 (1H, m)

Step 3: Synthesis of C7c: (S)-2-(tert-butyldimethylsilyloxy)-3-isopropoxypropanoic acid

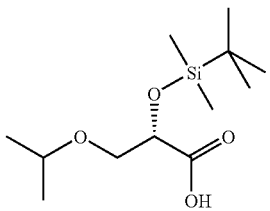

C7c was prepared in an analogous fashion to C4c from (S)-methyl 2-(tert-butyldimethylsilyloxy)-3-isopropoxypropanoate C7b.
$^1$H NMR (400 MHz, CDCl$_3$) δ 0.16 (3H, s), 0.17 (3H, s), 0.93 (9H, m), 1.14 (3H, d), 1.16 (3H, d), 3.58-3.74 (3H, m), 4.35-4.38 (1H, m), 9.31 (1H, s)

Step 4: Synthesis of C7d: (S)-2-(tert-butyldimethylsilyloxy)-3-isopropoxy-N-(5-methylpyridin-2-yl)propanamide

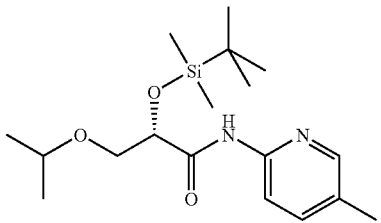

C7d was prepared in an analogous fashion to C4d from (S)-2-(tert-butyldimethylsilyloxy)-3-isopropoxypropanoic acid C7c and 5-methylpyridin-2-amine.

¹H NMR (400 MHz, CDCl₃) δ 0.16 (3H, s), 0.17 (3H, s), 1.01 (9H, s), 1.12 (3H, d), 1.13 (3H, d), 2.29 (3H, s), 3.56-3.62 (2H, m), 3.71-3.78 (1H, m), 4.40 (1H, dd), 7.47-7.51 (1H, m), 8.10-8.17 (2H, m), 9.01 (1H, s)

Step 5: Synthesis of C7: (S)-2-hydroxy-3-isopropoxy-N-(5-methylpyridin-2-yl)propanamide

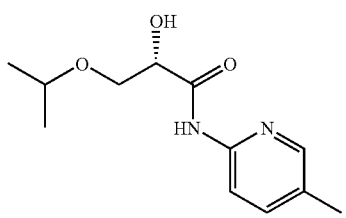

C7 was prepared in an analogous fashion to C4 (step 5) from (S)-2-(tert-butyldimethylsilyloxy)-3-isopropoxy-N-(5-methylpyridin-2-yl)propanamide C7d.

¹H NMR (400 MHz, CDCl₃) δ 1.19 (3H, d), 1.21 (3H, d), 2.30 (3H, s), 3.64-3.72 (2H, m), 3.76 (2H, d), 4.29-4.33 (1H, m), 7.52 (1H, dd), 8.09-8.14 (2H, m), 9.18 (1H, s), m/z (ESI+) (M+H)+=211; HPLC $t_R$=0.77 min.

Intermediate C8: (S)-2-hydroxy-3-isopropoxy-N-(5-methylpyrazin-2-yl)propanamide

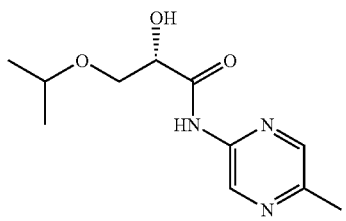

Step 1: Synthesis of C8a: (S)-2-(tert-butyldimethylsilyloxy)-3-isopropoxy-N-(5-methylpyrazin-2-yl)propanamide

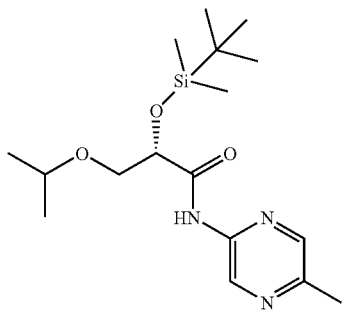

C8a was prepared in an analogous fashion to C4d from (S)-2-(tert-butyldimethylsilyloxy)-3-isopropoxypropanoic acid C7c and 5-methylpyrazin-2-amine. ¹H NMR (400 MHz, CDCl₃) δ 0.20 (3H, s), 0.21 (3H, s), 1.0 (9H, s), 1.14 (3H, d), 1.17 (3H, d), 2.54 (3H, s), 3.61-3.65 (2H, m), 3.77-3.80 (1H, m), 4.40 (1H, dd), 8.14 (1H, d), 9.01 (1H, s), 9.43 (1H, d)

Step 2: Synthesis of C8: (S)-2-hydroxy-3-isopropoxy-N-(5-methylpyrazin-2-yl)propanamide

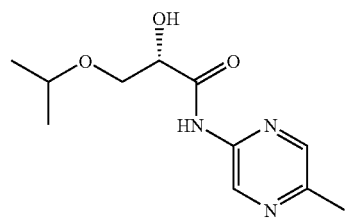

C8 was prepared in an analogous fashion to C4 (step 5) from (S)-2-(tert-butyldimethylsilyloxy)-3-isopropoxy-N-(5-methylpyrazin-2-yl)propanamide C8a.

¹H NMR (400 MHz, CDCl₃) δ 1.19 (3H, m), 1.21 (3H, d), 2.54 (3H, s), 3.42 (1H, d), 3.67-3.82 (3H, m), 4.31-4.35 (1H, m), 8.14 (1H, d), 9.14 (1H, s), 9.42 (1H, d)

Intermediate C 9: (S)-2-hydroxy-3-isopropoxy-N-(3-methyl-1,2,4-thiadiazol-5-yl)propanamide

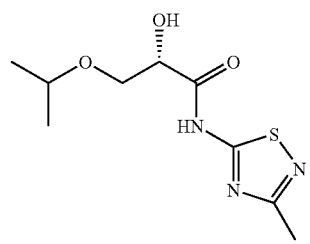

Step 1: Synthesis of C9a: (S)-2-(tert-butyldimethylsilyloxy)-3-isopropoxy-N-(3-methyl-1,2,4-thiadiazol-5-yl)propanamide

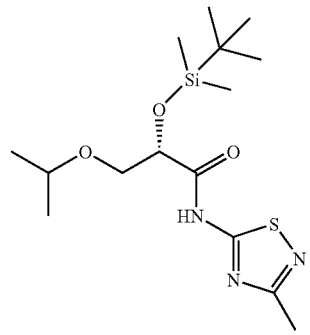

C9a was prepared in an analogous fashion to C4d from (S)-2-(tert-butyldimethylsilyloxy)-3-isopropoxypropanoic acid C7c and 3-methyl-1,2,4-thiadiazol-5-amine.

¹H NMR (400 MHz, CDCl₃) δ 0.17 (3H, s), 0.19 (3H, s), 0.96 (9H, s), 1.08 (3H, d), 1.13 (3H, d), 2.39 (3H, s), 3.42-3.66 (2H, m), 3.69-3.74 (1H, m), 4.50-4.53 (1H, m), 10.00 (1H, s)

Step 2: Synthesis of C9: (S)-2-hydroxy-3-isopropoxy-N-(3-methyl-1,2,4-thiadiazol-5-yl)propanamide

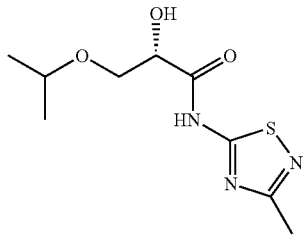

C9 was prepared in an analogous fashion to C4 (step 5) from (S)-2-(tert-butyldimethylsilyloxy)-3-isopropoxy-N-(3-methyl-1,2,4-thiadiazol-5-yl)propanamide C9a.

$^1$H NMR (400 MHz, CDCl$_3$) δ 1.1 (3H, m), 1.20 (3H, d), 2.55 (3H, s), 3.63-3.72 (1H, m), 3.75 (1H, broad s), 3.76-3.83 (2H, m), 4.47-4.50 (1H, m), 10.20 (1H, broad s)

Intermediate C10: (S)-2-hydroxy-3-methyl-N-(5-methylpyrazin-2-yl)butanamide

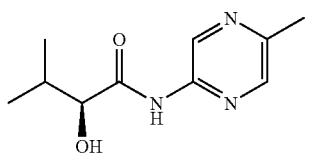

Step 1: Synthesis of C10a: (S)-tert-butyldimethylsilyl 2-(tert-butyldimethylsilyloxy)-3-methylbutanoate

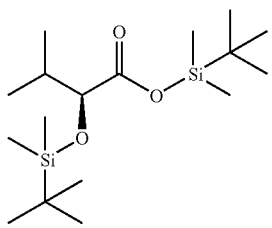

tert-Butyldimethylsilyl chloride (18.77 g, 124.54 mmol) was added to (S)-(+)-2-Hydroxy-3-methylbutyric acid (CAS 17407-55-5) (6.13 g, 51.9 mmol) and 1H-imidazole (16.96 g, 249 mmol) in DMF (259 mL) at 23° C. under nitrogen. The resulting solution was stirred at ambient for 60 hours. The reaction mixture was diluted with EtOAc (1400 mL) and the organic phase was washed sequentially with saturated aqueous citric acid (3×500 mL), saturated aqueous sodium hydrogen carbonate (3×500 mL) and saturated brine (3×500 mL). The organic layer was dried over MgSO$_4$, filtered and evaporated to provide (S)-tert-butyldimethylsilyl 2-(tert-butyldimethylsilyloxy)-3-methylbutanoate (18.0 g, 100%). This material was used without further purification.

Step 2: Synthesis of C10b: (S)-2-(tert-butyldimethylsilyloxy)-3-methyl-N-(5-methylpyrazin-2-yl)butanamide

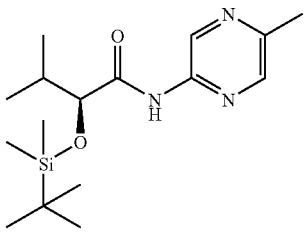

DMF (cat.) was added to a stirred solution of (S)-tert-butyldimethylsilyl 2-(tert-butyldimethylsilyloxy)-3-methylbutanoate C10a (17.99 g, 51.90 mmol) and oxalyl chloride (5.89 mL, 67.47 mmol) in DCM (259 mL) at 23° C. under nitrogen. The resulting solution was stirred at ambient temperature for 2 hours. The reaction mixture was concentrated under reduced pressure and azeotroped with toluene (50 mL). The resulting oil was dissolved in DCM (250 mL) and 5-methylpyrazin-2-amine (6.23 g, 57.1 mmol) added. The resulting solution was stirred for 4 hours at ambient temperature. The reaction mixture was washed sequentially with water (150 mL) and saturated NaHCO$_3$ (150 mL). The organic layer was dried over MgSO$_4$, filtered and evaporated to afford crude product. Purification by flash silica chromatography, elution gradient 0 to 70% EtOAc in isohexane afforded (S)-2-(tert-butyldimethylsilyloxy)-3-methyl-N-(5-methylpyrazin-2-yl)butanamide C10b (2.53 g). $^1$H NMR (400 MHz, CDCl$_3$) δ 0.11 (3H, s), 0.15 (3H, s), 0.95 (3H, d), 1.00 (9H, s), 1.02 (3H, d), 2.15-2.18 (1H, m), 2.54 (3H, s), 4.10 (1H, d), 8.13 (1H, d), 8.76 (1H, s), 9.45 (1H, d), m/z (ESI+) (M+H)+=324; HPLC $t_R$=3.25 min.

Step 3: Synthesis of C10: (S)-2-hydroxy-3-methyl-N-(5-methylpyrazin-2-yl)butanamide

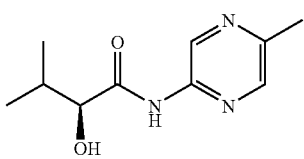

C10 was prepared in an analogous fashion to C4 (step 5) from (S)-2-(tert-butyldimethylsilyloxy)-3-methyl-N-(5-methylpyrazin-2-yl)butanamide C10b.

$^1$H NMR (400 MHz, DMSO-d$_6$) δ 0.88 (3H, d), 0.98 (3H, d), 2.05-2.16 (1H, m), 2.50 (3H, s), 3.99 (1H, dd), 5.84 (1H, d), 8.34 (1H, s), 9.26 (1H, d), 9.89 (1H, s), m/z (ESI+) (M+H)+=210; HPLC $t_R$=1.24 min.

Intermediate B15: 4-chloro-1-(3-chloropyridin-2-yl)-1H-pyrazolo[3,4-d]pyrimidine

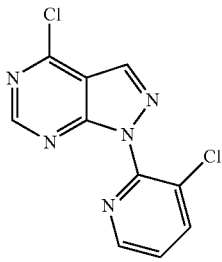

Step 1: Synthesis of B15a: 5-amino-1-(3-chloropyridin-2-yl)-1H-pyrazole-4-carbonitrile

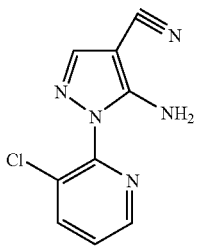

3-Chloro-2-hydrazinylpyridine (CAS 22841-92-5) (19.1 g, 133.03 mmol) was suspended in MeOH (200 mL) under nitrogen at −5° C. 2-(ethoxymethylene)malononitrile (CAS 123-06-8) (16.25 g, 133.03 mmol) was added portionwise and the resulting mixture stirred at ~0° C. for 2 hours. The reaction mixture was heated to reflux for 2 hours then cooled and evaporated to provide 5-amino-1-(3-chloropyridin-2-yl)-1H-pyrazole-4-carbonitrile (29.2 g). $^1$H NMR (400 MHz, DMSO-$d_6$) δ 6.87 (2H, s), 7.61 (1H, dd), 7.79 (1H, s), 8.21 (1H, dd), 8.55 (1H, dd), m/z (ESI+) (M+H)+=220; HPLC $t_R$=1.17 min.

Step 2: Synthesis of B15b: 1-(3-chloropyridin-2-yl)-1H-pyrazolo[3,4-d]pyrimidin-4(7H)-one

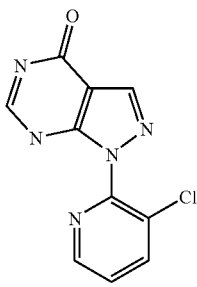

Concentrated sulphuric acid (10.87 mL, 203.92 mmol) was added to a stirred solution of 5-amino-1-(3-chloropyridin-2-yl)-1H-pyrazole-4-carbonitrile B15a (29.2 g, 132.95 mmol) in formic acid (200 mL). The resulting solution was stirred at 100° C. for 3 hours. The reaction mixture was cooled and evaporated to approx. half volume. Water (250 mL) was added and the resulting mixture was stirred for 1 hour. A precipitate formed which was collected by filtration and washed with water (3×50 mL) then dried in vacuo at 50° C. to provide 1-(3-chloropyridin-2-yl)-1H-pyrazolo[3,4-d]pyrimidin-4(7H)-one (30.5 g).
$^1$H NMR (400 MHz, DMSO-$d_6$) δ 7.72 (1H, dd), 8.10 (1H, s), 8.30 (1H, dd), 8.37 (1H, s), 8.64 (1H, dd), 12.43 (1H, s), m/z (ESI+) (M+H)+=248; HPLC $t_R$=0.99 min.

Step 3: Synthesis of B15: 4-chloro-1-(3-chloropyridin-2-yl)-1H-pyrazolo[3,4-d]pyrimidine

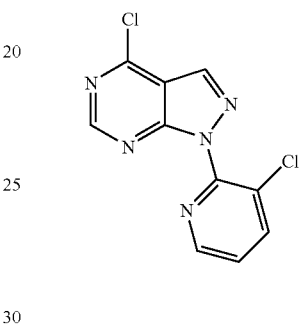

Phosphoryl trichloride (235 mL, 2455.17 mmol) was added to 1-(3-chloropyridin-2-yl)-1H-pyrazolo[3,4-d]pyrimidin-4-ol B15b (30.4 g, 122.76 mmol). The resulting solution was stirred at 100° C. for 4 hours. The mixture was concentrated in vacuo and to the residue was added an ice/water mixture. The resulting mixture was stirred for 1 hour during which time a solid precipitated. The solid was collected by filtration and washed with water (3×75 mL). The crude product was dissolved in EtOAc (500 mL) and dried over MgSO$_4$, filtered and evaporated to afford 4-chloro-1-(3-chloropyridin-2-yl)-1H-pyrazolo[3,4-d]pyrimidine (28.7 g). $^1$H NMR (400 MHz, DMSO-$d_6$) δ 7.78 (1H, dd), 8.37 (1H, dd), 8.69 (1H, dd), 8.83 (1H, s), 8.92 (1H, s), m/z (ESI+) (M+H)+=266; HPLC $t_R$=1.72 min.

Intermediate B16: 4-chloro-1-(2-chloro-4-fluorophenyl)-1H-pyrazolo[3,4-d]pyrimidine

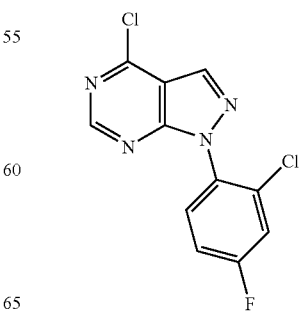

Step 1: Synthesis of B16a: 5-amino-1-(2-chloro-4-fluorophenyl)-1H-pyrazole-4-carbonitrile

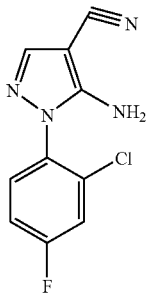

2-Chloro-4-fluorophenyl hydrazine hydrochloride (CAS 497959-29-2) (25.0 g, 126.9 mmol) was partitioned between DCM (250 mL) and 2M NaOH (100 mL). The organic phase was separated and washed sequentially with water (2×150 mL) and brine (150 mL), dried over MgSO$_4$ and evaporated to give the free base. This oil was dissolved in MeOH (200 mL) under nitrogen at −5° C. and 2-(ethoxymethylene)malononitrile (15.5 g, 127 mmol) was added portionwise. The resulting mixture was stirred at 0° C. for 2 hours then at reflux for a further 2 hours. After cooling, the mixture was evaporated to provide 5-amino-1-(2-chloro-4-fluorophenyl)-1H-pyrazole-4-carbonitrile (28.9 g).

$^1$H NMR (400 MHz, DMSO-d$_6$) δ 6.68 (2H, s), 7.37 (1H, ddd), 7.58 (1H, dd), 7.69 (1H, dd), 7.75 (1H, s), m/z (ESI+) (M+H)+=237; HPLC t$_R$=1.62 min.

Step 2: Synthesis of B16b: 1-(2-chloro-4-fluorophenyl)-1H-pyrazolo[3,4-d]pyrimidin-4(7H)-one

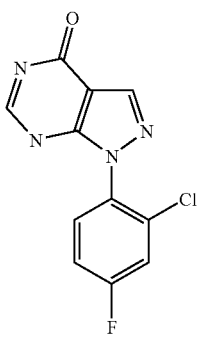

B16b (sulphate salt) was prepared in an analogous fashion to B15b from 5-amino-1-(2-chloro-4-fluorophenyl)-1H-pyrazole-4-carbonitrile B15a.

$^1$H NMR (400 MHz, DMSO-d$_6$) δ 7.44 (1H, ddd), 7.72 (1H, dd), 7.77 (1H, dd), 8.08 (1H, s), 8.33 (1H, s), 12.38 (1H, s), m/z (ESI−) (M−H)−=263; HPLC t$_R$=1.44 min.

Step 3: Synthesis of B16: 4-chloro-1-(2-chloro-4-fluorophenyl)-1H-pyrazolo[3,4-d]pyrimidine

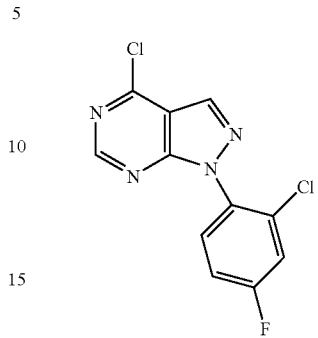

B16 was prepared in an analogous fashion to B15 (step 3) from 1-(2-chloro-4-fluorophenyl)-1H-pyrazolo[3,4-d]pyrimidin-4(7H)-one B16b.

$^1$H NMR (400 MHz, DMSO-d$_6$) δ 7.48-7.53 (1H, m), 7.79-7.83 (2H, m), 8.79 (1H, s), 8.89 (1H, s), m/z (ESI+) (M+H)+=283; HPLC t$_R$=2.39 min.

Intermediate B17: 2-(4-chloro-1H-pyrazolo[3,4-d]pyrimidin-1-yl)benzonitrile

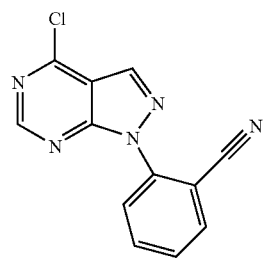

Step 1: Synthesis of B17a: 5-amino-1-(2-bromophenyl)-1H-pyrazole-4-carbonitrile

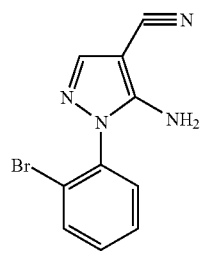

B17a was prepared in an analogous fashion to B16a from (2-bromophenyl) hydrazine hydrochloride (CAS 50709-33-6). m/z (ESI+) (M+H)$^+$=265; HPLC t$_R$=1.52 min.

Step 2: Synthesis of B17b:
1-(2-bromophenyl)-1H-pyrazolo[3,4-d]pyrimidin-4-ol

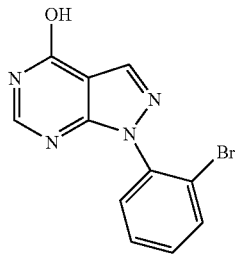

B17b (sulphate salt) was prepared in an analogous fashion to B15b from B16a.

$^1$H NMR (400 MHz, DMSO-d$_6$) δ 7.51-7.55 (1H, m), 7.56-7.61 (2H, m), 7.86-7.88 (1H, m), 8.04-8.08 (1H, m), 8.30-8.33 (1H, m), 12.35 (1H, s), m/z (ESI+) (M+H)$^+$=293; HPLC t$_R$=1.34 min.

Step 3: Synthesis of B17c: 2-(4-hydroxy-1H-pyrazolo[3,4-d]pyrimidin-1-yl)benzonitrile

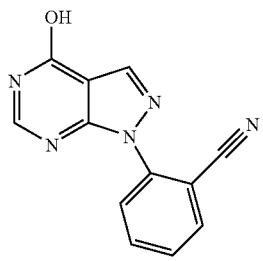

1-(2-bromophenyl)-1H-pyrazolo[3,4-d]pyrimidin-4-ol B17b (1.456 g, 5 mmol) and zinc cyanide (0.528 g, 4.50 mmol) were dissolved in DMF (15 mL) and sealed into a microwave tube. The tube was evacuated and back flushed with nitrogen several times. 9,9-Dimethyl-4,5-bis(diphenylphosphino)xanthene (0.289 g, 0.50 mmol) and tris(dibenzylideneacetone)dipalladium(0) (0.229 g, 0.25 mmol) were added. The reaction was heated to 160° C. for 10 minutes in the microwave reactor and cooled to RT. This was repeated on exactly the same scale. The two reaction mixtures were combined and diluted with EtOAc (200 mL) and water (30 mL). The biphasic mixture was filtered, and the organic phase separated and washed with brine (20 mL) then dried over MgSO$_4$, filtered and evaporated. The residue was purified by hot filtration, then crystallization from MeOH, providing 2-(4-hydroxy-1H-pyrazolo[3,4-d]pyrimidin-1-yl)benzonitrile (1.225 g). $^1$H NMR (400 MHz, DMSO-d$_6$) δ 7.70-7.75 (1H, m), 7.86-7.88 (1H, m), 7.91-7.95 (1H, m), 8.08-8.10 (1H, m), 8.17 (1H, s), 8.43 (1H, s), 12.49 (1H, s), m/z (ESI+) (M+H)+=238; HPLC t$_R$=1.15 min.

Step 4: Synthesis of B17: 2-(4-chloro-1H-pyrazolo[3,4-d]pyrimidin-1-yl)benzonitrile

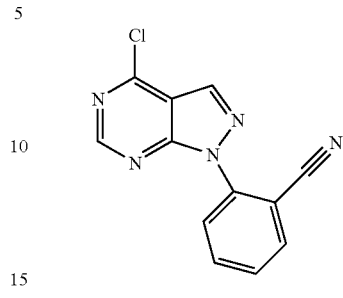

B17 was prepared in an analogous fashion to B15 from B17c. The final material was purified by flash silica chromatography, elution gradient 0 to 5% MeOH in DCM to afford B17 as a solid (0.495 g). $^1$H NMR (400 MHz, DMSO-d$_6$) δ 7.74-7.81 (1H, m), 7.96-8.02 (2H, m), 8.14-8.17 (1H, m), 8.89 (1H, s), 8.98 (1H, s), m/z (ESI+) (M+H)$^+$=256; HPLC t$_R$=1.97 min.

Intermediate D1: (2R)-2-(1-(2-chlorophenyl)-1H-pyrazolo[3,4-d]pyrimidin-4-yloxy)-3-isopropoxypropanoic acid

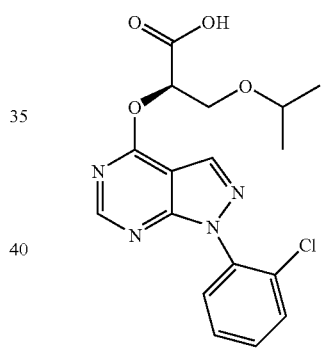

Step 1: Synthesis of D1a: (R)-methyl 2-hydroxy-3-isopropoxypropanoate

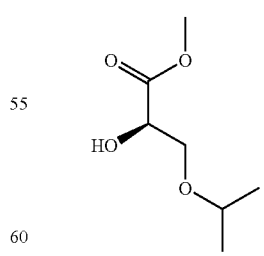

D1a was prepared in an analogous fashion to C4a from (R)-methyl oxirane-2-carboxylate (CAS 111058-32-3) and isopropanol. $^1$H NMR (400 MHz, CDCl$_3$) δ 1.12-1.16 (6H, m), 3.04-3.06 (1H, m), 3.58-3.64 (1H, m), 3.68-3.75 (2H, m), 3.80 (3H, s), 4.29-4.32 (1H, m)

Step 2: Synthesis of D1b: (2R)-methyl 2-(1-(2-chlorophenyl)-1H-pyrazolo[3,4-d]pyrimidin-4-yloxy)-3-isopropoxypropanoate

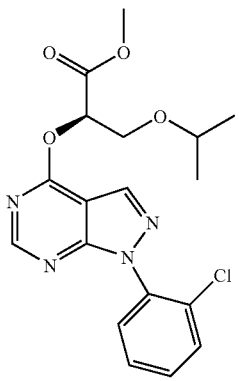

(R)-methyl 2-hydroxy-3-isopropoxypropanoate D1a (500 mg, 3.08 mmol), 4-chloro-1-(2-chlorophenyl)-1H-pyrazolo[3,4-d]pyrimidine B1 (817 mg, 3.08 mmol) and potassium carbonate (0.186 mL, 3.08 mmol) were suspended in acetonitrile (15 mL). The reaction was heated to 130° C. for 4 hours in the microwave reactor and cooled to ambient temperature. The reaction mixture was evaporated to dryness and the resulting residue was dissolved in EtOAc (25 mL), and washed sequentially with saturated NH$_4$Cl (50 mL) and saturated brine (50 mL). The organic layer was dried over MgSO$_4$, filtered and evaporated to afford crude product. Purification by flash silica chromatography, elution gradient 20 to 50% EtOAc in isohexane afforded (2R)-methyl 2-(1-(2-chlorophenyl)-1H-pyrazolo[3,4-d]pyrimidin-4-yloxy)-3-isopropoxypropanoate D1b (965 mg).

$^1$H NMR (400 MHz, CDCl$_3$) δ 1.22-1.26 (6H, m), 3.71-3.79 (1H, m), 3.80 (3H, s), 4.01-4.06 (2H, m), 5.79-5.81 (1H, m), 7.44-7.54 (3H, m), 7.61-7.63 (1H, m), 8.38 (1H, s), 8.54 (1H, s), m/z (ESI+) (M+H)+=391; HPLC t$_R$=2.51 min.

Step 3: Synthesis of D1: (2R)-2-(1-(2-chlorophenyl)-1H-pyrazolo[3,4-d]pyrimidin-4-yloxy)-3-isopropoxypropanoic acid

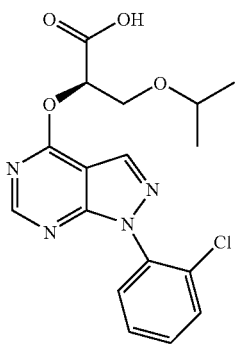

Sodium hydroxide (0.755 mL, 1.51 mmol) was added to a solution of (2R)-methyl 2-(1-(2-chlorophenyl)-1H-pyrazolo[3,4-d]pyrimidin-4-yloxy)-3-isopropoxypropanoate D1b (472 mg, 1.21 mmol) in THF (7 mL) and water (3.5 mL) at ambient temperature. The reaction mixture was stirred for 1 hour. The reaction mixture was diluted with EtOAc (50 mL) and acidified to pH 4 with 2M HCl. The organic layer was separated and the aqueous layer extracted with EtOAc (2×50 mL). The combined organics were dried over MgSO$_4$, filtered and concentrated to afford D1 (325 mg, 70% ee). $^1$H NMR (400 MHz, CDCl$_3$) δ 1.21-1.25 (6H, m), 3.73-3.81 (1H, m), 4.05-4.08 (2H, m), 5.82-5.84 (1H, m), 7.42-7.54 (3H, m), 7.58-7.61 (1H, m), 8.38 (1H, s), 8.57 (1H, s), m/z (ESI+) (M+H)+=377; HPLC t$_R$=2.15 min.

Intermediate D2: (2S)-2-(1-(2-chlorophenyl)-1H-pyrazolo[3,4-d]pyrimidin-4-yloxy)-3-isopropoxypropanoic acid

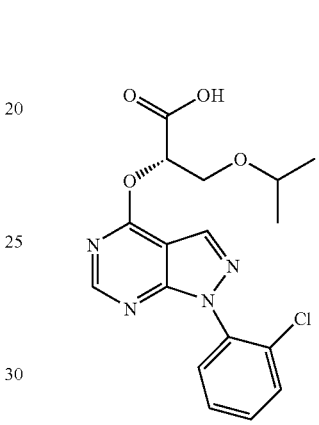

Step 1: Synthesis of D2a: (2S)-methyl 2-(1-(2-chlorophenyl)-1H-pyrazolo[3,4-d]pyrimidin-4-yloxy)-3-isopropoxypropanoate

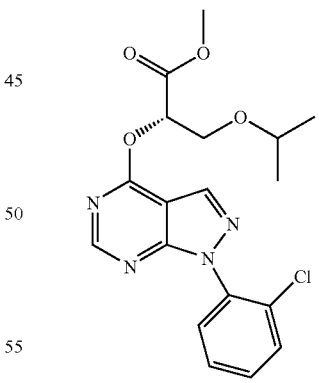

D2a was prepared in an analogous fashion to D1b from (S)-methyl 2-hydroxy-3-isopropoxypropanoate C7a and B1.

$^1$H NMR δ$_H$ (400 MHz, CDCl$_3$) 1.20-1.26 (6H, m), 3.71-3.75 (1H, m), 3.80 (3H, s), 4.01-4.08 (2H, m), 5.79-5.82 (1H, m), 7.43-7.50 (2H, m), 7.51-7.54 (1H, m), 7.60 (1H t, J=1.6 Hz), 8.37 (1H, s), 8.54 (1H, s), m/z (ESI+) (M+H)+=391; HPLC t$_R$=2.42 min

Step 2: Synthesis of D2: (2S)-2-(1-(2-chlorophenyl)-1H-pyrazolo[3,4-d]pyrimidin-4-yloxy)-3-isopropoxypropanoic acid

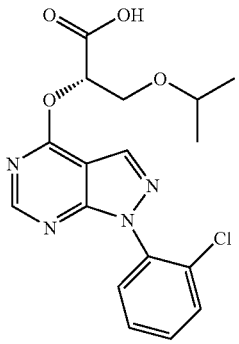

D2 was prepared in an analogous fashion to D1 from (2S)-methyl 2-(1-(2-chlorophenyl)-1H-pyrazolo[3,4-d]pyrimidin-4-yloxy)-3-isopropoxypropanoate D2a. 60% ee. $\delta_H$ (400 MHz, CDCl$_3$) 1.22-1.26 (6H, m), 3.75-3.81 (1H, m), 4.04-4.10 (2H, m), 5.83-5.86 (1H, m), 7.43-7.54 (3H, m), 7.59-7.62 (1H, m), 8.38 (1H, s), 8.57 (1H, s), m/z (ESI+) (M+H)+= 377; HPLC $t_R$=2.12 min.

Intermediate E1: (S)-2-hydroxy-3-methoxy-N-(3-methyl-1,2,4-thiadiazol-5-yl)propanamide

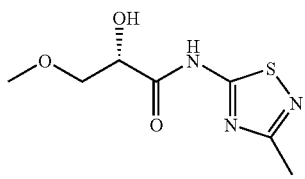

A solution of tetrabutylammonium fluoride (1M in THF) (2.353 mL, 2.35 mmol) was added in one portion to a stirred solution of (S)-2-(tert-butyldimethylsilyloxy)-3-methoxy-N-(3-methyl-1,2,4-thiadiazol-5-yl)propanamide (Intermediate E2) (390 mg, 1.18 mmol) in tetrahydrofuran (10 mL). The resulting solution was stirred at ambient temperature for 4 hours. The reaction mixture was diluted with EtOAc (20 mL), and washed sequentially with water (10 mL) and saturated brine (10 mL). The organic layer was dried (MgSO$_4$), filtered and evaporated. The residue was purified by flash silica chromatography, elution gradient 0 to 100% EtOAc in isohexane to afford (S)-2-hydroxy-3-methoxy-N-(3-methyl-1,2,4-thiadiazol-5-yl)propanamide (192 mg, 75%). $^1$H NMR (400 MHz, CDCl$_3$) δ 2.49 (3H, s), 3.37 (3H, s), 3.60 (1H, d), 3.72 (2H, d), 4.46 (1H, q), 10.20 (1H, s); m/z (ESI+) (M+H)+= 218.30; HPLC $t_R$=0.89 min.

Intermediate E2: (S)-2-(tert-butyldimethylsilyloxy)-3-methoxy-N-(3-methyl-1,2,4-thiadiazol-5-yl)propanamide

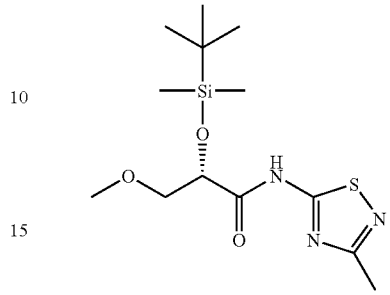

A solution of 1-chloro-N,N,2-trimethylprop-1-en-1-amine (1.521 mL, 11.50 mmol) in DCM (2 mL) was added dropwise to a stirred solution of (S)-2-(tert-butyldimethylsilyloxy)-3-methoxypropanoic acid (Intermediate C4c) (2.45 g, 10.45 mmol) in DCM (10 mL) over a period of 1 minute under nitrogen. The resulting pale yellow solution was stirred at ambient temperature for 30 minutes Anhydrous pyridine (1.262 mL, 15.68 mmol) was added in one portion (solution turns deeper yellow) followed by 3-methyl-1,2,4-thiadiazol-5-amine (CAS no. 17467-35-5) (1.204 g, 10.45 mmol) in DCM (3 mL) dropwise over a period of 1 minute. The resulting solution was stirred at ambient temperature for 1 hour. 1M citric acid (50 mL) added and extracted with EtOAc (50 mL). Organic phase washed with water (25 mL) and brine (25 mL), dried (MgSO$_4$), filtered and evaporated. The residue was purified by flash silica chromatography, elution gradient 0 to 30% EtOAc in isohexane to afford (S)-2-(tert-butyldimethylsilyloxy)-3-methoxy-N-(3-methyl-1,2,4-thiadiazol-5-yl)propanamide (390 mg, 11%). $^1$H NMR (400 MHz, CDCl$_3$) δ 0.11 (6H, dd), 0.89 (9H, s), 2.49 (3H, s), 3.30 (3H, s), 3.61 (2H, t), 4.46 (1H, dd), 9.75-9.90 (1H, s); m/z (ESI+) (M+H)+= 332.30; HPLC $t_R$=2.77 min.

Intermediate F1: (S)-2-Hydroxy-4-methoxy-N-(5-methylpyridin-2-yl)butanamide

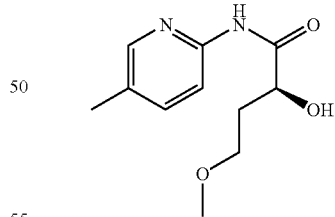

Aqueous potassium carbonate 1M (5.257 mL, 5.26 mmol) was added to a solution of (S)-4-methoxy-1-(5-methylpyridin-2-ylamino)-1-oxobutan-2-yl acetate (Intermediate F2) (170 mg, 0.64 mmol) in MeOH (0.3 mL) at 0° C. and the mixture was stirred at room temperature for 2 h. The reaction mixture was neutralized with aqueous KHSO$_4$ (1.0 M, 0.29 mL). The reaction mixture was concentrated and the residue was purified by flash silica chromatography, elution gradient 0 to 100% EtOAc in isohexane to afford (S)-2-hydroxy-4-methoxy-N-(5-methylpyridin-2-yl)butanamide (142 mg, 99%).

¹H NMR (400 MHz, CDCl₃) δ 2.02-2.11 (1H, m), 2.23-2.26 (1H, m), 2.30 (3H, s), 3.38 (3H, s), 3.64-3.75 (2H, m), 4.38-4.41 (1H, m), 4.64-4.78 (1H, m), 7.51-7.53 (1H, m), 8.13 (2H, t), 9.30 (1H, s); m/z (ESI+) (M+H)+=225; HPLC t$_R$=0.86 min.

Intermediate F2: (S)-4-methoxy-1-(5-methylpyridin-2-ylamino)-1-oxobutan-2-yl acetate

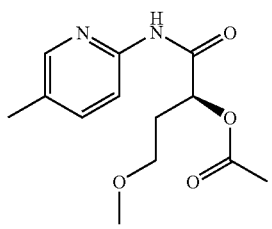

5-Methylpyridin-2-amine (CAS no. 1603-41-4) (460 mg, 4.26 mmol) was added to (S)-2-acetoxy-4-methoxybutanoic acid (Intermediate F3) (500 mg, 2.84 mmol), in THF (8 mL) under nitrogen. The resulting suspension was stirred at 23° C. for 30 minutes. 4-(4,6-Dimethoxy[1.3.5]triazin-2-yl)-4-methylmorpholinium chloride hydrate (CAS no. 3945-69-5) (1.18 g, 4.26 mmol) was added and the suspension stirred for 40 hrs. The reaction mixture was concentrated and purified by flash silica chromatography, elution gradient 0 to 50% EtOAc in isohexane to afford (S)-4-methoxy-1-(5-methylpyridin-2-ylamino)-1-oxobutan-2-yl acetate (410 mg, 54%). ¹H NMR (400 MHz, CDCl₃) δ 2.13-2.28 (5H, m), 2.30 (3H, s), 3.31 (3H, s), 3.48-3.53 (2H, m), 5.37-5.40 (1H, m), 7.50-7.53 (1H, m), 8.09-8.11 (2H, m), 8.52 (1H, s); m/z (ESI+) (M+H)+=267; HPLC t$_R$=1.22 min.

Intermediate F3: (S)-2-Acetoxy-4-methoxybutanoic acid

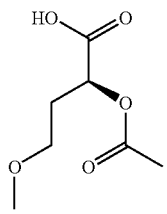

Sodium nitrate (4.93 g, 57.98 mmol) was added portionwise to (S)-2-amino-4-methoxybutanoic acid (CAS no. 3311-01-1) (3.86 g, 29.0 mmol) in acetic acid (88 mL) at room temperature (with intermittent cooling with an ice bath to keep the temperature near to room temperature). Once the addition was complete, the mixture was left to stir at room temperature for 24 h. The solvent was then removed in vacuo, the residue was dissolved in ether (250 mL), and the ethereal solution was washed with water (3×100 mL). The organic layer was extracted with saturated NaHCO₃ solution (3×100 mL). The aqueous extracts were then acidified with 2N HCl and extracted with ether (3×100 mL). The combined organic layers were dried (MgSO₄) and reduced in vacuo to give crude (S)-2-acetoxy-4-methoxybutanoic acid (0.600 g, 11.8%) which was used without further purification.

Intermediate G1: (2S)-3-Ethoxy-2-hydroxy-N-(5-methylpyridin-2-yl)propanamide

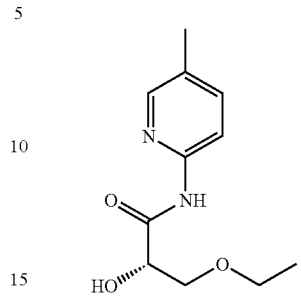

A solution of tetrabutylammonium fluoride (1M in THF) (3.25 mL, 3.25 mmol) was added in one portion to a stirred solution of (S)-2-(tert-butyldimethylsilyloxy)-3-ethoxy-N-(5-methylpyridin-2-yl)propanamide (Intermediate G2) (1.1 g, 3.25 mmol) in tetrahydrofuran (25 mL). The resulting solution was stirred at ambient temperature for 4 hours. The reaction mixture was concentrated and diluted with EtOAc (50 mL) washed sequentially with water (20 mL) and saturated brine (20 mL). The organic layer was dried (MgSO₄) and evaporated. The residue was purified by flash silica chromatography, elution gradient 50 to 100% EtOAc in isohexane to afford (2S)-3-ethoxy-2-hydroxy-N-(5-methylpyridin-2-yl)propanamide (730 mg, 100%). ¹H NMR (400 MHz, CDCl₃) δ 1.24 (3H, t), 2.30 (3H, s), 3.60 (2H, q), 3.76-3.79 (2H, m), 3.87 (1H, s), 4.33-4.38 (1H, m), 7.52 (1H, dd), 8.11-8.13 (2H, m), 9.20 (1H, s); m/z (ESI+) (M+H)+=225; HPLC t$_R$=0.96 min.

Intermediate G2: (2S)-2-(tert-butyl-dimethylsilyl)oxy-3-ethoxy-N-(5-methylpyridin-2-yl)propanamide

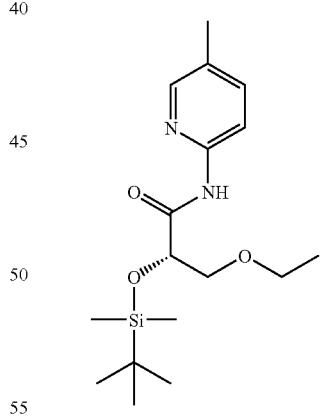

A solution of trimethylaluminium (2M in hexane, 2.75 mL, 5.49 mmol) was added dropwise to a stirred solution of 5-methylpyridin-2-amine (0.594 g, 5.49 mmol) in toluene (10 mL) cooled to 0° C., over a period of 5 minutes under nitrogen. The resulting solution was stirred for 15 minutes. A solution of (S)-methyl 2-(tert-butyldimethylsilyloxy)-3-ethoxypropanoate (Intermediate G3) (1.31 g, 4.99 mmol) in toluene (5 mL) was added dropwise over a period of 2 minutes. The resulting solution was allowed to warm to ambient temperature and then heated to reflux for 7 hours then allowed to cool to room temperature and 1M citric acid (20 mL) added, diluted with water (25 mL) and the mixture extracted with ethyl acetate (25 mL). The aqueous was re-extracted with ethyl acetate (25 mL), the organic phases combined, washed with water (5 mL) and brine (20 mL), dried over $MgSO_4$, filtered and evaporated. The residue was purified by flash silica chromatography, elution gradient 10 to 100% EtOAc in isohexane to give (2S)-2-(tert-butyl-dimethylsilyl)oxy-3-ethoxy-N-(5-methylpyridin-2-yl)propanamide (1.1 g, 65%). $^1$H NMR (400 MHz, $CDCl_3$) δ 0.18 (3H, s), 2.00 (3H, s), 0.99 (9H, s), 1.18 (3H, t), 2.30 (3H, s), 3.51-3.61 (2H, m), 3.63-3.67 (1H, m), 3.78-3.81 (1H, m), 4.41-4.43 (1H, m), 7.51 (1H, dd), 8.13-8.18 (2H, m), 9.03 (1H, s); m/z (ESI+) (M+H)+=339; HPLC $t_R$=3.31 min.

Intermediate G3: Methyl (2S)-2-(tert-butyl-dimethylsilyl)oxy-3-ethoxypropanoate

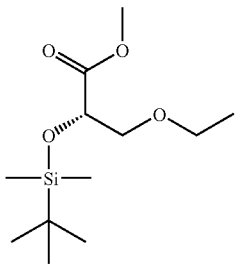

A solution of tert-butylchlorodimethylsilane (17.71 g, 117.52 mmol) in dry DMF (50 mL) was added dropwise to a stirred solution of (S)-methyl 2-hydroxy-3-ethoxypropanoate (14.51 g, 97.94 mmol) and 1H-imidazole (13.33 g, 195.87 mmol) in dry DMF (70 mL) at 20° C., over a period of 2 minutes. The resulting solution was stirred at ambient temperature for 20 hours. The reaction mixture was concentrated and diluted with EtOAc (500 mL), washed sequentially with water (4×100 mL) and saturated brine (100 mL). The organic layer was dried ($MgSO_4$) and evaporated. The residue was purified by flash silica chromatography, elution gradient 20 to 50% EtOAc in isohexane to afford methyl (2S)-2-(tert-butyl-dimethylsilyl)oxy-3-ethoxypropanoate (14.8 g, 57%). $^1$H NMR (400 MHz, $CDCl_3$) δ 0.10 (6H, d), 0.93 (9H, s), 1.19 (3H, t), 3.50-3.65 (3H, m), 3.57-3.73 (1H, m), 3.75 (3H, s), 4.37-4.40 (1H, m), 7.18 (2H, d).

Intermediate G4: Methyl (2S)-3-ethoxy-2-hydroxypropanoate

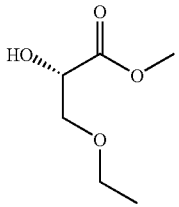

Magnesium trifluoromethanesulphonate (11.85 g, 36.73 mmol) was added in one portion to (S)-methyl oxirane-2-carboxylate (15.0 g, 146.93 mmol) and ethanol (10.29 ml, 176.32 mmol) cooled to 10° C. The resulting suspension was stirred at 10° C. for 20 minutes, allowed to warm to ambient temperature and then warmed to 50° C. for 30 hours. The mixture was allowed to cool and diluted with 9:1 DCM:ether (75 mL), filtered through Celite and washed through with 9:1 DCM:ether (3×50 mL) and evaporated. The residue was purified by flash silica chromatography, elution gradient 10 to 50% $Et_2O$ in DCM to give methyl (2S)-3-ethoxy-2-hydroxypropanoate (11.6 g, 53%). $^1$H NMR (400 MHz, $CDCl_3$) δ 1.19 (3H, t), 3.00 (1H, d), 3.47-3.58 (2H, m), 3.72 (2H, d), 3.81 (3H, s), 4.23-4.34 (1H, m).

Intermediate H1: (2S)-3-ethoxy-2-hydroxy-N-(5-methylpyrazin-2-yl)propanamide

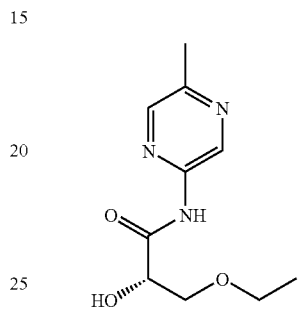

A solution of tetrabutylammonium fluoride (1M in THF) (4.27 mL, 4.27 mmol) was added in one portion to a stirred solution of (S)-2-(tert-butyldimethylsilyloxy)-3-ethoxy-N-(5-methylpyrazin-2-yl)propanamide (Intermediate H2) (1.45 g, 4.27 mmol) in tetrahydrofuran (25 mL). The resulting solution was stirred at ambient temperature for 4 hours. The reaction mixture was concentrated and diluted with EtOAc (50 mL) washed sequentially with water (20 mL) and saturated brine (20 mL). The organic layer was dried ($MgSO_4$) and evaporated. The residue was purified by flash silica chromatography eluting with 50% to 100% EtOAc in isohexane to afford (2S)-3-ethoxy-2-hydroxy-N-(5-methylpyrazin-2-yl)propanamide (700 mg, 73%). $^1$H NMR (400 MHz, $CDCl_3$) δ 1.24 (3H, t), 2.54 (3H, s), 3.49 (1H, d), 3.61 (2H, q), 3.75-3.83 (2H, m), 4.35-4.39 (1H, m), 8.14 (1H, d), 9.13 (1H, s), 9.43 (1H, d); m/z (ESI+) (M+H)+=226; HPLC $t_R$=1.00 min.

Intermediate H2: (2S)-2-(tert-butyl-dimethylsilyl)oxy-3-ethoxy-N-(5-methylpyrazin-2-yl)propanamide

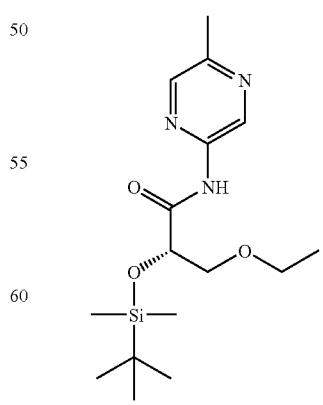

A solution of trimethylaluminium (2M in hexane, 5.51 mL, 11.02 mmol) was added dropwise to a stirred solution of 5-methylpyrazin-2-amine (CAS no. 5521-58-4) (1.20 g, 11.0 mmol) in toluene (20 mL) cooled to 0° C., over a period of 5 minutes under nitrogen. The resulting solution was stirred for 15 minutes. A solution of (S)-methyl 2-(tert-butyldimethylsilyloxy)-3-ethoxypropanoate (Intermediate G3) (2.63 g, 10.0 mmol) in toluene (5 mL) was added dropwise over a period of 2 minutes. The resulting solution was allowed to warm to ambient temperature and then heated to reflux for 3 hours. 20% Sodium potassium tartrate solution (50 mL) then water (25 mL) were added and the mixture extracted with ethyl acetate (25 mL). The aqueous was re-extracted with ethyl acetate (25 mL). The organic phases were combined, washed with water (5 mL) and brine (20 mL), dried (MgSO$_4$) and evaporated The residue was purified by flash silica chromatography, elution gradient 20 to 100% EtOAc in isohexane to give (2S)-2-(tert-butyl-dimethylsilyl)oxy-3-ethoxy-N-(5-methylpyrazin-2-yl)propanamide (1.45 g, 42%).

$^1$H NMR (400 MHz, CDCl$_3$) δ 0.18 (3H, s), 0.20 (3H, s), 0.98 (9H, s), 1.20 (3H, t), 2.54 (3H, s), 3.50-3.59 (2H, m), 3.65-3.69 (1H, m), 3.77-3.80 (1H, m), 4.42-4.44 (1H, m), 8.14 (1H, d), 9.01 (1H, s), 9.44 (1H, d); m/z (ESI+) (M+H)+= 340; HPLC t$_R$=3.04 min.

Intermediate H3: (S)—N-(5-chloropyridin-2-yl)-3-ethoxy-2-hydroxypropanamide

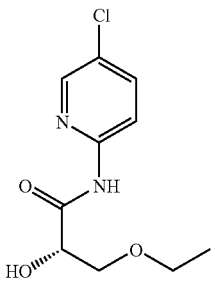

Prepared using analogous procedures to those described for G1 and G2, using 5-chloropyridine-2-amine (CAS no. 1072-98-6) and Intermediate G3. $^1$H NMR (400 MHz, CDCl$_3$) δ 1.24 (3H t), 3.57-3.64 (3H, m), 3.74-3.81 (2H, m), 4.34-4.36 (1H, m), 7.66-7.69 (1H, m), 8.21-8.23 (1H, m), 9.27 (1H, s); m/z (ESI+) (M+H)+=245; HPLC t$_R$=1.63 min.

Intermediate H4: (S)—N-(5-cyanopyridin-2-yl)-3-ethoxy-2-hydroxypropanamide

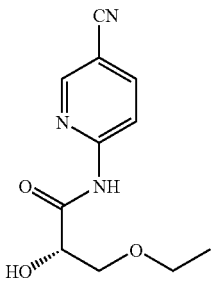

Prepared using a procedure analogous to that described for G1 and G2, using Intermediate G3 and 2-amino-5-cyanopyridine.

$^1$H NMR (400 MHz, CDCl$_3$) δ 1.24 (3H, t), 3.38 (1H, d), 3.61 (2H, q), 3.73-3.84 (2H, m), 4.37 (1H, q), 7.92-7.98 (1H, m), 8.35-8.40 (1H, m), 8.56-8.61 (1H, m), 9.44 (1H, s); m/z (ES+) (M+H)+=236.35; HPLC t$_R$=1.28 min.

Intermediate I1: 2-Hydrazinyl-3-methylpyrazine

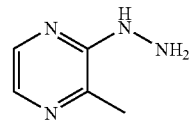

Hydrazine hydrate (9.66 mL, 311.14 mmol) was added to 2-chloro-3-methylpyrazine (CAS no. 95-58-9) (8 g, 62.23 mmol) in ethanol (25 mL). The resulting solution was stirred at 90° C. for 16 hours. The resulting solution was evaporated to dryness and the crude product was purified by crystallisation from toluene (125 mL) to afford 2-hydrazinyl-3-methylpyrazine (6.2 g, 80%). $^1$H NMR (400 MHz, DMSO-d$_6$) δ 2.24 (3H, s), 7.61 (1H, d), 7.61 (1H, d), 7.87 (1H, d).

Intermediate I2: 5-Amino-1-(3-methylpyrazin-2-yl)-1H-pyrazole-4-carbonitrile

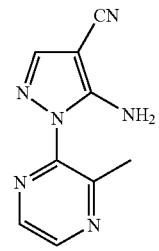

Prepared in an analogous fashion to B15a from 2-hydrazinyl-3-methylpyrazine (Intermediate I1). $^1$H NMR (400 MHz, DMSO-d$_6$) 2.45 (3H, s), 7.84 (1H, s), 8.48-8.49 (1H, m), 8.66 (1H, d), m/z (ESI+) (M+H)+=201; HPLC t$_R$=1.04 min.

Intermediate I3: 1-(3-methylpyrazin-2-yl)-1H-pyrazolo[3,4-d]pyrimidin-4(7H)-one

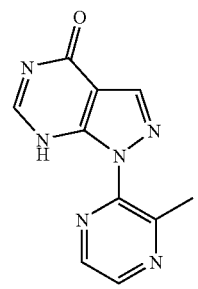

Prepared in an analogous fashion to B15b from 5-amino-1-(3-methylpyrazin-2-yl)-1H-pyrazole-4-carbonitrile (Intermediate I2). $^1$H NMR (400 MHz, DMSO-d$_6$) 2.40 (3H, s), 8.12-8.13 (1H, m), 8.41 (1H, s), 8.62 (1H, d), 8.80 (1H, d), 12.45 (1H, s); m/z (ESI+) (M+H)+=229; HPLC t$_R$=0.85 min.

Intermediate I4 : 4-Chloro-1-(3-methylpyrazin-2-yl)-1H-pyrazolo[3,4-d]pyrimidine

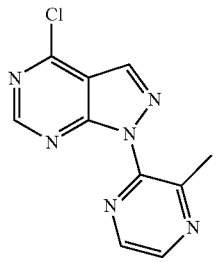

Prepared in an analogous fashion to Intermediate B15 from 1-(3-methylpyrazin-2-yl)-1H-pyrazolo[3,4-d]pyrimidin-4(7H)-one (Intermediate I3). ¹H NMR (400 MHz, DMSO-d₆) 2.43 (3H, s), 8.64-8.65 (1H, m), 8.84 (2H, t), 8.93 (1H, s); m/z (ESI+) (M+H)+=247; HPLC t_R=1.38 min.

Intermediate J1: 2-Hydrazinyl-3-methylpyridine

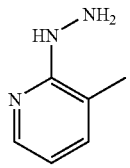

2-Bromo-3-methylpyridine (5.16 g, 30.00 mmol) and hydrazine hydrate (10.92 mL, 224.97 mmol) were mixed. The reaction was heated to 110° C. for 20 hours with stirring. The mixture was cooled to ambient temperature during which a white solid precipitated. This was then collected filtration, washed with ether (3×10 mL), slurried in DCM (50 mL), stirred for 10 minutes and then passed through a phase separation cartridge to remove water. The organic liquors were evaporated and dried under high vacuum to give 2-hydrazinyl-3-methylpyridine (2.5 g, 68%). ¹H NMR (400 MHz, CDCl₃) δ 2.08 (3H, s), 4.02 (2H, s), 5.50 (1H, s), 6.64 (1H, dd), 7.20-7.30 (1H, m), 8.08 (1H, dd). MP=119° C. (Lit 122° C.).

Intermediate J2: 5-Amino-1-(3-methylpyridin-2-yl)-1H-pyrazole-4-carbonitrile

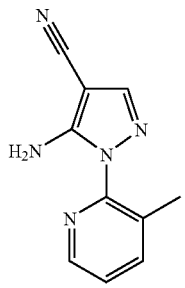

Prepared in an analogous fashion to B15a from 2-hydrazinyl-3-methylpyridine (Intermediate J1). ¹H NMR (400 MHz, DMSO-d₆) δ 2.23 (3H, s), 6.82 (2H, s), 7.42-7.45 (1H, m), 7.78 (1H, s), 7.88-7.90 (1H, m), 8.38-8.39 (1H, m). m/z (ESI+) (M+H)+=200; HPLC t_R=1.14 min.

Intermediate J3: 1-(3-methylpyridin-2-yl)-1H-pyrazolo[3,4-d]pyrimidin-4(7H)-one

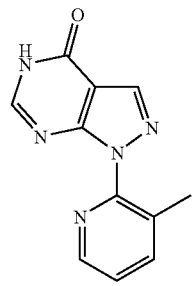

Prepared in an analogous fashion to B15b from 5-amino-1-(3-methylpyridin-2-yl)-1H-pyrazole-4-carbonitrile (Intermediate J2). ¹H NMR (400 MHz, DMSO-d₆) δ 2.08 (3H, s), 7.53-7.56 (1H, m), 7.94-7.97 (1H, d), 8.05 (1H, s), 8.31 (1H, s), 8.46-8.47 (1H, m), 12.34 (1H, s). m/z (ESI+) (M+H)+=228; HPLC t_R=0.92 min.

Intermediate J4: 4-Chloro-1-(3-methylpyridin-2-yl)-1H-pyrazolo[3,4-d]pyrimidine

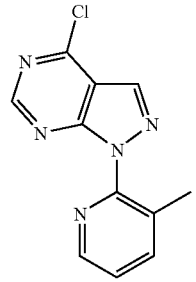

Prepared in an analogous fashion to B15 from 1-(3-methylpyridin-2-yl)-1H-pyrazolo[3,4-d]pyrimidin-4(7H)-one (Intermediate J3). ¹H NMR (400 MHz, DMSO-d₆) δ 2.12 (3H, s), 7.59-7.62 (1H, m), 8.00-8.03 (1H, m), 8.50-8.52 (1H, m), 8.76 (1H, s), 8.88 (1H, s). m/z (ESI+) (M+H)+=246; HPLC t_R=1.51 min.

Intermediate J5: (2S)-Methyl 3-isopropoxy-2-(1-(3-methylpyridin-2-yl)-1H-pyrazolo[3,4-d]pyrimidin-4-yloxy)propanoate

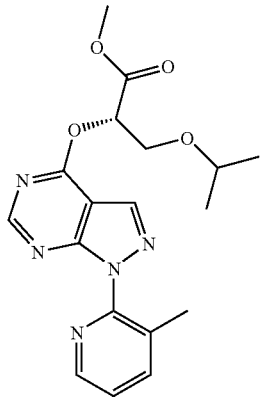

60% Sodium hydride (0.720 g, 18.00 mmol) was added to a solution of (S)-methyl 2-hydroxy-3-isopropoxypropanoate (2.353 g, 12.00 mmol) in anhydrous THF (100 mL) at 5° C., under nitrogen. The resulting suspension was stirred at 5° C. for 10 minutes and then a solution of 4-chloro-1-(3-methylpyridin-2-yl)-1H-pyrazolo[3,4-d]pyrimidine (Intermediate J4) (2.95 g, 12 mmol) in dry THF (50 mL) was added dropwise maintaining a temperature below 5° C. The reaction mixture was stirred at 5° C. for 10 mins and then allowed to warm to room temperature. The reaction was stirred at room temperature for 1 hour. The reaction mixture was neutralised with HCl (1M, aq). The majority of the THF was evaporated in vacuo and then EtOAc (75 mL) and water (50 mL) were added. The organic layer was separated and the aqueous layer re-extracted with EtOAc (2×50 mL). The combined organics were washed with saturated brine (50 mL), dried (MgSO$_4$), filtered and concentrated in vacuo. The crude product was purified by flash silica chromatography (120 g), elution gradient 30 to 80% EtOAc in isohexane to afford (2S)-methyl 3-isopropoxy-2-(1-(3-methylpyridin-2-yl)-1H-pyrazolo[3,4-d]pyrimidin-4-yloxy)propanoate (3.53 g, 79%). $^1$H NMR (400 MHz, DMSO-d$_6$) δ 1.11-1.14 (6H, m), 2.11 (3H, s), 3.68-3.74 (4H, m), 3.95-4.03 (2H, m), 5.79-5.81 (1H, m), 7.56-7.59 (1H, dd), 7.98-8.00 (1H, d), 8.49 (1H, m), 8.57 (2H, d). m/z (ESI+) (M+H)+=372; HPLC t$_R$=1.99 min.

Intermediate K1: 5-Amino-1-(5-chloro-3-(trifluoromethyl)pyridin-2-yl)-1H-pyrazole-4-carbonitrile

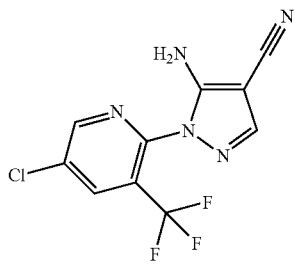

Prepared in an analogous fashion to B15a from 5-chloro-2-hydrazinyl-3-(trifluoromethyl)pyridine (CAS no. 129015-69-6). $^1$H NMR (400 MHz, DMSO) δ 6.87 (2H, s), 7.69 (1H, s), 8.58 (1H, d), 8.83 (1H, d).

Intermediate K2: 1-(5-Chloro-3-(trifluoromethyl)pyridin-2-yl)-1H-pyrazolo[3,4-d]pyrimidin-4-ol

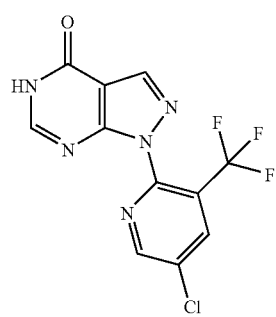

Prepared in an analogous fashion to B15b from 5-amino-1-(5-chloro-3-(trifluoromethyl)pyridin-2-yl)-1H-pyrazole-4-carbonitrile (Intermediate K1).

$^1$H NMR (400 MHz, DMSO-d$_6$) δ 8.10 (1H, s), 8.39 (1H, s), 8.80 (1H, d), 9.05 (1H, d), 12.49 (1H, s). m/z (ESI+) (M+H)+=316; HPLC t$_R$=1.48 min.

Intermediate K3: 4-Chloro-1-(5-chloro-3-(trifluoromethyl)pyridin-2-yl)-1H-pyrazolo[3,4-d]pyrimidine

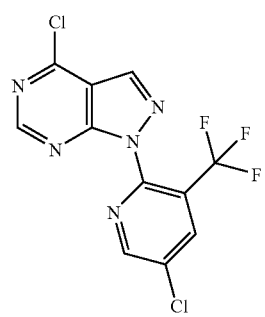

Prepared in an analogous fashion to B15 from 1-(5-chloro-3-(trifluoromethyl)pyridin-2-yl)-1H-pyrazolo[3,4-d]pyrimidin-4-ol (Intermediate K2). $^1$H NMR (400 MHz, DMSO-d$_6$) δ 8.88-8.88 (1H, m), 8.95 (1H, s), 9.10 (1H, d), 9.48 (1H, s). m/z (ESI+) (M+H)+=334; HPLC t$_R$=2.32 min. (93%)

Intermediate K4: (2S)-methyl 2-(1-(5-chloro-3-(trifluoromethyl)pyridin-2-yl)-1H-pyrazolo[3,4-d]pyrimidin-4-yloxy)-3-isopropoxypropanoate

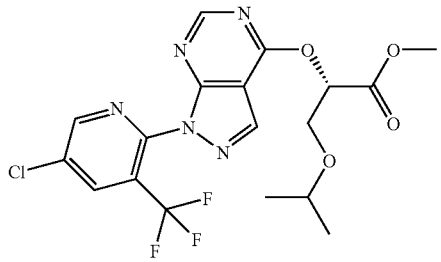

Prepared in an analogous fashion to J5 from 4-chloro-1-(5-chloro-3-(trifluoromethyl)pyridin-2-yl)-1H-pyrazolo[3,4-d]pyrimidine (Intermediate K3).

$^1$H NMR (400 MHz, DMSO-d$_6$) δ 1.10-1.14 (6H, m), 3.67-3.74 (4H, m), 3.96-4.01 (2H, m), 5.80-5.82 (1H, m), 8.60 (1H, s), 8.67 (1H, s), 8.83 (1H, d), 9.09 (1)H, d). m/z (ESI+) (M+H)+=460; HPLC t$_R$=2.65 min.

Intermediate K6: (2S)-2-(1-(5-Chloro-3-(trifluoromethyl)pyridin-2-yl)-1H-pyrazolo[3,4-d]pyrimidin-4-yloxy)-3-isopropoxy-N-(5-methylpyridin-2-yl)propanamide

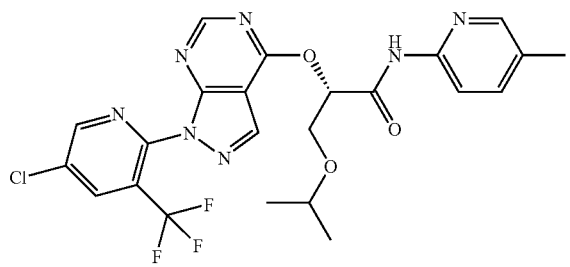

Prepared in an analogous fashion to Example 125 from (2S)-methyl 2-(1-(5-chloro-3-(trifluoromethyl)pyridin-2-yl)-1H-pyrazolo[3,4-d]pyrimidin-4-yloxy)-3-isopropoxypropanoate (Intermediate K4). $^1$H NMR (400 MHz, DMSO) δ 1.10-1.12 (6H, m), 2.24 (3H, s), 3.72-3.78 (1H, m), 3.95-4.07 (2H, m), 5.89 (1H, s), 7.58 (1H, d), 8.17 (1H, s), 8.57 (1H, s), 8.68 (1H, s), 8.83 (1H, d), 9.08 (1H, d), 10.81 (1H, s); m/z (ESI+) (M+H)+=536; HPLC t$_R$=2.72 min.

Intermediate L1: (2S)-Methyl 2-(1-(3-chloropyridin-2-yl)-1H-pyrazolo[3,4-d]pyrimidin-4-yloxy)-3-isopropoxypropanoate

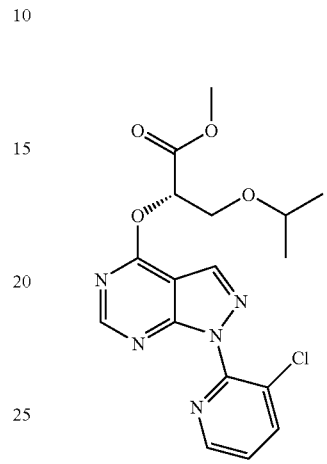

Sodium hydride (1.84 g, 45.9 mmol) was added to a stirred solution of (S)-methyl 2-hydroxy-3-isopropoxypropanoate (Intermediate C7a) (6.0 g, 30.6 mmol) in anhydrous THF (200 mL) at 0° C., under nitrogen. The resulting suspension was stirred at 0° C. for 10 minutes and then a solution of 4-chloro-1-(3-chloropyridin-2-yl)-1H-pyrazolo[3,4-d]pyrimidine (Intermediate B15) (8.14 g, 30.59 mmol) in dry THF (50 mL) was added dropwise, maintaining the temperature below 5° C. The reaction mixture was stirred at 0° C. for 10 minutes. Then allowed to warm to ambient temperature and stirred for 1 hour. The reaction mixture was neutralised with 1M HCl. The majority of the THF was evaporated in vacuo and then EtOAc (100 mL) was added. The organic layer was separated and the aqueous layer re-extracted with EtOAc (2×100 mL). The combined organics were washed with saturated brine (75 mL), dried (MgSO$_4$) and evaporated. The crude product was purified by flash silica chromatography, elution gradient 20 to 70% EtOAc in isohexane to afford (2S)-methyl 2-(1-(3-chloropyridin-2-yl)-1H-pyrazolo[3,4-d]pyrimidin-4-yloxy)-3-isopropoxypropanoate (7.76 g, 64.8%), ee 53%. A sample of this (1.48 g) was purified by preparative chiral-HPLC on a 50 mm 20um chiralcel OJ column, eluting with 30% isopropanol in isohexane (modified with 0.1% TEA), to give (2S)-methyl 2-(1-(3-chloropyridin-2-yl)-1H-pyrazolo[3,4-d]pyrimidin-4-yloxy)-3-isopropoxypropanoate (1.03 g, 99% ee). $^1$H NMR (400 MHz, DMSO-d$_6$) δ 1.10-1.14 (6H, m), 3.68-3.75 (4H, m), 3.98-4.00 (2H, m), 5.80-5.82 (1H, m), 7.74-7.77 (1H, m), 8.33-8.35 (1H, d), 8.59 (1H, s), 8.64 (1H, s), 8.67-8.68 (1H, m); m/z (ESI+) (M+H)+=392; HPLC t$_R$=2.13 min.

Intermediate L2: Methyl (2S)-2-[1-(3-chloropyridin-2-yl)pyrazolo[4,5-e]pyrimidin-4-yl]oxy-3-ethoxypropanoate

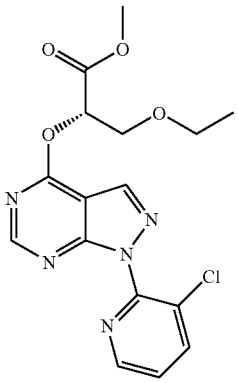

60% sodium hydride in mineral oil (0.96 g, 24.1 mmol) was added portionwise to (S)-methyl 3-ethoxy-2-hydroxypropanoate (Intermediate G4) (2.97 g, 20.1 mmol) in tetrahydrofuran (50 mL) cooled to 0° C. over a period of 1 minute under nitrogen. The resulting solution was stirred at 0° C. for 10 minutes. A solution of 4-chloro-1-(3-chloropyridin-2-yl)-1H-pyrazolo[3,4-d]pyrimidine (Intermediate B15) (5.87 g, 22.1 mmol) in tetrahydrofuran (50 mL) was added dropwise over a period of 2 minutes. The resulting mixture was allowed to warm to ambient temperature and stirred for 2 hour. The reaction was cooled to ~10° C., 1M citric acid (20 mL) added and the mixture was extracted with EtOAc (2×50 mL). The organic extracts were washed with water (25 mL) and saturated brine (25 mL), dried over MgSO$_4$, filtered and evaporated. The residue was purified by flash silica chromatography, elution gradient 50 to 100% EtOAc in isohexane to give the methyl (2S)-2-[1-(3-chloropyridin-2-yl)pyrazolo[4,5-e]pyrimidin-4-yl]oxy-3-ethoxypropanoate (5.7 g, 70% ee). This was further purified by chiral HPLC on Chiralcel OJ eluting with isohexane/isopropanol/triethylamine (70:30:0.1) at 60 mL/min. to give the enantiomerically pure product (3.8 g, 50%) as a colourless gum. $^1$H NMR (400 MHz, CDCl$_3$) δ 1.25 (3H, t), 3.60-3.73 (2H, m), 3.79 (3H, s), 4.00-4.11 (2H, m), 5.85 (1H, dd), 7.45 (1H, dd), 8.00 (1H, dd), 8.42 (1H, s), 8.58 (1H, s), 8.61 (1H, dd), m/z (ESI+) (M+H)+=378; HPLC t$_R$=1.84 min.

Intermediate M1: 4-Chloro-1-(3-methylpyridin-4-yl)pyrazolo[5,4-d]pyrimidine

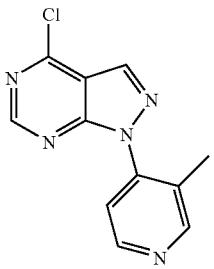

Phosphoryl trichloride (7.59 mL, 79.2 mmol) was added to 1-(3-methylpyridin-4-yl)-7H-pyrazolo[4,5-e]pyrimidin-4-one (Intermediate M2) (900 mg, 3.96 mmol) and the resulting suspension was stirred at 100° C. for 24 hours during which a solution formed. This was evaporated, triturated with ether (3×10 mL) and dried in vacuo. The resulting solid was suspended in DCM (50 mL) and stirred with 10 g of polymer supported carbonate for 2 hours. The mixture was filtered and evaporated to afford 4-chloro-1-(3-methylpyridin-4-yl)pyrazolo[5,4-d]pyrimidine (700 mg, 72%). $^1$H NMR (400 MHz, DMSO-d$_6$) δ 2.25 (3H, s), 7.62 (1H, d), 8.64 (1H, d), 8.74 (1H, s), 8.83 (1H, s), 8.94 (1H, s); m/z (ESI+) (M+H)+=246; HPLC t$_R$=1.22 min.

Intermediate M2: 1-(3-Methylpyridin-4-yl)-7H-pyrazolo[4,5-e]pyrimidin-4-one

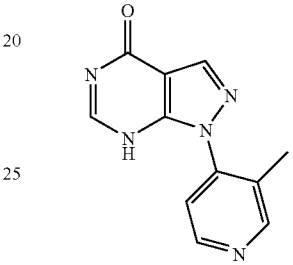

Concentrated sulphuric acid (0.241 mL, 4.52 mmol) was added to a stirred solution of 5-amino-1-(3-methylpyridin-4-yl)-1H-pyrazole-4-carbonitrile (Intermediate M3) (900 mg, 4.52 mmol) in formic acid (10 mL) and the resulting solution stirred at 100° C. for 3 hours. The mixture was cooled and evaporated to ~half volume, water (10 mL) added and stirred. The mixture was adjusted to pH 3-4 with 2M NaOH and stirred for 1 hour. The solid that formed was collected by filtration, washed with water (2×7.5 mL), acetonitrile (10 mL) and diethyl ether (2×10 mL) and dried to afford 1-(3-methylpyridin-4-yl)-7H-pyrazolo[4,5-e]pyrimidin-4-one (750 mg, 71%). $^1$H NMR (400 MHz, DMSO-d$_6$) δ 2.22 (3H, s), 7.51 (1H, d), 8.13 (1H, s), 8.38 (1H, s), 8.59 (1H, d), 8.68 (1H, s), 12.48 (1H, s), m/z (ESI+) (M+H)+=228; HPLC t$_R$=0.73 min.

Intermediate M3: 5-Amino-1-(3-methylpyridin-4-yl)pyrazole-4-carbonitrile

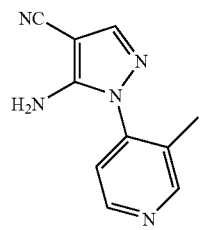

4-Hydrazinyl-3-methylpyridine (CAS no. 114913-51-8) (700 mg, 5.68 mmol) was suspended in MeOH (30 mL) under nitrogen at −5° C. 2-(ethoxymethylene)malononitrile (694 mg, 5.68 mmol) was added portionwise over 2 mins and the mixture stirred at ~0° C. for 0.5 hours then heated at reflux for 2 hours. The mixture was allowed to cool and was then evaporated under reduced pressure to afford the crude 5-amino-1-(3-methylpyridin-4-yl)pyrazole-4-carbonitrile which was used without further purification. ¹H NMR (400 MHz, DMSO-d₆) δ 2.09 (3H, m), 7.07 (1H, d), 7.87 (2H, m), 7.98 (1H, d), 10.22 (1H, s).

Intermediate N1: 1-(2-(methylsulfonyl)phenyl)-1H-pyrazolo[3,4-d]pyrimidin-4(5H)-one

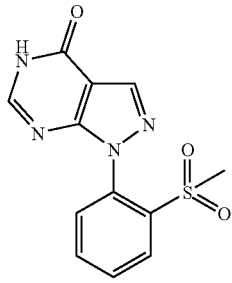

Prepared in an analogous fashion to B15b from N2. ¹H NMR (400 MHz, DMSO-d₆) δ 3.36 (3H, s), 7.69-7.71 (1H, m), 7.85-7.89 (1H, m), 7.92-7.96 (1H, m), 8.06-8.07 (1H, m), 8.15-8.17 (1H, m), 8.33 (1H, s), 12.36 (1H, s). m/z (ESI+) (M+H)+=291; HPLC $t_R$=0.96 min.

Intermediate N2: 5-Amino-1-(2-(methylsulfonyl)phenyl)-1H-pyrazole-4-carbonitrile

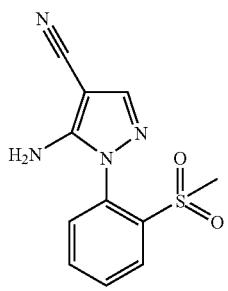

Prepared in an analogous fashion to B15a from (2-methanesulfonyl)phenylhydrazine (CAS no. 704-42-7). ¹H NMR (400 MHz, DMSO-d₆) δ 3.26 (3H, s), 6.62 (2H, s), 7.53-7.55 (1H, m), 7.79 (1H, s), 7.79-7.83 (1H, m), 7.86-7.90 (1H, m), 8.09-8.12 (1H, m). m/z (ESI+) (M+H)+=263; HPLC $t_R$=1.11 min.

Intermediate O1: (2S)-5-(tert-butyl-dimethylsilyl)oxy-2-[1-(3-chloropyridin-2-yl)pyrazolo[4,5-e]pyrimidin-4-yl]oxy-N-(5-methylpyridin-2-yl)pentanamide A solution of trimethylaluminium (2M in hexane) (0.491 mL, 0.98 mmol) was added dropwise to a stirred solution of 5-methylpyridin-2-amine (92 mg, 0.85 mmol) in toluene (5 mL) cooled to 0° C., over a period of 1 minute under nitrogen. The resulting solution was stirred at 0° C. for 20 minutes. A solution of (2S)-methyl 5-(tert-butyldimethylsilyloxy)-2-(1-(3-chloropyridin-2-yl)-1H-pyrazolo[3,4-d]pyrimidin-4-yloxy)pentanoate (Intermediate O2) (420 mg, 0.85 mmol) in toluene (5 mL) was added dropwise over a period of 2 minutes. The resulting solution was stirred at 0° C. for 10 minutes allowed to warm to ambient temperature and then heated at 60° C. for 20 hours. The mixture was cooled and 1M citric acid (10 mL) added with vigorous stirring. The mixture was diluted with ethyl acetate (35 mL), washed with water (10 mL) and brine (10 mL), dried (MgSO₄) and evaporated. The crude product was purified by flash silica chromatography, eluting with 50 to 100% ethyl acetate in isohexane to give the product (180 mg, 37%). ¹H NMR (400 MHz, CDCl₃) δ 0.04 (3H, s), 0.05 (3H, s), 0.89 (9H, s), 1.78-1.81 (2H, m), 2.20-2.30 (2H, m), 2.29 (3H, s), 3.71 (2H, t), 5.90-5.93 (1H, m), 7.45 (1H, dd), 7.51 (1H, dd), 7.99 (1H, dd), 8.07-8.08 (1H, m), 8.14 (1H, d), 8.42 (1H, s), 8.53 (1H, s), 8.60 (1H, dd), 8.62 (1H, s); m/z (ESI+) (M+H)+=568; HPLC $t_R$=3.33 min.

Intermediate O2: Methyl (2S)-5-(tert-butyl-dimethyl-silyl)oxy-2-[1-(3-chloropyridin-2-yl)pyrazolo[4,5-e]pyrimidin-4-yl]oxypentanoate

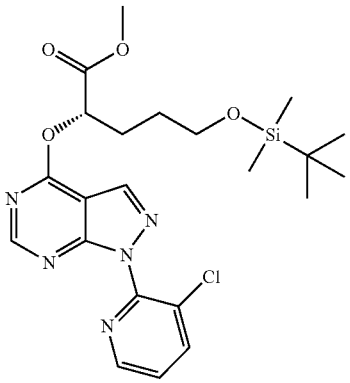

60% Sodium hydride in mineral oil (0.256 g, 6.40 mmol) was added portionwise to methyl 5-(tert-butyldimethylsilyloxy)-2-hydroxypentanoate (Intermediate O3) (1.4 g, 5.34 mmol) in tetrahydrofuran (7 mL) cooled to 0° C. over a period of 1 minute under nitrogen. The resulting solution was stirred at 0° C. for 10 minutes. A solution of 4-chloro-1-(3-chloropyridin-2-yl)-1H-pyrazolo[3,4-d]pyrimidine (1.562 g, 5.87 mmol) in tetrahydrofuran (7 mL) was added dropwise over a period of 2 minutes, the mixture was allowed to warm to ambient temperature and stirred for 2 hours. The mixture was cooled to 10° C., 1M citric acid (20 mL) was added and extracted with ethyl acetate (2×50 mL). Organic extracts washed with water (25 mL) and saturated brine (25 mL), dried (MgSO$_4$) and evaporated. The crude product was purified by flash silica chromatography, eluting with 30 to 100% ethyl acetate in isohexane to give the racemic product. This was purified by chiral HPLC to afford the product (850 mg, 32%). $^1$H NMR (400 MHz, CDCl$_3$) δ 0.08 (6H, s), 0.90 (9H, s), 1.80-1.90 (2H, m), 2.16-2.24 (2H, m), 3.72 (2H, t), 3.77 (3H, s), 5.62 (1H, t), 7.47 (1H, dd), 7.99 (1H, dd), 8.36 (1H, s), 8.57 (1H, s), 8.59 (1H, dd); m/z (ESI+) (M+H)+=492; HPLC tR=3.32 min.

Intermediate O3: Methyl 5-(tert-butyl-dimethylsilyl)oxy-2-hydroxypentanoate

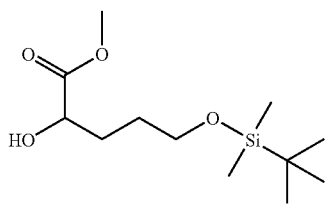

A solution of 1.6M butyllithium (6.42 mL, 10.27 mmol) was added dropwise to a stirred solution of diisopropylamine (1.583 mL, 11.20 mmol) in THF (20 mL) cooled to −78° C., over a period of 2 minutes under nitrogen. The resulting solution was stirred at −78° C. for 10 minutes and a solution of methyl 5-(tert-butyldimethylsilyloxy)pentanoate (Intermediate O4) (2.3 g, 9.33 mmol) in THF (10 mL) was added dropwise over a period of 5 minutes. The resulting solution was stirred at −78° C. for 10 minutes and then warmed to ambient temperature. The enolate solution was added dropwise over a period of 10 minutes to iodine (2.65 g, 10.45 mmol) in THF (20 mL) at −78° C. under nitrogen, stirred for 10 minutes and allowed to warm to ambient temperature. The mixture was re-cooled to −78° C., poured into 1M citric acid (50 mL) and extracted with ether (2×75 mL). The organic extracts were washed with 1M sodium metabisulfite (50 mL), water and brine, dried (MgSO$_4$) and evaporated. The residue was dissolved in 1:1 diethyl ether acetonitrile (60 mL), (2,2,2-trifluoroacetoxy)silver (2.350 g, 10.64 mmol) and silver(I) oxide (3.46 g, 14.93 mmol) were added and the mixture was stirred for 20 hours at room temperature. The mixture was filtered, evaporated. The residue was purified by flash silica chromatography, eluting with 30 to 60% ethyl acetate in isohexane to afford the product (1.4 g). $^1$H NMR (400 MHz, CDCl$_3$) δ 0.06 (6H, s), 0.90 (9H, s), 1.56-1.80 (3H, m), 1.83-1.95 (1H, m), 3.22 (1H, d), 3.66 (2H, t), 3.78 (3H, s), 4.23-4.30 (1H, m)

Intermediate O4: methyl 5-(tert-butyl-dimethylsilyl)oxypentanoate

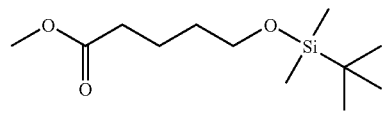

A solution of tert-butylchlorodimethylsilane (27.1 g, 179.79 mmol) in DCM (50 mL) was added dropwise to a stirred solution of methyl 5-hydroxypentanoate (CAS no. 14273-92-8, Huckstep, M.; Taylor, R. J. K.; Caton, M. P. L. Synthesis 1982, 10, 881) (19.8 g, 149.82 mmol) and 1H-imidazole (15.30 g, 224.73 mmol) in DCM (200 mL) at 5° C., over a period of 10 minutes under nitrogen. The resulting suspension was stirred at ambient temperature for 6 hours. The reaction mixture was diluted with DCM (250 mL), and washed sequentially with water (2×200 mL) and saturated brine (200 mL). The organic layer was dried (MgSO$_4$) and evaporated. The residue was purified by flash silica chromatography, eluting with 10 to 50% ethyl acetate in isohexane to afford the product (19.3 g, 52%).
$^1$H NMR (400 MHz, CDCl$_3$) δ 0.05 (6H, s), 0.90 (9H, s), 1.50-1.59 (2H, m), (2H, m), 1.65-1.72 (2H, m), 2.35 (2H, t), 3.62 (2H, t), 3.65 (3H, s).

Intermediate P1: 4-Chloro-1-[2-(trifluoromethyl)phenyl]pyrazolo[5,4-d]pyrimidine

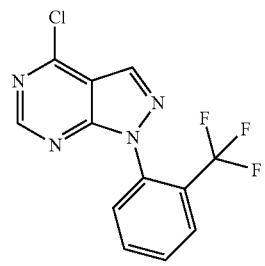

Phosphoryl trichloride (34.2 ml, 356.88 mmol) was added to 1-(2-(trifluoromethyl)phenyl)-1H-pyrazolo[3,4-d]pyrimidin-4-ol (Intermediate P2) (5.0 g, 17.84 mmol). The resulting solution was stirred at 100° C. for 4 hours. The mixture was evaporated and the residue added to ice (~200 g) with vigorous stirring. The mixture was stirred for 30 mins and the solid was collected by filtration washed with water (3×50 mL) and dried by suction. The solid was dissolved in ethyl acetate (250 mL), dried (MgSO₄) and evaporated to give the product (4.5 g, 85%). ¹H NMR (400 MHz, DMSO) δ 7.75-7.80 (1H, m), 7.88-7.91 (1H, m), 7.95-7.98 (1H, m), 8.05-8.07 (1H, m), 8.79 (1H, s), 8.88 (1H, s); m/z (ESI+) (M+H)+=299; HPLC tR=2.39 min.

Intermediate P2: 1-[2-(trifluoromethyl)phenyl]-5H-pyrazolo[4,5-e]pyrimidin-4-one

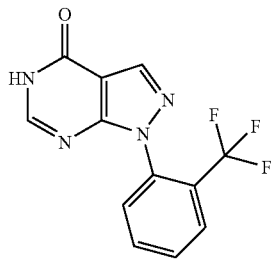

Concentrated sulfuric acid (5.43 mL, 101.96 mmol) in was added to a stirred solution of 5-amino-1-(2-(trifluoromethyl)phenyl)-1H-pyrazole-4-carbonitrile (Intermediate P3) (14.3 g, 56.70 mmol) in formic acid (100 mL). The resulting solution was stirred at 100° C. for 4 hours. The mixture was evaporated to approximately half its original volume and water (75 mL) was added. The mixture was stirred for 1 hour, and the solid was collected by filtration, washed with water (3×30 mL) and dried in vacuo at 50° C. to give the product (10.2 g, 64%). ¹H NMR (400 MHz, DMSO) δ 7.67 (1H, d), 7.85-7.92 (1H, m), 7.93-7.97 (1H, m), 7.98-8.01 (1H, m), 8.05 (1H, s), 8.32 (1H, s), 12.37 (1H, s); m/z (ESI+) (M+H)+= 281; HPLC tR=1.45 min.

Intermediate P3: 5-amino-1-[2-(trifluoromethyl)phenyl]pyrazole-4-carbonitrile

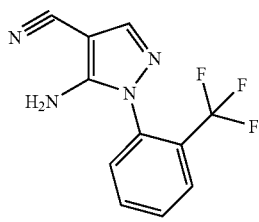

(2-(Trifluoromethyl)phenyl)hydrazine (CAS no. 365-34-4) (10.0 g, 56.77 mmol) was dissolved in MeOH (150 mL) under nitrogen at 0° C. 2-(ethoxymethylene)malononitrile (6.93 g, 56.77 mmol) added portionwise over 2 mins and the mixture stirred at ~0° C. for 0.5 hours. The reaction was heated at reflux for 2 hours. Further methanol (15 mL) was added to aid mobility. The mixture was allowed to cool and was evaporated to give the product (14.3 g, 100%) which was used without further purification. ¹H NMR (400 MHz, DMSO) δ 6.63 (2H, s), 7.53 (1H, d), 7.73 (1H, s), 7.74-7.77 (1H, m), 7.82-7.86 (1H, m), 7.91-7.94 (1H, m); m/z (ESI+) (M+H)+=253; HPLC tR=1.60 min.

Intermediate Q1: Methyl (2S)-3-ethoxy-2-[1-[3-(trifluoromethyl)pyridin-2-yl]pyrazolo[4,5-e]pyrimidin-4-yl]oxypropanoate

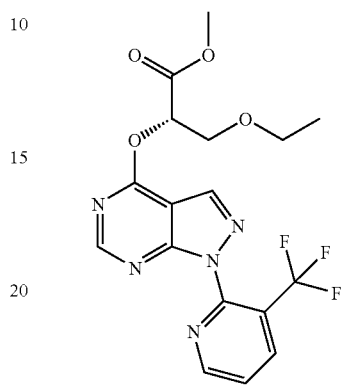

(2S)-Methyl 2-(1-(5-chloro-3-(trifluoromethyl)pyridin-2-yl)-1H-pyrazolo[3,4-d]pyrimidin-4-yloxy)-3-ethoxypropanoate (Intermediate Q2) (800 mg, 1.79 mmol) and 10% palladium on carbon (200 mg) in MeOH (30 mL) was stirred under an atmosphere of hydrogen for 24 hours. The mixture was filtered, 10% palladium on carbon (200 mg) and ammonium formate (1.0 g) were added and the mixture was heated to reflux for 2 hours. The mixture was allowed to cool and was filtered and evaporated. The residue was purified by flash silica chromatography, eluting with 50 to 100% ethyl acetate in isohexane to afford the product (400 mg, 54%). ¹H NMR (400 MHz, CDCl₃) δ 1.25 (3H, t), 3.62-3.73 (2H, m), 3.79 (3H, s), 4.00-4.11 (2H, m), 5.84 (1H, dd), 7.63-7.66 (1H, m), 8.27-8.29 (1H, m), 8.38 (1H, s), 8.58 (1H, s), 8.88-8.89 (1H, m); m/z (ESI+) (M+H)+=412; HPLC tR=2.13 min.

Intermediate Q2: Methyl (2S)-2-[1-[5-chloro-3-(trifluoromethyl)pyridin-2-yl]pyrazolo[4,5-e]pyrimidin-4-yl]oxy-3-ethoxypropanoate

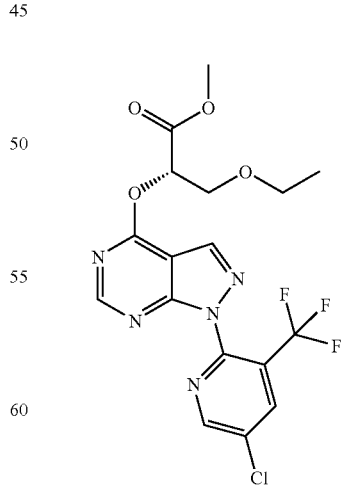

60% Sodium hydride in mineral oil (0.316 g, 7.90 mmol) was added portionwise to (S)-methyl 3-ethoxy-2-hydroxypropanoate (Intermediate G4) (0.976 g, 6.59 mmol) in tetrahydrofuran (50 mL) cooled to 5° C. over a period of 1 minute under nitrogen. The resulting solution was stirred at 0° C. for 10 minutes. A solution of 4-chloro-1-(5-chloro-3-(trifluoromethyl)pyridin-2-yl)-1H-pyrazolo[3,4-d]pyrimidine (Intermediate K3) (1.1 g, 3.29 mmol) was added portionwise over a period of 1 minute. The resulting mixture was allowed to warm to ambient temperature and stirred for 2 hours. The mixture was cooled to 10° C., quenched with 1M citric acid (20 mL) and extracted with ethyl acetate (2×50 mL). The combined organic extracts were washed with water (25 mL) and saturated brine (25 mL), dried (MgSO$_4$) and evaporated. The crude product was purified by flash silica chromatography, eluting with 20 to 50% ethyl acetate in isohexane to give the product (1.1 g, 73%). $^1$H NMR (400 MHz, CDCl$_3$) δ 1.25 (3H, t), 3.72 (2H, d), 3.81 (3H, s), 3.99-4.13 (2H, m), 5.84 (1H, dd), 8.22-8.24 (1H, m), 8.38 (1H, s), 8.57 (1H, s), 8.81-8.82 (1H, m); m/z (ESI+) (M+H)+=446; HPLC tR=2.52 min.

Intermediate R1: (2S)-3-cyclobutyloxy-2-hydroxy-N-(5-methylpyrazin-2-yl)propanamide

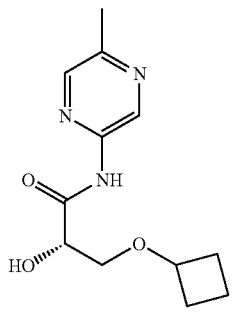

A solution of tetrabutylammonium fluoride (1M in THF) (7.39 mL, 7.39 mmol) was added in one portion to a stirred solution of (S)-2-(tert-butyldimethylsilyloxy)-3-cyclobutoxy-N-(5-methylpyrazin-2-yl)propanamide (Intermediate R2) (2.7 g, 7.39 mmol) in tetrahydrofuran (25 mL) and the resulting solution was stirred at ambient temperature for 4 hours. The reaction mixture was concentrated under vacuum, diluted with ethyl acetate (50 mL) and washed sequentially with water (20 mL) and saturated brine (20 mL). The organic layer was dried (MgSO$_4$) and evaporated. The residue was purified by flash silica chromatography, eluting with ethyl acetate to afford the product (1.5 g, 81%). $^1$H NMR (400 MHz, CDCl$_3$) δ 1.48-1.56 (1H, m), 1.70-1.76 (1H, m), 1.90-2.00 (2H, m), 2.19-2.26 (2H, m), 2.54 (3H, s), 3.61 (1H, d), 3.67-3.73 (2H, m), 3.97-4.05 (1H, m), 4.35-4.38 (1H, m), 8.14 (1H, d), 9.15 (1H, s), 9.43 (1H, d); m/z (ESI+) (M+H)+=252; HPLC t$_R$=1.31 min.

Intermediate R2: (2S)-2-(tert-butyl-dimethylsilyl)oxy-3-cyclobutyloxy-N-(5-methylpyrazin-2-yl)propanamide

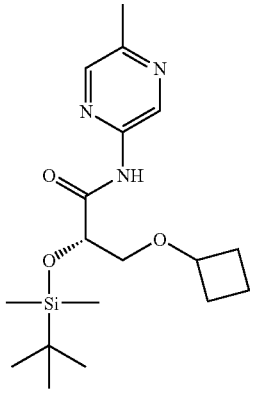

A solution of trimethylaluminium (2M in hexane) (11.44 mL, 22.88 mmol) was added dropwise to a stirred solution of 5-methylpyrazin-2-amine (CAS no. 5521-58-4) (2.497 g, 22.88 mmol) in toluene (50 mL) cooled to 0° C., over a period of 5 minutes under nitrogen.

The resulting solution was stirred at 0° C. for 15 minutes. A solution of (S)-methyl 2-(tert-butyldimethylsilyloxy)-3-cyclobutoxypropanoate (Intermediate R3) (6.0 g, 20.80 mmol) in toluene (10 mL) was added dropwise over a period of 2 minutes. The resulting solution was allowed to warm to ambient temperature and then heated to reflux for 2 hours. The mixture was allowed to cool, 20% sodium potassium tartrate (50 mL) and water (25 mL) were added and the mixture extracted with ethyl acetate (25 mL). The aqueous was re-extracted with ethyl acetate (25 mL). The organic phases were combined, washed with water (5 mL) and brine (20 mL), dried (MgSO$_4$) and evaporated. The crude product was purified by flash silica chromatography, eluting with 20 to 100% ethyl acetate in isohexane to give the product (2.7 g, 36%). $^1$H NMR (400 MHz, CDCl$_3$) δ 0.19 (3H, s), 2.00 (3H, s), 0.99 (9H, s), 1.48-1.51 (1H, m), 1.67-1.70 (1H, m), 1.91-1.94 (2H, m), 2.16-2.21 (2H, m), 2.54 (3H, s), 3.55 (1H, dd), 3.69 (1H, dd), 3.93-3.97 (1H, m), 4.39-4.41 (1H, m), 8.14 (1H, d), 9.00 (1H, s), 9.43 (1H, d); m/z (ESI+) (M+H)+=366; HPLC t$_R$=3.28 min.

Intermediate R3: (S)-methyl 2-(tert-butyldimethylsilyloxy)-3-cyclobutoxypropanoate

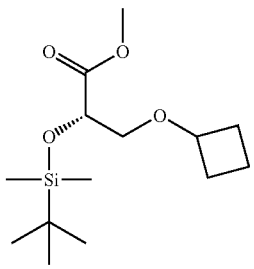

Prepared using a procedure analogous to that described for Intermediate C7a using cyclobutanol. $^1$H NMR (400 MHz, DMSO) δ 0.00 (d, 6H), 0.81 (s, 9H), 1.31-1.44 (m, 1H), 1.50-1.60 (m, 1H), 1.65-1.79 (m, 2H), 2.01-2.11 (m, 2H), 3.35-3.45 (m, 2H), 3.59 (s, 3H), 3.83-3.92 (m, 1H), 4.27-4.32 (m, 1H); m/z (EI+) M-C4H9=231.1069; GC tR=10.95 min.

Intermediate R4: (S)-2-(tert-butyldimethylsilyloxy)-3-cyclobutoxypropanoic acid

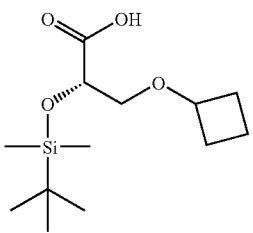

Lithium iodide (1.986 g, 14.84 mmol) was added to (S)-methyl 2-(tert-butyldimethylsilyloxy)-3-cyclobutoxypropanoate (Intermediate R3) (1.07 g, 3.71 mmol) in ethyl acetate (15 mL). The resulting suspension was protected from light and stirred at reflux (75° C.) for 6 hours. The reaction mixture was diluted with ethyl acetate (75 mL) washed sequentially with 1M sodium metabisulphite (25 mL), water (25 mL) and saturated brine (25 mL). The organic layer was dried (MgSO4) and evaporated to afford the crude product (0.920 g, 90%) that was used without further purification. $^1$H NMR (400 MHz, DMSO) δ 0.09 (d, 6H), 0.91 (s, 9H), 1.40-1.54 (m, 1H), 1.59-1.71 (m, 1H), 1.75-1.90 (m, 2H), 2.10-2.22 (m, 2H), 3.40-3.57 (m, 2H), 3.90-4.02 (m, 1H), 4.25-4.31 (m, 1H), 12.55 (s, 1H); m/z (EI+) M+=274; GC tR=11.09 min.

Intermediate R5: (S)-2-(tert-butyldimethylsilyloxy)-3-cyclobutoxy-N-(5-methylpyridin-2-yl)propanamide

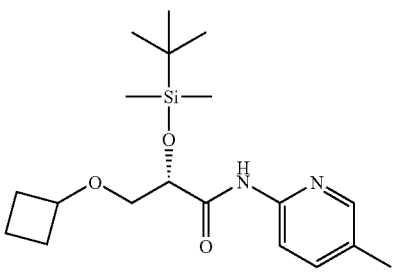

1-Chloro-N,N,2-trimethylprop-1-en-1-amine (0.133 mL, 1.00 mmol) was added to a stirred solution of (S)-2-(tert-butyldimethylsilyloxy)-3-cyclobutoxypropanoic acid (Intermediate R4) (250 mg, 0.91 mmol) in DCM (5 mL) at room temperature under nitrogen. The resulting solution was stirred at room temperature for 30 minutes. Pyridine (0.147 mL, 1.82 mmol) was added followed by a solution of 5-methylpyridin-2-amine (108 mg, 1.00 mmol) in DCM (5 mL) and the resulting solution was stirred at ambient temperature for 1 hour. 1M citric acid (10 mL) and DCM (50 mL) were added and the phases were separated. The organic phase washed with water (10 mL) and brine (10 mL), dried (MgSO4), filtered and evaporated. The crude product was purified by flash silica chromatography, eluting with 0 to 30% ethyl acetate in isohexane to afford the product (195 mg, 58.7%). $^1$H NMR (400 MHz, DMSO) δ 0.01 (d, 6H), 0.80 (s, 9H), 1.24-1.37 (m, 1H), 1.43-1.53 (m, 1H), 1.59-1.72 (m, 2H), 1.94-2.06 (m, 2H), 2.13 (s, 3H), 3.33-3.44 (m, 2H), 3.77-3.87 (m, 1H), 4.29-4.34 (m, 1H), 7.49-7.54 (m, 1H), 7.86 (d, 1H), 8.02-8.06 (m, 1H), 9.25 (s, 1H); m/z (ESI+) (M+H)+=365.47; HPLC tR=3.60 min.

Intermediate R6: (S)-3-cyclobutoxy-2-hydroxy-N-(5-methylpyridin-2-yl)propanamide

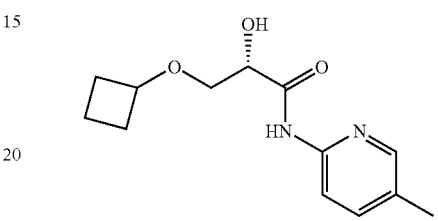

A solution of tetrabutylammonium fluoride (1M in THF) (0.439 mL, 0.44 mmol) was added to a stirred solution of (S)-2-(tert-butyldimethylsilyloxy)-3-cyclobutoxy-N-(5-methylpyridin-2-yl)propanamide (Intermediate R5) (80 mg, 0.22 mmol) in tetrahydrofuran (5 mL). The resulting solution was stirred at room temperature for 4 hours. The reaction mixture was concentrated and diluted with ethyl acetate (20 mL) and washed sequentially with water (5 mL) and saturated brine (5 mL). The organic layer was dried (MgSO4) and evaporated. The crude product was purified by flash silica chromatography, eluting with 0 to 60% ethyl acetate in isohexane to afford the product (46.0 mg, 84%).
$^1$H NMR (400 MHz, DMSO) δ 1.34-1.49 (m, 1H), 1.52-1.64 (m, 1H), 1.71-1.85 (m, 2H), 2.05-2.16 (m, 2H), 2.24 (s, 3H), 3.46-3.56 (m, 2H), 3.87-3.97 (m, 1H), 4.17-4.24 (m, 1H), 6.02 (d, 1H), 7.59-7.66 (m, 1H), 7.98 (d, 1H), 8.12-8.17 (m, 1H), 9.48 (s, 1H) m/z (ESI+) (M+H)+=251.33; HPLC tR=1.31 min.

Intermediate S1: (2S)-2-(1-(3-chloropyridin-2-yl)-1H-pyrazolo[3,4-d]pyrimidin-4-yloxy)-3-ethoxy-N-(5-(methylthio)pyridin-2-yl)propanamide

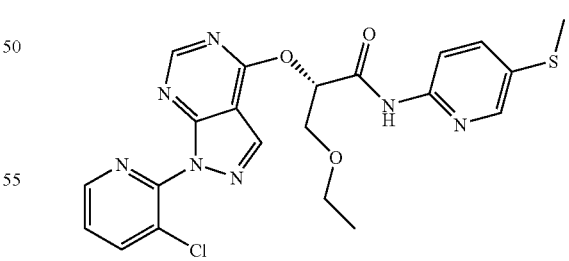

2M Trimethylaluminium in hexane (0.457 mL, 0.91 mmol) was added to 5-(methylthio)pyridin-2-amine (CAS no. 77618-99-6) (0.111 g, 0.79 mmol) in toluene (22 mL) at 0° C. under nitrogen. The resulting solution was stirred at 0° C. for 20 minutes. (2S)-methyl 2-(1-(3-chloropyridin-2-yl)-1H-pyrazolo[3,4-d]pyrimidin-4-yloxy)-3-ethoxypropanoate (Intermediate L2) (0.300 g, 0.79 mmol) in toluene (6 mL) was added dropwise at this temperature. After the addition was complete, the solution was allowed to warm to ambient temperature and was then heated at reflux for 16 hours. The mixture was allowed to cool to ambient temperature and left standing for 2 days. The reaction mixture was concentrated, diluted with ethyl acetate (100 mL) then washed with saturated brine (50 mL). The organic layer was dried (MgSO$_4$) and evaporated. The residue was purified by flash silica chromatography, eluting with 0 to 3% MeOH in DCM to afford the product.

$^1$H NMR (400 MHz, CDCl$_3$) δ 1.14 (3H, t), 2.41 (3H, s), 3.52-3.61 (2H, m), 3.99-4.07 (2H, m), 5.99 (1H, t), 7.38-7.42 (1H, m), 7.57-7.60 (1H, m), 7.93-7.95 (1H, m), 8.11-8.15 (2H, m), 8.40 (1H, s), 8.54-8.56 (2H, m), 8.64 (1H, s); m/z (ES+) (M+H)$^+$=486; HPLC tR=2.26 min.

Intermediate T1: (3S)-3-(1-(3-chloropyridin-2-yl)-1H-pyrazolo[3,4-d]pyrimidin-4-yloxy)dihydrouran-2(3H)-one

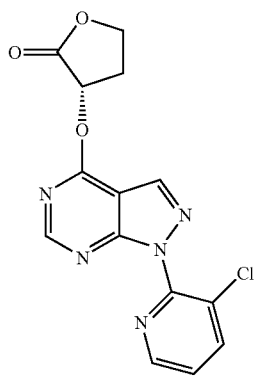

60% Sodium hydride in mineral oil (0.470 g, 11.75 mmol) was added to (S)-3-hydroxydihydrofuran-2(3H)-one (0.764 mL, 9.80 mmol) in anhydrous THF (30 mL) at 0° C. under nitrogen. The resulting solution was stirred at 0° C. for 10 minutes and then 4-chloro-1-(3-chloropyridin-2-yl)-1H-pyrazolo[3,4-d]pyrimidine (CAS no. 52079-23-9) (2.87 g, 10.77 mmol) was added portionwise maintaining the temperature below 5° C. The reaction mixture was allowed to warm to room temperature and stirred for 1 hour. The reaction mixture was neutralised with 1M citric acid and the majority of the THF removed in vacuo. The reaction mixture diluted with water (20 mL) and ethyl acetate (50 mL). The organic layer was separated and the aqueous layer re-extracted with ethyl acetate (2×100 mL). The combined organics were washed with saturated brine (75 mL), water (75 mL) dried (MgSO$_4$), filtered and evaporated. The residue was purified by flash silica chromatography, eluting with 50 to 100% ethyl acetate in isohexane to afford the product (1.970 g, 61%). $^1$H NMR (400 MHz, CDCl$_3$) 2.52-2.62 (1H, m), 2.92-3.00 (1H, m), 4.41-4.47 (1H, m), 4.59-4.64 (1H, m), 6.11-6.16 (1H, m), 7.46-7.49 (1H, m), 8.00-8.02 (1H, m), 8.37 (1H, s), 8.61-8.63 (1H, m), 8.64 (1H, s); m/z (ESI+) (M+H)+=332; HPLC t$_R$=1.51 min.

Intermediate T2: (3S)-3-(1-(2-chlorophenyl)-1H-pyrazolo[3,4-d]pyrimidin-4-yloxy)dihydrofuran-2(3H)-one

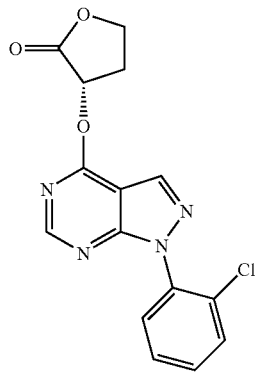

Prepared using an analogous procedure to that described for Intermediate T1 using Intermediate B1 $^1$H NMR (400 MHz, CDCl$_3$) 2.53-2.63 (1H, m), 2.92-2.99 (1H, m), 4.41-4.47 (1H, m), 4.59-4.65 (1H, m), 6.12-6.16 (1H, m), 7.44-7.55 (3H, m), 7.60-7.63 (1H, m), 8.33 (1H, s), 8.60 (1H, s); m/z (ESI+) (M+H)+=331; HPLC t$_R$=1.98 min.

Intermediate U1: (S)-3-cyclobutoxy-2-hydroxy-N-(5-methylpyridin-2-yl)propanamide

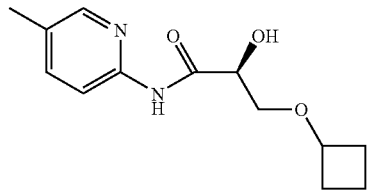

Prepared in an analogous fashion to Intermediate H1 from (S)-2-(tert-butyldimethylsilyloxy)-3-cyclobutoxy-N-(5-methylpyridin-2-yl)propanamide (Intermediate U2) $^1$H NMR (400 MHz, CDCl$_3$) 1.45-1.60 (1H, m), 1.64-1.74 (1H, m), 1.90-2.04 (2H, m), 2.17-2.26 (2H, m), 2.30 (3H, s), 3.63-3.74 (2H, m), 3.97-4.04 (1H, m), 4.11-4.17 (1H, m), 4.34-4.36 (1H, m), 7.51-7.54 (1H, m), 8.07-8.13 (2H, m), 9.26 (1H, s); m/z (ESI+) (M+H)+=251; HPLC t$_R$=1.30 min.

Intermediate U2: (S)-2-(tert-butyldimethylsilyloxy)-3-cyclobutoxy-N-(5-methylpyridin-2-yl)propanamide

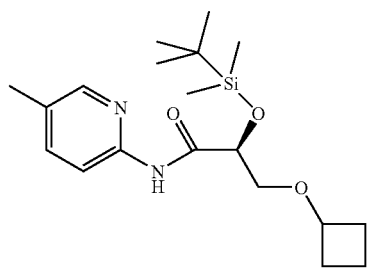

Prepared in an analogous fashion to Intermediate E2 from (S)-2-(tert-butyldimethylsilyloxy)-3-cyclobutoxypropanoic acid (Intermediate R4). $^1$H NMR (400 MHz, CDCl$_3$) 0.19 (6H, d), 0.99 (9H, s), 1.46-1.52 (1H, m), 1.67-1.70 (1H, m), 1.89-1.94 (2H, m), 2.16-2.20 (2H, m), 2.30 (3H, s), 3.49-3.54 (1H, m), 3.67-3.70 (1H, m), 3.93-3.97 (1H, m), 4.36-4.38 (1H, m), 7.49-7.52 (1H, m), 8.10-8.14 (2H, m), 9.01 (1H, s); m/z (ESI+) (M+H)+=365; HPLC $t_R$=3.57 min.

Intermediate V1: di-tert-butyl 1-(2-methylpyridin-3-yl)hydrazine-1,2-dicarboxylate

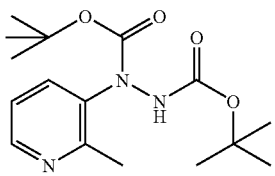

Prepared using a procedure analogous to that described for Intermediate X1 using 3-bromo-2-methylpyridine (CAS no. 38749-79-0). $^1$H NMR (400 MHz, DMSO) δ 1.07-1.32 (m, 18H), 3.09 (s, 3H), 7.01-7.12 (m, 1H), 7.41-7.50 (m, 1H), 8.12-8.18 (m, 1H), 9.39-9.62 (m, 1H); m/z (ESI+) (M+H)+=324.39; HPLC $t_R$=1.57 min.

Intermediate V2: 3-hydrazinyl-2-methylpyridine hydrochloride

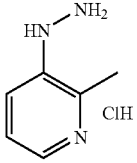

is Hydrogen chloride in dioxane (5.67 mL, 22.67 mmol) was added to a solution of di-tert-butyl 1-(2-methylpyridin-3-yl)hydrazine-1,2-dicarboxylate (Intermediate V1) (733 mg, 2.27 mmol) in IPA (10 mL). The reaction mixture was heated at reflux for 20 mins. The reaction mixture was allowed to cool and then diluted with diethyl ether (30 mL). The resultant precipitate was collected by filtration and dried in vacuo to afford 3-hydrazinyl-2-methylpyridine hydrochloride (362 mg, 100%). $^1$H NMR (400 MHz, DMSO) δ 2.66 (3H, s), 7.80-7.83 (1H, m), 7.95-7.97 (1H, m), 8.23-8.25 (1H, m), 9.15 (1H, s), 11.30 (1H, s); no ion in LCMS (1NH missing).

Intermediate V3: 5-amino-1-(2-methylpyridin-3-yl)-1H-pyrazole-4-carbonitrile

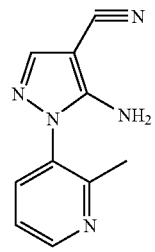

MP-carbonate (2.64 mmol/g) (2.6 g, 6.80 mmol) was added to 3-hydrazinyl-2-methylpyridine hydrochloride (Intermediate V2) (362 mg, 2.27 mmol) in DCM (10 mL). The reaction mixture was stirred at room temperature for 6 hours. The reaction mixture was filtered and evaporated. 2-(Ethoxymethylene)malononitrile (277 mg, 2.27 mmol) was added to suspension of the above solid in MeOH (6 mL) under nitrogen cooled to −5° C. The reaction mixture was stirred at 0° C. for 30 mins and then allowed to warm to room temperature and heated at reflux under nitrogen for 2 hours. The reaction mixture was allowed to cool and evaporated to dryness to afford the product (210 mg, 46.5%) which was used without further purification. $^1$H NMR (400 MHz, DMSO) δ 2.23 (3H, s), 6.65 (2H, s), 7.39-7.43 (1H, m), 7.74 (1H d), 7.79 (1H, s), 8.58-8.60 (1H, m), m/z (ESI+) (M+H)+=200; HPLC $t_R$=1.21 min.

Intermediate V4: 1-(2-methylpyridin-3-yl)-1H-pyrazolo[3,4-d]pyrimidin-4(7H)-one

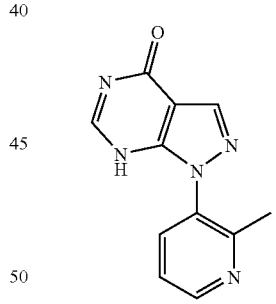

Concentrated sulfuric acid (0.258 mL, 4.85 mmol) was added to a stirred solution of 5-amino-1-(2-methylpyridin-3-yl)-1H-pyrazole-4-carbonitrile (Intermediate V3) (878 mg, 4.41 mmol) in formic acid (5 mL). The resulting solution was stirred at 100° C. for 1 hour. The reaction was allowed to cool to room temperature and evaporated to approximately half volume and water (25 mL) added. The reaction mixture was adjusted to pH 4 with 2M NaOH. The resultant precipate was collected by filtration, washing well with water, and then dried in vacuo to afford 1-(2-methylpyridin-3-yl)-1H-pyrazolo[3,4-d]pyrimidin-4(7H)-one (525 mg, 52%). $^1$H NMR (400 MHz, DMSO) δ 2.28 (3H, s), 7.44-7.47 (1H, m), 7.85-7.87 (1H, m), 8.09 (1H, s), 8.35 (1H, s), 8.61-8.63 (1H, m), 12.3 (1H, s); m/z (ESI+) (M+H)+=228; HPLC $t_R$=0.65 min.

Intermediate V5: 4-chloro-1-(2-methylpyridin-3-yl)-1H-pyrazolo[3,4-d]pyrimidine

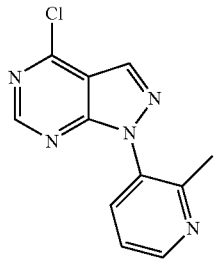

Prepared using a procedure analogous to that described for Intermediate X5 using Intermediate V4.

$^1$H NMR (400 MHz, DMSO) δ 2.32 (s, 3H), 7.51-7.56 (m, 1H), 7.96-8.00 (m, 1H), 8.67-8.70 (m, 1H), 8.81 (s, 1H), 8.91 (s, 1H). m/z (ESI+) (M+H)+=246.29; HPLC tR=1.29 min

Intermediate W1: 6-amino-N,N-dimethylnicotinamide

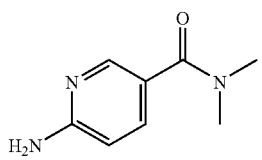

N-Ethyl-N-isopropylpropan-2-amine (12.61 mL, 72.40 mmol) was added to 6-aminonicotinic acid (CAS no. 3167-49-5) (5 g, 36.20 mmol), dimethylamine (2M in THF) (21.72 mL, 43.44 mmol) and EDCI (9.02 g, 47.06 mmol) in THF (150 mL) under nitrogen. The resulting suspension was stirred at r.t. for 18 hours. The reaction mixture was dry loaded onto silica and purified by flash silica chromatography, eluting with 0 to 10% MeOH in ethyl acetate to the product (4.50 g, 75%). $^1$H NMR (400 MHz, DMSO) δ 2.95 (6H, s), 6.28 (2H, s), 6.38-6.44 (1H, m), 7.42-7.47 (1H, m), 7.99-8.04 (1H, m)

Intermediate X1: di-tert-butyl 1-(4-methylpyridin-3-yl)hydrazine-1,2-dicarboxylate

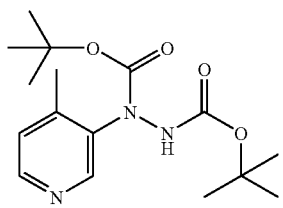

Isopropylmagnesium chloride. lithium chloride complex (0.96 M) (23.62 mL, 22.67 mmol) was added to 3-bromo-4-methylpyridine (CAS no. 3430-22-6) (3 g, 17.44 mmol) in THF (60 mL) cooled to 0° C. under nitrogen. The resulting solution was warmed to room temperature and stirred for 3 hours. The reaction temperature was cooled to 0° C. and di-tert-butyl azodicaboxylate (6.02 g, 26.16 mmol) in THF (10 ml) was added dropwise maintaining the temperature below 10° C. The reaction was warmed to room temperature and stirred for 1.5 hours. The reaction mixture was quenched with saturated NH$_4$Cl (50 mL) and extracted with ethyl acetate (3×75 mL). The organic layer was dried (MgSO$_4$) and evaporated. The crude product was purified by flash silica chromatography, eluting with 0 to 90% ethyl acetate in iso-hexane to afford the product (4.50 g, 80%).

$^1$H NMR (400 MHz, CDCl$_3$) δ 1.41-1.49 (18H, m), 2.34 (3H, s), 6.90 (1H, s), 7.13 (1H, d), 8.36 (1H, d), 8.60 (1H, s); m/z (ESI+) (M+H)+=324; HPLC tR=2.15 min.

Intermediate X2: 3-hydrazinyl-4-methylpyridine hydrochloride

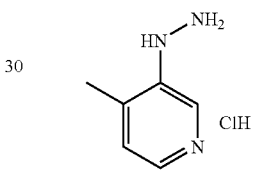

Prepared using a procedure analogous to that described for Intermediate V2 using Intermediate X1. $^1$H NMR (400 MHz, DMSO) δ 2.44 (3H, s), 7.79-7.80 (1H, m), 8.38 (2H, d), 9.07 (1H, s), 11.4 (2H, s)

Intermediate X3: 5-amino-1-(4-methylpyridin-3-yl)-1H-pyrazole-4-carbonitrile

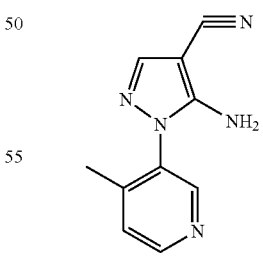

Prepared using a procedure analogous to that described for Intermediate V3 using Intermediate X2. $^1$H NMR (400 MHz, DMSO) δ 2.09 (3H, s), 6.68 (2H, s), 7.50 (1H, d), 7.80 (1H, s), 8.44-8.48 (1H, m), 8.57 (1H, d); m/z (ESI+) (M+H)+=200; HPLC tR=1.47 min.

Intermediate X4: 1-(4-methylpyridin-3-yl)-1H-pyrazolo[3,4-d]pyrimidin-4(7H)-one

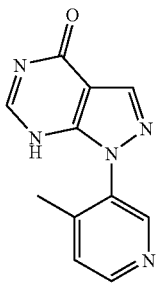

Prepared using a procedure analogous to that described for Intermediate V4 using Intermediate X3. $^1$H NMR (400 MHz, DMSO) δ 2.15 (3H, s), 7.51 (1H, d), 8.09 (1H, s), 8.37 (1H, s), 8.57-8.59 (2H, m), 12.5 (1H, s); m/z (ESI+) (M+H)+=228; HPLC $t_R$=1.36 min.

Intermediate X5: 4-chloro-1-(4-methylpyridin-3-yl)-1H-pyrazolo[3,4-d]pyrimidine

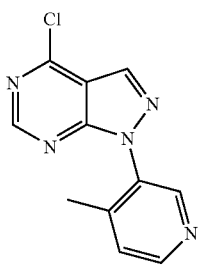

Phosphorus oxychloride (5.10 ml, 54.75 mmol) was added to 1-(4-methylpyridin-3-yl)-1H-pyrazolo[3,4-d]pyrimidin-4-ol (0.622 g, 2.74 mmol). The resulting solution was stirred at 100° C. for 2 hours. The reaction mixture was evaporated. Toluene was added to the residue and the reaction mixture was concentrated. This was repeated to remove excess POCl$_3$. The residue was dissolved in DMF (15 mL) and MP carbonate was added (~3 g) and allowed to stir overnight. The DMF was evaporated in vacuo to afford crude product which was used without further purification. $^1$H NMR (400 MHz, DMSO) δ 2.1 (3H, s), 7.60 (1H, d), 8.65 (1H, d), 8.68 (1H, s), 8.82 (1H, s), 8.91 (1H, s); m/z (ES+) (M+H)+=246; HPLC tR=1.69 min.

Intermediate Y1: (S)-methyl 2-(tert-butyldimethylsilyloxy)-3-((S)-1-methoxypropan-2-yloxy)propanoate

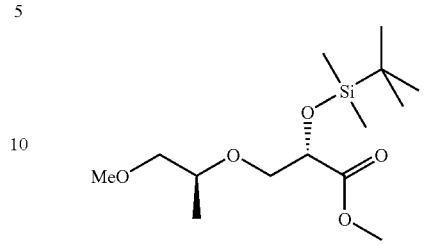

Magnesium perchlorate (2.79 g, 12.49 mmol) was added in one portion to (S)-methyl oxirane-2-carboxylate (CAS no. 118712-39-3) (5.1 g, 49.96 mmol) and (S)-1-methoxypropan-2-ol (CAS no. 26550-55-0) (4.50 g, 49.96 mmol) at ambient temperature. The resulting suspension was stirred at 50° C. for 16 hours. The reaction mixture was diluted with DMF (50 mL) before adding 1H-imidazole (6.80 g, 99.92 mmol) and tert-butylchlorodimethylsilane (9.04 g, 59.95 mmol). The resulting solution was stirred at 40° C. for 5 hours. The reaction mixture was evaporated to dryness and re-dissolved in ethyl acetate (125 mL), and washed sequentially with water (50 mL) and saturated brine (25 mL). The organic layer was dried (MgSO$_4$) and evaporated. The crude product was purified by flash silica chromatography, eluting with 0 to 50% ethyl acetate in isohexane to afford the product (4.52 g, 30%). $^1$H NMR (400 MHz, DMSO) δ 0.00 (d, 6H), 0.82 (s, 9H), 0.98 (d, 3H), 3.13-3.28 (m, 5H), 3.50-3.64 (m, 6H), 4.26-4.32 (m, 1H); m/z (ESI+) (M+H)+=307.19; HPLC $t_R$=10.82 min.

Intermediate Y2: (S)-2-(tert-butyldimethylsilyloxy)-3-((S)-1-methoxypropan-2-yloxy)-N-(5-methylpyrazin-2-yl)propanamide

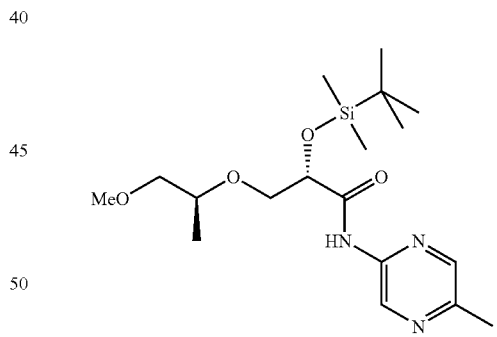

Trimethylaluminium (2M in hexane) (1.126 mL, 2.25 mmol) was added dropwise to 5-methylpyrazin-2-amine (214 mg, 1.96 mmol) in toluene (5 mL) cooled to 0° C. under nitrogen. The resulting solution was stirred for 20 minutes. A solution of (S)-methyl 2-(tert-butyldimethylsilyloxy)-3-((S)-1-methoxypropan-2-yloxy)propanoate (Intermediate Y1) (600 mg, 1.96 mmol) in toluene (2 mL) was added to the reaction mixture and the resulting solution was stirred at reflux for 5 hours. The reaction was allowed to cool to RT before adding ethyl acetate (30 mL) and 20% sodium potassium tartrate solution (30 mL), which was stirred vigorously for 16 hours. The phases were separated and the organic layer was washed with sat. brine (15 mL), dried (MgSO$_4$) and evaporated. The crude product was purified by flash silica chromatography, eluting with 0 to 60% ethyl acetate in isohexane to afford the product (230 mg, 31%). $^1$H NMR (400 MHz, CDCl$_3$) δ 0.17 (d, 6H), 0.98 (s, 9H), 1.16 (d, 3H), 2.53 (s, 3H), 3.25-3.32 (m, 4H), 3.35-3.42 (m, 1H), 3.60-3.68 (m, 1H), 3.74-3.80 (m, 1H), 3.82-3.87 (m, 1H), 4.35-4.40 (m, 1H), 8.12-8.13 (m, 1H), 8.98 (s, 1H), 9.42 (d, 1H); m/z (ESI+) (M+H)+=384.23; HPLC $t_R$=10.70 min.

Intermediate Y3: (S)-2-hydroxy-3-((S)-1-methoxypropan-2-yloxy)-N-(5-methylpyrazin-2-yl)propanamide

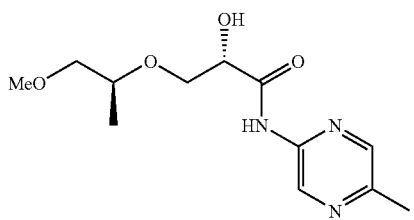

Tetrabutylammonium fluoride (1M in THF) (1199 µl, 1.20 mmol) was added to (S)-2-(tert-butyldimethylsilyloxy)-3-((S)-1-methoxypropan-2-yloxy)-N-(5-methylpyrazin-2-yl)propanamide (Intermediate Y2) (230 mg, 0.60 mmol) in THF (3.0 mL) at 20° C. The resulting solution was stirred at room temperature for 3 hours. The reaction mixture was concentrated and diluted with ethyl acetate (50 mL), and washed sequentially with water (25 mL) and saturated brine (10 mL). The organic layer was dried (MgSO$_4$) and evaporated. The crude product was purified by flash silica chromatography, eluting with 100% ethyl acetate to afford the product (80 mg, 50%). $^1$H NMR (400 MHz, CDCl$_3$) δ 1.16 (d, 3H), 2.53 (s, 3H), 3.34-3.45 (m, 5H), 3.66-3.81 (m, 2H), 3.97-4.03 (m, 1H), 4.30 (d, 1H), 4.34-4.39 (m, 1H), 8.13 (d, 1H), 9.30 (s, 1H), 9.41 (d, 1H); m/z (ESI+) (M+H)+=270.29; HPLC $t_R$=0.95 min.

Intermediate Y4: (S)-2-(tert-butyldimethylsilyloxy)-3-((S)-1-methoxypropan-2-yloxy)-N-(5-methylpyridin-2-yl)propanamide

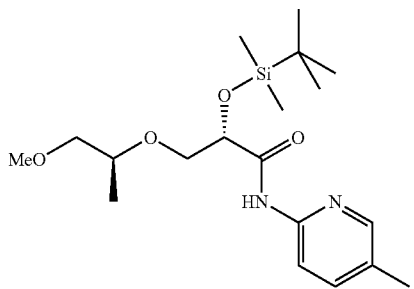

Trimethylaluminium (2M in hexane) (0.938 mL, 1.88 mmol) was added dropwise to 5-methylpyridin-2-amine (194 mg, 1.79 mmol) in toluene (5 mL) cooled to 0° C. under nitrogen. The resulting solution was stirred for 20 minutes. A solution of (S)-methyl 2-(tert-butyldimethylsilyloxy)-3-((S)-1-methoxypropan-2-yloxy) propanoate (Intermediate Y1) (500 mg, 1.63 mmol) in toluene (2 mL) was added to the reaction mixture and the resulting solution was stirred at reflux for 5 hours. The reaction was allowed to cool to room temperature before adding ethyl acetate (30 mL) and 20% sodium potassium tartrate solution (30 mL), which was stirred vigourously for 16 hours. The phases were separated and the organic layer was washed with sat. brine (15 mL), dried (MgSO$_4$) and evaporated. The crude product was purified by flash silica chromatography, eluting with 0 to 60% ethyl acetate in isohexane to afford the product (388 mg, 62%). $^1$H NMR (400 MHz, DMSO) δ 0.01 (d, 6H), 0.81 (s, 9H), 0.93 (d, 3H), 2.13 (s, 3H), 3.06-3.21 (m, 5H), 3.44-3.53 (m, 1H), 3.57 (d, 2H), 4.29 (t, 1H), 7.49-7.55 (m, 1H), 7.87 (d, 1H), 8.01-8.05 (m, 1H), 9.25 (s, 1H); m/z (ESI+) (M+H)+=383.24; HPLC $t_R$=11.31 min.

Intermediate Y5: (S)-2-hydroxy-3-((S)-1-methoxypropan-2-yloxy)-N-(5-methylpyridin-2-yl)propanamide

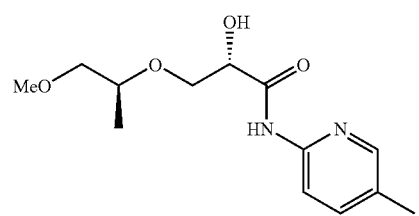

Tetrabutylammonium fluoride (1M in THF) (2028 µl, 2.03 mmol) was added to (S)-2-(tert-butyldimethylsilyloxy)-3-((S)-1-methoxypropan-2-yloxy)-N-(5-methylpyridin-2-yl)propanamide (Intermediate Y4) (388 mg, 1.01 mmol) in THF (5 mL) at 20° C. The resulting solution was stirred at room temperature for 3 hours. The reaction mixture was concentrated, diluted with ethyl acetate (50 mL), and washed sequentially with water (25 mL) and saturated brine (10 mL). The organic layer was dried (MgSO$_4$) and evaporated. The crude product was purified by flash silica chromatography, eluting with 0 to 10% s MeOH in DCM to afford the product (200 mg, 74%). $^1$H NMR (400 MHz, DMSO) δ 1.04 (d, 3H), 2.24 (s, 3H), 3.17-3.23 (m, 4H), 3.25-3.31 (m, 1H), 3.55-3.73 (m, 3H), 4.16-4.23 (m, 1H), 5.94 (d, 1H), 7.59-7.65 (m, 1H), 7.98 (d, 1H), 8.12-8.16 (m, 1H), 9.48 (s, 1H); m/z (ESI+) (M+H)+=269.31; HPLC $t_R$=1.11 min.

Intermediate Y6: (S)-methyl 2-hydroxy-3-((R)-1-methoxypropan-2-yloxy)propanoate

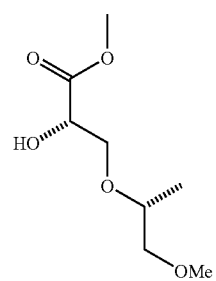

Magnesium perchlorate (2.73 g, 12.24 mmol) was added in one portion to (S)-methyl oxirane-2-carboxylate (CAS no. 118712-39-3) (5 g, 48.98 mmol) and (R)-1-methoxypropan-2-ol (CAS no. 4984-22-9) (4.41 g, 48.98 mmol) at room temperature. The resulting suspension was stirred at 50° C. for 16 hours. The reaction mixture was diluted with ethyl acetate (50 mL) and washed with water (20 mL), dried (MgSO$_4$) and evaporated. This was not isolated and used crude in next step.

$^1$H NMR (400 MHz, CDCl$_3$) δ 1.11 (d, 3H), 3.31-3.40 (m, 5H), 3.64-3.72 (m, 1H), 3.75-3.80 (m, 4H), 3.89-3.95 (m, 1H), 4.27-4.30 (m, 1H), OH not observed.

Intermediate Y7: (2S)-methyl 2-(1-(2-chlorophenyl)-1H-pyrazolo[3,4-d]pyrimidin-4-yloxy)-3-((R)-1-methoxypropan-2-yloxy)propanoate

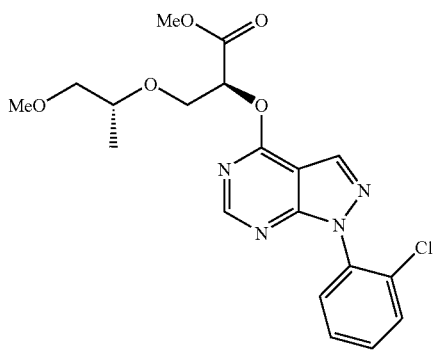

Sodium hydride (94 mg, 2.34 mmol) was added to (S)-methyl 2-hydroxy-3-((R)-1-methoxypropan-2-yloxy)propanoate (Intermediate Y6) (300 mg, 1.56 mmol) in anhydrous THF (5 mL) at 0° C. under nitrogen. The resulting solution was stirred at 0° C. for 10 minutes and then 4-chloro-1-(2-chlorophenyl)-1H-pyrazolo[3,4-d]pyrimidine (Intermediate B1) (538 mg, 2.03 mmol) was added. The reaction mixture was allowed to warm up to room temperature and stirred for 30 minutes. The reaction mixture was neutralized with 1M citric acid, diluted with ethyl acetate (20 mL), and washed sequentially with water (10 mL) and saturated brine (5 mL). The organic layer was dried (MgSO$_4$) and evaporated. The crude product was purified by flash silica chromatography, eluting with 0-100% ethyl acetate in isohexane to afford the product (358 mg, 54.5%).

$^1$H NMR (400 MHz, DMSO) δ 1.07 (d, 3H), 3.23-3.40 (m, 5H), 3.68-3.77 (m, 4H), 4.05-4.10 (m, 2H), 5.81 (t, 1H), 7.56-7.71 (m, 3H), 7.73-7.79 (m, 1H), 8.57 (s, 1H), 8.58 (s, 1H); m/z (ESI+) (M+H)+=421.17; HPLC t$_R$=1.86 min.

Intermediate Y8: (2S)-methyl 2-(1-(3-chloropyridin-2-yl)-1H-pyrazolo[3,4-d]pyrimidin-4-yloxy)-3-((R)-1-methoxypropan-2-yloxy)propanoate

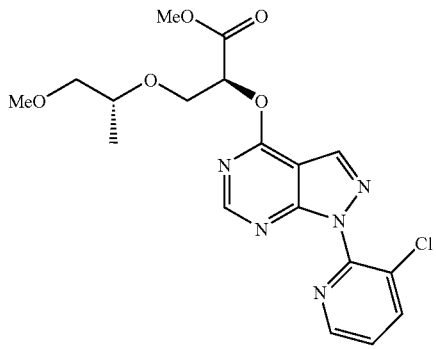

Sodium hydride (62.4 mg, 1.56 mmol) was to (S)-methyl 2-hydroxy-3-((R)-1-methoxypropan-2-yloxy)propanoate (Intermediate Y6) (200 mg, 1.04 mmol) in anhydrous THF (5 mL) at 0° C. under nitrogen. The resulting mixture was stirred for 10 minutes at 0° C. and then 4-chloro-1-(3-chloropyridin-2-yl)-1H-pyrazolo[3,4-d]pyrimidine (Intermediate B15) (360 mg, 1.35 mmol) was added and the reaction was allowed to warm up to room temperature and stirred for 1 hour. The reaction mixture was diluted with ethyl acetate (20 mL), and washed sequentially with water (10 mL) and saturated brine (5 mL). The organic layer was dried (MgSO$_4$) and evaporated. The crude product was purified by flash silica chromatography, eluting with 0-100% ethyl acetate in isohexane to afford the product (245 mg, 55.8%). $^1$H NMR (400 MHz, CDCl$_3$) δ 1.19 (d, 3H), 3.33-3.48 (m, 5H), 3.74-3.82 (m, 4H), 4.13-4.18 (m, 2H), 5.81-5.86 (m, 1H), 7.43-7.48 (m, 1H), 7.98-8.02 (m, 1H), 8.39-8.41 (m, 1H), 8.58 (s, 1H), 8.60-8.63 (m, 1H); m/z (ESI+) (M+H)+=422.36; HPLC t$_R$=1.93 min.

Intermediate Y9: (S)-methyl 2-(tert-butyldimethylsilyloxy)-3-((R)-1-methoxypropan-2-yloxy)propanoate

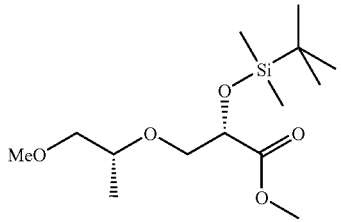

tert-Butylchlorodimethylsilane (7.09 g, 47.01 mmol) was added to (S)-methyl 2-hydroxy-3-((R)-1-methoxypropan-2-yloxy)propanoate (Intermediate Y6) (7.53 g, 39.18 mmol) and 1H-imidazole (5.33 g, 78.35 mmol) in DMF (50 mL) at room temperature under nitrogen. The resulting solution was stirred at 40° C. for 5 hours. The reaction mixture was evaporated to dryness and re-dissolved in ethyl acetate (125 mL), and washed sequentially with water (50 mL) and saturated brine (25 mL). The organic layer was dried (MgSO$_4$) and evaporated. The crude product was purified by flash silica chromatography, eluting with 0 to 50% ethyl acetate in isohexane to afford the product (2.58 g, 21.5%). $^1$H NMR (400 MHz, DMSO) δ −0.01 (d, 6H), 0.81 (s, 9H), 0.97 (d, 3H), 3.13-3.29 (m, 5H), 3.49-3.64 (m, 6H), 4.26-4.31 (m, 1H); m/z (ESI+) M-C$_4$H$_9$=249; GC t$_R$=10.92 min.

Intermediate Y10: (S)-2-(tert-butyldimethylsilyloxy)-3-((R)-2-methoxypropoxy)propanoic acid

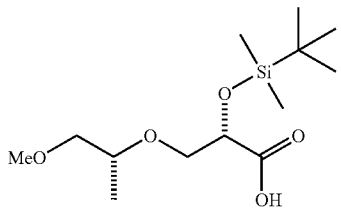

Lithium iodide (4.51 g, 33.67 mmol) was added to (S)-methyl 2-(tert-butyldimethylsilyloxy)-3-((R)-2-methoxypropoxy) propanoate (Intermediate Y9) (2.58 g, 8.42 mmol) in ethyl acetate (15 mL). The resulting suspension was protected from light and stirred at reflux (75° C.) for 6 hours. The reaction mixture was diluted with ethyl acetate (75 mL) washed sequentially with 1M sodium metabisulphite (25 mL), water (25 mL) and saturated brine (25 mL). The organic layer was dried (MgSO$_4$) and evaporated to afford crude product (1.166 g, 47.4%) that was used without further purification.

Intermediate Y11: (S)-2-(tert-butyldimethylsilyloxy)-3-((R)-1-methoxypropan-2-yloxy)-N-(5-methylpyrazin-2-yl)propanamide

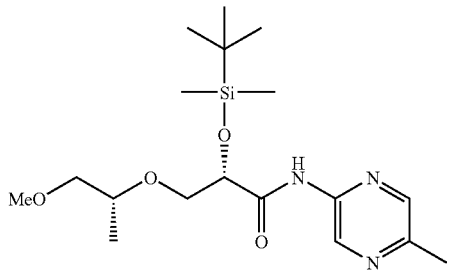

1-Chloro-N,N,2-trimethylprop-1-en-1-amine (0.170 mL, 1.28 mmol) was added to a stirred solution of (S)-2-(tert-butyldimethylsilyloxy)-3-((R)-1-methoxypropan-2-yloxy) propanoic acid (Intermediate Y10) (250 mg, 0.85 mmol) in DCM (5 mL) at room temperature under nitrogen. The resulting solution was stirred at room temperature for 30 minutes. A solution of 5-methylpyrazin-2-amine (140 mg, 1.28 mmol) in DCM (5 mL) was added to the reaction mixture and the resulting solution was stirred at room temperature for 16 hours. The reaction mixture was quenched with water (20 mL), extracted with DCM (2×25 mL), the combined organic layers were dried (MgSO$_4$) and evaporated. The crude product was purified by flash silica chromatography, eluting with 0 to 90% ethyl acetate in isohexane to afford the product (170 mg, 51.8%). $^1$H NMR (400 MHz, DMSO) δ 0.01 (d, 6H), 0.80 (s, 9H), 0.91 (d, 3H), 2.35 (s, 3H), 3.09-3.23 (m, 5H), 3.47-3.63 (m, 3H), 4.35-4.40 (m, 1H), 8.20 (s, 1H), 9.09 (s, 1H), 9.63 (s, 1H); m/z (ESI+) (M+H)+=384.43; HPLC t$_R$=2.99 min.

Intermediate Y12: (S)-2-hydroxy-3-((R)-2-methoxypropoxy)-N-(5-methylpyrazin-2-yl)propanamide

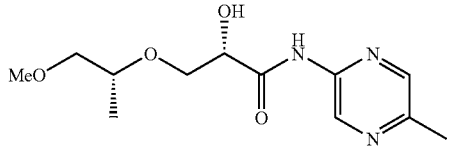

Tetrabutylammonium fluoride (881 µl, 0.88 mmol) was added to (S)-2-(tert-butyldimethylsilyloxy)-3-((R)-2-methoxypropoxy)-N-(5-methylpyrazin-2-yl)propanamide (Intermediate Y11) (169 mg, 0.44 mmol) in THF (2203 µl) at room temperature under nitrogen. The resulting solution was stirred at room temperature for 3 hours. The reaction mixture was quenched with water (5 mL), extracted with ethyl acetate (3×10 mL), the organic layer was back washed with water (5 mL), dried (MgSO$_4$) and evaporated. The crude product was purified by flash silica chromatography, eluting with 0 to 100% ethyl acetate in isohexane to afford the product (64.0 mg, 53.9%). $^1$H NMR (400 MHz, CDCl$_3$) δ 1.13 (d, 3H), 2.53 (s, 3H), 3.33-3.43 (m, 5H), 3.68-3.82 (m, 2H), 4.04-4.11 (m, 1H), 4.33 (t, 1H), 4.53 (s, 1H), 8.12-8.15 (m, 1H), 9.19 (s, 1H), 9.43 (d, 1H); m/z (ESI+) (M+H)+=270.24; HPLC t$_R$=1.04 min.

Intermediate Z1: 4-phenoxy-1-(2-(trifluoromethyl)phenyl)-1H-pyrazolo[3,4-d]pyrimidine

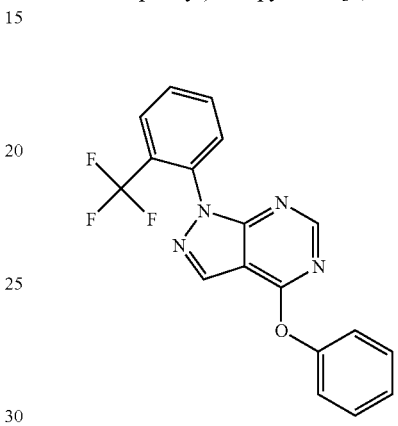

(2-(trifluoromethyl)phenyl)hydrazine (CAS no. 365-34-4) (102 mg, 0.58 mmol) was added to 4,6-diphenoxypyrimidine-5-carbaldehyde (Intermediate Z2) (169 mg, 0.58 mmol) in THF (2 mL) the resulting solution was stirred at room temperature for 5 minutes. 2-tert-butylimino-2-diethylamino-1,3-dimethyl-perhydro-1,3,2-diazaphosphorine on polystyrene (526 mg, 1.16 mmol) was added and sealed into a microwave tube. The reaction was heated to 150° C. for 10 hours in a microwave reactor and cooled to RT. The reaction mixture was filtered and evaporated to dryness. The crude product was purified by flash silica chromatography, eluting with 10 to 80% ethyl acetate in isohexane to afford the product (88 mg, 42.7%). $^1$H NMR (400 MHz, CDCl$_3$) δ 7.29-7.33 (2H, m), 7.34-7.39 (1H, m), 7.49-7.58 (3H, m), 7.67-7.71 (1H, m), 7.74-7.78 (1H, m), 7.90-7.92 (1H, m), 8.08 (1H, s), 8.56 (1H, s); m/z (ES+) (M+H)+=357; HPLC tR=2.66 min.

Intermediate Z2: (S)-2-acetoxy-4-methoxybutanoic acid

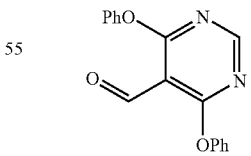

Potassium carbonate (6.08 g, 44.00 mmol) was added to phenol (2.070 g, 22.00 mmol) in THF (20 mL) under nitrogen. The resulting suspension was stirred at room temperature for 30 minutes. 4,6-Dichloro-5-pyrimidinecarbaldehyde (1.770 g, 10 mmol) was added and the mixture stirred overnight under nitrogen. The reaction mixture was evaporated to dryness and redissolved in DCM (100 mL), and washed sequentially with water (150 mL). The organic layer was dried (MgSO₄) and evaporated. The crude product was purified by flash silica chromatography, eluting with 0 to 50% ethyl acetate in isohexane to afford the product (2.54 g, 87%). ¹H NMR (400 MHz, CDCl₃) δ 7.19 (4H, d), 7.31 (2H, t), 7.44-7.48 (4H, m), 8.40 (1H, s), 10.67 (1H, s); m/z (ES+) (M+H)+=293; HPLC tR=2.48 min.

Intermediate AA1: (2S)-methyl 2-(1-(2-chlorophenyl)-1H-pyrazolo[3,4-d]pyrimidin-4-yloxy)-4-(methylsulfonyl)butanoate

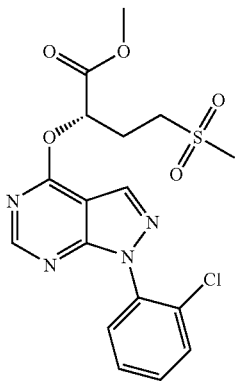

Sodium hydride (58.7 mg, 1.47 mmol) was added to (S)-methyl 2-hydroxy-4-(methylsulfonyl)butanoate (Intermediate AA2) (120 mg, 0.61 mmol) in anhydrous THF (50 mL) at 0° C. under nitrogen. The resulting solution was stirred at 0° C. for 10 minutes and then 4-chloro-1-(2-chlorophenyl)-1H-pyrazolo[3,4-d]pyrimidine (Intermediate B1) (357 mg, 0.67 mmol) was added. The reaction mixture was allowed to warm to room temperature and stirred for 3 hour. The reaction mixture was neutralised with 1M citric acid and the majority of the THF removed in vacuo. The reaction mixture was diluted with water (20 mL) and ethyl acetate (50 mL). The organic layer was separated and the aqueous layer re-extracted with ethyl acetate (2×100 mL). The combined organics were washed with saturated brine (75 mL), dried (MgSO₄) and evaporated. The crude product was purified by flash silica chromatography, eluting with 50 to 100% ethyl acetate in isohexane to afford the product (160 mg, 61.6%). ¹H NMR (400 MHz, CDCl₃) δ 2.60-2.75 (2H, m), 3.01 (3H, s), 3.25-3.38 (2H, m), 3.82 (3H, s), 5.79-5.82 (1H, m), 7.44-7.54 (3H, m), 7.61-7.63 (1H, m), 8.34 (1H, s), 8.54 (1H, s); m/z (ES+) (M+H)+=425; HPLC tR=2.01 min.

Intermediate AA2: (S)-methyl 2-hydroxy-4-(methylsulfonyl)butanoate

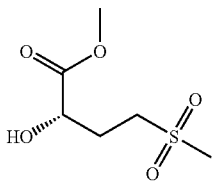

Tetrabutylammonium fluoride (1M in THF) (2071 µl, 2.07 mmol) was added to (S)-methyl 2-(tert-butyldiphenylsilyloxy)-4-(methylsulfonyl)butanoate (Intermediate AA3) (450 mg, 1.04 mmol) in THF (3106 µl) under nitrogen. The resulting mixture was stirred at ambient temperature for 2 hours. The reaction mixture was quenched with saturated NH₄Cl (10 mL), extracted with Et₂O (3×15 mL). The combined organic layers were back washed with water (10 mL), dried (MgSO₄) and evaporated. The crude product was purified by flash silica chromatography, eluting with 0 to 100% ethyl acetate in isohexane to afford the product (120 mg, 59%). ¹H NMR (400 MHz, CDCl₃) δ 2.10-2.20 (1H, m), 2.38-2.46 (1H, m), 2.94 (4H, m), 3.10-3.24 (2H, m), 3.84 (3H, s), 4.34 (1H, q), 7.26 (3H, s).

Intermediate AA3: (S)-methyl 2-(tert-butyldiphenylsilyloxy)-4-(methylsulfonyl)butanoate

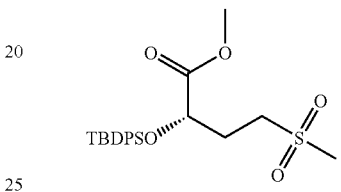

3-Chloroperoxybenzoic acid (753 mg, 3.05 mmol) was added in one portion to (S)-methyl 2-(tert-butyldiphenylsilyloxy)-4-(methylthio)butanoate (Intermediate AA4) (410 mg, 1.02 mmol) in dichloromethane (20 mL) at 25° C. The resulting suspension was stirred at 25° C. for 2 hours. The reaction mixture was quenched with saturated NaHCO3 (50 mL), washed with water (1×50 mL), the organic layer was dried (MgSO₄) and evaporated to afford the product (420 mg, 95%) which was used without further purification. ¹H NMR (400 MHz, CDCl₃) δ 1.10 (9H, s), 2.18-2.24 (2H, m), 2.83 (3H, s), 3.00-3.04 (1H, m), 3.12-3.18 (1H, m), 3.52 (3H, s), 4.38 (1H, t), 7.35-7.47 (6H, m), 7.61-7.65 (4H, m); m/z (ESI+) (M+NH4)+=452; HPLC tR=3.0 min.

Intermediate AA4: (S)-methyl 2-(tert-butyldiphenylsilyloxy)-4-(methylthio)butanoate

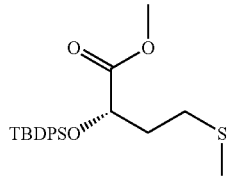

Sodium thiomethoxide (0.187 g, 2.67 mmol) was added to (S)-3-(tert-butyldiphenylsilyloxy)dihydrofuran-2(3H)-one (CAS no. 220351-82-6: Klar, U.; Schwede, W.; Skuballa, W.; Buchmann, B.; Schirner, M. Ger. Offen. 1999 DE 19735575 A1) (0.826 g, 2.43 mmol) in DMF (2 mL) at 0° C. The resulting solution was stirred at room temperature for 16 hours. The reaction mixture was neutralised with 2M HCl and diluted with ethyl acetate. The organic layer was extracted with water (3×100 mL), the organic layer was dried (MgSO₄) and evaporated to afford (S)-2-(tert-butyldiphenylsilyloxy)-4-(methylthio)butanoic acid (0.160 g, 16.98%) which was used without further purification. A solution of trimethylsilyldiazomethane (2M solution in ether, 0.412 ml, 0.82 mmol) was added dropwise to a stirred solution of methyl alcohol (0.167 ml, 4.12 mmol) and (S)-2-(tert-butyldiphenylsily-loxy)-4-(methylthio)butanoic acid (0.160 g, 0.41 mmol) in toluene (0.174 ml) over a period of 2 minutes. The resulting solution was stirred at ambient temperature for 2 hours. The reaction mixture was quenched with acetic acid (0.071 ml, 1.24 mmol) and stirred at ambient temperature for 10 minutes. The reaction mixture was evaporated. The residue was purified by flash silica chromatography, eluting with 0 to 50% ethyl acetate in isohexane to afford the product (0.120 g, 72.4%). $^1$H NMR (400 MHz, CDCl$_3$) δ 1.09 (9H, s), 1.94-2.05 (5H, m), 2.48-2.60 (2H, m), 3.47 (3H, s), 4.33-4.36 (1H, m), 7.34-7.45 (6H, m), 7.62-7.67 (4H, m); m/z (ES+) (M-Ph)-= 325; HPLC tR=3.63 min Intermediate AB1: (2S)-3-(2-(tert-butyldiphenylsily-loxy)ethoxy)-2-(1-(3-chloropyridin-2-yl)-1H-pyra-zolo[3,4-d]pyrimidin-4-yloxy)-N-(5-cyanopyridin-2-yl)propanamide

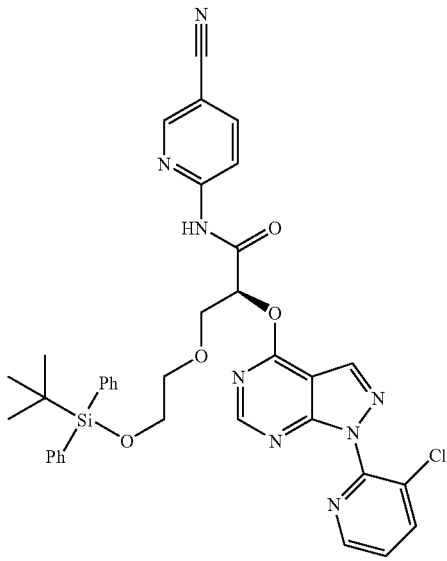

Trimethylaluminium (2M in hexane) (0.455 mL, 0.91 mmol) was added to 6-aminonicotinonitrile (104 mg, 0.87 mmol) in toluene (10 mL) cooled to 0° C. under nitrogen. The resulting solution was stirred at 0° C. for 20 minutes. (2S)-methyl 3-(2-(tert-butyldiphenylsilyloxy)ethoxy)-2-(1-(3-chloropyridin-2-yl)-1H-pyrazolo[3,4-d]pyrimidin-4-yloxy) propanoate (Intermediate AB2) (500 mg, 0.79 mmol) in toluene (2 mL) was added and the reaction was allowed to warm to room temperature. The temperature was increased to 60° C. and stirred for 4 hours, then heated at reflux for 24 hours. The reaction mixture was concentrated in vacuo and neutralised with citric acid (1M, aq) and then diluted with water (10 ml) and DCM (10 mL). The mixture was poured onto a phase separator and the organic layer was evaporated in vacuo. The crude product was purified by preparative HPLC (Waters XBridge Prep C18 OBD column, 5µ silica, 50 mm diameter, 150 mm length), using decreasingly polar mixtures of water (containing 0.1% formic acid) and MeCN as eluents. Fractions containing the desired compound were neutralised with MP-carbonate and evaporated to dryness to afford the product (100 mg, 17.6%). m/z (ES+) (M+H)+=719.51; HPLC tR=3.58 min.

Intermediate AB2: (2S)-methyl 3-(2-(tert-butyldiphe-nylsilyloxy)ethoxy)-2-(1-(3-chloropyridin-2-yl)-1H-pyrazolo[3,4-d]pyrimidin-4-yloxy)propanoate

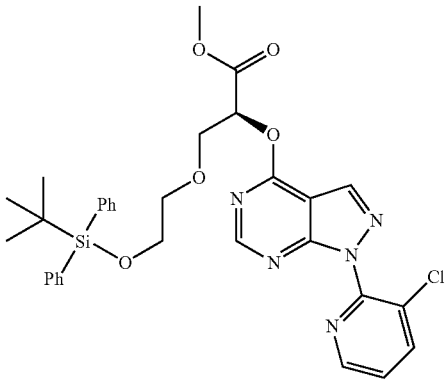

60% Sodium hydride in mineral oil (1.013 g, 25.34 mmol) was added to (S)-methyl 3-(2-(tert-butyldiphenylsilyloxy) ethoxy)-2-hydroxypropanoate (Intermediate AB3) (8.5 g, 21.12 mmol) in tetrahydrofuran (150 mL) cooled to 0° C. under nitrogen. The resulting solution was stirred at 0° C. for 10 minutes. A solution of 4-chloro-1-(3-chloropyridin-2-yl)-1H-pyrazolo[3,4-d]pyrimidine (6.18 g, 23.23 mmol) in tetrahydrofuran (20 mL) was added dropwise over a period of 5 minutes. The resulting mixture was allowed to warm to ambient temperature and stirred for 2 hours. The reaction mixture was quenched with 1M citric acid and extracted with ethyl acetate. The organic layer was washed with brine, dried (MgSO$_4$) and evaporated. The crude product was purified by flash silica chromatography, eluting with 0 to 100% ethyl acetate in isohexane to afford the product (7.15 g, 53.6%).
$^1$H NMR (400 MHz, CDCl$_3$) δ 1.05 (9H, s), 3.68-3.79 (5H, m), 3.85 (2H, t), 4.08-4.23 (2H, m), 5.84-5.89 (1H, m), 7.33-7.48 (7H, m), 7.65-7.73 (4H, m), 7.97-8.03 (1H, m), 8.34 (1H, s), 8.58 (1H, s), 8.59-8.63 (1H, m); m/z (ESI+) (M+H)+=632; HPLC tR=3.68 min.

Intermediate AB3: (S)-methyl 3-(2-(tert-butyldiphe-nylsilyloxy)ethoxy)-2-hydroxypropanoate

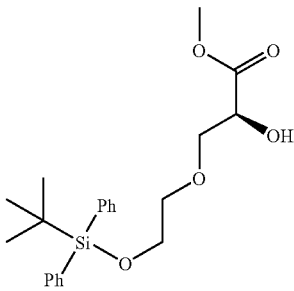

Magnesium trifluoromethanesulfonate (3.95 g, 12.24 mmol) was added in one portion to (S)-methyl oxirane-2-carboxylate (5 g, 48.98 mmol) and 2-(tert-butyldiphenylsily-loxy)ethanol (14.72 g, 48.98 mmol) at 10° C. The resulting suspension was stirred at 10° C. for 10 minutes and then warmed to 45° C. and stirred for 3 days. The crude product was purified by flash silica chromatography, eluting with 0 to 30% ethyl acetate in isohexane to afford the product (8.50 g, 43.1%). ¹H NMR (400 MHz, CDCl₃) δ 1.05 (9H, s), 3.10 (1H, d), 3.62 (2H, t), 3.74-3.87 (7H, m), 4.26-4.34 (1H, m), 7.35-7.46 (6H, m), 7.63-7.71 (4H, m); m/z (ESI+) (M+Na)+= 425.37; HPLC tR=3.15 min.

Intermediate AB4: (2S)-3-(2-(tert-butyldiphenylsilyloxy)ethoxy)-N-(5-chloropyridin-2-yl)-2-(1-(3-chloropyridin-2-yl)-1H-pyrazolo[3,4-d]pyrimidin-4-yloxy)propanamide

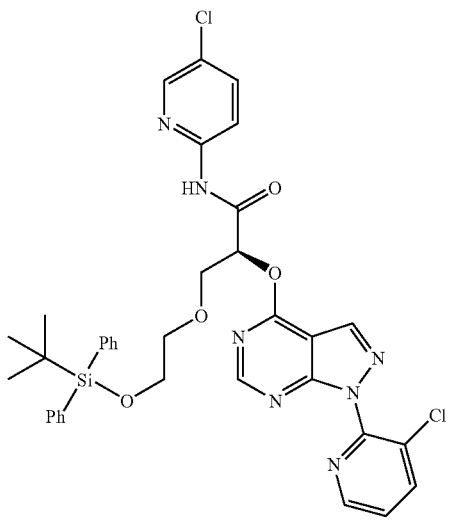

Trimethylaluminium (2M in hexane) (0.455 mL, 0.91 mmol) was added to 5-chloropyridin-2-amine (112 mg, 0.87 mmol) in toluene (10 mL) cooled to 0° C. under nitrogen. The resulting solution was stirred at 0° C. for 20 minutes. (2S)-methyl 3-(2-(tert-butyldiphenylsilyloxy)ethoxy)-2-(1-(3-chloropyridin-2-yl)-1H-pyrazolo[3,4-d]pyrimidin-4-yloxy)propanoate (Intermediate AB2) (500 mg, 0.79 mmol) in toluene (2 mL) was added and the reaction was heated to reflux for 24 hours. The reaction mixture was concentrated in vacuo and neutralised with citric acid (1M, aq) and then diluted with water (10 ml) and DCM (10 mL). The mixture was poured onto a phase separator and the organic layer collected and evaporated. The crude material was used without purification.

Intermediate AC1: (3S)-3-(1-(2-chlorophenyl)-1H-pyrazolo[3,4-d]pyrimidin-4-yloxy)-1-(methylsulfonyl)pyrrolidin-2-one

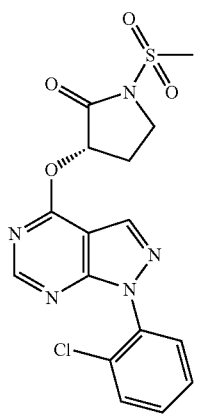

Butyllithium (1.6M in hexane, 1.668 mL, 2.67 mmol) was added dropwise to (3S)-3-(1-(2-chlorophenyl)-1H-pyrazolo[3,4-d]pyrimidin-4-yloxy)pyrrolidin-2-one (Intermediate AC2) (800 mg, 2.43 mmol) in THF (15 mL) cooled to −78° C. under nitrogen. The resulting solution was allowed to warm to r.t., then recooled to −78° C. methanesulfonyl chloride (0.207 mL, 2.67 mmol) was added dropwise and the resulting solution was stirred at r.t. for 2 hours. The reaction mixture was quenched with water (20 mL) and extracted with ethyl acetate (2×50 mL). The combined organic layers were dried (MgSO₄) and evaporated (995 mg). The crude product was purified by flash silica chromatography, eluting with 50 to 100% ethyl acetate in isohexane to afford the product (368 mg, 37.2%). ¹H NMR (400 MHz, CDCl₃) δ 2.35-2.47 (1H, m), 2.83-2.92 (1H, m), 3.37 (3H, s), 3.85-3.94 (1H, m), 4.06-4.16 (1H, m), 6.13 (1H, t), 7.44-7.56 (3H, m), 7.59-7.66 (1H, m), 8.32 (1H, s), 8.57 (1H, s); m/z (ES+) (M+H)+=408.29; HPLC tR=2.10 min.

Intermediate AC2: (3S)-3-(1-(2-chlorophenyl)-1H-pyrazolo[3,4-d]pyrimidin-4-yloxy)pyrrolidin-2-one

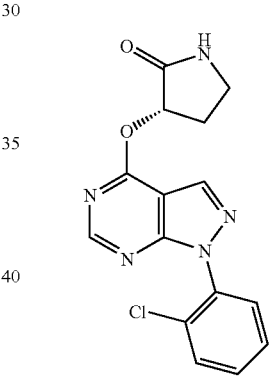

Sodium hydride (60% in oil) (0.435 g, 10.88 mmol) was added to (S)-3-hydroxypyrrolidin-2-one (CAS no. 34368-52-0) (1 g, 9.89 mmol) in THF (50 mL) at 0° C. under nitrogen. The resulting suspension was stirred at 0° C. for 10 minutes. A solution of 4-chloro-1-(2-chlorophenyl)-1H-pyrazolo[3,4-d]pyrimidine (Intermediate B15) (4.01 g, 15.13 mmol) in DMF (25 mL) was added and the resulting mixture was stirred at r.t. for 16 hours. The reaction mixture was quenched with water (20 mL) and extracted with ethyl acetate (2×50 mL). The combined organic layers were dried (MgSO₄) and evaporated (3.8 g). The crude product was purified by flash silica chromatography, eluting with 0-50% MeOH in ethyl acetate to afford the product (0.810 g, 24.8%). ¹H NMR (400 MHz, CDCl₃) δ 2.30-2.42 (1H, m), 2.81-2.91 (1H, m), 3.45-3.64 (2H, m), 6.05 (1H, t), 6.44 (1H, s), 7.42-7.51 (2H, m), 7.51-7.56 (1H, m), 7.57-7.66 (1H, m), 8.33 (1H, s), 8.60 (1H, s); m/z (ES+) (M+H)+=330.27; HPLC tR=1.61 min.

Intermediate AD1: (2S)-3-[3-(tert-butyl-dimethylsilyl)oxyazetidin-1-yl]-N-(5-chloropyridin-2-yl)-2-[1-(3-chloropyridin-2-yl)pyrazolo[4,5-e]pyrimidin-4-yl]oxypropanamide

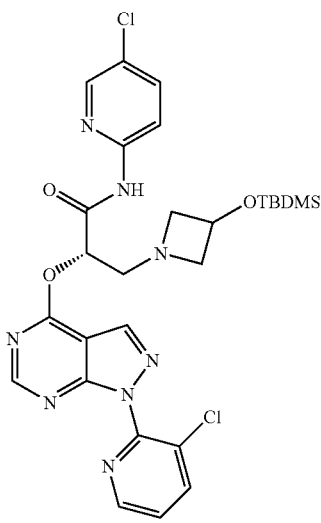

Sodium hydride (0.715 g, 17.88 mmol) was added to (S)-3-(3-(tert-butyldimethylsilyloxy)azetidin-1-yl)-N-(5-chloropyridin-2-yl)-2-hydroxypropanamide (Intermediate AD2) (2.3 g, 5.96 mmol) in anhydrous THF (25 mL) at 0° C. under nitrogen. The resulting solution was stirred at 0° C. for 10 minutes and then 4-chloro-1-(3-chloropyridin-2-yl)-1H-pyrazolo[3,4-d]pyrimidine (Intermediate B15) (2.265 g, 5.96 mmol) was added. The reaction mixture was allowed to warm to room temperature and stirred for 3 hours. The reaction mixture was neutralised with 1M citric acid and diluted with water (25 mL) and EtOAc (50 mL). The organic layer was separated and washed with saturated brine (25 mL), dried (MgSO$_4$) and evaporated to give the product (3.67 g, 100%) which was used for the next stage without purification. m/z (ESI+) (M+H)$^+$=615; HPLC t$_R$=2.43 min.

Intermediate AD2: (2S)-3-[3-(tert-butyl-dimethylsilyl)oxyazetidin-1-yl]-N-(5-chloropyridin-2-yl)-2-hydroxypropanamide

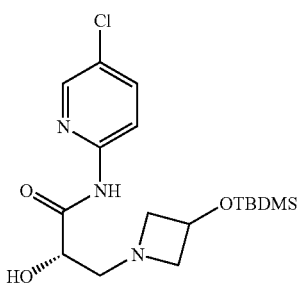

Trimethylaluminium (5.75 mL, 11.50 mmol) was added to 5-chloropyridin-2-amine (1.285 g, 10.00 mmol) in toluene (50 mL) cooled to 0° C. under nitrogen. The resulting solution was stirred at 0° C. for 10 minutes, (S)-methyl 3-(3-(tert-butyldimethylsilyloxy)azetidin-1-yl)-2-hydroxypropanoate (Intermediate AD3) (2.894 g, 10.00 mmol) in toluene (20 mL) was added, the reaction allowed to warm to room temperature and then heated at 80° C. for 4 hours. The reaction mixture was cooled, concentrated in vacuo and the residue neutralised with 1M citric acid (30 mL), diluted with water (25 mL) and extracted with EtOAc (2×30 mL). The combined organic extracts were dried (MgSO$_4$) and evaporated to afford crude product which was purified by flash silica chromatography with EtOAc as eluent to afford the product (2.5 g, 65%). 1H NMR (400 MHz, DMSO) δ 0.01 (6H, s), 0.84 (9H, m), 2.65-2.70 (2H, m), 2.76-2.83 (2H, m), 3.56-3.59 (2H, m), 4.07-4.10 (1, m), 4.28-4.34 (1H, m), 5.78 (1H, s), 7.92 (1H, dd), 8.12 (1H, dd), 8.36-8.37 (1H, m), 9.87 (1H, s); m/z (ESI+) (M+H)$^+$=386; HPLC t$_R$=1.64 min.

Intermediate AD3: Methyl (2S)-3-[3-(tert-butyl-dimethylsilyl)oxyazetidin-1-yl]-2-hydroxypropanoate

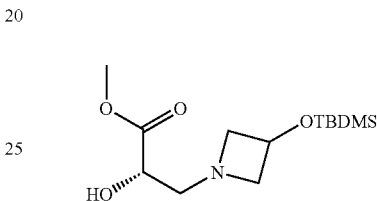

3-(tert-butyldimethylsilyloxy)azetidine (Intermediate AD4) (11.0 g, 58.71 mmol) and (S)-methyl oxirane-2-carboxylate (5.99 g, 58.71 mmol) were dissolved in butyronitrile (75 mL) and heated to 100° C. for 90 minutes. Reaction turns from colourless to yellow during the period of heating. The resulting mixture was cooled and evaporated. The crude product was purified by flash silica chromatography, elution gradient 0 to 5% MeOH in EtOAc to afford the product (9.6 g, 56%). 1H NMR (400 MHz, CDCl$_3$) δ 0.04 (6H, s), 0.85 (9H, s), 2.71-2.79 (2H, m), 2.87-2.95 (2H, m), 3.58-3.68 (2H, m), 3.75 (3H, s), 4.10-4.12 (1H, m), 4.35-4.39 (1H, t) (OH signal not observed).

The procedure may also be carried out in an analogous manner using azetidin-3-yloxy-tert-butyl-dimethylsilane and diphenylmethane (1:1) (Intermediate AD5).

Intermediate AD4: Azetidin-3-yloxy-tert-butyl-dimethylsilane

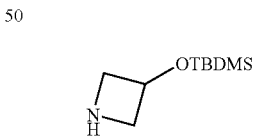

A solution of tert-butylchlorodimethylsilane (12.01 g, 79.69 mmol) in DCM (20 mL) was added dropwise to a stirred solution of azetidin-3-ol hydrochloride (CAS no. 18621-18-6) (8.73 g, 79.69 mmol) and anhydrous N-ethyl-N-isopropylpropan-2-amine (34.1 mL, 199.22 mmol) in DCM (20 mL) cooled to 10° C., over a period of 2 minutes under nitrogen. The resulting solution was stirred at ambient temperature for 20 hours. The reaction mixture was concentrated, diluted with EtOAc (75 mL), and washed sequentially with saturated NaHCO$_3$ (25 mL), water (20 mL), and saturated brine (20 mL). The organic layer was dried (MgSO$_4$), filtered and evaporated to afford the product (11.1 g, 74%). 1H NMR (400 MHz, CDCl$_3$) δ 0.04 (6H, s), 0.87 (9H, m), 2.80 (1H, s), 3.57-3.61 (2H, m), 3.67-3.71 (2H, m), 4.57-4.64 (1H, m).

Intermediate AD5:
Azetidin-3-yloxy-tert-butyl-dimethylsilane and diphenylmethane (1:1)

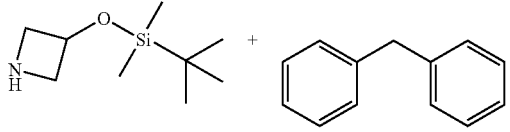

1-benzhydryl-3-(tert-butyldimethylsilyloxy)azetidine (Intermediate AD6) (3.12 g, 8.82 mmol) and palladium on carbon (0.3 g, 0.28 mmol) in methanol (60 mL) were stirred under an atmosphere of hydrogen at ambient temperature for 18 hours. The reaction mixture was filtered and concentrated to a colourless liquid, 3-(tert-butyldimethylsilyloxy)azetidine compound with diphenylmethane (1:1) (3.02 g, 96%). This was used without further purification. 1H NMR (400 MHz, CDCl$_3$) δ 0.00 (6H, s), 0.84 (9H, s), 3.52-3.58 (2H, m), 3.61-3.67 (2H, m), 3.95 (2H, s), 4.55-4.63 (1H, m), 7.12-7.27 (10H, m), 7.64 (1H, s).

Intermediate AD6: (1-Benzhydrylazetidin-3-yl)oxy-tert-butyl-dimethylsilane

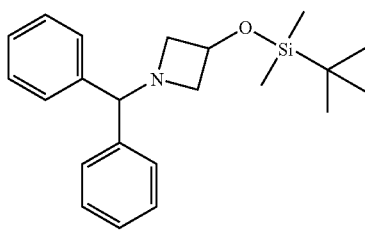

tert-Butyldimethylsilyl chloride (1.524 g, 10.11 mmol) was added to 1-benzhydrylazetidin-3-ol (CAS no. 18621-17-5) (2.2 g, 9.19 mmol) and imidazole (1.565 g, 22.98 mmol) in DCM (46.0 mL) at r.t. under nitrogen. The resulting solution was stirred at r.t. for 3 hours. The reaction mixture was quenched with water, poured onto a phase separator and evaporated to afford the product (3.66 g, 113%). 1H NMR (400 MHz, CDCl$_3$) δ 0.00 (6H, s), 0.85 (9H, s), 2.81 (2H, s), 3.52 (2H, s), 4.35 (1H, s), 4.40-4.49 (1H, m), 7.08-7.43 (10H, m); m/z (ES+) (M+H)$^+$=354.55; HPLC t$_R$=2.04 min.

Intermediate AD7: (2S)-3-(3-(tert-butyldimethylsilyloxy)azetidin-1-yl)-2-(1-(2-chlorophenyl)-1H-pyrazolo[3,4-d]pyrimidin-4-yloxy)-N-(5-methylpyridin-2-yl)propanamide

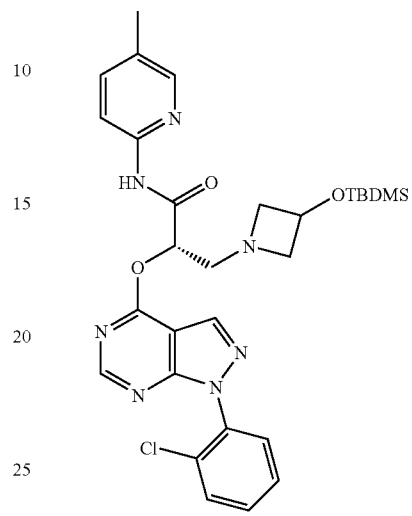

Sodium hydride (132 mg, 3.30 mmol) was added to (S)-3-(3-(tert-butyldimethylsilyloxy)azetidin-1-yl)-2-hydroxy-N-(5-methylpyridin-2-yl)propanamide (Intermediate AD8) (482 mg, 1.32 mmol) in anhydrous THF (5 mL) at 0° C. under nitrogen. The resulting solution was stirred at 0° C. for 10 minutes and then 4-chloro-1-(2-chlorophenyl)-1H-pyrazolo [3,4-d]pyrimidine (Intermediate B1) (385 mg, 1.45 mmol) was added. The reaction mixture was allowed to warm to room temperature and stirred for 3 hours. The reaction mixture was neutralised with 1M citric acid and diluted with water and EtOAc. The organic layer was separated and washed with saturated brine, dried (MgSO$_4$) and evaporated to afford the product (908 mg) which was used without further purification. m/z (ES+) (M+H)$^+$=594.52; HPLC t$_R$=1.87 min.

Intermediate AD8: (S)-3-(3-(tert-butyldimethylsilyloxy)azetidin-1-yl)-2-hydroxy-N-(5-methylpyridin-2-yl)propanamide

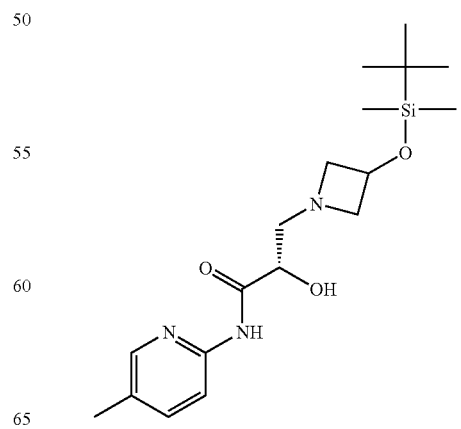

Trimethylaluminium (2M in toluene) (0.993 mL, 1.99 mmol) was added to 5-methylpyridin-2-amine (205 mg, 1.90 mmol) in toluene (10 mL) cooled to 0° C. under nitrogen. The resulting solution was stirred at 0° C. for 10 minutes. (S)-methyl 3-(3-(tert-butyldimethylsilyloxy)azetidin-1-yl)-2-hydroxypropanoate (Intermediate AD3) (500 mg, 1.73 mmol) in toluene (4 mL) was added and the reaction was allowed to warm to room temperature and then heated at 80° C. for 4 hours. The reaction mixture was concentrated in vacuo. The residue was neutralised with citric acid (1M, aq) and then diluted with water and extracted with EtOAc. The combined organics were dried (MgSO$_4$) and evaporated to afford the product (482 mg, 76%). 1H NMR (400 MHz, CDCl$_3$) δ 0.05 (6H, s), 0.88 (9H, s), 2.30 (3H, s), 3.15-3.23 (1H, m), 3.37-3.51 (3H, m), 4.15-4.30 (2H, m), 4.32-4.39 (1H, m), 4.58-4.66 (1H, m), 7.48-7.53 (1H, m), 8.04 (1H, d), 8.12-8.15 (1H, m), 9.46 (1H, s); m/z (ES+) (M+H)$^+$=366.53; HPLC t$_R$=1.50 min.

Intermediate AD9: (2S)-3-(3-(tert-butyldimethylsilyloxy)azetidin-1-yl)-2-(1-(3-chloropyridin-2-yl)-1H-pyrazolo[3,4-d]pyrimidin-4-yloxy)-N-(5-methylpyridin-2-yl)propanamide

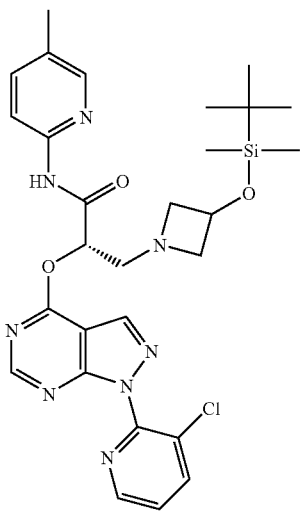

Sodium hydride (15.76 mg, 0.39 mmol) was added to (S)-3-(3-(tert-butyldimethylsilyloxy)azetidin-1-yl)-2-hydroxy-N-(5-methylpyridin-2-yl)propanamide (Intermediate AD8) (120 mg, 0.33 mmol) in anhydrous THF (5 mL) at 0° C. under nitrogen. The resulting solution was stirred at 0° C. for 10 minutes and then 4-chloro-1-(3-chloropyridin-2-yl)-1H-pyrazolo[3,4-d]pyrimidine (Intermediate B15) (96 mg, 0.36 mmol) was added. The reaction mixture was allowed to warm to room temperature and stirred for 5 hours. A further portion of Sodium hydride (15.76 mg, 0.39 mmol) was added and stirring continued for 1 hour more. The reaction mixture was neutralised with 1M citric acid and diluted with water and EtOAc. The organic layer was separated and washed with saturated brine, dried (MgSO$_4$) and evaporated to afford the product (195 mg). m/z (ES+) (M+H)$^+$=595.61; HPLC t$_R$=1.83 min.

Intermediate AE1: (2S)-3-[2-(tert-butyl-diphenylsilyl)oxyethoxy]-2-[1-(3-chloro-2-methylphenyl)pyrazolo[4,5-e]pyrimidin-4-yl]oxy-N-(5-cyanopyridin-2-yl)propanamide A solution of 2M Trimethyl aluminium in toluene (1.790 mL, 3.58 mmol) in toluene (15 mL) was added dropwise to a stirred suspension of 6-aminonicotinonitrile (0.426 g, 3.58 mmol) in toluene (15 mL) cooled to 0° C., over a period of 2 minutes under nitrogen and the resulting suspension stirred for 20 minutes at 0° C. A solution of (2S)-methyl 3-(2-(tert-butyldiphenylsilyloxy)ethoxy)-2-(1-(3-chloro-2-methylphenyl)-1H-pyrazolo[3,4-d]pyrimidin-4-yloxy)propanoate (Intermediate AE2) (1.05 g, 1.63 mmol) in toluene (10 mL) was added dropwise over 2 minutes, the mixture allowed to warm to ambient temperature and then heated to 60° C. for 20hrs. Cooled to ~5° C. and a 10% solution of Rochelle's salt (25 mL) added followed by ethyl acetate (30 mL) and stirred at ambient temperature for 30 minutes. The organic phase was separated, washed with water (20 mL) and brine (20 mL), dried (MgSO$_4$), filtered and evaporated to a yellow gum. The crude product was purified by flash silica chromatography, elution gradient 20 to 50% EtOAc in isohexane to afford the product (1.1 g, 92%). $^1$H NMR (400 MHz, DMSO) δ 0.89 (9H, s), 2.03 (3H, s), 3.71-3.78 (4H, m), 4.05-4.10 (1H, m), 4.14-4.19 (1H, m), 6.00-6.02 (1H, m), 7.34-7.45 (8H, m), 7.59-7.61 (4H, m), 7.67-7.69 (1H, m), 8.11-8.14 (1H, m), 8.20-8.23 (1H, m), 8.51 (1H, s), 8.84 (1H, s), 8.80-8.82 (1H, m), 11.55 (1H, s); m/z (ESI+) (M+H)$^+$=732; HPLC t$_R$=3.48 min.

323

Intermediate AE2: (2S)-Methyl 3-[2-(tert-butyl-diphenylsilyl)oxyethoxy]-2-[1-(3-chloro-2-methylphenyl)pyrazolo[4,5-e]pyrimidin-4-yl]oxypropanoate

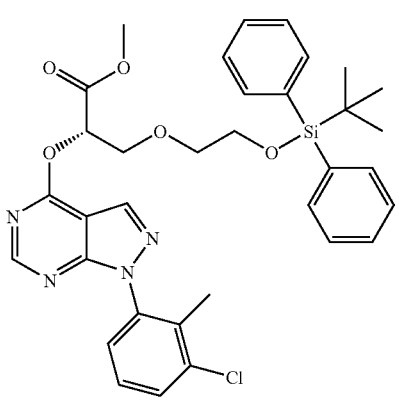

Sodium hydride (60% in mineral oil) (0.191 g, 4.77 mmol) was added in one portion to (S)-methyl 3-(2-(tert-butyldiphenylsilyloxy)ethoxy)-2-hydroxypropanoate (Intermediate AB3) (1.6 g, 3.97 mmol) in THF (15 mL) cooled to 0° C. under nitrogen. Slow gas evolution. The resulting suspension was stirred at 0° C. for 10 minutes. A solution of 4-chloro-1-(3-chloro-2-methylphenyl)-1H-pyrazolo[3,4-d]pyrimidine (Intermediate AE5) (1.109 g, 3.97 mmol) in THF (10 mL) was added dropwise over 2 minutes. The resulting suspension was stirred at 0° C. for 10 minutes, allowed to warm to ambient temperature and stirred for 72 hours to give an orange solution. Cooled to ~5° C., 1M citric acid (30 mL) added, the mixture stirred for 10 minutes, diluted with EtOAc (50 mL), the organic phase separated and washed sequentially with water (25 mL) and saturated brine (25 mL). The organic layer was dried (MgSO$_4$), filtered and evaporated in vacuo. The crude product was purified by flash silica chromatography, elution gradient 20 to 50% EtOAc in isohexane to afford the product (2.1 g, 82%). $^1$H NMR (400 MHz, DMSO) δ 0.95 (9H, s), 2.03 (3H, s), 3.68 (3H, s), 3.67-3.74 (2H, m), 3.78-3.82 (2H, m), 4.04-4.07 (1H, m), 5.87-5.91 (1H, m), 7.37-7.45 (8H, m), 7.61-7.65 (4H, m), 7.67-7.69 (1H, m), 8.48 (1H, s), 8.57 (1H, s); m/z (ESI+) (M+H)$^+$=645; HPLC t$_R$=3.65 min.

324

Intermediate AE3: (2S)-3-[2-(tert-butyl-dimethylsilyl)oxyethoxy]-2-[1-(3-chloro-2-methylphenyl)pyrazolo[4,5-e]pyrimidin-4-yl]oxy-N-(5-methylpyridin-2-yl)propanamide

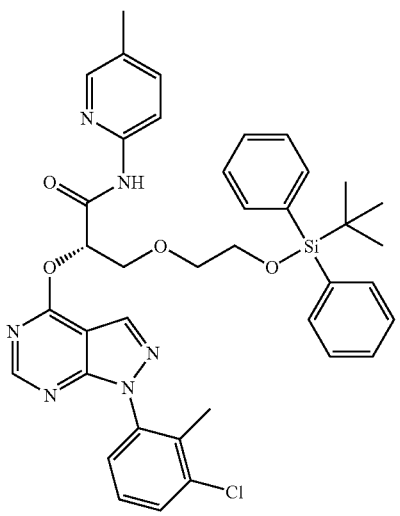

A solution of 2M trimethyl aluminium in toluene (1.790 mL, 3.58 mmol) in toluene (15 mL) was added dropwise to a stirred suspension of 5-methylpyridin-2-amine (0.387 g, 3.58 mmol) in toluene (15 mL) cooled to 0° C., over a period of 2 minutes under nitrogen and the resulting suspension was stirred at 0° C. for 20 minutes. A solution of (2S)-methyl 3-(2-(tert-butyldiphenylsilyloxy)ethoxy)-2-(1-(3-chloro-2-methylphenyl)-1H-pyrazolo[3,4-d]pyrimidin-4-yloxy)propanoate (Intermediate AE2) (1.05 g, 1.63 mmol) in toluene (10 mL) was added dropwise over 2 minutes, the mixture allowed to warm to ambient temperature and then heated to 60° C. for 20hrs. The reaction was cooled to ~5° C. and a 10% solution of Rochelles salt (25 mL) added followed by ethyl acetate (30 mL). The organic phase was separated, washed with water (20 mL) and brine (20 mL), dried (MgSO$_4$), filtered and evaporated. The crude product was purified by flash silica chromatography, elution gradient 20 to 50% EtOAc in iso-hexane to afford the product (1.1 g, 94%). $^1$H NMR (400 MHz, DMSO) δ 0.89 (9H, s), 2.03 (3H, s), 2.24 (3H, s), 3.70-3.79 (4H, m), 4.03-4.07 (1H, m), 4.12-4.16 (1H, m), 5.99-6.00 (1H, m), 7.33-7.47 (8H, m), 7.55-7.62 (5H, m), 7.67-7.69 (1H, m), 7.86-7.89 (1H, m), 8.17-8.18 (1H, m), 8.50 (1H, s), 8.53 (1H, s), 10.87 (1H, s); m/z (ESI+) (M+H)$^+$= 721; HPLC t$_R$=3.63 min.

Intermediate AE4: (2S)-3-[2-(tert-butyl-diphenylsilyl)oxyethoxy]-2-[1-(3-chloro-2-methylphenyl)pyrazolo[4,5-e]pyrimidin-4-yl]oxy-N-(5-chloropyridin-2-yl)propanamide

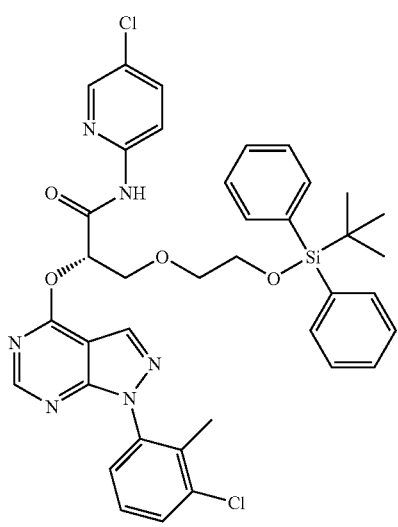

Sodium hydride (60% in mineral oil) (88 mg, 2.20 mmol) was added in one portion to (S)-3-(2-(tert-butyldiphenylsilyloxy)ethoxy)-N-(5-chloropyridin-2-yl)-2-hydroxypropanamide (Intermediate AU3) (499 mg, 1.00 mmol) in THF (25 mL) cooled to 0° C. under nitrogen. Slow gas evolution and the resulting suspension was stirred at 0° C. for 10 minutes. 4-chloro-1-(3-chloro-2-methylphenyl)-1H-pyrazolo[3,4-d]pyrimidine (Intermediate AE5) (279.1 mg, 1.00 mmol) was added in one portion, stirred at 0° C. for 10 minutes, allowed to warm to ambient temperature and stirred for 20 hours. Cooled to ~5° C., 1M citric acid (30 mL) added and the mixture stirred for 10 minutes. The mixture was diluted with EtOAc (50 mL), the organic phase separated and washed sequentially with water (25 mL) and saturated brine (25 mL). The organic layer was dried (MgSO$_4$), filtered and evaporated to afford crude product which was purified by flash silica chromatography, elution gradient 20 to 50% EtOAc in isohexane to afford the product (550 mg, 74%). $^1$H NMR (400 MHz, DMSO) δ 0.89 (9H, s), 2.03 (3H, s), 3.70-3.79 (4H, m), 4.02-4.18 (2H, m), 5.98-6.03 (1H, d), 7.32-7.47 (8H, m), 7.59-7.62 (4H, m), 7.67-7.69 (1H, m), 7.86-7.88 (1H, m), 8.00-8.03 (1H, m), 8.39 (1H, dd), 8.51 (1H, s), 8.54 (1H, s), 11.19 (1H, s); m/z (ESI+) (M+H)$^+$=741/743/745 (Cl$_2$ pattern); HPLC t$_R$=3.83 min.

Intermediate AE5: 4-Chloro-1-(3-chloro-2-methylphenyl)pyrazolo[5,4-d]pyrimidine

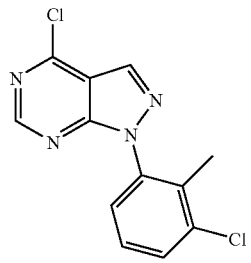

Phosphoryl trichloride (16.09 mL, 172.63 mmol) was added in one portion to 1-(3-chloro-2-methylphenyl)-1H-pyrazolo[3,4-d]pyrimidin-4-ol (Intermediate AE6) (3.0 g, 11.51 mmol) and the resulting suspension was heated to 100° C. to give a solution and stirred for 4 hours. Evaporated, the residue poured into ice/water and stirred for 30 minutes. The solids were filtered, washed with water (4×20 mL), dissolved in ethyl acetate (100 mL), dried (MgSO$_4$), filtered and evaporated to afford the product (2.8 g) which was used without further purification. $^1$H NMR (400 MHz, DMSO) δ 2.06 (3H, s), 7.41-7.54 (2H, m), 7.71-7.73 (1H, m), 8.79 (1H, s), 8.89 (1H, s); m/z (ESI+) (M+H)$^+$=279; HPLC t$_R$=2.59 min.

Intermediate AE6: 1-(3-chloro-2-methylphenyl)-1H-pyrazolo[3,4-d]pyrimidin-4-ol

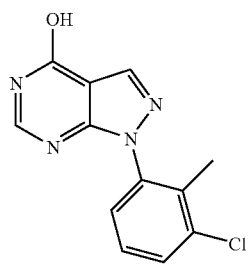

Concentrated sulfuric acid (1.595 mL, 29.93 mmol) was added to a stirred solution of 5-amino-1-(3-chloro-2-methylphenyl)-1H-pyrazole-4-carbonitrile (Intermediate AE7) (6.33 g, 27.21 mmol) in formic acid (40 mL). The resulting solution was stirred at 100° C. for 24 hours. The reaction was allowed to cool to room temperature and evaporated to ~half volume, water (100 mL) added and stirred for 1 hour. The formed ppt was filtered off, washed well with water and dried overnight in a vacuum over P$_2$O$_5$ to afford the product (5.82 g, 82%). $^1$H NMR (400 MHz, DMSO) δ 2.04 (3H, s), 7.37-7.46 (2H, m), 7.64-7.68 (1H, m), 8.06 (1H, d), 8.33 (1H, s), 12.35 (1H, s); m/z (ES−) (M−H)−=259.24; HPLC t$_R$=1.68 min.

Intermediate AE7: 5-amino-1-(3-chloro-2-methylphenyl)-1H-pyrazole-4-carbonitrile

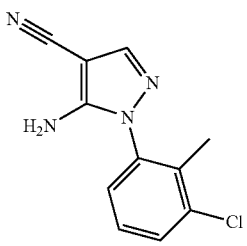

(3-Chloro-2-methylphenyl)hydrazine hydrochloride (CAS no. 65208-12-0) (9 g, 46.61 mmol) was partitioned between EtOAc (100 mL) and NaOH (2M, aq) (60 mL). The organic layer separated and washed with water (50 mL), brine (50 mL), dried (MgSO$_4$), filtered and concentrated. The resultant oil was suspended in MeOH (100 mL) under nitrogen at −5° C. 2-(Ethoxymethylene)malononitrile (5.69 g, 46.61 mmol) was added portionwise over 5 mins and the mixture stirred at ~0° C. for 30 mins. The reaction mixture was allowed to warm to room temperature and then heated at reflux under nitrogen for 2 hours. The reaction mixture was allowed to cool and evaporated to dryness. The crude product was purified by flash silica chromatography, elution gradient 0 to 50% EtOAc in isohexane to afford the product(6.33 g, 58.4%). $^1$H NMR (400 MHz, DMSO) δ 2.02 (3H, s), 6.57 (2H, s), 7.25-7.32 (1H, m), 7.37 (1H, t), 7.58-7.64 (1H, m), 7.77 (1H); m/z (ES+) (M+H)$^+$=233.28; HPLC t$_R$=1.89 min.

Intermediate AF1: (2S)-3-[2-(tert-butyl-dimethylsilyl)oxyethoxy]-N-(5-cyanopyridin-2-yl)-2-[1-(3-fluoro-2-methylphenyl)pyrazolo[4,5-e]pyrimidin-4-yl]oxypropanamide

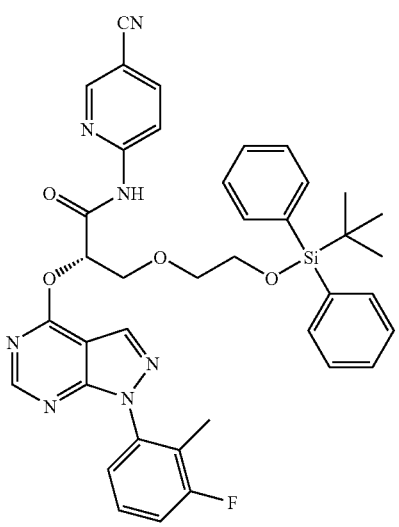

Prepared using a procedure analogous to that described for Intermediate AE1 using (2S)-methyl 3-(2-(tert-butyldiphenylsilyloxy)ethoxy)-2-(1-(3-fluoro-2-methylphenyl)-1H-pyrazolo[3,4-d]pyrimidin-4-yloxy)propanoate (Intermediate AF4) and 6-aminonicotinonitrile. $^1$H NMR (400 MHz, DMSO) d 0.89 (9H, s), 1.96 (3H, d), 3.83-3.69 (4H, m), 4.12-4.04 (1H, m), 4.17 (1H, dd), 6.02 (1H, m), 7.51-7.27 (9H, m), 7.60 (4H, m), 8.13 (1H, d), 8.22 (1H, dd), 8.51 (1H, s), 8.55 (1H, s), 8.81 (1H, d), 11.56 (1H, s). m/z (ES+) (M+H)$^+$=716; HPLC t$_R$=3.29 min.

Intermediate AF2: (2S)-3-[2-(tert-butyl-dimethylsilyl)oxyethoxy]-2-[1-(3-fluoro-2-methylphenyl)pyrazolo[4,5-e]pyrimidin-4-yl]oxy-N-(5-methylpyridin-2-yl)propanamide

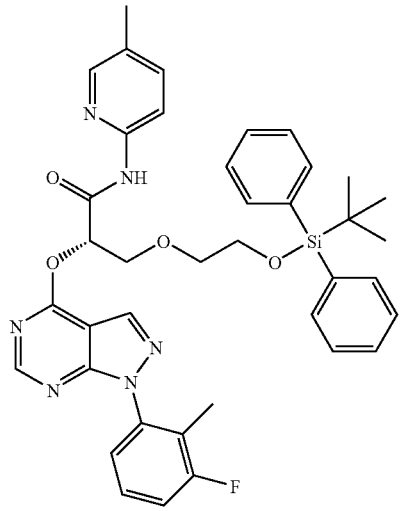

Prepared using a procedure analogous to that described for Intermediate AE1 using (2S)-methyl 3-(2-(tert-butyldiphenylsilyloxy)ethoxy)-2-(1-(3-fluoro-2-methylphenyl)-1H-pyrazolo[3,4-d]pyrimidin-4-yloxy)propanoate (Intermediate AF4) and 5-methylpyridin-2-amine. $^1$H NMR (400 MHz, DMSO) d 0.88 (9H, s), 1.96 (3H, d), 2.24 (3H, s), 3.75 (4H, m), 4.08-4.02 (1H, m), 4.14 (1H, m), 5.99 (1H, m), 7.50-7.29 (9H, m), 7.63-7.54 (5H, m), 7.89 (1H, d), 8.17 (1H, s), 8.51 (1H, s), 8.55 (1H, s), 10.94 (1H, s).
m/z (ES+) (M+H)$^+$=705; HPLC t$_R$=3.42 min.

Intermediate AF3: (2S)-3-[2-(tert-butyl-dimethylsilyl)oxyethoxy]-N-(5-chloropyridin-2-yl)-2-[1-(3-fluoro-2-methylphenyl)pyrazolo[4,5-e]pyrimidin-4-yl]oxypropanamide

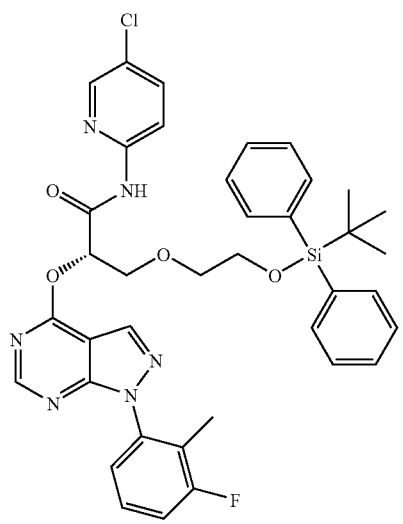

Prepared using a procedure analogous to that described for Intermediate AE1 using (2S)-methyl 3-(2-(tert-butyldiphenylsilyloxy)ethoxy)-2-(1-(3-fluoro-2-methylphenyl)-1H-pyrazolo[3,4-d]pyrimidin-4-yloxy)propanoate (Intermediate AF4) and 5-chloropyridin-2-amine. ¹H NMR (400 MHz, DMSO) d 0.87 (9H, s), 1.96 (3H, d), 3.75 (4H, m), 4.10-4.02 (1H, m), 4.15 (1H, m), 6.00 (1H, m), 7.38 (9H, m), 7.63-7.57 (4H, m), 7.88 (1H, dd), 8.03 (1H, d), 8.40 (1H, d), 8.52 (1H, s), 8.56 (1H, s), 11.25 (1H, s).

m/z (ES+) (M+H)⁺=725; HPLC $t_R$=3.63 min.

Intermediate AF4: (2S)-methyl 3-(2-(tert-butyldiphenylsilyloxy)ethoxy)-2-(1-(3-fluoro-2-methylphenyl)-1H-pyrazolo[3,4-d]pyrimidin-4-yloxy)propanoate

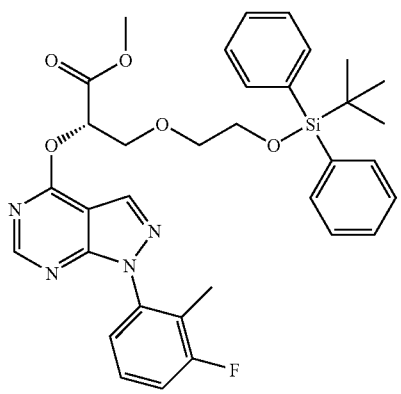

Prepared using a procedure analogous to that described for Intermediate AE2 using (S)-methyl 3-(2-(tert-butyldiphenylsilyloxy)ethoxy)-2-hydroxypropanoate (Intermediate AB3) and 4-chloro-1-(3-fluoro-2-methylphenyl)-1H-pyrazolo[3,4-d]pyrimidine (Intermediate AF5). ¹H NMR (400 MHz, DMSO) d 0.94 (9H, s), 1.96 (3H, d), 3.81-3.63 (7H, m), 4.09-4.02 (1H, m), 4.13 (1H, m), 5.89 (1H, m), 7.50-7.30 (9H, m), 7.63 (4H, m), 8.49 (1H, s), 8.59 (1H, s). m/z (ES+) (M+H)⁺=629; HPLC $t_R$=3.43 min.

Intermediate AF5: 4-chloro-1-(3-fluoro-2-methylphenyl)-1H-pyrazolo[3,4-d]pyrimidine

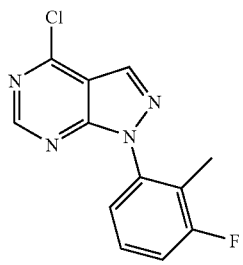

Prepared using a procedure analogous to that described for Intermediate AE5 using 1-(3-fluoro-2-methylphenyl)-1H-pyrazolo[3,4-d]pyrimidin-4-ol (Intermediate AF6). ¹H NMR (400 MHz, DMSO) d 1.99 (3H, d), 7.37 (1H, d), 7.45 (2H, m), 8.77 (1H, s), 8.89 (1H, s).

m/z (ES+) (M+H)⁺=263; HPLC $t_R$=2.38 min.

Intermediate AF6: 1-(3-fluoro-2-methylphenyl)-1H-pyrazolo[3,4-d]pyrimidin-4-ol

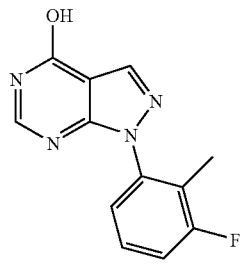

Prepared using a procedure analogous to that described for Intermediate AE6 using 5-amino-1-(3-fluoro-2-methylphenyl)-1H-pyrazole-4-carbonitrile (Intermediate AF7)
¹H NMR (400 MHz, DMSO) d 1.97 (3H, d), 7.28 (1H, d), 7.48-7.35 (2H, m), 8.07 (1H, d), 8.33 (1H, s), 12.34 (1H, s); m/z (ES+) (M+H)⁺=245; HPLC $t_R$=1.43 min.

Intermediate AF7: 5-amino-1-(3-fluoro-2-methylphenyl)-1H-pyrazole-4-carbonitrile

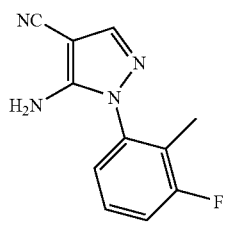

Prepared using a procedure analogous to that described for Intermediate AE7 using (3-fluoro-2-methylphenyl)hydrazine hydrochloride. ¹H NMR (400 MHz, DMSO) d 1.94 (3H, d), 6.56 (2H, s), 7.15 (1H, d), 7.42-7.30 (2H, m), 7.76 (1H, s); m/z (ES+) (M+H)⁺=217; HPLC $t_R$=1.63 min.

Intermediate AG1: (2S)-3-[2-(tert-butyl-dimethylsilyl)oxyethoxy]-2-[1-(2-chlorophenyl)pyrazolo[4,5-e]pyrimidin-4-yl]oxy-N-(5-chloropyridin-2-yl)propanamide

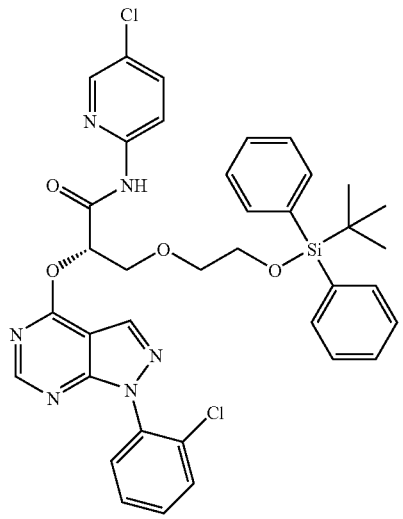

Prepared from (2S)-methyl 3-(2-(tert-butyldiphenylsilyloxy)ethoxy)-2-(1-(2-chlorophenyl)-1H-pyrazolo[3,4-d]pyrimidin-4-yloxy)propanoate (Intermediate AG2) (950 mg, 1.51 mmol) according to the method for Intermediate AE3 using 5-chloropyridin-2-amine. $^1$H NMR (400 MHz, DMSO) δ 0.88 (9H, s), 3.71-3.84 (4H, m), 4.02-4.07 (1H, m), 4.13-4.18 (1H, m), 5.97-5.99 (1H, m), 7.34-7.43 (6H, m), 7.56-7.67 (7H, m), 7.74-7.77 (1H, m), 7.86-7.89 (1H, m), 8.00-8.03 (1H, m), 8.40-8.41 (1H, m), 8.52 (1H, s), 8.57 (1H, s), 11.25 (1H, s); m/z (ESI+) (M+H)$^+$=727; HPLC $t_R$=3.49 min.

Intermediate AG2: Methyl (2S)-3-[2-(tert-butyl-diphenylsilyl)oxyethoxy]-2-[1-(2-chlorophenyl)pyrazolo[4,5-e]pyrimidin-4-yl]oxypropanoate

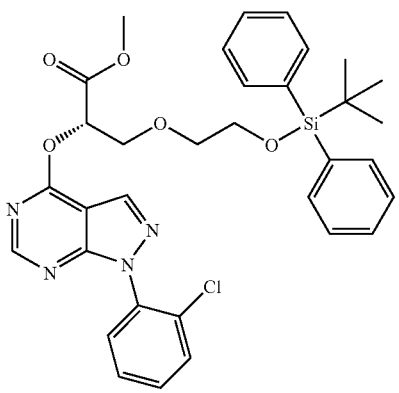

Prepared according to the method for Intermediate AE2 from (S)-methyl 3-(2-(tert-butyldiphenylsilyloxy)ethoxy)-2-hydroxypropanoate (Intermediate AB3) and 4-chloro-1-(2-chlorophenyl)-1H-pyrazolo[3,4-d]pyrimidine (Intermediate B1). $^1$H NMR (400 MHz, DMSO) δ 0.94 (9H, s), 3.56-3.75 (4H, m), 3.68 (3H, s), 3.90-4.09 (2H, m), 5.80-5.85 (1H, m), 7.29-7.43 (6H, m), 7.50-7.67 (7H, m), 7.67-7.74 (1H, m), 8.43 (1H, s), 8.52 (1H, s); m/z (ESI+) (M+H)$^+$=631; HPLC $t_R$=3.38 min.

Intermediate AG3: (2S)-3-[2-(tert-butyl-diphenylsilyl)oxyethoxy]-2-[1-(2-chlorophenyl)pyrazolo[4,5-e]pyrimidin-4-yl]oxy-N-(5-cyanopyridin-2-yl)propanamide

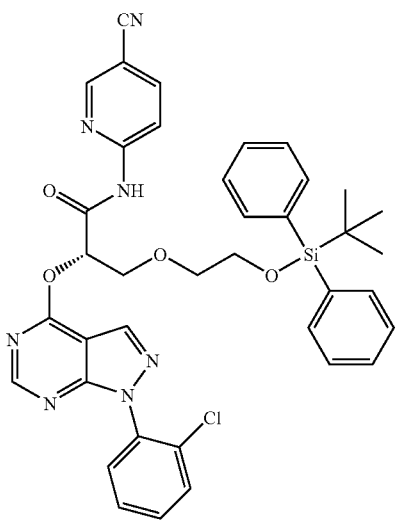

Prepared according to the method for (Intermediate AE1) from (2S)-methyl 3-(2-(tert-butyldiphenylsilyloxy)ethoxy)-2-(1-(2-chlorophenyl)-1H-pyrazolo[3,4-d]pyrimidin-4-yloxy)propanoate (Intermediate AG2). $^1$H NMR (400 MHz, DMSO) δ 0.91 (9H, s), 3.68-3.80 (4H, m), 4.09-4.19 (2H, m), 5.98-6.04 (1H, m), 7.34-7.48 (6H, m), 7.56-7.68 (7H, m), 7.74-7.77 (1H, m), 8.11-8.15 (1H, m), 8.21-8.24 (1H, m), 8.52 (1H, s), 8.54 (1H, s), 8.82-8.83 (1H, m), 11.60 (1H, s); m/z (ESI+) (M+H)$^+$=718; HPLC $t_R$=3.13 min.

Intermediate AG4: (2S)-3-(2-(tert-butyldiphenylsilyloxy)ethoxy)-2-(1-(2-chlorophenyl)-1H-pyrazolo[3,4-d]pyrimidin-4-yloxy)-N-(5-methylpyridin-2-yl)propanamide

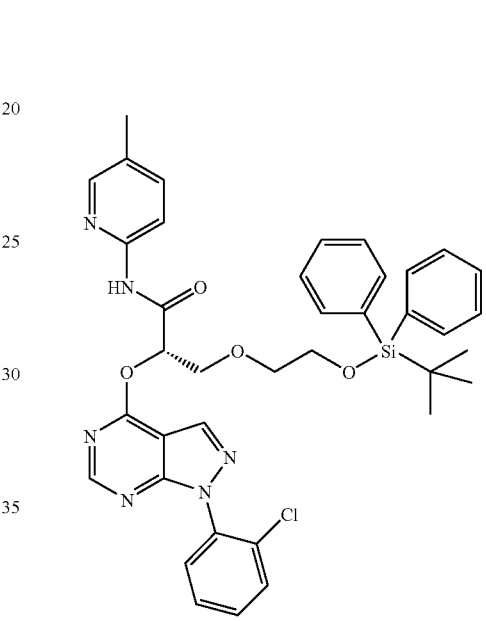

Sodium hydride (14.21 mg, 0.36 mmol) was added to (S)-3-(2-(tert-butyldiphenylsilyloxy)ethoxy)-2-hydroxy-N-(5-methylpyridin-2-yl)propanamide (Intermediate AU2) (85 mg, 0.18 mmol) in anhydrous THF (5 mL) at 0° C. under nitrogen. The resulting solution was stirred at 0° C. for 10 minutes and then 4-chloro-1-(2-chlorophenyl)-1H-pyrazolo[3,4-d]pyrimidine (47.1 mg, 0.18 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×20 mL). The combined organics were washed with saturated brine (10 mL), dried (MgSO$_4$) and evaporated. The crude product was purified by flash silica chromatography, eluting with 0 to 20% EtOAc in isohexane to give (2S)-3-(2-(tert-butyldiphenylsilyloxy)ethoxy)-2-(1-(2-chlorophenyl)-1H-pyrazolo[3,4-d]pyrimidin-4-yloxy)-N-(5-methylpyridin-2-yl)propanamide (126 mg, 100%). $^1$H NMR (400 MHz, CDCl$_3$) δ 0.99 (s, 9H), 2.29 (s, 3H), 3.67-3.73 (m, 2H), 3.77-3.84 (m, 2H), 4.13-4.25 (m, 2H), 6.07 (t, 1H), 7.29-7.54 (m, 10H), 7.59-7.69 (m, 5H), 8.06-8.16 (m, 2H), 8.38 (s, 1H), 8.58 (s, 1H), 8.66 (s, 1H); m/z (ES+), (M+H)=707.62; HPLC $t_R$=3.81 min

Intermediate AH1: di-tert-butyl 1-(2-bromo-6-chlorophenyl)hydrazine-1,2-dicarboxylate

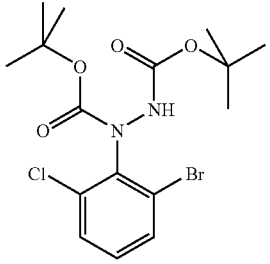

To a stirred solution of 2.5 M Butyllithium in hexanes (13.79 mL, 34.47 mmol) at −20° C. was added dropwise 2,2,6,6-tetramethylpiperidine (5.82 mL, 34.47 mmol) in THF (30 mL). This was stirred for 30 minutes. This solution was cooled down to −78° C., and a solution of 1-bromo-3-chlorobenzene (6 g, 31.34 mmol) in THF (20 mL) was added dropwise so as to maintain the temperature at <−70° C. After 2 hours (Z)-di-tert-butyl diazene-1,2-dicarboxylate (10.82 g, 47.01 mmol) in THF (30 mL) added dropwise at −78° C. Stirred at this temperature for 2 hours, then allowed to warm to room temperature overnight. Water (150 mL) added. The mixture was extracted with EtOAc (2×300 mL). The extracts were combined, washed with brine (100 mL), dried (MgSO$_4$) and reduced go give a residue which was purified by flash silica chromatography, elution gradient 0-10% EtOAc in hexane. Fractions containing suspected product were combined, and reduced to give di-tert-butyl 1-(2-bromo-6-chlorophenyl)hydrazine-1,2-dicarboxylate (9.59 g, 72.5%) $^1$H NMR (400 MHz, DMSO) δ 1.30-1.50 (18H, s), 7.28 (1H, m), 7.55 (1H, dd), 7.67 (1H, dd), 9.18 (1H, s). m/z (ES+) (M+Na)$^+$=443; HPLC t$_R$=10.76 min.

Intermediate AH2: (2-bromo-6-chlorophenyl)hydrazine hydrochloride

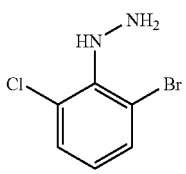

4M Hydrogen chloride in dioxane (28.2 mL, 112.64 mmol) was added to di-tert-butyl 1-(2-bromo-6-chlorophenyl)hydrazine-1,2-dicarboxylate (Intermediate AH1) (9.5 g, 22.53 mmol) in iPrOH (30 mL) at ambient temperature. The resulting solution was heated to 60° C. and stirred for 20 minutes. The reaction mixture was allowed to cool to ambient temperature. A solid was filtered off, and dried under vacuum to afford the product (4.71 g). $^1$H NMR (400 MHz, DMSO) d 6.97 (1H, s), 7.06 (1H, t), 7.41 (1H, dd), 7.52 (1H, dd), 9.83 (3H, s). m/z M$^+$=220; GC-MS tR=10.419 min.

Intermediate AH3: 5-amino-1-(2-bromo-6-chlorophenyl)-1H-pyrazole-4-carbonitrile

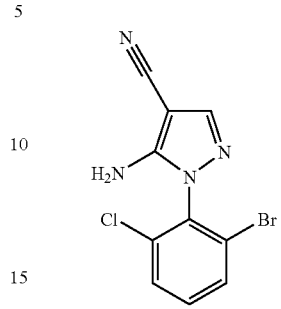

(2-Bromo-6-chlorophenyl)hydrazine hydrochloride (Intermediate AH2) (4.71 g, 18.26 mmol) was partitioned between DCM (300 mL) and 2M NaOH (20 mL). Allowed to Stir for 1 hour. The two phases were separated. The organic phase was reduced under vacuum to give the free base. This was dissolved in MeOH (60 mL), and stirred in a cooling bath at 0° C. (Ethoxymethylene)malononitrile (2.230 g, 18.26 mmol) added portionwise. The reaction mixture was then allowed to warm to ambient temperature and stirred for 1 hour. The mixture was then heated to reflux and stirred for 16 hours. Allowed to cool to ambient temperature. The reaction mixture was concentrated to give a solid, which was triturated under MeOH. A solid was filtered off. This was dried to afford the product (4.59 g, 85%).

$^1$H NMR (400 MHz, DMSO) δ 6.79 (2H, s), 7.54-7.47 (1H, m), 7.70 (1H, dd), 7.79 (1H, s), 7.81 (1H, d). m/z (ES+) (M+H)$^+$=299; HPLC t$_R$=1.70 min.

Intermediate AH4: 1-(2-bromo-6-chlorophenyl)-1H-pyrazolo[3,4-d]pyrimidin-4(5H)-one

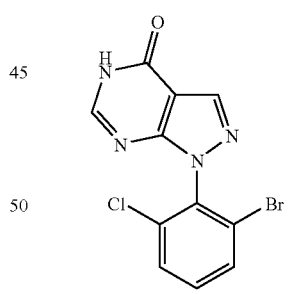

Concentrated sulfuric acid (0.905 mL, 16.97 mmol) was added to a stirred solution of 5-amino-1-(2-bromo-6-chlorophenyl)-1H-pyrazole-4-carbonitrile (Intermediate AH3) (4.59 g, 15.43 mmol) in formic acid (30 mL). The resulting solution was heated to 100° C. and stirred for 4 hours. The reaction mixture was allowed to cool to ambient temperature. The reaction mixture was evaporated to dryness. The residue was triturated under water. A solid was filtered off. This was dried under vacuum to afford the product (3.71 g, 73.8%).

$^1$H NMR (400 MHz, DMSO) δ 7.58 (1H, t), 7.80-7.76 (1H, m), 7.88 (1H, dd), 8.08 (1H, d), 8.40 (1H, s), 12.44 (1H, s). m/z (ES+) (M+H)$^+$=327; HPLC t$_R$=1.48 min.

Intermediate AH5: 3-chloro-2-(4-hydroxy-1H-pyrazolo[3,4-d]pyrimidin-1-yl)benzonitrile

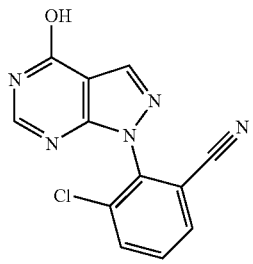

1-(2-bromo-6-chlorophenyl)-1H-pyrazolo[3,4-d]pyrimidin-4(5H)-one (Intermediate AH4)(1012 mg, 3.11 mmol) and zinc cyanide (329 mg, 2.80 mmol) were dissolved in DMF (15 mL). Sealed into a microwave tube. The tube was purged with nitrogen. 9,9-Dimethyl-4,5-bis(diphenylphosphino)xanthene (180 mg, 0.31 mmol) and tris(dibenzylideneacetone)dipalladium(0) (142 mg, 0.16 mmol) added. The reaction was heated to 160° C. for 15 minutes in the microwave reactor, then allowed to cool to ambient temperature. The DMF was removed by evaporation. The crude product was absorbed onto silica and then purified by flash silica chromatography, elution gradient 0 to 10% MeOH in DCM to afford the product (769 mg, 91%). $^1$H NMR (400 MHz, DMSO) δ 7.89-7.83 (1H, t), 8.14 (1H, s), 8.15 (2H, d), 8.49 (1H, s), 12.56 (1H, s); m/z (ES+) (M+H)$^+$=272; HPLC $t_R$=1.29 min.

Intermediate AH6: 3-Chloro-2-(4-chloro-1H-pyrazolo[3,4-d]pyrimidin-1-yl)benzonitrile

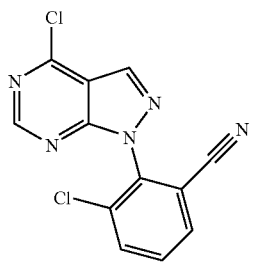

Phosphorus oxychloride (7.93 mL, 85.03 mmol) was added to 3-chloro-2-(4-hydroxy-1H-pyrazolo[3,4-d]pyrimidin-1-yl)benzonitrile (Intermediate AH5) (1.155 g, 4.25 mmol).

The resulting mixture was heated to 100° C. and stirred for 4 hours. The reaction mixture was allowed to cool to ambient temperature. The reaction mixture was evaporated to near dryness. Poured onto ice/water with stirring. A solid precipitate was collected by filtration. This was dried overnight under vacuum to afford the product (0.928 g, 75%). $^1$H NMR (400 MHz, DMSO) δ 8.02-7.96 (1H, t), 8.26 (1H, d), 8.28 (1H, s), 9.05 (2H, d). m/z M$^+$=289; GCMS tR=13.82 min.

Intermediate AH7: (2S)-3-(2-(tert-butyldiphenylsilyloxy)ethoxy)-2-(1-(2-chloro-6-cyanophenyl)-1H-pyrazolo[3,4-d]pyrimidin-4-yloxy)-N-(5-chloropyridin-2-yl)propanamide

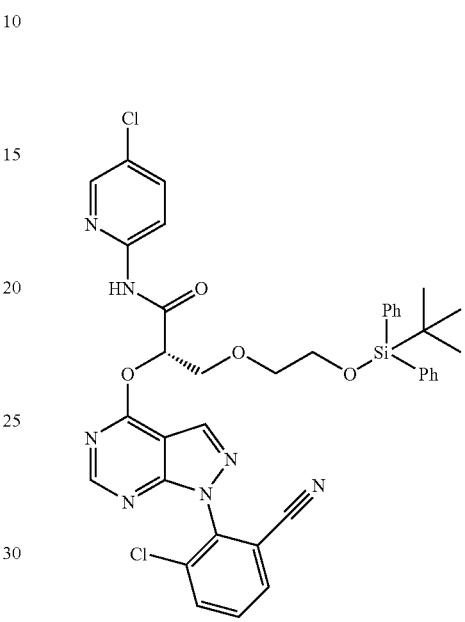

60% Sodium hydride (95 mg, 2.38 mmol) was added to (S)-3-(2-(tert-butyldiphenylsilyloxy)ethoxy)-N-(5-chloropyridin-2-yl)-2-hydroxypropanamide (Intermediate AU3) (540 mg, 1.08 mmol) in anhydrous THF (15 mL), at 0° C., under nitrogen. The resulting solution was stirred at 0° C. for 10 minutes. 3-chloro-2-(4-chloro-1H-pyrazolo[3,4-d]pyrimidin-1-yl)benzonitrile (Intermediate AH6) (314 mg, 1.08 mmol) was added. The reaction mixture was allowed to warm to room temperature and was then stirred for 2 hours. The reaction mixture was neutralised with 1M citric acid and then diluted with water (50 mL) and EtOAc (100 mL). The organic layer was separated and the aqueous layer re-extracted with EtOAc (2×100 mL). The combined organics were washed with saturated brine (50 mL), dried (MgSO$_4$), filtered and concentrated in vacuo. The crude product was purified by flash silica chromatography, elution gradient 30 to 50% EtOAc in isohexane. Fractions were evaporated to dryness to afford (2S)-3-(2-(tert-butyldiphenylsilyloxy)ethoxy)-2-(1-(2-chloro-6-cyanophenyl)-1H-pyrazolo[3,4-d]pyrimidin-4-yloxy)-N-(5-chloropyridin-2-yl)propanamide (466 mg, 57.2%). $^1$H NMR (400 MHz, DMSO) δ 0.89 (9H, d), 3.83-3.66 (4H, m), 4.11-4.04 (1H, m), 4.20-4.12 (1H, m), 6.00 (1H, s), 7.44-7.31 (6H, m), 7.60 (4H, m), 7.87 (2H, m), 8.03 (1H, t), 8.22-8.13 (2H, m), 8.39 (1H, d), 8.62 (1H, d), 8.68 (1H, d), 11.23 (1H, s). m/z (ES+) (M+H)$^+$=752; HPLC $t_R$=3.89 min.

Intermediate AH8: (2S)-2-(1-(2-chloro-6-cyanophenyl)-1H-pyrazolo[3,4-d]pyrimidin-4-yloxy)-N-(5-methylpyridin-2-yl)-3-((R)-1-(triisopropylsilyloxy)propan-2-yloxy)propanamide

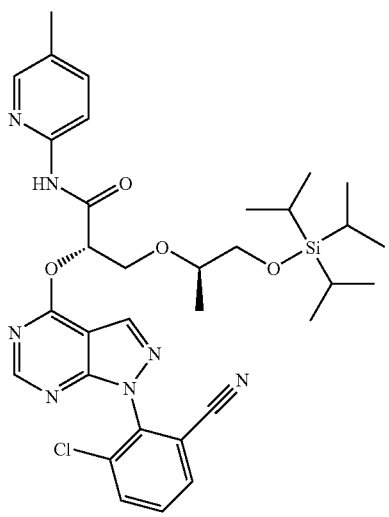

Sodium hydride (64.3 mg, 1.61 mmol) was added to (S)-2-hydroxy-N-(5-methylpyridin-2-yl)-3-((R)-1-(triisopropylsilyloxy)propan-2-yloxy)propanamide (Intermediate AU4) (300 mg, 0.73 mmol) in anhydrous THF (10 mL) at 0° C. under nitrogen. The resulting solution was stirred at 0° C. for 10 minutes and then 3-chloro-2-(4-chloro-1H-pyrazolo[3,4-d]pyrimidin-1-yl)benzonitrile (Intermediate AH6) (212 mg, 0.73 mmol) added. The reaction mixture was allowed to warm to ambient temperature and stirred for 2 hours. The reaction mixture was neutralised with 1M citric acid and then diluted with water (50 mL) and EtOAc (100 mL). The organic layer was separated and the aqueous layer re-extracted with EtOAc (2×100 mL). The combined organics were washed with saturated brine (50 mL), dried (MgSO$_4$), filtered and concentrated in vacuo. The crude product was purified by flash silica chromatography, elution gradient 20 to 40% EtOAc in isohexane to afford the product (334 mg, 68.8%). $^1$H NMR (400 MHz, DMSO) δ 0.98-0.86 (21H, m), 1.09 (3H, d), 2.24 (3H, s), 3.58-3.47 (1H, m), 3.64 (1H, m), 3.81-3.71 (1H, m), 4.10 (2H, m), 5.92 (1H, s), 7.58 (1H, d), 7.89 (2H, t), 8.18 (3H, m), 8.59 (1H, s), 8.72 (1H, s), 10.88 (1H, s). m/z (ES+) (M+H)$^+$=664; HPLC t$_R$=3.99 min.

Intermediate AH9: (2S)-3-(2-(tert-butyldiphenylsilyloxy)ethoxy)-2-(1-(2-chloro-6-cyanophenyl)-1H-pyrazolo[3,4-d]pyrimidin-4-yloxy)-N-(5-methylpyridin-2-yl)propanamide

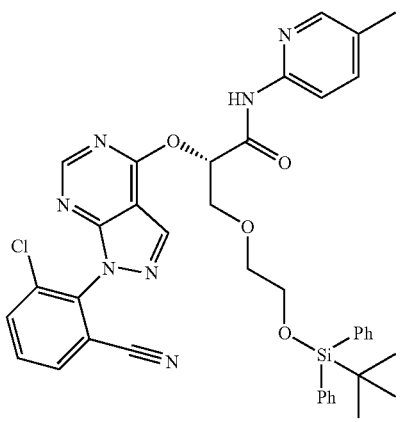

Prepared using a procedure analogous to that described with Intermediate AH7 using (S)-3-(2-(tert-butyldiphenylsilyloxy)ethoxy)-N-(5-methylpyridin-2-yl)-2-hydroxypropanamide (Intermediate AU2) and 3-chloro-2-(4-chloro-1H-pyrazolo[3,4-d]pyrimidin-1-yl)benzonitrile (Intermediate AH6). m/z (ES+) (M+H)$^+$=732; HPLC t$_R$=3.76 min

Intermediate AI1: (S)-2-(tert-butyldimethylsilyloxy)-3-isopropoxy-N-(5-(methylthio)pyridin-2-yl)propanamide

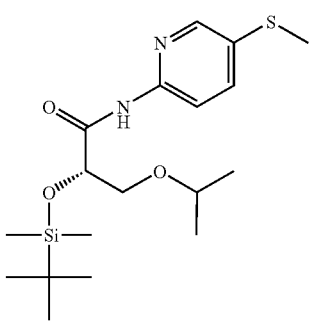

Trimethylaluminium (2M in toluene) (10.40 mL, 20.80 mmol) was added to 5-(methylthio)pyridin-2-amine (CAS no. 77618-99-6) (2.54 g, 18.09 mmol) in toluene (100 mL) cooled to 0° C. under nitrogen. The resulting solution was stirred at 0° C. for 20 minutes. (S)-methyl 2-(tert-butyldimethylsilyloxy)-3-isopropoxypropanoate (Intermediate C7b) (5 g, 18.09 mmol) was added and the reaction was allowed to warm to room temperature. The reaction was allowed to stir at room temperature for 1 hour. The temperature was increased to 60° C. and stirred for a further 24 hours. The reaction mixture was neutralised with citric acid (1M, aq) and then diluted with water and EtOAc (200 mL). The organic layer was separated and the aqueous layer re-extracted with EtOAc (100 mL). The combined organics were dried (MgSO$_4$), filtered and evaporated in vacuo. The crude product was purified by flash silica chromatography, elution gradient 0 to 50%

Et2O in isohexane to afford the product (3.95 g, 56.8%). $^1$H NMR (400 MHz, DMSO) δ 0.10-0.13 (6H, d), 0.90-0.92 (9H, m), 1.04-1.07 (6H, m), 2.40 (3H +DMSO, s), 3.54-3.63 (3H, m), 4.42-4.44 (1H, m), 7.77-7.80 (1H, dd), 8.03-8.06 (1H, d), 8.26 (1H, d), 9.49 (1H, s); m/z (ES+) (M+H)$^+$=385; HPLC $t_R$=3.66 min.

Intermediate AI2: (S)-2-hydroxy-3-isopropoxy-N-(5-(methylthio)pyridin-2-yl)propanamide

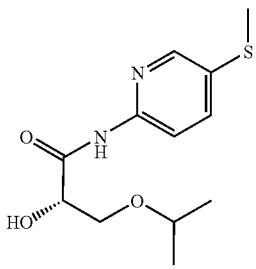

A solution of tetrabutylammonium fluoride (1M in THF) (10.04 mL, 10.04 mmol) was added in one portion to a stirred solution of (S)-2-(tert-butyldimethylsilyloxy)-3-isopropoxy-N-(5-(methylthio)pyridin-2-yl)propanamide (Intermediate AI1) in tetrahydrofuran (50 mL). The resulting solution was stirred at ambient temperature for 30 minutes. The majority of the THF was evaporated in vacuo. The residue was diluted with EtOAc (100 mL), washed sequentially with water (25 mL) and saturated brine (25 mL). The organic layer was dried (MgSO$_4$), filtered and evaporated to afford crude product. The crude product was purified by flash silica chromatography, elution gradient 30 to 50% EtOAc in isohexane to afford the product (2.38 g, 88%). 1H NMR (400 MHz, DMSO) δ 1.03-1.07 (6H, m), 3.28 (3H, s), 3.53-3.64 (3H, m), 4.19-4.22 (1H, m), 5.95 (1H, d), 7.77-7.80 (1H, d), 8.04-8.06 (1H, d), 8.24-8.25 (1H, s), 9.60 (1H, s); m/z (ES+) (M+H)$^+$=271; HPLC $t_R$=1.74 min.

Intermediate AI3: (2S)-2-(1-(3-chloropyridin-2-yl)-1H-pyrazolo[3,4-d]pyrimidin-4-yloxy)-3-isopropoxy-N-(5-(methylthio)pyridin-2-yl)propanamide

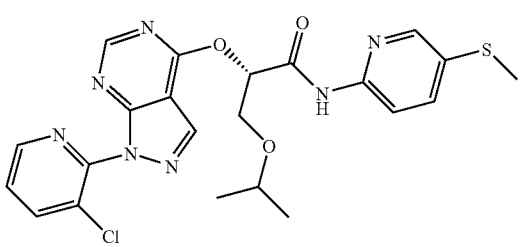

60% Sodium hydride (111 mg, 2.77 mmol) was added to a solution of (S)-2-hydroxy-3-isopropoxy-N-(5-(methylthio)pyridin-2-yl)propanamide (Intermediate AI2) (500 mg, 1.85 mmol) in anhydrous THF (30 mL) at 0° C. under nitrogen. The resulting suspension was stirred at 0° C. for 10 minutes and then a solution of 4-chloro-1-(3-chloropyridin-2-yl)-1H-pyrazolo[3,4-d]pyrimidine (Intermediate B15) (492 mg, 1.85 mmol) in dry THF (10 mL) added dropwise, maintaining the temperature below 5° C. The reaction mixture was stirred at 0° C. for 10 minutes and then allowed to warm to room temperature. The reaction was stirred at room temperature for 1 hour. The reaction mixture was neutralised with HCl (1M, aq). The majority of the THF was evaporated in vacuo and then EtOAc (100 mL) was added. The organic layer was separated and the aqueous layer re-extracted with EtOAc (2×100 mL). The combined organics were washed with saturated brine (75 mL), dried (MgSO$_4$), filtered and concentrated in vacuo. The crude product was purified by flash silica chromatography (330 g), elution gradient 20 to 70% EtOAc in isohexane to afford the product (609 mg, 65.9%). $^1$H NMR (400 MHz, DMSO) δ 1.12 (6H, dd), 3.28 (3H, s), 3.76 (1H, dt), 4.07-3.96 (2H, m), 5.90 (1H, s), 7.78-7.72 (2H, m), 7.95 (1H, d), 8.27 (1H, dd), 8.33 (1H, dd), 8.56 (1H, s), 8.65 (1H, s), 8.67 (1H, dd), 10.97 (1H, s). m/z (ES+) (M+H)$^+$=500; HPLC $t_R$=2.43 min.

Intermediate AJ1: (2S)-3-(2-(tert-butyldiphenylsilyloxy)ethoxy)-N-(5-chloropyridin-2-yl)-2-(1-(2,5-dimethylphenyl)-1H-pyrazolo[3,4-d]pyrimidin-4-yloxy)propanamide

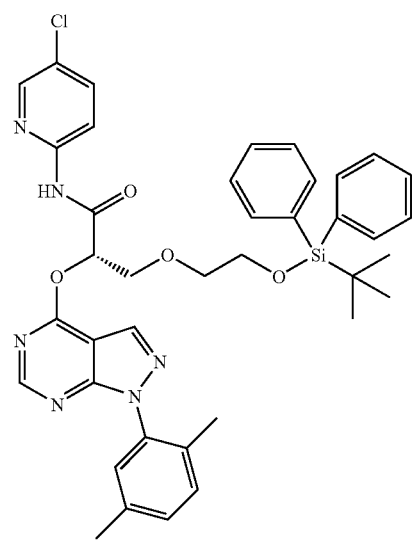

Trimethylaluminium (2M in toluene) (0.692 mL, 1.38 mmol) was added dropwise to a stirred solution of 5-chloropyridin-2-amine (163 mg, 1.27 mmol) in toluene (15 mL), under nitrogen at 0° C. The resulting solution was allowed to stir at this temperature for a further 20 minutes. (2S)-Methyl 3-(2-(tert-butyldiphenylsilyloxy)ethoxy)-2-(1-(2,5-dimethylphenyl)-1H-pyrazolo[3,4-d]pyrimidin-4-yloxy)propanoate (Intermediate AJ2) (721 mg, 1.15 mmol) in toluene (6 mL) was added slowly to the mixture at 0° C. The reaction mixture was then heated to 100° C. and was stirred for 5 hours using the microwave. The reaction mixture was allowed to cool to ambient temperature, then was evaporated to afford a crude product. The crude product was purified by flash silica chromatography. Fractions were evaporated to dryness to afford a crude product (428 mg).

Trimethylaluminium (2M in toluene) (0.258 mL, 0.52 mmol) was added dropwise to a stirred solution of 5-chloropyridin-2-amine (66.3 mg, 0.52 mmol) in toluene (6 mL), under nitrogen at 0° C. The resulting solution was allowed to stir at this temperature for a further 20 minutes. The crude product in toluene (6 mL) was added slowly to the mixture at 0° C. The reaction mixture was then heated to 100° C. and was stirred for 5 hours using the microwave. The reaction mixture was allowed to cool to ambient temperature, then was evaporated to afford a crude product. This was purified by flash silica chromatography, elution gradient 0 to 30% EtOAc in isohexane to afford the product (328 mg). m/z (ES+) (M+H)$^+$= 721; HPLC t$_R$=3.76 min.

Intermediate AJ2: (2S)-methyl 3-(2-(tert-butyldiphenylsilyloxy)ethoxy)-2-(1-(2,5-dimethylphenyl)-1H-pyrazolo[3,4-d]pyrimidin-4-yloxy)propanoate

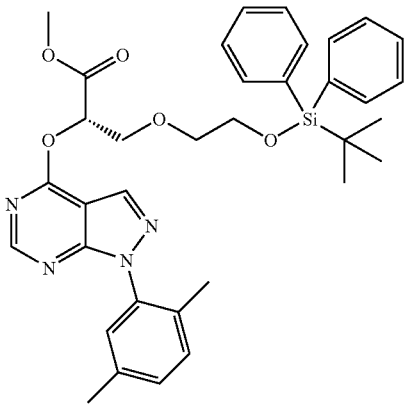

60% sodium hydride (0.187 g, 4.67 mmol) was added to (S)-methyl 3-(2-(tert-butyldiphenylsilyloxy)ethoxy)-2-hydroxypropanoate (Intermediate AB3) (1.568 g, 3.90 mmol) in anhydrous THF (20 mL) at 0° C. under nitrogen. The resulting solution was stirred at 0° C. for 10 minutes and then 4-chloro-1-(2,5-dimethylphenyl)-1H-pyrazolo[3,4-d]pyrimidine (Intermediate AJ3)(1.008 g, 3.90 mmol) was added. The reaction mixture was allowed to warm to room temperature and stirred for 1 hour. The reaction mixture was neutralised with 1M citric acid and the majority of the THF removed in vacuo. The residue was diluted with water (20 mL) and EtOAc (100 mL). The organic layer was separated and the aqueous layer re-extracted with EtOAc (100 mL). The combined organics were washed with saturated brine (75 mL), dried (MgSO$_4$) and evaporated to give the crude product. This was purified by flash silica chromatography, elution gradient 0 to 20% EtOAc in isohexane to afford the product (1.400 g, 57.5%). m/z (ES+) (M+H)$^+$=625; HPLC t$_R$=3.53 min.

Intermediate AJ3: 4-Chloro-1-(2,5-dimethylphenyl)-1H-pyrazolo[3,4-d]pyrimidine

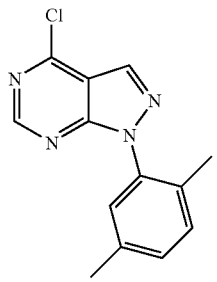

Phosphorus oxychloride (7.76 mL, 83.24 mmol) was added to 1-(2,5-dimethylphenyl)-1H-pyrazolo[3,4-d]pyrimidin-4-ol (1 g, 4.16 mmol). The resulting solution was stirred at 100° C. for 2 hours. LCMS showed reaction was complete. The reaction mixture was evaporated. Ice/water and then EtOAc were added. The organic layer was separated and the aqueous layer re-extracted with EtOAc. The combined organics were washed with water, dried (MgSO4) and concentrated to give crude product (1.077 g, 100%) which was used without purification. $^1$H NMR (400 MHz, DMSO) δ 2.00 (3H, s), 2.35 (3H, s), 7.26-7.37 (3H, m), 8.72 (1H, s), 8.86 (1H, s); m/z (ES+) (M+H)$^+$=259; HPLC t$_R$=2.48 min.

Intermediate AJ4: 1-(2,5-dimethylphenyl)-1H-pyrazolo[3,4-d]pyrimidin-4-ol

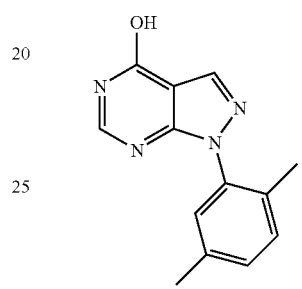

Concentrated sulfuric acid (3.06 mL, 57.37 mmol) was added to a stirred solution of 5-amino-1-(2,5-dimethylphenyl)-1H-pyrazole-4-carbonitrile (Intermediate AJ5) (11.07 g, 52.16 mmol) in formic acid (70 mL). The resulting solution was stirred at 100° C. for 24 hours. The reaction was allowed to cool to room temperature and evaporated to ~half volume, water (100 mL) added and stirred for 1 hour. The formed ppt was filtered off, washed well with water and dried overnight in a vacuum over P$_2$O$_5$ to afford the product (8.71 g, 69.5%) which was used without purification. $^1$H NMR (400 MHz, DMSO) δ 2.00 (3H, s), 2.33 (3H, s), 3.43 (2H, s), 7.18 (1H, s), 7.24-7.31 (2H, m), 8.04 (1H, d), 8.28 (1H, s), 12.27 (1H, s); m/z (ES+) (M+H)$^+$=241; HPLC t$_R$=1.6 min.

Intermediate AJ5: 5-amino-1-(2,5-dimethylphenyl)-1H-pyrazole-4-carbonitrile

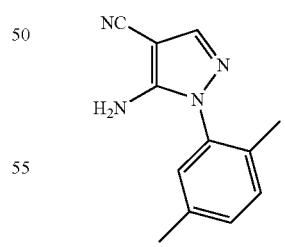

2,5-Dimethylphenylhydrazine hydrochloride (CAS no. 56737-78-1) (10 g, 57.92 mmol) was partitioned between EtOAc (100 mL) and NaOH (2M, aq) (60 mL). The organic layer separated and washed with water (50 mL), brine (50 mL), dried (MgSO4), filtered and concentrated to afford free base of the starting material. The resultant oil was suspended in MeOH (100 mL) under nitrogen at −5° C. 2-(ethoxymethylene)malononitrile (7.07 g, 57.92 mmol) added portionwise over 5 mins and the mixture stirred at ~0° C. for 30 mins. The reaction mixture was allowed to warm to room temperature and then heated at reflux under nitrogen for 2 hours. The reaction mixture was allowed to cool and evaporated to dryness to afford the product (11.07 g, 90%) which was used without purification. $^1$H NMR (400 MHz, DMSO) δ 1.98 (3H, s), 2.31 (3H, s), 6.39 (2H, s), 7.07 (1H, s), 7.21-7.28 (2H, m), 7.72 (1H, s); m/z (ES+) (M+H)$^+$=213; HPLC $t_R$=1.79 min.

Intermediate AK1: 5-amino-1-(5-fluoro-2-methylphenyl)-1H-pyrazole-4-carbonitrile

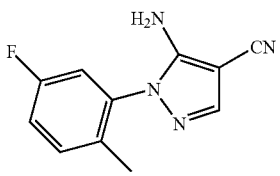

(Ethoxymethylene)malononitrile (CAS no. 123-06-8) (3.18 g, 26.04 mmol) was added portionwise to the stirred solution of (5-fluoro-2-methylphenyl)hydrazine hydrochloride (CAS no. 325-50-8) (4.6 g, 26.04 mmol) and N,N-diisopropylethylamine (5.90 mL, 33.86 mmol) in MeOH (50 mL), under nitrogen at 5° C. The resulting solution was allowed to stir for a further 30 minutes at this temperature. The reaction mixture was then heated to reflux and was stirred for 3 hours. The reaction mixture was allowed to cool to ambient temperature. The reaction mixture was evaporated to dryness, redissolved in EtOAc (200 mL), washed with water (50 mL), and saturated brine (50 mL). The organic layer was dried (MgSO$_4$), filtered and evaporated to afford crude product. This was purified by flash silica chromatography, elution gradient 0 to 50% EtOAc in isohexane to afford the product (1.076 g, 19.11%). $^1$H NMR (400 MHz, DMSO) δ 2.00 (3H, s), 6.56 (2H, s), 7.20 (1H, dd), 7.29 (1H, td), 7.43 (1H, t), 7.75 (1H, s); m/z (ES+) (M+H)$^+$=217; HPLC $t_R$=1.61 min.

Intermediate AK2: 1-(5-fluoro-2-methylphenyl)-1H-pyrazolo[3,4-d]pyrimidin-4(5H)-one

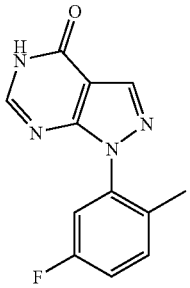

Sulfuric acid (0.353 mL, 6.61 mmol) was added to a stirred solution of 5-amino-1-(5-fluoro-2-methylphenyl)-1H-pyrazole-4-carbonitrile (Intermediate AK1) (1.3 g, 6.01 mmol) in formic acid (10 mL), under nitrogen at 5° C. The reaction mixture was then heated to 100° C. and was stirred for 16 hours. The reaction mixture was allowed to cool to ambient temperature, then was evaporated to half volume. A percipitate was filtered off. This solid was washed with water, then dried under vacuum to afford the product (0.713 g, 48.6%). $^1$H NMR (400 MHz, DMSO) δ 2.05 (3H, s), 7.30-7.36 (2H, m), 7.45-7.51 (1H, m), 8.08 (1H, s), 8.32 (1H, s), 12.33 (1H, s). m/z (ES+) (M+H)$^+$=245; HPLC $t_R$=1.43 min.

Intermediate AK3: 4-chloro-1-(5-fluoro-2-methylphenyl)-1H-pyrazolo[3,4-d]pyrimidine

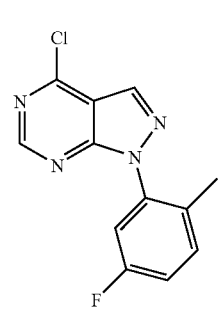

Phosphorus oxychloride (5442 µl, 58.39 mmol) was added to 1-(5-fluoro-2-methylphenyl)-1H-pyrazolo[3,4-d]pyrimidin-4(5H)-one (Intermediate AK2) (713 mg, 2.92 mmol), at ambient temperature. The resulting mixture was heated to 100° C. and stirred for 4 hours. The mixture was allowed to cool to ambient temperature. The reaction mixture was evaporated to near dryness. Dissolved into toluene, evaporated, dissolved, in toluene and evaporated to dryness again. The solid was dried under vacuum to give crude product. This was partitioned between EtOAc (70 mL), and water (25 mL). The organic phase was dried (MgSO$_4$), evaporated, then dried under vacuum to afford the product (732 mg, 95%). $^1$H NMR (400 MHz, DMSO) δ 2.13 (3H, s), 7.52-7.42 (2H, m), 7.64-7.58 (1H, m), 8.83 (1H, s), 8.96 (1H, s); m/z (ES+) (M+H)$^+$=263; HPLC $t_R$=2.39 min.

Intermediate AK4: (2S)-methyl 3-(2-(tert-butyldiphenylsilyloxy)ethoxy)-2-(1-(5-fluoro-2-methylphenyl)-1H-pyrazolo[3,4-d]pyrimidin-4-yloxy)propanoate

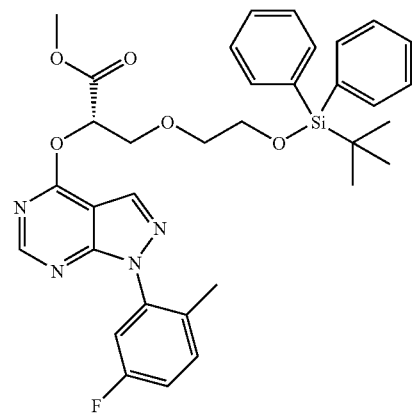

60% Sodium hydride (156 mg, 3.89 mmol) was added to (S)-methyl 3-(2-(tert-butyldiphenylsilyloxy)ethoxy)-2-hydroxypropanoate (Intermediate AB3) (1119 mg, 2.78 mmol) in anhydrous THF (15 mL) at 0° C. under nitrogen. The resulting solution was stirred at 0° C. for 10 minutes and then 4-chloro-1-(5-fluoro-2-methylphenyl)-1H-pyrazolo[3,4-d]pyrimidine (Intermediate AK3) (730 mg, 2.78 mmol) was added. The reaction mixture was allowed to warm to room temperature and stirred for 1 hour. The reaction mixture was neutralised with 1M citric acid and the majority of the THF removed in vacuo. The residue was diluted with water (20 mL) and EtOAc (100 mL). The organic layer was separated and the aqueous layer re-extracted with EtOAc (100 mL). The combined organics were washed with saturated brine (75 mL), dried (MgSO₄) and evaporated. The crude product was purified by flash silica (120 g) chromatography, elution gradient 0 to 20% EtOAc in isohexane to afford the product (932 mg, 53.3%). ¹H NMR (400 MHz, DMSO) δ 0.94 (9H, s), 2.03 (3H, s), 3.80-3.65 (7H, m), 4.16-4.03 (2H, m), 5.89 (1H, dd), 7.46-7.33 (8H, m), 7.54-7.48 (1H, m), 7.65-7.61 (4H, m), 8.48 (1H, s), 8.59 (1H, s); m/z (ES+) (M+H)⁺=629; HPLC $t_R$=3.41 min.

Intermediate AK5: (2S)-3-(2-(tert-butyldiphenylsilyloxy)ethoxy)-N-(5-chloropyridin-2-yl)-2-(1-(5-fluoro-2-methylphenyl)-1H-pyrazolo[3,4-d]pyrimidin-4-yloxy)propanamide

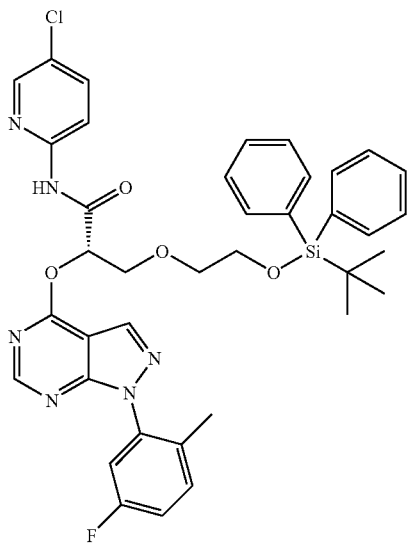

Trimethylaluminium (2M in toluene) (0.556 mL, 1.11 mmol) was added dropwise to a stirred solution of 5-chloropyridin-2-amine (143 mg, 1.11 mmol) in toluene (10 mL), under nitrogen at 0° C. The resulting solution was allowed to stir at this temperature for a further 20 minutes. (2S)-methyl 3-(2-(tert-butyldiphenylsilyloxy)ethoxy)-2-(1-(5-fluoro-2-methylphenyl)-1H-pyrazolo[3,4-d]pyrimidin-4-yloxy)propanoate (Intermediate AK4) (466 mg, 0.74 mmol) in toluene (5 mL) was added slowly to the mixture at 0° C. The reaction mixture was then heated to 100° C. and was stirred for 6 hours using the microwave. The reaction mixture was allowed to cool to ambient temperature, then evaporated to afford a gum. This was dissolved in EtOAc (75 mL), and washed sequentially with Rochelle's solution (20 mL), and water (20 mL). The organic layer was dried (MgSO₄), filtered and evaporated to afford crude product. The crude product was purified by flash silica chromatography, elution gradient 10 to 30% EtOAc in isohexane to afford the product (390 mg, 72.6%). ¹H NMR (400 MHz, DMSO) δ 0.88 (9H, s), 2.03 (3H, s), 3.82-3.67 (4H, m), 4.05 (1H, m), 4.15 (1H, m), 6.00 (1H, m), 7.45-7.31 (8H, m), 7.50 (1H, t), 7.60 (4H, m), 7.87 (1H, dd), 8.02 (1H, d), 8.40 (1H, d), 8.51 (1H, s), 8.56 (1H, s), 11.25 (1H, s); m/z (ES+) (M+H)⁺=725; HPLC $t_R$=3.63 min.

Intermediate AK6: (2S)-3-(2-(tert-butyldiphenylsilyloxy)ethoxy)-N-(5-cyanopyridin-2-yl)-2-(1-(5-fluoro-2-methylphenyl)-1H-pyrazolo [3,4-d]pyrimidin-4-yloxy)propanamide

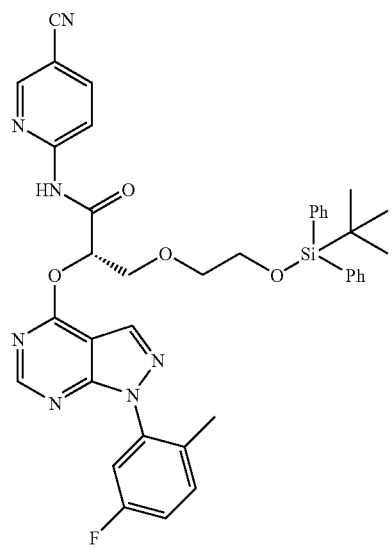

Prepared in an analogous fashion to Intermediate AL1 using Intermediate AK3 and Intermediate AK7. ¹H NMR (400 MHz, CDCl₃) 0.99 (9H, s), 2.13 (3H, s), 3.70-3.73 (2H, m), 3.84 (2H, t), 4.19-4.21 (2H, m), 6.04 (1H, t), 7.13-7.17 (2H, m), 7.32-7.42 (7H, m), 7.63-7.66 (4H, m), 7.91-7.94 (1H, m), 8.35 (1H, s), 8.36-8.38 (1H, m), 8.51 (1H, q), 8.57 (1H, s), 9.02 (1H, s); m/z (ES+) (M+H)⁺=716.5; HPLC $t_R$=3.69 min.

Intermediate AK7: (S)-3-(2-(tert-butyldiphenylsilyloxy)ethoxy)-N-(5-cyanopyridin-2-yl)-2-hydroxypropanamide

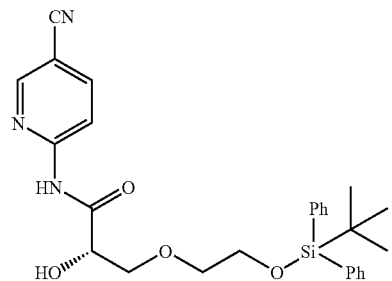

Trimethylaluminium (2M in toluene) (0.621 mL, 1.24 mmol) was added to a solution of 6-aminonicotinonitrile (148 mg, 1.24 mmol) in toluene (10 mL) at 0° C. under nitrogen. The reaction mixture was stirred at 0° C. for 20 mins and then (S)-methyl 3-(2-(tert-butyldiphenylsilyloxy)ethoxy)-2-hydroxypropanoate (Intermediate AB3) (250 mg, 0.62 mmol) was added. The reaction mixture was allowed to warm to room temperature and then heated at reflux under nitrogen for 4 hours. The reaction mixture was allowed to cool to room temperature and the concentrated in vacuo. The residue was neutralised with citric acid (1M, aq) and then diluted with water and DCM (50 mL). The organic layer was separated and the aqueous layer re-extracted with DCM (30 mL). The combined organics were dried (MgSO$_4$), filtered and evaporated in vacuo. The crude product was purified by flash silica chromatography, elution gradient 20 to 50% EtOAc in isohexane to afford the product (202 mg, 66.4%). $^1$H NMR (400 MHz, CDCl$_3$) 1.04 (9H, s), 3.65-3.67 (2H, m), 3.81-3.91 (4H, m), 4.36 (1H, t), 7.35-7.45 (6H, m), 7.65-7.67 (4H, m), 7.92-7.95 (1H, m), 8.36-8.39 (1H, m), 8.54-8.56 (1H m), 9.43 (1H, s); m/z (ES+) (M+H)$^+$=490; HPLC t$_R$=3.08 min.

Intermediate AL1: (S)-2-(1-benzyl-1H-pyrazolo[3,4-d]pyrimidin-4-yloxy)-3-(2-(tert-butyldiphenylsilyloxy)ethoxy)-N-(5-methylpyridin-2-yl)propanamide

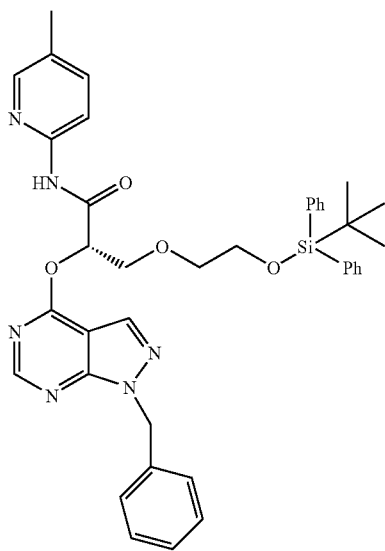

Sodium hydride (90 mg, 2.25 mmol) was added to (S)-3-(2-(tert-butyldiphenylsilyloxy)ethoxy)-2-hydroxy-N-(5-methylpyridin-2-yl)propanamide (538 mg, 1.12 mmol) (Intermediate AU2) in anhydrous THF (20 mL) at 0° C. under nitrogen. The resulting solution was stirred at 0° C. for 10 minutes and then 1-benzyl-4-chloro-1H-pyrazolo[3,4-d]pyrimidine (Intermediate AL2) (250 mg, 1.02 mmol) was added. The reaction mixture was allowed to warm to room temperature and stirred overnight. The reaction mixture was neutralised with 1M citric acid, diluted with water (20 mL) and EtOAc (50 mL). The organic layer was separated and the aqueous layer re-extracted with EtOAc (2×50 mL). The combined organics were washed with saturated brine (75 mL), dried (MgSO$_4$), filtered and concentrated in vacuo. The crude product was purified by flash silica chromatography, elution gradient 30 to 50% EtOAc in isohexane to afford the product (540 mg, 77%). m/z (ES+) (M+H)$^+$=687; HPLC t$_R$=3.89 min.

Intermediate AL2: 1-benzyl-4-chloro-1H-pyrazolo[3,4-d]pyrimidine

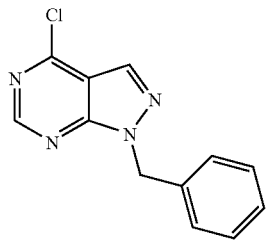

Triethylamine (1.181 mL, 8.48 mmol) was added to 4,6-dichloropyrimidine-5-carbaldehyde (CAS no. 5305-40-8) (500 mg, 2.83 mmol) and benzylhydrazine dihydrochloride (CAS no. 20570-96-1) (551 mg, 2.83 mmol) in THF (15 mL) at room temperature under nitrogen. The resulting suspension was stirred at room temperature for 10 minutes and then heated at 65° C. for 50 mins. Silica was added to the reaction mixture and concentrated in vacuo. The crude product was purified by flash silica chromatography, elution gradient 20 to 50% EtOAc in isohexane to afford the product (500 mg, 72.3%). $^1$H NMR (400 MHz, CDCl$_3$) 5.67 (2H, s), 7.28-7.38 (5H, m), 8.16 (1H, s), 8.79 (1H, s); m/z (ES+) (M+H)$^+$=245; HPLC t$_R$=2.29 min.

Intermediate AM1: (2S)-3-(2-(tert-butyldiphenylsilyloxy)ethoxy)-2-(1-(5-cyano-2-methylphenyl)-1H-pyrazolo[3,4-d]pyrimidin-4-yloxy)-N-(5-cyanopyridin-2-yl)propanamide

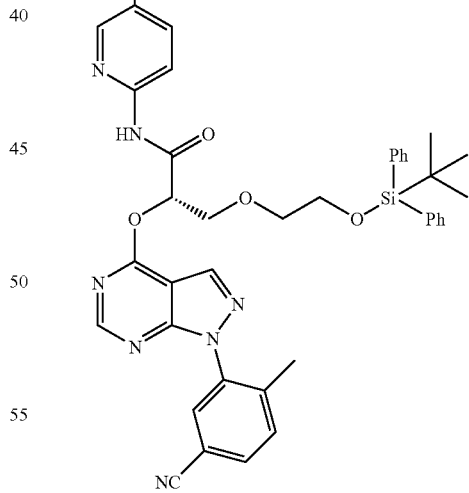

Prepared in an analogous fashion to Intermediate AL1 using Intermediate AM2 and Intermediate AK7.

1H NMR (400 MHz, CDCl$_3$) 1.00 (9H, s), 2.28 (3H, s), 3.70-3.74 (2H, m), 3.84 (2H, t), 4.12 4.20-4.21 (2H, m), 6.04 (1H, t), 7.32-7.43 (6H, m), 7.52-7.54 (1H, m), 7.63-7.73 (6H, m), 7.91-7.94 (1H, m), 8.35-8.38 (2H, m), 8.51 (1H, q), 8.57 (1H, s), 9.02 (1H, s); m/z (ES+) (M+H)$^+$=723.5; HPLC t$_R$=3.57 min.

Intermediate AM2: 3-(4-chloro-1H-pyrazolo[3,4-d]pyrimidin-1-yl)-4-methylbenzonitrile

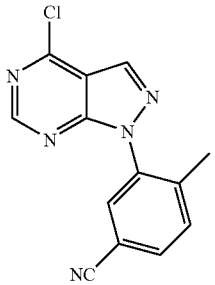

Phosphorus oxychloride (8.90 mL, 95.52 mmol) was added to 3-(4-hydroxy-1H-pyrazolo[3,4-d]pyrimidin-1-yl)-4-methylbenzonitrile (Intermediate AM3) (1.2 g, 4.78 mmol). The resulting solution was stirred at 100° C. for 4 hours. The reaction mixture was evaporated and then azetroped with toluene to remove any residual POCl$_3$. Ice/water was added and the formed precipitate was filtered washing well with water and dried overnight in vacuo over P$_2$O$_5$ to afford 3-(4-chloro-1H-pyrazolo[3,4-d]pyrimidin-1-yl)-4-methylbenzonitrile (1.16 g, 90%). $^1$H NMR (400 MHz, DMSO) 2.21 (3H, s), 7.73 (1H, d), 7.97-8.00 (1H, m), 8.06 (1H, d), 8.81 (1H, s), 8.91 (1H, s); HPLC $t_R$=2.05 min.

Intermediate AM3: 3-(4-hydroxy-1H-pyrazolo[3,4-d]pyrimidin-1-yl)-4-methylbenzonitrile

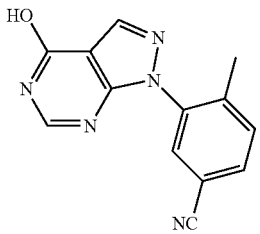

1-(5-Bromo-2-methylphenyl)-1H-pyrazolo[3,4-d]pyrimidin-4-ol (Intermediate AM4) (1.38 g, 4.52 mmol), and zinc cyanide (0.478 g, 4.07 mmol) were dissolved in DMF (15 mL) and sealed into a microwave tube. The reaction mixture was evacuated and back flushed with nitrogen several times. 9,9-Dimethyl-4,5-bis(diphenylphosphino)xanthene (0.262 g, 0.45 mmol) and tris(dibenzylideneacetone)dipalladium(0) (0.207 g, 0.23 mmol) were added. The reaction was heated to 160° C. for 10 minutes in the microwave reactor and cooled to RT. The reaction mixture was diluted with EtOAc (100 mL) and water (50 mL) and then filtered. Solid was taken up in hot methanol, filtered and dried under vacuum to afford the product (0.99 g, 89%) which was used without further purification. $^1$H NMR (400 MHz, DMSO) 2.19 (3H, s), 7.67 (1H, d), 7.92-7.96 (2H, m), 8.10 (1H, s), 8.35 (1H, s), 12.38 (1H, s); m/z (ES−) (M−H)−=250; HPLC $t_R$=1.23 min.

Intermediate AM4: 1-(5-bromo-2-methylphenyl)-1H-pyrazolo[3,4-d]pyrimidin-4(7H)-one

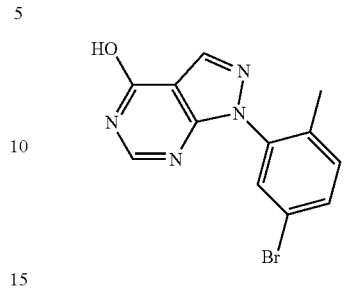

Concentrated sulfuric acid (1.160 mL, 21.76 mmol) was added to a stirred solution of 5-amino-1-(5-bromo-2-methylphenyl)-1H-pyrazole-4-carbonitrile (Intermediate AM5) (5.481 g, 19.78 mmol) in formic acid (35 mL). The resulting solution was stirred at 100° C. for 24 hours. The reaction was allowed to cool to room temperature and evaporated to approximately half the volume, water (50 mL) added and stirred for 1 hour. The formed precipitate was filtered off, washed well with water and dried overnight under vacuum over P$_2$O$_5$ to afford the product (4.47 g, 74.0%). $^1$H NMR (400 MHz, DMSO) 2.05 (3H, s), 7.40-7.42 (1H, m), 7.63-7.67 (2H, m), 8.08-8.09 (1H, m), 8.32 (1H, s), m/z (ES−) (M−H)−=305, 303; HPLC $t_R$=1.62 min.

Intermediate AM5: 5-amino-1-(5-bromo-2-methylphenyl)-1H-pyrazole-4-carbonitrile

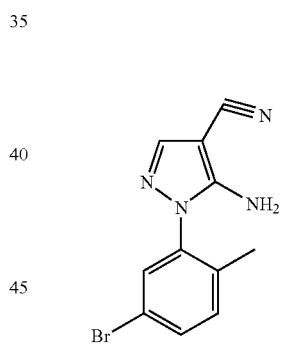

5 (5-Bromo-2-methylphenyl)hydrazine hydrochloride (CAS no. 214915-80-7) (5 g, 21.05 mmol) was partitioned between EtOAc (50 mL) and NaOH (2M, aq) (30 mL). The organic layer separated and washed with water (50 mL), brine (50 mL), dried (MgSO$_4$), filtered and concentrated to afford free base of the starting material. The resultant oil was suspended in MeOH (50 mL) under nitrogen at −5° C. 2-(ethoxymethylene)malononitrile (2.57 g, 21.05 mmol) added portionwise over 5 mins and the mixture stirred at ~0° C. for 30 mins. The reaction mixture was allowed to warm to room temperature and then heated at reflux under nitrogen for 2 hours. The reaction mixture was allowed to cool and evaporated to dryness to afford the product (5.48 g, 94%). $^1$H NMR (400 MHz, DMSO) 1.99 (3H, s), 6.59 (2H, s), 7.36 (1H, d), 7.49 (1H, d), 7.60-7.63 (1H, m), 7.76 (1H, s); m/z (ES+) (M+H)$^+$=277+279; HPLC $t_R$=2.01 min.

Intermediate AM6: (2S)-3-(2-(tert-butyldiphenylsilyloxy)ethoxy)-2-(1-(5-cyano-2-methylphenyl)-1H-pyrazolo[3,4-d]pyrimidin-4-yloxy)-N-(5-methylpyridin-2-yl)proanamide

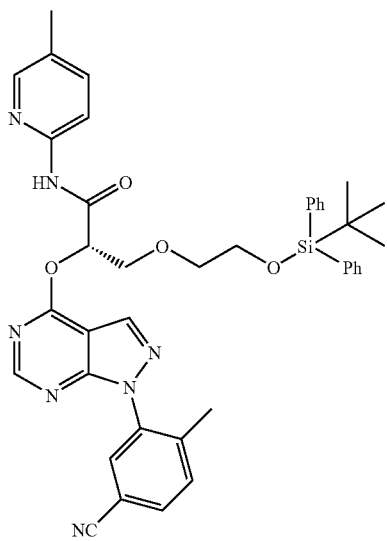

Trimethylaluminium (2M in toluene) (0.472 mL, 0.94 mmol) was added to a solution of 5-methylpyridin-2-amine (102 mg, 0.94 mmol) in toluene (10 mL) at 0° C. under nitrogen in a microwave vial. The reaction mixture was stirred at 0° C. for 20 mins and then (2S)-methyl 3-(2-(tert-butyldiphenylsilyloxy)ethoxy)-2-(1-(5-cyano-2-methylphenyl)-1H-pyrazolo[3,4-d]pyrimidin-4-yloxy)propanoate (Intermediate AM7) (300 mg, 0.47 mmol) was added. The reaction mixture was allowed to warm to room temperature and then heated in the microwave at 120° C. for 2 hours. The reaction mixture was allowed to cool to room temperature and the concentrated in vacuo. The residue was neutralised with citric acid (1M, aq) and then diluted with water and DCM (50 mL). The organic layer was separated and the aqueous layer re-extracted with DCM (30 mL). The combined organics were dried (MgSO$_4$), filtered and evaporated in vacuo. The crude product was purified by flash silica chromatography, elution gradient 20 to 50% Et2O in isohexane to afford the product (125 mg, 37.2%). $^1$H NMR (400 MHz, CDCl$_3$) 0.99 (9H, s), 2.27 (3H, s), 2.29 (3H, s), 3.69-3.72 (2H, m), 3.81 (2H, t), 4.16-4.24 (2H, m), 6.07-6.09 (1H, m), 7.16-7.41 (6H, m), 7.51 (1H, s), 7.53 (1H, s), 7.63-7.65 (4H, m), 7.68-7.72 (2H, m), 8.08-8.08 (1H, m), 8.14 (1H, d), 8.37 (1H, s), 8.57 (1H, s), 8.67 (1H, s); m/z (ES+) (M+H)$^+$=712.6; HPLC t$_R$=3.65 min.

Intermediate AM7: (2S)-methyl 3-(2-(tert-butyldiphenylsilyloxy)ethoxy)-2-(1-(5-cyano-2-methylphenyl)-1H-pyrazolo[3,4-d]pyrimidin-4-yloxy)propanoate

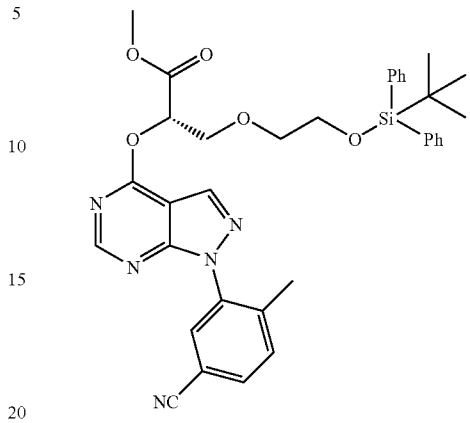

Sodium hydride (108 mg, 2.69 mmol) was added to (S)-methyl 3-(2-(tert-butyldiphenylsilyloxy)ethoxy)-2-hydroxypropanoate (795 mg, 1.97 mmol) (Intermediate AB3) in anhydrous THF (20 mL) at 0° C. under nitrogen. The resulting solution was stirred at 0° C. for 10 minutes and then 3-(4-chloro-1H-pyrazolo[3,4-d]pyrimidin-1-yl)-4-methylbenzonitrile (Intermediate AM2) (484 mg, 1.79 mmol) was added. The reaction mixture was allowed to warm to room temperature and stirred for 1 hour. The reaction mixture was neutralised with 1M citric acid and the reaction mixture diluted with water (10 mL) and EtOAc (30 mL). The organic layer was separated and the aqueous layer re-extracted with EtOAc (2×30 mL). The combined organics were washed with saturated brine (75 mL),dried (MgSO$_4$), filtered and concentrated in vacuo. The crude product was purified by flash silica chromatography, elution gradient 30 to 50% Et$_2$O in isohexane to afford the product (300 mg, 26.3%). m/z (ES+) (M+H)$^+$=636.5; HPLC t$_R$=3.65 min.

Intermediate AM8: (2S)-3-(2-(tert-butyldiphenylsilyloxy)ethoxy)-N-(5-chloropyridin-2-yl)-2-(1-(5-cyano-2-methylphenyl)-1H-pyrazolo[3,4-d]pyrimidin-4-yloxy)propanamide

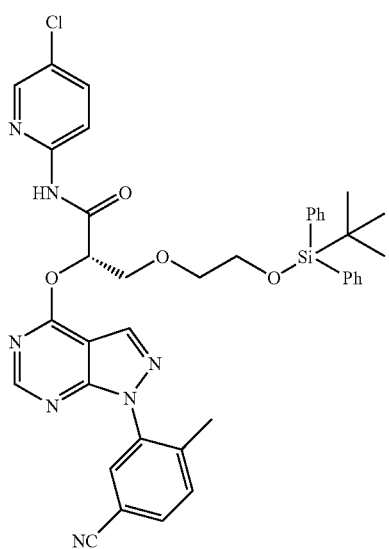

Prepared in an analogous fashion to Intermediate AM6 using 5-chloropyridyl-2-amine. m/z (ES+) (M+H)⁺=732.5; HPLC $t_R$=3.77 min.

Intermediate AN1: (S)-Methyl 3-((R)-1-(tert-butyldimethylsilyloxy)propan-2-yloxy)-2-hydroxypropanoate

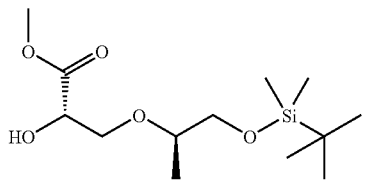

Magnesium trifluoromethanesulfonate (1.165 g, 3.61 mmol) was added in one portion to (S)-methyl oxirane-2-carboxylate (1.475 g, 14.45 mmol) and (R)-1-(tert-butyldimethylsilyloxy)propan-2-ol (CAS no. 136918-07-5) (2.75 g, 14.45 mmol) cooled to 10° C. The resulting suspension was stirred at 10° C. for 10 minutes and then warmed to 45° C. and stirred for 2 days. The crude product was purified by flash silica chromatography, eluting with 0 to 30% EtOAc in isohexane to afford the product (1.680 g, 39.8%). ¹H NMR (400 MHz, DMSO) δ0.00 (s, 6H), 0.83 (s, 9H), 0.98 (d, 3H), 3.35-3.45 (m, 2H), 3.47-3.65 (m, 3H), 3.66 (s, 3H), 4.09-4.15 (m, 1H), 5.37 (d, 1H).

Intermediate AN2: (2S)-methyl 3-((R)-1-(tert-butyldimethylsilyloxy)propan-2-yloxy)-2-(1-(3-chloropyridin-2-yl)-1H-pyrazolo[3,4-d]pyrimidin-4-yloxy)propanoate

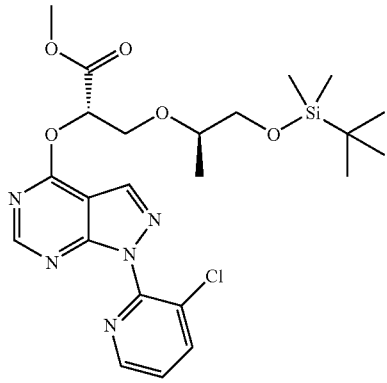

Sodium hydride (0.164 g, 4.10 mmol) was added to (S)-methyl 3-((R)-1-(tert-butyldimethylsilyloxy)propan-2-yloxy)-2-hydroxypropanoate (Intermediate AN1) (1 g, 3.42 mmol) in anhydrous THF (20 mL) at 0° C. under nitrogen. The resulting solution was stirred at 0° C. for 10 minutes and then 4-chloro-1-(3-chloropyridin-2-yl)-1H-pyrazolo[3,4-d]pyrimidine (Intermediate B15) (0.910 g, 3.42 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×50 mL). The combined organics were washed with saturated brine (25 mL), dried (MgSO₄) and evaporated. The crude product was purified by flash silica chromatography, eluting with 40 to 70% EtOAc in isohexane to afford the product (0.911 g, 51.0%). ¹H NMR (400 MHz, DMSO) δ0.00 (d, 6H), 0.81 (s, 9H), 1.04 (d, 3H), 3.47-3.62 (m, 3H), 3.68 (s, 3H), 4.08 (d, 2H), 5.81 (t, 1H), 7.71-7.77 (m, 1H), 8.29-8.34 (m, 1H), 8.54-8.58 (m, 2H), 8.64-8.67 (m/z (ES+), (M+H)⁺= 522.50; HPLC $t_R$=3.38 min Intermediate AN3: (2S)-3-((R)-1-(tert-butyldimethylsilyloxy)propan-2-yloxy)-2-(1-(3-chloropyridin-2-yl)-1H-pyrazolo[3,4-d]pyrimidin-4-yloxy)-N-(5-cyanopyridin-2-yl)propanamide

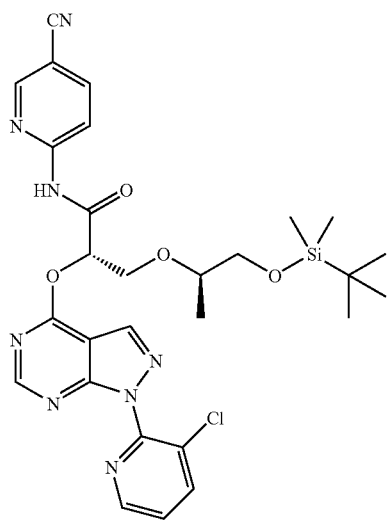

Trimethylaluminium (2M in hexanes) (1.839 mL, 3.68 mmol) was added to 6-aminonicotinonitrile (CAS no. 4214-73-7) (411 mg, 3.45 mmol) in DCM (8 mL) cooled to 0° C. under nitrogen. The resulting solution was stirred at 0° C. for 20 minutes. (2S)-methyl 3-((R)-1-(tert-butyldimethylsilyloxy)propan-2-yloxy)-2-(1-(3-chloropyridin-2-yl)-1H-pyrazolo[3,4-d]pyrimidin-4-yloxy)propanoate (Intermediate AN2) (600 mg, 1.15 mmol) in toluene (8 mL) was added and the reaction was allowed to warm to room temperature and then heated to 100° C. for 5 hours in the microwave reactor. The reaction was allowed to cool to room temperature before adding EtOAc (50 mL) and 20% sodium potassium tartrate solution (30 mL), which was stirred vigorously for 16 hours. The phases were separated and the organic layer was washed with sat. brine (15 mL), dried (MgSO₄) and evaporated. The crude product was purified by flash alumina chromatography, eluting with 0 to 50% EtOAc in isohexane to afford the product (395 mg, 56.4%). ¹H NMR (400 MHz, DMSO) δ-0.01 (d, 6H), 0.80 (s, 9H), 1.08 (d, 3H), 3.47-3.62 (m, 2H), 3.67-3.77 (m, 1H), 4.09-4.21 (m, 2H), 5.92-5.97 (m, 1H), 7.75-7.80 (m, 1H), 8.13-8.17 (m, 1H), 8.22-8.29 (m, 1H), 8.34-8.37 (m, 1H), 8.58 (s, 1H), 8.63 (s, 1H), 8.67-8.71 (m, 1H), 8.82-8.85 (m, 1H), 11.55 (s, 1H); m/z (ES+), (M+H)⁺= 607.47; HPLC $t_R$=3.27 min

Intermediate AN4: (2S)-3-((R)-1-(tert-butyldimethylsilyloxy)propan-2-yloxy)-N-(5-chloropyridin-2-yl)-2-(1-(3-chloropyridin-2-yl)-1H-pyrazolo[3,4-d]pyrimidin-4-yloxy)propanamide

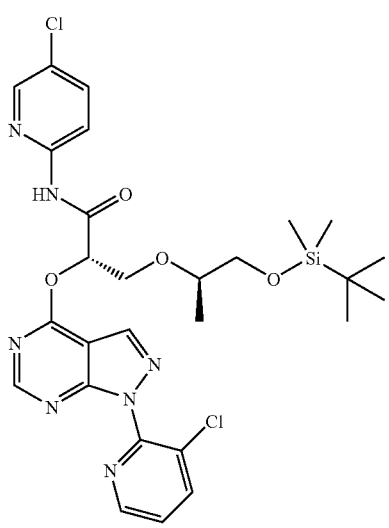

Trimethylaluminium (2M in Hexanes) (0.551 mL, 1.10 mmol) was added to 5-chloropyridin-2-amine (135 mg, 1.05 mmol) in toluene (5 mL) cooled to 0° C. under nitrogen. The resulting solution was stirred at 0° C. for 20 minutes. (2S)-methyl 3-((R)-1-(tert-butyldimethylsilyloxy)propan-2-yloxy)-2-(1-(3-chloropyridin-2-yl)-1H-pyrazolo[3,4-d]pyrimidin-4-yloxy)propanoate (Intermediate AN2) (500 mg, 0.96 mmol) in toluene (5 mL) was added and the reaction was allowed to warm to room temperature and then heated to 100° C. for 5 hours in the microwave reactor. The reaction was allowed to cool to room temperature before adding EtOAc (50 mL) and 20% sodium potassium tartrate solution (30 mL), which was stirred vigorously for 16 hours. The phases were separated and the organic layer was washed with sat. brine (15 mL), dried (MgSO$_4$) and evaporated. The crude product was purified by flash silica chromatography, eluting with 30 to 50% EtOAc in isohexane afford the product (460 mg, 78%). $^1$H NMR (400 MHz, DMSO) δ-0.01 (d, 6H), 0.80 (s, 9H), 1.08 (d, 3H), 3.47-3.63 (m, 2H), 3.67-3.76 (m, 1H), 4.07-4.19 (m, 2H), 5.89-5.96 (m, 1H), 7.75-7.80 (m, 1H), 7.89-7.94 (m, 1H), 8.02-8.07 (m, 1H), 8.33-8.37 (m, 1H), 8.41-8.43 (m, 1H), 8.58 (s, 1H), 8.63 (s, 1H), 8.67-8.72 (m, 1H), 11.18 (s, 1H); m/z (ES+), (M+H)$^+$=618.44; HPLC t$_R$=3.53 min

Intermediate AN5: (2S)-3-((R)-1-(tert-butyldimethylsilyloxy)propan-2-yloxy)-2-(1-(3-chloropyridin-2-yl)-1H-pyrazolo[3,4-d]pyrimidin-4-yloxy)-N-(5-fluoropyridin-2-yl)propanamide

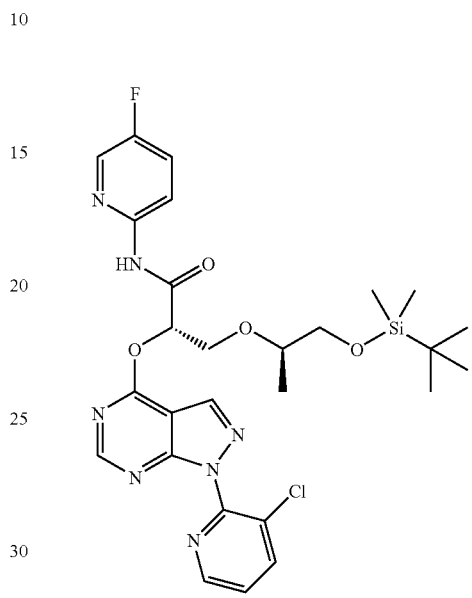

Trimethylaluminium (2M in hexane)(0.474 mL, 0.95 mmol) was added to 5-fluoropyridin-2-amine (102 mg, 0.91 mmol) in toluene (7 mL) cooled to 0° C. under nitrogen. The resulting solution was stirred at 0° C. for 20 minutes. (2S)-Methyl 3-((R)-1-(tert-butyldimethylsilyloxy)propan-2-yloxy)-2-(1-(3-chloropyridin-2-yl)-1H-pyrazolo[3,4-d]pyrimidin-4-yloxy)propanoate (Intermediate AN2) (430 mg, 0.82 mmol) in toluene (7 mL) was added and the reaction was allowed to warm to room temperature and then heated to 100° C. for 5 hours in the microwave reactor. The reaction was allowed to cool to room temperature before adding EtOAc (30 mL) and 20% sodium potassium tartrate solution (30 mL), which was stirred vigorously for 16 hours. The phases were separated and the organic layer was washed with sat. brine (15 mL), dried (MgSO$_4$) and evaporated. The crude product was purified by flash silica chromatography, eluting with 30 to 50% EtOAc in isohexane to give (2S)-3-((R)-1-(tert-butyldimethylsilyloxy)propan-2-yloxy)-2-(1-(3-chloropyridin-2-yl)-1H-pyrazolo[3,4-d]pyrimidin-4-yloxy)-N-(5-fluoropyridin-2-yl)propanamide (303 mg, 61.1%). $^1$H NMR (400 MHz, DMSO) δ-0.01 (d, 6H), 0.80 (s, 9H), 1.09 (d, 3H), 3.46-3.63 (m, 2H), 3.67-3.77 (m, 1H), 4.07-4.20 (m, 2H), 5.90-5.95 (m, 1H), 7.71-7.80 (m, 2H), 8.02-8.08 (m, 1H), 8.33-8.39 (m, 2H), 8.58 (s, 1H), 8.63 (s, 1H), 8.67-8.71 (m, 1H), 11.09 (s, 1H); m/z (ES+), (M+H)$^+$=602.48; HPLC t$_R$=3.33 min

Intermediate AO1: (S)-Methyl 3-((S)-1-(tert-butyldimethylsilyloxy)propan-2-yloxy)-2-hydroxypropanoate

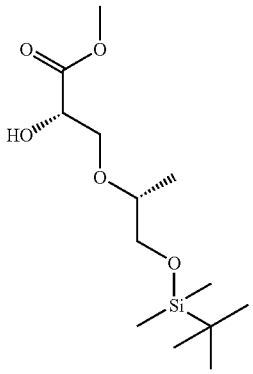

Magnesium trifluoromethanesulfonate (0.974 g, 3.02 mmol) was added in one portion to (S)-methyl oxirane-2-carboxylate (1.234 g, 12.08 mmol) and (S)-1-(tert-butyldimethylsilyloxy)propan-2-ol (CAS no. 113534-13-7) (2.30 g, 12.08 mmol) in EtOAc (5 mL) cooled to 10° C. The resulting suspension was stirred at 10° C. for 10 minutes and then warmed to 45° C. and stirred for 2 days. The crude product was purified by flash silica chromatography, eluting with 0 to 30% EtOAc in isohexane to afford the product (1.336 g, 37.8%). $^1$H NMR (400 MHz, DMSO) δ 0.00 (s, 6H), 0.83 (s, 9H), 0.98 (d, 3H), 3.34-3.53 (m, 3H), 3.55-3.64 (m, 5H), 4.11 (q, 1H), 5.39 (d, 1H)

Intermediate AO2: (2S)-methyl 3-((S)-1-(tert-butyldimethylsilyloxy)propan-2-yloxy)-2-(1-(3-chloropyridin-2-yl)-1H-pyrazolo[3,4-d]pyrimidin-4-yloxy)propanoate

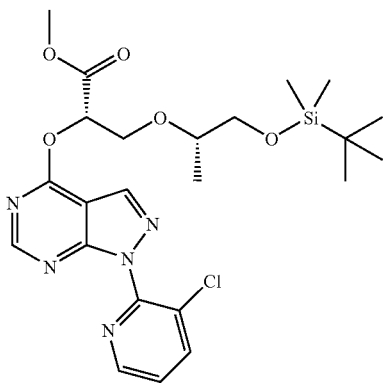

Sodium hydride (0.219 g, 5.48 mmol) was added to (S)-methyl 3-((S)-1-(tert-butyldimethylsilyloxy)propan-2-yloxy)-2-hydroxypropanoate (Intermediate AO1) (1.336 g, 4.57 mmol) in anhydrous THF (30 mL) at 0° C. under nitrogen. The resulting solution was stirred at 0° C. for 10 minutes and then 4-chloro-1-(3-chloropyridin-2-yl)-1H-pyrazolo[3,4-d]pyrimidine (1.216 g, 4.57 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×50 mL). The combined organics were washed with saturated brine (25 mL), dried (MgSO$_4$) and evaporated. The crude product was purified by flash silica chromatography, eluting with 30 to 60% EtOAc in isohexane to give (2S)-methyl 3-((S)-1-(tert-butyldimethylsilyloxy)propan-2-yloxy)-2-(1-(3-chloropyridin-2-yl)-1H-pyrazolo[3,4-d]pyrimidin-4-yloxy)propanoate (1.658 g, 69.5%). m/z (ES+), (M+H)$^+$=522.50; HPLC $t_R$=3.35 min

Intermediate AO3: (2S)-3-((S)-1-(tert-butyldimethylsilyloxy)propan-2-yloxy)-2-(1-(3-chloropyridin-2-yl)-1H-pyrazolo[3,4-d]pyrimidin-4-yloxy)-N-(5-fluoropyridin-2-yl)propanamide

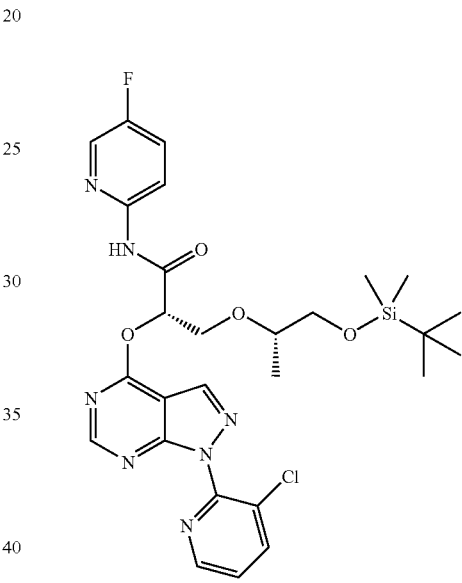

Trimethylaluminium (2M in hexanes)(0.608 mL, 1.22 mmol) was added to 5-fluoropyridin-2-amine (130 mg, 1.16 mmol) in toluene (8 mL) cooled to 0° C. under nitrogen. The resulting solution was stirred at 0° C. for 20 minutes. (2S)-methyl 3-((S)-1-(tert-butyldimethylsilyloxy)propan-2-yloxy)-2-(1-(3-chloropyridin-2-yl)-1H-pyrazolo[3,4-d]pyrimidin-4-yloxy)propanoate (Intermediate AO2) (552 mg, 1.06 mmol) in toluene (8 mL) was added and the reaction was heated to 100° C. for 5 hours in the microwave reactor. The reaction was allowed to cool to room temperature before adding EtOAc (30 mL) and 20% sodium potassium tartrate solution (30 mL), which was stirred vigorously for 16 hours. The phases were separated and the organic layer was washed with sat. brine (15 mL), dried (MgSO$_4$) and evaporated to afford the product (638 mg, 100%) which was used without further purification. $^1$H NMR (400 MHz, CDCl$_3$) δ 0.05 (d, 6H), 0.87 (s, 9H), 1.17 (d, 3H), 3.51-3.58 (m, 1H), 3.60-3.69 (m, 2H), 4.18-4.22 (m, 2H), 6.00 (t, 1H), 7.40-7.49 (m, 2H), 7.98-8.03 (m, 1H), 8.13 (d, 1H), 8.22-8.28 (m, 1H), 8.44 (s, 1H), 8.60-8.64 (m, 2H), 8.94 (s, 1H); m/z (ES+), (M+H)$^+$=602.55; HPLC $t_R$=3.35 min Intermediate AO4: (2S)-3-((S)-1-(tert-butyldimethyl-silyloxy)propan-2-yloxy)-N-(5-chloropyridin-2-yl)-2-(1-(3-chloropyridin-2-yl)-1H-pyrazolo [3,4-d]pyrimidin-4-yloxy)propanamide

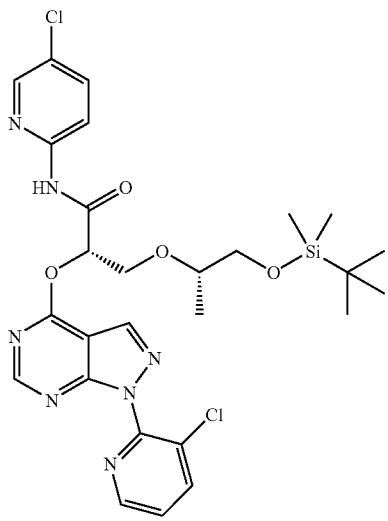

Trimethylaluminium (2M in hexanes)(0.551 mL, 1.10 mmol) was added to 5-chloropyridin-2-amine (135 mg, 1.05 mmol) in toluene (8 mL) cooled to 0° C. under nitrogen. The resulting solution was stirred at 0° C. for 20 minutes. (2S)-methyl 3-((S)-1-(tert-butyldimethylsilyloxy)propan-2-yloxy)-2-(1-(3-chloropyridin-2-yl)-1H-pyrazolo[3,4-d]pyrimidin-4-yloxy)propanoate (Intermediate AO2) (500 mg, 0.96 mmol) in toluene (8 mL) was added and the reaction was heated to 100° C. for 5 hours in the microwave reactor. The reaction was allowed to cool to room temperature before adding EtOAc (30 mL) and 20% sodium potassium tartrate solution (30 mL), which was stirred vigorously for 16 hours. The phases were separated and the organic layer was washed with sat. brine (15 mL), dried (MgSO$_4$) and evaporated to give crude product (300 mg) that was used without further purification. m/z (ES+), (M+H)$^+$=618.44; HPLC t$_R$=23.55 min Intermediate AP1:
6-chloro-N4-(2-chlorophenyl)pyrimidine-4,5-diamine

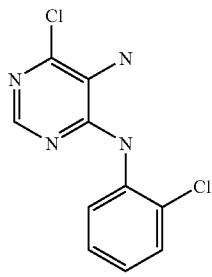

4,6-Dichloropyrimidin-5-amine (CAS no. 5413-85-4) (2 g, 12.20 mmol) and 2-chloroaniline (CAS no. 95-51-2) (1.556 g, 12.20 mmol) were dissolved in ethylene glycol (12 mL) and sealed into a microwave tube. The reaction was heated to 100° C. for 1 hour in the microwave reactor and cooled to room temperature. The reaction mixture was quenched with water (50 mL), extracted with EtOAc (3×50 mL), the organic layer was dried (MgSO$_4$), filtered and evaporated to afford crude product. The crude product was purified by flash silica chromatography, eluting with 0 to 60% EtOAc in isohexane to afford the product (2.65 g, 85%). $^1$H NMR (400 MHz, DMSO) 65.38 (s, 2H), 7.19-7.25 (m, 1H), 7.32-7.38 (m, 1H), 7.49-7.54 (m, 1H), 7.57-7.62 (m, 1H), 7.73 (s, 2H), 7.19-7.25 (s, 1H); m/z (ES+), (M+H)$^+$=255.25; HPLC t$_R$=1.82 min.

Intermediate AP2: 7-chloro-3-(2-chlorophenyl)-3H-[1,2,3]triazolo[4,5-d]pyrimidine

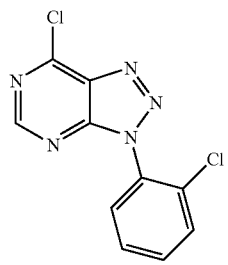

Sodium nitrite (0.298 g, 4.31 mmol) was added to 6-chloro-N4-(2-chlorophenyl)pyrimidine-4,5-diamine (Intermediate AP1) (1 g, 3.92 mmol) in acetic acid (50% Aq, 25 mL) and DCM (25 mL) at room temperature. The resulting solution was stirred at room temperature for 15 minutes. The reaction mixture was separated and the organic phase was washed with water (10 mL), dried (MgSO$_4$) and evaporated to give crude product (0.600 g) that was used without further purification. $^1$H NMR (400 MHz, CDCl$_3$) δ δ7.52-7.65 (m, 3H), 7.68-7.73 (m, 1H), 8.97 (s, 1H); m/z (ES+), (M+H)$^+$= 266.21; HPLC t$_R$=2.33 min Intermediate AP3: (2S)-3-(2-(tert-butyldiphenylsilyloxy)ethoxy)-2-(3-(2-chlorophenyl)-3H-[1,2,3]triazolo[4,5-d]pyrimidin-7-yloxy)-N-(5-chloropyridin-2-yl)propanamide

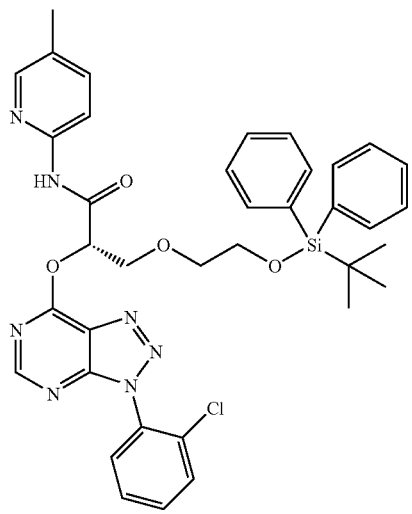

Sodium hydride (50.1 mg, 1.25 mmol) was added to (S)-3-(2-(tert-butyldiphenylsilyloxy)ethoxy)-2-hydroxy-N-(5-methylpyridin-2-yl)propanamide (Intermediate AU2) (250 mg, 0.52 mmol) in anhydrous THF (5 mL) at 0° C. under nitrogen. The resulting solution was stirred at 0° C. for 10 minutes and then 7-chloro-3-(2-chlorophenyl)-3H-[1,2,3]triazolo[4,5-d]pyrimidine (Intermediate AP2) (278 mg, 1.04 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×50 mL). The combined organics were washed with saturated brine (15 mL), dried (MgSO$_4$) and evaporated. The crude product was purified by flash silica chromatography, eluting with 0 to 50% EtOAc in isohexane to give (2S)-3-(2-(tert-butyldiphenylsilyloxy)ethoxy)-2-(3-(2-chlorophenyl)-3H-[1,2,3]triazolo[4,5-d]pyrimidin-7-yloxy)-N-(5-methylpyridin-2-yl)propanamide (335 mg, 91%). $^1$H NMR (400 MHz, CDCl$_3$) δ0.97 (s, 9H), 2.28 (s, 3H), 3.67-3.84 (m, 4H), 4.26 (d, 2H), 6.15 (t, 1H), 7.30-7.41 (m, 5H), 7.48-7.71 (m, 10H), 8.06-8.14 (m, 2H), 8.68 (s, 1H), 8.76 (s, 1H); m/z (ES+), (M+H)$^+$=708.65; HPLC t$_R$=3.84 min Intermediate AP4: (2S)-3-(2-(tert-butyldiphenylsilyloxy)ethoxy)-2-(3-(2-chlorophenyl)-3H-[1,2,3]triazolo[4,5-d]pyrimidin-7-yloxy)-N-(5-chloropyridin-2-yl)propanamide

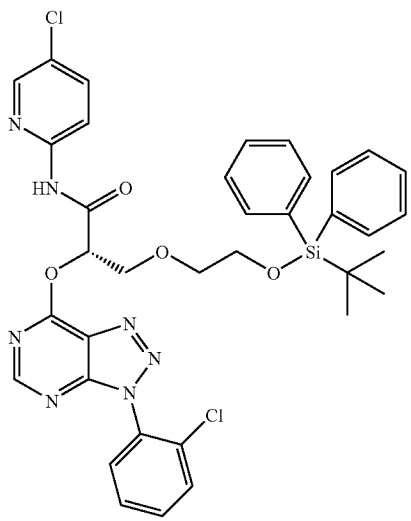

Sodium hydride (38.5 mg, 0.96 mmol) was added to (S)-3-(2-(tert-butyldiphenylsilyloxy)ethoxy)-N-(5-chloropyridin-2-yl)-2-hydroxypropanamide (Intermediate AU3) (200 mg, 0.40 mmol) in anhydrous THF (5 mL) at 0° C. under nitrogen. The resulting solution was stirred at 0° C. for 10 minutes and then 7-chloro-3-(2-chlorophenyl)-3H-[1,2,3]triazolo[4,5-d]pyrimidine (Intermediate AP2) (107 mg, 0.40 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×50 mL). The combined organics were washed with saturated brine (25 mL), dried (MgSO$_4$) and evaporated. The crude product was purified by flash silica chromatography, eluting with 0 to 50% EtOAc in isohexane to give (2S)-3-(2-(tert-butyldiphenylsilyloxy)ethoxy)-2-(3-(2-chlorophenyl)-3H-[1,2,3]triazolo[4,5-d]pyrimidin-7-yloxy)-N-(5-chloropyridin-2-yl)propanamide (290 mg, 99%). m/z (ES+), (M+H)$^+$=728.38: HPLC t$_R$=3.91 min Intermediate AP5: 6-chloro-N4-o-tolylpyrimidine-4,5-diamine

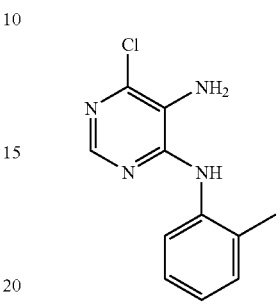

4,6-dichloropyrimidin-5-amine (2 g, 12.20 mmol) and o-toluidine (1.309 mL, 12.20 mmol) were dissolved in ethylene glycol (10 mL) and sealed into a microwave tube. The reaction was heated to 100° C. for 1 hour in the microwave reactor and cooled to room temperature. The reaction mixture was quenched with water (20 mL), extracted with EtOAc (3×20 mL), the organic layer was dried (MgSO$_4$), filtered and evaporated to afford crude product. The crude product was purified by flash silica chromatography, eluting with 0 to 50% EtOAc in isohexane to afford the product (2.300 g, 80%). $^1$H NMR (400 MHz, DMSO) δ2.15 (s, 3H), 5.28 (s, 2H), 7.08-7.33 (m, 4H), 7.68 (s, 1H), 8.18 (s, 1H); m/z (ES+), (M+H)$^+$=235.34; HPLC t$_R$=1.54 min.

Intermediate AP6: 7-chloro-3-o-tolyl-3H-[1,2,3]triazolo[4,5-d]pyrimidine

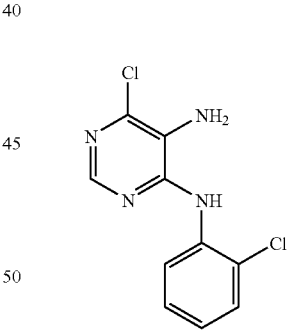

Sodium nitrite (0.323 g, 4.69 mmol) was added to 6-chloro-N4-o-tolylpyrimidine-4,5-diamine (Intermediate AP5)(1 g, 4.26 mmol) in acetic acid (50% Aq) (25 mL)and DCM (25 mL) at room temperature. The resulting solution was stirred at room temperature for 15 minutes. The reaction mixture was separated and the organic phase was washed with water (10 mL), dried (MgSO$_4$) and evaporated to give crude 7-chloro-3-o-tolyl-3H-[1,2,3]triazolo[4,5-d]pyrimidine (0.980 g, 94%) that was used without further purification.

$^1$H NMR (400 MHz, CDCl$_3$) δ2.19 (s, 3H), 7.42-7.57 (m, 4H), 8.95 (s, 1H)

m/z (ES+), (M+H)$^+$=246.29; HPLC t$_R$=2.28 min

Intermediate AP7: (2S)-3-(2-(tert-butyldiphenylsilyloxy)ethoxy)-N-(5-chloropyridin-2-yl)-2-(3-o-tolyl-3H-[1,2,3]triazolo[4,5-d]pyrimidin-7-yloxy)propanamide

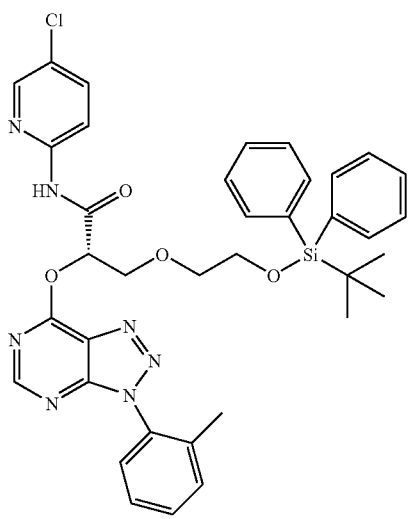

Sodium hydride (57.7 mg, 1.44 mmol) was added to (S)-3-(2-(tert-butyldiphenylsilyloxy)ethoxy)-N-(5-chloropyridin-2-yl)-2-hydroxypropanamide (Intermediate AU3) (300 mg, 0.60 mmol) in anhydrous THF (7 ml) at 0° C. under nitrogen. The resulting solution was stirred at 0° C. for 10 minutes and then 7-chloro-3-o-tolyl-3H-[1,2,3]triazolo[4,5-d]pyrimidine (148 mg, 0.60 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×50 mL). The combined organics were washed with saturated brine (15 mL), dried (MgSO$_4$) and evaporated. The crude product was purified by flash silica chromatography, eluting with 0 to 50% EtOAc in isohexane to give (2S)-3-(2-(tert-butyldiphenylsilyloxy)ethoxy)-N-(5-chloropyridin-2-yl)-2-(3-o-tolyl-3H-[1,2,3]triazolo[4,5-d]pyrimidin-7-yloxy)propanamide (410 mg, 100%). $^1$H NMR (400 MHz, CDCl$_3$) δ 0.97 (s, 9H), 2.19 (s, 3H), 3.67-3.85 (m, 4H), 4.26 (d, 2H), 6.14 (t, 1H), 7.31-7.54 (m, 10H), 7.60-7.68 (m, 5H), 8.18-8.23 (m, 2H), 8.66 (s, 1H), 8.91 (s, 1H); m/z (ES+), (M+H)$^+$=708.61; HPLC t$_R$=4.02 min

Intermediate AQ1: (2S)-3-(2-(tert-butyldiphenylsilyloxy)ethoxy)-N-(pyridin-2-yl)-2-(1-(2-(trifluoromethyl)phenyl)-1H-pyrazolo[3,4-d]pyrimidin-4-yloxy)propanamide

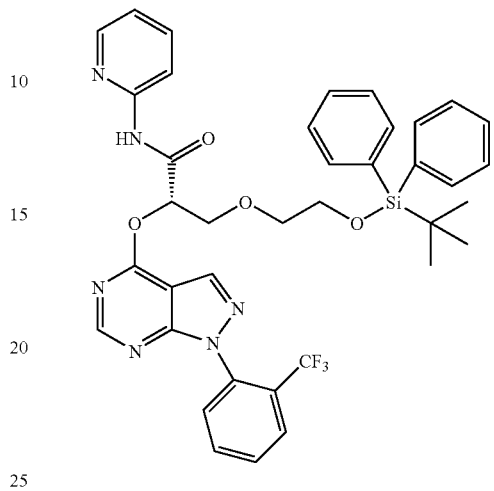

Sodium hydride (117 mg, 2.93 mmol) was added to (S)-3-(2-(tert-butyldiphenylsilyloxy)ethoxy)-2-hydroxy-N-(pyridin-2-yl)propanamide (618 mg, 1.33 mmol) (Intermediate AQ2) in anhydrous THF (20 mL) at 0° C. under nitrogen. The resulting solution was stirred at 0° C. for 10 minutes and then 4-chloro-1-(2-(trifluoromethyl)phenyl)-1H-pyrazolo[3,4-d]pyrimidine (514 mg, 1.46 mmol) (Intermediate B4) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×100 mL). The combined organics were washed with saturated brine (75 mL), dried (MgSO$_4$) and evaporated. The crude product was purified by flash silica chromatography, eluting with 50 to 100% EtOAc in isohexane to afford the product (919 mg, 95%). $^1$H NMR: (400 MHz, CDCl$_3$) δ 0.99 (9H, t), 3.70-3.72 (2H, m), 3.82 (2H, t), 4.16-4.25 (2H, m), 6.05-6.07 (1H, m), 7.04-7.07 (1H, m), 7.31-7.75 (14H, m), 7.89-7.92 (1H, m), 8.24-8.28 (2H, m), 8.36 (1H, s), 8.55 (1H, s), 8.73 (1H, s); m/z (ES+) (M+H)$^+$=279.1; HPLC Rt=3.71 min.

Intermediate AQ2: (S)-3-(2-(tert-butyldiphenylsilyloxy)ethoxy)-2-hydroxy-N-(pyridin-2-yl)propanamide

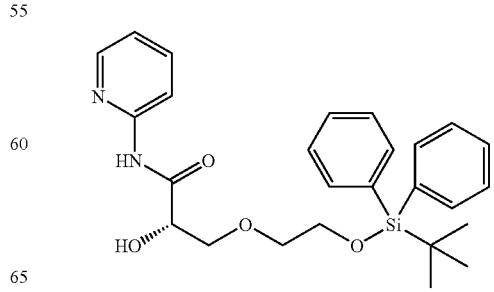

Trimethylaluminium (3.73 mL, 7.45 mmol) was added to pyridin-2-amine (0.701 g, 7.45 mmol) in toluene (6 ml) cooled to 0° C. under nitrogen. The resulting solution was stirred at 0° C. for 20 minutes. (S)-methyl 3-(2-(tert-butyldiphenylsilyloxy)ethoxy)-2-hydroxypropanoate (1.5 g, 3.73 mmol) (Intermediate AB3) in toluene (6 ml) was added and the reaction was allowed to warm to room temperature and then heated to 110 for 5 hours in a microwave. The reaction mixture was allowed to cool and concentrated in vacuo. The residue was neutralised with citric acid (1M, aq) and then diluted with water (25 mL) and extracted with EtOAc (2×50 mL). The combined organics were washed with brine (20 ml), then dried (MgSO$_4$), filtered and evaporated. The crude product was purified by flash silica chromatography, eluting with 30 to 50% EtOAc in isohexane to afford the product (1.085 g, 62.7%). $^1$H NMR: (400 MHz, CDCl$_3$) δ 1.05 (9H, t), 3.60-3.66 (2H, m), 3.67 (1H, d), 3.82-3.84 (2H d, m), 3.80-3.85 (2H, m), 4.33-4.35 (1H, m), 7.03-7.06 (1H, m), 7.35-7.68 (10H, m), 7.70 (1H, d), 8.22 (1H, d), 8.29-8.30 (1H, m), 9.15 (1H, s); m/z (ES+) (M+H)$^+$=465.42; HPLC t$_R$=3.13 min.

Intermediate AQ3: (2S)-2-(1-(2-chlorophenyl)-1H-pyrazolo[3,4-d]pyrimidin-4-yloxy)-N-(pyridin-2-yl)-3-((R)-1-(triisopropylsilyloxy)propan-2-yloxy)propanamide

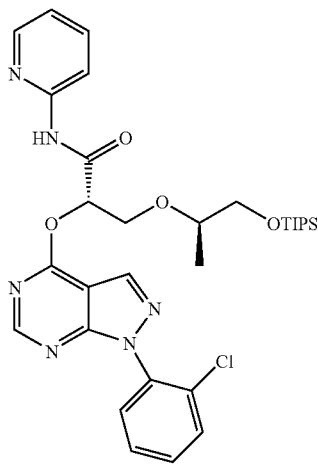

Sodium hydride (78 mg, 1.95 mmol) was added to (S)-2-hydroxy-N-(pyridin-2-yl)-3-((R)-1-(triisopropylsilyloxy)propan-2-yloxy)propanamide (Intermediate AQ4) (387 mg, 0.98 mmol) in anhydrous THF (20 mL). The resulting solution was stirred at 0° C. for 10 minutes and then 4-chloro-1-(2-chlorophenyl)-1H-pyrazolo[3,4-d]pyrimidine (Intermediate B1) (250 mg, 0.89 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×100 mL). The combined organics were washed with saturated brine (75 mL), dried (MgSO$_4$) and evaporated. The crude product was purified by flash silica chromatography, eluting with 50 to 100% EtOAc in isohexane to afford the product (329 mg, 59.4%). $^1$H NMR (400 MHz, CDCl$_3$) δ 1.01-1.15 (24H, m), 3.55-3.78 (3H, m), 4.19-4.35 (2H, m), 6.03 (1H, t), 7.05 (1H, t) 7.40-7.65 (4H, m), 7.7 (1H, t), 8.2-8.3 (2H, m), 8.43 (1H, s), 8.58 (1H, s)8.75 (1H, s); m/z (ES+) M+=625.44; HPLC t$_R$=4.02 min., Intermediate AQ4: (S)-2-hydroxy-N-(pyridin-2-yl)-3-((R)-1-(triisopropylsilyloxy)propan-2-yloxy)propanamide

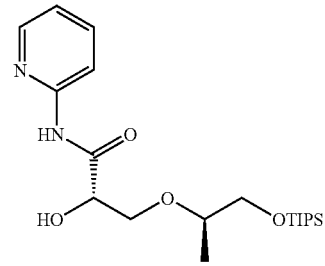

Trimethylaluminium (2M in toluene) (2.99 ml, 5.98 mmol) was added to pyridin-2-amine (0.563 g, 5.98 mmol) in toluene (20.18 ml) cooled to 0° C. under nitrogen. The resulting solution was stirred at 0° C. for 20 minutes. (S)-methyl 2-hydroxy-3-((R)-1-(triisopropylsilyloxy)propan-2-yloxy)propanoate (1 g, 2.99 mmol) (Intermediate AN1) in toluene (6.73 mL) was added and the reaction was allowed to warm to room temperature and then heated at reflux for 5 hours. The reaction mixture was allowed to cool and concentrated in vacuo. The residue was neutralised with citric acid (1M, aq) and then diluted with water (25 mL) and extracted with EtOAc (2×50 mL). The combined organics were washed with brine (20 ml), then dried (MgSO$_4$) and evaporated. The crude product was purified by flash silica chromatography, eluting with 30 to 50% EtOAc in isohexane to afford the product (0.657 g, 55.4%). $^1$H NMR (400 MHz, CDCl$_3$) δ 1.03-1.17 (24H, m), 3.61-3.69 (3H, m), 3.82-3.86 (1H, m), 4.00-4.04 (1H, m), 4.13 (1H, d), 4.32 (1H, q), 7.02-7.06 (1H, m), 7.67-7.72 (1H, m), 8.23 (1H, d), 8.29-8.31 (1H, m), 9.20 (1H, s); m/z (ES+) (M+H)$^+$=397.44; HPLC t$_R$=3.36 min.

Intermediate AQ5: (2S)-3-(2-(tert-butyldiphenylsilyloxy)ethoxy)-2-(1-(2-chlorophenyl)-1H-pyrazolo[3,4-d]pyrimidin-4-yloxy)-N-(pyridin-2-yl)propanamide

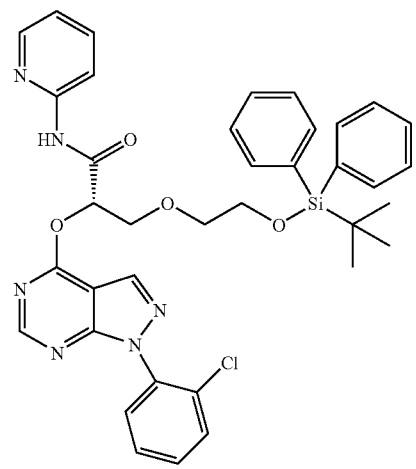

Sodium hydride (91 mg, 2.27 mmol) was added to (S)-3-(2-(tert-butyldiphenylsilyloxy)ethoxy)-2-hydroxy-N-(pyridin-2-yl)propanamide (Intermediate AQ4) (480 mg, 1.03 mmol) (intermediate 3) in anhydrous THF (20 mL) at 0° C. under nitrogen. The resulting solution was stirred at 0° C. for 10 minutes and then 4-chloro-1-(2-chlorophenyl)-1H-pyrazolo[3,4-d]pyrimidine (Intermediate B1) (320 mg, 1.14 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×100 mL). The combined organics were washed with saturated brine (75 mL), dried (MgSO$_4$) and evaporated. The crude product was purified by flash silica chromatography, eluting with 50 to 100% EtOAc in isohexane to afford the product (682 mg, 95%). $^1$H NMR: (400 MHz, CDCl$_3$) δ 0.98-1.00 (9H, m), 3.69-3.72 (2H, m), 3.81 (2H, t), 4.16-4.25 (2H, m), 6.06-6.09 (1H, m), 7.04-7.07 (1H, m), 7.31-7.66 (14H, m), 7.68-7.73 (1H, m), 8.24-8.28 (2H, m), 8.38 (1H, s), 8.58 (1H, s), 8.75 (1H, s); m/z (ES+) M+=693.61; HPLC t$_R$=3.79 min.

Intermediate AR1: (2S)-Methyl 3-(2-(tert-butyldiphenylsilyloxy)ethoxy)-2-(1-(2,3-dichlorophenyl)-1H-pyrazolo[3,4-d]pyrimidin-4-yloxy)propanoate

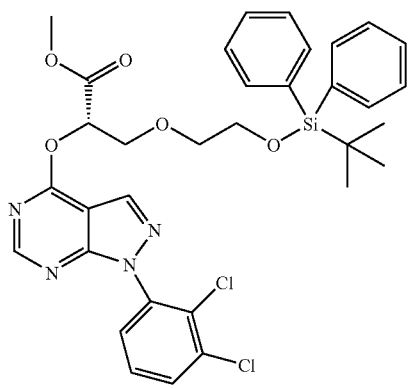

Sodium hydride (0.167 g, 4.17 mmol) was added to (S)-methyl 3-(2-(tert-butyldiphenylsilyloxy)ethoxy)-2-hydroxypropanoate (Intermediate AB3) (1.4 g, 3.48 mmol) in anhydrous THF (25 ml) at 0° C. under nitrogen. The resulting solution was stirred at 0° C. for 10 minutes and then 4-chloro-1-(2,3-dichlorophenyl)-1H-pyrazolo[3,4-d]pyrimidine (Intermediate AR2) (1.432 g, 3.83 mmol) was added. The reaction mixture was allowed to warm to room temperature and stirred for 1 hour. The reaction mixture was neutralised with 1M citric acid and the majority of the THF removed in vacuo. The reaction mixture was diluted with water (20 mL) and EtOAc (50 mL). The organic layer was separated and the aqueous layer re-extracted with EtOAc (2×100 mL). The combined organics were washed with saturated brine (75 mL), dried (MgSO$_4$) and evaporated. The crude product was purified by flash silica chromatography, eluting with 50 to 100% EtOAc in isohexane. Fractions containing the product were evaporated to dryness to afford crude product which unfortunately was contaminated with starting alcohol and Methyl glycidate. The crude product was repurified by flash silica chromatography, elution gradient 0 to 30% EtOAc in toluene to afford the product (0.860 g, 37.1%). $^1$H NMR (400 MHz, CDCl$_3$) δ 1.04 (9H, s), 3.80-3.69 (5H, m), 3.85 (2H, t), 4.15-4.08 (1H, m), 4.20 (1H, dd), 5.87 (1H, dd), 7.48-7.33 (8H, m), 7.75-7.60 (5H, m), 8.32 (1H, s), 8.54 (1H, s). m/z (ES+) (M+H)$^+$=667; HPLC t$_R$=3.8 min.

Intermediate AR2: 4-chloro-1-(2,3-dichlorophenyl)-1H-pyrazolo[3,4-d]pyrimidine

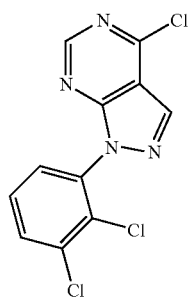

Phosphorus oxychloride (26.5 ml, 284.60 mmol) was added to 1-(2,3-dichlorophenyl)-1H-pyrazolo[3,4-d]pyrimidin-4-ol (Intermediate AR3) (4 g, 14.23 mmol), at ambient temperature. The resulting mixture was stirred at 100° C. for 4 hours. Allowed to cool to Ambient temperature. The reaction mixture was evaporated to near dryness, dissolved in toluene, evaporated, re-dissolved in toluene and evaporated to dryness again. The solid was triturated with EtOH. A solid was filtered off and dried under vacuum to give the product (2.450 g, 57.5%). $^1$H NMR (400 MHz, DMSO) δ 7.65 (1H, m), 7.73-7.75 (1H, dd), 7.94-7.97 (1H, dd), 8.83 (1H, s), 8.91 (1H, s); m/z (ES+) (M+H)$^+$=518; HPLC t$_R$=1.89 min.

Intermediate AR3: 1-(2,3-Dichlorophenyl)-1H-pyrazolo[3,4-d]pyrimidin-4-ol

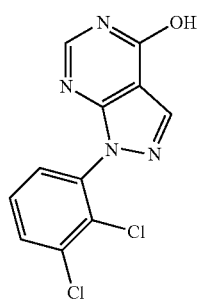

Concentrated sulfuric acid (1.666 mL, 31.25 mmol) in was added to a stirred solution of 5-amino-1-(2,3-dichlorophenyl)-1H-pyrazole-4-carbonitrile (Intermediate AR4) (7.19 g, 28.41 mmol) in formic acid (40 mL). The resulting solution was stirred at 100° C. for 16 hours. Allowed to cool to ambient temperature. The reaction mixture was evaporated to dryness. The residue was triturated under water. A solid was filtered off and dried under vacuum to give the product (6.64 g, 83%). $^1$H NMR (400 MHz, DMSO) δ 7.57-7.61 (1H, m), 7.63-7.66 (1H, m), 7.88-7.91 (1H, dd), 8.09 (1H, d), 8.36 (1H, s), 12.40 (1H, s); m/z (ES+) (M+H)$^+$=281; HPLC t$_R$=1.61 min.

Intermediate AR4: 5-amino-1-(2,3-dichlorophenyl)-1H-pyrazole-4-carbonitrile

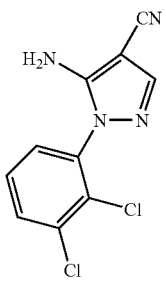

(2,3-Dichlorophenyl)hydrazine hydrochloride (CAS no. 21938-47-6) (6.06 g, 28.4 mmol) was partitioned between EtOAc and 2M NaOH. Separated. The organic solution was dried (MgSO₄), filtered and reduced to give the free base. 2-(Ethoxymethylene)malononitrile (3.47 g, 28.39 mmol) was added portionwise to a stirred solution of (2,3-dichlorophenyl)hydrazine in MeOH (50 mL), under nitrogen at 5° C. The resulting solution was allowed to stir for a further 1 hour. The reaction mixture was then heated to reflux and was stirred for 3 hours. The reaction mixture was allowed to cool to ambient temperature, then was evaporated to afford the product (7.19 g, 100%) which was used without further purification. ¹H NMR (400 MHz, DMSO) δ 6.75 (2H, s), 7.48-7.53 (2H, m), 7.77 (1H, s), 7.79-7.84 (1H, m).

Intermediate AS1: (2S)-3-((S)-2-(tert-butyldimethylsilyloxy)propoxy)-2-(1-(3-chloropyridin-2-yl)-1H-pyrazolo[3,4-d]pyrimidin-4-yloxy)-N-(5-methylpyridin-2-yl)propanamide

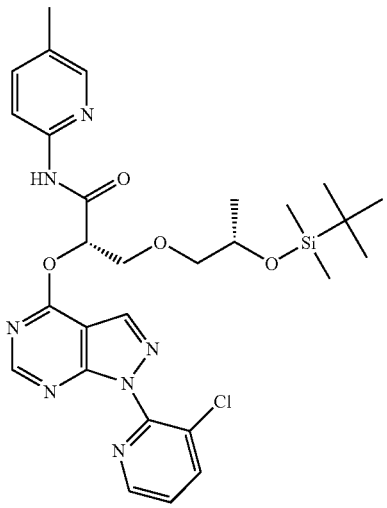

Sodium hydride (134 mg, 3.36 mmol) was added to (S)-3-((S)-2-(tert-butyldimethylsilyloxy)propoxy)-2-hydroxy-N-(5-methylpyridin-2-yl)propanamide (Intermediate AS2) (495 mg, 1.34 mmol) in anhydrous THF (5 mL) at 0° C. under nitrogen. The resulting solution was stirred at 0° C. for 10 minutes and then 4-chloro-1-(3-chloropyridin-2-yl)-1H-pyrazolo[3,4-d]pyrimidine (Intermediate B15) (393 mg, 1.48 mmol) was added. The reaction mixture was allowed to warm to room temperature and stirred for 2 hours. The reaction mixture was neutralised with 1M citric acid and diluted with water and EtOAc. The organic layer was separated and washed with saturated brine, dried (MgSO₄) and evaporated to give (2S)-3-((S)-2-(tert-butyldimethylsilyloxy)propoxy)-2-(1-(3-chloropyridin-2-yl)-1H-pyrazolo[3,4-d]pyrimidin-4-yloxy)-N-(5-methylpyridin-yl)propanamide (843 mg, 105%). m/z (ES+) (M+H)⁺=598.58; HPLC t$_R$=3.36 min.

Intermediate AS2: (S)-3-((S)-2-(tert-Butyldimethylsilyloxy)propoxy)-2-hydroxy-N-(5-methylpyridin-2-yl)propanamide

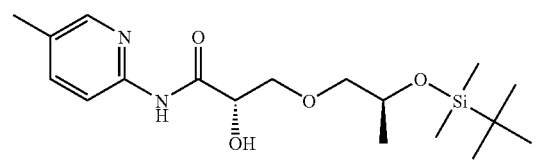

Trimethylaluminium (1.966 mL, 3.93 mmol) was added slowly to 5-methylpyridin-2-amine (0.407 g, 3.76 mmol) in toluene (20 mL) cooled to 0° C. under nitrogen. The resulting solution was stirred at 0° C. for 10 minutes. (S)-methyl 3-((S)-2-(tert-butyldimethylsilyloxy)propoxy)-2-hydroxypropanoate (Intermediate AS3) (1 g, 3.42 mmol) in toluene (4 mL) was added and the reaction was allowed to warm to room temperature and then heated at reflux for 4 hours (a further 5ml toluene was added to aid stirring). The reaction mixture was concentrated in vacuo. The residue was neutralised with citric acid (1M, aq) and then diluted with water and extracted with EtOAc. The combined organics were dried (MgSO₄) and evaporated to afford the product (0.994 g) which was used without further purification. ¹H NMR (400 MHz, CDCl₃) δ 0.07 (6H, d), 0.88 (9H, s), 1.15 (3H, d), 2.30 (3H, s), 2.79-3.11 (1H, m), 3.39-3.51 (2H, m), 3.80-3.91 (2H, m), 3.94-4.03 (1H, m), 4.31-4.36 (1H, m), 7.49-7.56 (1H, m), 8.09-8.16 (2H, m), 9.20 (1H, s); m/z (ES+) (M+H)⁺=369.52; HPLC t$_R$=2.73 min.

Intermediate AS3: (S)-Methyl 3-((S)-2-(tert-butyldimethylsilyloxy)propoxy)-2-hydroxypropanoate

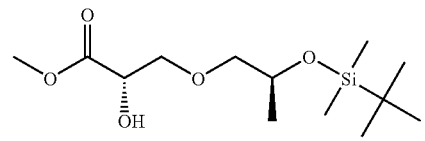

Magnesium trifluoromethanesulfonate (1.779 g, 5.52 mmol) was added in one portion to (S)-2-(tert-butyldimethylsilyloxy)propan-1-ol (Intermediate AS4) (4.2 g, 22.06 mmol) and (S)-methyl oxirane-2-carboxylate (2.252 g, 22.06 mmol) in EtOAc (25 mL). The resulting suspension was stirred at 80° C. for 24 hours. A further 1.5 g of the oxirane was added and the reaction stirred for 4 days. The reaction mixture was diluted with EtOAc, filtered through celite and evaporated to dryness. The crude product was purified by flash silica chromatography, elution gradient 0 to 30% EtOAc in isohexane to afford the product (2.70 g, 41.8%). ¹H NMR (400 MHz, CDCl₃) δ 0.00 (6H, d), 0.82 (9H, s), 1.06 (3H, d), 3.04 (1H, d), 3.25-3.39 (2H, m), 3.65-3.78 (5H, m), 3.83-3.92 (1H, m), 4.19-4.27 (1H, m)

Intermediate AS4:
(S)-2-(tert-butyldimethylsilyloxy)propan-1-ol

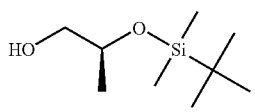

Diisobutylaluminum hydride (1M in DCM) (41.4 mL, 41.42 mmol) was added dropwise to a stirred solution of (S)-ethyl 2-(tert-butyldimethylsilyloxy)propanoate (CAS no. 106513-42-2) (5 mL, 18.83 mmol) in diethyl ether (25 mL) at ~78° C. under nitrogen. The resulting mixture was stirred at r.t. for 2 hours. The reaction mixture was carefully quenched with 20% Rochelle's solution (>100 ml) and at −78° C. and allowed to warm to r.t. After 2 hours of vigourous stirring the mixture was extracted with Et2O ×2, the organic layer was dried (MgSO$_4$), filtered and evaporated to afford colourless liquid, (S)-2-(tert-butyldimethylsilyloxy)propan-1-ol (3.50 g, 98%). $^1$H NMR (400 MHz, CDCl$_3$) δ 0.00 (6H, s), 0.81 (9H, s), 1.03 (3H, d), 1.71-1.90 (1H, m), 3.24-3.33 (1H, m), 3.35-3.44 (1H, m), 3.78-3.87 (1H, m).

Intermediate AT1: (2S)-3-(2-(tert-Butyldiphenylsilyloxy)ethoxy)-2-(1-(3-cyano-2-methylphenyl)-1H-pyrazolo[3,4-d]pyrimidin-4-yloxy)-N-(5-cyanopyridin-2-yl)propanamide

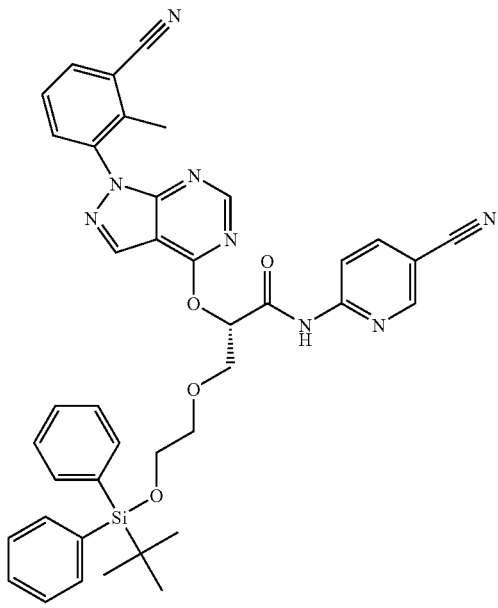

Sodium hydride (60% in oil) (87 mg, 2.17 mmol) was added to (S)-3-(2-(tert-butyldiphenylsilyloxy)ethoxy)-N-(5-cyanopyridin-2-yl)-2-hydroxypropanamide (Intermediate AU1) (484 mg, 0.99 mmol) in anhydrous THF (25 ml) at 0° C. under nitrogen. The resulting solution was stirred at 0° C. for 10 minutes and then 3-(4-chloro-1H-pyrazolo[3,4-d]pyrimidin-1-yl)-2-methylbenzonitrile (Intermediate AT2) (267 mg, 0.99 mmol) was added. The reaction mixture was allowed to warm to room temperature and stirred for 4 hours. The reaction mixture was neutralised with 1M citric acid and diluted with water and EtOAc. The organic layer was separated and the aqueous layer re-extracted with EtOAc. The combined organics were washed with saturated brine, dried (MgSO$_4$) and evaporated. The crude product was purified by flash silica chromatography, eluting with 0 to 50% EtOAc in isohexane to afford the product (251 mg, 35.1%). m/z (ES+) (M+H)$^+$= 723.67; HPLC t$_R$=3.75 min.

Intermediate AT2: 3-(4-chloro-1H-pyrazolo[3,4-d]pyrimidin-1-yl)-2-methylbenzonitrile

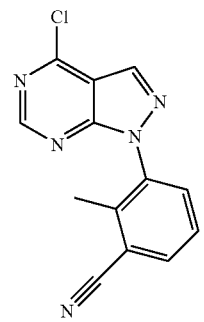

Phosphoryl trichloride (9.92 ml, 103.49 mmol) was added to 3-(4-hydroxy-1H-pyrazolo[3,4-d]pyrimidin-1-yl)-2-methylbenzonitrile (Intermediate AT3) (1.3 g, 5.17 mmol). The resulting solution was stirred at 100° C. for 2 hours. The reaction mixture was evaporated (azeotroping with toluene × 3) giving a brown oil which was triturated with ice/water to give afford the product (1.200 g) which was used without further purification.
$^1$H NMR (400 MHz, DMSO) δ 2.28 (3H, s), 7.65 (1H, t), 7.86 (1H, d), 8.06 (1H, d), 8.81 (1H, s), 8.90 (1H, s)

Intermediate AT3: 3-(4-hydroxy-1H-pyrazolo[3,4-d]pyrimidin-1-yl)-2-methylbenzonitrile

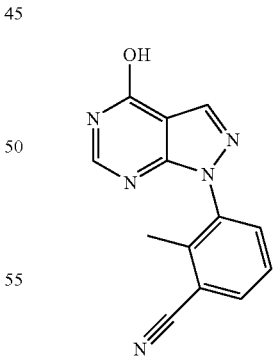

1-(3-bromo-2-methylphenyl)-1H-pyrazolo[3,4-d]pyrimidin-4-ol (Intermediate AT4) (2 g, 6.55 mmol) and Zinc cyanide (0.693 g, 5.90 mmol) were dissolved in DMF (30 mL) and sealed into a microwave tube. The tube was purged with nitrogen. 9,9-Dimethyl-4,5-bis(diphenylphosphino) xanthene (0.379 g, 0.66 mmol) and tris(dibenzylideneacetone)dipalladium(0) (0.300 g, 0.33 mmol) added. The reaction was heated to 160° C. for 10 minutes in the microwave reactor and cooled to RT. The reaction mixture was filtered and the solid washed with DMF (until the filtrate was colourless) to afford the product (1.340 g, 81%) which was used without further purification. ¹H NMR (400 MHz, DMSO) δ 2.19 (3H, s), 7.54 (1H, t), 7.71 (1H, d), 7.94 (1H, d), 8.02 (1H, s), 8.30 (1H, s), 12.32 (1H, s)

Intermediate AT4: 1-(3-bromo-2-methylphenyl)-1H-pyrazolo[3,4-d]pyrimidin-4(7H)-one

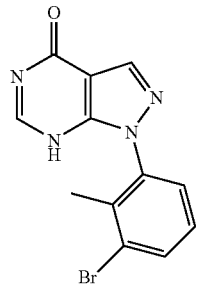

Concentrated sulfuric acid (2.67 mL, 50.01 mmol) was added to a stirred solution of 5-amino-1-(3-bromo-2-methylphenyl)-1H-pyrazole-4-carbonitrile (Intermediate AT5) (12.6 g, 45.47 mmol) in formic acid (80 mL). The resulting solution was stirred at 100° C. for 18 hours. The reaction was allowed to cool to room temperature and evaporated to ~half volume, water (100 mL) added and stirred for 2 hours. The formed ppt was filtered off, washed well with water and dried overnight in a vacuum over $P_2O_5$. The resulting solid was then slurried in DCM (100 mL), filtered and dried to afford the product (9.30 g, 67.0%) which was used without further purification. ¹H NMR (400 MHz, DMSO) δ 2.06 (3H, s), 7.34 (1H, t), 7.43 (1H, d), 7.82 (1H, d), 8.06 (1H, d), 8.33 (1H, s), 12.34 (1H, s); m/z (ES−) (M−H)−=303.26, 305.21; HPLC $t_R$=1.72 min.

Intermediate AT5: 5-amino-1-(3-bromo-2-methylphenyl)-1H-pyrazole-4-carbonitrile

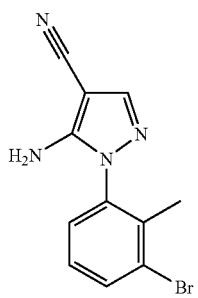

(3-Bromo-2-methylphenyl)hydrazine (CAS no. 459817-67-5) (10 g, 49.74 mmol) was suspended in MeOH (100 mL) under nitrogen at 0° C. 2-(Ethoxymethylene)malononitrile (6.07 g, 49.74 mmol) added portionwise over 5 mins and the mixture stirred at ~0° C. for 2 hours. The reaction mixture was allowed to warm to room temperature and then heated at reflux under nitrogen for 2 hours. No reaction. The starting material was NMRed and found to be a salt, so N-ethyl-N-isopropylpropan-2-amine (17.33 mL, 99.47 mmol) was added and stirred for a further 16 hours. The reaction mixture was evaporated to dryness and redissolved in EtOAc, and washed sequentially with water ×2 and saturated brine. The organic layer was dried (MgSO₄), filtered and evaporated to afford crude product, 5-amino-1-(3-bromo-2-methylphenyl)-1H-pyrazole-4-carbonitrile (12.60 g, 91%). m/z (ES+) (M+H)⁺=279.25; HPLC $t_R$=1.95 min.

Intermediate AT6: (2S)-3-(2-(tert-butyldiphenylsilyloxy)ethoxy)-2-(1-(3-cyano-2-methylphenyl)-1H-pyrazolo[3,4-d]pyrimidin-4-yloxy)-N-(5-methylpyridin-2-yl)propanamide

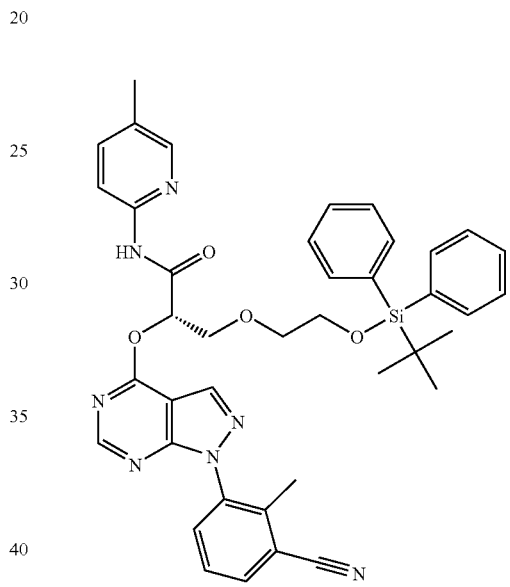

Sodium hydride (60% in oil) (92 mg, 2.30 mmol) was added to (S)-3-(2-(tert-butyldiphenylsilyloxy)ethoxy)-2-hydroxy-N-(5-methylpyridin-2-yl)propanamide (Intermediate AU2) (500 mg, 1.04 mmol) in anhydrous THF (25 ml) at 0° C. under nitrogen. The resulting solution was stirred at 0° C. for 10 minutes and then 3-(4-chloro-1H-pyrazolo[3,4-d]pyrimidin-1-yl)-2-methylbenzonitrile (Intermediate AT2) (282 mg, 1.04 mmol) was added. The reaction mixture was allowed to warm to room temperature and stirred for 4 hours. The reaction mixture was neutralised with 1M citric acid and diluted with water and EtOAc. The organic layer was separated and the aqueous layer re-extracted with EtOAc. The combined organics were washed with saturated brine, dried (MgSO₄) and evaporated. The crude product was purified by flash silica chromatography, eluting with 0 to 50% EtOAc in isohexane. No separation was achieved. The column was repeated with a 0-10% MeOH/DCM gradient. Still no separation! Mixed fractions were evaporated to dryness to afford (2S)-3-(2-(tert-butyldiphenylsilyloxy)ethoxy)-2-(1-(3-cyano-2-methylphenyl)-1H-pyrazolo[3,4-d]pyrimidin-4-yloxy)-N-(5-methylpyridin-2-yl)propanamide (313 mg, 42.1%). m/z (ES+) (M+H)⁺=712.63; HPLC $t_R$=3.85 min.

Intermediate AT7: (2S)-3-(2-(tert-butyldiphenylsily-loxy)ethoxy)-N-(5-chloropyridin-2-yl)-2-(1-(3-cy-ano-2-methylphenyl)-1H-pyrazolo[3,4-d]pyrimidin-4-yloxy)propanamide

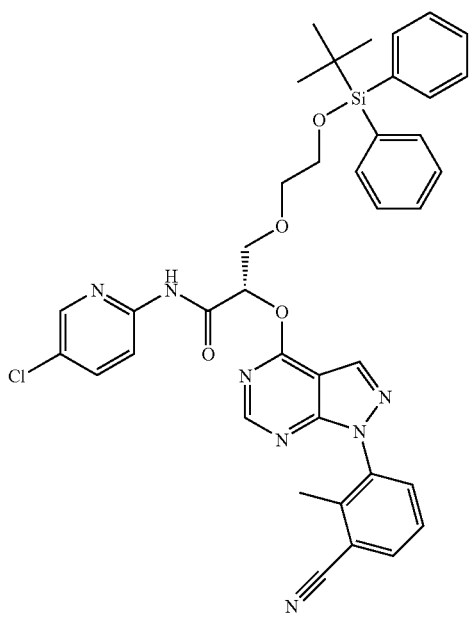

Trimethylaluminium (2M in toluene) (1.850 mL, 3.70 mmol) was added to 5-chloropyridin-2-amine (260 mg, 2.02 mmol) in toluene (8 mL) cooled to 0° C. under nitrogen. The resulting solution was stirred at 0° C. for 15 minutes. (S)-3-(2-(tert-Butyldiphenylsilyloxy)ethoxy)-N-(5-chloropyridin-2-yl)-2-hydroxypropanamide (Intermediate AU3) in toluene (2 mL) was added and the reaction was allowed to warm to room temperature and then heated at reflux for 18 hours. The reaction mixture was allowed to cool and concentrated in vacuo. The residue was neutralised with citric acid (1M, aq) and then diluted with water and extracted with EtOAc ×2. The combined organics were washed with brine, dried (MgSO$_4$) and evaporated to afford the product (860 mg) which was used without further purification. m/z (ES+) (M+H)$^+$=732.66; HPLC t$_R$=3.89 min.

Intermediate AU1: (S)-3-(2-(tert-butyldiphenylsily-loxy)ethoxy)-N-(5-cyanopyridin-2-yl)-2-hydrox-ypropanamide

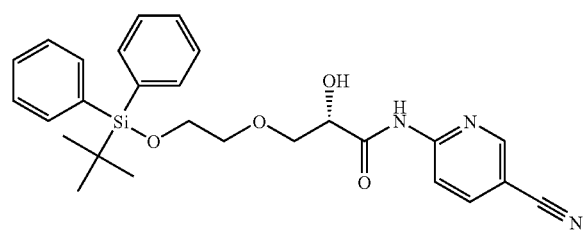

Trimethylaluminium (2M in toluene) (6.21 mL, 12.42 mmol) was added to 6-aminonicotinonitrile (1.480 g, 12.42 mmol) in toluene (80 mL) at 0° C. under nitrogen. The resulting solution was stirred at 0° C. for 15 minutes. (S)-Methyl 3-(2-(tert-butyldiphenylsilyloxy)ethoxy)-2-hydroxypro-panoate (Intermediate AB3) (2.5 g, 6.21 mmol) in toluene (20 mL) was added. The reaction was heated to 110° C. for 2 hours and cooled to RT. The reaction mixture was concentrated. The residue was neutralised with citric acid (1M, aq) and then diluted with water and extracted with EtOAc. The combined organics were dried (MgSO$_4$) and evaporated. The crude product was purified by flash silica chromatography, elution gradient 20 to 50% EtOAc in isohexane to afford the product (1.780 g, 58.5%). $^1$H NMR (400 MHz, CDCl$_3$) δ 1.04 (9H, s), 3.65-3.69 (3H, m), 3.81-3.91 (4H, m), 4.35 (1H, q), 7.35-7.45 (6H, m), 7.65-7.67 (4H, m), 7.92-7.95 (1H, m), 8.36-8.38 (1H, m), 8.55-8.56 (1H, m), 9.40 (1H, s); m/z (ES+) (M+H)$^+$=490; HPLC t$_R$=3.07 min.

Intermediate AU2: (S)-3-(2-(tert-butyldiphenylsily-loxy)ethoxy)-2-hydroxy-N-(5-methylpyridin-2-yl)propanamide

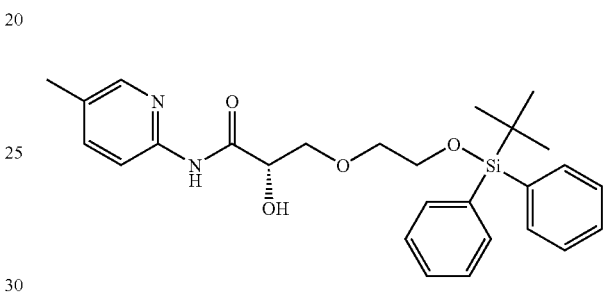

Trimethylaluminium (2M in toluene) (4.97 mL, 9.94 mmol) was added carefully to 5-methylpyridin-2-amine (1.075 g, 9.94 mmol) in toluene (20 mL) at 0° C. under nitrogen. The resulting solution was stirred at 0° C. for 15 minutes. (S)-methyl 3-(2-(tert-butyldiphenylsilyloxy)ethoxy)-2-hydroxypropanoate (Intermediate AB3) (2 g, 4.97 mmol) in toluene (4 mL) was added. The reaction was heated to 120° C. for 1 hour in the microwave reactor and cooled to RT. The reaction mixture was concentrated. The residue was neutralised with citric acid (1M, aq) and then diluted with water and extracted with EtOAc. The combined organics were dried (MgSO$_4$) and evaporated. The crude product was purified by flash silica chromatography, elution gradient 0 to 50% EtOAc in isohexane to afford the product (1.800 g, 76%). $^1$H NMR (400 MHz, CDCl$_3$) δ 1.04 (9H, s), 2.29 (3H, s), 3.65 (2H, t), 3.76-3.90 (5H, m), 4.31-4.37 (1H, m), 7.34-7.45 (6H, m), 7.48-7.54 (1H, m), 7.64-7.71 (4H, m), 8.07-8.13 (2H, m), 9.13 (1H, s); m/z (ES+) (M+H)$^+$=479.60; HPLC t$_R$=3.16 min.

Intermediate AU3: (S)-3-(2-(tert-Butyldiphenylsily-loxy)ethoxy)-N-(5-chloropyridin-2-yl)-2-hydrox-ypropanamide

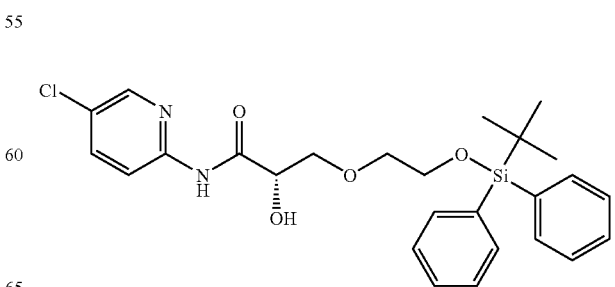

Trimethylaluminium (2M in toluene) (4.97 mL, 9.94 mmol) was added carefully to 5-chloropyridin-2-amine (1.277 g, 9.94 mmol) in toluene (10 mL) at 0° C. under nitrogen. The resulting solution was stirred at 0° C. for 15 minutes. (S)-Methyl 3-(2-(tert-butyldiphenylsilyloxy) ethoxy)-2-hydroxypropanoate (Intermediate AB3) (2 g, 4.97 mmol) in toluene (2 mL) was added. The reaction was heated to 120° C. for 2 hours in the microwave reactor. The reaction mixture was allowed to cool. The residue was neutralised with citric acid (1M, aq) and then diluted with water and extracted with EtOAc. The combined organics were dried (MgSO$_4$) and evaporated. The crude product was purified by flash silica chromatography, elution gradient 0 to 50% EtOAc in isohexane to afford the product (1.52 g, 61.3%). $^1$H NMR (400 MHz, CDCl$_3$) δ 1.04 (9H, s), 3.63-3.68 (3H, m), 3.79-3.83 (2H, m), 3.85 (2H, d), 4.33 (1H, q), 7.34-7.46 (6H, m), 7.63-7.69 (5H, m), 8.18-8.25 (2H, m), 9.19 (1H, s); m/z (ES+) (M+H)$^+$=499.55; HPLC $t_R$=3.43 min.

Intermediate AU4: (S)-2-hydroxy-N-(5-methylpyridin-2-yl)-3-((R)-1-(triisopropylsilyloxy)propan-2-yloxy)propanamide

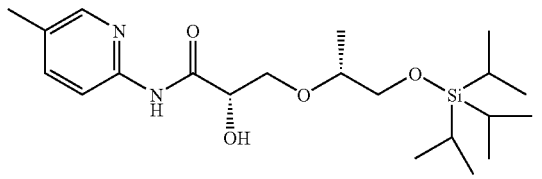

Trimethylaluminium (2M in toluene) (8.97 ml, 17.94 mmol) was added to 5-methylpyridin-2-amine (1.940 g, 17.94 mmol) in toluene (70 ml) cooled to 0° C. under nitrogen. The resulting solution was stirred at 0° C. for 20 minutes. (S)-methyl 2-hydroxy-3-((R)-1-(triisopropylsilyloxy)propan-2-yloxy)propanoate (Intermediate AU5) (3.0 g, 8.97 mmol) in toluene (20 ml) was added and the reaction was allowed to warm to room temperature and then heated at reflux for 5 hours. The reaction mixture was allowed to cool and concentrated in vacuo. The residue was neutralised with citric acid (1M, aq) and then diluted with water (50 mL) and extracted with EtOAc (2×100 mL). The combined organics were dried (MgSO$_4$) filtered and evaporated. The crude product was purified by flash silica chromatography, eluting with 30 to 50% EtOAc in isohexane to afford the product (2.40 g, 65.2%). $^1$H NMR (400 MHz, CDCl$_3$) δ 1.03-1.15 (24H, m), 2.29 (3H, s), 3.60-3.68 (3H, m), 3.82-3.86 (1H, m), 3.98-4.02 (1H, m), 4.14-4.15 (1H, m), 4.30-4.34 (1H, m), 7.49-7.52 (1H, m), 8.11-8.13 (2H, m), 9.14 (1H, s); m/z (ES+) (M+H)$^+$= 411.44; HPLC $t_R$=3.46 min.

Intermediate AU5: (S)-methyl 2-hydroxy-3-((R)-1-(triisopropylsilyloxy)propan-2-yloxy)propanoate

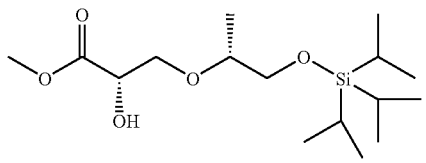

Prepared using a procedure analogous to that described for Intermediate AN1 using (R)-1-(triisopropylsilyloxy)propan-2-ol (CAS no. 871657-72-6). $^1$H NMR (400 MHz, CDCl$_3$) δ 1.04-1.16 (24H, m), 3.39 (1H, d), 3.54-3.59 (2H, m), 3.67-3.72 (1H, m), 3.78 (3H, s), 3.80-3.91 (2H, m), 4.27-4.31 (1H, m).

Intermediate AU5: (R)-methyl 2-hydroxy-3-((S)-1-(triisopropylsilyloxy)propan-2-yloxy)propanoate
Alternative Procedure Magnesium trifluoromethanesulfonate (1.263 g, 3.92 mmol) was added to a mixture of (S)-1-(triisopropylsilyloxy) propan-2-ol (4.55 g, 19.59 mmol) and (R)-methyl oxirane-2-carboxylate (2 g, 19.59 mmol) in ethyl acetate (40 mL). The resulting suspension was heated to 80° C. for 72 hours. Further (R)-methyl oxirane-2-carboxylate (2 g, 19.59 mmol) was added and the mixture stirred at 80° C. for 48 hrs. Further (R)-methyl oxirane-2-carboxylate (2 g, 19.59 mmol) was added and the mixture stirred for 24hrs. The mixture was allowed to cool, filtered through a bed of silica (~10 g), washed through with EtOAc and evaporated. The crude product was purified by flash silica chromatography, elution gradient 10 to 50% EtOAc in isohexane, to afford the product (2.7 g, 41%).

Intermediate AV1: 1-(1-methyl-1H-imidazol-2-yl)-4-phenoxy-1H-pyrazolo[3,4-d]pyrimidine

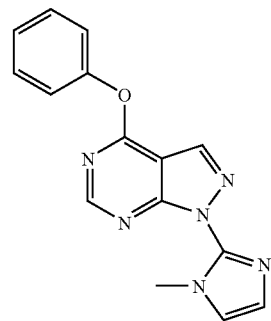

2-Hydrazinyl-1-methyl-1H-imidazole hydrochloride (Intermediate AV2) (305 mg, 2.05 mmol) was added to 4,6-diphenoxypyrimidine-5-carbaldehyde (Intermediate Z2) (600 mg, 2.05 mmol) in THF (15 mL) the resulting solution was stirred at room temperature for 5 minutes. 2-tert-Butylimino-2-diethylamino-1,3-dimethyl-perhydro-1,3,2-diazaphosphorine on polystyrene (2.8 g, 6.2 mmol) was added and sealed into a microwave tube. The reaction was heated to 120° C. for 10 hours in the microwave reactor and cooled to RT. The reaction mixture was filtered and evaporated to dryness. The crude product was purified by flash silica chromatography eluting with 0 to 5% MeOH in DCM to afford the product (190 mg, 32%). $^1$H NMR (400 MHz, CDCl$_3$) δ 3.59 (3H, s), 6.95 (1H, d), 7.11 (1H, d), 7.24-7.20 (2H, m), 7.32-7.26 (1H, m), 7.44 (2H, m), 8.03 (1H, s), 8.59 (1H, s); m/z (ES$^+$) (M+H)$^+$=293; HPLC $t_R$=1.65 min.

Intermediate AV2:
2-Hydrazinyl-1-methyl-1H-imidazole hydrochloride

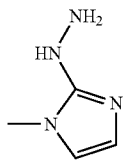

4 M Hydrogen chloride in dioxane (50 mL, 200.00 mmol) was added to di-tert-butyl 1-(1-methyl-1H-imidazol-2-yl)hydrazine-1,2-dicarboxylate (Intermediate AV3) (5.9 g, 18.89 mmol) in ethyl acetate (50 mL) at 22° C. The resulting solution was stirred at 22° C. for 20 hours. The reaction mixture was evaporated to dryness to afford the product (2.80 g) which was used without purification. 1H NMR (400 MHz, DMSO) δ 3.38 (3H, s), 6.90 (1H, d), 6.96 (1H, d).

Intermediate AV3: di-tert-Butyl 1-(1-methyl-1H-imidazol-2-yl)hydrazine-1,2-dicarboxylate

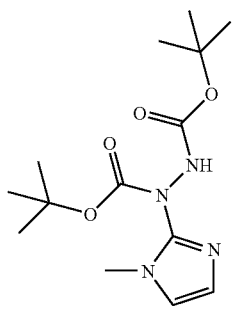

n-Butyllithium (1.6M in hexane, 20.76 mL, 33.22 mmol) was added dropwise to 1-methyl-1H-imidazole (CAS no. 616-47-7) (3 g, 36.54 mmol), in THF (10 mL) cooled to −70° C. over a period of 10 minutes under nitrogen. The resulting solution was stirred at −70° C. for 10 minutes. di-tert-Butyl diazene-1,2-dicarboxylate (CAS no. 870-50-8) (7.65 g, 33.22 mmol) in THF (6 ml) added dropwise over 10 minutes, not allowing the solution to rise above −65° C. After the addition was complete the solution was allowed to warm to ambient temperature overnight. Water (20 mL) added at RT. The THF was removed under vacuum. Extracted with EtOAc (2×40 mL). The organic extracts were combined, washed with brine (15 mL), dried over MgSO4 and reduced to give crude product. The crude product was purified by flash silica chromatography eluting with 20 to 100% EtOAc in isohexane to afford the product (6.17 g, 59.5%). m/z (ESI+) (M+H)$^+$=313; HPLC $t_R$=1.36 min.

Intermediate AW1: (2S)-5-(tert-butyldimethylsilyloxy)-N-(5-chloropyridin-2-yl)-2-(1-(3-chloropyridin-2-yl)-1H-pyrazolo[3,4-d]pyrimidin-4-yloxy)pentanamide

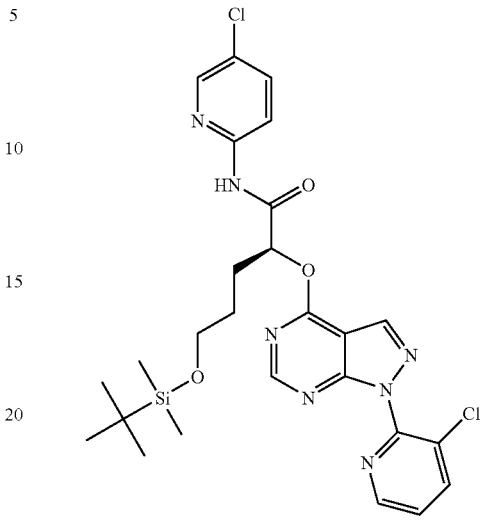

A solution of trimethylaluminium (2M in toluene) (0.795 mL, 1.59 mmol) was added dropwise to a stirred solution of 5-chloropyridin-2-amine (178 mg, 1.38 mmol) in toluene (5 mL) cooled to 0° C. under nitrogen. The resulting solution was stirred at 0° C. for 15 minutes. A solution of (2S)-methyl 5-(tert-butyldimethylsilyloxy)-2-(1-(3-chloropyridin-2-yl)-1H-pyrazolo[3,4-d]pyrimidin-4-yloxy)pentanoate (Intermediate O2) (680 mg, 1.38 mmol) in toluene (5 mL) was added dropwise. The resulting solution was stirred at 0° C. for 10 minutes allowed to warm to ambient temperature and then heated at reflux for 18 hours. The reaction mixture was allowed to cool to r.t. and concentrated. The residue was diluted with ethyl acetate and treated with 1M citric acid (2ml). The layers were separated and the organics were washed with water and brine, dried (MgSO4) and concentrated to a yellow foam, (2S)-5-(tert-butyldimethylsilyloxy)-N-(5-chloropyridin-2-yl)-2-(1-(3-chloropyridin-2-yl)-1H-pyrazolo[3,4-d]pyrimidin-4-yloxy)pentanamide (693 mg, 85%). m/z (ES+) (M+H)$^+$=588.46; HPLC $t_R$=3.54 min.

Intermediate AW2: (2S)-5-(tert-butyldimethylsilyloxy)-2-(1-(3-chloropyridin-2-yl)-1H-pyrazolo[3,4-d]pyrimidin-4-yloxy)-N-(5-cyanopyridin-2-yl)pentanamide

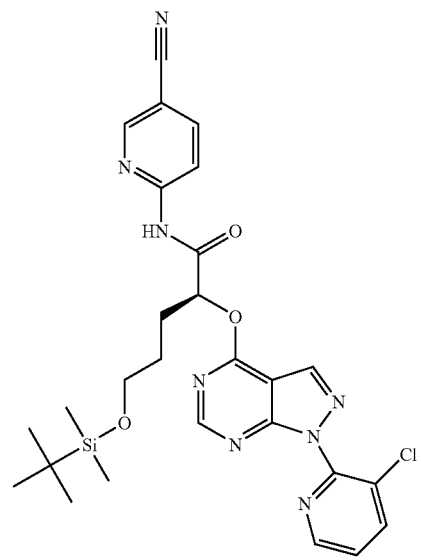

A solution of trimethylaluminium (2M in toluene) (0.795 mL, 1.59 mmol) was added dropwise to a stirred solution of 6-aminonicotinonitrile (165 mg, 1.38 mmol) in toluene (5 mL) cooled to 0° C., over a period of 1 minute under nitrogen. The resulting solution was stirred at 0° C. for 20 minutes. A solution of (2S)-methyl 5-(tert-butyldimethylsilyloxy)-2-(1-(3-chloropyridin-2-yl)-1H-pyrazolo[3,4-d]pyrimidin-4-yloxy)pentanoate (Intermediate O2) (680 mg, 1.38 mmol) in toluene (5 mL) was added dropwise. The resulting solution was stirred at 0° C. for 10 minutes allowed to warm to ambient temperature and then heated at reflux for 18 hours. The reaction mixture was allowed to cool to r.t. and concentrated. The residue was diluted with ethyl acetate and treated with 1M citric acid (2 ml). The layers were separated and the organics were washed with water and brine, dried ($MgSO_4$) and evaporated to afford the product (797 mg) which was used without further purification. m/z (ES−) (M−H)−=577.45; HPLC $t_R$=3.29 min.

Intermediate AX1: (2S)-3-(3-(tert-butyldimethylsilyloxy)azetidin-1-yl)-2-(1-(2-chlorophenyl)-1H-pyrazolo[3,4-d]pyrimidin-4-yloxy)-N-(5-fluoropyridin-2-yl)propanamide

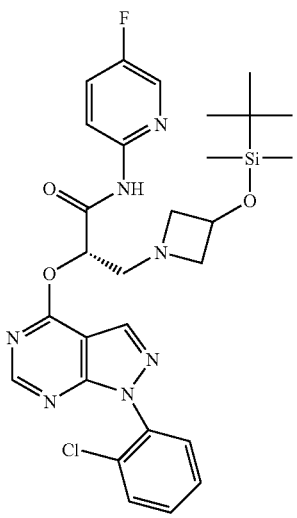

Sodium hydride (60% dispersion in mineral oil) (0.682 g, 17.05 mmol) was added to (S)-3-(3-(tert-butyldimethylsilyloxy)azetidin-1-yl)-N-(5-fluoropyridin-2-yl)-2-hydroxypropanamide (Intermediate AX2) (3.0 g, 8.12 mmol) in anhydrous THF (80 mL) at 0° C. under nitrogen. The resulting solution was stirred at 0° C. for 10 minutes and then 4-chloro-1-(2-chlorophenyl)-1H-pyrazolo[3,4-d]pyrimidine (Intermediate B1) (2.63 g, 8.93 mmol) was added. The reaction mixture was allowed to warm to room temperature and stirred for 3 hours. The reaction mixture was neutralised with 1M citric acid and then diluted with water (50 mL) and EtOAc (100 mL). The organic layer was separated and the aqueous layer re-extracted with EtOAc (100 mL). The combined organics were washed with saturated brine (75 mL), dried ($MgSO_4$), filtered and concentrated in vacuo. The crude product was purified by flash silica chromatography, elution gradient 30 to 70% EtOAc in isohexane to afford the product (4.29 g, 88%). $^1$H NMR (400 MHz, $CDCl_3$) δ 0.04 (6H, s), 0.88 (9H, s), 3.06-3.10 (2H, m), 3.15-3.19 (1H, m), 3.27-3.31 (1H, m), 3.87-3.90 (2H, m), 4.41-4.48 (1H, m), 5.89-5.92 (1H, m), 7.40-7.55 (4H, m), 7.61-7.63 (1H, m), 8.15 (1H, d), 8.22-8.26 (1H, m), 8.36 (1H, s), 8.59 (1H, s), 9.82 (1H, s); m/z (ES$^+$) (M+H)$^+$=598; HPLC $t_R$=2.82 min.

Intermediate AX2: (S)-3-(3-(tert-butyldimethylsilyloxy)azetidin-1-yl)-N-(5-fluoropyridin-2-yl)-2-hydroxypropanamide

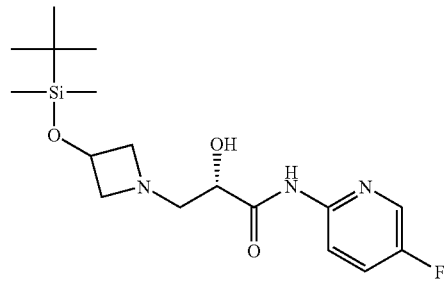

Trimethylaluminium (2M solution in toluene) (15.89 mL, 31.79 mmol) was added to 5-fluoropyridin-2-amine (3.10 g, 27.64 mmol) in toluene (80 mL) cooled to 0° C. under nitrogen over a period of 10 minutes. The resulting solution was stirred at 0° C. for 10 minutes. (S)-methyl 3-(3-(tert-butyldimethylsilyloxy)azetidin-1-yl)-2-hydroxypropanoate (Intermediate AD3) (8 g, 27.64 mmol) in toluene (20 mL) was added over 10 minutes and the reaction was allowed to warm to room temperature and then heated at 90° C. for 2 hours. The reaction mixture was cooled and poured into a 20% solution of Rochelle's salt (50 mL), diluted with ethyl acetate (200 mL) and stirred for 2 hours. The organic phase was separated, washed with water and brine, dried ($MgSO_4$) filtered and evaporated. The crude product was purified by flash silica chromatography, elution gradient 80 to 100% EtOAc in isohexane to afford the product (5.28 g, 51.7%). $^1$H NMR (400 MHz, $CDCl_3$) δ 0.028 (3H, s), 0.033 (3H, s), 0.87 (9H, s), 2.90 (2H, d), 3.02-3.08 (2H, m), 3.68-3.74 (2H, m), 4.00 (1H, t), 4.41-4.48 (1H, m), 7.41-7.45 (1H, m), 8.15 (1H, d), 8.21-8.24 (1H, m), 9.85 (1H, s); m/z (ES$^+$) (M+H)$^+$=370; HPLC $t_R$=1.97 min.

Intermediate AY1: (2S)-2-(1-(2-chloro-6-cyanophenyl)-1H-pyrazolo[3,4-d]pyrimidin-4-yloxy)-N-(5-chloropyridin-2-yl)-3-((R)-1-(triisopropylsilyloxy)propan-2-yloxy)propanamide

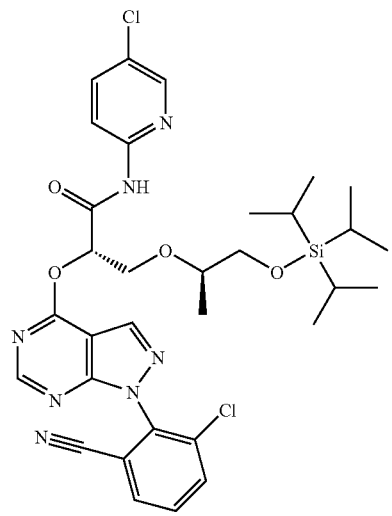

Sodium hydride (60% dispersion in mineral oil) (93 mg, 2.32 mmol) was added to (S)—N-(5-chloropyridin-2-yl)-2-hydroxy-3-((R)-1-(triisopropylsilyloxy)propan-2-yloxy)propanamide (Intermediate AY2) (500 mg, 1.16 mmol) in anhydrous THF (25 mL) at 0° C. under nitrogen. The resulting solution was stirred at 0° C. for 10 minutes and then 3-chloro-2-(4-chloro-1H-pyrazolo[3,4-d]pyrimidin-1-yl)benzonitrile (Intermediate AH6) (370 mg, 1.28 mmol) was added. The reaction mixture was allowed to warm to room temperature and stirred overnight. The reaction mixture was adjusted to pH 7 by addition of 1M citric acid and then diluted with water (20 mL) and EtOAc (50 mL). The organic layer was separated and the aqueous layer re-extracted with EtOAc (2×50 mL). The combined organics were washed with saturated brine (75 mL), dried (MgSO$_4$), filtered and concentrated in vacuo. The crude product was purified by flash silica chromatography, elution gradient 50 to 100% EtOAc in isohexane to afford the product (626 mg, 79%). $^1$H NMR (400 MHz, CDCl$_3$) δ 0.98-1.09 (21H, m), 1.13-1.17 (3H, m), 3.60-3.77 (3H, m), 4.20-4.33 (2H, m), 5.99-6.03 (1H, m), 7.60-7.70 (2H, m), 7.78-7.81 (1H, m), 7.85-5 7.87 (1H, m), 8.22-8.25 (2H, m), 8.50 (1H, d), 8.60 (1H, d), 8.82 (1H, s); m/z (ES$^-$) (M−H)$^-$=682; HPLC $t_R$=4.04 min.

Intermediate AY2: (S)—N-(5-chloropyridin-2-yl)-2-hydroxy-3-((R)-1-(triisopropylsilyloxy)propan-2-yloxy)propanamide

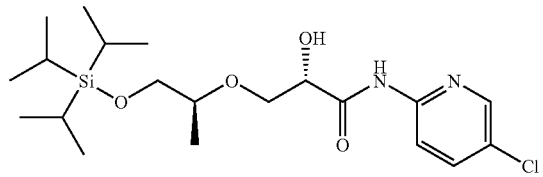

Trimethylaluminium (2M solution in toluene) (2.99 mL, 5.98 mmol) was added to a solution of 5-chloropyridin-2-amine (0.769 g, 5.98 mmol) in toluene (20 mL) at 0° C. under nitrogen. The reaction mixture was stirred at 0° C. for 20 mins and then (S)-methyl 2-hydroxy-3-((R)-1-(triisopropylsilyloxy)propan-2-yloxy)propanoate (Intermediate AU5) (1 g, 2.99 mmol) was added. The reaction mixture was allowed to warm to room temperature and then heated at reflux under nitrogen for 4 hours. The reaction mixture was allowed to cool to room temperature and the concentrated in vacuo. The residue was neutralised with citric acid (1M, aq.) and then diluted with water and DCM (50 mL). The organic layer was separated and the aqueous layer re-extracted with DCM (30 mL). The combined organics were dried (MgSO$_4$), filtered and evaporated in vacuo. The crude product was purified by flash silica chromatography, elution gradient 20 to 50% EtOAc in isohexane to afford the product (0.935 g, 72.6%). $^1$H NMR (400 MHz, CDCl$_3$) δ 1.05-1.13 (24H, m), 3.62-3.67 (3H, m), 3.81-3.84 (1H, m), 4.02-4.06 (1H, m), 4.20 (1H, d), 4.31 (1H, q), 7.65-7.67 (1H, m), 8.22-8.25 (2H, m), 9.23 (1H, s); m/z (ES$^-$) (M−H)$^-$=429; HPLC $t_R$=3.81 min.

Intermediate AZ1: (2S)-2-(1-(2-chloro-6-cyanophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide

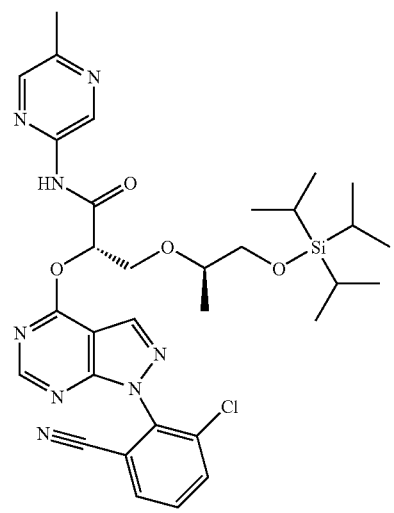

Sodium hydride (60% dispersion in mineral oil) (0.116 g, 2.89 mmol) was added to (S)-2-hydroxy-5-methylpyrazin-2-yl)-3-((R)-1-(triisopropylsilyloxy)propan-2-yloxy)propanamide (Intermediate AZ2) (0.595 g, 1.45 mmol) in anhydrous THF (20 mL) at 0° C. under nitrogen. The resulting solution was stirred at 0° C. for 10 minutes and then 3-chloro-2-(4-chloro-1H-pyrazolo[3,4-d]pyrimidin-1-yl)benzonitrile (Intermediate AH6) (0.438 g, 1.31 mmol) was added. The reaction mixture was allowed to warm to room temperature and stirred for 1 hour. The reaction mixture was adjusted to pH 7 by addition of 1M citric acid and the majority of the THF removed in vacuo. The reaction mixture was diluted with water (20 mL) and EtOAc (50 mL). The organic layer was separated and the aqueous layer re-extracted with EtOAc (2×100 mL). The combined organics were washed with saturated brine (75 mL), dried (MgSO$_4$) and evaporated. The crude product was purified by flash silica chromatography, eluting with 50 to 100% EtOAc in isohexane to afford the product (0.590 g, 67.5%). $^1$H NMR (400 MHz, CDCl$_3$) δ 0.98-1.08 (21H, m), 1.12-1.17 (3H, m), 2.54 (3H, s), 3.59-3.78 (3H, m), 4.21-4.26 (1H, m), 4.29-4.36 (1H, m), 6.02-6.06 (1H, m), 7.60-7.65 (1H, m), 7.78-7.81 (1H, m), 7.85-7.87 (1H, m), 8.11-8.13 (1H, m), 8.50 (1H, d), 8.61 (1H, d), 8.71 (1H, d), 9.44 (1H, t); m/z (ES$^+$) M$^+$=665.26; HPLC $t_R$=4.02 min.

Intermediate AZ1: (2S)-2-[1-(2-chloro-6-cyanophenyl)pyrazolo[4,5-e]pyrimidin-4-yl]oxy-N-(5-methylpyrazin-2-yl)-3-[(2R)-1-tri(propan-2-yl)silyloxypropan-2-yl]oxypropanamide. Alternative preparation.

Intermediate AZ2: (S)-2-hydroxy-N-(5-methylpyrazin-2-yl)-3-((R)-1-(triisopropylsilyloxy)propan-2-yloxy)propanamide

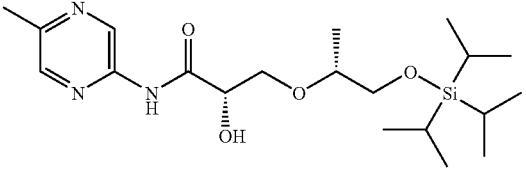

Trimethylaluminium (2M solution in toluene) (5.98 mL, 11.96 mmol) was added to 5-methylpyrazin-2-amine (1.305 g, 11.96 mmol) in toluene (20 mL) cooled to 0° C. under nitrogen. The resulting solution was stirred at 0° C. for 20 minutes. (R)-methyl 2-hydroxy-3-((S)-1-(triisopropylsilyloxy)propan-2-yloxy)propanoate (Intermediate AU5) (2 g, 5.98 mmol) in toluene (6 mL) was added and the reaction was allowed to warm to room temperature and then refluxed for 6 hours. The reaction mixture was allowed to cool and concentrated in vacuo. The residue was neutralised with citric acid (1M, aq.) and then diluted with water (25 mL) and extracted with EtOAc (2×50 mL). The combined organics were washed with brine (20 mL), then dried (MgSO$_4$) and evaporated. The crude product was purified by flash silica chromatography, eluting with 30 to 50% EtOAc in isohexane to afford the product (1.390 g, 56.5%). $^1$H NMR (400 MHz, CDCl$_3$) δ 1.04-1.17 (24H, m), 2.54 (3H, s), 3.62-3.67 (3H, m), 3.81-3.85 (1H, m), 4.05-4.09 (1H, m), 4.22 (1H, d), 4.34 (1H, q), 8.13 (1H, d), 9.12 (1H, s), 9.44 (1H, d); m/z (ES$^+$) (M+H)$^+$ 412.34; HPLC t$_R$=3.82 min.

Intermediate AZ2: (S)-2-hydroxy-N-(5-methylpyrazin-2-yl)-3-((R)-1-(triisopropylsilyloxy)propan-2-yloxy)propanamide. Alternative preparation.

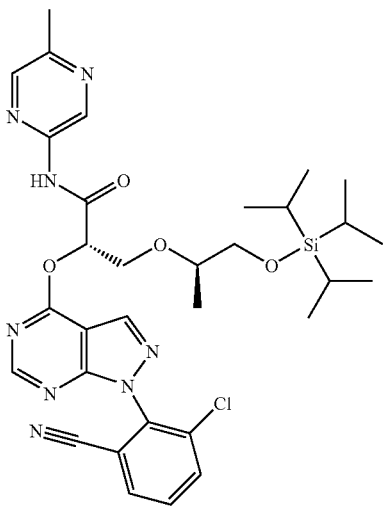

Tris(dibenzylideneacetone)dipalladium(0) (0.261 g, 0.29 mmol) was added in one portion to a de-gassed mixture of (2S)-2-(1-(2-bromo-6-chlorophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide (Intermediate BO1) (4.1 g, 5.70 mmol), zinc cyanide (0.335 g, 2.85 mmol) and 9,9-dimethyl-4,5-bis(diphenylphosphino)xanthene (0.330 g, 0.57 mmol) in N-methylpyrrolidone (41 mL) at 20° C. under nitrogen. The resulting suspension was degassed under vacuum with inlet of nitrogen four times and then heated to 110° C. (internal temperature) for 1 hour. The mixture was cooled, poured into water (100 mL) and extracted with ethyl acetate (2×50 mL). The organic layers were combined and washed with water (4×50 mL) and brine (50 mL), dried over MgSO$_4$, filtered and evaporated. The crude product was purified by flash silica chromatography, elution gradient 30 to 100% EtOAc in isohexane to afford the product (3.0 g, 79%).

1H NMR (400.13 MHz, DMSO-d$_6$) δ 0.90-1.08 (21H, m), 1.09-1.11 (3H, m), 2.45 (3H, s), 3.53-3.58 (1H, m), 3.60-3.66 (1H, m), 3.75-3.78 (1H, m), 4.10-4.15 (2H, m), 5.94-5.99 (1H, m), 7.87-7.91 (1H, m), 8.16-8.19 (2H, m), 8.31-8.33 (1H, m), 8.60-8.61 (1H, m), 8.73 (1H, s), 9.10-9.12 (1H, d), 11.20 (1H, s); m/z (ES$^-$) (M−H)$^-$=663; HPLC t$_R$=3.79 min.

Trimethylaluminium (2M solution in toluene) (72.5 mL, 145 mmol) was added to 5-methylpyrazin-2-amine (13.64 g, 125.0 mmol) in toluene (520 mL) cooled to 0° C. under nitrogen. The resulting solution was stirred at 0° C. for 20 minutes. (R)-methyl 2-hydroxy-3-((S)-1-(triisopropylsilyloxy)propan-2-yloxy)propanoate (Intermediate AU5) (33.5 g, 100.0 mmol) in toluene (130 mL) was added and the reaction was allowed to warm to room temperature and then stirred at 72° C. for 2.5 hours. The reaction mixture was allowed to cool then poured into a stirred mixture of ethyl acetate (500 mL) and aqueous solution of Rochelle salt (20% w/v, 500 mL). The mixture was stirred for 15 minutes then the organics separated and washed with water (500 mL) followed by brine (500 mL), then dried (MgSO$_4$), filtered and concentrated. The residues were dissolved in iso-hexane (300 mL) and stood for 15 minutes at 20° C. before cooling to 5° C. over 30 minutes. The solid formed was isolated by filtration, washed with iso-hexane cooled to 5° C. (200 mL) and dried at 40° C. under high vacuum to afford the product (26.7 g, 64%). The filtrates were combined and concentrated to 100 mL total volume and the mixture stood for 16 hours. The solid formed was isolated by filtration, washed with iso-hexane cooled to 5° C. (100 mL), dried at 40° C. under high vacuum and combined with the initial batch to afford the product (30.1 g, 73%). $^1$H NMR (400 MHz, CDCl$_3$) δ 1.04-1.17 (24H, m), 2.54 (3H, s), 3.62-3.67 (3H, m, 3.81-3.85 (1H, m), 4.05-4.09 (1H, m), 4.22 (1H, d), 4.34 (1H, q), 8.13 (1H, d), 9.12 (1H, s), 9.44 (1H, d); m/z (ES$^+$) (M+H)$^+$=412.34; HPLC t$_R$=3.82 min.

Intermediate BA1: (S)-3-(2-(tert-butyldiphenylsilyloxy)ethoxy)-2-(1-(2,6-dichlorophenyl)-1H-pyrazolo[3,4-d]pyrimidin-4-yloxy)-N-(5-fluoropyridin-2-yl)propanamide

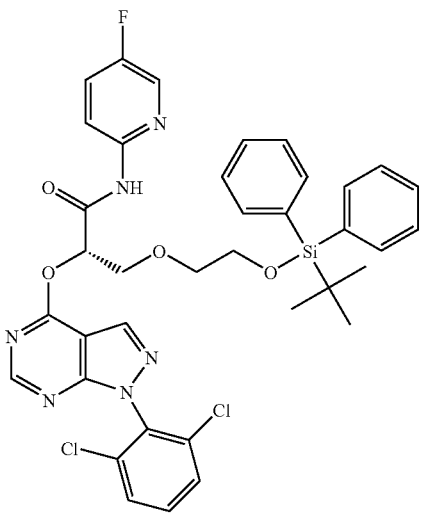

Sodium hydride (60% dispersion in mineral oil) (83 mg, 2.07 mmol) was added to (S)-3-(2-(tert-butyldiphenylsilyloxy)ethoxy)-N-(5-fluoropyridin-2-yl)-2-hydroxypropanamide (Intermediate BA2) (500 mg, 1.04 mmol) in anhydrous THF (20 mL) at 0° C. under nitrogen. The resulting solution was stirred at 0° C. for 10 minutes and then 4-chloro-1-(2,6-dichlorophenyl)-1H-pyrazolo[3,4-d]pyrimidine (Intermediate BA3) (310 mg, 1.04 mmol) was added. The reaction mixture was allowed to warm to room temperature and stirred overnight. The reaction mixture was adjusted to pH 7 by addition of 1M citric acid and the reaction mixture diluted with water (20 mL) and EtOAc (50 mL). The organic layer was separated and the aqueous layer re-extracted with EtOAc (2×50 mL). The combined organics were washed with saturated brine (75 mL), dried (MgSO$_4$), filtered and concentrated in vacuo. The crude product was purified by flash silica chromatography, elution gradient 25 to 100% EtOAc in isohexane to afford the product (637 mg, 82%). $^1$H NMR (400 MHz, CDCl$_3$) δ 0.99 (9H, t), 3.69-3.72 (2H, m), 3.82 (2H, t), 4.16-4.24 (2H, m), 6.06 (1H, t), 7.31-7.47 (8H, m), 7.52-7.55 (2H, m), 7.63-7.66 (4H, m), 8.12 (1H, d), 8.26-8.29 (1H, m), 8.42 (1H, s), 8.58 (1H, s), 8.79 (1H, s).

Intermediate BA2: (S)-3-(2-(tert-butyldiphenylsilyloxy)ethoxy)-N-(5-fluoropyridin-2-yl)-2-hydroxypropanamide

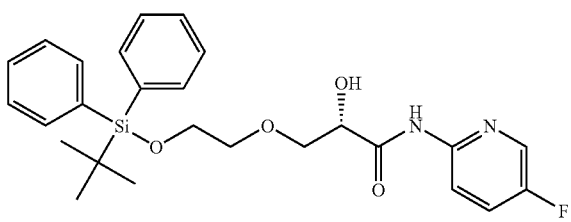

Trimethylaluminium (2M solution in toluene) (2.86 mL, 5.71 mmol) was added to 5-fluoropyridin-2-amine in toluene (8 mL) cooled to 0° C. under nitrogen. The resulting solution was stirred at 0° C. for 20 minutes. (S)-Methyl 3-(2-(tert-butyldiphenylsilyloxy)ethoxy)-2-hydroxypropanoate (Intermediate AB3) in toluene (8 mL) was added and the reaction was allowed to warm to room temperature and then heated at reflux for 24 hours. The reaction mixture was allowed to cool and concentrated in vacuo. The residue was neutralised with citric acid (1M, aq.) and then diluted with water (30 mL) and extracted with EtOAc (2×50 mL). The combined organics were dried (MgSO$_4$) and evaporated. The crude product was purified by flash silica chromatography, eluting with 30 to 50% EtOAc in isohexane to afford the product (1.32 g, 55%). $^1$H NMR (400 MHz, CDCl$_3$) δ 1.05 (s, 9H), 3.60-3.68 (m, 3H), 3.79-3.83 (m, 2H), 3.86 (d, 2H), 4.31-4.35 (m, 1H), 7.34-7.46 (m, 7H), 7.64-7.69 (m, 4H), 8.14 (d, 1H), 8.22-8.28 (m, 1H), 9.18 (s, 1H); m/z (ES$^+$), (M+H)$^+$=483.63; HPLC t$_R$=3.08 min.

Intermediate BA3: 4-chloro-1-(2,6-dichlorophenyl)-1H-pyrazolo[3,4-d]pyrimidine

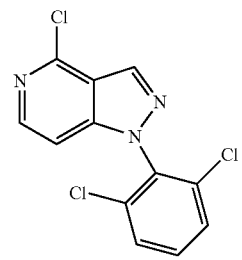

Phosphorus oxychloride (7.96 mL, 85.38 mmol) was added to 1-(2,6-dichlorophenyl)-1H-pyrazolo[3,4-d]pyrimidin-4-ol (Intermediate BA4) (1.2 g, 4.27 mmol). The resulting solution was stirred at 100° C. for 20 hours. LCMS showed reaction was complete. The reaction mixture was evaporated. Ice/water and then EtOAc were added. The organic layer was separated and the aqueous layer re-extracted with EtOAc. The combined organics were washed with water, dried (MgSO$_4$) and concentrated to give the product (1.110 g, 87%) which was used without further purification. $^1$H NMR (400 MHz, CDCl$_3$) δ 7.46-7.58 (3H, m), 8.45 (1H, s), 8.82 (1H, s); m/z (ES$^+$) (M+H)$^+$=299; HPLC t$_R$=2.77 min.

Intermediate BA4: 1-(2,6-dichlorophenyl)-1H-pyrazolo[3,4-d]pyrimidin-4-ol

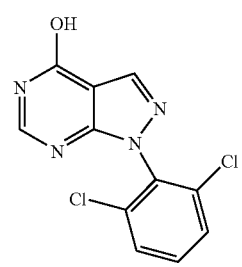

Concentrated sulfuric acid (1.297 mL, 24.34 mmol) was added to a stirred solution of 5-amino-1-(2,6-dichlorophenyl)-1H-pyrazole-4-carbonitrile (Intermediate BA5) (5.6 g, 22.13 mmol) in formic acid (35 mL). The resulting solution was stirred at 100° C. for 24 hours. The reaction was allowed to cool to room temperature and evaporated to ~half volume, water (100 mL) added and stirred for 1 hour. The formed precipitate was filtered off, washed well with water and dried overnight in a vacuum over $P_2O_5$ to afford the product (4.07 g, 65.4%) which was used without further purification. $^1$H NMR (400 MHz, DMSO) δ 7.65-7.69 (1H, m), 7.75-7.78 (2H, m), 8.09 (1H, d), 8.41 (1H, s), 12.44 (1H, s); m/z (ES$^-$) (M−H)$^-$= 279; HPLC $t_R$=1.41 min.

Intermediate BA5: 5-amino-1-(2,6-dichlorophenyl)-1H-pyrazole-4-carbonitrile

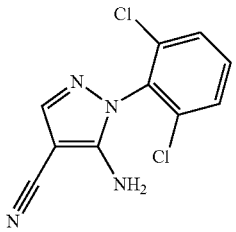

(2,6-Dichlorophenyl)hydrazine hydrochloride (5 g, 23.42 mmol) was partitioned between EtOAc (100 mL) and NaOH (2M, aq) (40 mL). The organic layer separated and washed with water (50 mL), brine (50 mL), dried (MgSO$_4$), filtered and concentrated. The resultant oil was suspended in methanol (50 mL) under nitrogen at −5° C. 2-(Ethoxymethylene)malononitrile (2.86 g, 23.42 mmol) added portionwise over 5 mins and the mixture stirred at 0° C. for 30 mins. The reaction mixture was allowed to warm to room temperature and then heated at reflux under nitrogen for 2 hours. The reaction mixture was allowed to cool and evaporated to dryness to afford the product (5.60 g, 94%) which was used without further purification. $^1$H NMR (400 MHz, CDCl$_3$) δ 4.47 (2H, s), 7.43-7.47 (1H, m), 7.51-7.53 (2H, m), 7.73 (1H, s); m/z (ES$^+$) (M+H)$^+$=253; HPLC $t_R$=1.62 min.

Intermediate BB1: (2S)-3-(3-(tert-butyldimethylsilyloxy)azetidin-1-yl)-2-(1-(2-chlorophenyl)-1H-pyrazolo[3,4-d]pyrimidin-4-yloxy)-N-(5-methylpyrazin-2-yl)propanamide

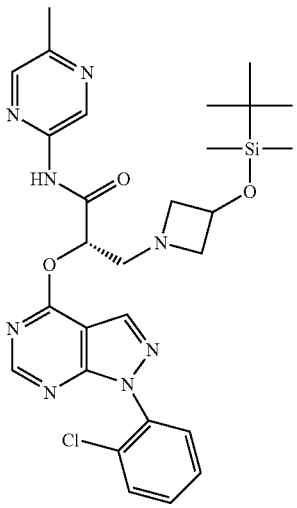

Sodium hydride (87 mg, 2.18 mmol) was added to (S)-3-(3-(tert-butyldimethylsilyloxy)azetidin-1-yl)-2-hydroxy-N-(5-methylpyrazin-2-yl)propanamide (Intermediate BB2) (400 mg, 1.09 mmol) in anhydrous tetrahydrofuran (15 mL) at 0° C. under nitrogen. The resulting solution was stirred at 0° C. for 10 minutes and then 4-chloro-1-(2-chlorophenyl)-1H-pyrazolo[3,4-d]pyrimidine (318 mg, 1.20 mmol) was added. The reaction mixture was allowed to warm to room temperature and stirred for 2 hours. The reaction mixture was adjusted to pH 7 by addition of 1M citric acid and then diluted with water (30 mL) and ethyl acetate (50 mL). The organic layer was separated and the aqueous layer re-extracted with ethyl acetate (50 mL). Te combined organics were washed with saturated brine (75 mL), dried (MgSO$_4$), filtered and evaporated. The crude product was purified by flash silica chromatography, eluting with 40 to 100% ethyl acetate in isohexane followed by 0-20% methanol in ethyl acetate to afford the product (532 mg, 82%). 1H NMR (400 MHz, CDCl$_3$) δ 0.00 (6H, s), 0.83 (9H, s), 2.45 (3H, s), 3.61-3.90 (4H, m), 4.47-4.60 (2H, m), 4.69 (1H, m), 6.22 (1H, m), 7.36-7.48 (3H, m), 7.51-7.57 (1H, m), 8.03 (1H, s), 8.38 (1H, s), 8.50 (1H, s), 9.27 (1H, s), 10.31 (1H, s); m/z (ES$^+$) (M+H)$^+$= 595; HPLC $t_R$=2.63 min.

Intermediate BB2: (S)-3-(3-(tert-butyldimethylsilyloxy)azetidin-1-yl)-2-hydroxy-N-(5-methylpyrazin-2-yl)propanamide

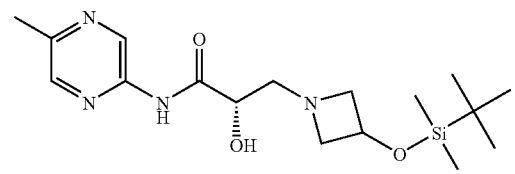

Trimethylaluminum (6.22 mL, 12.44 mmol) was added to 5-methylpyrazin-2-amine (1.357 g, 12.44 mmol) in anhydrous toluene (20 mL) cooled to 0° C. under nitrogen. The resulting solution was stirred at 0° C. for 10 minutes. (S)-methyl 3-(3-(tert-butyldimethylsilyloxy)azetidin-1-yl)-2-hydroxypropanoate (Intermediate AD3) (2 g, 6.91 mmol) in anhydrous toluene (10 mL) was added and the resulting solution was allowed to warm to room temperature and then heated at 80° C. overnight. The reaction was allowed to cool to room temperature and a solution of Rochelle salt in water (20%, 75 ml) was added. The mixture diluted with water (25 mL) and ethyl acetate (75 mL) and allowed to stir for 2 hours. The organic layer was separated and the aqueous was extracted with ethyl acetate (75 mL). The combined organics were washed with brine (75 mL), dried (MgSO$_4$), filtered and evaporated. The crude product was purified by flash silica chromatography, eluting with 20 to 50% ethyl acetate in isohexane. This was further purified by flash silica chromatography, eluting with 0 to 10% methanol in dichloromethane, to afford the product (1.50 g, 59.2%). $^1$H NMR (400 MHz, CDCl$_3$) δ 0.03 (3H, d), 0.04 (3H, s), 0.87 (9H, q), 2.54 (3H, s), 2.93 (2H, d), 3.09 (2H, q), 3.71-3.77 (2H, m), 4.04 (1H, t), 4.46 (1H, t), 8.13 (1H, d), 9.39 (1H, d), 9.81 (1H, s); m/z (ES$^+$) (M+H)$^+$=367.34; HPLC $t_R$=1.76 min.

Intermediate BB3: (S)-3-(3-(tert-butyldimethylsilyloxy)azetidin-1-yl)-2-(1-(2,6-dichlorophenyl)-1H-pyrazolo[3,4-d]pyrimidin-4-yloxy)-N-(5-methylpyrazin-2-yl)propanamide

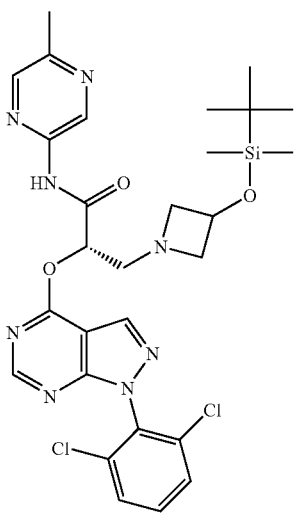

Sodium hydride (87 mg, 2.18 mmol) was added to (S)-3-(3-(tert-butyldimethylsilyloxy)azetidin-1-yl)-2-hydroxy-N-(5-methylpyrazin-2-yl)propanamide (Intermediate BB2) (400 mg, 1.09 mmol) in anhydrous tetrahydrofuran (15 mL) at 0° C. under nitrogen. The resulting solution was stirred at 0° C. for 10 minutes and then 4-chloro-1-(2,6-dichlorophenyl)-1H-pyrazolo[3,4-d]pyrimidine (Intermediate BA3) (360 mg, 1.20 mmol) was added. The reaction mixture was allowed to warm to room temperature and stirred for 2 hours. The reaction mixture was neutralised with 1M citric acid and then diluted with water (30 mL) and ethyl acetate (50 mL). The organic layer was separated and the aqueous layer re-extracted with ethyl acetate (50 mL). The combined organics were washed with saturated brine (75 mL), dried (MgSO$_4$), filtered and evaporated. The crude product was purified by flash silica chromatography, eluting with 40 to 80% ethyl acetate in isohexane, to afford the product (395 mg, 57.5%). $^1$H NMR (400 MHz, CDCl$_3$) δ 0.04 (6H, s), 0.88 (9H, s), 2.54 (3H, s), 3.09-3.13 (2H, m), 3.16-3.21 (1H, m), 3.29-3.34 (1H, m), 3.87-3.92 (2H, m), 4.51 (1H, qn), 5.92-5.95 (1H, m), 7.43-7.47 (1H, m), 7.52-7.55 (2H, m), 8.14 (1H, d), 8.41 (1H, s), 8.59 (1H, s), 9.42 (1H, d), 9.96 (1H, s); m/z (ES$^+$) (M+H)$^+$= 631; HPLC t$_R$=2.94 min.

Intermediate BC1: (S)-3-(azetidin-1-yl)-2-hydroxy-N-(pyridin-2-yl)propanamide

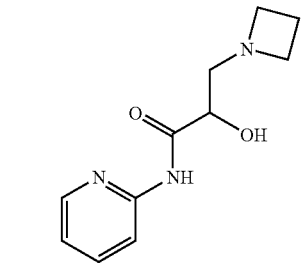

Trimethylaluminium (8.31 mL, 16.62 mmol) was added to pyridin-2-amine (1.360 g, 14.45 mmol) in toluene (30 mL) cooled to 0° C. under nitrogen. The resulting solution was stirred at 0° C. for 10 minutes. (S)-Methyl 3-(azetidin-1-yl)-2-hydroxypropanoate (Intermediate BC2) (2.3 g, 14.45 mmol) in toluene (10 mL) and THF (5 mL) was added and the resulting solution was allowed to warm to room temperature and then heated at 60° C. for 8 hours. The reaction cooled and 20% Rochelle salt (50 mL) added followed by EtOAc (50 mL) and the mixture stirred at ambient temperature overnight. The organic phase separated and the aqueous phase re-extracted with EtOAc (2×50 mL). The organic phases were combined, dried (MgSO$_4$) and evaporated to afford the product (2.7 g) which was used without further purification.

1H NMR (400 MHz, CDCl$_3$) δ 2.10-2.17 (2H, m), 2.86 (2H, d), 3.36 (4H, t), 4.00 (1H, t), 7.02-7.06 (1H, m), 7.67-7.72 (1H, m), 8.19-8.23 (1H, m), 8.29-8.32 (1H, m), 9.91 (1H, s)

Intermediate BC2: (S)-methyl 3-(azetidin-1-yl)-2-hydroxypropanoate

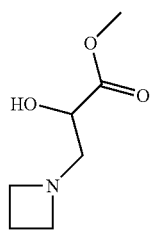

(S)-Methyl oxirane-2-carboxylate (1475 mg, 14.45 mmol) in acetonitrile (2 mL) was added to azetidine (825 mg, 14.45 mmol) in acetonitrile (8 mL). The reaction was heated to 100° C. for 60 minutes in the microwave reactor and cooled to room temperature. The mixture was evaporated to afford the crude product (2.3 g) which was used without further purification.

1H NMR (400 MHz, CDCl$_3$) δ 2.04-2.14 (2H, m), 2.71-2.81 (2H, m), 3.27 (4H, t), 3.77 (3H, s), 4.11-4.13 (1H, m)

The following intermediates were prepared using a procedure analogous to that described for Intermediate BB1 using the appropriate intermediates.

| Intermediate number | Structure | 1H NMR (400 MHz) δ | LCMS | Intermediate refs. |
|---|---|---|---|---|
| BD1 | 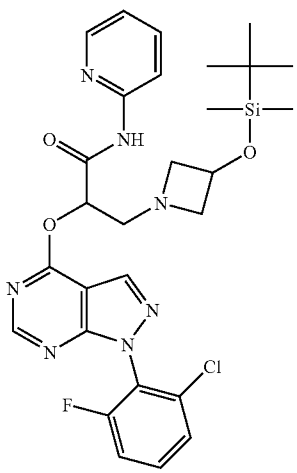 | (DMSO-d6) 0.02 (6H, s), 0.84 (9H, q), 3.02-3.25 (4H, s), 3.70-3.79 (2H, m), 4.35-4.42 (1H, m), 5.75-5.79 (1H, m), 7.11-7.14 (1H, m), 7.54-7.60 (1H, m), 7.65-7.67 (1H, m), 7.71-7.78 (2H, m), 7.94-7.99 (1H, m), 8.33-8.35 (1H, m), 8.56 (1H, d), 8.67 (1H, d), 10.94 (1H, d) | m/z (ES+) (M + H)+ = 598; HPLC tR = 3.19 min. | BI1, BH1 |
| BD2 | 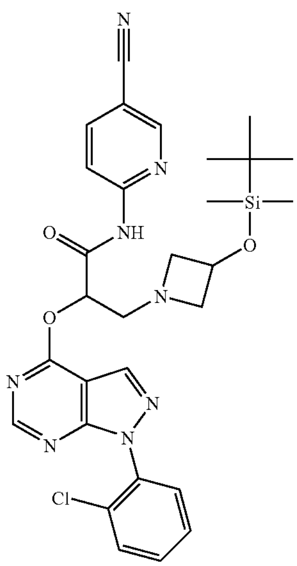 | | m/z (ES+) (M + H)+ = 605; HPLC tR = 1.95 min. | BE1, B1 |
| BD3 | 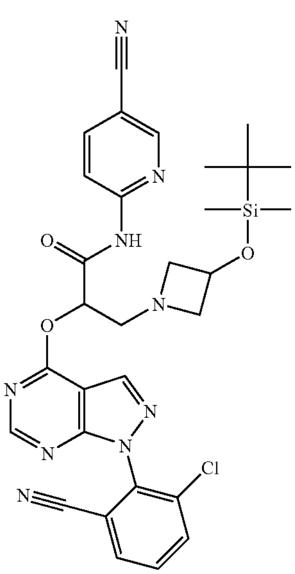 | | m/z (ES+) (M + H)+ = 630; HPLC tR = 1.89 min. | BE1, AH6 |

| Intermediate number | Structure | 1H NMR (400 MHz) δ | LCMS | Intermediate refs. |
|---|---|---|---|---|
| BD4 | 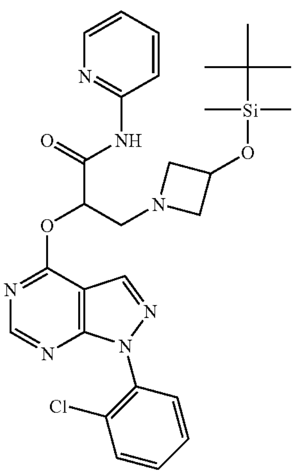 | | m/z (ES+) (M + H)+ = 580; HPLC tR = 2.46 min. | BE2, B1 |
| BD5 | 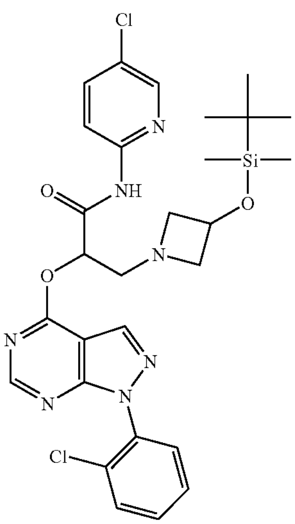 | (DMSO-d6) 0.03 (6H, s), 0.85 (9H, s), 2.90-2.95 (1H, m), 3.00-3.06 (1H, m), 3.10-3.16 (1H, m), 3.62-3.69 (2H, m), 4.30-4.39 (1H, m), 5.71-5.77 (1H, d), 7.54-7.65 (3H, m), 7.74-7.77 (1H, m), 7.87-7.90 (1H, m), 7.99-8.03 (1H, d), 8.39-8.40 (1H, m), 8.52 (1H, s), 8.58 (1H, s), 11.12 (1H, s) | m/z (ES+) (M + H)+ = 614; HPLC tR = 2.91 min. | AD2, B1 |
| BD6 | 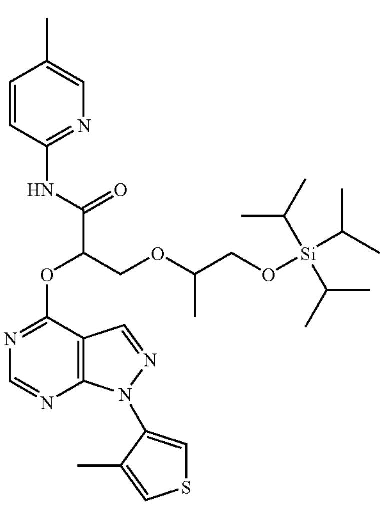 | (DMSO-d6) 0.91-1.04 (18H, m), 1.08 (3H, d), 2.09 (3H, d), 2.24 (3H, s), 3.50-3.54 (1H, m), 3.62-3.66 (1H, m), 3.68-3.74 (1H, m), 4.06-4.14 (2H, m), 5.87-5.94 (1H, m), 7.40-7.41 (1H, m), 7.57-7.60 (1H, m), 7.82 (1H, d), 7.86-7.89 (1H, m), 8.17-8.17 (1H, m), 8.50 (1H, s), 8.55 (1H, s), 10.82 (1H, s) | m/z (ES+) (M + H)+ = 625; HPLC tR = 3.77 min. | AU4, BF1 |

-continued

| Intermediate number | Structure | 1H NMR (400 MHz) δ | LCMS | Intermediate refs. |
|---|---|---|---|---|
| BD7 | 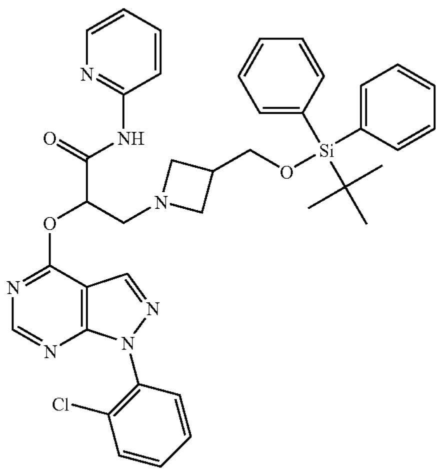 | | m/z (ES+) (M + H)+ = 718; HPLC tR = 3.17 min. | BG1, B1 |
| BD8 | 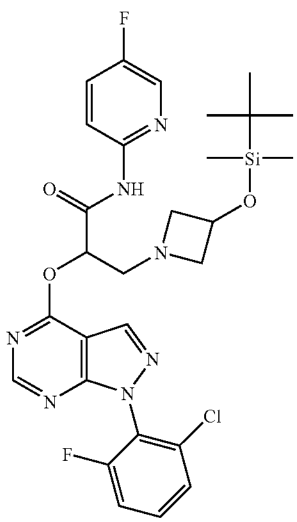 | (CDCl$_3$) 0.04 (6H, s), 0.88 (9H, s), 3.06-3.10 (2H, m), 3.15-3.20 (1H, m), 3.26-3.32 (1H, m), 3.86-3.91 (2H, m), 4.49-4.52 (1H, m), 5.89-5.92 (1H, m), 7.22-7.27 (1H, m), 7.40-7.44 (2H, m), 7.44-7.52 (1H, m), 8.15-8.16 (1H, m), 8.22-8.26 (1H, m), 8.41 (1H, d), 8.59 (1H, s), 9.83 (1H, d) | m/z (ES+) (M + H)+ = 616; HPLC tR = 3.02 min. | AX2, BH1 |
| BD9 | 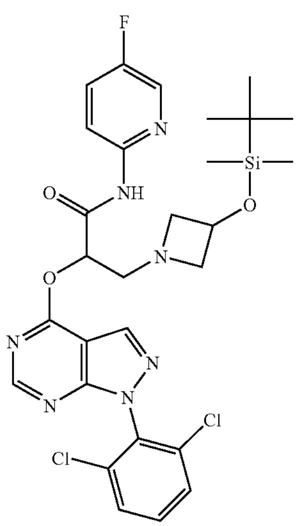 | (CDCl$_3$) 0.05 (6H, s), 0.89 (9H, s), 3.07-3.11 (2H, m), 3.17-3.21 (1H, m), 3.28-3.33 (1H, m), 3.89-3.92 (2H, m), 4.52 (1H, qn), 5.90-5.93 (1H, m), 7.42-7.48 (2H, m), 7.53-7.56 (2H, m), 8.17 (1H, d), 8.24-8.28 (1H, m), 8.42 (1H, s), 8.59 (1H, s), 9.85 (1H, s) | m/z (ES+) (M + H)+ = 632; HPLC tR = 3.05 min. | AX2, BA3 |

-continued

| Intermediate number | Structure | 1H NMR (400 MHz) δ | LCMS | Intermediate refs. |
|---|---|---|---|---|
| BD10 | 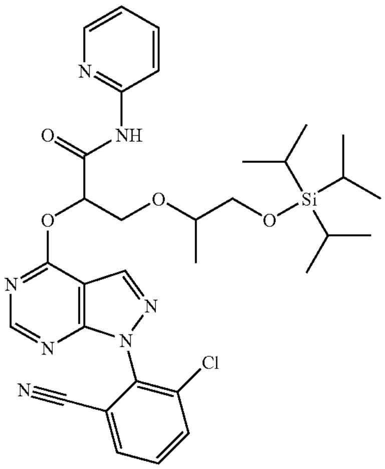 | (DMSO-d6) 0.91-1.01 (21H, m), 1.10 (3H, d), 3.52-3.57 (1H, m), 3.62-3.68 (1H, m), 3.75-3.78 (1H, m), 4.11-4.14 (2H, m), 5.94 (1H, s), 7.11-7.14 (1H, m), 7.74-7.79 (1H, m), 7.87-7.91 (1H, m), 7.99 (1H, t), 8.16-8.19 (2H, m), 8.33-8.36 (1H, m), 8.60 (1H, s), 8.73 (1H, s), 10.99 (1H, s) | m/z (ES+) (M + H)+ = 650; HPLC tR = 4.07 min. | AQ4, AH6 |
| BD11 | 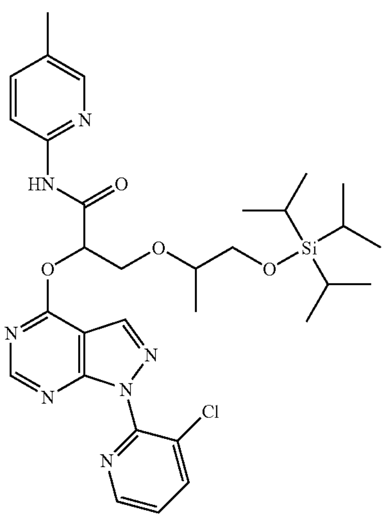 | (CDCl₃) 1.00-1.04 (21H, m), 1.13 (3H, d), 2.29 (3H, s), 3.56-3.74 (3H, m), 4.20-4.31 (2H, m), 6.00-6.03 (1H, m), 7.45-7.48 (1H, m), 7.51-7.53 (1H, m), 7.99-8.02 (1H, m), 8.08-8.09 (1H, m), 8.13 (1H, d), 8.46 (1H, s), 8.61-8.62 (2H, m), 8.65 (1H, s) | m/z (ES+) (M + H)+ = 640; HPLC tR = 3.90 min. | AU2, B15 |

Intermediate BD1 (2S)-3-(3-(tert-butyldimethylsilyloxy)azetidin-1-yl)-2-(1-(2-chloro-6-fluorophenyl)-1H-pyrazolo [3,4-d]pyrimidin-4-yloxy)-N-(pyridin-2-yl)propanamide Intermediate BD2 (2S)-3-(3-(tert-butyldimethylsilyloxy)azetidin-1-yl)-2-(1-(2-chlorophenyl)-1H-pyrazolo [3,4-d]pyrimidin-4-yloxy)-N-(5-cyanopyridin-2-yl)propanamide Intermediate BD3 (2S)-3-(3-(tert-butyldimethylsilyloxy)azetidin-1-yl)-2-(1-(2-chloro-6-cyanophenyl)-1H-pyrazolo [3,4-d]pyrimidin-4-yloxy)-N-(5-cyanopyridin-2-yl)propanamide Intermediate BD4 (2S)-3-(3-(tert-butyldimethylsilyloxy)azetidin-1-yl)-2-(1-(2-chlorophenyl)-1H-pyrazolo [3,4-d]pyrimidin-4-yloxy)-N-(pyridin-2-yl)propanamide Intermediate BD5 (2S)-3-(3-(tert-butyldimethylsilyloxy)azetidin-1-yl)-2-(1-(2-chlorophenyl)-1H-pyrazolo [3,4-d]pyrimidin-4-yloxy)-N-(5-chloropyridin-2-yl)propanamide Intermediate BD6 (2S)—N-(5-methylpyridin-2-yl)-2-(1-(4-methylthiophen-3-yl)-1H-pyrazolo[3,4-d]pyrimidin-4-yloxy)-3-((R)-1-(triisopropylsilyloxy)propan-2-yloxy)propanamide Intermediate BD7 (2S)-3-(3-((tert-butyldiphenylsilyloxy)methyl)azetidin-1-yl)-2-(1-(2-chlorophenyl)-1H-pyrazolo[3,4-d]pyrimidin-4-yloxy)-N-(pyridin-2-yl)propanamide Intermediate BD8 (2S)-3-(3-(tert-butyldimethylsilyloxy)azetidin-1-yl)-2-(1-(2-chloro-6-fluorophenyl)-1H-pyrazolo[3,4-d]pyrimidin-4-yloxy)-N-(5-fluoropyridin-2-yl)propanamide Intermediate BD9 (S)-3-(3-(tert-butyldimethylsilyloxy)azetidin-1-yl)-2-(1-(2,6-dichlorophenyl)-1H-pyrazolo[3,4-d]pyrimidin-4-yloxy)-N-(5-fluoropyridin-2-yl)propanamide Intermediate BD10 (2S)-2-(1-(2-chloro-6-cyanophenyl)-1H-pyrazolo[3,4-d]pyrimidin-4-yloxy)-N-(pyridin-2-yl)-3-((R)-1-(triisopropylsilyloxy)propan-2-yloxy)propanamide Intermediate BD11 (2S)-2-(1-(3-chloropyridin-2-yl)-1H-pyrazolo[3,4-d]pyrimidin-4-yloxy)-N-(5-methylpyridin-2-yl)-3-((R)-1-(triisopropylsilyloxy)propan-2-yloxy)propanamide Intermediate BD12: (S)-3-(3-(tert-butyldimethylsilyloxy)azetidin-1-yl)-2-(1-(2,6-dichlorophenyl)-1H-pyrazolo[3,4-d]pyrimidin-4-yloxy)-N-(pyridin-2-yl)propanamide combined organics were dried (MgSO$_4$), filtered and evaporated. The crude product was purified by flash silica chromatography, elution gradient 20 to 50% EtOAc in isohexane to afford the product (151 mg, 67.9%).

$^1$H NMR (400 MHz, CDCl$_3$) δ 0.04 (6H, s), 0.88 (9H, s), 3.05-3.09 (2H, m), 3.17-3.31 (2H, m), 3.86-3.91 (2H, m), 4.50 (1H, t), 5.89-5.92 (1H, m), 7.04-7.07 (1H, m), 7.42-7.47 (1H, m), 7.52-7.55 (2H, m), 7.68-7.72 (1H, m), 8.22-8.24 (1H, m), 8.29-8.31 (1H, m), 8.42 (1H, s), 8.58 (1H, s), 9.63 (1H, s); m/z (ES$^+$) (M+H)$^+$=616; HPLC $t_R$=1.95 min.

Intermediate BD13: (S)-3-(3-(tert-butyldimethylsilyloxy)azetidin-1-yl)-N-(5-cyanopyridin-2-yl)-2-(1-(2,6-dichlorophenyl)-1H-pyrazolo[3,4-d]pyrimidin-4-yloxy)propanamide

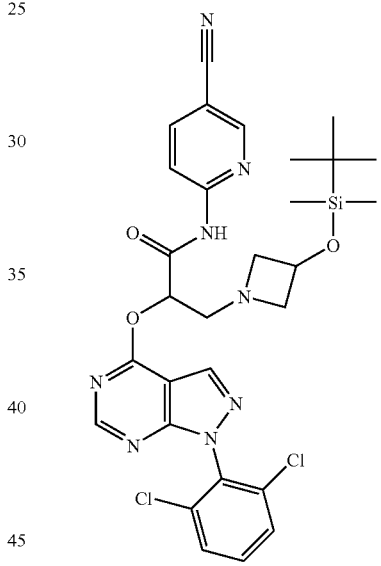

Trimethylaluminium (0.362 mL, 0.72 mmol) was added to a solution of pyridin-2-amine (68.1 mg, 0.72 mmol) in toluene (8 mL) at 0° C. under nitrogen. The reaction mixture was stirred at 0° C. for 20 mins and then (S)-methyl 3-(3-(tert-butyldimethylsilyloxy)azetidin-1-yl)-2-(1-(2,6-dichlorophenyl)-1H-pyrazolo [3,4-d]pyrimidin-4-yloxy)propanoate (Intermediate BJ1) (200 mg, 0.36 mmol) in toluene (4 mL) was added. The reaction mixture was allowed to warm to room temperature and then heated at reflux under nitrogen for 4 hours. The reaction mixture was allowed to cool to room temperature and the concentrated. The residue was neutralised to pH 7 with citric acid (1M, aq) and then diluted with water and DCM (50 mL). The organic layer was separated and the aqueous layer re-extracted with DCM (30 mL). The Using a procedure analogous to that described for Intermediate BD12 using 6-aminonicotinonitrile and (S)-methyl 3-(3-(tert-butyldimethylsilyloxy)azetidin-1-yl)-2-(1-(2,6-dichlorophenyl)-1H-pyrazolo[3,4-d]pyrimidin-4-yloxy)propanoate (Intermediate BJ1).

$^1$H NMR (400 MHz, CDCl$_3$) δ 0.06 (6H, s), 0.89 (9H, s), 3.11-3.19 (3H, m), 3.30-3.35 (1H, m), 3.90-3.94 (2H, m), 4.54 (1H, t), 5.87-5.91 (1H, m), 7.43-7.47 (1H, m), 7.52-7.55 (2H, m), 7.92-7.94 (1H, m), 8.33-8.36 (1H, m), 8.40 (1H, s), 8.57 (1H, s), 8.59 (1H, q), 10.57 (1H, s); m/z (ES$^+$) M$^+$=639; HPLC $t_R$=2.02 min.

The following intermediates were prepared using a procedure analogous to that described for Intermediate BB1 using the appropriate intermediates.

| Intermediate number | Structure | 1H NMR (400 MHz) δ | LCMS | Intermediate refs. |
|---|---|---|---|---|
| BD14 | 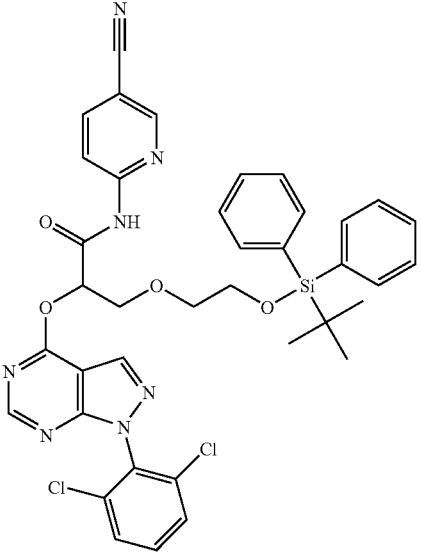 | | m/z (ES+) (M + H)+ = 752; HPLC tR = 3.78 min. | AK7, BA3 |
| BD15 | 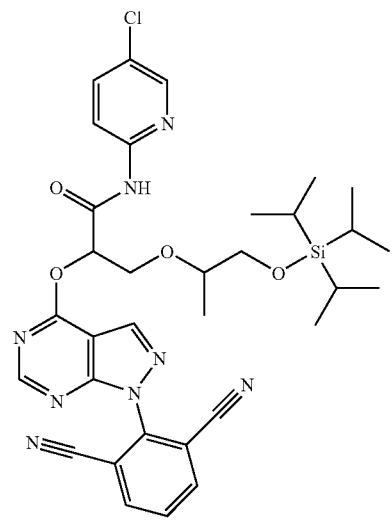 | (CDCl$_3$) 0.95-1.09 (m, 21H), 1.15 (d, 3H), 3.58-3.79 (m, 3H), 4.18-4.25 (m, 1H), 4.27-4.34 (m, 1H), 6.01 (t, 1H), 7.65-7.70 (m, 1H), 7.78 (t, 1H), 8.10 (d, 2H), 8.20-8.25 (m, 2H), 8.56 (s, 1H), 8.66 (s, 1H), 8.78 (s, 1H) | | AY2, BK1 |

-continued
| Intermediate number | Structure | 1H NMR (400 MHz) δ | LCMS | Intermediate refs. |
|---|---|---|---|---|
| BD16 | 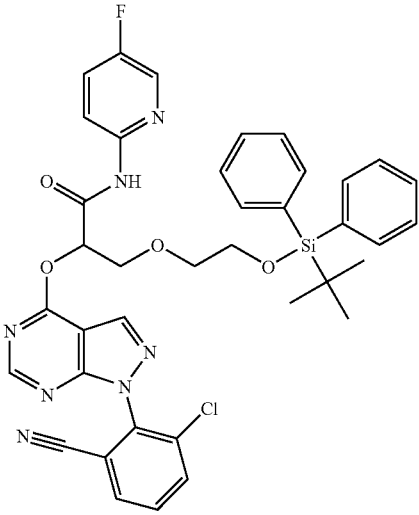 | (DMSO-d6) 0.88 (s, 9H), 3.62-3.78 (m, 4H), 3.93-4.12 (m, 2H), 5.93-5.99 (m, 1H), 7.24-7.35 (m, 6H), 7.50-7.59 (m, 5H), 7.73-7.80 (m, 1H), 7.89-7.96 (m, 1H), 7.98-8.04 (m, 2H), 8.17-8.21 (m, 1H), 8.47-8.52 (m, 2H), 10.50 (s, 1H) | m/z (ES+), (M + H)+ = 736.55; HPLC tR = 3.66 min | BA1, AH6 |
| BD17 | 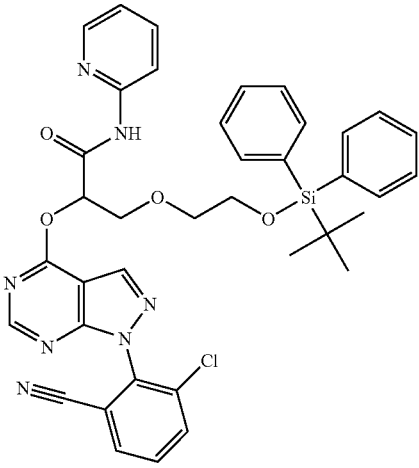 | (DMSO-d6) 0.97 (s, 9H), 3.71-3.90 (m, 4H), 4.08-4.22 (m, 2H), 6.03-6.10 (m, 1H), 7.07-7.13 (m, 1H), 7.33-7.45 (m, 6H), 7.60-7.66 (m, 5H), 7.71-7.78 (m, 1H), 7.85 (t, 1H), 7.94-7.99 (m, 1H), 8.06-8.13 (m, 2H), 8.30-8.34 (m, 1H), 8.57-8.60 (m, 1H), 10.43 (s, 1H) | m/z (ES+), (M + H)+ = 718.58; HPLC tR = 3.59 min | AQ2, AH6 |
| BD18 | 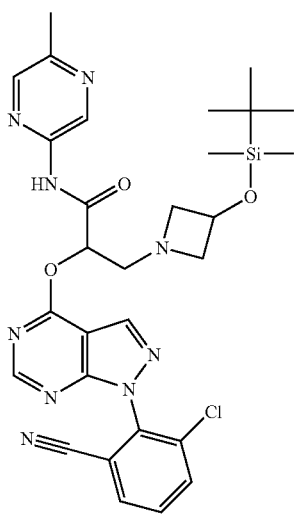 | (CDCl3) 0.00 (6H, s), 0.81 (9H, s), 2.47 (3H, s), 2.99-3.09 (2H, m), 3.11 (2H, d), 4.40-4.50 (1H, m), 3.81-3.88 (2H, m), 5.83-5.88 (1H, m), 7.53-7.58 (1H, m), 7.70-7.74 (1H, m), 7.77-7.81 (1H, m), 8.07 (1H, s), 8.33-8.41 (1H, m), 8.54 (1H, d), 9.32-9.36 (1H, m), 10.08 (1H, s), 9.71 (0H, s) | m/z (ES+), (M + H)+ = 620; 5 min, Acid, HPLC tR = 1.81 min | BB2, AH6 |

-continued
| Intermediate number | Structure | 1H NMR (400 MHz) δ | LCMS | Intermediate refs. |
|---|---|---|---|---|
| BD19 | 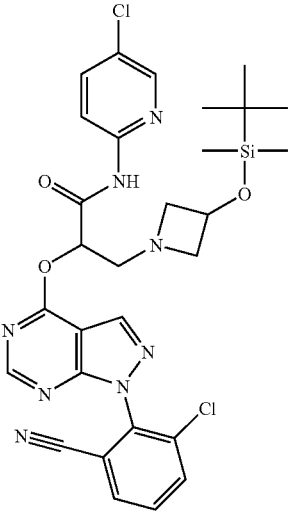 | (CDCl₃) 0.00 (6H, d), 0.78-0.82 (9H, m), 3.06 (2H, q), 3.23 (1H, d), 3.85 (2H, d), 4.43-4.46 (1H, m), 5.81-5.84 (1H, m), 7.19 (1H, s), 7.54 (1H, d), 7.57-7.61 (1H, m), 7.70-7.74 (1H, m), 7.77-7.80 (1H, m), 8.11-8.14 (1H, m), 8.18-8.19 (1H, m), 8.38 (1H, d), 8.53 (1H, d), 10.00 (1H, s) | m/z (ES+), (M + H)+ = 639; 5 min Acid, HPLC tR = 2.01 min | AD2, AH6 |
| BD20 | 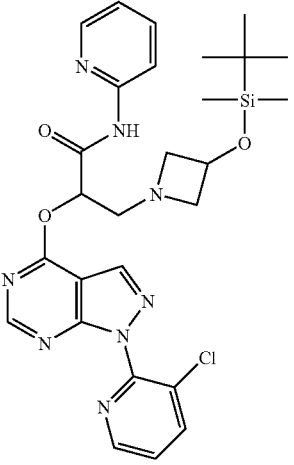 | (CDCl₃) 0.05 (6H, t), 0.89 (9H, t), 3.05-3.10 (2H, m), 3.17-3.22 (1H, m), 3.30 (1H, q), 3.86-3.91 (2H, m), 4.50 (1H, t), 5.91-5.94 (1H, m), 7.04-7.08 (1H, m), 7.42-7.49 (1H, m), 7.68-7.73 (1H, m), 8.00-8.03 (1H, m), 8.21-8.24 (1H, m), 8.30-8.32 (1H, m), 8.42 (1H, s), 8.62-8.64 (2H, m), 9.59 (1H, s) | m/z (ES+) M+ = 581.36; HPLC tR = 2.57 min. | BE2, B15 |
| BD21 | 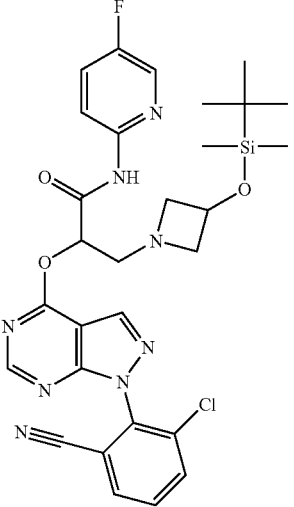 | (CDCl₃) 0.03-0.06 (6H, m), 0.88-0.89 (9H, m), 3.07-3.33 (4H, m), 3.91 (2H, s), 4.50-4.54 (1H, m), 5.89 (1H, d), 7.40-7.46 (1H, m), 7.62 (1H, t), 7.77-7.81 (1H, m), 7.84-7.87 (1H, m), 8.16 (1H, d), 8.22-8.26 (1H, m), 8.45 (1H, d), 8.60 (1H, d), 9.74-10.00 (1H, m) | m/z (ES+) M+ = 623.20; HPLC tR = 2.81 min. | AX2, AH6 |

-continued
| Intermediate number | Structure | 1H NMR (400 MHz) δ | LCMS | Intermediate refs. |
|---|---|---|---|---|
| BD22 | 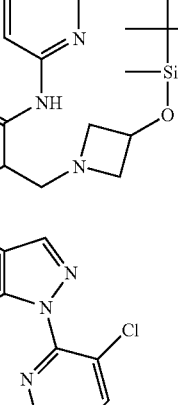 | (CDCl₃) 0.04 (6H s), 0.88 (9H s), 3.07-3.29 (4H, m), 3.89 (2H, s), 4.50 (1H, t), 5.91 (1H, t), 7.40-7.52 (2H, m), 8.00-8.02 (1H, m), 8.15 (1H, d), 8.22-8.25 (1H, m), 8.40 (1H, s), 8.61-8.63 (2H, m), 9.79 (1H, s) | m/z (ES+) (M + H)+ = 623.20; HPLC tR = 2.81 min. | AX2, B15 |
| BD23 | 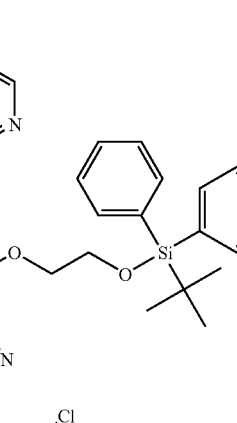 | (CDCl₃) 0.99 (9H, d), 3.68-3.72 (2H, m), 3.81-3.84 (2H, m), 4.18-4.21 (2H, m), 6.06 (1H, t), 7.22-7.27 (1H, m), 7.31-7.52 (9H, m), 7.63-7.68 (4H, m), 8.11 (1H, t), 8.25-8.29 (1H, m), 8.42 (1H, d), 8.58 (1H, d), 8.77 (1H, d) | m/z (ES+) (M + H)+ = 729.22; HPLC tR = 3.76 min. | BA2, BH1 |
| BD24 | 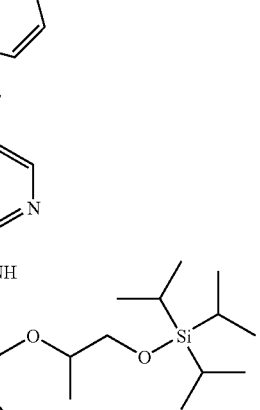 | (CDCl₃) 0.98-1.07 (21H, m), 1.14 (3H, d), 3.59-3.67 (1H, m), 3.61-3.66 (1H, m), 3.71-3.75 (1H, m), 4.20-4.24 (1H, m), 4.28-4.32 (1H, m), 6.02 (1H, t), 7.42-7.45 (1H, m), 7.46-7.49 (2H, m), 7.52-7.55 (1H, m), 7.61-7.63 (1H, m), 8.13 (1H, d), 8.26-8.29 (1H, m), 8.42 (1H, s), 8.58 (1H, s), 8.79 (1H, s) | m/z (ES+) M+ = 643.39; HPLC tR = 3.96 min. | BL1, B1 |

-continued

| Intermediate number | Structure | 1H NMR (400 MHz) δ | LCMS | Intermediate refs. |
|---|---|---|---|---|
| BD25 | 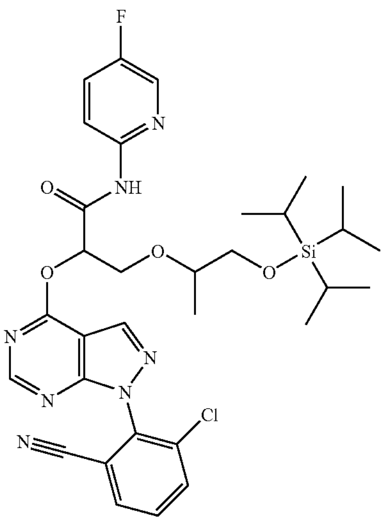 | (CDCl₃) 0.98-1.07 (21H, m), 1.13-1.17 (3H, m), 3.59-3.77 (3H, m), 4.21-4.33 (2H, m), 6.00-6.04 (1H, m), 7.43-7.47 (1H, m), 7.60-7.65 (1H, m), 7.78-7.81 (1H, m), 7.85-7.87 (1H, m), 8.14 (1H, t), 8.25-8.29 (1H, m), 8.51 (1H, d), 8.60 (1H, d), 8.80 (1H, s) | | BL1, AH6 |
| BD26 | 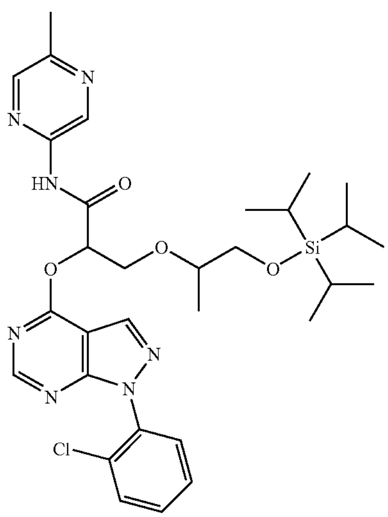 | (CDCl₃) 0.98-1.08 (21H, m), 1.15 (3H, d), 2.04 (3H, s), 2.54 (3H, s), 3.59-3.68 (2H, m), 3.71-3.75 (1H, m), 4.21-4.33 (2H, m), 6.04 (1H, t), 7.46-7.50 (2H, m), 7.51-7.55 (1H, m), 7.61-7.63 (1H, m), 8.11 (1H, d), 8.41 (1H, s), 8.59 (1H, s), 8.70 (1H, s), 9.44 (1H, d) | m/z (ES+) = 641.87; HPLC tR = 4.08 min. | AZ2, B1 |
| BD27 | 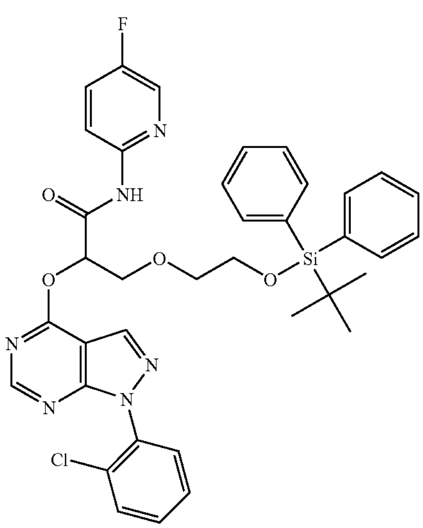 | (CDCl₃) 0.99 (9H, s), 3.69-3.72 (2H, m), 3.81-3.86 (2H, m), 4.16-4.24 (2H, m), 6.07 (1H, t), 7.31-7.68 (15H, m), 8.11 (1H, s), 8.25-8.28 (1H, m), 8.37 (1H, s), 8.58 (1H, s), 8.77 (1H, s) | m/z (ES+) (M + H)+ = 711.41; HPLC tR = 3.79 min. | BA2, B1 |

-continued
| Intermediate number | Structure | 1H NMR (400 MHz) δ | LCMS | Intermediate refs. |
|---|---|---|---|---|
| BD28 | 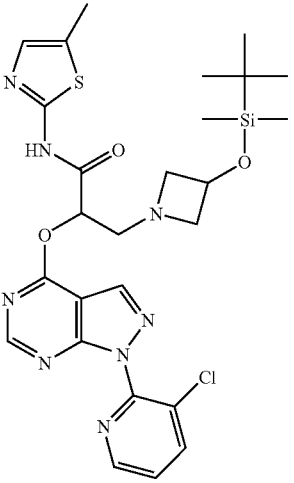 | (CDCl₃) 0.05 (6H, s), 0.88 (9H, s), 2.38-2.41 (3H, m), 3.05-3.16 (3H, m), 3.29-3.36 (1H, m), 3.90-3.96 (2H, m), 4.50-4.58 (1H, m), 5.96-6.01 (1H, m), 7.08-7.12 (1H, m), 7.44-7.49 (1H, m), 7.98-8.02 (1H, m), 8.37 (1H, s), 8.60-8.64 (2H, m), 11.11-11.47 (1H, m) | m/z (ES+) (M + H)+ = 601.39; HPLC tR = 2.61 min. | BM1, B15 |
| BD29 | 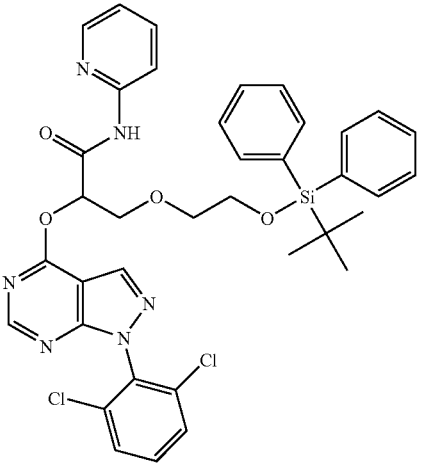 | (CDCl₃) 0.99 (9H, t), 3.69-3.72 (2H, m), 3.82 (2H, t), 4.16-4.25 (2H, m), 6.06-6.08 (1H, m), 7.04-7.07 (1H, m), 7.31-7.46 (7H, m), 7.51-7.54 (2H, m), 7.63-7.73 (5H, m), 8.26-8.29 (1H, m), 8.43 (1H, s), 8.58 (1H, s), 8.76 (1H, s) | m/z (ES+) (M + H)+ = 727.48; HPLC tR = 3.98 min. | AQ2, BA3 |
| BD30 | 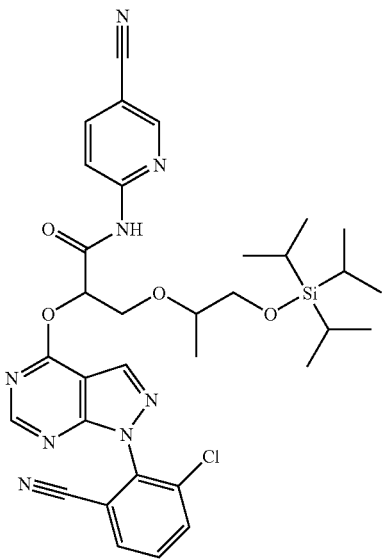 | (DMSO-d6) 0.88-1.01 (21H, m), 1.09 (3H, d), 3.52-3.56 (1H, m), 3.65 (1H, q), 3.73-3.77 (1H, m), 4.10-4.16 (2H, m), 5.93-5.95 (1H, m), 7.87-7.91 (1H, m), 8.12-8.19 (3H, m), 8.23-8.27 (1H, m), 8.60 (1H, s), 8.73 (1H, d), 8.82-8.83 (1H, m), 11.57 (1H, s) | m/z (ES+) (M + H)+ = 673.49 & 675.57; HPLC tR = 4 min. | BN1, AH6 |

-continued

| Intermediate number | Structure | 1H NMR (400 MHz) δ | LCMS | Intermediate refs. |
|---|---|---|---|---|
| BD31 | 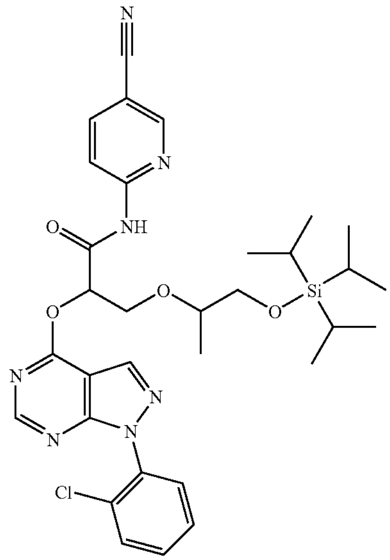 | (CDCl₃) 0.98-1.08 (21H, m), 1.15 (3H, t), 3.61-3.76 (3H, m), 4.20-4.24 (1H, m), 4.30-4.34 (1H, m), 6.00 (1H, t), 7.46-7.54 (3H, m), 7.61-7.64 (1H, m), 7.94-7.97 (1H, m), 8.37-8.41 (2H, m), 8.56-8.58 (2H, m), 9.05 (1H, s) | m/z (ES+) (M + H)+ = 648.54 & 650.50; HPLC tR = 4.08 min. | BN1, B1 |

Intermediate BD14 (S)-3-(2-(tert-butyldiphenylsilyloxy)ethoxy)-N-(5-cyanopyridin-2-yl)-2-(1-(2,6-dichlorophenyl)-1H-pyrazolo [3,4-d]pyrimidin-4-yloxy)propanamide Intermediate BD15 (S)—N-(5-chloropyridin-2-yl)-2-(1-(2,6-dicyanophenyl)-1H-pyrazolo[3,4-d]pyrimidin-4-yloxy)-3-((R)-1-(triisopropylsilyloxy)propan-2-yloxy)propanamide Intermediate BD16 (2S)-3-(2-(tert-butyldiphenylsilyloxy)ethoxy)-2-(1-(2-chloro-6-cyanophenyl)-1H-pyrazolo [3,4-d]pyrimidin-4-yloxy)-N-(5-fluoropyridin-2-yl)propanamide Intermediate BD17 (2S)-3-(2-(tert-butyldiphenylsilyloxy)ethoxy)-2-(1-(2-chloro-6-cyanophenyl)-1H-pyrazolo [3,4-d]pyrimidin-4-yloxy)-N-(pyridin-2-yl)propanamide Intermediate BD18 (2S)-3-(3-(tert-butyldimethylsilyloxy)azetidin-1-yl)-2-(1-(2-chloro-6-cyanophenyl)-1H-pyrazolo [3,4-d]pyrimidin-4-yloxy)-N-(5-methylpyrazin-2-yl)propanamide Intermediate BD19 (2S)-3-(3-(tert-butyldimethylsilyloxy)azetidin-1-yl)-2-(1-(2-chloro-6-cyanophenyl)-1H-pyrazolo [3,4-d]pyrimidin-4-yloxy)-N-(5-chloropyridin-2-yl)propanamide Intermediate BD20 (2S)-3-(3-(tert-butyldimethylsilyloxy)azetidin-1-yl)-2-(1-(3-chloropyridin-2-yl)-1H-pyrazolo [3,4-d]pyrimidin-4-yloxy)-N-(pyridin-2-yl)propanamide Intermediate BD21 (2S)-3-(3-(tert-butyldimethylsilyloxy)azetidin-1-yl)-2-(1-(2-chloro-6-cyanophenyl)-1H-pyrazolo [3,4-d]pyrimidin-4-yloxy)-N-(5-fluoropyridin-2-yl)propanamide Intermediate BD22 (2S)-3-(3-(tert-butyldimethylsilyloxy)azetidin-1-yl)-2-(1-(3-chloropyridin-2-yl)-1H-pyrazolo [3,4-d]pyrimidin-4-yloxy)-N-(5-fluoropyridin-2-yl)propanamide Intermediate BD23 (2S)-3-(2-(tert-butyldiphenylsilyloxy)ethoxy)-2-(1-(2-chloro-6-fluorophenyl)-1H-pyrazolo [3,4-d]pyrimidin-4-yloxy)-N-(5-fluoropyridin-2-yl)propanamide Intermediate BD24 (2S)-2-(1-(2-chlorophenyl)-1H-pyrazolo [3,4-d]pyrimidin-4-yloxy)-N-(5-fluoropyridin-2-yl)-3-((R)-1-(triisopropylsilyloxy)propan-2-yloxy)propanamide Intermediate BD25 (2S)-2-(1-(2-chloro-6-cyanophenyl)-1H-pyrazolo [3,4-d]pyrimidin-4-yloxy)-N-(5-fluoropyridin-2-yl)-3-((R)-1-(triisopropylsilyloxy)propan-2-yloxy)propanamide Intermediate BD26 (2S)-2-(1-(2-chlorophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide Intermediate BD27 (2S)-3-(2-(tert-butyldiphenylsilyloxy)ethoxy)-2-(1-(2-chlorophenyl)-1H-pyrazolo[3,4-d]pyrimidin-4-yloxy)-N-(5-fluoropyridin-2-yl)propanamide Intermediate BD28 (2S)-3-(3-(tert-butyldimethylsilyloxy)azetidin-1-yl)-2-(1-(3-chloropyridin-2-yl)-1H-pyrazolo[3,4-d]pyrimidin-4-yloxy)-N-(5-methylthiazol-2-yl)propanamide

Intermediate BD29 (S)-3-(2-(tert-butyldiphenylsilyloxy)ethoxy)-2-(1-(2,6-dichlorophenyl)-1H-pyrazolo[3,4-d]pyrimidin-4-yloxy)-N-(pyridin-2-yl)propanamide

Intermediate BD30 (2S)-2-(1-(2-chloro-6-cyanophenyl)-1H-pyrazolo[3,4-d]pyrimidin-4-yloxy)-N-(5-cyanopyridin-2-yl)-3-((R)-1-(triisopropylsilyloxy)propan-2-yloxy)propanamide

Intermediate BD31 (2S)-2-(1-(2-chlorophenyl)-1H-pyrazolo[3,4-d]pyrimidin-4-yloxy)-N-(5-cyanopyridin-2-yl)-3-((R)-1-(triisopropylsilyloxy)propan-2-yloxy)propanamide

Intermediate BE1: (S)-3-(3-(tert-butyldimethylsilyloxy)azetidin-1-yl)-N-(5-cyanopyridin-2-yl)-2-hydroxypropanamide

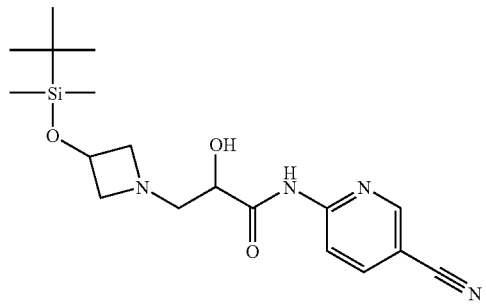

Trimethylaluminium (7.95 mL, 15.89 mmol) was added to 6-aminonicotinonitrile (1.646 g, 13.82 mmol) in toluene (50 mL) cooled to 0° C. under nitrogen. The resulting solution was stirred at 0° C. for 10 minutes. (S)-Methyl 3-(3-(tert-butyldimethylsilyloxy)azetidin-1-yl)-2-hydroxypropanoate (Intermediate AD3) (4.0 g, 13.82 mmol) in toluene (20 mL) was added and the resulting solution was allowed to warm to room temperature and then heated at 60° C. for 3 hours. The mixture was cooled to ~10° C. and quenched by the addition of 20% Rochelle salt solution. It was then diluted with EtOAc (50 mL) and stirred for 2 hours. The organic phase was separated, washed with water and brine, dried (MgSO$_4$), filtered and evaporated. The residue was purified by flash chromatography on silica with EtOAc as eluent to afford the product containing some 6-aminonicotinonitrile (4.1 g). This was used without further purification.

$^1$H NMR (400 MHz, DMSO-d6) δ 0.02 (6H, s), 0.83 (9H, s), 2.69-2.71 (2H, m), 2.76-2.82 (2H, m), 3.56-3.61 (2H, m), 4.12-4.14 (1H, m), 4.30-4.38 (1H, m), 5.85 (1H, s), broad), 8.20-8.32 (3H, m), 10.30 (1H, s, broad); m/z (ES$^+$) (M+H)$^+$= 377; HPLC t$_R$=1.43 min.

Intermediate BE2: (S)-3-(3-(tert-butyldimethylsilyloxy)azetidin-1-yl)-2-hydroxy-N-(pyridin-2-yl)propanamide Trimethylaluminium (2.384 mL, 4.77 mmol) was added to pyridin-2-amine (0.390 g, 4.15 mmol) in toluene (30 mL) cooled to 0° C. under nitrogen. The resulting solution was stirred at 0° C. for 10 minutes. (S)-methyl 3-(3-(tert-butyldimethylsilyloxy)azetidin-1-yl)-2-hydroxypropanoate (Intermediate AD3) (1.2 g, 4.15 mmol) in toluene (10 mL) was added and the reaction was allowed to warm to room temperature and then heated at 80° C. for 4 hours. The reaction mixture was cooled, 20% Rochelle salt in water (75 mL) added and stirred for 2 hours. The mixture was extracted with ethyl acetate (2×5 mL) and the combined organic extracts washed with water (50 mL) and brine (50 mL), dried (MgSO$_4$), filtered and evaporated. The crude product was purified by flash silica chromatography, elution gradient 0 to 10% MeOH in EtOAc to afford the product (1.25 g).

$^1$H NMR (400 MHz, DMSO-d6) δ 0.03 (6H, s), 0.83 (9H, m), 2.65-2.74 (2H, m), 2.78-2.88 (2H, m), 3.56-3.60 (2H, m), 4.07-4.12 (1H, m), 4.27-4.36 (1H, m), 5.77-5.83 (1H, m), 7.11-7.14 (1H, m), 7.78-7.82 (1H, m), 8.05-8.10 (1H, m), 8.30-8.32 (1H, m), 9.65 (1H, s) m/z (ES) (M+H)$^+$=352; HPLC t$_R$=1.25 min.

Intermediate BF1: 4-chloro-1-(4-methylthiophen-3-yl)-1H-pyrazolo[3,4-d]pyrimidine Phosphoryl trichloride (4.2 mL, 45 mmol) was added in one portion to 1-(4-methylthiophen-3-yl)-1H-pyrazolo[3,4-d]pyrimidin-4-ol (Intermediate BF2) (700 mg, 3.01 mmol). The resulting suspension was heated to 100° C. to give a solution and stirred for 2 hours. The mixture was evaporated and ice added to the residue and stirred for 30 minutes. It was then filtered and the solids washed with water (3×10 mL). The crude product was dissolved in ethyl acetate (40 mL), dried with MgSO$_4$, filtered and evaporated to give the product (700 mg, 93%).

Intermediate BF2: 1-(4-methylthiophen-3-yl)-1H-pyrazolo[3,4-d]pyrimidin-4(7H)-one

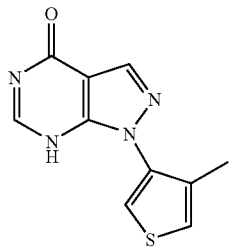

Concentrated sulfuric acid (0.237 mL, 4.46 mmol) was added to a stirred solution of 5-amino-1-(4-methylthiophen-3-yl)-1H-pyrazole-4-carbonitrile (Intermediate BF3) (910 mg, 4.46 mmol) in formic acid (15 mL). The resulting solution was stirred at 100° C. for 20 hours. It was then cooled and evaporated to ~half volume. Water (10 mL) was added and stirred for 1 hour. It was then filtered, washed with water (3×5 mL) and dried under high vacuum at 45° C. to afford the product (700 mg, 67%) which was used without further purification.

$^1$H NMR (400 MHz, DMSO-d6) δ 2.07 (3H, d), 7.36-7.38 (1H, m), 7.77 (1h, d), 8.09 (1H, s), 8.28 (1H, s), 12.31 (1H, s); m/z (ES$^+$) (M+H)$^+$=233; HPLC $t_R$=1.29 min.

Intermediate BF3: 5-amino-1-(4-methylthiophen-3-yl)-1H-pyrazole-4-carbonitrile

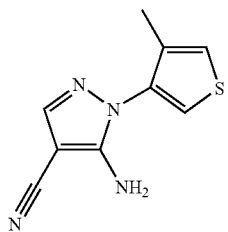

(4-Methylthiophen-3-yl)hydrazine (Intermediate BF4) (910 mg, 7.10 mmol) was suspended in MeOH (30 mL) under nitrogen, 2-(ethoxymethylene)malononitrile (867 mg, 7.10 mmol) added in one portion and the mixture stirred at ambient temperature for 1 hour then heated at reflux for 2 hours. The mixture was cooled, evaporated and dried under high vacuum. The crude product was purified by flash silica chromatography, elution gradient 30 to 100% EtOAc in isohexane to afford the product (780 mg, 54%).

$^1$H NMR (400 MHz, DMSO-d6) δ 1.97 (3H, s), 6.51 (2H, s), 7.34-7.35 (1H, m), 7.69-7.72 (1H, m), 7.73 (1H, s); m/z (ES$^+$) (M+H)$^+$=205; HPLC $t_R$=1.40 min.

Intermediate BF4: (4-methylthiophen-3-yl)hydrazine

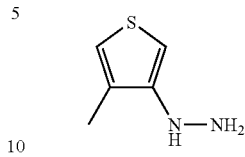

A solution of 4M HCl in dioxane (43.4 mL, 173.55 mmol) was added dropwise to a stirred solution of di-tert-butyl 1-(4-methylthiophen-3-yl)hydrazine-1,2-dicarboxylate (Intermediate BF5) (5.7 g, 17.36 mmol) in isopropanol (50 mL) over a period of 1 minute. The resulting solution was stirred at reflux for 2 hours. The mixture was evaporated, co-evaporated with 1,4-dioxane (3×50 mL) and dried under high vacuum. The residue was suspended in DCM and washed with 1M NaOH. The organic phase was washed with water, dried by passing through a phase separating membrane and evaporated to afford the product (910 mg) which was used without further purification.

$^1$H NMR (400 MHz, DMSO-d6) δ 1.96 (3H, s), 3.85 (2H, s), 6.14 (1H, s), 6.17 (1H, d), 6.91-6.92 (1H, m).

Intermediate BF5: di-tert-butyl 1-(4-methylthiophen-3-yl)hydrazine-1,2-dicarboxylate

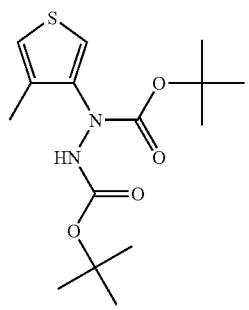

Isopropylmagnesium chloride-lithium chloride complex (0.96M) (40.5 mL, 38.91 mmol) was added to 3-bromo-4-methylthiophene (CAS no. 30318-99-1) (5.3 g, 29.93 mmol) in THF (60 mL) cooled to 0° C. under nitrogen. The resulting solution was warmed to room temperature and stirred for 3 hours. The reaction temperature was cooled to 0° C. and di-tert-butyl azodicarboxylate (10.34 g, 44.90 mmol) in THF (30 mL) was added dropwise maintaining the temperature below 10° C. The reaction was warmed to room temperature and stirred for 20 hours. The reaction mixture was cooled to ~10° C., saturated NH$_4$Cl (150 mL) added, and extracted with EtOAc (3×75 mL). The combined organic layers were dried over MgSO$_4$, filtered and evaporated. The residue was purified by flash silica chromatography, elution gradient 20 to 50% Et2O in isohexane to give the product (7.0 g).

$^1$H NMR (400 MHz, DMSO-d6) δ 1.37-1.40 (18H, m), 2.08 (3H, s), 7.06 (1H, d), 7.26 (1H, d), 8.68 (1H, s)

---

$^1$H NMR (400 MHz, DMSO-d6) δ 2.09 (3H, d), 7.43-7.45 (1H, m), 7.89 (1H, d), 8.72 (1H, s), 8.90 (1H, s); m/z (ES$^-$) (M+H)$^+$=251; HPLC $t_R$=2.26 min.

Intermediate BG1: (S)-3-(3-((tert-butyldiphenylsilyloxy)methyl)azetidin-1-yl)-2-hydroxy-N-(pyridin-2-yl)propanamide

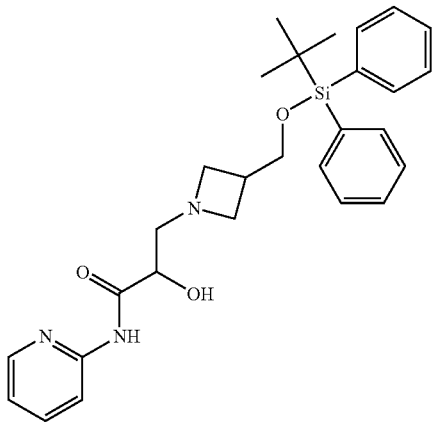

Trimethylaluminium (1.344 mL, 2.69 mmol) was added to pyridin-2-amine (220 mg, 2.34 mmol) in toluene (20 mL) cooled to 0° C. under nitrogen over a period of 10 minutes. The resulting solution was stirred at 0° C. for 10 minutes. (S)-Methyl 3-(3-((tert-butyldiphenylsilyloxy)methyl)azetidin-1-yl)-2-hydroxypropanoate (Intermediate BG2) (1.43 g, 2.34 mmol) in toluene (5 mL) was added over 10 minutes and the reaction was allowed to warm to room temperature and then heated at 110° C. for 2 hours. The reaction mixture was cooled and poured into a 20% solution of Rochelle salt (30 mL), diluted with ethyl acetate (80 mL) and stirred for 1 hour. The organic phase was separated, washed with water and brine, dried over MgSO$_4$ filtered and evaporated. The crude product was purified by flash silica chromatography, elution gradient 0 to 100% (10% MeOH in DCM) in DCM to afford the product (681 mg, 59.5%).

m/z (ES$^-$) (M+H)$^+$=491; HPLC $t_R$=2.67 min.

Intermediate BG2: (S)-methyl 3-(3-((tert-butyldiphenylsilyloxy)methyl)azetidin-1-yl)-2-hydroxypropanoate

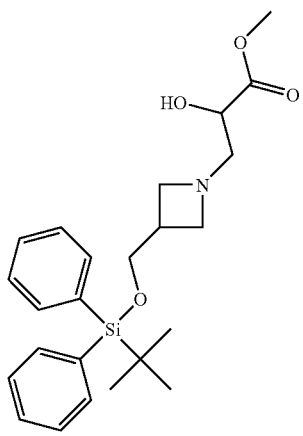

3-((tert-Butyldiphenylsilyloxy)methyl)azetidine (Intermediate BG3) (7.461 g, 22.92 mmol) and (S)-methyl oxirane-2-carboxylate (2.340 g, 22.92 mmol) were dissolved in acetonitrile (50 mL) and heated to 85° C. for 90 minutes. The resulting mixture was cooled and evaporated to dryness. The crude product was purified by flash silica chromatography, elution gradient 0 to 5% MeOH in DCM to afford the product (9.6 g, 56%).

$^1$H (400 MHz, CDCl$_3$) δ 1.05 (9H s), 2.69 (1H, t), 2.73-2.82 (2H, m), 3.08 (2H, q), 3.38 (2H, q), 3.70-3.78 (5H, m), 4.09-4.12 (1H, m), 7.36-7.45 (6H, m), 7.62-7.66 (4H, m); m/z (ES$^+$) (M+H)$^+$=428.41; HPLC $t_R$=2.43 min.

Intermediate BG3: 3-((tert-butyldiphenylsilyloxy)methyl)azetidine

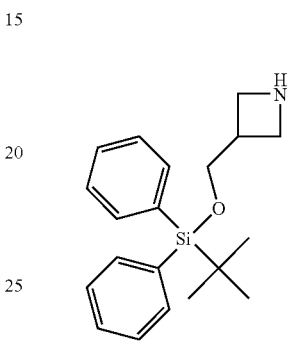

2,2,2-Trifluoroacetic acid (42.9 mL, 556.53 mmol) was added to tert-butyl 3-((tert-butyldiphenylsilyloxy)methyl)azetidine-1-carboxylate (Intermediate BG4) (9.87 g, 23.19 mmol) in anhydrous DCM (50 mL) at 0° C. then allowed to stirred at room temperature for 1 hour. The solution was concentrated and made basic using sodium hydroxide (250 mL, 2M) was added. the suspension was extracted with DCM and dried with Na$_2$SO$_4$ to afford the product (7.46 g, 99%)

$^1$H (400 MHz, CDCl$_3$) δ 1.03-1.07 (9H, m), 2.87-2.95 (1H, m), 3.47-3.51 (2H, m), 3.60 (2H, t), 3.77 (2H, d), 7.35-7.45 (6H, m), 7.62-7.73 (4H, m); m/z (ES$^+$) (M+H)$^+$=326.22; HPLC $t_R$=2.45 min.

Intermediate BG4: tert-butyl 3-((tert-butyldiphenylsilyloxy)methyl)azetidine-1-carboxylate

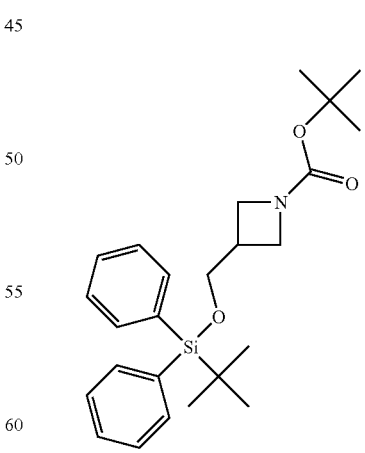

A solution of tert-butylchlorodiphenylsilane (5.56 mL, 21.36 mmol) in DCM (20 mL) was added dropwise to a stirred solution of tert-butyl 3-(hydroxymethyl)azetidine-1-carboxylate (CAS no. 142253-56-3) (4.0 g, 21 mmol) and anhydrous N-ethyl-N-isopropylpropan-2-amine (9.1 mL, 53 mmol) in DCM (45 mL) cooled to 10° C., over a period of 2 minutes under nitrogen. The resulting solution was stirred at ambient temperature for 3 hours 4-dimethylaminopyridine (100 mg) was added and the reaction was left overnight. The reaction mixture was concentrated and diluted with EtOAc (75 mL), and washed sequentially with saturated NaHCO$_3$ (25 mL), water (20 mL) and saturated brine (20 mL). The organic layer was dried over MgSO$_4$, filtered and evaporated to afford the crude product (9.87 g) which was used without further purification.

$^1$H (400 MHz, CDCl$_3$) δ 1.06 (9H, q), 1.44 (9H, d), 2.68 (1H, s), 3.72-3.75 (4H, m), 3.92 (2H, t), 7.36-7.45 (6H, m), 7.63-7.73 (4H, m); HPLC $t_R$=3.75 min.

Intermediate BH1: 4-chloro-1-(2-chloro-6-fluorophenyl)-1H-pyrazolo[3,4-d]pyrimidine

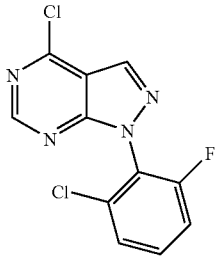

Phosphorus oxychloride (17.54 mL, 188.18 mmol) was added to 1-(2-chloro-6-fluorophenyl)-1H-pyrazolo[3,4-d]pyrimidin-4-ol (Intermediate BH2) (2.49 g, 9.41 mmol). The resulting solution was stirred at 100° C. for 1 hour. The reaction mixture was evaporated. Ice/water (100 mL) and then EtOAc (100 mL) were added. The organic layer was separated and the aqueous layer re-extracted with EtOAc (100 mL). The combined organics were washed with water (100 mL), dried (MgSO$_4$) and concentrated to give the crude product (2.48 g) which was used without further purification.

$^1$H (400 MHz, DMSO-d6) δ 7.60-7.65 (1H, m), 7.67-7.70 (1H, m), 7.75-7.81 (1H, m), 8.89 (1H, s), 8.92-8.95 (1H, m).

Intermediate BH2: 1-(2-chloro-6-fluorophenyl)-1H-pyrazolo[3,4-d]pyrimidin-4-ol

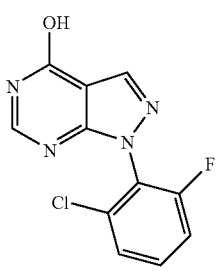

Concentrated sulfuric acid (0.867 mL, 16.27 mmol) was added to a stirred solution of 5-amino-1-(2-chloro-6-fluorophenyl)-1H-pyrazole-4-carbonitrile (Intermediate BH3) (3.5 g, 14.79 mmol) in formic acid (25 mL). The resulting solution was stirred at 100° C. for 24 hours. The reaction was allowed to cool to room temperature and evaporated to approximately half volume, water (100 mL) added and stirred for 1 hour. The formed precipitate was filtered off, washed well with water and dried overnight in a vacuum over P$_2$O$_5$ to afford the product (2.51 g, 64.1%) which was used without further purification.

$^1$H (400 MHz, DMSO-d6) δ 7.53-7.58 (1H, m), 7.61-7.64 (1H, m), 7.68-7.74 (1H, m), 8.09-8.10 (1H, m), 8.41 (1H, s), 12.46 (1H, s); m/z (ES$^+$) (M+H)$^+$=265; HPLC $t_R$=1.79 min.

Intermediate BH3: 5-amino-1-(2-chloro-6-fluorophenyl)-1H-pyrazole-4-carbonitrile

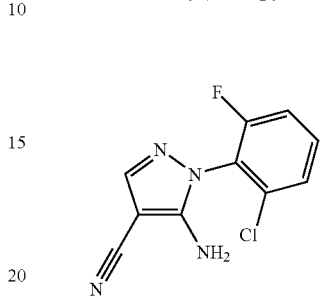

(2-Chloro-6-fluorophenyl)hydrazine hydrochloride (CAS no. 529512-79-6) (5 g, 25.38 mmol) was partitioned between EtOAc (100 mL) and NaOH (2M, aq) (40 mL). The organic layer separated and washed with water (50 mL), brine (50 mL), dried (MgSO$_4$), filtered and concentrated. The resultant oil was suspended in MeOH (50 mL) under nitrogen at -5° C. 2-(Ethoxymethylene)malononitrile (3.10 g, 25.38 mmol) added portionwise over 5 mins and the mixture stirred at ~0° C. for 30 mins. The reaction mixture was allowed to warm to room temperature and then heated at reflux under nitrogen for 2 hours. The reaction mixture was allowed to cool and evaporated to dryness to afford the product (3.52 g) which was used without further purification.

$^1$H (400 MHz, CDCl$_3$) δ 4.51 (2H, s), 7.21-7.26 (1H, m), 7.39-7.42 (1H, m), 7.47-7.53 (1H, m), 7.72 (1H, s); m/z (ES$^+$) (M+H)$^+$=237; HPLC $t_R$=1.54 min.

Intermediate BI1: (S)-3-(3-(tert-butyldimethylsilyloxy)azetidin-1-yl)-2-hydroxy-N-(pyridin-2-yl)propanamide

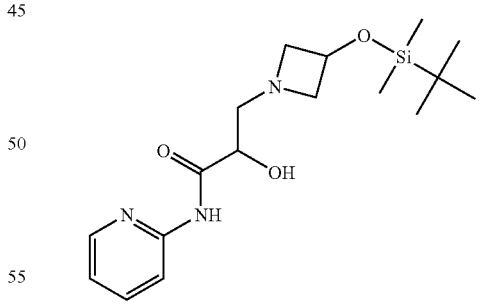

Trimethylaluminium (7.60 mL, 15.20 mmol) was added to pyridin-2-amine (1.431 g, 15.20 mmol) in anhydrous toluene (30 mL) cooled to 0° C. under nitrogen. The resulting solution was stirred at 0° C. for 10 minutes. (S)-Methyl 3-(3-(tert-butyldimethylsilyloxy)azetidin-1-yl)-2-hydroxypropanoate (Intermediate AD3) (2.2 g, 7.60 mmol) in anhydrous toluene (10 mL) was added and the resulting solution was allowed to warm to room temperature and then heated at 80° C. for 4 hours. The mixture was cooled to room temperature, neutralised with Rochelle salt in water (20%, 75 mL), diluted with water (50 mL) and extracted with EtOAc (2×50 mL). The organic phase was separated, washed with brine, dried over MgSO₄, filtered and evaporated. The crude product was purified by flash silica chromatography, elution gradient 20 to 50% EtOAc in isohexane to give impure product. This was shown to contain the starting amine so was re-purified by flash silica chromatography, elution gradient 0 to 10% MeOH in DCM to afford the product (1.928 g, 72.2%).

$^1$H (400 MHz, CDCl$_3$) δ 0.02-0.04 (6H, m), 0.87 (9H s), 2.90-2.92 (2H, m), 3.05 (2H, q), 3.69-3.77 (2H, m), 4.02 (1H, t), 4.41-4.48 (1H, m), 7.03-7.06 (1H, m), 7.67-7.72 (1H, m), 8.19-8.21 (1H, m), 8.30-8.32 (1H, m), 9.78 (1H, s); m/z (ES$^+$) (M+H)$^+$=353.12; HPLC t$_R$=1.93 min.

Intermediate BJ1: (S)-methyl 3-(3-(tert-butyldimethylsilyloxy)azetidin-1-yl)-2-(1-(2,6-dichlorophenyl)-1H-pyrazolo [3,4-d]pyrimidin-4-yloxy)propanoate

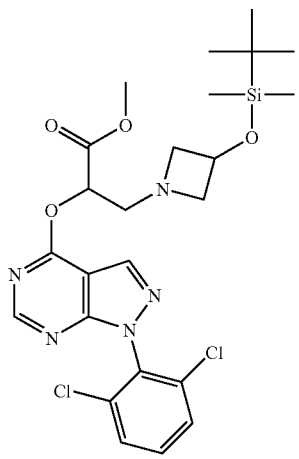

Sodium hydride (60% dispersion in mineral oil) (127 mg, 3.17 mmol) was added to (S)-methyl 3-(3-(tert-butyldimethylsilyloxy)azetidin-1-yl)-2-hydroxypropanoate (Intermediate AD3) (765 mg, 2.64 mmol) in anhydrous THF (30 mL) at 0° C. under nitrogen. The resulting solution was stirred at 0° C. for 10 minutes and then 4-chloro-1-(2,6-dichlorophenyl)-1H-pyrazolo[3,4-d]pyrimidine (Intermediate BA3) (871 mg, 2.91 mmol) was added. The reaction mixture was allowed to warm to room temperature and stirred overnight. The reaction mixture was neutralised with 1M citric acid and the reaction mixture diluted with water (20 mL) and EtOAc (50 mL). The organic layer was separated and the aqueous layer re-extracted with EtOAc (2×50 mL). The combined organics were washed with saturated brine (75 mL),dried (MgSO₄), filtered and concentrated in vacuo. The crude product was purified by flash silica chromatography, elution gradient 50 to 100% EtOAc in isohexane to afford the product (445 mg, 30.5%).

$^1$H (400 MHz, CDCl$_3$) δ 0.05 (6H, s), 0.89 (9H, s), 3.03-3.11 (3H, m), 3.18-3.23 (1H, m), 3.77-3.79 (1H, m), 3.80 (3H, s), 3.86 (1H, d), 4.46 (1H, t), 5.66 (1H, q), 7.45 (1H, t), 7.51-7.55 (2H, m), 8.37 (1H, s), 8.53 (1H, s); m/z (ES$^+$) (M+H)$^+$=554.8; HPLC t$_R$=1.95 min.

Intermediate BK1: 2-(4-chloro-1H-pyrazolo[3,4-d]pyrimidin-1-yl)isophthalonitrile

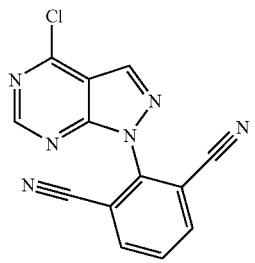

Phosphoryl trichloride (6842 μl, 71.40 mmol) was added to 2-(4-hydroxy-1H-pyrazolo[3,4-d]pyrimidin-1-yl)isophthalonitrile (Intermediate BK2) (1872 mg, 7.14 mmol). The resulting solution was stirred at 100° C. for 4 hours. The reaction mixture was evaporated and ice/water added to the residue. After stirring for 1 hour a precipitate formed that was filtered off and washed with water (3×5 mL) to give a yellow solid. This was dried under high vacuum for 20 hours to give the product (879 mg, 43.9%) which was used without further purification.

$^1$H NMR (400 MHz, DMSO) δ 8.01 (t, 1H), 8.49 (d, 2H), 9.01 (d, 2H); m/z (ES$^-$), (M−H)$^-$=279.15; HPLC t$_R$=2.17 min.

Intermediate BK2: 2-(4-hydroxy-1H-pyrazolo[3,4-d]pyrimidin-1-yl)isophthalonitrile

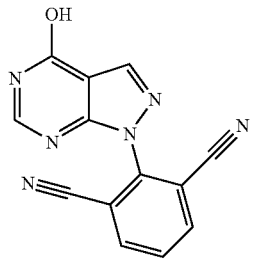

1-(2,6-dibromophenyl)-1H-pyrazolo[3,4-d]pyrimidin-4-ol (Intermediate BK3) (686 mg, 1.85 mmol) and zinc cyanide (392 mg, 3.34 mmol) were dissolved in DMF (9270 μl) and sealed into a microwave tube. The tube was purged with nitrogen. 9,9-Dimethyl-4,5-bis(diphenylphosphino)xanthene (215 mg, 0.37 mmol) and tris(dibenzylideneacetone)dipalladium(0) (170 mg, 0.19 mmol) were added. The reaction was heated to 150° C. for 5 minutes in the microwave reactor and cooled to room temperature. The solvent was evaporated. The crude product was absorbed onto celite and purified by flash silica chromatography, elution gradient 0 to 10% MeOH in DCM to afford the product (420 mg, 86%).

$^1$H NMR (400 MHz, DMSO) δ 8.02 (t, 1H), 8.23 (s, 1H), 8.49 (d, 2H), 8.58 (s, 1H), 12.67 (s, 1H); m/z (ES$^-$) (M−H)$^-$=261.13; HPLC t$_R$=1.42 min.

Intermediate BK3: 1-(2,6-dibromophenyl)-1H-pyrazolo[3,4-d]pyrimidin-4-ol

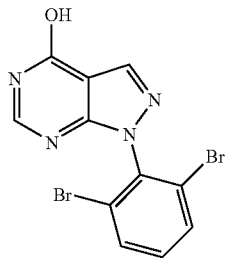

Conc. sulfuric acid (1.323 mL, 24.83 mmol) was added to a stirred solution of 5-amino-1-(2,6-dibromophenyl)-1H-pyrazole-4-carbonitrile (Intermediate BK4) (5.66 g, 16.55 mmol) in formic acid (50 mL). The resulting solution was stirred at 100° C. for 3 hours. The reaction mixture was cooled and evaporated to approximately half volume, water (20 mL) added and stirred for 1 hour. The resulting precipitate was filtered, washed with water (3×10 mL) and dried in vacuo at 50° C. to give the product (3.60 g, 58.8%) which was used without further purification.

$^1$H NMR (400 MHz, DMSO) δ 7.49 (t, 1H), 7.90 (d, 2H), 8.07-8.10 (m, 1H), 8.39 (s, 1H), 12.43 (s, 1H); m/z (ES$^+$), (M+H)$^+$=371.07; HPLC $t_R$=1.92 min.

Intermediate BK4: 5-amino-1-(2,6-dibromophenyl)-1H-pyrazole-4-carbonitrile

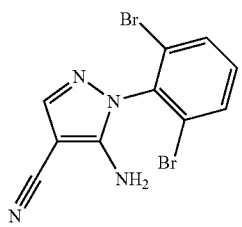

2-(Ethoxymethylene)malononitrile (197 mg, 1.62 mmol) was added portionwise to a stirred solution of (2,6-dibromophenyl)hydrazine (CAS no. 14763-29-2) (430 mg, 1.62 mmol) in MeOH (8085 µl), under nitrogen at 5° C. The resulting solution was allowed to stir for a further 1 hour. The reaction mixture was then heated to reflux and was stirred for 3 hours. The reaction mixture was allowed to cool to ambient temperature, then was evaporated to afford crude product which was used without further purification.

m/z (ES$^-$), (M+H)$^-$=343.06; HPLC $t_R$=1.91 min.

Intermediate BL1: (S)—N-(5-fluoropyridin-2-yl)-2-hydroxy-3-((S)-1-(triisopropylsilyloxy)propan-2-yloxy)propanamide

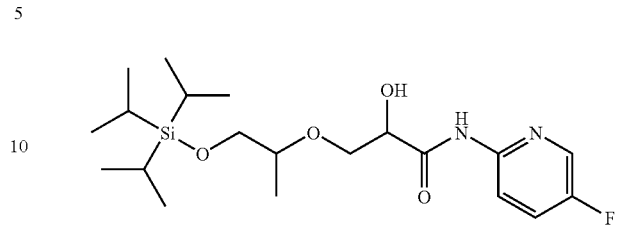

Trimethylaluminium (5.98 mL, 11.96 mmol) was added to 5-fluoropyridin-2-amine (1.340 g, 11.96 mmol) in toluene (20 mL) cooled to 0° C. under nitrogen. The resulting solution was stirred at 0° C. for 20 minutes. (S)-Methyl 2-hydroxy-3-((R)-1-(triisopropylsilyloxy)propan-2-yloxy)propanoate (Intermediate AU5) (2 g, 5.98 mmol) in toluene (6 mL) was added and the reaction was allowed to warm to room temperature and then refluxed for 6 hours. The reaction mixture was allowed to cool and concentrated in vacuo. The residue was neutralised with citric acid (1M, aq) and then diluted with water (25 mL) and extracted with EtOAc (2×50 mL). The combined organics were washed with brine (20 mL), then dried (MgSO$_4$) and evaporated. The crude product was purified by flash silica chromatography, eluting with 30 to 50% EtOAc in isohexane to afford the product (1.863 g, 75%).

$^1$H (400 MHz, CDCl$_3$) δ 1.03-1.17 (24H, m), 3.61-3.68 (3H, m), 3.81-3.85 (1H, m), 4.02-4.06 (1H, m), 4.16 (1H, d), 4.31 (1H, t), 7.40-7.45 (1H, m), 8.14 (1H, d), 8.25-8.28 (1H, m), 9.22 (1H, s); m/z (ES$^+$) (M+H)$^+$=415.31; HPLC $t_R$=3.9 min.

Intermediate BM1: (S)-3-(3-(tert-butyldimethylsilyloxy)azetidin-1-yl)-2-hydroxy-N-(5-methylthiazol-2-yl)propanamide

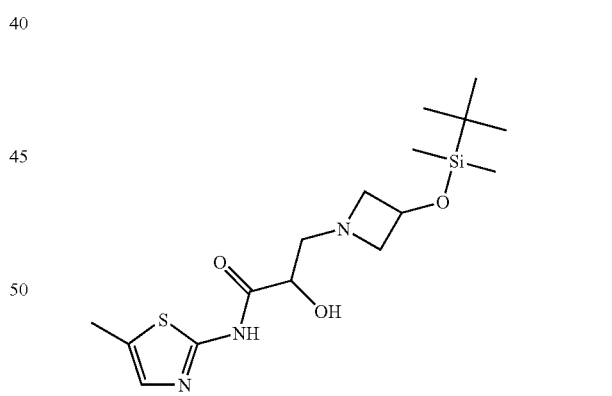

Trimethylaluminium (1M in heptane) (3.97 mL, 3.97 mmol) was added to 5-methylthiazol-2-amine (0.434 g, 3.80 mmol) in DCM (40 mL) cooled to 0° C. under nitrogen. The resulting solution was stirred at 0° C. for 10 minutes. (S)-Methyl 3-(3-(tert-butyldimethylsilyloxy)azetidin-1-yl)-2-hydroxypropanoate (Intermediate AD3) (1 g, 3.45 mmol) in DCM (10 mL) was added and the reaction was allowed to warm to room temperature and then heated at reflux for 2 hours, then left to cool to room temperature overnight. Rochelle solution (20%; 50 mL) was added and the resulting mixture was stirred vigorously for 90 mins. The mixture was diluted with DCM (50 mL) and the layers separated. The organics were dried (MgSO$_4$) and evaporated (733 mg). The residue was purified by flash silica chromatography, elution gradient 0 to 5% MeOH in EtOAc to afford the product (0.300 g, 23.37%).

$^1$H NMR (400 MHz, CDCl$_3$) δ 0.03 (6H, s), 0.87 (9H, s), 2.40 (3H, s), 2.90 (2H, d), 2.99-3.10 (2H, m), 3.66-3.79 (2H, m), 4.04 (1H, t), 4.41-4.50 (1H, m), 7.08-7.10 (1H, m); m/z (ES$^+$) (M+H)$^+$=372.39; HPLC t$_R$=2.13 min.

Intermediate BN1: (S)—N-(5-cyanopyridin-2-yl)-2-hydroxy-3-((R)-1-(triisopropylsilyloxy)propan-2-yloxy)propanamide

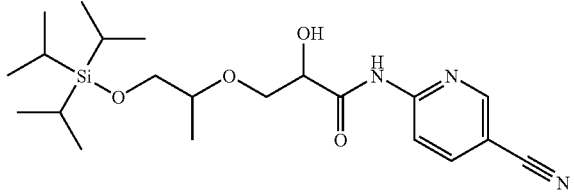

Trimethylaluminium (5.98 mL, 11.96 mmol) was added to 6-aminonicotinonitrile (1.424 g, 11.96 mmol) in toluene (20 mL) cooled to 0° C. under nitrogen. The resulting solution was stirred at 0° C. for 20 minutes. (S)-Methyl 2-hydroxy-3-((R)-1-(triisopropylsilyloxy)propan-2-yloxy)propanoate (Intermediate AU5) (2 g, 5.98 mmol) in toluene (6 mL) was added and the reaction was allowed to warm to room temperature and then refluxed for 6 hours. The reaction mixture was allowed to cool and concentrated in vacuo. The residue was neutralised with citric acid (1M, aq) and then diluted with water (25 mL) and extracted with EtOAc (2×50 mL). The combined organics were washed with brine (20 mL), then dried (MgSO$_4$) and evaporated. The crude product was purified by flash silica chromatography, eluting with 30 to 50% EtOAc in isohexane to afford the product (1.760 g, 69.8%).

$^1$H (400 MHz, CDCl$_3$) δ 1.05-1.18 (27H, m), 1.25 (2H, q), 1.53 (11H, s), 2.04)1H, s), 2.26 (1H, d), 3.63-3.67 (3H, m), 3.81-3.84 (1H, m), 4.08-4.15 (1H, m), 4.32 (2H, d), 7.92-7.95 (1H, m), 8.38-8.40 (1H, m), 8.58 (1H, q), 9.45 (1H, s); m/z (ES$^+$) (M+H)$^+$=422.26; HPLC t$_R$=3.85 min.

Intermediate BO1: (2S)-2-[1-(2-bromo-6-chlorophenyl)pyrazolo [4,5-e]pyrimidin-4-yl]oxy-N-(5-methylpyrazin-2-yl)-3-[(2R)-1-tri(propan-2-yl)silyloxypropan-2-yl]oxypropanamide

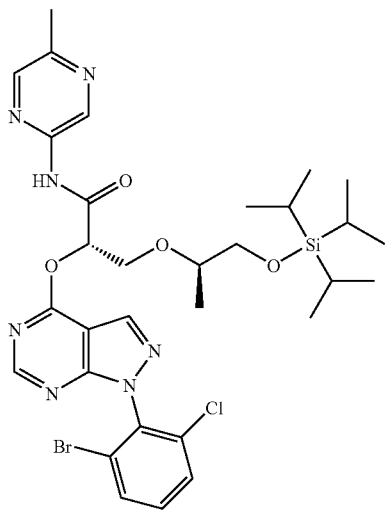

Sodium hydride (0.875 g, 21.87 mmol) was added to (S)-2-hydroxy-N-(5-methylpyrazin-2-yl)-3-((R)-1-(triisopropylsilyloxy)propan-2-yloxy)propanamide (Intermediate AZ2) (3.0 g, 7.29 mmol) in anhydrous THF (35 mL) at 0° C. under nitrogen. The resulting solution was stirred at 0° C. for 10 minutes and then a solution of 1-(2-bromo-6-chlorophenyl)-4-chloro-1H-pyrazolo[3,4-d]pyrimidine (Intermediate BO2) (2.507 g, 7.29 mmol) in anhydrous THF (20 mL) was added dropwise over 1 minute. The mixture was stirred at 0° C. for 10minutes and then allowed to warm to ambient temperature for 6 hours.

It was then cooled to ~0° C., the mixture poured into ice cold 1M citric acid and diluted with EtOAc (50 mL). It was stirred vigorously for 10 minutes. The organic phase was separated, washed with water and brine, dried over MgSO$_4$, filtered and evaporated.

The crude product was purified by flash silica chromatography, elution gradient 20 to 50% EtOAc in isohexane to afford the product (4.90 g, 93%).

1H NMR (400.13 MHz, DMSO-d$_6$) δ 0.88-1.03 (21H, m), 1.09-1.11 (3H, m), 2.44 (3H, s), 3.52-3.57 (1H, m), 3.63-3.67 (1H, m), 3.73-3.78 (1H, m), 4.09-4.18 (2H, m), 5.92-5.98 (1H, m), 7.60-7.64 (1H, m), 7.80-7.83 (1H, m), 7.91-7.93 (1H, m), 8.30-8.31 (1H, m), 8.53-8.54 (1H, m), 8.63 (1H, s), 9.11 (1H, s), 11.19 (1H, s); m/z (ES$^-$) (M−H)$^-$=718; HPLC t$_R$=3.95 min.

Intermediate BO2: 1-(2-bromo-6-chlorophenyl)-4-chloropyrazolo[4,5-e]pyrimidine

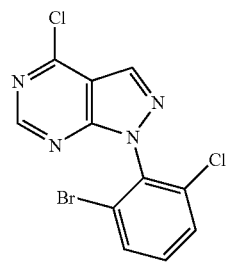

Phosphoryl trichloride (30.4 ml, 326.37 mmol) was added in one portion to 1-(2-bromo-6-chlorophenyl)-1H-pyrazolo [3,4-d]pyrimidin-4-ol (Intermediate AH4) (4.25 g, 13.05 mmol) and the resulting suspension was stirred at 100° C. for 2 hours.

It was then cooled and evaporated. The residue was dissolved in toluene (60 mL), poured onto ice, diluted with ethyl acetate (40 mL) and stirred for 1 hour. The organic phase was separated, washed with water (4×25 mL) and brine (25 mL), dried over MgSO$_4$, filtered and evaporated to a pale yellow oil that crystallised on standing to afford the product (4.3 g, 95%) which was used without further purification.

1H NMR (400.13 MHz, DMSO-d6) δ 7.66 (1H, dd), 7.84 (1H, dd), 7.94 (1H, dd), 8.89 (1H, s), 8.93 (1H, s); m/z (ES$^-$) (M+H)$^+$=345; HPLC t$_R$=2.90 min.

Biological Tests:

The biological effects of the compounds of formula (I) may be tested in the following way:

(1) Enzymatic Activity

Enzymatic activity of recombinant human pancreatic GLK may be measured by incubating GLK, ATP and glucose. The rate of product formation may be determined by coupling the assay to a G-6-P dehydrogenase, NADP/NADPH system and measuring the linear increase with time of optical density at 340 nm as described in Brocklehurst et al (Diabetes 2004, 53, 535-541).

Compounds of the invention generally activate glucokinase with an $EC_{50}$ of less than about 100 μM with the exception of Examples 2, 5, 8, 11, 14, 23, 32, 36 and 76.

Examples of the invention have been found to have the following mean $EC_{50}$s (μM):

| Ex. No. | EC50/ uM |
|---|---|
| 1 | 0.62 |
| 2 | >93 |
| 3 | 0.17 |
| 4 | 3.4 |
| 5 | >100 |
| 6 | 0.68 |
| 7 | 3.7 |
| 8 | 91 |
| 9 | 0.52 |
| 10 | 2.7 |
| 11 | >52 |
| 12 | 2.4 |
| 13 | 1.4 |
| 14 | >82 |
| 15 | 2.7 |
| 16 | 0.29 |
| 17 | 0.064 |
| 18 | 32 |
| 19 | 0.095 |
| 20 | 9.3 |
| 21 | 0.032 |
| 22 | 0.19 |
| 23 | >100 |
| 24 | 0.12 |
| 25 | 1.2 |
| 26 | 35 |
| 27 | 1 |
| 28 | 0.11 |
| 29 | 0.058 |
| 30 | 4.8 |
| 31 | 0.35 |
| 32 | >80 |
| 33 | >1.7 |
| 34 | 1.9 |
| 35 | 2.1 |
| 36 | >82 |
| 37 | 1.3 |
| 38 | 0.02 |
| 39 | 11 |
| 40 | 0.14 |
| 41 | 0.12 |
| 42 | 0.41 |
| 43 | 4.2 |
| 44 | 3.4 |
| 45 | 1.4 |
| 46 | 1.6 |
| 47 | 1 |
| 48 | 11 |
| 49 | 34 |
| 50 | 0.59 |
| 51 | 4.4 |
| 52 | 2.9 |
| 53 | 0.78 |
| 54 | 4 |
| 55 | >20 |
| 56 | 3.1 |
| 57 | 30 |
| 58 | 1.95 |
| 59 | 0.65 |
| 60 | 1.7 |
| 61 | 1.7 |
| 62 | 12 |
| 63 | >4.5 |
| 64 | 10 |
| 65 | >91 |
| 66 | >91 |
| 67 | 2.4 |
| 68 | >8.4 |
| 69 | 0.52 |
| 70 | 15 |
| 71 | 1.6 |
| 72 | 2.9 |
| 73 | >18 |
| 74 | >100 |
| 75 | >100 |
| 76 | >36 |
| 81 | 4.7 |
| 82 | 0.1 |
| 83 | 0.87 |
| 84 | 0.47 |
| 85 | 9.5 |
| 86 | 1.5 |
| 87 | 0.32 |
| 88 | 5.1 |
| 89 | 1.5 |
| 90 | 5.4 |
| 91 | 0.16 |
| 92 | 0.42 |
| 93 | 3.3 |
| 94 | 9.2 |
| 95 | 39 |
| 96 | 1.3 |
| 97 | 1.2 |
| 97a | 0.46 |
| 98 | 0.11 |
| 99 | 9.3 |
| 100 | 1 |
| 101 | 5 |
| 102 | 0.13 |
| 103 | 0.28 |
| 104 | 1.2 |
| 105 | 0.51 |
| 106 | 6.9 |
| 107 | 3.6 |
| 108 | 1.3 |
| 109 | 3.2 |
| 110 | 1 |
| 111 | 0.33 |
| 111a | 0.21 |
| 112 | 0.26 |
| 112a | 0.22 |
| 113 | 0.3 |
| 113a | 0.3 |
| 114 | 2.1 |
| 115 | 0.11 |
| 115a | 0.098 |
| 116 | 2.3 |
| 117 | 6.8 |
| 118 | 0.15 |
| 118a | 0.12 |
| 119 | 1.2 |
| 120 | 0.54 |
| 125 | 0.31 |
| 126 | 0.57 |
| 127 | 6 |
| 127a | 1.1 |
| 127b | 0.84 |
| 127c | 0.67 |
| 127d | 0.67 |
| 127e | 0.55 |
| 127f | 1.1 |

-continued

| Ex. No. | EC50/ uM |
|---|---|
| 127g | 0.3 |
| 127h | 6.4 |
| 127i | 0.36 |
| 127j | 0.58 |
| 127k | 0.56 |
| 127l | 0.5 |
| 128 | 0.92 |
| 128a | 0.62 |
| 129 | 1.3 |
| 130 | 1.1 |
| 131 | 0.41 |
| 132 | 0.47 |
| 133 | 1.1 |
| 134 | 0.44 |
| 135 | 5.9 |
| 136 | 2.1 |
| 137 | 0.35 |
| 138 | 0.81 |
| 139 | 1.4 |
| 140 | 1.2 |
| 141 | 0.34 |
| 142 | 2.4 |
| 143 | 0.18 |
| 143a | 2.6 |
| 143b | 0.26 |
| 143c | 0.61 |
| 143d | 0.59 |
| 143e | 0.53 |
| 143f | 0.98 |
| 144 | 0.51 |
| 145 | 0.23 |
| 146 | 0.96 |
| 147 | 7.8 |
| 148 | 0.93 |
| 149 | 0.66 |
| 150 | 1 |
| 151 | 1.7 |
| 152 | 0.49 |
| 153 | 0.28 |
| 154 | 1.2 |
| 155 | 0.76 |
| 156 | 0.087 |
| 157 | 0.14 |
| 158 | 0.15 |
| 159 | 0.85 |
| 160 | 0.28 |
| 161 | 0.61 |
| 162 | 1.5 |
| 163 | 0.58 |
| 164 | 0.93 |
| 165 | 0.37 |
| 166 | 2.9 |
| 167 | 1.1 |
| 168 | 3.9 |
| 169 | 1.7 |
| 170 | 1.5 |
| 171 | 0.33 |
| 172 | 0.81 |
| 173 | 0.92 |
| 174 | 0.23 |
| 175 | 0.27 |
| 176 | 0.38 |
| 177 | 1.5 |
| 178 | 4.3 |
| 179 | 0.62 |
| 180 | 0.94 |
| 181 | 3.3 |
| 182 | 3 |
| 183 | 7.7 |
| 184 | 1.5 |
| 185 | 3.7 |
| 186 | 1.8 |
| 187 | 1.7 |
| 188 | 1.1 |
| 189 | 0.6 |
| 190 | 0.37 |
| 191 | 0.84 |

-continued

| Ex. No. | EC50/ uM |
|---|---|
| 192 | 0.36 |
| 193 | 3.3 |
| 194 | 0.58 |
| 195 | 2 |
| 196 | 1.7 |
| 197 | 0.6 |
| 198 | 2.2 |
| 199 | 1.1 |
| 200 | 0.44 |
| 201 | 0.65 |
| 202 | 0.34 |
| 203 | 0.83 |
| 204 | 1.3 |
| 205 | 0.24 |
| 206 | 0.57 |
| 207 | 5 |
| 208 | 2.8 |
| 209 | 1.5 |
| 210 | 1.2 |
| 211 | 1.1 |
| 212 | 0.49 |
| 213 | 1.1 |
| 214 | 0.32 |
| 215 | 0.2285 |
| 216 | 0.1634 |
| 217 | 0.4415 |
| 218 | 0.2147 |
| 219 | 0.28 |
| 220 | 0.22 |
| 221 | 0.31 |
| 222 | 0.14 |
| 223 | 0.31 |
| 224 | 0.51 |
| 225 | 0.22 |
| 226 | 0.13 |
| 227 | 0.32 |
| 228 | 0.46 |
| 229 | 0.11 |
| 230 | 0.11 |
| 231 | 0.26 |
| 232 | 0.54 |
| 233 | 0.21 |
| 234 | 0.21 |
| 235 | 0.4 |
| 236 | 0.74 |
| 237 | 0.47 |
| 238 | 0.42 |
| 239 | 0.49 |
| 240 | 0.45 |
| 241 | 0.35 |
| 242 | 0.22 |
| 243 | 0.57 |
| 244 | 0.33 |
| 245 | 0.47 |
| 246 | 0.22 |
| 247 | 0.59 |
| 248 | 0.64 |
| 249 | 0.59 |
| 250 | 0.23 |
| 251 | 0.35 |
| 252 | 0.45 |

The following compounds were also found to have a mean $EC_{50}$ of more than about 100 μM:

2-[1-(2-chlorophenyl)pyrazolo[4,5-e]pyrimidin-4-yl]sulfanyl-N-(5-methyl-2-pyridyl)octanamide;

2-[1-(2-chlorophenyl)pyrazolo[4,5-e]pyrimidin-4-yl]sulfanyl-4-(2-methoxyethoxy)-N-(5-methyl-2-pyridyl)butanamide;

2-(1-methylpyrazolo[4,5-e]pyrimidin-4-yl)oxy-N-(5-methyl-2-pyridyl)-4-methylsulfonyl-butanamide;

(R)-4-methoxy-N-(5-methyl-2-pyridyl)-2-[1-(2-pyridyl)pyrazolo[4,5-e]pyrimidin-4-yl]oxy-butanamide;

(R)-2-[1-(2-methoxyphenyl)pyrazolo[4,5-e]pyrimidin-4-yl]oxy-N-(5-methyl-2-pyridyl)propanamide;
2-[1-(2-chlorophenyl)pyrazolo[4,5-e]pyrimidin-4-yl]oxy-3-isopropoxy-N-(5-methyl-1,3,4-oxadiazol-2-yl)propanamide;
2-[1-(2-chlorophenyl)pyrazolo[4,5-e]pyrimidin-4-yl]oxy-N-(4-cyano-2-pyridyl)-3-isopropoxy-propanamide;
2-[1-(2-chlorophenyl)pyrazolo[4,5-e]pyrimidin-4-yl]oxy-3-isopropoxy-N-pyrimidin-2-yl-propanamide;
(2S)-2-[1-(3-chloro-2-pyridyl)pyrazolo[4,5-e]pyrimidin-4-yl]oxy-3-isopropoxy-N-(3-methyl-2-pyridyl)propanamide;
(2S)-2-[1-(3-chloro-2-pyridyl)pyrazolo[4,5-e]pyrimidin-4-yl]oxy-3-isopropoxy-N-(4-methoxy-2-pyridyl)propanamide;
(2S)-2-[1-(3-chloro-2-pyridyl)pyrazolo[4,5-e]pyrimidin-4-yl]oxy-N-(1,5-dimethyl-1,2,4-triazol-3-yl)-3-isopropoxy-propanamide.

Production of Recombinant GLK:

Human GLK was obtained by PCR from human pancreatic mRNA respectively, using established techniques described in Sambrook J, Fritsch E F & Maniatis T, 1989. PCR primers were designed according to the GLK cDNA sequences shown in Tanizawa et al 1991 and Bonthron, D. T. et at 1994 (later corrected in Warner, J. P. 1995).

Cloning in Bluescript II Vectors

GLK was cloned in *E. coli* using pBluescript II, (Short et al 1998) a recombinant cloning vector system similar to that employed by Yanisch-Perron C et at (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

Transformations

*E. Coli* transformations were generally carried out by electroporation. 400 mL cultures of strains DH5a or BL21(DE3) were grown in L-broth to an OD 600 of 0.5 and harvested by centrifugation at 2,000 g. The cells were washed twice in ice-cold deionised water, resuspended in 1 mL 10% glycerol and stored in aliquots at −70° C. Ligation mixes were desalted using Millipore V Series™ membranes (0.0025 mm) pore size). 40 mL of cells were incubated with 1 mL of ligation mix or plasmid DNA on ice for 10 minutes in 0.2 cm electroporation cuvettes, and then pulsed using a Gene Pulser™ apparatus (BioRad) at 0.5 kVcm$^{-1}$, 250 mF. Transformants were selected on L-agar supplemented with tetracyline at 10 mg/mL or ampicillin at 100 mg/mL.

Expression

GLK was expressed from the vector pTB375NBSE in *E. coli* BL21 cells, producing a recombinant protein containing a 6-His tag immediately adjacent to the N-terminal methionine. Alternatively, another suitable vector is pET21(+)DNA, Novagen, Cat number 697703. The 6-His tag was used to allow purification of the recombinant protein on a column packed with nickel-nitrilotriacetic acid agarose purchased from Qiagen (cat no 30250).

(2) Oral Glucose Tolerance Test (OGTT) or Glucose Profile

Oral glucose tolerance tests were done on conscious Zucker obese fa/fa rats (age 12-13 weeks or older). The animals were fasted for 2 hours before use for experiments. A test compound or a vehicle was given orally 120 minutes before oral administration of a glucose solution at a dose of 2 g/kg body weight. Blood glucose levels were measured using a Accucheck glucometer from tail bled samples taken at different time points before and after administration of glucose (time course of 60 minutes). A time curve of the blood glucose levels was generated and the area-under-the-curve (AUC) for 120 minutes was calculated (the time of glucose administration being time zero). Percent reduction in glucose excursion was determined using the AUC in the vehicle-control group as zero percent reduction.

For Glucose profile a test compound or vehicle was given 60 minutes before conscious Zucker obese fa/fa rats (age 12-13 weeks or older) entered a dark cycle (12-hours). Blood glucose mevels were measured using a Accucheck glucometer from tail bled samples taken at different time points during the 12-hour dark cycle. A time curve of the blood glucose levels was generated and the area-under-the-curve (AUC) for 12-hours was calculated (the beginning of the dark cycle being time zero). Percent reduction in glucose excursion was determined using the AUC in the vehicle-control group as zero percent reduction.

The invention claimed is:

1. A compound or a pharmaceutically acceptable salt thereof, selected from the group consisting of, 2-{[1-(2-chlorophenyl)-1H-pyrazolo[3,4-d]pyrimidin-4-yl]oxy}-3-methoxy-N-(5-methylpyridin-2-yl)propanamide;
(R)-2-{[1-(2-chlorophenyl)-1H-pyrazolo[3,4-d]pyrimidin-4-yl]oxy}-3-methoxy-N-(5-methylpyridin-2-yl)propanamide;
(S)-2-{[1-(2-chlorophenyl)-1H-pyrazolo[3,4-d]pyrimidin-4-yl]oxy}-3-methoxy-N-(5-methylpyridin-2-yl)propanamide;
3-methoxy-2-{[1-(2-methoxyphenyl)-1H-pyrazolo[3,4-d]pyrimidin-4-yl]oxy}-N-(5-methylpyridin-2-yl)propanamide;
(R)-3-methoxy-2-{[1-(2-methoxyphenyl)-1H-pyrazolo[3,4-d]pyrimidin-4-yl]oxy}-N-(5-methylpyridin-2-yl)propanamide;
(S)-3-methoxy-2-{[1-(2-methoxyphenyl)-1H-pyrazolo[3,4-d]pyrimidin-4-yl]oxy}-N-(5-methylpyridin-2-yl)propanamide;
2-{[1-(2,4-dichlorophenyl)-1H-pyrazolo[3,4-d]pyrimidin-4-yl]oxy}-3-methoxy-N-(5-methylpyridin-2-yl)propanamide;
3-methoxy-2-[(1-methyl-1H-pyrazolo[3,4-d]pyrimidin-4-yl)oxy]-N-(5-methylpyridin-2-yl)propanamide;
2-{[1-(2-chlorophenyl)-1H-pyrazolo[3,4-d]pyrimidin-4-yl]oxy}-N-(5-methylpyridin-2-yl)-4-(methylsulfonyl)butanamide;
2-{[1-(2-methoxyphenyl)-1H-pyrazolo[3,4-d]pyrimidin-4-yl]oxy}-N-(5-methylpyridin-2-yl)-4-(methylsulfonyl)butanamide;
(R)-2-{[1-(2-methoxyphenyl)-1H-pyrazolo[3,4-d]pyrimidin-4-yl]oxy}-N-(5-methylpyridin-2-yl)-4-(methylsulfonyl)butanamide;
(S)-2-{[1-(2-methoxyphenyl)-1H-pyrazolo[3,4-d]pyrimidin-4-yl]oxy}-N-(5-methylpyridin-2-yl)-4-(methylsulfonyl)butanamide;
4-methoxy-2-{[1-(3-methoxyphenyl)-1H-pyrazolo[3,4-d]pyrimidin-4-yl]oxy}-N-(5-methylpyridin-2-yl)butanamide;
(R)-4-methoxy-2-{[1-(3-methoxyphenyl)-1H-pyrazolo[3,4-d]pyrimidin-4-yl]oxy}-N-(5-methylpyridin-2-yl)butanamide;
(S)-4-methoxy-2-{[1-(3-methoxyphenyl)-1H-pyrazolo[3,4-d]pyrimidin-4-yl]oxy}-N-(5-methylpyridin-2-yl)butanamide;
4-methoxy-2-{[1-(2-methylphenyl)-1H-pyrazolo[3,4-d]pyrimidin-4-yl]oxy}-N-(5-methylpyridin-2-yl)butanamide;

(S)-4-methoxy-2-{[1-(2-methylphenyl)-1H-pyrazolo[3,4-d]pyrimidin-4-yl]oxy}-N-(5-methylpyridin-2-yl)butanamide;
(R)-4-methoxy-2-{[1-(2-methylphenyl)-1H-pyrazolo[3,4-d]pyrimidin-4-yl]oxy}-N-(5-methylpyridin-2-yl)butanamide;
2-{[1-(2-chlorophenyl)-1H-pyrazolo[3,4-d]pyrimidin-4-yl]oxy}-4-methoxy-N-(5-methylpyridin-2-yl)butanamide;
(R)-2-{[1-(2-chlorophenyl)-1H-pyrazolo[3,4-d]pyrimidin-4-yl]oxy}-4-methoxy-N-(5-methylpyridin-2-yl)butanamide;
(S)-2-{[1-(2-chlorophenyl)-1H-pyrazolo[3,4-d]pyrimidin-4-yl]oxy}-4-methoxy-N-(5-methylpyridin-2-yl)butanamide;
4-methoxy-2-{[1-(2-methoxyphenyl)-1H-pyrazolo[3,4-d]pyrimidin-4-yl]oxy}-N-(5-methylpyridin-2-yl)butanamide;
(R)-4-methoxy-2-{[1-(2-methoxyphenyl)-1H-pyrazolo[3,4-d]pyrimidin-4-yl]oxy}-N-(5-methylpyridin-2-yl)butanamide;
(S)-4-methoxy-2-{[1-(2-methoxyphenyl)-1H-pyrazolo[3,4-d]pyrimidin-4-yl]oxy}-N-(5-methylpyridin-2-yl)butanamide;
2-{[1-(2,4-difluorophenyl)-1H-pyrazolo[3,4-d]pyrimidin-4-yl]oxy}-4-methoxy-N-(5-methylpyridin-2-yl)butanamide;
(R)-2-{[1-(2,4-difluorophenyl)-1H-pyrazolo[3,4-d]pyrimidin-4-yl]oxy}-4-methoxy-N-(5-methylpyridin-2-yl)butanamide;
(S)-2-{[1-(2,4-difluorophenyl)-1H-pyrazolo[3,4-d]pyrimidin-4-yl]oxy}-4-methoxy-N-(5-methylpyridin-2-yl)butanamide;
4-methoxy-N-(5-methylpyridin-2-yl)-2-({1-[2-(trifluoromethyl)phenyl]-1H-pyrazolo[3,4-d]pyrimidin-4-yl}oxy)butanamide;
(S)-4-methoxy-N-(5-methylpyridin-2-yl)-2-({1-[2-(trifluoromethyl)phenyl]-1H-pyrazolo[3,4-d]pyrimidin-4-yl}oxy)butanamide;
(R)-4-methoxy-N-(5-methylpyridin-2-yl)-2-({1-[2-(trifluoromethyl)phenyl]-1H-pyrazolo[3,4-d]pyrimidin-4-yl}oxy)butanamide;
4-methoxy-2-{[1-(3-methylphenyl)-1H-pyrazolo[3,4-d]pyrimidin-4-yl]oxy}-N-(5-methylpyridin-2-yl)butanamide;
(R)-4-methoxy-2-{[1-(3-methylphenyl)-1H-pyrazolo[3,4-d]pyrimidin-4-yl]oxy}-N-(5-methylpyridin-2-yl)butanamide;
(S)-4-methoxy-2-{[1-(3-methylphenyl)-1H-pyrazolo[3,4-d]pyrimidin-4-yl]oxy}-N-(5-methylpyridin-2-yl)butanamide;
4-methoxy-N-(5-methylpyridin-2-yl)-2-[(1-pyridin-2-yl-1H-pyrazolo[3,4-d]pyrimidin-4-yl)oxy]butanamide;
4-methoxy-2-{[1-(2-methoxyphenyl)-1H-pyrazolo[3,4-d]pyrimidin-4-yl]oxy}-N-(4-methyl-1,3-thiazol-2-yl)butanamide;
(R)-4-methoxy-2-{[1-(2-methoxyphenyl)-1H-pyrazolo[3,4-d]pyrimidin-4-yl]oxy}-N-(4-methyl-1,3-thiazol-2-yl)butanamide;
(S)-4-methoxy-2-{[1-(2-methoxyphenyl)-1H-pyrazolo[3,4-d]pyrimidin-4-yl]oxy}-N-(4-methyl-1,3-thiazol-2-yl)butanamide;
2-{[1-(2-chlorophenyl)-1H-pyrazolo[3,4-d]pyrimidin-4-yl]oxy}-N-(5-methylpyridin-2-yl)hexanamide;
2-[(1-methyl-1H-pyrazolo[3,4-d]pyrimidin-4-yl)oxy]-N-(5-methylpyridin-2-yl)hexanamide;
2-{[1-(2-chlorophenyl)-1H-pyrazolo[3,4-d]pyrimidin-4-yl]oxy}-N-(5-methylpyrazin-2-yl)hexanamide;
2-{[1-(2-chlorophenyl)-1H-pyrazolo[3,4-d]pyrimidin-4-yl]thio}-N-(4-methyl-1,3-thiazol-2-yl)hexanamide;
2-{[1-(2-methoxyphenyl)-1H-pyrazolo[3,4-d]pyrimidin-4-yl]oxy}-N-(5-methylpyridin-2-yl)butanamide;
(2R)-2-{[1-(2-methoxyphenyl)-1H-pyrazolo[3,4-d]pyrimidin-4-yl]oxy}-N-(5-methylpyridin-2-yl)butanamide;
2-{[1-(2-methoxyphenyl)-1H-pyrazolo[3,4-d]pyrimidin-4-yl]oxy}-N-(5-methylpyridin-2-yl)propanamide;
(2S)-2-{[1-(2-chlorophenyl)-1H-pyrazolo[3,4-d]pyrimidin-4-yl]oxy}-4-(dimethylamino)-N-(5-methylpyridin-2-yl)butanamide;
3-acetamido-2-{[1-(2-chlorophenyl)-1H-pyrazolo[3,4-d]pyrimidin-4-yl]oxy}-N-(4-methyl-1,3-thiazol-2-yl)propanamide;
4-{[1-(2-chlorophenyl)-1H-pyrazolo[3,4-d]pyrimidin-4-yl]oxy}-5-[(5-methylpyridin-2-yl)amino]-5-oxopentanoic acid;
2-{[1-(2-chlorophenyl)-1H-pyrazolo[3,4-d]pyrimidin-4-yl]oxy}-N1-(5-methylpyridin-2-yl)pentanediamide;
2-{[1-(2-chlorophenyl)-1H-pyrazolo[3,4-d]pyrimidin-4-yl]oxy}-N5-methyl-N1-(5-methylpyridin-2-yl)pentanediamide;
2-{[1-(2-chlorophenyl)-1H-pyrazolo[3,4-d]pyrimidin-4-yl]thio}-4-(2-methoxyethoxy)-N-(4-methyl-1,3-thiazol-2-yl)butanamide;
2-{[1-(2-chlorophenyl)-1H-pyrazolo[3,4-d]pyrimidin-4-yl]thio}-4-methoxy-N-(4-methyl-1,3-thiazol-2-yl)butanamide;
2-{[1-(2-chlorophenyl)-1H-pyrazolo[3,4-d]pyrimidin-4-yl]thio}-3-methyl-N-(4-methyl-1,3-thiazol-2-yl)pentanamide;
2-{[1-(2-chlorophenyl)-1H-pyrazolo[3,4-d]pyrimidin-4-yl]thio}-N-isoxazol-3-yl-3-methylpentanamide;
2-{[1-(2-chlorophenyl)-1H-pyrazolo[3,4-d]pyrimidin-4-yl]thio}-3-methyl-N-(5-methylpyridin-2-yl)pentanamide;
2-[(1-isopropyl-1H-pyrazolo[3,4-d]pyrimidin-4-yl)thio]-4-(2-methoxyethoxy)-N-(5-methylpyridin-2-yl)butanamide;
2-[(1-isopropyl-1H-pyrazolo[3,4-d]pyrimidin-4-yl)thio]-4-(2-methoxyethoxy)-N-(5-methylpyridin-2-yl)butanamide;
2-{[1-(2-chlorophenyl)-1H-pyrazolo[3,4-d]pyrimidin-4-yl]thio}-N-(4-methyl-1,3-thiazol-2-yl)hexanamide;
2-{[1-(2-chlorophenyl)-1H-pyrazolo[3,4-d]pyrimidin-4-yl]thio}-N-isoxazol-3-ylhexanamide;
2-{[1-(2-Chlorophenyl)-1H-pyrazolo[3,4-d]pyrimidin-4-yl]thio}-4-(2-methoxyethoxy)-N-(4-methyl-1,3-thiazol-2-yl)butanamide;
2-{[1-(2-Chlorophenyl)-1H-pyrazolo[3,4-d]pyrimidin-4-yl]thio}-3-methoxy-N-(5-methylpyridin-2-yl)propanamide;
2-{[1-(2-chlorophenyl)-1H-pyrazolo[3,4-d]pyrimidin-4-yl]thio}-N-(4-methyl-1,3-thiazol-2-yl)octanamide;
2-{[1-(2-chlorophenyl)-1H-pyrazolo[3,4-d]pyrimidin-4-yl]thio}-N-isoxazol-3-yloctanamide;
2-ethoxy-2-{[1-(2-methoxyphenyl)-1H-pyrazolo[3,4-d]pyrimidin-4-yl]thio}-N-(4-methyl-1,3-thiazol-2-yl)acetamide;
2-ethoxy-N-isoxazol-3-yl-2-{[1-(2-methoxyphenyl)-1H-pyrazolo[3,4-d]pyrimidin-4-yl]thio}acetamide;
2-[(1-isopropyl-1H-pyrazolo[3,4-d]pyrimidin-4-yl)oxy]-4-methoxy-N-(5-methylpyridin-2-yl)butanamide;
(R)-2-{[1-(2-chlorophenyl)-1H-pyrazolo[3,4-d]pyrimidin-4-yl]thio}-N-(4-methyl-1,3-thiazol-2-yl)hexanamide;

(S)-2-{[1-(2-chlorophenyl)-1H-pyrazolo[3,4-d]pyrimidin-4-yl]thio}-N-(4-methyl-1,3-thiazol-2-yl)hexanamide;
2-(1-(2-chlorophenyl)-1H-pyrazolo[3,4-d]pyrimidin-4-yloxy)-3-methyl-N-(5-methylpyridin-2-yl)butanamide;
(2S)-2-(1-(2-chlorophenyl)-1H-pyrazolo[3,4-d]pyrimidin-4-yloxy)-3-methyl-N-(5-methylpyridin-2-yl)butanamide;
(2R)-2-(1-(2-chlorophenyl)-1H-pyrazolo[3,4-d]pyrimidin-4-yloxy)-3-methyl-N-(5-methylpyridin-2-yl)butanamide;
(2S)-2-(1-(3-chloropyridin-2-yl)-1H-pyrazolo[3,4-d]pyrimidin-4-yloxy)-3-methyl-N-(5-methylpyridin-2-yl)butanamide;
(2S)-2-(1-(2-chlorophenyl)-1H-pyrazolo[3,4-d]pyrimidin-4-yloxy)-3-methoxy-N-(5-methylpyridin-2-yl)propanamide;
(2R)-2-(1-(2-chlorophenyl)-1H-pyrazolo[3,4-d]pyrimidin-4-yloxy)-3-methoxy-N-(5-methylpyridin-2-yl)propanamide;
(2S)-2-(1-(3-chloropyridin-2-yl)-1H-pyrazolo[3,4-d]pyrimidin-4-yloxy)-3-methoxy-N-(5-methylpyridin-2-yl)propanamide;
(2S)-2-(1-(3-chloropyridin-2-yl)-1H-pyrazolo[3,4-d]pyrimidin-4-yloxy)-3-methoxy-N-(5-methylpyrazin-2-yl)propanamide;
(2S)-2-(1-(3-chloropyridin-2-yl)-1H-pyrazolo[3,4-d]pyrimidin-4-yloxy)-3-isopropoxy-N-(5-methylpyridin-2-yl)propanamide;
(2S)-2-(1-(3-chloropyridin-2-yl)-1H-pyrazolo[3,4-d]pyrimidin-4-yloxy)-3-isopropoxy-N-(5-methylpyrazin-2-yl)propanamide;
(2S)-2-(1-(3-chloropyridin-2-yl)-1H-pyrazolo[3,4-d]pyrimidin-4-yloxy)-3-isopropoxy-N-(3-methyl-1,2,4-thiadiazol-5-yl)propanamide;
(2S)-2-(1-(3-chloropyridin-2-yl)-1H-pyrazolo[3,4-d]pyrimidin-4-yloxy)-3-methyl-N-(5-methylpyrazin-2-yl)butanamide;
(2S)-2-(1-(2-chloro-4-fluorophenyl)-1H-pyrazolo[3,4-d]pyrimidin-4-yloxy)-3-methoxy-N-(5-methylpyrazin-2-yl)propanamide;
(2S)-2-(1-(2-chloro-4-fluorophenyl)-1H-pyrazolo[3,4-d]pyrimidin-4-yloxy)-3-methoxy-N-(5-methylpyridin-2-yl)propanamide;
(2S)-2-(1-(2-cyanophenyl)-1H-pyrazolo[3,4-d]pyrimidin-4-yloxy)-3-methoxy-N-(5-methylpyridin-2-yl)propanamide;
(2S)-2-(1-(2-chlorophenyl)-1H-pyrazolo[3,4-d]pyrimidin-4-yloxy)-3-isopropoxy-N-(5-methylpyridin-2-yl)propanamide;
(2R)-2-(1-(2-chlorophenyl)-1H-pyrazolo[3,4-d]pyrimidin-4-yloxy)-3-isopropoxy-N-(5-methylpyridin-2-yl)propanamide; and/or
(2S)-2-[1-(2-cyanophenyl)pyrazolo[4,5-e]pyrimidin-4-yl]oxy-N-(5-methylpyridin-2-yl)-3-propan-2-yloxypropanamide;
(2S)-2-[1-(2-chlorophenyl)pyrazolo[4,5-e]pyrimidin-4-yl]oxy-N-(3-methyl-1,2,4-thiadiazol-5-yl)-3-propan-2-yloxypropanamide;
(2S)-2-(1-(2-chlorophenyl)-1H-pyrazolo[3,4-d]pyrimidin-4-yloxy)-3-methoxy-N-(3-methyl-1,2,4-thiadiazol-5-yl)propanamide;
(2S)-2-(1-(3-chloropyridin-2-yl)-1H-pyrazolo[3,4-d]pyrimidin-4-yloxy)-4-methoxy-N-(5-methylpyridin-2-yl)butanamide;
(2S)-2-[1-(3-chloropyridin-2-yl)pyrazolo[4,5-e]pyrimidin-4-yl]oxy-3-ethoxy-N-(5-methylpyridin-2-yl)propanamide;
(2S)-2-[1-(3-chloropyridin-2-yl)pyrazolo[4,5-e]pyrimidin-4-yl]oxy-3-ethoxy-N-(5-methylpyrazin-2-yl)propanamide;
(2S)-2-[1-(2-chlorophenyl)pyrazolo[4,5-e]pyrimidin-4-yl]oxy-3-ethoxy-N-(5-methylpyrazin-2-yl)propanamide;
(2S)-3-isopropoxy-N-(5-methylpyrazin-2-yl)-2-(1-(3-methylpyrazin-2-yl)-1H-pyrazolo[3,4-d]pyrimidin-4-yloxy)propanamide;
(S)-3-methoxy-N-(5-methylpyridin-2-yl)-2-(1-phenyl-1H-pyrazolo[3,4-d]pyrimidin-4-yloxy)propanamide;
2-[1-(2-chlorophenyl)pyrazolo[4,5-e]pyrimidin-4-yl]oxy-3-isopropoxy-N-pyrazin-2-yl-propanamide;
2-[1-(2-chlorophenyl)pyrazolo[4,5-e]pyrimidin-4-yl]oxy-3-isopropoxy-N-(5-methyl-1,3,4-thiadiazol-2-yl)propanamide;
2-[1-(2-chlorophenyl)pyrazolo[4,5-e]pyrimidin-4-yl]oxy-3-isopropoxy-N-(5-methylisoxazol-3-yl)propanamide;
2-[1-(2-chlorophenyl)pyrazolo[4,5-e]pyrimidin-4-yl]oxy-3-isopropoxy-N-(5-methylthiazol-2-yl)propanamide;
2-[1-(2-chlorophenyl)pyrazolo[4,5-e]pyrimidin-4-yl]oxy-N-(5-fluoro-2-pyridyl)-3-isopropoxy-propanamide;
2-[1-(2-chlorophenyl)pyrazolo[4,5-e]pyrimidin-4-yl]oxy-N-(5-cyano-2-pyridyl)-3-isopropoxy-propanamide;
2-[1-(2-chlorophenyl)pyrazolo[4,5-e]pyrimidin-4-yl]oxy-3-isopropoxy-N-(1,2,4-thiadiazol-5-yl)propanamide;
2-[1-(2-chlorophenyl)pyrazolo[4,5-e]pyrimidin-4-yl]oxy-N-(5-chloro-2-pyridyl)-3-isopropoxy-propanamide;
2-[1-(2-chlorophenyl)pyrazolo[4,5-e]pyrimidin-4-yl]oxy-3-isopropoxy-N-(4-methyl-2-pyridyl)propanamide;
2-[1-(2-chlorophenyl)pyrazolo[4,5-e]pyrimidin-4-yl]oxy-3-isopropoxy-N-(1,3,4-thiadiazol-2-yl)propanamide;
2-[1-(2-chlorophenyl)pyrazolo[4,5-e]pyrimidin-4-yl]oxy-3-isopropoxy-N-(2-pyridyl)propanamide;
2-[1-(2-chlorophenyl)pyrazolo[4,5-e]pyrimidin-4-yl]oxy-3-isopropoxy-N-isoxazol-3-yl-propanamide;
2-[1-(2-chlorophenyl)pyrazolo[4,5-e]pyrimidin-4-yl]oxy-3-isopropoxy-N-pyrimidin-4-yl-propanamide;
(2S)-2-[1-(2-chlorophenyl)pyrazolo[4,5-e]pyrimidin-4-yl]oxy-3-isopropoxy-N-(5-methylthiazol-2-yl)propanamide;
(2S)-2-[1-(2-chlorophenyl)pyrazolo[4,5-e]pyrimidin-4-yl]oxy-N-(5-fluoro-2-pyridyl)-3-isopropoxy-propanamide;
(2S)-2-[1-(2-chlorophenyl)pyrazolo[4,5-e]pyrimidin-4-yl]oxy-N-(5-cyano-2-pyridyl)-3-isopropoxy-propanamide;
(2S)-2-[1-(2-chlorophenyl)pyrazolo[4,5-e]pyrimidin-4-yl]oxy-N-(5-chloro-2-pyridyl)-3-isopropoxy-propanamide;
(2S)-2-[1-(2-chlorophenyl)pyrazolo[4,5-e]pyrimidin-4-yl]oxy-3-isopropoxy-N-(2-pyridyl)propanamide;
(2S)-3-isopropoxy-N-(5-methylpyridin-2-yl)-2-(1-(3-methylpyridin-2-yl)-1H-pyrazolo[3,4-d]pyrimidin-4-yloxy)propanamide;
(2S)-3-isopropoxy-N-(5-methylpyridin-2-yl)-2-(1-(3-(trifluoromethyl)pyridin-2-yl)-1H-pyrazolo[3,4-d]pyrimidin-4-yloxy)propanamide;
(2S)-2-[1-(3-chloro-2-pyridyl)pyrazolo[4,5-e]pyrimidin-4-yl]oxy-3-isopropoxy-N-(6-methylpyridazin-3-yl)propanamide;
(2S)—N-(5-cyanopyridin-2-yl)-3-isopropoxy-2-(1-(3-methylpyridin-2-yl)-1H-pyrazolo[3,4-d]pyrimidin-4-yloxy)propanamide;

(2S)—N-(5-chloropyridin-2-yl)-3-isopropoxy-2-(1-(3-methylpyridin-2-yl)-1H-pyrazolo[3,4-d]pyrimidin-4-yloxy)propanamide;

(2S)-2-[1-(3-chloro-2-pyridyl)pyrazolo[4,5-e]pyrimidin-4-yl]oxy-N-(5-cyano-2-pyridyl)-3-ethoxy-propanamide;

(2S)-2-[1-(3-chloro-2-pyridyl)pyrazolo[4,5-e]pyrimidin-4-yl]oxy-3-ethoxy-N-(5-fluoro-2-pyridyl)propanamide;

(2S)-2-[1-(3-chloro-2-pyridyl)pyrazolo[4,5-e]pyrimidin-4-yl]oxy-3-ethoxy-N-(2-pyridyl)propanamide;

(2S)-2-[1-(3-chloro-2-pyridyl)pyrazolo[4,5-e]pyrimidin-4-yl]oxy-3-ethoxy-N-pyrimidin-4-yl-propanamide;

(2S)—N-(5-chloro-2-pyridyl)-2-[1-(3-chloro-2-pyridyl)pyrazolo[4,5-e]pyrimidin-4-yl]oxy-3-ethoxy-propanamide;

(2S)-2-[1-(3-chloro-2-pyridyl)pyrazolo[4,5-e]pyrimidin-4-yl]oxy-N-(4-cyanothiazol-2-yl)-3-isopropoxy-propanamide;

(2S)—N-(5-chloro-2-pyridyl)-2-[1-(3-chloro-2-pyridyl)pyrazolo[4,5-e]pyrimidin-4-yl]oxy-3-isopropoxy-propanamide;

(2S)-2-[1-(3-chloro-2-pyridyl)pyrazolo[4,5-e]pyrimidin-4-yl]oxy-N-(5-cyano-2-pyridyl)-3-isopropoxy-propanamide;

(2S)-2-[1-(3-chloro-2-pyridyl)pyrazolo[4,5-e]pyrimidin-4-yl]oxy-3-isopropoxy-N-(2-pyridyl)propanamide;

(2S)-2-[1-(3-chloro-2-pyridyl)pyrazolo[4,5-e]pyrimidin-4-yl]oxy-N-(5-fluoro-2-pyridyl)-3-isopropoxy-propanamide;

(2S)—N-(5-chloropyridin-2-yl)-3-ethoxy-2-[1-(3-methylpyridin-4-yl)pyrazolo[4,5-e]pyrimidin-4-yl]oxypropanamide;

(2S)—N-(5-chloropyridin-2-yl)-3-ethoxy-2-(1-(3-methylpyridin-2-yl)-1H-pyrazolo[3,4-d]pyrimidin-4-yloxy)propanamide;

(2S)-3-isopropoxy-N-(5-methylpyridin-2-yl)-2-(1-(2-(methylsulfonyl)phenyl)-1H-pyrazolo[3,4-d]pyrimidin-4-yloxy)propanamide;

(2S)—N-(5-chloropyridin-2-yl)-3-ethoxy-2-(1-(2-(methylsulfonyl)phenyl)-1H-pyrazolo[3,4-d]pyrimidin-4-yloxy)propanamide;

(2R)-2-[1-(3-chloro-2-pyridyl)pyrazolo[4,5-e]pyrimidin-4-yl]oxy-5-hydroxy-N-(5-methyl-2-pyridyl)pentanamide;

(2S)—N-(5-cyano-2-pyridyl)-3-ethoxy-2-[1-[2-(trifluoromethyl)phenyl]pyrazolo[4,5-e]pyrimidin-4-yl]oxy-propanamide;

(2S)-3-ethoxy-N-(5-methylpyrazin-2-yl)-2-[1-[2-(trifluoromethyl)phenyl]pyrazolo[4,5-e]pyrimidin-4-yl]oxy-propanamide;

(2S)—N-(5-chloro-2-pyridyl)-3-ethoxy-2-[1-[3-(trifluoromethyl)-2-pyridyl]pyrazolo[4,5-e]pyrimidin-4-yl]oxy-propanamide;

(2S)-3-isopropoxy-N-(5-methyl-2-pyridyl)-2-[1-(3-methyl-4-pyridyl)pyrazolo[4,5-e]pyrimidin-4-yl]oxy-propanamide;

(2S)-3-(cyclobutoxy)-N-(5-methylpyrazin-2-yl)-2-[1-(3-methyl-4-pyridyl)pyrazolo[4,5-e]pyrimidin-4-yl]oxy-propanamide;

(2S)-3-(cyclobutoxy)-N-(5-methylpyrazin-2-yl)-2-[1-[3-(trifluoromethyl)-2-pyridyl]pyrazolo[4,5-e]pyrimidin-4-yl]oxy-propanamide;

(2S)-2-[1-[5-chloro-3-(trifluoromethyl)-2-pyridyl]pyrazolo[4,5-e]pyrimidin-4-yl]oxy-3-(cyclobutoxy)-N-(5-methylpyrazin-2-yl)propanamide;

(2S)-2-[1-(3-chloro-2-pyridyl)pyrazolo[4,5-e]pyrimidin-4-yl]oxy-3-ethoxy-N-(5-methylsulfonyl-2-pyridyl)propanamide;

(2S)-3-(cyclobutoxy)-N-(5-methylpyrazin-2-yl)-2-[1-(2-methylsulfonylphenyl)pyrazolo[4,5-e]pyrimidin-4-yl]oxy-propanamide;

(2S)-3-(cyclobutoxy)-N-(5-methylpyrazin-2-yl)-2-[1-(3-methyl-2-pyridyl)pyrazolo[4,5-e]pyrimidin-4-yl]oxy-propanamide;

(2S)-3-(cyclobutoxy)-N-(5-methylpyrazin-2-yl)-2-(1-phenylpyrazolo[4,5-e]pyrimidin-4-yl)oxy-propanamide;

(2S)-2-[1-(3-chloro-2-pyridyl)pyrazolo[4,5-e]pyrimidin-4-yl]oxy-4-hydroxy-N-(5-methyl-2-pyridyl)butanamide;

(2S)-3-(cyclobutoxy)-2-[1-(3-methylpyrazin-2-yl)pyrazolo[4,5-e]pyrimidin-4-yl]oxy-N-(5-methyl-2-pyridyl)propanamide;

(2S)-2-[1-(2-chlorophenyl)pyrazolo[4,5-e]pyrimidin-4-yl]oxy-4-hydroxy-N-(5-methyl-2-pyridyl)butanamide;

(2S)-3-isopropoxy-N-(5-methyl-2-pyridyl)-2-[1-(2-methyl-3-pyridyl)pyrazolo[4,5-e]pyrimidin-4-yl]oxy-propanamide;

6-[[(2S)-2-[1-(3-chloro-2-pyridyl)pyrazolo[4,5-e]pyrimidin-4-yl]oxy-3-ethoxy-propanoyl]amino]-N,N-dimethyl-pyridine-3-carboxamide;

(2S)-3-isopropoxy-N-(5-methyl-2-pyridyl)-2-[1-(4-methyl-3-pyridyl)pyrazolo[4,5-e]pyrimidin-4-yl]oxy-propanamide;

(2S)-3-(cyclobutoxy)-N-(5-methylpyrazin-2-yl)-2-[1-(2-methyl-3-pyridyl)pyrazolo[4,5-e]pyrimidin-4-yl]oxy-propanamide;

(2S)—N-(5-chloro-2-pyridyl)-3-ethoxy-2-[1-(2-methyl-3-pyridyl)pyrazolo[4,5-e]pyrimidin-4-yl]oxy-propanamide;

(2S)-2-[1-(2-chlorophenyl)pyrazolo[4,5-e]pyrimidin-4-yl]oxy-3-[(1S)-2-methoxy-1-methyl-ethoxy]-N-(5-methylpyrazin-2-yl)propanamide;

(2S)-2-[1-(2-chlorophenyl)pyrazolo[4,5-e]pyrimidin-4-yl]oxy-3-[(1S)-2-methoxy-1-methyl-ethoxy]-N-(5-methyl-2-pyridyl)propanamide;

(2S)-2-[1-(2-chlorophenyl)pyrazolo[4,5-e]pyrimidin-4-yl]oxy-3-[(1R)-2-methoxy-1-methyl-ethoxy]-N-(5-methyl-2-pyridyl)propanamide;

(2S)-2-[1-(3-chloro-2-pyridyl)pyrazolo[4,5-e]pyrimidin-4-yl]oxy-3-[(1R)-2-methoxy-1-methyl-ethoxy]-N-(5-methyl-2-pyridyl)propanamide;

(2R)-2-[1-(2-chlorophenyl)pyrazolo[4,5-e]pyrimidin-4-yl]oxy-3-[(1S)-2-methoxy-1-methyl-ethoxy]-N-(5-methylpyrazin-2-yl)propanamide;

(2S)-2-[1-(2-chlorophenyl)pyrazolo[4,5-e]pyrimidin-4-yl]oxy-3-(cyclobutoxy)-N-(5-methylpyrazin-2-yl)propanamide;

(2S)-2-[1-(3-chloro-2-pyridyl)pyrazolo[4,5-e]pyrimidin-4-yl]oxy-3-(cyclobutoxy)-N-(5-methylpyrazin-2-yl)propanamide;

(2S)-2-[1-(3-chloro-2-pyridyl)pyrazolo[4,5-e]pyrimidin-4-yl]oxy-3-(cyclobutoxy)-N-(5-methyl-2-pyridyl)propanamide;

[(3S)-3-[1-(3-chloro-2-pyridyl)pyrazolo[4,5-e]pyrimidin-4-yl]oxy-4-[(5-methyl-2-pyridyl)amino]-4-oxo-butyl]acetate;

(2S)-3-isopropoxy-N-(5-methyl-2-pyridyl)-2-[1-[2-(trifluoromethyl)phenyl]pyrazolo[4,5-e]pyrimidin-4-yl]oxy-propanamide;

(2S)-2-[1-(2-chlorophenyl)pyrazolo[4,5-e]pyrimidin-4-yl]oxy-N-(5-methyl-2-pyridyl)-4-methylsulfonyl-butanamide;

(2S)-2-[1-(3-chloro-2-pyridyl)pyrazolo[4,5-e]pyrimidin-4-yl]oxy-N-(5-cyano-2-pyridyl)-3-(2-hydroxyethoxy)propanamide;

(2S)—N-(5-chloro-2-pyridyl)-2-[1-(3-chloro-2-pyridyl)pyrazolo[4,5-e]pyrimidin-4-yl]oxy-3-(2-hydroxyethoxy)propanamide;

(2S)-2-[1-(2-chlorophenyl)pyrazolo[4,5-e]pyrimidin-4-yl]oxy-4-methanesulfonamido-N-(5-methyl-2-pyridyl)butanamide;

(2S)-2-[1-(3-chloro-2-pyridyl)pyrazolo[4,5-e]pyrimidin-4-yl]oxy-4-hydroxy-N-(5-methylpyrazin-2-yl)butanamide;

(2S)—N-(5-chloro-2-pyridyl)-2-[1-(3-chloro-2-pyridyl)pyrazolo[4,5-e]pyrimidin-4-yl]oxy-4-hydroxy-butanamide;

(2S)-2-[1-(3-chloro-2-pyridyl)pyrazolo[4,5-e]pyrimidin-4-yl]oxy-4-hydroxy-N-(2-pyridyl)butanamide;

(2S)-2-[1-(3-chloro-2-pyridyl)pyrazolo[4,5-e]pyrimidin-4-yl]oxy-N-(5-fluoro-2-pyridyl)-4-hydroxy-butanamide;

(2S)-2-[1-(3-chloro-2-pyridyl)pyrazolo[4,5-e]pyrimidin-4-yl]oxy-N-(5-cyano-2-pyridyl)-4-hydroxy-butanamide;

(2S)-2-[1-(3-chloro-2-pyridyl)pyrazolo[4,5-e]pyrimidin-4-yl]oxy-4-hydroxy-N-pyrimidin-4-yl-butanamide;

(2S)—N-(5-chloropyridin-2-yl)-2-[1-(3-chloropyridin-2-yl)pyrazolo[4,5-e]pyrimidin-4-yl]oxy-3-(3-hydroxyazetidin-1-yl)propanamide;

(2S)-2-[1-(3-chloro-2-methylphenyl)pyrazolo[4,5-e]pyrimidin-4-yl]oxy-N-(5-cyanopyridin-2-yl)-3-(2-hydroxyethoxy)propanamide;

(2S)-2-[1-(3-chloro-2-methylphenyl)pyrazolo[4,5-e]pyrimidin-4-yl]oxy-3-(2-hydroxyethoxy)-N-(5-methylpyridin-2-yl)propanamide;

(2S)—N-(5-cyanopyridin-2-yl)-2-[1-(3-fluoro-2-methylphenyl)pyrazolo[4,5-e]pyrimidin-4-yl]oxy-3-(2-hydroxyethoxy)propanamide;

(2S)-2-[1-(3-fluoro-2-methylphenyl)pyrazolo[4,5-e]pyrimidin-4-yl]oxy-3-(2-hydroxyethoxy)-N-(5-methylpyridin-2-yl)propanamide;

(2S)—N-(5-chloropyridin-2-yl)-2-[1-(3-fluoro-2-methylphenyl)pyrazolo[4,5-e]pyrimidin-4-yl]oxy-3-(2-hydroxyethoxy)propanamide;

(2S)-2-[1-(2-chlorophenyl)pyrazolo[4,5-e]pyrimidin-4-yl]oxy-N-(5-chloropyridin-2-yl)-3-(2-hydroxyethoxy)propanamide;

(2S)-2-[1-(2-chlorophenyl)pyrazolo[4,5-e]pyrimidin-4-yl]oxy-N-(5-cyanopyridin-2-yl)-3-(2-hydroxyethoxy)propanamide;

(2S)-2-[1-(3-chloro-2-methylphenyl)pyrazolo[4,5-e]pyrimidin-4-yl]oxy-N-(5-chloropyridin-2-yl)-3-(2-hydroxyethoxy)propanamide;

(2S)-2-(1-(2-chloro-6-cyanophenyl)-1H-pyrazolo[3,4-d]pyrimidin-4-yloxy)-N-(5-chloropyridin-2-yl)-3-(2-hydroxyethoxy)propanamide;

(2S)-2-(1-(2-chloro-6-cyanophenyl)-1H-pyrazolo[3,4-d]pyrimidin-4-yloxy)-3-((R)-1-hydroxypropan-2-yloxy)-N-(5-methylpyridin-2-yl)propanamide;

(2S)-2-(1-(2-chloro-6-cyanophenyl)-1H-pyrazolo[3,4-d]pyrimidin-4-yloxy)-3-(2-hydroxyethoxy)-N-(5-methylpyridin-2-yl)propanamide;

(2S)-2-(1-(3-chloropyridin-2-yl)-1H-pyrazolo[3,4-d]pyrimidin-4-yloxy)-3-isopropoxy-N-(5-(methylsulfonyl)pyridin-2-yl)propanamide;

6-((2S)-2-(1-(3-chloropyridin-2-yl)-1H-pyrazolo[3,4-d]pyrimidin-4-yloxy)-3-isopropoxypropanamido)-N,N-dimethylnicotinamide;

(2S)—N-(5-chloropyridin-2-yl)-2-(1-(2,5-dimethylphenyl)-1H-pyrazolo[3,4-d]pyrimidin-4-yloxy)-3-(2-hydroxyethoxy)propanamide;

(2S)—N-(5-chloropyridin-2-yl)-2-(1-(5-fluoro-2-methylphenyl)-1H-pyrazolo[3,4-d]pyrimidin-4-yloxy)-3-(2-hydroxyethoxy)propanamide;

(S)-2-(1-benzyl-1H-pyrazolo[3,4-d]pyrimidin-4-yloxy)-3-(2-hydroxyethoxy)-N-(5-methylpyridin-2-yl)propanamide;

(2S)—N-(5-cyanopyridin-2-yl)-2-(1-(5-fluoro-2-methylphenyl)-1H-pyrazolo[3,4-d]pyrimidin-4-yloxy)-3-(2-hydroxyethoxy)propanamide;

(2S)-2-(1-(5-cyano-2-methylphenyl)-1H-pyrazolo[3,4-d]pyrimidin-4-yloxy)-N-(5-cyanopyridin-2-yl)-3-(2-hydroxyethoxy)propanamide;

(2S)-2-(1-(5-cyano-2-methylphenyl)-1H-pyrazolo[3,4-d]pyrimidin-4-yloxy)-3-(2-hydroxyethoxy)-N-(5-methylpyridin-2-yl)propanamide;

(2S)—N-(5-chloropyridin-2-yl)-2-(1-(5-cyano-2-methylphenyl)-1H-pyrazolo[3,4-d]pyrimidin-4-yloxy)-3-(2-hydroxyethoxy)propanamide;

(2S)—N-(5-cyanopyridin-2-yl)-2-(1-(2,5-dimethylphenyl)-1H-pyrazolo[3,4-d]pyrimidin-4-yloxy)-3-ethoxypropanamide;

(2S)—N-(5-cyanopyridin-2-yl)-3-ethoxy-2-(1-(4-methylpyridin-3-yl)-1H-pyrazolo[3,4-d]pyrimidin-4-yloxy)propanamide;

(2S)-3-cyclobutoxy-N-(5-methylpyrazin-2-yl)-2-(1-(4-methylpyridin-3-yl)-1H-pyrazolo[3,4-d]pyrimidin-4-yloxy)propanamide;

(2S)-2-(1-(3-chloropyridin-2-yl)-1H-pyrazolo[3,4-d]pyrimidin-4-yloxy)-N-(5-cyanopyridin-2-yl)-3-((R)-1-hydroxypropan-2-yloxy)propanamide;

(2S)—N-(5-chloropyridin-2-yl)-2-(1-(3-chloropyridin-2-yl)-1H-pyrazolo[3,4-d]pyrimidin-4-yloxy)-3-((R)-1-hydroxypropan-2-yloxy)propanamide;

(2S)-2-(1-(3-chloropyridin-2-yl)-1H-pyrazolo[3,4-d]pyrimidin-4-yloxy)-N-(5-fluoropyridin-2-yl)-3-((R)-1-hydroxypropan-2-yloxy)propanamide;

(2S)-2-(1-(3-chloropyridin-2-yl)-1H-pyrazolo[3,4-d]pyrimidin-4-yloxy)-N-(5-fluoropyridin-2-yl)-3-((S)-1-hydroxypropan-2-yloxy)propanamide;

(2S)—N-(5-chloropyridin-2-yl)-2-(1-(3-chloropyridin-2-yl)-1H-pyrazolo[3,4-d]pyrimidin-4-yloxy)-3-((S)-1-hydroxypropan-2-yloxy)propanamide;

(2S)-2-(1-(2-chlorophenyl)-1H-pyrazolo[3,4-d]pyrimidin-4-yloxy)-3-(2-hydroxyethoxy)-N-(5-methylpyridin-2-yl)propanamide;

(2S)-3-(2-hydroxyethoxy)-N-(pyridin-2-yl)-2-(1-(2-(trifluoromethyl)phenyl)-1H-pyrazolo[3,4-d]pyrimidin-4-yloxy)propanamide;

(2S)-2-(1-(2-chlorophenyl)-1H-pyrazolo[3,4-d]pyrimidin-4-yloxy)-3-((R)-1-hydroxypropan-2-yloxy)-N-(pyridin-2-yl)propanamide;

(2S)-2-(1-(2-chlorophenyl)-1H-pyrazolo[3,4-d]pyrimidin-4-yloxy)-3-(2-hydroxyethoxy)-N-(pyridin-2-yl)propanamide;

(2S)—N-(5-chloropyridin-2-yl)-2-(1-(2,3-dichlorophenyl)-1H-pyrazolo[3,4-d]pyrimidin-4-yloxy)-3-(2-hydroxyethoxy)propanamide;

(2S)—N-(5-cyanopyridin-2-yl)-2-(1-(2,3-dichlorophenyl)-1H-pyrazolo[3,4-d]pyrimidin-4-yloxy)-3-(2-hydroxyethoxy)propanamide;

(2S)-2-(1-(3-chloropyridin-2-yl)-1H-pyrazolo[3,4-d]pyrimidin-4-yloxy)-3-((S)-2-hydroxypropoxy)-N-(5-methylpyridin-2-yl)propanamide;

(2S)-2-(1-(2-chlorophenyl)-1H-pyrazolo[3,4-d]pyrimidin-4-yloxy)-3-(3-hydroxyazetidin-1-yl)-N-(5-methylpyridin-2-yl)propanamide;

(2S)-2-(1-(3-chloropyridin-2-yl)-1H-pyrazolo[3,4-d]pyrimidin-4-yloxy)-3-(3-hydroxyazetidin-1-yl)-N-(5-methylpyridin-2-yl)propanamide;

(2S)-2-(1-(3-cyano-2-methylphenyl)-1H-pyrazolo[3,4-d]pyrimidin-4-yloxy)-N-(5-cyanopyridin-2-yl)-3-(2-hydroxyethoxy)propanamide;

(2S)-2-(1-(3-cyano-2-methylphenyl)-1H-pyrazolo[3,4-d]pyrimidin-4-yloxy)-3-(2-hydroxyethoxy)-N-(5-methylpyridin-2-yl)propanamide;

(2S)—N-(5-chloropyridin-2-yl)-2-(1-(3-cyano-2-methylphenyl)-1H-pyrazolo[3,4-d]pyrimidin-4-yloxy)-3-(2-hydroxyethoxy)propanamide;

(2S)—N-(5-chloropyridin-2-yl)-3-ethoxy-2-(1-(1-methyl-1H-imidazol-2-yl)-1H-pyrazolo[3,4-d]pyrimidin-4-yloxy)propanamide;

(2S)-3-isopropoxy-2-(1-(1-methyl-1H-imidazol-2-yl)-1H-pyrazolo[3,4-d]pyrimidin-4-yloxy)-N-(5-methylpyridin-2-yl)propanamide;

(2S)—N-(5-chloropyridin-2-yl)-2-(1-(3-chloropyridin-2-yl)-1H-pyrazolo[3,4-d]pyrimidin-4-yloxy)-5-hydroxypentanamide;

(2S)-2-(1-(3-chloropyridin-2-yl)-1H-pyrazolo[3,4-d]pyrimidin-4-yloxy)-N-(5-cyanopyridin-2-yl)-5-hydroxypentanamide;

(2S)—N-(5-cyanopyridin-2-yl)-2-(1-(2,3-dichlorophenyl)-1H-pyrazolo[3,4-d]pyrimidin-4-yloxy)-3-ethoxypropanamide;

(2S)-2-[1-(2-chlorophenyl)pyrazolo[4,5-e]pyrimidin-4-yl]oxy-N-(5-fluoro-2-pyridyl)-3-(3-hydroxyazetidin-1-yl)propanamide;

(2S)-2-[1-(2-chloro-6-cyano-phenyl)pyrazolo[4,5-e]pyrimidin-4-yl]oxy-N-(5-chloro-2-pyridyl)-3-[(1R)-2-hydroxy-1-methyl-ethoxy]propanamide;

(2S)-2-[1-(2,6-dichlorophenyl)pyrazolo[4,5-e]pyrimidin-4-yl]oxy-N-(5-fluoro-2-pyridyl)-3-(2-hydroxyethoxy)propanamide;

(2S)-2-[1-(2-chlorophenyl)pyrazolo[4,5-e]pyrimidin-4-yl]oxy-3-(3-hydroxyazetidin-1-yl)-N-(5-methylpyrazin-2-yl)propanamide;

(2S)-3-(azetidin-1-yl)-2-[1-(2-chloro-6-cyano-phenyl)pyrazolo[3,4-d]pyrimidin-4-yl]oxy-N-(2-pyridyl)propanamide;

(2S)-2-[1-(2-chloro-6-fluoro-phenyl)pyrazolo[3,4-d]pyrimidin-4-yl]oxy-3-(3-hydroxyazetidin-1-yl)-N-(2-pyridyl)propanamide;

(2S)-2-[1-(2-chlorophenyl)pyrazolo[3,4-d]pyrimidin-4-yl]oxy-N-(5-cyano-2-pyridyl)-3-(3-hydroxyazetidin-1-yl)propanamide;

(2S)-2-[1-(2-chloro-6-cyano-phenyl)pyrazolo[3,4-d]pyrimidin-4-yl]oxy-N-(5-cyano-2-pyridyl)-3-(3-hydroxyazetidin-1-yl)propanamide;

(2S)-2-[1-(2-chlorophenyl)pyrazolo[3,4-d]pyrimidin-4-yl]oxy-3-(3-hydroxyazetidin-1-yl)-N-(2-pyridyl)propanamide;

(2S)-2-[1-(2-chlorophenyl)pyrazolo[3,4-d]pyrimidin-4-yl]oxy-N-(5-chloro-2-pyridyl)-3-(3-hydroxyazetidin-1-yl)propanamide;

(2S)-3-[(1R)-2-hydroxy-1-methyl-ethoxy]-N-(5-methyl-2-pyridyl)-2-[1-(4-methyl-3-thienyl)pyrazolo[3,4-d]pyrimidin-4-yl]oxy-propanamide;

(2S)-2-[1-(2-chlorophenyl)pyrazolo[3,4-d]pyrimidin-4-yl]oxy-3-[3-(hydroxymethyl)azetidin-1-yl]-N-(2-pyridyl)propanamide;

(2S)-2-[1-(2-chloro-6-fluoro-phenyl)pyrazolo[3,4-d]pyrimidin-4-yl]oxy-N-(5-fluoro-2-pyridyl)-3-(3-hydroxyazetidin-1-yl)propanamide;

(2S)-2-[1-(2,6-dichlorophenyl)pyrazolo[3,4-d]pyrimidin-4-yl]oxy-N-(5-fluoro-2-pyridyl)-3-(3-hydroxyazetidin-1-yl)propanamide;

(2S)-2-[1-(2-chloro-6-cyano-phenyl)pyrazolo[3,4-d]pyrimidin-4-yl]oxy-3-[(1R)-2-hydroxy-1-methyl-ethoxy]-N-(2-pyridyl)propanamide;

(2S)-2-[1-(3-chloro-2-pyridyl)pyrazolo[3,4-d]pyrimidin-4-yl]oxy-3-[(1R)-2-hydroxy-1-methyl-ethoxy]-N-(5-methyl-2-pyridyl)propanamide;

(2S)-2-[1-(2,6-dichlorophenyl)pyrazolo[3,4-d]pyrimidin-4-yl]oxy-3-(3-hydroxyazetidin-1-yl)-N-(2-pyridyl)propanamide;

(2S)—N-(5-cyano-2-pyridyl)-2-[1-(2,6-dichlorophenyl)pyrazolo[3,4-d]pyrimidin-4-yl]oxy-3-(3-hydroxyazetidin-1-yl)propanamide;

(2S)—N-(5-cyano-2-pyridyl)-2-[1-(2,6-dichlorophenyl)pyrazolo[3,4-d]pyrimidin-4-yl]oxy-3-(2-hydroxyethoxy)propanamide;

(2S)—N-(5-chloro-2-pyridyl)-2-[1-(2,6-dicyanophenyl)pyrazolo[3,4-d]pyrimidin-4-yl]oxy-3-[(1R)-2-hydroxy-1-methyl-ethoxy]propanamide;

(2S)-2-[1-(2-chloro-6-cyano-phenyl)pyrazolo[3,4-d]pyrimidin-4-yl]oxy-N-(5-fluoro-2-pyridyl)-3-(2-hydroxyethoxy)propanamide;

(2S)-2-[1-(2-chloro-6-cyano-phenyl)pyrazolo[3,4-d]pyrimidin-4-yl]oxy-3-(2-hydroxyethoxy)-N-(2-pyridyl)propanamide;

(2S)-2-[1-(2-chloro-6-cyano-phenyl)pyrazolo[3,4-d]pyrimidin-4-yl]oxy-3-(3-hydroxyazetidin-1-yl)-N-(5-methylpyrazin-2-yl)propanamide;

(2S)-2-[1-(2-chloro-6-cyano-phenyl)pyrazolo[3,4-d]pyrimidin-4-yl]oxy-N-(5-chloro-2-pyridyl)-3-(3-hydroxyazetidin-1-yl)propanamide;

(2S)-2-[1-(3-chloro-2-pyridyl)pyrazolo[3,4-d]pyrimidin-4-yl]oxy-3-(3-hydroxyazetidin-1-yl)-N-(2-pyridyl)propanamide;

(2S)-2-[1-(2-chloro-6-cyano-phenyl)pyrazolo[3,4-d]pyrimidin-4-yl]oxy-N-(5-fluoro-2-pyridyl)-3-(3-hydroxyazetidin-1-yl)propanamide;

(2S)-2-[1-(3-chloro-2-pyridyl)pyrazolo[3,4-d]pyrimidin-4-yl]oxy-N-(5-fluoro-2-pyridyl)-3-(3-hydroxyazetidin-1-yl)propanamide;

(2S)-2-[1-(2-chloro-6-fluoro-phenyl)pyrazolo[3,4-d]pyrimidin-4-yl]oxy-N-(5-fluoro-2-pyridyl)-3-(2-hydroxyethoxy)propanamide;

(2S)-2-[1-(2-chlorophenyl)pyrazolo[3,4-d]pyrimidin-4-yl]oxy-N-(5-fluoro-2-pyridyl)-3-[(1R)-2-hydroxy-1-methyl-ethoxy]propanamide;

(2S)-2-[1-(2-chloro-6-cyano-phenyl)pyrazolo[3,4-d]pyrimidin-4-yl]oxy-N-(5-fluoro-2-pyridyl)-3-[(1R)-2-hydroxy-1-methyl-ethoxy]propanamide;

(2S)-2-[1-(2-chlorophenyl)pyrazolo[3,4-d]pyrimidin-4-yl]oxy-3-[(1R)-2-hydroxy-1-methyl-ethoxy]-N-(5-methylpyrazin-2-yl)propanamide;

(2S)-2-[1-(2-chlorophenyl)pyrazolo[3,4-d]pyrimidin-4-yl]oxy-N-(5-fluoro-2-pyridyl)-3-(2-hydroxyethoxy)propanamide;

(2S)-2-[1-(3-chloro-2-pyridyl)pyrazolo[3,4-d]pyrimidin-4-yl]oxy-3-(3-hydroxyazetidin-1-yl)-N-(5-methylthiazol-2-yl)propanamide;

(2S)-2-[1-(2,6-dichlorophenyl)pyrazolo[3,4-d]pyrimidin-4-yl]oxy-3-(2-hydroxyethoxy)-N-(2-pyridyl)propanamide;

(2S)-2-[1-(2-chloro-6-cyano-phenyl)pyrazolo[3,4-d]pyrimidin-4-yl]oxy-N-(5-cyano-2-pyridyl)-3-[(1R)-2-hydroxy-1-methyl-ethoxy]propanamide; and (2S)-2-[1-(2-chlorophenyl)pyrazolo[3,4-d]pyrimidin-4-yl]oxy-N-(5-cyano-2-pyridyl)-3-[(1R)-2-hydroxy-1-methyl-ethoxy]propanamide.

2. A compound or a pharmaceutically acceptable salt thereof as claimed in claim 1 selected from the group consisting of:

(2S)—N-(5-chloropyridin-2-yl)-2-(1-(3-chloropyridin-2-yl)-1H-pyrazolo[3,4-d]pyrimidin-4-yloxy)-3-(3-hydroxyazetidin-1-yl)propanamide;

(2S)-2-(1-(2-chloro-6-cyanophenyl)-1H-pyrazolo[3,4-d]pyrimidin-4-yloxy)-N-(5-chloropyridin-2-yl)-3-(2-hydroxyethoxy)propanamide;

(2S)—N-(5-chloropyridin-2-yl)-2-(1-(3-chloropyridin-2-yl)-1H-pyrazolo[3,4-d]pyrimidin-4-yloxy)-3-((R)-1-hydroxypropan-2-yloxy)propanamide;

(2S)-2-[1-(2-chlorophenyl)pyrazolo[4,5-e]pyrimidin-4-yl]oxy-N-(5-fluoro-2-pyridyl)-3-(3-hydroxyazetidin-1-yl)propanamide;

(2S)-2-[1-(2-chloro-6-cyano-phenyl)pyrazolo[4,5-e]pyrimidin-4-yl]oxy-N-(5-chloro-2-pyridyl)-3-[(1R)-2-hydroxy-1-methyl-ethoxy]propanamide;

(2S)-2-[1-(2,6-dichlorophenyl)pyrazolo[4,5-e]pyrimidin-4-yl]oxy-N-(5-fluoro-2-pyridyl)-3-(2-hydroxyethoxy)propanamide;

(2S)-2-[1-(2-chlorophenyl)pyrazolo[4,5-e]pyrimidin-4-yl]-3-(3-hydroxyazetidin-1-yl)-N-(5-methylpyrazin-2-yl)propanamide;

(2S)-2-[1-(2-chlorophenyl)pyrazolo[3,4-d]pyrimidin-4-yl]oxy-N-(5-chloro-2-pyridyl)-3-(3-hydroxyazetidin-1-yl)propanamide;

(2S)-2-[1-(2,6-dichlorophenyl)pyrazolo[3,4-d]pyrimidin-4-yl]oxy-N-(5-fluoro-2-pyridyl)-3-(3-hydroxyazetidin-1-yl)propanamide; and (2S)-2-[1-(2-chloro-6-cyano-phenyl)pyrazolo[3,4-d]pyrimidin-4-yl]oxy-N-(5-fluoro-2-pyridyl)-3-(3-hydroxyazetidin-1-yl)propanamide.

3. A pharmaceutical composition comprising a compound according to claim 1, or a pharmaceutically-acceptable salt thereof, together with a pharmaceutically acceptable diluent or carrier.

* * * * *